US012746242B2

(12) United States Patent
O'Farrell et al.

(10) Patent No.: US 12,746,242 B2
(45) **Date of Patent: *Sep. 29, 2026**

(54) COMBINATION THERAPIES OF FASN INHIBITORS WITH THYROID HORMONE RECEPTOR AGONISTS

(71) Applicant: Sagimet Biosciences Inc., San Mateo, CA (US)

(72) Inventors: Anne-Marie O'Farrell, Burlingame, CA (US); George Kemble, Saratoga, CA (US); Wen-Wei Tsai, San Mateo, CA (US)

(73) Assignee: Sagimet Biosciences Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/228,638

(22) Filed: Jun. 4, 2025

(65) Prior Publication Data

US 2026/0048061 A1 Feb. 19, 2026

Related U.S. Application Data

(63) Continuation of application No. 18/749,069, filed on Jun. 20, 2024.

(60) Provisional application No. 63/509,267, filed on Jun. 20, 2023.

(51) Int. Cl.

| | |
|---|---|
| ***A61K 31/53*** | (2006.01) |
| ***A61K 31/4155*** | (2006.01) |
| ***A61K 31/454*** | (2006.01) |
| ***A61P 1/16*** | (2006.01) |

(52) U.S. Cl.
CPC .......... *A61K 31/53* (2013.01); *A61K 31/4155* (2013.01); *A61K 31/454* (2013.01); *A61P 1/16* (2018.01)

(58) Field of Classification Search
None
See application file for complete search history.

(56) References Cited

U.S. PATENT DOCUMENTS

| | | | |
|---|---|---|---|
| 3,625,214 | A | 12/1971 | Higuchi |
| 4,789,734 | A | 12/1988 | Pierschbacher |
| 4,897,268 | A | 1/1990 | Tice et al. |
| 4,906,474 | A | 3/1990 | Langer et al. |
| 4,925,673 | A | 5/1990 | Steiner et al. |
| 5,075,109 | A | 12/1991 | Tice et al. |
| 5,190,029 | A | 3/1993 | Byron et al. |
| 5,376,359 | A | 12/1994 | Johnson |
| 5,776,434 | A | 7/1998 | Purewal et al. |
| 5,811,128 | A | 9/1998 | Tice et al. |
| 5,814,344 | A | 9/1998 | Tice et al. |
| 5,820,883 | A | 10/1998 | Tice et al. |
| 5,853,763 | A | 12/1998 | Tice et al. |
| 5,928,647 | A | 7/1999 | Rock |
| 5,942,252 | A | 8/1999 | Tice et al. |
| 9,624,173 | B2 | 4/2017 | Oslob et al. |
| 2019/0381045 | A1 | 12/2019 | Harriman et al. |
| 2020/0248261 | A1 | 8/2020 | Hanf et al. |
| 2022/0023299 | A1 | 1/2022 | Esler et al. |
| 2022/0411405 | A1 | 12/2022 | Bestvater et al. |

FOREIGN PATENT DOCUMENTS

| | | | |
|---|---|---|---|
| WO | 2008059214 | A1 | 5/2008 |
| WO | 2012122391 | A1 | 9/2012 |
| WO | 2014008197 | A1 | 1/2014 |
| WO | 2015095767 | A1 | 6/2015 |
| WO | 2015105860 | A1 | 7/2015 |
| WO | 2016025816 | A1 | 2/2016 |
| WO | 2016149271 | A1 | 9/2016 |
| WO | 2018089904 | A1 | 5/2018 |
| WO | 2022165227 | A1 | 8/2022 |
| WO | 2023085931 | A1 | 5/2023 |
| WO | 2023086483 | A1 | 5/2023 |
| WO | 2024251076 | A1 | 12/2024 |
| WO | 2024263785 | A1 | 12/2024 |
| WO | 2025020955 | A1 | 1/2025 |
| WO | 2025080818 | A1 | 4/2025 |
| WO | 2025086054 | A1 | 5/2025 |
| WO | 2025155977 | A1 | 7/2025 |

OTHER PUBLICATIONS

Harrison et al. "Resmetirom (MGL-3196) for the Treatment of Non-Alcoholic Steatohepatitis: A Multicentre, Randomised, Double-Blind, Placebo-Controlled, Phase 2 Trial". Lancet. 2019; 394:2012-2024. (Year: 2019).*

Loomba et al. "TVB-2640 (Fasn Inhibitor) for the Treatment of Nonalcoholic Steatohepatitis: Fascinate-1, a Randomized, Placebo-Controlled Phase 2a Trial". Gastroenterology. 2021; 161:1475-1486. (Year: 2021).*

Brol et al. "The Pathogenesis of Hepatic Fibrosis: Basic Facts and Clinical Challenges—Assessment of Liver Fibrosis: A Narrative Review". Dig Med Res. Jun. 30, 2022; 5:24. (Year: 2022).*

National Cancer Institute (NCI) Dictionary [Online]. "Denifanstat". [Retrieved Dec. 12, 2025]. Retrieved from the Internet: <URL: https://www.cancer.gov/publications/dictionaries/cancer-drug/def/denifanstat>. One page. (Year: 2025).*

Harrison et al. "Effects of Resmetirom on Noninvasive Endpoints in a 36-Week Phase 2 Active Treatment Extension Study in Patients with NASH". Hepatology Communications. 2021; 5(4):573-588. (Year: 2021).*

(Continued)

*Primary Examiner* — Leslie A. Royds Draper

(74) *Attorney, Agent, or Firm* — Goodwin Procter LLP

(57) ABSTRACT

Therapeutic combinations of fatty acid synthesis modulators and thyroid hormone receptor agonists are provided. The combinations may be used to treat disorders including metabolic disorders and liver disorders, such as nonalcoholic steatohepatitis/metabolic dysfunction-associated steatohepatitis (NASH/MASH).

18 Claims, 21 Drawing Sheets

(56) References Cited

OTHER PUBLICATIONS

Tsai et al. "Combination of Fatty Acid Synthase (FASN) Inhibitor and Thyroid Hormone Receptor Beta (THRb) Agonist, Resmetirom, Improved Markers of NASH and Cardiovascular Health in LDL Receptor Knockout Mice", Journal of Hepatology, Jun. 5-8, 2024; 80( S1), Abstract THU-231, p. S575-576. (Year: 2024).*
Donnelly et al., "Sources of Fatty Acids Stored in Liver and Secreted via Lipoproteins in Patients with Nonalcoholic Fatty Liver Disease," J. Clin. Invest. 115 (5). 2005, 1343-51.
Lambert et al., Increased De Novo Lipogenesis Is a Distinct Characteristic of Individuals with Nonalcoholic Fatty Liver Disease, Gastroenterology, 146 (3), pp. 726-735, Mar. 2014.
Wei, "Saturated Fatty Acids Induce Endoplasmic Reticulum Stress and Apoptosis Independently of Ceramide in Liver Cells," Am. J. Physio. Endocrinol. Metab. 291 (2): 2006, E275-81.
Kakazu et al., Hepatocytes Release Ceramide-rich Proinflammatory Extracellular Vesicles in an IRE1alpha dependent manner, Journal of Lipid Research, vol. 57, pp. 233-245, 2016.
Roncari DA. Mammalian fatty acid synthetase. I. Purification and properties of human liver complex. Can J Biochem., 52(3):221, Mar. 1974.
Thompson BJ, Smith S. Biosynthesis of fatty acids by lactating human breast epithelial cells: an evaluation of the contribution to the overall composition of human milk fat. Pediatr Res. Jan. 1985;19(1):139-43.
Park SH, et al., Phosphorylation-activity relationships of AMPK and acetyl-CoA carboxylase in muscle. J Appl Physiol (1985). Jun. 2002;92(6):2475-82.
Hardie DG. Regulation of fatty acid and cholesterol metabolism by the AMP-activated protein kinase. Biochim Biophys Acta., 1123(3):231-8, Feb. 1992.
Chakravarthy et al., "New hepatic fat activates PPARalpha to maintain glucose, lipid, and cholesterol homeostasis," Cell Metabol. 1(5), 2005, 309-322.
Wu, M. et al. Antidiabetic and antisteatotic effects of the selective fatty acid synthase (FAS) inhibitor platensimycin in mouse models of diabetes. Proc Natl Acad Sci U S A. Mar. 29, 2011; 108(13):5378-83. doi: 10.1073/pnas.1002588108. Epub Mar. 9, 2011.
Francis et. al., "De novo lipogenesis in the liver in health and disease: more than just a shunting yard for glucose." Biol. Rev. (2016), 91, pp. 452-468.
Bae et. al., "Combined effect of nonalcoholic fatty liver disease and impaired fasting glucose on the development of type 2 diabetes." Diabetes Care, 2011, 34, 727-729.
"A Novel Fatty Acid Synthase Inhibitor (FASi) Suppresses De Novo Lipogenesis but induces Hepatic Steatosis, Dermatitis and does not enhance Insulin Sensitivity in Obese Zucker Rats," Am. Diabetes Assoc. 68th Scientific Sessions, Jun. 6-10, 2008, San Francisco, CA, poster 58LB.
Tesmer LA, et al., Th17 cells in human disease. Immunol Rev. Jun. 2008;223:87-113.
Lee et. al. Unexpected targets and triggers of autoimmunity. J. Clin. Immunol., 34 Suppl 1, 2014, S56-60.
Flavin et al. Fatty acid synthase as a potential therapeutic target in cancer. Future Oncol. Apr. 2010;6(4):551-62.
Orita et al. Selective inhibition of fatty acid synthase for lung cancer treatment. Clin Cancer Res. Dec. 1, 2007;13 (23):7139-45.
Puig et al. A novel inhibitor of fatty acid synthase shows activity against HER2+ breast cancer xenografts and is active in anti-HER2 drug-resistant cell lines. Breast Cancer Res. 2011;13(6):R131.
Browne et al., Inhibition of endothelial cell proliferation and angiogenesis by orlistat, a fatty acid synthase inhibitor. FASEB J., 20(12), pp. 2027-2035, Oct. 2006.
Jain, K.K Trends in Pharmacological Sciences, vol. 19, Issue 5, 155-157, 1998.
Bangham et al., Diffusion of univalent ions across the lamellae of swollen phospholipids. J Mol Biol. Aug. 1965;13(1):238-52.
Szoka et al., Procedure for preparation of liposomes with large internal aqueous space and high capture by reverse-phase evaporation. Proc Natl Acad Sci U S A. Sep. 1978;75(9):4194-8.
Klausner et al., 2003 "Novel gastroretentive dosage forms: evaluation of gastroretentivity and its effect on levodopa in humans." Pharm. Res. 20, 1466-73.
Hoffman et al., Pharmacokinetic and pharmacodynamic aspects of gastroretentive dosage forms. Int J Pharm. Jun. 11, 2004;277(1-2):141-53.
Streubel et al., Gastroretentive drug delivery systems. Expert Opin Drug Deliv., 3(2):217-33, Mar. 2006.
Chavanpatil et al., Novel sustained release, swellable and bioadhesive gastroretentive drug delivery system for ofloxacin. Int J Pharm. Jun. 19, 2006;316(1-2):86-92.
Chung et al. A fluorescence-based thiol quantification assay for ultra-high-throughput screening for inhibitors of coenzyme A production. Assay Drug Dev Technol. Jun. 2008;6(3):361-74.
PCT/US2024/034827 International Search Report and Written Opinion issued Nov. 5, 2024 (16 pages).
Miyazaki et al., Effects of fenofibrate on lipid profiles, cholesterol estertransfer activity, and in-stent intimal hyperplasia in patients after elective coronary stenting, Lipids in Health and Disease, 9:122, 9 pages, 2010.
The Accord Group Study, Effects of Combination Lipid Therapy in Type 2 Diabetes Mellitus, The New England Journal of Medicine, vol. 362, No. 17, 12 pages, Apr. 2010.
The effects of lowering LDL cholesterol with statin therapy in people at low risk of vascular disease: meta-analysis of individual data from 27 randomised trials, Cholesterol Treatment Trialists (CTT) Collaborators, Lancet, 380, pp. 581-590, May 2012.

* cited by examiner

| | | | | | | | | | |
|---|---|---|---|---|---|---|---|---|---|
| TVB | | | | low | high | low | high | low | high |
| Combinatorial drug | | MGL low | MGL high | | | MGL low | MGL low | MGL high | MGL high |
| | NASH | | | | | | | | |
| lipids | TGs | U | U | D | D | D | D | D | D |
| Inflammation | MCP1 | U | U | U | U | U | U | D | U |
| | IL6 | U | U | D | U | | U | D | U |
| | MIP1a | U | U | U | U | D | D | D | D |
| | TNFa | | D | D | U | D | U | D | D |
| | IP10 | U | U | D | U | D | D | | U |
| | IP8 | U | U | U | U | D | D | D | U |
| Fibrosis | PC1-d7 | U | U | U | U | U | D | D | D |
| | PC1-d10 | | D | U | U | U | D | D | D |
| | PC3-d10 | D | U | D | D | D | | | U |

COMBINATION THERAPIES OF FASN INHIBITORS WITH THYROID HORMONE RECEPTOR AGONISTS

CROSS-REFERENCE TO RELATED APPLICATIONS

The present application is a continuation of U.S. patent application Ser. No. 18/749,069, filed Jun. 20, 2024, which claims priority from U.S. Prov. Application Ser. No. 63/509,267, filed Jun. 20, 2023, the disclosures of which are incorporated herein by reference.

FIELD

The present disclosure relates generally to therapeutic combinations of fatty acid synthase inhibitors with thyroid hormone receptor agonists for the treatment of liver diseases.

BACKGROUND

Metabolic dysfunction-associated steatotic liver disease (MASLD) (formerly known as non-alcoholic liver disease (NAFLD)), a condition in which the liver contains more than 5% fat by weight and is not caused by excessive alcohol consumption, is a disease which currently affects ~20-30% of the US and general western world population, and is associated with a significant increased risk of morbidity extending beyond the liver to cardiovascular disease (i.e., carotid atherosclerotic plaques and endothelial dysfunction), chronic kidney disease and malignancy. Obesity, type 2 diabetes and metabolic syndrome are three key risk factors for NAFLD/MASLD which are characterized as an imbalance in energy utilization and storage. This imbalance leads to dysregulated metabolic pathways and inflammatory responses that drive further changes leading to liver damage and comorbid conditions. Along with the progression of metabolic syndrome, NAFLD/MASLD leads to more advanced liver disease starting with metabolic dysfunction-associated steatohepatitis (MASH) (formerly known as non-alcoholic steatohepatitis (NASH)) which can then progress to significant cirrhosis and hepatocellular carcinoma.

In 2023, global liver disease medical societies and patient groups formalized the decision to rename non-alcoholic fatty liver disease (NAFLD) to metabolic dysfunction-associated steatotic liver disease (MASLD) and nonalcoholic steatohepatitis (NASH) to metabolic dysfunction-associated steatohepatitis (MASH). Additionally, an overarching term, steatotic liver disease (SLD), was established to capture multiple types of liver diseases associated with fat buildup in the liver.

The synthesis of fatty acids in the liver, a pathway termed hepatic de novo lipogenesis (DNL), is increased in subjects with metabolic syndrome and NAFLD/MASLD (Donnelly, K. L, et. al., "Sources of Fatty Acids Stored in Liver and Secreted via Lipoproteins in Patients with Nonalcoholic Fatty Liver Disease," *J. Clin. Invest.* 115 (5). 2005, 1343-51; Lambert, J. E, et. al., "Increased De Novo Lipogenesis Is a Distinct Characteristic of Individuals with Nonalcoholic Fatty Liver Disease," *Gastroenterology* 146 (3).2014, 726-35). The DNL pathway not only produces fatty acids that contribute to elevated liver stores of triglycerides, but the fatty acids that are produced are saturated fatty acid species, primarily palmitate, which contribute to signaling events that increase liver inflammation (Wei, Y., "Saturated Fatty Acids Induce Endoplasmic Reticulum Stress and Apoptosis Independently of Ceramide in Liver Cells," *Am. J. Physio. Endocrinol. Metab.* 291 (2): 2006, E275-81; Kakazu, E., et al., "Hepatocytes Release Ceramide-rich Proinflammatory Extracellular Vesicles in an IRE1alpha dependent manner," Abstract 58. AASLD—The Liver Meeting, San Francisco, CA, USA, 13-17, Nov. 2015). One of the key enzymes in the DNL pathway is fatty acid synthase (FASN) which is solely responsible for synthesizing palmitate. Thus, DNL is an important pathway for therapeutic intervention to reduce the consequences associated with metabolic syndrome and NAFLD/MASLD.

Inhibition of FASN has the potential to be a treatment for a wide range of diseases including cancer, viral disease, metabolic disease, NAFLD/MASLD, NASH/MASH, and inflammatory diseases, (i.e., rheumatoid arthritis, gout, pulmonary fibrosis, COPD, IBD and transplant rejection). Additionally, FASN inhibition may provide therapeutic benefits in cardiovascular disease, atherosclerosis, type II diabetes, and metabolic syndrome. Successful treatment of these diseases is still a highly unmet need.

FASN inhibition not only reduces liver fat but also acts directly on immune and hepatic stellate cells reducing inflammation and fibrosis. WO2012/122391, WO2014/008197 and WO2015/105860 describe heterocyclic FASN inhibitors and WO2018/089904 describes uses of some of the above-referenced FASN inhibitors for the treatment of NAFLD/MASLD and NASH/MASH. The content of the above-referenced disclosures is incorporated by reference herein. One of the compounds described in the above-reference applications, Denifanstat (TVB-2640) is a first in class FASN inhibitor that has demonstrated improvements in liver fat and biomarkers associated with inflammation and fibrosis in NASH/MASH trials.

Thyroid hormone receptor beta (THRβ) agonists increase lipid oxidation which decreases liver fat and THRβ agonist resmetirom recently demonstrated significant NASH/MASH resolution and fibrosis improvement in a Phase III clinical trial and has been approved for the treatment of non-cirrhotic NASH/MASH. While promising, the efficacy of THRβ agonist resmetirom does not approach 50% histology response rates.

There is a need for combinations of FASN inhibitors with other agents such as THRβ agonists that can complement and potentiate the activity of FASN inhibitors in steatotic liver diseases such as NASH/MASH and NAFLD/MASLD. Additionally, there is a need for combinations of THRβ agonists with other agents such as FASN inhibitors that can complement and potentiate the activity of THRβ agonists in steatotic liver diseases such as NASH/MASH and NAFLD/MASLD.

SUMMARY

The present disclosure addresses the deficiencies for metabolic disease treatments by providing novel therapeutic combinations of heterocyclic modulators of lipid synthesis with thyroid hormone receptor agonists. This provides a multi-pronged therapy for metabolic disease with complex pathophysiology. FASN inhibitors target inflammation (e.g., immune cells) and fibrosis (e.g., hepatic stellate cells), directly, as well as indirectly via lowering liver fat by inhibiting de novo lipogenesis. THR-β agonists may reduce inflammation and fibrosis indirectly, as a result of lowering liver fat effect by increasing liver fat breakdown and/or fatty acid beta oxidation.

These different mechanisms have potential to be additive or synergistic and broaden or deepen the efficacy response rate.

In a first aspect, the present disclosure relates to methods of treating a disease (e.g., a steatotic liver disease, e.g., NAFLD/MASLD or NASH/MASH), comprising administering to a subject in need thereof a fatty acid synthase inhibitor and a thyroid hormone receptor (THR) agonist (e.g., a thyroid hormone receptor-beta (THR-β)) agonist.

In some embodiments, the fatty acid synthase inhibitor is a compound of Formula (IX-1):

(IX-1)

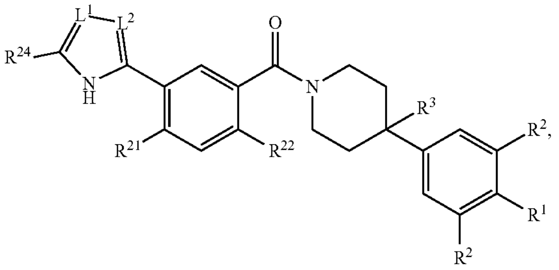

or a pharmaceutically acceptable salt thereof, wherein:

$R^1$ is H, —CN, halogen, $C_1$-$C_4$ straight or branched alkyl, —O—($C_3$-$C_5$ cycloalkyl), —O-(4- to 6-membered heterocycle), or —O—($C_1$-$C_4$ straight or branched alkyl), wherein when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

$L^1$ is N; and $L^2$ is N.

In some embodiments of Formula (IX-1), $R^1$ is H, —CN, halogen, or $C_1$-$C_4$ straight or branched alkyl; each $R^2$ is independently H; $R^3$ is H or halogen; $R^{21}$ is $C_1$-$C_4$ straight or branched alkyl or $C_3$-$C_5$ cycloalkyl; $R^{22}$ is H or $C_1$-$C_2$ alkyl; and $R^{24}$ is H or $C_1$-$C_4$ straight or branched alkyl.

In some embodiments of Formula (IX-1), $R^1$ is —CN; each $R^2$ is independently H; $R^3$ is H; $R^{21}$ is $C_3$-$C_5$ cycloalkyl; $R^{22}$ is H or $C_1$-$C_2$ alkyl; and $R^{24}$ is $C_1$-$C_4$ straight or branched alkyl.

In some embodiments, the compound of Formula (IX-1) has the following structure:

(Compound 001-152)

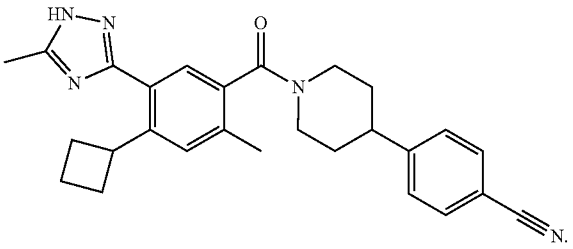

In some embodiments, the fatty acid synthase inhibitor is a compound of Formula (XII-1):

(XII-1)

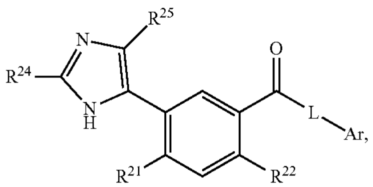

or pharmaceutically acceptable salts thereof, wherein:

L-Ar is

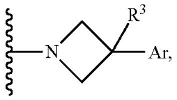

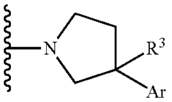

or

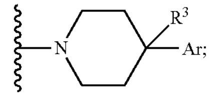

Ar is

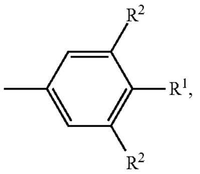

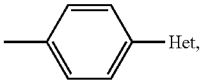

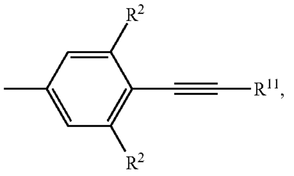

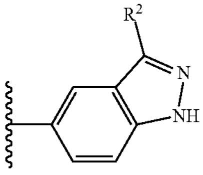

or

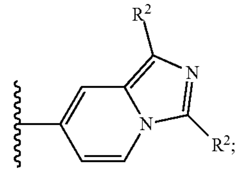

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently H, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl;

$R^{24}$ is H, —CN, —($C_1$-$C_4$ alkyl)-CN, $C_1$-$C_4$ alkyl, $C_1$-$C_4$ haloalkyl, —($C_1$-$C_4$ alkyl)-OH, —($C_1$-$C_4$ alkyl)-N$(R^{241})_2$, —$(C_1$-$C_4$ alkyl$)_t$-$O_u$—($C_3$-$C_6$ cycloalkyl), —$(C_1$-$C_4$ alkyl$)_t$-$O_u$-(4- to 6-membered heterocycle) or —($C_1$-$C_4$ alkyl)-O—($C_1$-$C_4$ alkyl), wherein:

t is 0 or 1;

u is 0 or 1;

each $R^{241}$ is independently H or $C_1$-$C_2$ alkyl; and $R^{25}$ is halogen, —CN, —($C_1$-$C_4$ alkyl)-CN, $C_1$-$C_2$ alkyl, $C_1$-$C_4$ haloalkyl, —($C_1$-$C_4$ alkyl)-O—($C_1$-$C_4$ alkyl), or cyclopropyl.

In some embodiments of Formula (XII-1), L-Ar is

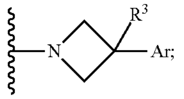

Ar is

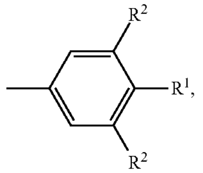

$R^1$ is H, —CN, halogen, or $C_1$-$C_4$ alkyl; each $R^2$ is independently H; $R^3$ is H or F; $R^{21}$ is H, halogen, or $C_1$-$C_4$ alkyl; $R^{22}$ is H, halogen, or $C_1$-$C_2$ alkyl; $R^{24}$ is $C_1$-$C_4$ alkyl, $C_1$-$C_4$ haloalkyl, —$(C_1$-$C_4$ alkyl$)_t$-$O_u$-(4- to 6-membered heterocycle), or —($C_1$-$C_4$ alkyl)-O—($C_1$-$C_4$ alkyl); $R^{25}$ is $C_1$-$C_2$ alkyl, $C_1$-$C_4$ haloalkyl, or —($C_1$-$C_4$ alkyl)-O—($C_1$-$C_4$ alkyl).

In some embodiments of Formula (XII-1), L-Ar is

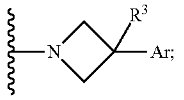

Ar is

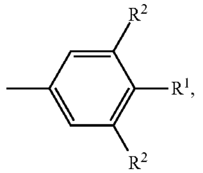

$R^1$ is —CN; each $R^2$ is independently H; $R^3$ is H; $R^{21}$ is $C_1$-$C_4$ alkyl; $R^{22}$ is H or $C_1$-$C_2$ alkyl; $R^{24}$ is $C_1$-$C_4$ haloalkyl, or —$(C_1$-$C_4$ alkyl$)_t$-$O_u$-(4- to 6-membered heterocycle), and $R^{25}$ is —($C_1$-$C_4$ alkyl)-O—($C_1$-$C_4$ alkyl).

In some embodiments, the compound of Formula (XII-1) has the following structure:

(Compound 002-386)

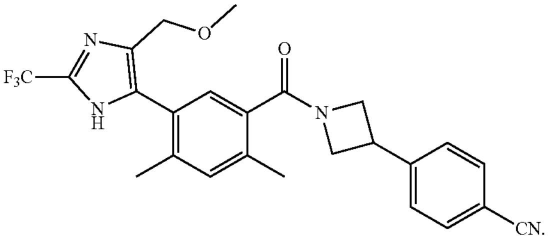

In some embodiments, the fatty acid synthase inhibitor is a compound of Formula (XIII-1):

(XIII-1)

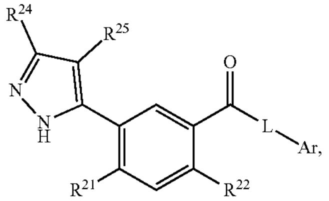

or pharmaceutically acceptable salts thereof, wherein:

L-Ar is

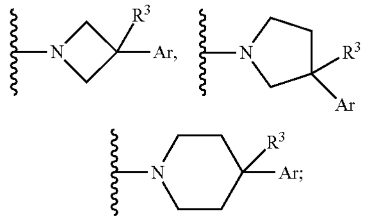

Ar is

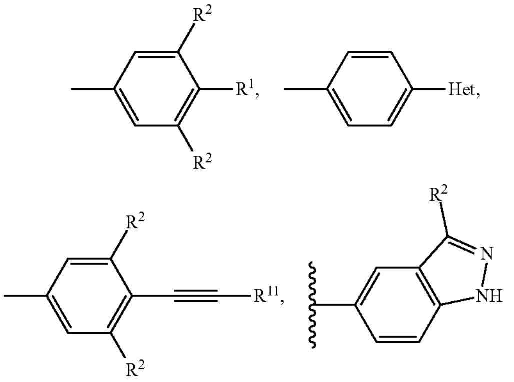

-continued

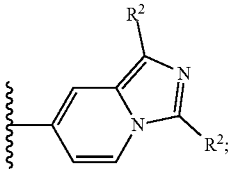

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and each $R^{24}$ and $R^{25}$ is independently H, halogen, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_5$ cycloalkyl), —($C_1$-$C_4$ alkyl)$_t$-O$_u$-(4- to 6-membered heterocycle) or —($C_1$-$C_4$ alkyl)$_t$-O—($C_1$-$C_4$ alkyl), wherein:

each t is independently 0 or 1;

each u is independently 0 or 1; and each $R^{241}$ is independently H or $C_1$-$C_2$ alkyl.

In some embodiments of Formula (XIII-1), L-Ar is

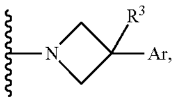

Ar is

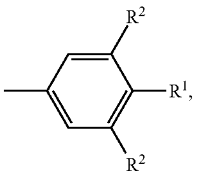

$R^1$ is H, —CN, halogen, or $C_1$-$C_4$ alkyl; each $R^2$ is independently H; $R^3$ is H or F; $R^{21}$ is H, halogen, or $C_1$-$C_4$ alkyl; $R^{22}$ is H, halogen, or $C_1$-$C_2$ alkyl; and each $R^{24}$ and $R^{25}$ is independently halogen, $C_1$-$C_4$ alkyl, or —($C_1$-$C_4$ alkyl)-O—($C_1$-$C_4$ alkyl).

In some embodiments of Formula (XIII-1), L-Ar is

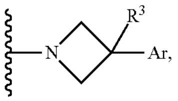

Ar is

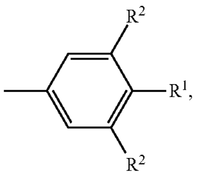

$R^1$ is —CN; each $R^2$ is independently H; $R^3$ is H; $R^{21}$ is $C_1$-$C_4$ alkyl; $R^{22}$ is H or $C_1$-$C_2$ alkyl; and each $R^{24}$ and $R^{25}$ is independently halogen, $C_1$-$C_4$ alkyl, or —($C_1$-$C_4$ alkyl)$_t$-O—($C_1$-$C_4$ alkyl).

In some embodiments, the compound of Formula (XIII-1) has the following structure:

(Compound 002-242)

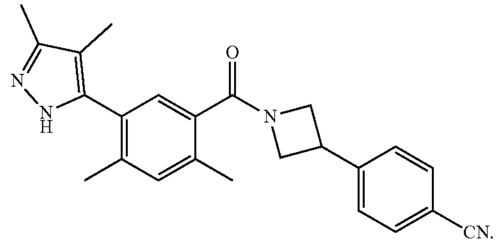

In some embodiments, the fatty acid synthase inhibitor is a compound of Formula (XX-1):

(XX-1)

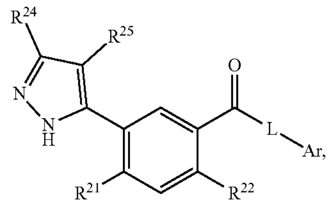

or a pharmaceutically acceptable salt thereof, wherein:

L-Ar is

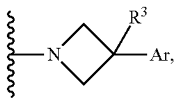

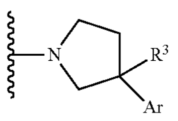

or

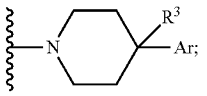

Ar is

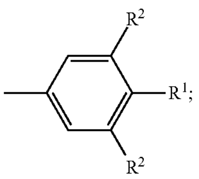

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogen;

each $R^2$ is independently hydrogen, halogen or $C_1$-$C_4$ alkyl;

$R^3$ is H or F;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl;

$R^{24}$ is —O—($C_1$-$C_4$ alkyl), —O—($C_1$-$C_4$ alkyl)-O—($C_1$-$C_4$ alkyl), —O—($C_3$-$C_5$ cycloalkyl), or —O-(4- to 6-membered heterocycle), wherein $R^{24}$ is optionally substituted with one or more hydroxyl or halogen; and $R^{25}$ is H, halogen, $C_1$-$C_4$ alkyl or $C_3$-$C_5$ cycloalkyl, wherein $R^{25}$ is optionally substituted with one or more halogen.

In some embodiments of Formula (XX-1), L-Ar is

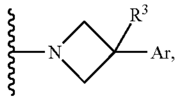

Ar is

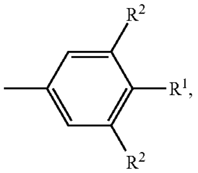

$R^1$ is —CN or —O—($C_1$-$C_4$ alkyl) optionally substituted with one or more halogen; each $R^2$ is independently H; $R^3$ is H or F; $R^{21}$ is H or $C_1$-$C_4$ alkyl; $R^{22}$ is H or $C_1$-$C_2$ alkyl; $R^{24}$ is —O—($C_1$-$C_4$ alkyl), —O—($C_1$-$C_4$ alkyl)-O—($C_1$-$C_4$ alkyl), or —O-(4- to 6-membered heterocycle), wherein $R^{24}$ is optionally substituted with one or more hydroxyl or halogen; and $R^{25}$ is H, halogen, or $C_1$-$C_4$ alkyl.

In some embodiments of Formula (XX-1), L-Ar is

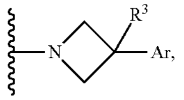

Ar is

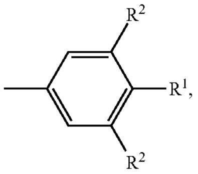

$R^1$ is —CN or —O—($C_1$-$C_4$ alkyl) optionally substituted with one or more halogen; each $R^2$ is independently H; $R^3$ is H or F; $R^{21}$ is H or $C_1$-$C_4$ alkyl; $R^{22}$ is H or $C_1$-$C_2$ alkyl;

$R^{24}$ is —O—($C_1$-$C_4$ alkyl) substituted with one or more hydroxyl or halogen; and $R^{25}$ is $C_1$-$C_4$ alkyl.

In some embodiments, the compound of Formula (XX-1) has one of the following structures:

(Compound 005-2)

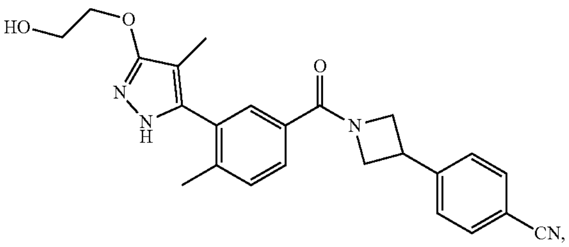

(Compound 005-5)

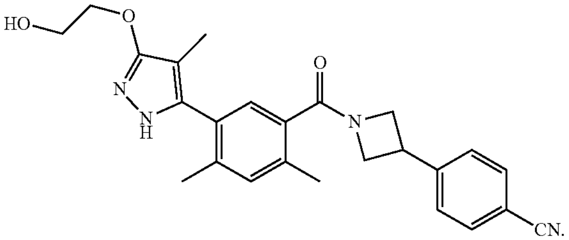

In some embodiments, the fatty acid synthase inhibitor is a compound of Formula (IX-1), (XII-1), (XIII-1), or (XX-1), or a pharmaceutically acceptable salt thereof.

In some embodiments, the fatty acid synthase inhibitor is a compound selected from: Compound 001-152, Compound 002-386, Compound 002-242, Compound 005-2, and Compound 005-5, or a pharmaceutically acceptable salt thereof.

In some embodiments, the fatty acid synthase inhibitor is a compound selected from: Compound 001-152 and Compound 005-2, or a pharmaceutically acceptable salt thereof.

In some embodiments, the fatty acid synthase inhibitor is a compound selected from Table C-1, or a pharmaceutically acceptable salt thereof.

In some embodiments, the fatty acid synthase inhibitor is a compound selected from Table C-2, or a pharmaceutically acceptable salt thereof.

In some embodiments, the fatty acid synthase inhibitor is a compound selected from Table C-3, or a pharmaceutically acceptable salt thereof.

In various aspects, the present disclosure provides pharmaceutical compositions comprising any one of the compounds disclosed herein, and a and a pharmaceutically acceptable carrier, excipient, or diluent.

In some embodiments, the thyroid hormone receptor agonist is a compound of Formula (XXI):

(XXI)

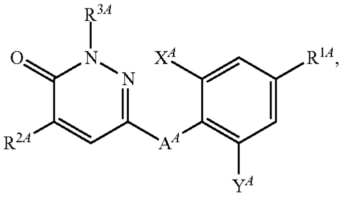

or a pharmaceutically acceptable salt thereof, wherein:

$A^A$ is O, $CH_2$, S, SO or $SO_2$;

$X^A$ and $Y^A$ are each independently selected from the group consisting of Br, Cl and $CH_3$;

$R^{1A}$ is selected from the group consisting of: $-(CH_2)_nCOOH$, $-OCH_2COOH$, $-NHC(=O)COOH$, $-NHCH_2COOH$,

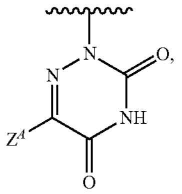

and

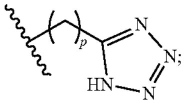

;

$Z^A$ is H, or $-C\equiv N$;

$R^{2A}$ is lower alkyl having from 1 to 4 C atoms;

$R^3$ is H or lower alkyl;

n is 1 or 2; and p is 1 or 2.

In some embodiments, the thyroid hormone receptor agonist is a compound of Formula (XXI-1):

(XXI-1)

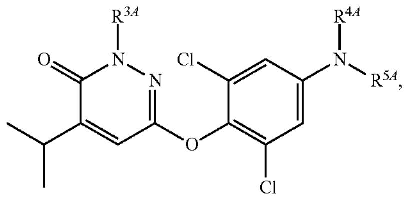

or a pharmaceutically acceptable salt thereof, wherein:

$R^{3A}$ is H or $CH_2R^{3B}$;

$R^{3B}$ is hydroxyl, O-linked amino acid, $-OP(O)(OH)_2$ or $-OC(O)R^{3C}$, wherein $R^{3C}$ is lower alkyl, alkoxy, alkyl acid, cycloalkyl, aryl, heteroaryl, or $-(CH_2)_n$-heteroaryl, wherein n is 0 or 1;

$R^{4A}$ is H, and $R^{5A}$ is $CH_2COOH$, $C(O)CO_2H$, or an ester or amide thereof, or $R^{4A}$ and $R^5$ together are $-N=C(R^{4B})-C(O)-NH-C(O)-$; wherein $R^{4B}$ is H or cyano.

In some embodiments, the thyroid hormone receptor agonist of Formula (XXI) has the following structure:

(Compound A)

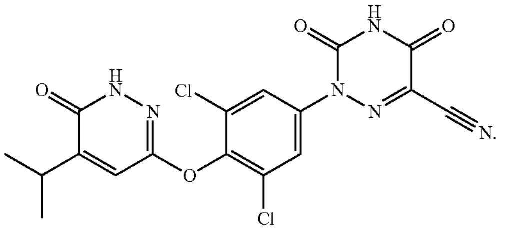

Compound A is also known as MGL-3196 or resmetirom and is marketed as Rezdifra™ for the treatment of non-cirrhotic NASH.

In some embodiments of the combinations and methods of the disclosure, the fatty acid synthase inhibitor has a formula of:

(a) Formula (IX)

(IX)

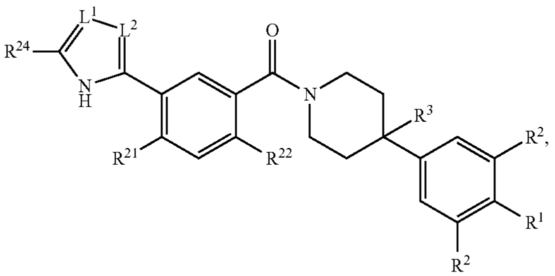

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

$C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

$L^1$ is $CR^{23}$ or N;

$L^2$ is CH or N;

at least one of $L^1$ or $L^2$ is N; and $R^{23}$ is H or $C_1$-$C_4$ straight or branched alkyl; or (b) Formula (X):

(X)

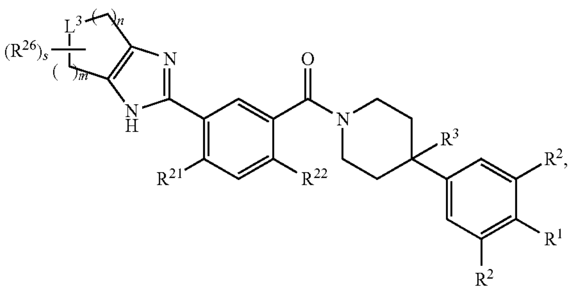

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

the $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH or halogen;

$L^3$ is $C(R^{60})_2$, O or $NR^{50}$;

each $R^{60}$ is independently H, —OH, —CN, —$O_t$—($C_3$-$C_5$ cycloalkyl), —O—($C_1$-$C_4$ straight or branched alkyl), or —C(O)—$N(R^{601})_2$ wherein:

t is 0 or 1, and the $C_3$-$C_5$ cycloalkyl optionally includes an oxygen or nitrogen heteroatom;

each $R^{50}$ is independently H, —C(O)—$O_t$—($C_1$-$C_4$ straight or branched alkyl), —C(O)—$O_t$—($C_3$-$C_5$ cyclic alkyl), —$C_3$-$C_5$ cyclic alkyl optionally containing an oxygen or nitrogen heteroatom, —C(O)—N$(R^{501})_2$, $C_1$-$C_4$ straight or branched alkyl wherein:

t is 0 or 1, and the $C_3$-$C_5$ cycloalkyl optionally includes an oxygen or nitrogen heteroatom;

n is 1, 2 or 3;

m is 1 or 2;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom $R^{22}$ is H, halogen, $C_1$-$C_2$ alkyl;

each $R^{26}$ is independently —OH, —CN, halogen, $C_1$-$C_4$ straight or branched alkyl, —($C_1$-$C_4$ alkyl)$_t$-$O_t$—($C_3$-$C_5$ cycloalkyl), —($C_1$-$C_4$ alkyl)$_t$-O—($C_1$-$C_4$ straight or branched alkyl), —C(O)—$O_t$—($C_1$-$C_4$ alkyl), or —C(O)—$N(R^{501})_2$ wherein:

t is 0 or 1, and the $C_3$-$C_5$ cycloalkyl optionally includes an oxygen or nitrogen heteroatom;

s is 0, 1 or 2;

each $R^{601}$ and $R^{501}$ is independently H or $C_1$-$C_4$ straight or branched alkyl; and wherein two of $R^{26}$, $R^{60}$, $R^{50}$, $R^{501}$ and $R^{601}$ optionally join to form a ring wherein the two of $R^{26}$, $R^{60}$, $R^{50}$, $R^{501}$ and $R^{601}$ may be two $R^{26}$, two $R^{60}$, two $R^{50}$, two $R^{501}$ or two $R^{601}$; or (c) Formula (VI-J)

(VI-J)

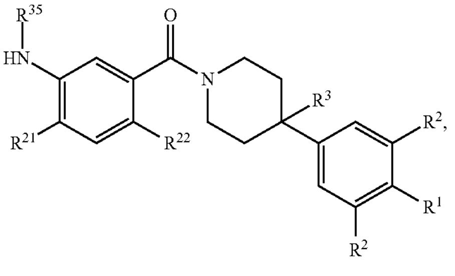

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

the $C_3$-$C_5$ cycloalkyl optionally includes an oxygen or nitrogen heteroatom; and when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is cyclobutyl, azetidin-1-yl, or cyclopropyl;

$R^{22}$ is H, halogen, or $C_1$-$C_2$ alkyl;

$R^{35}$ is —C(O)—$R^{351}$, —C(O)—$NHR^{351}$, —C(O)—O—$R^{351}$ or $S(O)_2R^{351}$; and $R^{351}$ is $C_1$-$C_6$ straight or branched alkyl, cycloalkyl, heterocyclyl, aryl or heteroaryl; or (d) Formula (XII):

(XII)

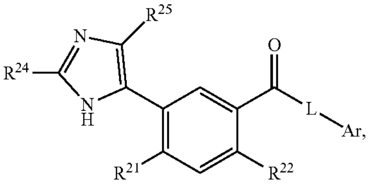

or pharmaceutically acceptable salts thereof, wherein:

L-Ar is

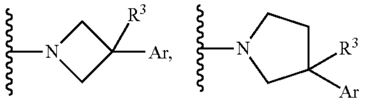

or

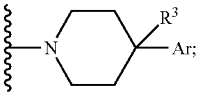

Ar is

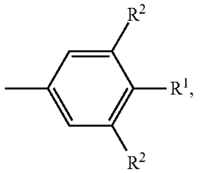

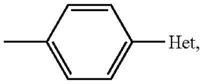

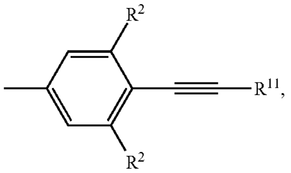

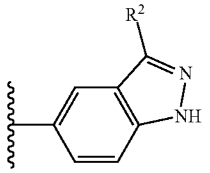

or

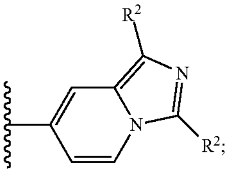

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl;

$R^{24}$ is H, —CN, —($C_1$-$C_4$ alkyl)-CN, $C_1$-$C_4$ alkyl, —($C_1$-$C_4$ alkyl)-OH, —($C_1$-$C_4$ alkyl)-$N(R^{241})_2$, —($C_1$-$C_4$ alkyl)$_t$-O$_u$—(C$_3$-C$_6$ cycloalkyl), —(C$_1$-C$_4$ alkyl)$_t$-O$_u$-(4- to 6-membered heterocycle) or —(C$_1$-C$_4$ alkyl)-O—(C$_1$-C$_4$ alkyl), wherein:

t is 0 or 1;

u is 0 or 1;

with the proviso that when u is 1, t is 1; and each $R^{241}$ is independently H or C$_1$-C$_2$ alkyl; and $R^{25}$ is halogen, —CN, —(C$_1$-C$_4$ alkyl)-CN, C$_1$-C$_2$ alkyl or cyclopropyl; or (e) Formula (XIII):

(XIII)

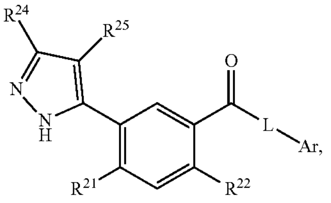

or pharmaceutically acceptable salts thereof, wherein:

L-Ar is

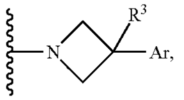 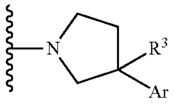 or 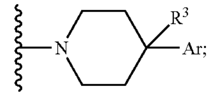

Ar is

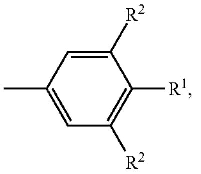 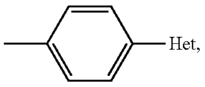

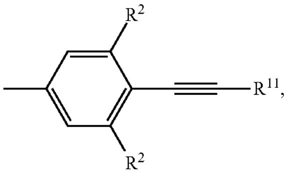 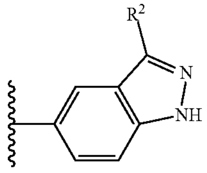 or

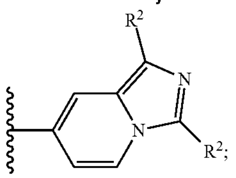

Het is a 5- to 6-membered heteroaryl;

$R^1$ is H, —CN, halogen, C$_1$-C$_4$ alkyl, —O—(C$_3$-C$_5$ cycloalkyl), —O-(4- to 6-membered heterocycle) or —O—(C$_1$-C$_4$ alkyl), wherein when $R^1$ is not H, —CN or halogen, $R^1$ is optionally substituted with one or more halogens;

each $R^2$ is independently hydrogen, halogen or C$_1$-C$_4$ alkyl;

$R^3$ is H or F;

$R^{11}$ is H or —CH$_3$;

$R^{21}$ is H, halogen, C$_1$-C$_4$ alkyl, C$_3$-C$_5$ cycloalkyl or 4- to 6-membered heterocycle;

$R^{22}$ is H, halogen or C$_1$-C$_2$ alkyl; and each $R^{24}$ and $R^{25}$ is independently H, halogen, —CN, —(C$_1$-C$_4$ alkyl)-CN, C$_1$-C$_4$ alkyl, —(C$_1$-C$_4$ alkyl)-OH, —(C$_1$-C$_4$ alkyl)-N($R^{241}$)$_2$, —(C$_1$-C$_4$ alkyl)$_t$-O$_u$—(C$_3$-C$_5$ cycloalkyl), —(C$_1$-C$_4$ alkyl)$_t$-O$_u$-(4- to 6-membered heterocycle) or —(C$_1$-C$_4$ alkyl)$_t$-O—(C$_1$-C$_4$ alkyl), wherein:

each t is independently 0 or 1;

each u is independently 0 or 1; and each $R^{241}$ is independently H or C$_1$-C$_2$ alkyl; or (f) Formula (XIV):

(XIV)

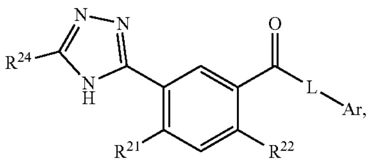

or pharmaceutically acceptable salts thereof, wherein:

L-Ar is

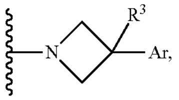 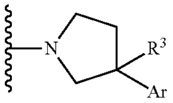 or 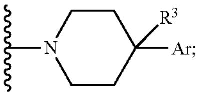

Ar is

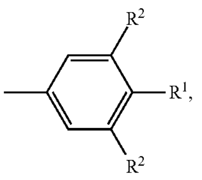 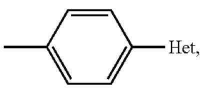

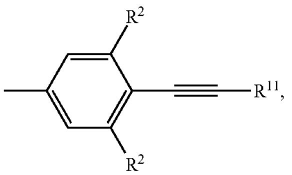 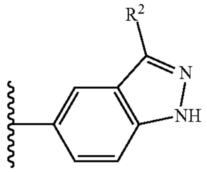 or

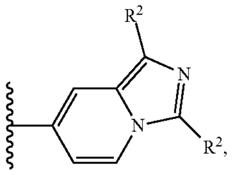

with the proviso that when L-Ar is

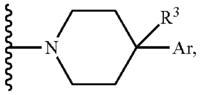

Ar is not

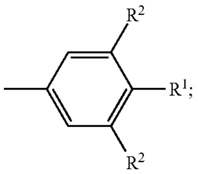

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl; and $R^{24}$ is H, $C_1$-$C_4$ alkyl, —($C_1$-$C_4$ alkyl)-OH, —($C_1$-$C_4$ alkyl), —$N(R^{241})_2$, —($C_1$-$C_4$ alkyl)$_t$-$O_t$—($C_3$-$C_5$ cycloalkyl), —($C_1$-$C_4$ alkyl)$_t$-$O_t$-(4- to 6-membered heterocycle) or —($C_1$-$C_4$ alkyl)$_t$-O—($C_1$-$C_4$ alkyl), wherein:

each t is independently 0 or 1; and each $R^{241}$ is independently H or $C_1$-$C_2$ alkyl; or (g) Formula (XV):

(XV)

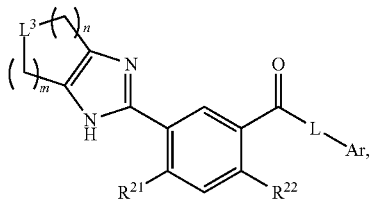

or pharmaceutically acceptable salts thereof, wherein:

$L^3$ is —$CH_2$—, —$CHR^{50}$—, —O—, —$NR^{50}$, —NC(O)$R^{50}$— or —NC(O)$OR^{50}$—, wherein $R^{50}$ is $C_1$-$C_6$ alkyl, $C_3$-$C_5$ cycloalkyl, or 4- to 6-membered heterocycle;

n is 1, 2, or 3;

m is 1 or 2 with the proviso that n+m≥3;

L-Ar is

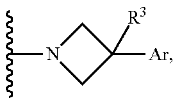

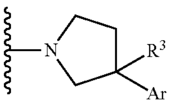

or

-continued

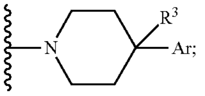

Ar is

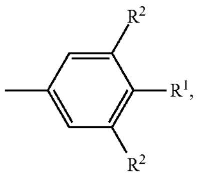

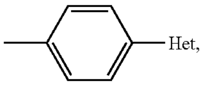

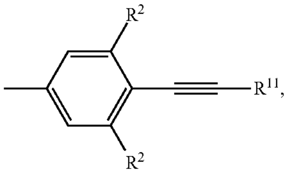

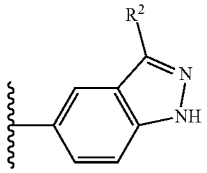

or

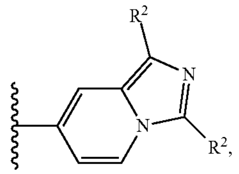

with the proviso that when L-Ar is

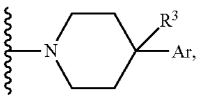

Ar is not

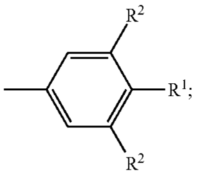

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or a 4- to 6-membered heterocycle; and $R^{22}$ is H, halogen, or $C_1$-$C_2$ alkyl; or (h) Formula (XVI):

(XVI)

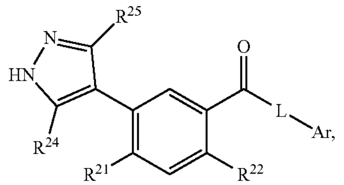

or pharmaceutically acceptable salts thereof, wherein:

L-Ar is

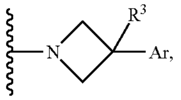

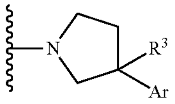

or

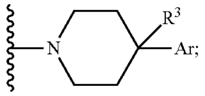

Ar is

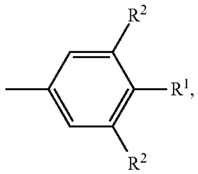

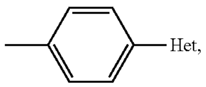

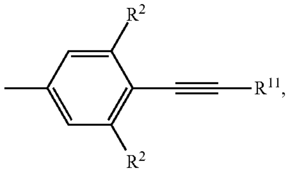

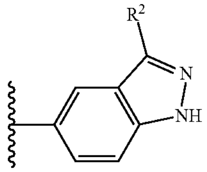

or

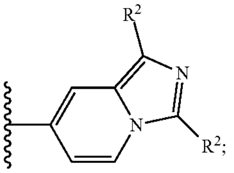

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and each of $R^{24}$ and $R^{25}$ is independently H, —$C_1$-$C_4$ alkyl, or halogen; or (i) Formula (XVII):

(XVII)

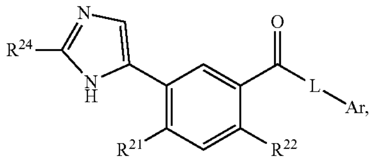

or pharmaceutically acceptable salts thereof, wherein:

L-Ar is

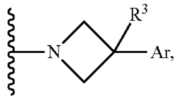

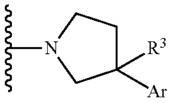

or

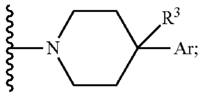

Ar is

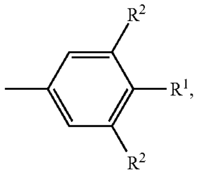

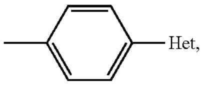

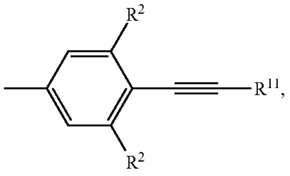

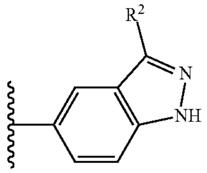

or

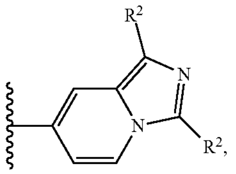

with the proviso that when L-Ar is

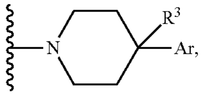

Ar is not

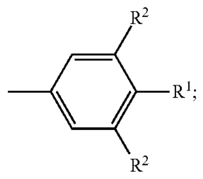

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and $R^{24}$ is H, $C_1$-$C_4$ alkyl, —($C_1$-$C_4$ alkyl)-OH, —($C_1$-$C_4$ alkyl)-$N(R^{241})_2$, —($C_1$-$C_4$ alkyl)$_t$-$O_u$—($C_3$-$C_5$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl), wherein:

t is 0 or 1;

u is 0 or 1;

with the proviso that when u is 1, t is 1; and $R^{241}$ is H or $C_1$-$C_2$ alkyl; or (j) Formula (XVIII):

(XVIII)

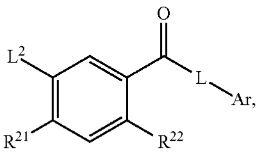

or pharmaceutically acceptable salts thereof, wherein:

L-Ar is

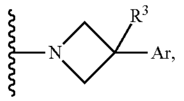

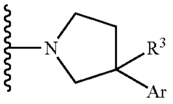

or

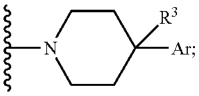

Ar is

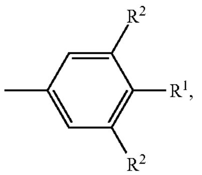

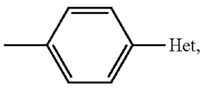

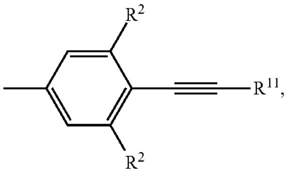

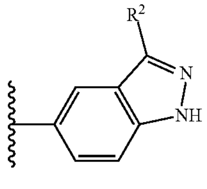

or

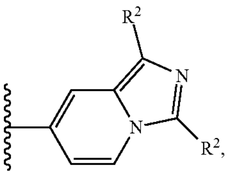

with the proviso that when L-Ar is

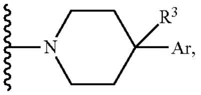

Ar is not

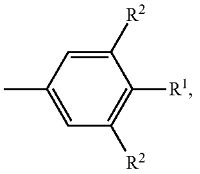

$L^2$ is —$NHR^{35}$ or —C(O)$NHR^{351}$, wherein $R^{351}$ is $C_1$-$C_6$ alkyl, $C_3$-$C_5$ cycloalkyl, 4- to 6-membered heterocycle, aryl or heteroaryl;

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle)$_t$-O—($C_1$-$C_4$ alkyl) wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl; and $R^{35}$ is —C(O)$R^{351}$, —C(O)$NHR^{351}$, C(O)$OR^{351}$ or $S(O)_2$ $R^{351}$ wherein $R^{351}$ is $C_1$-$C_6$ alkyl, $C_3$-$C_5$ cycloalkyl, 4- to 6-membered heterocycle, aryl or heteroaryl; or (k) Formula (XIX):

(XIX)

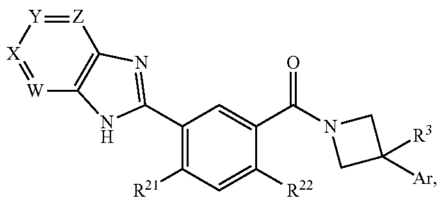

or pharmaceutically acceptable salts thereof, wherein:

each W, X, Y and Z is independently —N— or —$CR^{26}$— with the proviso that not more than 2 of W, X, Y and Z are —N—;

each $R^{26}$ is independently H, $C_1$-$C_4$ alkyl, —O—($C_1$-$C_4$ alkyl), —$N(R^{27})_2$, —$S(O)_2$—($C_1$-$C_4$ alkyl), or —C(O)—($C_1$-$C_4$ alkyl);

each $R^{27}$ is independently H or $C_1$-$C_4$ alkyl or both $R^{27}$ are $C_1$-$C_4$ alkyl and join to form a 3- to 6-membered ring together with the N to which they are attached and wherein the ring optionally includes one oxygen atom as one of the members of the ring;

Ar is

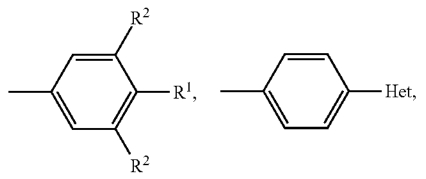

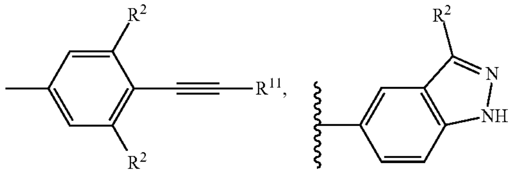

or

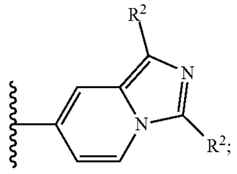

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle), —O—($C_1$-$C_4$ alkyl) wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or a 4- to 6-membered heterocycle; and $R^{22}$ is H, halogen or $C_1$-$C_2$ alkyl; or (l) Formula (XX):

(XX)

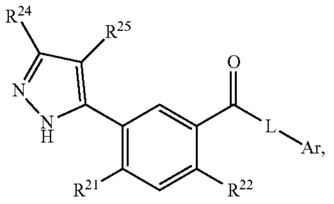

or a pharmaceutically acceptable salt thereof, wherein:

L-Ar is

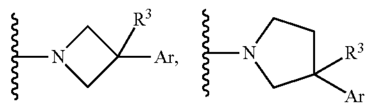

or

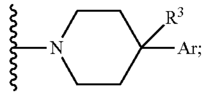

Ar is

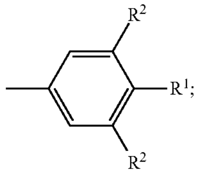

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogen;

each $R^2$ is independently hydrogen, halogen or $C_1$-$C_4$ alkyl;

$R^3$ is H or F;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl;

$R^{24}$ is —O—($C_1$-$C_4$ alkyl), —O—($C_1$-$C_4$ alkyl)-O—($C_1$-$C_4$ alkyl), —O—($C_3$-$C_5$ cycloalkyl), or —O-(4- to 6-membered heterocycle), wherein $R^{24}$ is optionally substituted with one or more hydroxyl or halogen; and $R^{25}$ is H, halogen, $C_1$-$C_4$ alkyl or $C_3$-$C_5$ cycloalkyl, wherein $R^{25}$ is optionally substituted with one or more halogen; or (m) Formula (XI):

(XI)

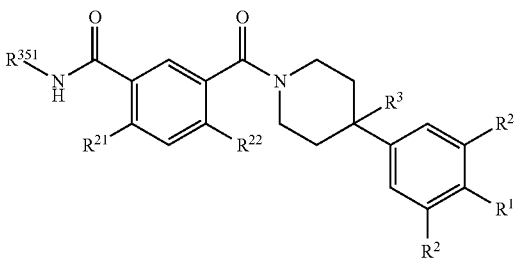

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

the $C_3$-$C_5$ cycloalkyl optionally includes an oxygen or nitrogen heteroatom; and when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is cyclobutyl, azetidin-1-yl, or cyclopropyl;

$R^{22}$ is H, halogen, $C_1$-$C_2$ alkyl; and $R^{351}$ is $C_1$-$C_2$ alkyl or $C_2$—O—($C_1$ or $C_2$ alkyl).

In various aspects, the present disclosure relates to a method of treating steatotic liver disease in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating steatotic liver disease in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating steatotic liver disease in a subject in need thereof, comprising administering to the subject a fatty acid synthase inhibitor and a thyroid hormone receptor agonist, wherein the fatty acid synthase inhibitor is:

(Compound 001-152)

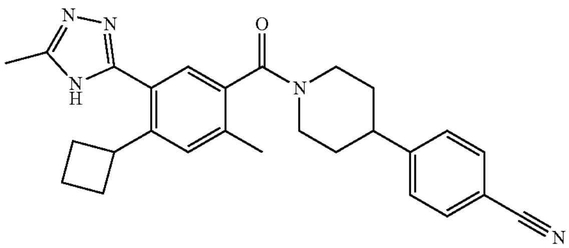

and the thyroid hormone receptor agonist is:

(Compound A)

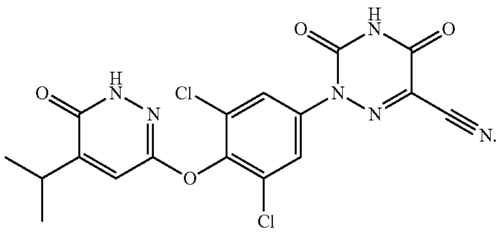

In various aspects, the present disclosure relates to a method of treating non-alcoholic steatohepatitis/metabolic dysfunction associated steatohepatitis (NASH/MASH) in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating nonalcoholic steatohepatitis/metabolic dysfunction-associated steatohepatitis (NASH/MASH) in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating non-alcoholic steatohepatitis/metabolic dysfunction-associated steatohepatitis (NASH/MASH) in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating non-alcoholic fatty liver disease/metabolic dysfunction-associated steatotic liver disease (NAFLD/MASLD) in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating non-alcoholic fatty liver disease/metabolic dysfunction-associated steatotic liver disease (NAFLD/MASLD) in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating non-alcoholic fatty liver disease/metabolic dysfunction-associated steatotic liver disease (NAFLD/MASLD) in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating metabolic syndrome in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating metabolic syndrome in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating metabolic syndrome in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating type II diabetes in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating type II diabetes in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating type II diabetes in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating atherosclerosis in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating atherosclerosis in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating atherosclerosis in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating liver cirrhosis in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating liver cirrhosis in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating liver cirrhosis in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating liver fibrosis in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating liver fibrosis in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating liver fibrosis in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating liver cancer in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating liver cancer in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating liver cancer in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating liver cancer in a subject in need thereof, wherein the liver cancer has developed from NAFLD/MASLD or NASH/MASH, comprising administering to the subject a fatty acid synthase inhibitor and a thyroid hormone receptor agonist (e.g., a thyroid hormone receptor-beta agonist). For example, in some embodiments, the present disclosure relates to a method of treating liver cancer in a subject in need thereof, wherein the liver cancer has developed from NAFLD/MASLD or NASH/MASH, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating liver cancer in a subject in need thereof, wherein the liver cancer has developed from NAFLD/MASLD or NASH/MASH, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating a hepatocellular carcinoma in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating a hepatocellular carcinoma in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating a hepatocellular carcinoma in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating a hepatocellular carcinoma in a subject in need thereof, wherein the hepatocellular carcinoma has developed from NAFLD/MASLD or NASH/MASH, comprising administering to the subject a fatty acid synthase inhibitor and a thyroid hormone receptor agonist (e.g., a thyroid hormone receptor-beta agonist). For example, in some embodiments, the present disclosure relates to a method of treating a hepatocellular carcinoma in a subject in need thereof, wherein the hepatocellular carcinoma has developed from NAFLD/MASLD or NASH/MASH, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating a hepatocellular carcinoma in a subject in need thereof, wherein the hepatocellular carcinoma has developed from NAFLD/MASLD or NASH/MASH, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating a cholangiocarcinoma in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating a cholangiocarcinoma in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating a cholangiocarcinoma in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating disease or condition in which interleukin 1 beta (IL1β) levels are elevated in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating disease or condition in which interleukin 1 beta (IL1B) levels are elevated in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating disease or condition in which interleukin 1 beta (IL1β) levels are elevated in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating disease or condition modulated by interleukin 1 beta (IL1β) in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating disease or condition modulated by interleukin 1 beta (IL1β) in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating a disease or condition modulated by interleukin 1 beta (IL1β) in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating a disease or condition in which t-helper (Th) cell levels are elevated in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating a disease or condition in which t-helper (Th) cell levels are elevated in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating a disease or condition in which t-helper (Th) cell levels are elevated in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating a disease or condition in which regulatory t cells ($T_{reg}$) are reduced or suppressed in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating a disease or condition in which regulatory t cells ($T_{reg}$) are reduced or suppressed in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating a disease or condition in which regulatory t cells ($T_{reg}$) are reduced or suppressed in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of reversing established non-alcoholic steatohepatitis/metabolic dysfunction-associated steatohepatitis (NASH/MASH) in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of reversing established non-alcoholic steatohepatitis/metabolic dysfunction-associated steatohepatitis (NASH/MASH) in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of reversing established non-alcoholic steatohepatitis/metabolic dysfunction-associated steatohepatitis (NASH/MASH) in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of reducing fibrotic gene expression in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of reducing fibrotic gene expression in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of reducing fibrotic gene expression in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating liver fibrosis in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating liver fibrosis in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating liver fibrosis in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating skin fibrosis in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating skin fibrosis in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating skin fibrosis in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating pulmonary fibrosis in a subject in need thereof, comprising administering to the subject a fatty acid synthase inhibitor and a thyroid hormone receptor agonist (e.g., a thyroid hormone receptor-beta agonist). For example, in some embodiments, the present disclosure relates to a method of treating pulmonary fibrosis in a subject in need thereof, comprising administering to the subject a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating pulmonary fibrosis in a subject in need thereof, comprising administering to the subject a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of reducing triglycerides in a subject in need thereof, including for example severe hypertriglyceridemia (sHTG), comprising administering a fatty acid synthase inhibitor and a thyroid hormone receptor agonist (e.g., a thyroid hormone receptor-beta agonist). For example, in some embodiments, the present disclosure relates to a method of reducing triglycerides in a subject in need thereof comprising administering a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of reducing triglycerides in a subject in need thereof comprising administering a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of improving or restoring liver function in a subject in need thereof, comprising administering a fatty acid synthase inhibitor and a thyroid hormone receptor agonist (e.g., a thyroid hormone receptor-beta agonist). For example, in some embodiments, the present disclosure relates to a method of improving or restoring liver function in a subject in need thereof comprising administering a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of improving or restoring liver function in a subject in need thereof comprising administering a fatty acid synthase inhibitor and a thyroid hormone receptor agonist, wherein the fatty acid synthase inhibitor is Compound 001-152 and the thyroid hormone receptor agonist is Compound A.

In various aspects, the present disclosure relates to a method of treating NASH/MASH with moderate to severe fibrosis in a subject in need thereof, comprising administering a fatty acid synthase inhibitor and a thyroid hormone receptor agonist (e.g., a thyroid hormone receptor-beta agonist). For example, in some embodiments, the present disclosure relates to a method of treating NASH/MASH with moderate to severe fibrosis in a subject in need thereof comprising administering a fatty acid synthase inhibitor of Formula (IX), (X), (VI-J), (XII), (XIII), (XIV), (XV), (XVI), (XVII), (XVIII), (XIX), (XX), or (XI) and a thyroid hormone receptor agonist of Formula (XXI). In some embodiments, the present disclosure relates to a method of treating NASH/MASH with moderate to severe fibrosis in a subject in need thereof comprising administering a fatty acid synthase inhibitor and a thyroid hormone receptor agonist, wherein the fatty acid synthase inhibitor is Compound 001-152 and the thyroid hormone receptor agonist is Compound A.

In various aspects, the disclosure further relates to pharmaceutical formulations comprising a FASN inhibitor or a pharmaceutically acceptable salt thereof and a thyroid hormone receptor agonist or a pharmaceutically acceptable salt thereof.

In yet other aspects, the disclosure further relates to pharmaceutical formulations Compound 001-152 or a pharmaceutically acceptable salt thereof and Compound A or a pharmaceutically acceptable salt thereof.

In various other aspects, the disclosure further relates to pharmaceutical formulations Compound 001-152 or a pharmaceutically acceptable salt thereof and a Form A of the Compound A.

In various other aspects, the disclosure relates to methods of treating of diseases and/or disorders described herein in which the methods of treating comprise administering Compound 001-152 or a pharmaceutically acceptable salt thereof and a Form A of the Compound A.

In various other aspects, the disclosure relates to methods of treating of diseases and/or disorders described herein in which the methods of treating comprise administering a pharmaceutical formulation comprising Compound 001-152 or a pharmaceutically acceptable salt thereof and a Form A of the Compound A.

In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for treating steatotic liver disease, non-alcoholic steatohepatitis/metabolic dysfunction-associated steatohepatitis (NASH/MASH), non-alcoholic fatty liver disease/metabolic dysfunction associated steatotic liver disease (NAFLD/MASLD), liver cirrhosis, liver fibrosis, liver cancer (e.g., a liver cancer that has developed from NAFLD/MASLD or NASH/MASH), a cholangiocarcinoma, or a hepatocellular carcinoma (e.g., a hepatocellular carcinoma that has developed from NAFLD/MASLD or NASH/MASH), or for improving or restoring liver function, wherein the medicament is for combined administration with a thyroid hormone receptor agonist (e.g., a thyroid hormone receptor-beta agonist, e.g., a compound of Formula (XXI)).

In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for treating a disease or condition in which interleukin 1 beta (IL1β) levels are elevated, a disease or condition modulated by interleukin 1 beta (IL1β), a disease or condition in which t-helper (Th) cell levels are elevated, or a disease or condition in which regulatory t cells ($T_{reg}$) are reduced or suppressed, wherein the medicament is for combined administration with a thyroid hormone receptor agonist (e.g., a thyroid hormone receptor-beta agonist, e.g., a compound of Formula (XXI)).

In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for reversing established non-alcoholic steatohepatitis (NASH/MASH), wherein the medicament is for combined administration with a thyroid hormone receptor agonist (e.g., a thyroid hormone receptor-beta agonist, e.g., a compound of Formula (XXI)).

In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for treating metabolic syndrome, wherein the medicament is for combined administration with a THR β agonist (e.g., a compound of Formula (XXI)).

In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for treating type II diabetes, wherein the medicament is for combined administration with a THR β agonist (e.g., a compound of Formula (XXI)).

In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for treating atherosclerosis, wherein the medicament is for combined administration with a THR β agonist (e.g., a compound of Formula (XXI)).

In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for reducing fibrotic gene expression, wherein the medicament is for combined administration with a THR β agonist (e.g., a compound of Formula (XXI)).

In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for treating liver fibrosis, wherein the medicament is for combined administration with a THR β agonist (e.g., a compound of Formula (XXI)).

In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for improving or restoring liver function, wherein the medicament is for combined administration with a THR β agonist (e.g., a compound of Formula (XXI)).

In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for treating NASH/MASH with moderate to severe fibrosis, wherein the medicament is for combined administration with a THR β agonist (e.g., a compound of Formula (XXI)). In various aspects, the disclosure relates to a fatty acid synthase inhibitor of Structure (IX), (X), (VI-J), (XII), (XIII), (XIV), (XV), (XVI), (XVII), (XVIII), (XIX), (XX), or (XI) in the manufacture of a medicament for treating skin fibrosis or pulmonary fibrosis, wherein the medicament is for combined administration with a thyroid hormone receptor agonist (e.g., a thyroid hormone receptor-beta agonist, e.g., a compound of Formula (XXI)).

In any of the foregoing aspects and embodiments, a fatty acid synthase inhibitor of Formula (IX), (X), (VI-J), (XII), (XIII), (XIV), (XV), (XVI), (XVII), (XVIII), (XIX), (XX), or (XI) is a compound selected from Tables C-1 to C-3.

DETAILED DESCRIPTION

Figure 1A:
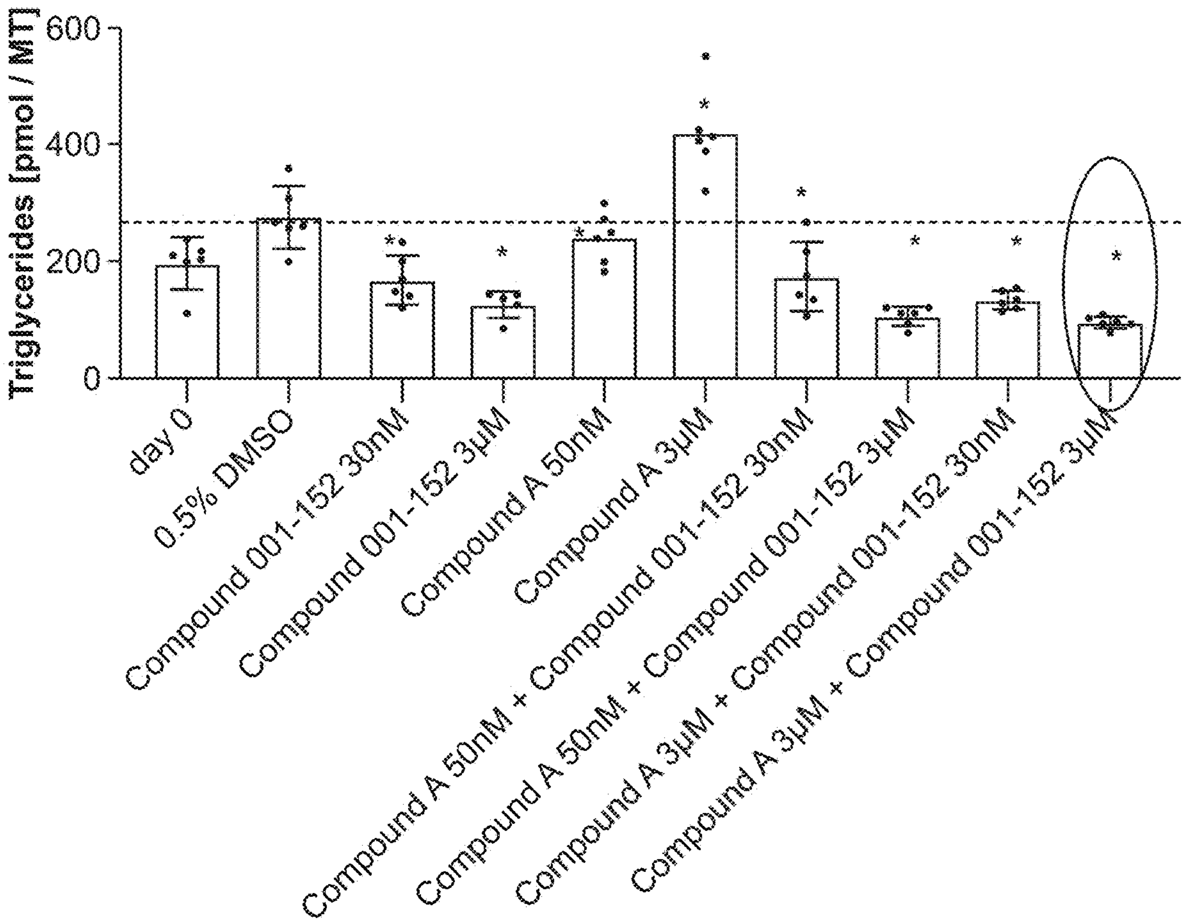
FIG. 1A is a graph showing the effect of Compound 001-152 and Compound A in a human liver microtissue model in hepatic de novo lipogenesis (DNL) condition as measured by intratissue Triglyceride content. Compound 001-152 (30 nM and 3 uM) single agent treatment reduces cellular triglycerides in vitro in a human liver microtissue model. Combination of Compound 001-152 with Compound A enhances the effect of Compound A and the combination has an increased efficacy overall versus single agent. This liver microtissue model comprises hepatocytes, Kupffer cells and liver endothelial cells. Liver microtissues were treated for 7 days. To model increased lipid accumulation within hepatocytes, microtissues were treated with sugar and free fatty acids (FFA). Graphs depict Mean±Standard Deviation (SD). A two-tailed t-test with Welch's correction *$p<0.05$ was used.

The present disclosure addresses the deficiencies in treating conditions characterized by dysregulation of the FASN function in a subject, such as liver disorders, liver cancer (e.g., cholangiocarcinoma, hepatocellular carcinoma) and metabolic disorders (e.g., type II diabetes), by providing novel treatment methods comprising the administration of a therapeutic combination of fatty acid synthase inhibitors and thyroid receptor hormone agonists, and/or pharmaceutical formulations comprising fatty acid synthase inhibitors and thyroid receptor hormone agonists.

Definitions

Chemical moieties referred to as univalent chemical moieties (e.g., alkyl, aryl, etc.) also encompass structurally permissible multivalent moieties, as understood by those skilled in the art. For example, while an "alkyl" moiety generally refers to a monovalent radical (e.g., $CH_3CH_2$—), in appropriate circumstances an "alkyl" moiety can also refer to a divalent radical (e.g., —$CH_2CH_2$—, which is equivalent to an "alkylene" group). Similarly, under circumstances where a divalent moiety is required, those skilled in the art will understand that the term "aryl" refers to the corresponding divalent arylene group.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is O the moiety is B and when a is 1 the moiety is AB.

Where a substituent can vary in the number of atoms or groups of the same kind (e.g., alkyl groups can be $C_1$, $C_2$, $C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1$, $C_2$, $C_3$, $C_{1-2}$, $C_{1-3}$, and $C_{2-3}$ alkyl.

"Alkanoyl" refers to a carbonyl group with a lower alkyl group as a substituent.

"Alkylamino" refers to an amino group substituted by an alkyl group.

"Alkoxy" refers to an O-atom substituted by an alkyl group as defined herein, for example, methoxy [—$OCH_3$, a $C_1$alkoxy]. The term "$C_{1-6}$ alkoxy" encompasses $C_1$ alkoxy, $C_2$ alkoxy, $C_3$ alkoxy, $C_4$ alkoxy, $C_5$ alkoxy, $C_6$ alkoxy, and any sub-range thereof.

"Alkoxycarbonyl" refers to a carbonyl group with an alkoxy group as a substituent.

"Alkyl," "alkenyl," and "alkynyl," refer to optionally substituted, straight and branched chain aliphatic groups having from 1 to 30 carbon atoms, or preferably from 1 to 15 carbon atoms, or more preferably from 1 to 6 carbon atoms. Examples of alkyl groups include, without limitation, methyl, ethyl, propyl, isopropyl, butyl, tert-butyl, isobutyl, pentyl, hexyl, vinyl, allyl, isobutenyl, ethynyl, and propynyl. The term "heteroalkyl" as used herein contemplates an alkyl with one or more heteroatoms.

"Alkylene" refers to an optionally substituted divalent radical which is a branched or unbranched hydrocarbon fragment containing the specified number of carbon atoms, and having two points of attachment. An example is propylene [—$CH_2CH_2CH_2$—, a $C_3$alkylene].

"Amino" refers to the group —$NH_2$.

"Aryl" refers to optionally substituted aromatic groups which have at least one ring having a conjugated pi electron system and includes carbocyclic aryl, and biaryl groups, all of which can be optionally substituted. Phenyl and naphthyl groups are preferred carbocyclic aryl groups.

"Aralkyl" or "arylalkyl" refer to alkyl-substituted aryl groups. Examples of aralkyl groups include butylphenyl, propylphenyl, ethylphenyl, methylphenyl, 3,5-dimethylphenyl, tert-butylphenyl.

"Carbamoyl" as used herein contemplates a group of the Formula

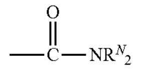

where in $R^N$ is selected from the group consisting of hydrogen, —OH, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, sulfonyl, sulfonate and sulfonamide.

"Carbonyl" refers to a group of the Formula

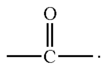

"Cycloalkyl" refers to an optionally substituted ring, which can be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Heterocycle" refers to an optionally substituted 5- to 7-membered cycloalkyl ring system containing 1, 2 or 3 heteroatoms, which can be the same or different, selected from N, O or S, and optionally containing one double bond.

"Halogen" refers to a chloro, bromo, fluoro or iodo atom radical. The term "halogen" also contemplates terms "halo" or "halide."

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present disclosure.

"Heteroaryl" refers to optionally substituted aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include thienyl, pyrrolyl, furyl, pyridyl, pyrimidyl, pyrazinyl, pyrazolyl, oxazolyl, isoxazolyl, imidazolyl, thiazolyl, pyranyl, tetrazolyl, pyrrolyl, pyrrolinyl, pyridazinyl, triazolyl, indolyl, isoindolyl, indolizinyl, benzimidazolyl, quinolyl, isoquinolyl, indazolyl, benzotriazolyl, tetrazolopyridazinyl, oxadiazolyl, benzoxazolyl, benzoxadiazolyl, thiadiazolyl, benzothiazolyl, benzothiadiazolyl, and the like.

An "optionally substituted" moiety can be substituted with from one to four, or preferably from one to three, or more preferably one or two non-hydrogen substituents. Unless otherwise specified, when the substituent is on a carbon, it is selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, none of which are further substituted. Unless otherwise specified, when the substituent is on a nitrogen, it is selected from the group consisting of $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, sulfonyl, sulfonate and sulfonamide none of which are further substituted.

The term "sulfonamide" as used herein contemplates a group having the Formula

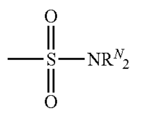

wherein $R^N$ is selected from the group consisting of hydrogen, —OH, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate and sulfonamide.

The term "sulfonate" as used herein contemplates a group having the Formula

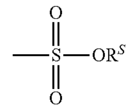

wherein $R^S$ is selected from the group consisting of hydrogen, $C_1$-$C_{10}$ alkyl, $C_2$-$C_{10}$ alkenyl, $C_2$-$C_{10}$ alkynyl, $C_1$-$C_{10}$ alkanoyl, or $C_1$-$C_{10}$ alkoxycarbonyl.

"Sulfonyl" as used herein alone or as part of another group, refers to an $SO_2$ group. The $SO_2$ moiety is optionally substituted.

Compounds of the present disclosure can exist as stereoisomers, wherein asymmetric or chiral centers are present. Stereoisomers are designated (R) or(S) depending on the configuration of substituents around the chiral carbon atom. The terms (R) and(S) used herein are configurations as defined in IUPAC 1974 Recommendations for Section E, Fundamental Stereochemistry, Pure Appl. Chem., (1976), 45:13-30, hereby incorporated by reference. The present disclosure contemplates various stereoisomers and mixtures thereof and are specifically included within the scope of the present disclosure. Stereoisomers include enantiomers, diastereomers, and mixtures of enantiomers or diastereomers. Individual stereoisomers of compounds of the present disclosure can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Also, moieties disclosed herein which exist in multiple tautomeric forms include all such forms encompassed by a given tautomeric Formula. For example, it is understood that Compound 001-152 when drawn as:

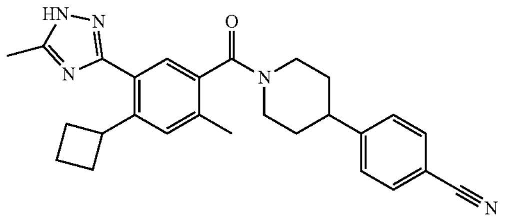 [SMILES: Cc1nc(-c2cc(C(=O)N3CCC(c4ccc(C#N)cc4)CC3)c(C)cc2C2CCC2)n[nH]1]

encompasses, e.g.:

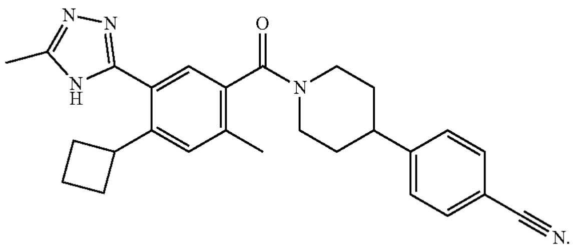 [SMILES: Cc1nnc(-c2cc(C(=O)N3CCC(c4ccc(C#N)cc4)CC3)c(C)cc2C2CCC2)[nH]1]

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism. One example of a moiety existing in several tautomeric forms is 1,2,4-triazole exists in tautomeric forms known as 1H-1,2,4-triazole, 4H-1,2,4-triazole and 3H-1,2,4-triazole which interconvert rapidly.

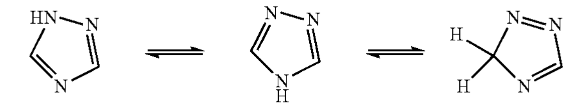

1H-1,2,4-triazole 4H-1,2,4-triazole 3H-1,2,4-triazole

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2 (1H)-ones and the corresponding pyridin-2-ols, as shown below.

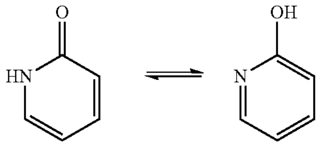

pyridin-2(1H)-one pyridin-2-ol.

Individual atoms in the disclosed compounds may be any isotope of that element. For example, hydrogen may be in the form of deuterium.

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts include, for example, acid addition salts and base addition salts.

"Acid addition salts" according to the present disclosure, are formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

"Base addition salts" according to the present disclosure are formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature can cause a single crystal form to dominate.

The term "treating" includes the administration of the compounds or agents of the present invention to a subject to prevent or delay, to alleviate, or to arrest or inhibit development of the symptoms or conditions associated with fatty acid synthase-associated disorders, e.g., tumor growth associated with cancer. A skilled medical practitioner will know how to use standard methods to determine whether a patient is suffering from a disease associated with activity of fatty acid synthase, e.g., by examining the patient and determining whether the patient is suffering from a disease known to be associated with fatty acid synthase activity or by assaying for fatty acid synthase levels in blood plasma or tissue of the individual suspected of suffering from fatty acid synthase associated disease and comparing fatty acid synthase levels in the blood plasma or tissue of the individual suspected of suffering from a fatty acid synthase associated disease with fatty acid synthase levels in the blood plasma or tissue of a healthy individual. Increased securin levels are indicative of disease. Accordingly, the present invention provides, inter alia, methods of administering a compound of the present invention to a subject and determining fatty acid synthase activity in the subject. Fatty acid synthase activity in the subject can be determined before and/or after administration of the compound.

A "therapeutically effective amount" or "pharmaceutically effective amount" means the amount that, when administered to a subject, produces effects for which it is administered. For example, a "therapeutically effective amount," when administered to a subject to inhibit fatty acid synthase activity, is sufficient to inhibit fatty acid synthase activity. A "therapeutically effective amount," when administered to a subject for treating a disease, is sufficient to effect treatment for that disease.

In some embodiments, the "term "therapeutically effective amount" refers to a synergistically effective amount or synergistically therapeutic amount.

"Synergistic" means that the therapeutic effect of FASN inhibitor when administered in combination as described herein with a THR agonist (e.g., THR-β agonist) is greater than the predicted additive therapeutic effects of the FASN inhibitor and THR agonist (e.g., THR-β agonist) when administered alone. The "term "synergistically therapeutic amount" or "synergistically effective amount" refers to a less than standard therapeutic amount of one or both drugs, meaning that the amount required for the desired effect is lower than when the drug is used alone. A synergistically therapeutic amount also includes cases where one drug is given at a standard therapeutic dose and another drug is administered in a less than standard therapeutic dose. For example, the FASN inhibitor could be given in a therapeutic dose and the THR agonist (e.g., THR-β agonist) could be given in a standard or less than standard therapeutic dose to provide a synergistic result, or vice versa.

The term "therapeutic combination" is intended to embrace administration of two or more therapeutic agents (e.g., a fatty acid synthase inhibitor of the disclosure and a THR-beta agonist of the disclosure) in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent (e.g., a fatty acid synthase inhibitor of the disclosure and a THR-beta agonist of the disclosure) or in multiple, single capsules for each of the therapeutic agents. Sequential or substantially simultaneous administration of each therapeutic agent (e.g., a fatty acid synthase inhibitor of the disclosure and a THR-beta agonist of the disclosure) can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary aspect of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that are associated with the targeted or suspected disease or condition. These and other routine methods allow the clinician to select patients in need of therapy using the methods and formulations of the present invention.

FASN Pathway Modulators

In some embodiments, the fatty acid synthase inhibitor is a compound of Formula (I):

(I)

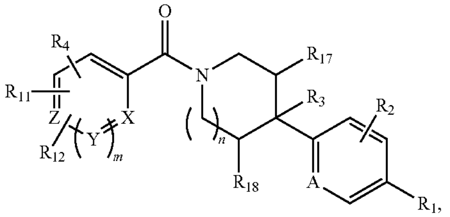

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

A is CH or N;

$R_1$ is hydrogen, cyano, halo, $C_{1-6}$ alkyl, $C_{1-6}$ alkoxy, $—C(=O)N(R_{13})(R_{14})$, $—(CH_2)_qC(=O)N(R^{13})(R^{14})$, $CF_3$, $—OCF_3$, or $—S(=O)_2R_{20}$;

q is 0, 1, 2, 3, or 4;

$R_{20}$ is hydrogen or $C_{1-6}$ alkyl, $C_{1-6}$ alkoxy, or $—N(R_{13})(R_{14})$;

$R_2$ is hydrogen, halo, $C_{1-6}$ alkoxy, or $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, $—C(=O)N(R_5R_6)$, $—N(R_7)C(=O)R_8$, $—N(R_9R_{10})$, $C_{1-6}$ alkyl, $C_{1-6}$ alkoxy, $—S(=O)_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, $—N(R_{13}R_{14})$, $CF_3$, $—OCF_3$, or $—S(=O)_2R_{20}$, or $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, $—N(R_{13}R_{14})$, $CF_3$, $—OCF_3$, or $—S(=O)_2R_{20}$, or $R_{11}$ and $R_{12}$ taken together with the atoms to which they are attached join together to form a heteroaryl;

$R_5$, $R_6$, $R_7$, $R_8$, $R_9R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, $—N(R_{15}R_{16})$, or $—S(=O)_2R_{20}$;

$R_{15}$ and $R_{16}$ are each independently hydrogen, $C_{1-6}$ alkyl, cycloalkyl, aryl, heterocyclyl, heteroaryl, or alkylamino;

$R_{17}$ and $R_{18}$ are each independently hydrogen or alkyl or can optionally join together to form a bond;

n is 1 or 2; and m is 0 or 1.

In certain embodiments of Formula (I), $R_3$ is F.

In certain embodiments of Formula (I), A is CH.

In certain embodiments of Formula (I), A is N.

In certain embodiments of Formula (I), X, Y, and Z are NR'.

In certain embodiments of Formula (I), $R_4$ is heteroaryl, heterocyclyl, $—C(=O)N(R_5R_6)$, $—N(R_7)C(=O)R_8$, $—N(R_9R_{10})$, $C_{1-6}$ alkyl, $C_{1-6}$ alkoxy, or $R_4$ and $R_{11}$ taken together with the atoms to which they are attached join together to form a heteroaryl.

In certain embodiments of Formula (I), $R_5$ is hydrogen and $R_6$ is aryl or heteroaryl.

In certain embodiments, the fatty acid synthase inhibitors of Formula (I) have one of the following Formulas (I-A) or (I-B):

(I-A)

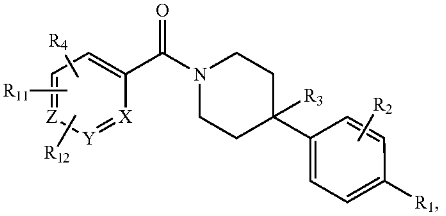

or (I-B)

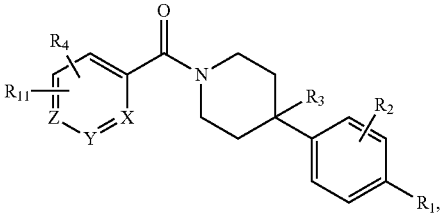

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

$R_1$ is hydrogen, cyano, halo, $C_{1-6}$ alkyl, $C_{1-6}$ alkoxy, —C(═O)N($R_{13}$)($R_{14}$), —$(CH_2)_q$C(═O)N($R_{13}$)($R_{14}$), $CF_3$, —$OCF_3$, or —S(═O)$_2R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(═O)N($R_5R_6$), —N($R_7$)C(═O)$R_8$, —N($R_9R_{10}$), $C_{1-6}$ alkyl, $C_{1-6}$ alkoxy, —S(═O)$_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), $CF_3$, —$OCF_3$, —S(═O)$_2R_{20}$, or $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —S(═O)$_2R_{20}$, or $R_{11}$ and $R_{12}$ taken together with the atoms to which they are attached join together to form a heteroaryl;

$R_5$, $R_6$, $R_7$, $R_8$, $R_9R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(═O)$_2R_{20}$;

$R_{15}$ and $R_{16}$ are each independently hydrogen, $C_{1-6}$ alkyl, cycloalkyl, aryl, heterocyclyl, heteroaryl, or alkylamino; and $R_{17}$ and $R_{18}$ are each independently hydrogen or alkyl or can optionally join together to form a bond.

In certain embodiments, the fatty acid synthase inhibitors of Formula (I) have one of the following Formulas (I-C) or (I-D):

(I-C)

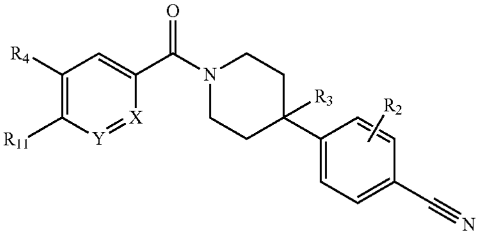

or (I-D)

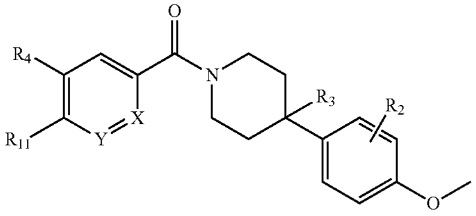

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

$R_2$ is hydrogen, halo, $C_{1-6}$ alkoxy, or $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, or $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(═O)N($R_5R_6$), —N($R_7$)C(═O)$R_8$, —N($R_9R_{10}$), $C_{1-6}$ alkyl, $C_{1-6}$ alkoxy, or —S(═O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitors of Formula (I) have one of the following Formulas (I-E), (I-F), (I-G), and (I-H):

(I-E)

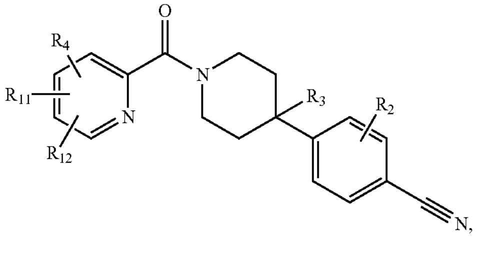

-continued (I-F)

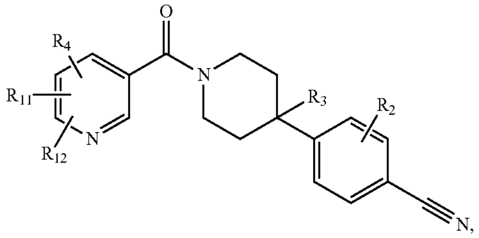

(I-G)

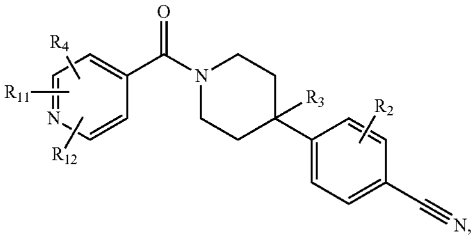

and (I-H)

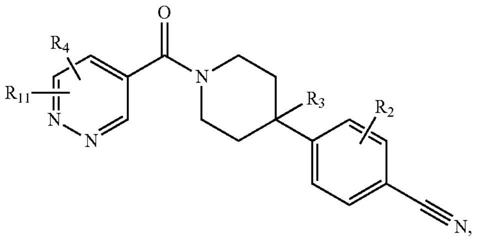

or a pharmaceutically acceptable salt thereof, wherein:

$R_2$ is hydrogen, halo, $C_{1-6}$ alkoxy, or $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, or $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(═O)N($R_5R_6$), —N($R_7$)C(═O)$R_8$, —N($R_9R_{10}$), $C_{1-6}$ alkyl, $C_{1-6}$ alkoxy, or —S(═O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$, or $R_4$ and $R_{11}$ taken together with the atoms to which they are attached join together to form a heteroaryl, or Rin and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitors of Formula (I) have one of the following Formulas (I-I), (I-J), and (I-K):

(I-I)

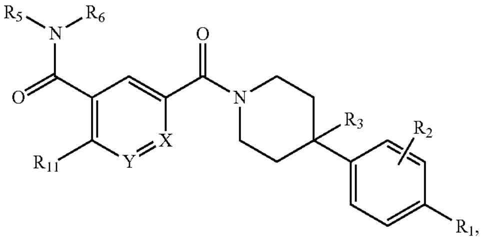

(I-J)

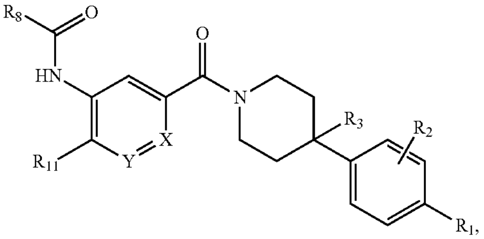

and (I-K)

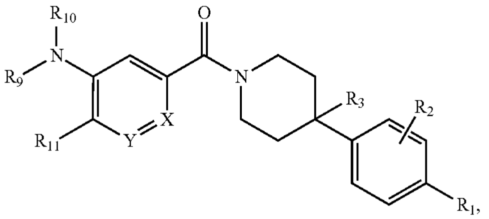

or a pharmaceutically acceptable salt thereof, wherein:

X and Y are each independently CR or NR', wherein R is H or $C_{1-6}$ alkyl and R' is H, $C_{1-6}$ alkyl, or absent;

$R_1$ is hydrogen, cyano, halo, $C_{1-6}$ alkyl, $C_{1-6}$ alkoxy, —C(═O)N($R_{13}$)($R_{14}$), —$(CH_2)_q$C(═O)N($R_{13}$)($R_{14}$), $CF_3$, —$OCF_3$, or —S(═O)$_2R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_{11}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitors of Formula (I) have the following Formula (I-L) or (I-M):

(I-L)

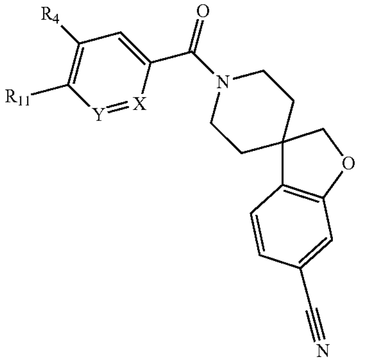

or (I-M)

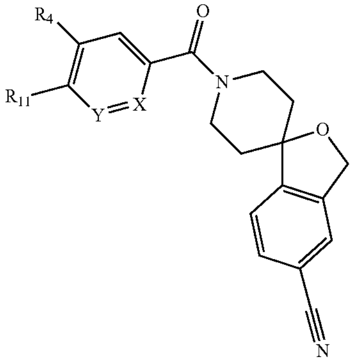

, or a pharmaceutically acceptable salt thereof, wherein:

X and Y are each independently CR or NR', wherein R is H or $C_{1-6}$ alkyl and R' is H, $C_{1-6}$ alkyl, or absent;

$R_4$ is hydrogen, heteroaryl, heterocyclyl, —C(═O)N($R_5R_6$), —N($R_7$)C(═O)$R_8$, —N($R_9R_{10}$), $C_{1-6}$ alkyl, $C_{1-6}$ alkoxy, or —S(═O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitor is Compound 001-346 or 001-495 of Table C-1, or a pharmaceutically acceptable salt thereof.

or a pharmaceutically acceptable salt thereof.

In certain embodiments, the fatty acid synthase inhibitors of Formula (I) have the following Formula (I-P):

(I-P)

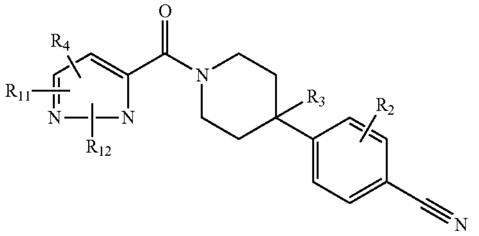

or a pharmaceutically acceptable salt thereof, wherein:

$R_2$ is hydrogen, halo, $C_{1-6}$ alkoxy, or $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, or $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(═O)N($R_5R_6$), —N($R_7$)C(═O)$R_8$, —N($R_9R_{10}$), $C_{1-6}$ alkyl, $C_{1-6}$ alkoxy, or —S(═O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$, or $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —S(═O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitor is Compound 001-385, 001-387, or 001-496, of Table C-1, or a pharmaceutically acceptable salt thereof.

In certain embodiments, the fatty acid synthase inhibitors of Formula (I) have the following Formula (I-T):

(I-T)

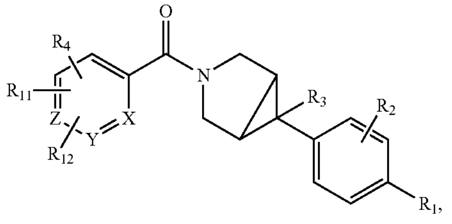

or a pharmaceutically acceptable salt thereof, wherein:

X, Y, and Z are each independently CR or NR', wherein R is H or $C_{1-6}$ alkyl and R' is H, $C_{1-6}$ alkyl, or absent;

$R_1$ is hydrogen, cyano, halo, $C_{1-6}$ alkyl, $C_{1-6}$ alkoxy, —C(═O)N($R_{13}$)($R_{14}$), —($CH_2$)$_q$C(═O)N($R_{13}$)($R_{14}$), $CF_3$, —$OCF_3$, or —S(═O)$_2R_{20}$;

q is 0, 1, 2, 3, or 4;

$R_{20}$ is hydrogen or $C_{1-6}$ alkyl, $C_{1-6}$ alkoxy, or —$N(R_{13})(R_{14})$;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(═O)N($R_5R_6$), —N($R_7$)C(═O)$R_8$, —N($R_9R_{10}$), $C_{1-6}$ alkyl, $C_{1-6}$ alkoxy, —S(═O)$_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$, or $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitor is Compound 001-118 of Table C-1, or a pharmaceutically acceptable salt thereof.

In certain embodiments, the fatty acid synthase inhibitors of Formula (I) have the following Formula (I-V):

(I-V)

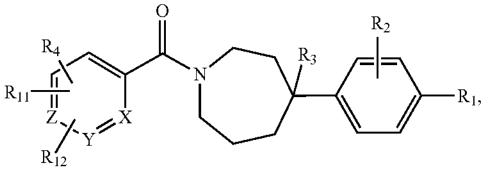

or a pharmaceutically acceptable salt thereof, wherein:

X, Y, and Z are each independently CR or NR', wherein R is H or $C_{1-6}$ alkyl and R' is H, $C_{1-6}$ alkyl, or absent;

$R_1$ is hydrogen, cyano, halo, $C_{1-6}$ alkyl, $C_{1-6}$ alkoxy, —C(═O)N($R_{13}$)($R_{14}$), —$(CH_2)_q$C(═O)N($R_{13}$)($R_{14}$), $CF_3$, —$OCF_3$, or —S(═O)$_2R_{20}$;

q is 0, 1, 2, 3, or 4;

$R_{20}$ is hydrogen or $C_{1-6}$ alkyl, $C_{1-6}$ alkoxy, or —$N(R_{13})(R_{14})$;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(═O)N($R_5R_6$), —N($R_7$)C(═O)$R_8$, —N($R_9R_{10}$), $C_{1-6}$ alkyl, $C_{1-6}$ alkoxy, or —S(═O)$_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$, or $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —S(═O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitor is Compound 001-40 of Table C-1, or a pharmaceutically acceptable salt thereof.

In certain embodiments, the fatty acid synthase inhibitor is a compound selected from Compounds 001-500, 001-27, 001-73, 001-348, 001-349, 001-123, 001-497, 001-383, 001-280, 001-121, and 001-289 of Table C-1, or a pharmaceutically acceptable salt thereof.

In some embodiments, the fatty acid synthase inhibitor is a compound of Formula (II):

(II)

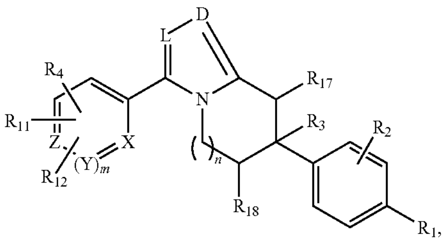

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

L and D are each independently C or N;

$R_1$ is hydrogen, cyano, halo, $C_{1-6}$ alkyl, $C_{1-6}$ alkoxy, —C(═O)N($R_{13}$)($R_{14}$), —$(CH_2)_q$C(═O)N($R_{13}$)($R_{14}$), $CF_3$, —$OCF_3$, or —S(═O)$_2R_{20}$;

q is 0, 1, 2, 3, or 4;

$R_{20}$ is hydrogen or $C_{1-6}$ alkyl, $C_{1-6}$ alkoxy, or —$N(R_{13})(R_{14})$;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(═O)N($R_5R_6$), —N($R_7$)C(═O)$R_8$, —N($R_9R_{10}$), $C_{1-6}$ alkyl, $C_{1-6}$ alkoxy, or —S(═O)$_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$, or $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, or —S(═O)$_2R_{20}$, or $R_{11}$ and $R_{12}$ taken together with the atoms to which they are attached join together to form a heteroaryl;

$R_5$, $R_6$, $R_7$, $R_8$, $R_9R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, $—N(R_{15}R_{16})$, or $—S(=O)_2R_{20}$;

$R_{15}$ and $R_{16}$ are each independently hydrogen, $C_{1-6}$ alkyl, cycloalkyl, aryl, heterocyclyl, heteroaryl, or alkylamino;

$R_{17}$ and $R_{18}$ are each independently hydrogen or alkyl or can optionally join together to form a bond;

n is 1 or 2; and m is 0 or 1.

In certain embodiments, the fatty acid synthase inhibitors of Formula (II) have the following Formula (II-A):

(II-A)

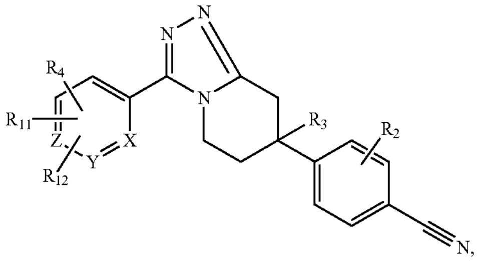

or a pharmaceutically acceptable salt thereof, wherein:

X, Y, and Z are each independently CR or NR', wherein R is H or $C_{1-6}$ alkyl and R' is H, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, $—C(=O)N(R_5R_6)$, $—N(R_7)C(=O)R_8$, $—N(R_9R_{10})$, $C_{1-6}$ alkyl, $C_{1-6}$ alkoxy, or $—S(=O)_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or $—N(R_{13})(R_{14})$;

$R_{11}$ is hydrogen, halo, cyano, $C_{1-6}$ alkyl, $C_{1-6}$ alkoxy, $—N(R_{13}R_{14})$, $CF_3$, $—OCF_3$, or $—S(=O)_2R_{20}$, or $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, $—N(R_{13}R_{14})$, $CF_3$, $—OCF_3$, or $—S(=O)_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or $—N(R_{15}R_{16})$; and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitors of Formula (II) have the following Formula (II-B):

(II-B)

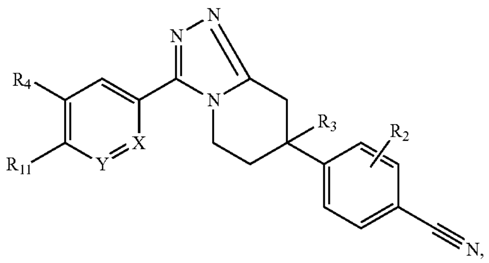

or a pharmaceutically acceptable salt thereof, wherein:

X and Y are each independently CR or NR', wherein R is H or $C_{1-6}$ alkyl and R' is H, $C_{1-6}$ alkyl, or absent;

$R_2$ is hydrogen, halo, $C_{1-6}$ alkoxy, or $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, or $C_{1-6}$ alkoxy, or $R_2$ and $R_3$ taken together with the atoms to which they are attached form a 5-membered heterocyclyl;

$R_4$ is hydrogen, heteroaryl, heterocyclyl, $—C(=O)N(R_5R_6)$, $—N(R_7)C(=O)R_8$, $—N(R_9R_{10})$, $C_{1-6}$ alkyl, $C_{1-6}$ alkoxy, or $—S(=O)_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or $—N(R_{13})(R_{14})$;

$R_{11}$ is hydrogen, halo, cyano, $C_{1-6}$ alkyl, $C_{1-6}$ alkoxy, $—N(R_{13}R_{14})$, $CF_3$, $—OCF_3$, or $—S(=O)_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or $—N(R_{15}R_{16})$; and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitors of Formula (II) have one of the following Formulas (II-C), (II-D), and (II-E):

(II-C)

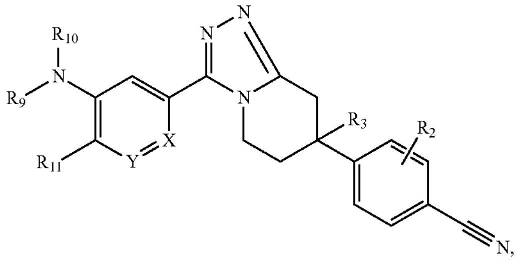

(II-D)

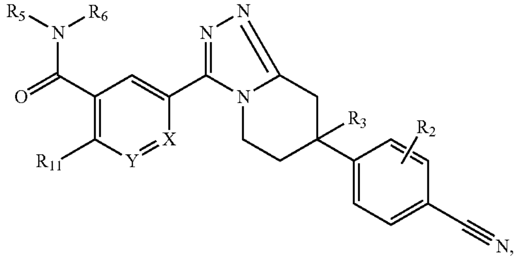

and

-continued (II-E)

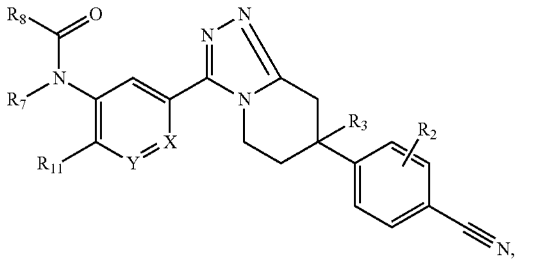

or a pharmaceutically acceptable salt thereof, wherein:

X and Y are each independently CR or NR', wherein R is H or $C_{1-6}$ alkyl and R' is H, $C_{1-6}$ alkyl, or absent;

$R_2$ is hydrogen, halo, $C_{1-6}$ alkoxy, or $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, or $C_{1-6}$ alkoxy, or $R_2$ and $R_3$ taken together with the atoms to which they are attached form a 5-membered heterocyclyl;

$R_{11}$ is hydrogen, halo, cyano, $C_{1-6}$ alkyl, $C_{1-6}$ alkoxy, —$N(R_{13}R_{14})$, $CF_3$, —$OCF_3$, or —$S(=O)_2R_{20}$;

$R_{20}$ is hydrogen or $C_{1-6}$ alkyl, $C_{1-6}$ alkoxy, or —$N(R_{13})(R_{14})$;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —$N(R_{15}R_{16})$; and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitor is Compound 001-347 of Table C-1, or a pharmaceutically acceptable salt thereof.

In some embodiments, the fatty acid synthase inhibitor is a compound of Formula (III):

(III)

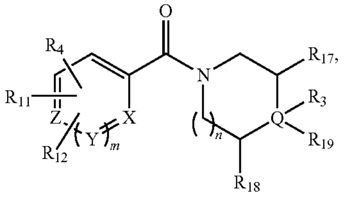

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

Q is C or N;

$R_3$ is hydrogen, hydroxyl, halo, $C_{1-6}$ alkyl, $C_{1-6}$ alkoxy, or if Q is N then $R_3$ is absent;

$R_4$ is hydrogen, heteroaryl, heterocyclyl, —$C(=O)N(R_5R_6)$, —$N(R_7)C(=O)R_8$, —$N(R_9R_{10})$, $C_{1-6}$ alkyl, $C_{1-6}$ alkoxy, or —$S(=O)_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —$N(R_{13}R_{14})$, $CF_3$, —$OCF_3$, —$S(=O)_2R_{20}$, or $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —$N(R_{13}R_{14})$, $CF_3$, —$OCF_3$, or —$S(=O)_2R_{20}$, or $R_{11}$ and $R_{12}$ taken together with the atoms to which they are attached join together to form a heteroaryl;

$R_{20}$ is hydrogen or $C_{1-6}$ alkyl, $C_{1-6}$ alkoxy, or —$N(R_{13})(R_{14})$;

$R_5$, $R_6$, $R_7$, $R_8$, $R_9R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, —$N(R_{15}R_{16})$, or —$S(=O)_2R_{20}$;

$R_{15}$ and $R_{16}$ are each independently hydrogen, $C_{1-6}$ alkyl, cycloalkyl, aryl, heterocyclyl, heteroaryl, or alkylamino;

$R_{17}$ and $R_{18}$ are each independently hydrogen or alkyl or can optionally join together to form a bond;

$R_{19}$ is aryl, heteroaryl, cycloalkyl, or heterocyclyl;

n is 0, 1, or 2; and m is 0 or 1.

In certain embodiments, the fatty acid synthase inhibitors of Formula (III) have one of the following Formulas (III-A), (III-B), and (III-C):

(III-A)

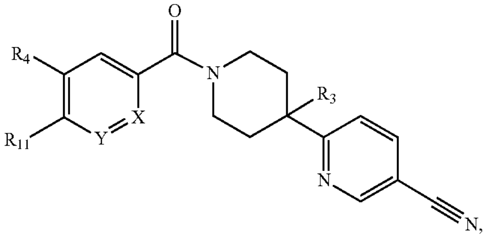

(III-B)

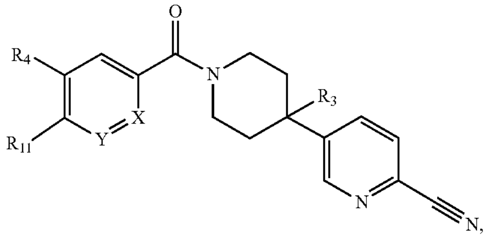

and (III-C)

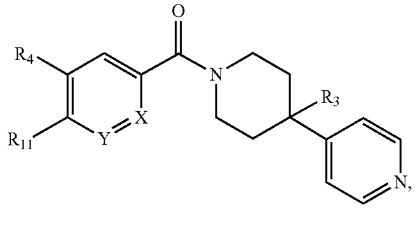

or a pharmaceutically acceptable salt thereof, wherein:

X and Y are each independently CR or NR', wherein R is H or $C_{1-6}$ alkyl and R' is H, $C_{1-6}$ alkyl, or absent;

$R_3$ is hydrogen, hydroxyl, halo, $C_{1-6}$ alkyl, or $C_{1-6}$ alkoxy;

$R_4$ is hydrogen, heteroaryl, heterocyclyl, —$C(=O)N(R_5R_6)$, —$N(R_7)C(=O)R_8$, —$N(R_9R_{10})$, $C_{1-6}$ alkyl, $C_{1-6}$ alkoxy, or —$S(=O)_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —$N(R_{13}R_{14})$, $CF_3$, —$OCF_3$, or —$S(=O)_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —$N(R_{15}R_{16})$; and $R_{15}$ and $R_{16}$ are each independently H, $C_{1-6}$ alkyl, cycloalkyl, aryl, heterocyclyl, heteroaryl, or alkylamino.

In certain embodiments, the fatty acid synthase inhibitor is a compound selected from Compounds 001-50, 001-51, and 001-326 of Table C-1, or a pharmaceutically acceptable salt thereof.

In some embodiments, the fatty acid synthase inhibitor is a compound of Formula (IV-A), (IV-B), or (IV-C):

(IV-A)

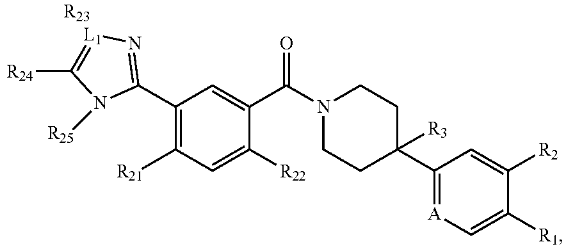

(IV-B)

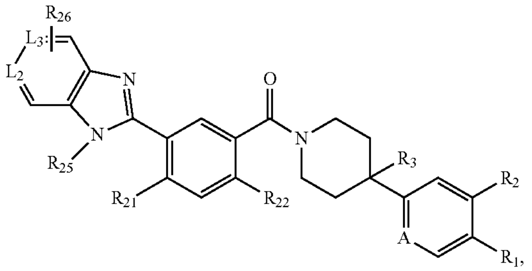

or (IV-C)

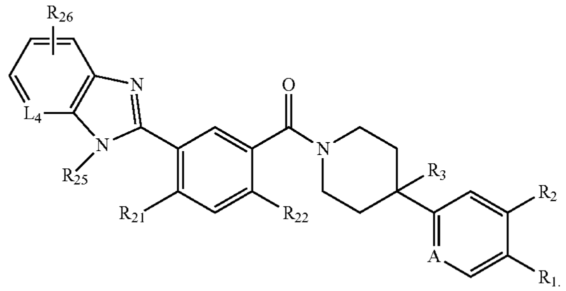

or a pharmaceutically acceptable salt thereof, wherein:

$L_1$, $L_2$, $L_3$, $L_4$, and A are each independently CH or N;

$R_1$ is hydrogen, cyano, halo, $C_{1-6}$ alkyl, $C_{1-6}$ alkoxy, —$C(=O)N(R_{13})(R_{14})$, —$(CH_2)_qC(=O)N(R_{13})(R_{14})$, $CF_3$, —$OCF_3$, or —$S(=O)_2R_{20}$;

q is 0, 1, 2, 3, or 4;

$R_{20}$ is hydrogen or $C_{1-6}$ alkyl, $C_{1-6}$ alkoxy, or —$N(R_{13})(R_{14})$;

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —$S(=O)_2R_{20}$;

$R_{23}$ is hydrogen, —$N(R_{13})(R_{14})$, $C_{1-6}$ alkyl, $C_{1-6}$ alkoxy, is absent if $L_1$ is N, or $R_{23}$ and $R_{24}$ taken together with the atoms to which they are attached join together to form a heterocyclyl, heteroaryl, or cycloalkyl;

$R_{24}$ is hydrogen, —$N(R_{13})(R_{14})$, $C_{1-6}$ alkyl, $C_{1-6}$ alkoxy, —($C_{1-6}$ alkoxy) (heterocyclyl), heterocyclyl, or $R_{23}$ and $R_{24}$ taken together with the atoms to which they are attached join together to form a heterocyclyl, heteroaryl, or cycloalkyl;

$R_{26}$ is hydrogen, heteroaryl, heterocyclyl, —$N(R_{13})(R_{14})$, or —$S(=O)_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —$N(R_{15}R_{16})$, or —$S(=O)_2R_{20}$;

$R_{25}$ is hydrogen, $C_{1-6}$ alkyl, or $C_{1-6}$ alkoxy; and $R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In certain embodiments, the fatty acid synthase inhibitors of Formula (IV) have one of the following Formulas (IV-D) and (IV-E):

(IV-D)

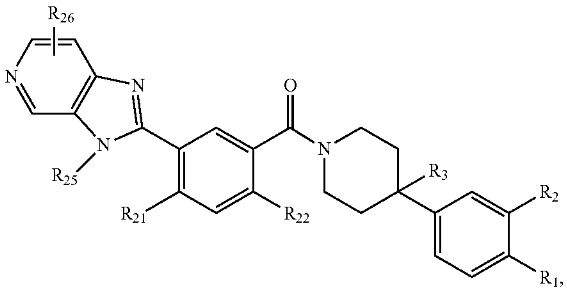

(IV-E)

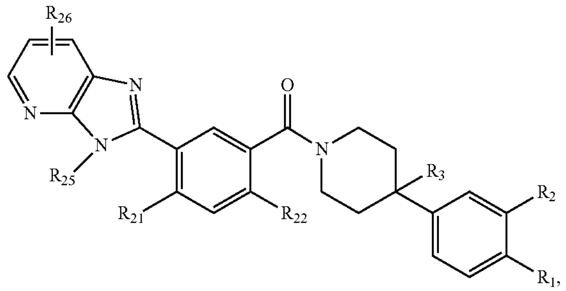

or a pharmaceutically acceptable salt thereof.

$R_1$ is hydrogen, cyano, halo, $C_{1-6}$ alkyl, $C_{1-6}$ alkoxy, —$C(=O)N(R_{13})(R_{14})$, —$(CH_2)_qC(=O)N(R_{13})(R_{14})$, $CF_3$, —$OCF_3$, or —$S(=O)_2R_{20}$;

q is 0, 1, 2, 3, or 4;

$R_{20}$ is hydrogen or $C_{1-6}$ alkyl, $C_{1-6}$ alkoxy, or —$N(R_{13})(R_{14})$;

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —$S(=O)_2R_{20}$;

$R_{26}$ is hydrogen, heteroaryl, heterocyclyl, —$N(R_{13})(R_{14})$, or —$S(=O)_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —$N(R_{15}R_{16})$, or —$S(=O)_2R_{20}$;

$R_{25}$ is hydrogen, $C_{1-6}$ alkyl, or $C_{1-6}$ alkoxy; and $R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In certain embodiments, the fatty acid synthase inhibitors of Formula (IV) have one of the following Formulas (IV-F) and (IV-G):

(IV-F)

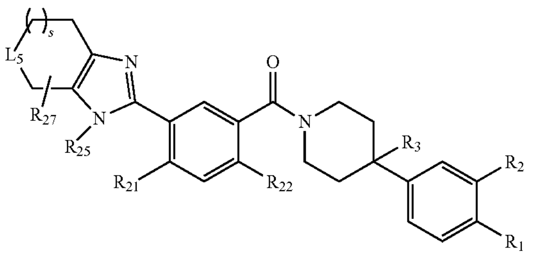

or (IV-G)

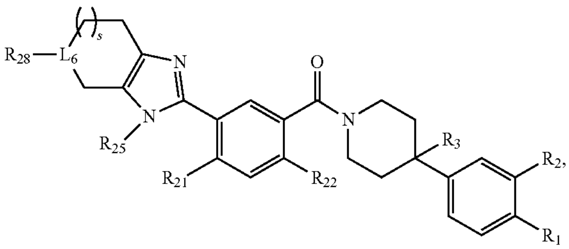

or a pharmaceutically acceptable salt thereof, wherein:

$R_1$ is hydrogen, cyano, halo, $C_{1-6}$ alkyl, $C_{1-6}$ alkoxy, —C(=O)N($R_{13}$)($R_{14}$), —$(CH_2)_q$C(=O)N($R_{13}$)($R_{14}$), $CF_3$, —$OCF_3$, or —S(=O)$_2R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —S(=O)$_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2R_{20}$;

$R_{25}$ is hydrogen, $C_{1-6}$ alkyl, or $C_{1-6}$ alkoxy;

$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino;

s is 0, 1, or 2;

$L^5$ is $CH_2$, NH, S, or O;

$L^6$ is CH or N;

$R_{27}$ is hydrogen, —C(=O)R", —S(=O)$_2R_{20}$;

$R_{28}$ is hydrogen, —C(=O)R", —S(=O)$_2R_{20}$, or is absent if $L^6$ is O; and R" is hydrogen, $C_{1-6}$ alkyl, $C_{1-6}$ alkoxy, —C(=O)N($R_{13}$)($R_{14}$), or —N($R_{13}$)($R_{14}$).

In certain embodiments of Formula (IV), $R_1$ is hydrogen, cyano, $C_{1-6}$ alkyl, $C_{1-6}$ alkoxy, or —C(=O)N($R_{13}$)($R_{14}$).

In certain embodiments of Formula (IV), $R_1$ is cyano.

In certain embodiments of Formula (IV), $R_2$ is hydrogen or halo; $R_2$ is hydrogen.

In certain embodiments of Formula (IV), $R_3$ is hydrogen.

In certain embodiments of Formula (IV), $R_{21}$ and $R_{22}$ are each independently hydrogen or $C_{1-6}$ alkyl.

In certain embodiments of Formula (IV), $R_{21}$ and $R_{22}$ are each independently $C_{1-6}$ alkyl.

In certain embodiments of Formula (IV), $R_{25}$ is hydrogen.

In certain embodiments of Formula (IV), $L^2$ is N.

In certain embodiments of Formula (IV), $L^1$ is CH.

In certain embodiments of Formula (IV), $L^3$ is CH.

In certain embodiments of Formula (IV), $L^4$ is CH.

In certain embodiments of Formula (IV), A is N.

In certain embodiments of Formula (IV), A is CH.

In certain embodiments of Formula (IV), $R_{26}$ is heterocyclyl.

In certain embodiments of Formula (IV), $R_{24}$ is —N($R_{13}$)($R_{14}$).

In certain embodiments of Formula (IV), $L_5$ and $L_6$ are each independently N. In certain embodiments of Formula (IV), s is 1.

In certain embodiments of Formula (IV), s is 0.

In certain embodiments, the fatty acid synthase inhibitor is a compound selected from Compounds 001-1, 001-3, 001-4, 001-14, 001-20, 001-27, 001-31, and 001-36 of Table C-1, or a pharmaceutically acceptable salt thereof.

In some embodiments, the fatty acid synthase inhibitor is a compound of Formula (V):

(V)

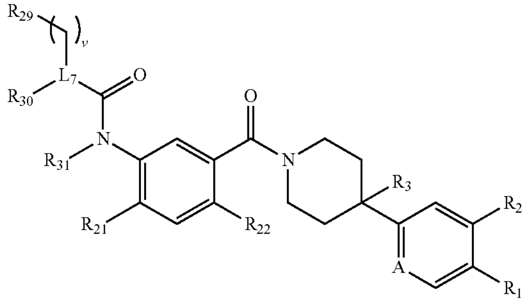

or a pharmaceutically acceptable salt thereof, wherein:

$L_7$ is N or O, wherein $R_{30}$ is absent if $L_7$ is O;

A is CH or N;

$R_1$ is hydrogen, cyano, halo, $C_{1-6}$ alkyl, $C_{1-6}$ alkoxy, —C(=O)N($R_{13}$)($R_{14}$), —$(CH_2)_q$C(=O)N($R_{13}$)($R_{14}$), $CF_3$, —$OCF_3$, or —S(=O)$_2R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —S(=O)$_2R_{20}$;

$R_{29}$ and $R_{30}$ are each independently hydrogen, $C_{1-6}$ alkyl, $C_{1-6}$ alkoxy, hydroxyalkyl, heteroaryl, heterocyclyl, —N($R_{15}R_{16}$), —C(=O)$R_{46}$, OR—$R_{48}$C(=O)$R_{47}$, or $R_{29}$ and $R_{30}$ taken together with the atoms to which they are attached join together to form a heteroaryl or heterocyclyl, wherein $R_{30}$ is absent if $L_7$ is O;

$R_{46}$ and $R_{47}$ are each independently hydrogen, $C_{1-6}$ alkyl, cycloalkyl, aryl, heterocyclyl, heteroaryl, hydroxyalkyl, —N($R_{15}R_{16}$), or —S(=O)$_2R_{20}$;

$R_{48}$ is alkyl or is absent;

$R_{31}$ is hydrogen, $C_{1-6}$ alkyl, or $C_{1-6}$ alkoxy;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino; and v is 0 or 1.

In certain embodiments, the fatty acid synthase inhibitors of Formula (V) have one of the following Formulas (V-A), (V-B), (V-C), and (V-D):

(V-A)

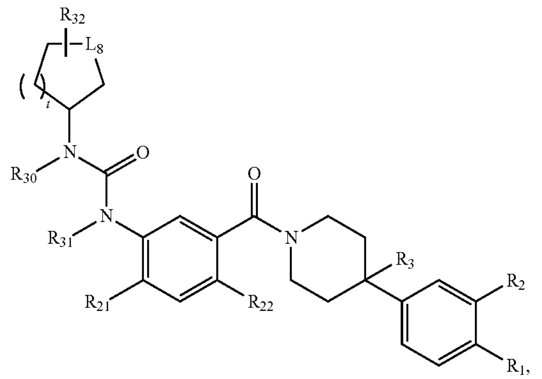

(V-B)

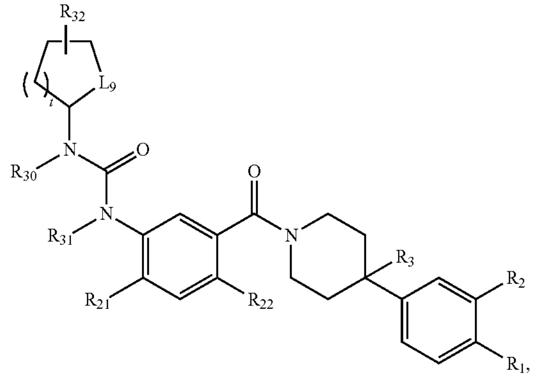

(V-C)

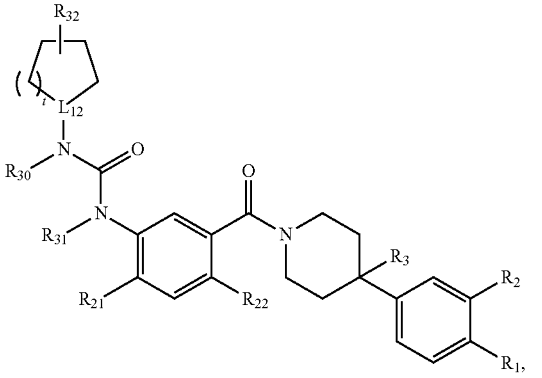

and

-continued (V-D)

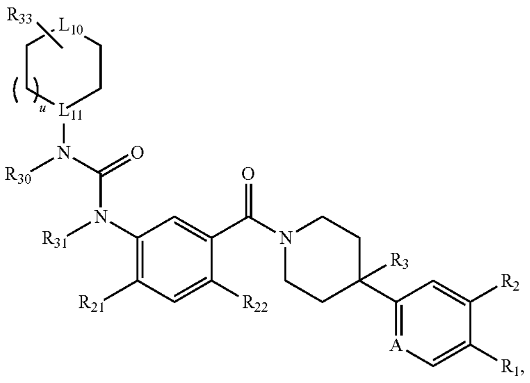

or a pharmaceutically acceptable salt thereof, wherein:

$R_1$ is hydrogen, cyano, halo, $C_{1-6}$ alkyl, $C_{1-6}$ alkoxy, $—C(=O)N(R_{13})(R_{14})$, $—(CH_2)_qC(=O)N(R_{13})(R_{14})$, $CF_3$, $—OCF_3$, or $—S(=O)_2R_{20}$;

q is 0, 1, 2, 3, or 4;

$R_{20}$ is hydrogen or $C_{1-6}$ alkyl, $C_{1-6}$ alkoxy, or $—N(R_{13})(R_{14})$;

$R_2$ is hydrogen, halo, $C_{1-6}$ alkoxy, or $C_{1-6}$ alkyl;

$R_3$ is halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, $—OCF_3$, or $—S(=O)_2R_{20}$;

$R_{30}$ is hydrogen, $C_{1-6}$ alkyl, $C_{1-6}$ alkoxy, hydroxyalkyl, heteroaryl, heterocyclyl, $—N(R_{15}R_{16})$, $—C(=O)R_{46}$, or $—R_{48}C(=O)R_{47}$, wherein $R_{30}$ is absent if $L_7$ is O;

$R_{46}$ and $R_{47}$ are each independently hydrogen, $C_{1-6}$ alkyl, cycloalkyl, aryl, heterocyclyl, heteroaryl, hydroxyalkyl, $—N(R_{15}R_{16})$, or $—S(=O)_2R_{20}$;

$R_{48}$ is alkyl or is absent;

$R_{31}$ is hydrogen, $C_{1-6}$ alkyl, or $C_{1-6}$ alkoxy;

$R_{13}$ and $R_{14}$ are each independently hydrogen, $C_{1-6}$ alkyl, cycloalkyl, aryl, heterocyclyl, heteroaryl, hydroxyalkyl, alkylamino, $—N(R_{15}R_{16})$, or $—S(=O)_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino;

$L_8$, $L_9$, and $L_{10}$ are each independently $CH_2$, NH, or O;

$L_{11}$ and $L_{12}$ are each independently CH or N;

$R_{32}$ and $R_{33}$ are each independently hydrogen, $C_{1-6}$ alkyl, $C_{1-6}$ alkoxy, $—S(=O)_2R_{20}$, $—C(=O)R_{46}$, hydroxyalkyl, hydroxyl, or are absent;

u is 0, 1, or 2; and t is 0, 1, or 2.

In certain embodiments of Formula (V), $L_7$ is N.

In certain embodiments of Formula (V), $L_7$ is O.

In certain embodiments of Formula (V), A is N.

In certain embodiments of Formula (V), A is CH.

In certain embodiments of Formula (V), $R_1$ is hydrogen, cyano, $C_{1-6}$ alkyl, $C_{1-6}$ alkoxy, or $—C(=O)N(R_{13})(R_{14})$.

In certain embodiments of Formula (V), $R_1$ is cyano.

In certain embodiments of Formula (V), $R_2$ is hydrogen or halo.

In certain embodiments of Formula (V), $R_2$ is hydrogen.

In certain embodiments of Formula (V), $R_3$ is fluorine.

In certain embodiments of Formula (V), $R_{21}$ and $R_{22}$ are each independently hydrogen or $C_{1-6}$ alkyl.

In certain embodiments of Formula (V), $R_{21}$ and $R_{22}$ are each independently $C_{1-6}$ alkyl.

In certain embodiments of Formula (V), $R_{31}$ is hydrogen.

In certain embodiments of Formula (V), $R_{30}$ is hydrogen.

In certain embodiments of Formula (V), $L_8$ is O.

In certain embodiments of Formula (V), $L_9$ is O.

In certain embodiments of Formula (V), $L_{10}$ is O and $L_{11}$ is N.

In certain embodiments of Formula (V), $L_{12}$ is N.

In certain embodiments of Formula (V), $R_{32}$ and $R_{33}$ are each independently hydrogen.

In certain embodiments, the fatty acid synthase inhibitor is a compound selected from Compounds 001-64, 001-65, 001-70, 001-78, 001-498, 001-336, and 001-338 of Table C-1, or a pharmaceutically acceptable salt thereof.

In some embodiments, the fatty acid synthase inhibitor is a compound of Formula (VI-A) or (VI-B):

(VI-A)

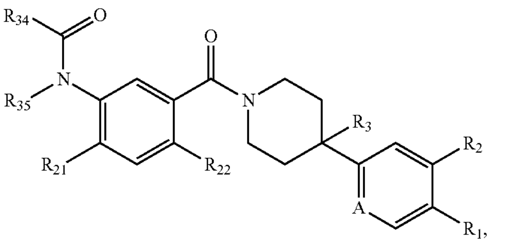

or (VI-B)

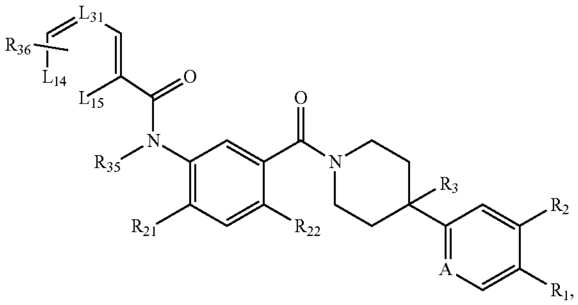

or a pharmaceutically acceptable salt thereof, wherein:

- $L_{13}$, $L_{14}$, $L_{15}$, and A are each independently CH or N;
- $R_1$ is hydrogen, cyano, halo, $C_{1-6}$ alkyl, $C_{1-6}$ alkoxy, —C(═O)N($R_{13}$)($R_{14}$), —$(CH_2)_q$C(═O)N($R_{13}$)($R_{14}$), $CF_3$, —$OCF_3$, or —S(═O)$_2$$R_{20}$;
- q is 0, 1, 2, 3, or 4;
- $R_{20}$ is hydrogen or $C_{1-6}$ alkyl, $C_{1-6}$ alkoxy, or —N($R_{13}$)($R_{14}$);
- $R_2$ is hydrogen, halo, $C_{1-6}$ alkoxy, or $C_{1-6}$ alkyl;
- $R_3$ is halo, $C_{1-6}$ alkyl, or $C_{1-6}$ alkoxy;
- $R_{21}$ and $R_{22}$ are each independently hydrogen, halo, cyano, $C_{1-6}$ alkyl, $C_{1-6}$ alkoxy, $CF_3$, —$OCF_3$, or —S(═O)$_2$$R_{20}$;
- $R_{34}$ is hydrogen, $C_{1-6}$ alkyl, $C_{1-6}$ alkoxy, cycloalkyl, hydroxyl, hydroxyalkyl, aryl, heterocyclyl, heteroaryl, alkylamino, $CF_3$, —$OCF_3$, —S(═O)$_2$$R_{20}$, or —N($R_{15}$$R_{16}$);
- $R_{35}$ is hydrogen, $C_{1-6}$ alkyl, or $C_{1-6}$ alkoxy;
- $R_{36}$ is hydrogen, $C_{1-6}$ alkyl, $C_{1-6}$ alkoxy, —N($R_{15}$$R_{16}$), heterocyclyl, or heteroaryl;
- $R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}$$R_{16}$), or —S(═O)$_2$$R_{20}$; and

- $R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In certain embodiments, the fatty acid synthase inhibitors of Formula (VI) have one of the following Formulas (VI-C) or (VI-D):

(VI-C)

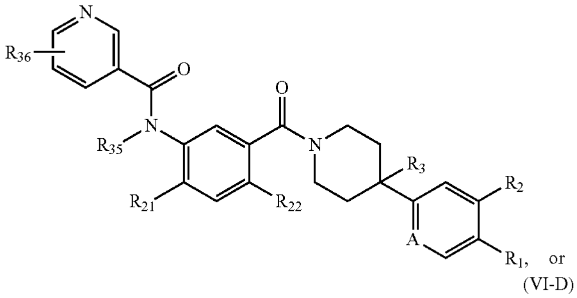

or (VI-D)

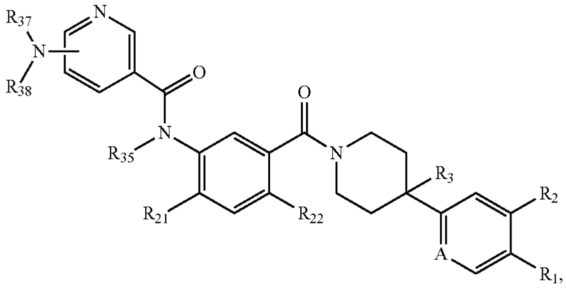

(VI-D), or a pharmaceutically acceptable salt thereof, wherein:

- $R_1$ is hydrogen, cyano, halo, $C_{1-6}$ alkyl, $C_{1-6}$ alkoxy, —C(═O)N($R_{13}$)($R_{14}$), —$(CH_2)_q$C(═O)N($R_{13}$)($R_{14}$), $CF_3$, —$OCF_3$, or —S(═O)$_2$$R_{20}$;
- q is 0, 1, 2, 3, or 4;
- $R_{20}$ is hydrogen or $C_{1-6}$ alkyl, $C_{1-6}$ alkoxy, or —N($R_{13}$)($R_{14}$);
- $R_2$ is hydrogen, halo, $C_{1-6}$ alkoxy, or $C_{1-6}$ alkyl;
- $R_3$ is halo, $C_{1-6}$ alkyl, or $C_{1-6}$ alkoxy;
- $R_{21}$ and $R_{22}$ are each independently hydrogen, halo, cyano, $C_{1-6}$ alkyl, $C_{1-6}$ alkoxy, $CF_3$, —$OCF_3$, or —S(═O)$_2$$R_{20}$;
- $R_{35}$ is hydrogen, $C_{1-6}$ alkyl, or $C_{1-6}$ alkoxy;
- $R_{36}$ is hydrogen, $C_{1-6}$ alkyl, $C_{1-6}$ alkoxy, —N($R_{15}$$R_{16}$), heterocyclyl, or heteroaryl;
- $R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}$$R_{16}$), or —S(═O)$_2$$R_{20}$;
- $R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino; and
- $R_{37}$ and $R_{38}$ are each independently hydrogen, $C_{1-6}$ alkyl, $C_{1-6}$ alkoxy, hydroxyalkyl, heteroaryl, heterocyclyl, or $R_{37}$ and $R_{38}$ taken together with the atoms to which they are attached join together to form a heteroaryl or heterocyclyl.

In certain embodiments of Formula (VI), $R_1$ is hydrogen, cyano, $C_{1-6}$ alkyl, $C_{1-6}$ alkoxy, or —C(═O)N($R_{13}$)($R_{14}$).

In certain embodiments of Formula (VI), $R_1$ is cyano.

In certain embodiments of Formula (VI), $R_2$ is hydrogen or halo.

In certain embodiments of Formula (VI), $R_2$ is hydrogen.

In certain embodiments of Formula (VI), $R_3$ is fluorine.

In certain embodiments of Formula (VI), $R_{21}$ and $R_{22}$ are each independently hydrogen or $C_{1-6}$ alkyl.

In certain embodiments of Formula (VI), $R_{21}$ and $R_{22}$ are each independently $C_{1-6}$ alkyl.

In certain embodiments of Formula (VI), $R_{35}$ is hydrogen.

In certain embodiments of Formula (VI), $R_{34}$ is heteroaryl;

In certain embodiments of Formula (VI), $R_{34}$ is thienyl, pyrryl, furyl, pyridyl, pyrimidyl, pyrazinyl, pyrazolyl, oxazolyl, isoxazolyl, imidazolyl, thiazolyl, pyranyl, tetrazolyl, pyrrolyl, pyrrolinyl, pyridazinyl, triazolyl, indolyl, isoindolyl, indolizinyl, benzimidazolyl, quinolyl, isoquinolyl, indazolyl, benzotriazolyl, tetrazolopyridazinyl, oxadiazolyl, benzoxazolyl, benzoxadiazolyl, thiadiazolyl, benzothiazolyl, or benzothiadiazolyl.

In certain embodiments of Formula (VI), $L_{13}$ is N.

In certain embodiments of Formula (VI), $L_{14}$ and Lis are each independently CH.

In certain embodiments of Formula (VI), A is N.

In certain embodiments of Formula (VI), A is CH.

In certain embodiments, the fatty acid synthase inhibitor is a compound selected from Compounds 001-42, 001-43, 001-48, 001-62, and 001-322 of Table C-1, or a pharmaceutically acceptable salt thereof.

In some embodiments, the fatty acid synthase inhibitor is a compound of Formula (VI-J):

(VI-J)

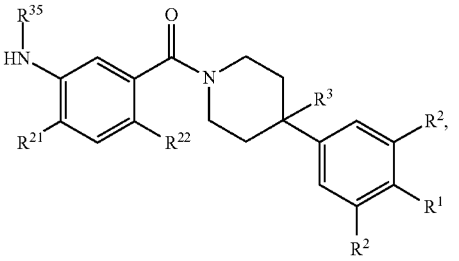

or a pharmaceutically acceptable salt thereof, wherein:

$R^1$ is H, —CN, halogen, $C_1$-$C_4$ straight or branched alkyl, —O—($C_3$-$C_5$ cycloalkyl), or —O—($C_1$-$C_4$ straight or branched alkyl) wherein:

the $C_3$-$C_5$ cycloalkyl optionally includes an oxygen or nitrogen heteroatom; and when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is cyclobutyl, azetidin-1-yl, or cyclopropyl;

$R^{22}$ is H, halogen, or $C_1$-$C_2$ alkyl;

$R^{35}$ is —C(O)—$R^{351}$, —C(O)—NH$R^{351}$, —C(O)—O—$R^{351}$ or S(O)$_2R^{351}$; and $R^{351}$ is $C_1$-$C_6$ straight or branched alkyl, cycloalkyl, heterocyclyl, aryl or heteroaryl.

In some embodiments of Formula (VI-J), $R^3$ is H or halogen.

In some embodiments of Formula (VI-J), $R^1$ is halogen, —CN or $C_1$-$C_2$ haloalkyl.

In some embodiments of Formula (VI-J), $R^{22}$ is $C_1$-$C_2$ alkyl.

In some embodiments of Formula (VI-J), $R^{21}$ is cyclobutyl and $R^{22}$ is $C_1$-$C_2$ alkyl.

In some embodiments of Formula (VI-J), $R^{21}$ is cyclobutyl.

In some embodiments of Formula (VI-J), $R^3$ is H or F.

In some embodiments of Formula (VI-J), $R^1$ is —CN.

In some embodiments of Formula (VI-J), $R^1$ is —$CF_3$.

In some embodiments of Formula (VI-J), $R^{22}$ is H, methyl or ethyl.

In some embodiments of Formula (VI-J), $R^{22}$ is H.

In some embodiments of Formula (VI-J), $R^{22}$ is methyl.

In some embodiments of Formula (VI-J), $R^{35}$ is —C(O)—NH$R^{351}$.

In some embodiments of Formula (VI-J), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl or(S)-tetrahydro-2H-pyran-3-yl.

In some embodiments of Formula (VI-J), $R^{351}$ is (R)-(tetrahydrofuran-2-yl)methyl or(S)-(tetrahydrofuran-2-yl) methyl.

In some embodiments of Formula (VI-J), $R^1$ is —CN, each $R^2$ is hydrogen, $R^3$ is H or F, $R^{21}$ is $C_3$-$C_4$ cycloalkyl, $R^{22}$ is H, $R^{35}$ is —C(O)—NH$R^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or(S)-tetrahydro-2H-pyran-3-yl.

In some embodiments of Formula (VI-J), $R^{35}$ is —C(O)—O—$R^{351}$.

In some embodiments of Formula (VI-J), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or(S)-tetrahydro-2H-pyran-3-yl.

In some embodiments of Formula (VI-J), $R^1$ is —CN, each $R^2$ is H, $R^3$ is H or F, $R^{21}$ is $C_3$-$C_4$ cycloalkyl, $R^{22}$ is H, $R^{35}$ is —C(O)—O—$R^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or(S)-tetrahydro-2H-pyran-3-yl.

In some embodiments of Formula (VI-J), $R^{351}$ is (R)-3-tetrahydrofuranyl or(S)-3-tetrahydrofuranyl.

In certain embodiments, the fatty acid synthase inhibitor is a compound selected from Compounds 001-443, 001-444, 001-490, 001-491, 001-492, and 001-493 of Table C-1, or a pharmaceutically acceptable salt thereof.

In some embodiments, the fatty acid synthase inhibitor is a compound of Formulas (VII-A) or (VII-B):

(VII-A)

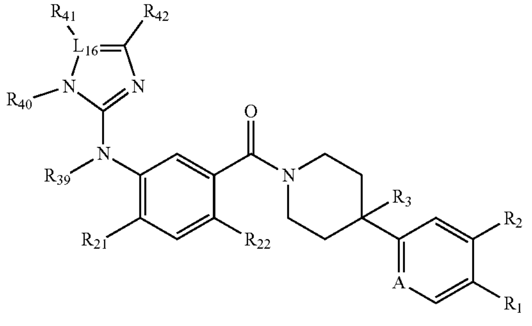

or

-continued (VII-B)

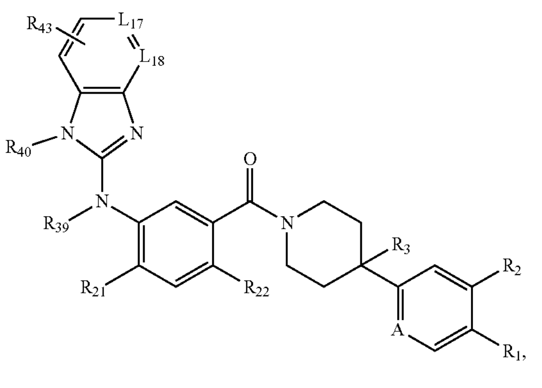

or a pharmaceutically acceptable salt thereof, wherein:

$L_{16}$ is C or N, wherein $R^{41}$ is absent if $L_{16}$ is N;

$L_{17}$, $L_{18}$, and A are each independently CH or N;

$R_1$ is hydrogen, cyano, halo, $C_{1-6}$ alkyl, $C_{1-6}$ alkoxy, $—C(=O)N(R_{13})(R_{14})$, $—(CH_2)_qC(=O)N(R_{13})(R_{14})$, $CF_3$, $—OCF_3$, or $—S(=O)_2R_{20}$;

q is 0, 1, 2, 3, or 4;

$R_{20}$ is hydrogen or $C_{1-6}$ alkyl, $C_{1-6}$ alkoxy, or $—N(R_{13})(R_{14})$;

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, $—OCF_3$, or $—S(=O)_2R_{20}$;

$R_{40}$, $R_{42}$, and $R_{43}$ are each independently hydrogen, $C_{1-6}$ alkyl, $C_{1-6}$ alkoxy, $—S(=O)_2R_{20}$, $—C(=O)R$, hydroxyalkyl, hydroxyl, or $—N(R_{13}R_{14})$, or $R_{41}$ and $R_{42}$ taken together with the atoms to which they are attached join together to form a heteroaryl or heterocyclyl;

$R_{41}$ is hydrogen, $C_{1-6}$ alkyl, $C_{1-6}$ alkoxy, $—S(=O)_2R_{20}$, $—C(=O)R$, hydroxyalkyl, hydroxyl, or $—N(R_{13}R_{14})$, or $R_{41}$ is absent if $L_{16}$ is N, or $R_{41}$ and $R_{42}$ taken together with the atoms to which they are attached join together to form a heteroaryl or heterocyclyl;

R is hydrogen, $C_{1-6}$ alkyl, cycloalkyl, aryl, heterocyclyl, heteroaryl, hydroxyalkyl, $—N(R_{15}R_{16})$, or $—S(=O)_2R_{20}$;

$R_{39}$ is hydrogen, $C_{1-6}$ alkyl, or $C_{1-6}$ alkoxy;

$R_{13}$ and $R_{14}$ are each independently hydrogen, $C_{1-6}$ alkyl, cycloalkyl, aryl, heterocyclyl, heteroaryl, hydroxyalkyl, alkylamino, $—N(R_{15}R_{16})$, or $—S(=O)_2R_{20}$; and $R_{15}$ and $R_{16}$ are each independently hydrogen, $C_{1-6}$ alkyl, cycloalkyl, aryl, heterocyclyl, heteroaryl, hydroxyalkyl, or alkylamino.

In certain embodiments of Formula (VII), $R_1$ is hydrogen, cyano, $C_{1-6}$ alkyl, $C_{1-6}$ alkoxy, or $—C(=O)N(R_{13})(R_{14})$.

In certain embodiments of Formula (VII), $R_1$ is cyano.

In certain embodiments of Formula (VII), $R_2$ is hydrogen or halo.

In certain embodiments of Formula (VII), $R_2$ is hydrogen.

In certain embodiments of Formula (VII), $R_3$ is hydrogen.

In certain embodiments of Formula (VII), $R_{21}$ and $R_{22}$ are each independently hydrogen or $C_{1-6}$ alkyl.

In certain embodiments of Formula (VII), $R_{21}$ and $R_{22}$ are each independently $C_{1-6}$ alkyl.

In certain embodiments of Formula (VII), $R_{39}$ is hydrogen.

In certain embodiments of Formula (VII), $R_{40}$ is hydrogen.

In certain embodiments of Formula (VII), $L_{16}$ is N.

In certain embodiments of Formula (VII), $L_{17}$ is N.

In certain embodiments of Formula (VII), $L_{18}$ is CH.

In certain embodiments of Formula (VII), $L_{18}$ is N.

In certain embodiments of Formula (VII), A is N.

In certain embodiments of Formula (VII), A is CH.

In certain embodiments of Formula (VII), $R_{42}$ is $C_{1-6}$ alkyl.

In certain embodiments of Formula (VII), $R_{41}$ is $C_{1-6}$ alkyl.

In certain embodiments, the fatty acid synthase inhibitor is Compound 001-161 or 001-499 of Table C-1, or a pharmaceutically acceptable salt thereof.

In some embodiments, the fatty acid synthase inhibitor is a compound of one of Formulae (VIII-A), (VIII-B), and (VIII-C):

(VIII-A)

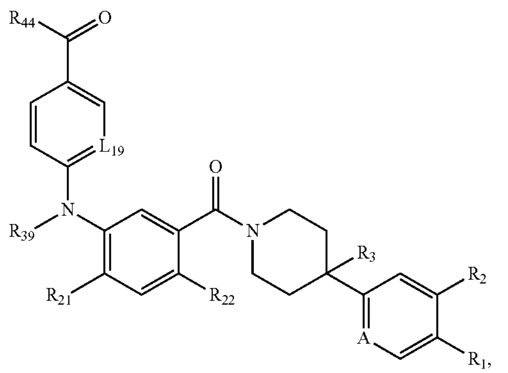

(VIII-B)

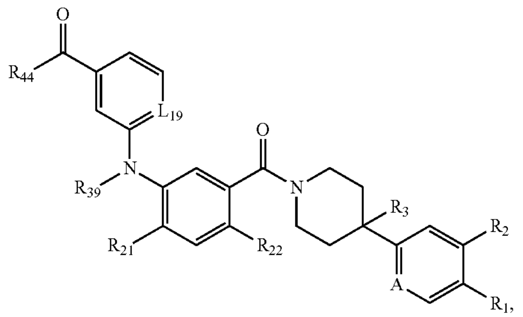

and (VIII-C)

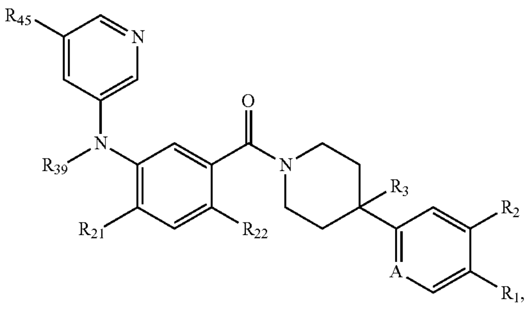

or a pharmaceutically acceptable salt thereof, wherein:

$L_{19}$ and A are each independently CH or N;

$R_1$ is hydrogen, cyano, halo, $C_{1-6}$ alkyl, $C_{1-6}$ alkoxy, $—C(=O)N(R_{13})(R_{14})$, $—(CH_2)_qC(=O)N(R_{13})(R_{14})$, $CF_3$, $—OCF_3$, or $—S(=O)_2R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —S(═O)$_2R_{20}$;

$R_{39}$ is hydrogen, $C_{1-6}$ alkyl, or $C_{1-6}$ alkoxy;

$R_{44}$ and $R_{45}$ are each independently hydrogen, $C_{1-6}$ alkyl, $C_{1-6}$ alkoxy, cycloalkyl, hydroxyalkyl, aryl, heterocyclyl, heteroaryl, alkylamino, —S(═O)$_2R_{20}$, —C(═O)R, or —N($R_{13}R_{14}$); and $R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(═O)$_2R_{20}$; and $R_{15}$ and $R_{16}$ are each independently hydrogen, $C_{1-6}$ alkyl, cycloalkyl, aryl, heterocyclyl, heteroaryl, hydroxyalkyl, or alkylamino.

In certain embodiments of Formula (VIII), $R_1$ is cyano.

In certain embodiments of Formula (VIII), $R_2$ is hydrogen or halo.

In certain embodiments of Formula (VIII), $R_2$ is hydrogen.

In certain embodiments of Formula (VIII), $R_3$ is hydrogen.

In certain embodiments of Formula (VIII), $R_{21}$ and $R_{22}$ are each independently hydrogen or $C_{1-6}$ alkyl.

In certain embodiments of Formula (VIII), $R_{21}$ and $R_{22}$ are each independently $C_{1-6}$ alkyl.

In certain embodiments of Formula (VIII), $R_{39}$ is hydrogen.

In certain embodiments of Formula (VIII), $L_{19}$ is N.

In certain embodiments of Formula (VIII), A is N.

In certain embodiments of Formula (VIII), A is CH.

In certain embodiments, the fatty acid synthase inhibitor is Compound 001-498 of Table C-1, or a pharmaceutically acceptable salt thereof.

In some embodiments, the fatty acid synthase inhibitor is a compound of Formula (IX):

(IX)

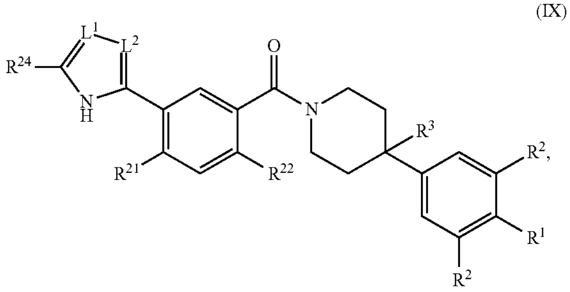

or a pharmaceutically acceptable salt thereof, wherein:

$R^1$ is H, —CN, halogen, $C_1$-$C_4$ straight or branched alkyl, —O—($C_3$-$C_5$ cycloalkyl), or —O—($C_1$-$C_4$ straight or branched alkyl) wherein:

$C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, or $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

$L^1$ is $CR^{23}$ or N;

$L^2$ is CH or N;

at least one of $L^1$ or $L^2$ is N; and $R^{23}$ is H or $C_1$-$C_4$ straight or branched alkyl.

In some embodiments of Formula (IX), $R^{24}$ is $C_1$-$C_4$ straight or branched alkyl or —($C_1$-$C_4$ alkyl)$_t$-O—($C_1$-$C_4$ straight or branched alkyl) wherein t is 0 or 1.

In some embodiments of Formula (IX), $R^{21}$ is halogen, $C_1$-$C_4$ straight or branched alkyl, $C_3$-$C_5$ cycloalkyl wherein the $C_3$-$C_5$ cycloalkyl optionally includes an oxygen or nitrogen heteroatom, or —S(O)$_u$—($C_1$-$C_4$ straight or branched alkyl) wherein u is 0 or 2, or —S(O)$_u$—($C_3$-$C_5$ cycloalkyl) wherein u is 0 or 2;

In some embodiments of Formula (IX), $R^3$ is H or halogen.

In some embodiments of Formula (IX), $R^1$ is halogen, —CN or $C_1$-$C_2$ haloalkyl.

In some embodiments of Formula (IX), both $L_1$ and $L_2$ are N.

In some embodiments of Formula (IX), $R^{21}$ is $C_1$-$C_2$ alkyl or $C_3$-$C_5$ cycloalkyl and $R^{22}$ is $C_1$-$C_2$ alkyl.

In some embodiments of Formula (IX), $R^{21}$ is $C_3$-$C_5$ cycloalkyl and $R^{22}$ is $C_1$-$C_2$ alkyl.

In some embodiments of Formula (IX), $R^{24}$ is —($C_1$-$C_2$ alkyl)$_t$-O—($C_1$-$C_2$ alkyl) wherein t is 0 or 1.

In some embodiments of Formula (IX), $R^{21}$ is $C_3$-$C_5$ cycloalkyl, $R^{22}$ is $C_1$-$C_2$ alkyl and $R^{24}$ is $C_1$-$C_2$ alkyl.

In some embodiments of Formula (IX), $R^{21}$ is cyclobutyl, $R^{22}$ is $C_1$-$C_2$ alkyl and $R^{24}$ is $C_1$-$C_2$ alkyl.

In some embodiments of Formula (IX), $R^{21}$ is cyclobutyl.

In some embodiments of Formula (IX), $R^3$ is H or F.

In some embodiments of Formula (IX), $R^1$ is —CN.

In some embodiments of Formula (IX), $R^1$ is —$CF_3$.

In some embodiments of Formula (IX), $R^{22}$ is H, methyl or ethyl.

In some embodiments of Formula (IX), $R^{22}$ is H.

In some embodiments of Formula (IX), $R^{22}$ is methyl.

In some embodiments of Formula (IX), $R^1$ is —CN, each $R^2$ is H, $R^3$ is H or F, $R^{21}$ is $C_3$-$C_4$ cycloalkyl, $R^{22}$ is methyl, $L^1$ and $L^2$ are N, and $R^{24}$ is methyl, ethyl, hydroxymethyl, methoxymethyl, 2-methoxyethyl.

In some embodiments of Formula (IX), $R^1$ is —CN, each $R^2$ is H, $R^3$ is H or F, $R^{21}$ is $C_3$-$C_4$ cycloalkyl, $R^{22}$ is methyl, $L^1$ and $L^2$ are N, and $R^{24}$ is methoxy or ethoxy.

In some embodiments of Formula (IX), $R^1$ is —CN, each $R^2$ is H, $R^3$ is H or F, $R^{21}$ is $C_3$-$C_4$ cycloalkyl, $R^{22}$ is methyl, $L^1$ is CH, $L^2$ is N, and $R^{24}$ is methyl, ethyl, hydroxymethyl, methoxymethyl, or 2-methoxyethyl.

In some embodiments of Formula (IX), $R^1$ is —CN, each $R^2$ is H, $R^3$ is H or F, $R^{21}$ is $C_3$-$C_4$ cycloalkyl, $R^{22}$ is methyl, $L^1$ is N, $L^2$ is CH, and $R^{24}$ is methyl, ethyl, hydroxymethyl, methoxymethyl, or 2-methoxyethyl.

In certain embodiments, the fatty acid synthase inhibitor is a compound selected from Compounds 001-152, 001-154, 001-156, and 001-246 of Table C-1, or a pharmaceutically acceptable salt thereof.

In some embodiments, the fatty acid synthase inhibitor is a compound of Formula (IX-1):

(IX-1)

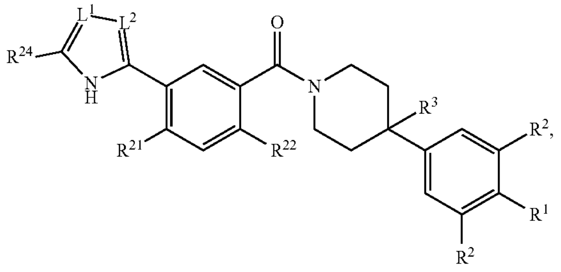

or a pharmaceutically acceptable salt thereof, wherein:

$R^1$ is H, —CN, halogen, $C_1$-$C_4$ straight or branched alkyl, —O—($C_3$-$C_5$ cycloalkyl), —O-(4- to 6-membered heterocycle), or —O—($C_1$-$C_4$ straight or branched alkyl), wherein when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl), —OH, —($C_1$-$C_4$ alkyl)$_t$-O$_t$—($C_3$-$C_5$ cycloalkyl), or —($C_1$-$C_4$ alkyl), —O—($C_1$-$C_4$ straight or branched alkyl) wherein:

t is 0 or 1;

the $C_3$-$C_5$ cycloalkyl optionally includes an oxygen or nitrogen heteroatom;

$L^1$ is N; and $L^2$ is N.

In some embodiments of Formula (IX-1), $R^1$ is H, —CN, halogen, or $C_1$-$C_4$ straight or branched alkyl; each $R^2$ is independently H; $R^3$ is H or halogen; $R^{21}$ is $C_1$-$C_4$ straight or branched alkyl or $C_3$-$C_5$ cycloalkyl; $R^{22}$ is H or $C_1$-$C_2$ alkyl; and $R^{24}$ is H or $C_1$-$C_4$ straight or branched alkyl.

In some embodiments of Formula (IX-1), $R^1$ is —CN; each $R^2$ is independently H; $R^3$ is H; $R^{21}$ is $C_3$-$C_5$ cycloalkyl; $R^{22}$ is H or $C_1$-$C_2$ alkyl; and $R^{24}$ is $C_1$-$C_4$ straight or branched alkyl.

In some embodiments, the fatty acid synthase inhibitor of Formula (IX-1) has the following structure:

(Compound 001-152)

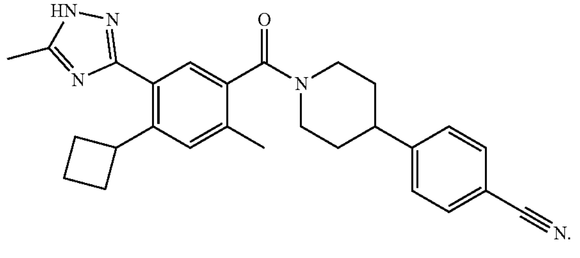

In some embodiments, the fatty acid synthase inhibitor is a compound of Formula (X):

(X)

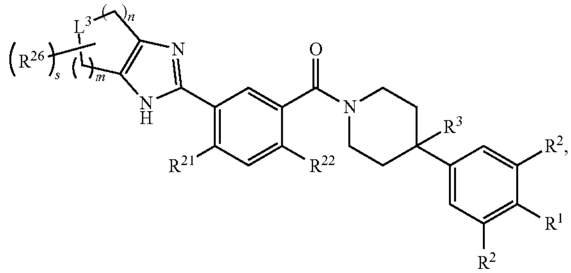

or a pharmaceutically acceptable salt thereof, wherein:

$R^1$ is H, —CN, halogen, $C_1$-$C_4$ straight or branched alkyl, —O—($C_3$-$C_5$ cycloalkyl), or —O—($C_1$-$C_4$ straight or branched alkyl) wherein:

the $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH or halogen;

$L^3$ is $C(R^{60})_2$, O or $NR^{50}$;

each $R^{60}$ is independently H, —OH, —CN, —O$_t$—($C_3$-$C_5$ cycloalkyl), —O—($C_1$-$C_4$ straight or branched alkyl), or —C(O)—N$(R^{601})_2$ wherein:

t is 0 or 1, and the $C_3$-$C_5$ cycloalkyl optionally includes an oxygen or nitrogen heteroatom;

each $R^{50}$ is independently H, —C(O)—O$_t$—($C_1$-$C_4$ straight or branched alkyl), —C(O)—O$_t$—($C_3$-$C_5$ cyclic alkyl), —$C_3$-$C_5$ cyclic alkyl optionally containing an oxygen or nitrogen heteroatom, —C(O)—N$(R^{501})_2$, or $C_1$-$C_4$ straight or branched alkyl wherein:

t is 0 or 1, and the $C_3$-$C_5$ cycloalkyl optionally includes an oxygen or nitrogen heteroatom;

n is 1, 2 or 3;

m is 1 or 2;

$R^{21}$ is H, halogen, $C_1$-$C_4$ straight or branched alkyl, or $C_3$-$C_5$ cycloalkyl wherein the $C_3$-$C_5$ cycloalkyl optionally includes an oxygen or nitrogen heteroatom $R^{22}$ is H, halogen, or $C_1$-$C_2$ alkyl;

each $R^{26}$ is independently —OH, —CN, halogen, $C_1$-$C_4$ straight or branched alkyl, —($C_1$-$C_4$ alkyl)$_t$-O$_t$—($C_3$-$C_5$ cycloalkyl), —($C_1$-$C_4$ alkyl)$_t$-O—($C_1$-$C_4$ straight or branched alkyl), —C(O)—O$_t$—($C_1$-$C_4$ alkyl), or —C(O)—N$(R^{501})_2$ wherein:

t is 0 or 1, and the $C_3$-$C_5$ cycloalkyl optionally includes an oxygen or nitrogen heteroatom;

s is 0, 1 or 2; and each $R^{601}$ and $R^{501}$ is independently H or $C_1$-$C_4$ straight or branched alkyl; and wherein two of $R^{26}$, $R^{60}$, $R^{50}$, $R^{501}$ and $R^{601}$ optionally join to form a ring wherein the two of $R^{26}$, $R^{60}$, $R^{50}$, $R^{501}$ and $R^{601}$ may be two $R^{26}$, two $R^{60}$, two $R^{50}$, two $R^{501}$ or two $R^{601}$.

In some embodiments of Formula (X), $R^{21}$ is halogen, $C_1$-$C_4$ straight or branched alkyl or $C_3$-$C_5$ cycloalkyl.

In some embodiments of Formula (X), $R^3$ is H or halogen.

In some embodiments of Formula (X), $R^1$ is —CN or $C_1$-$C_2$ haloalkyl.

In some embodiments of Formula (X), $R^3$ is H or F.

In some embodiments of Formula (X), $R^1$ is —CN.

In some embodiments of Formula (X), $R^1$ is $—CF_3$.

In some embodiments of Formula (X), n is 1.

In some embodiments of Formula (X), n is 2.

In some embodiments of Formula (X), m is 1

In some embodiments of Formula (X), m is 2.

In some embodiments of Formula (X), $R^{21}$ is $C_1$-$C_2$ alkyl or $C_3$-$C_5$ cycloalkyl and $R^{22}$ is $C_1$-$C_2$ alkyl.

In some embodiments of Formula (X), $R^{21}$ is $C_3$-$C_5$ cycloalkyl and $R^{22}$ is $C_1$-$C_2$ alkyl.

In some embodiments of Formula (X), n is 2, m is 1, $L^3$ is —N—C(O)—O—($C_1$-$C_2$ alkyl).

In some embodiments of Formula (X), $L^3$ is $NR^{50}$; $R^{50}$ is $C_1$-$C_2$ alkyl; $R^{21}$ is cyclobutyl; $R^{22}$ is H or methyl; $R^3$ is H; $R^1$ is —CN; m is 2 and n is 1 or 2.

In some embodiments of Formula (X), n is 2, m is 1, $L^3$ is O and s is 0.

In some embodiments of Formula (X), $R^{22}$ is H, methyl or ethyl.

In some embodiments of Formula (X), $R^{22}$ is methyl.

In some embodiments of Formula (X), $R^{22}$ is H.

In some embodiments of Formula (X), $R^1$ is —CN, each $R^2$ is H, $R^3$ is H or F, $R^{21}$ is $C_3$-$C_4$ cycloalkyl, $R^{22}$ is methyl, n is 2 and $L^3$ is $NR^{50}$ where $R^{50}$ is methyl or ethyl.

In some embodiments of Formula (X), $R^1$ is —CN, each $R^2$ is H, $R^3$ is H or F, $R^{21}$ is $C_3$-$C_4$ cycloalkyl, $R^{22}$ is methyl, n is 2 and $L^3$ is O.

In certain embodiments, the fatty acid synthase inhibitor is a compound selected from Compounds 001-406, 001-440, and 001-439 of Table C-1, or a pharmaceutically acceptable salt thereof.

In some embodiments, the fatty acid synthase inhibitor is a compound of Formula (XI):

(XI)

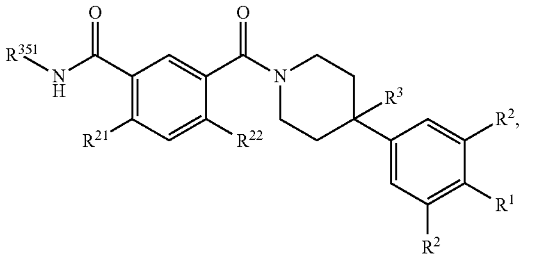

or a pharmaceutically acceptable salt thereof, wherein:

$R^1$ is H, —CN, halogen, $C_1$-$C_4$ straight or branched alkyl, —O—($C_3$-$C_5$ cycloalkyl), or —O—($C_1$-$C_4$ straight or branched alkyl) wherein:

the $C_3$-$C_5$ cycloalkyl optionally includes an oxygen or nitrogen heteroatom; and when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is cyclobutyl, azetidin-1-yl, or cyclopropyl;

$R^{22}$ is H, halogen, $C_1$-$C_2$ alkyl; and $R^{351}$ is $C_1$-$C_2$ alkyl or $C_2$—O—($C_1$ or $C_2$ alkyl).

In some embodiments of Formula (XI), $R^3$ is H or halogen.

In some embodiments of Formula (XI), $R^1$ is halogen, —CN or $C_1$-$C_2$ haloalkyl.

In some embodiments of Formula (XI), $R^{21}$ is $C_3$-$C_4$ cycloalkyl and $R^{22}$ is $C_1$-$C_2$ alkyl.

In some embodiments of Formula (XI), $R^{21}$ is cyclobutyl and $R^{22}$ is $C_1$-$C_2$ alkyl.

In some embodiments of Formula (XI), $R^{21}$ is cyclobutyl.

In some embodiments of Formula (XI), $R^3$ is H or F.

In some embodiments of Formula (XI), $R^1$ is —CN.

In some embodiments of Formula (XI), $R^1$ is $—CF_3$.

In some embodiments of Formula (XI), $R^{22}$ is H, methyl or ethyl.

In some embodiments of Formula (XI), $R^{22}$ is H.

In some embodiments of Formula (XI), $R^{22}$ is methyl.

In some embodiments of Formula (XI), $R^1$ is —CN, each $R^2$ is H, $R^3$ is H or F, $R^{21}$ is cyclobutyl, $R^{22}$ is methyl and $R^{351}$ is methyl or ethyl.

In certain embodiments, the fatty acid synthase inhibitor is Compound 001-254 or 001-256 of Table C-1, or a pharmaceutically acceptable salt thereof.

In some embodiments, the fatty acid synthase inhibitor is a compound of Formula (XII):

(XII)

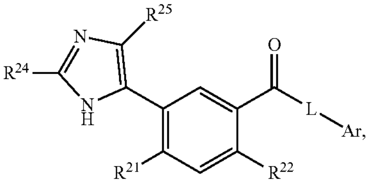

or pharmaceutically acceptable salts thereof, wherein:

L-Ar is

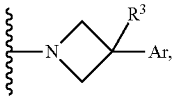

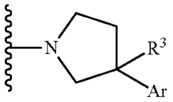

or

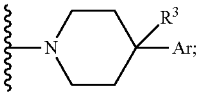

Ar is

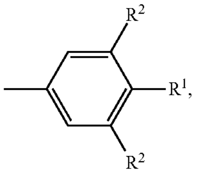

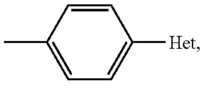

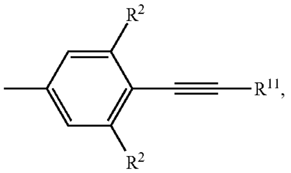

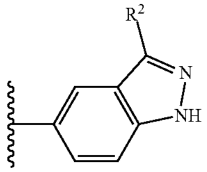

or

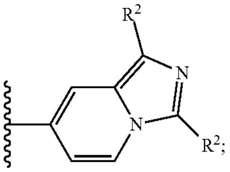

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl;

$R^{24}$ is H, —CN, —($C_1$-$C_4$ alkyl)-CN, $C_1$-$C_4$ alkyl, $C_1$-$C_4$ haloalkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_6$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl), wherein:

t is 0 or 1;

u is 0 or 1;

with the proviso that when u is 1, t is 1; and each $R^{241}$ is independently H or $C_1$-$C_2$ alkyl; and $R^{25}$ is halogen, —CN, —($C_1$-$C_4$ alkyl)-CN, $C_1$-$C_2$ alkyl, $C_1$-$C_4$ haloalkyl, —($C_1$-$C_4$ alkyl)-O—($C_1$-$C_4$ alkyl), or cyclopropyl.

In some embodiments of Formula (XII), L-Ar is

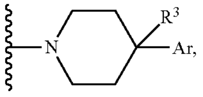

Ar is not

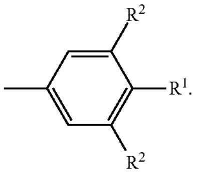

In some embodiments of Formula (XII), L-Ar is

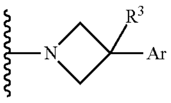

or

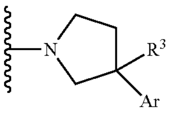

and Ar is

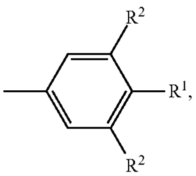

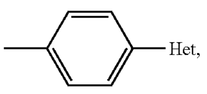

-continued

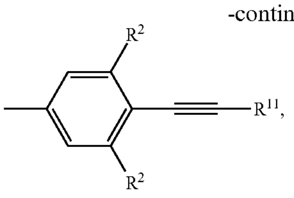

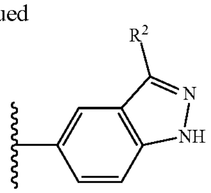

or

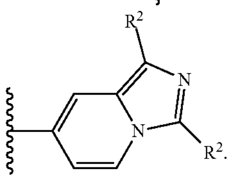

In some embodiments of Formula (XII), L-Ar is

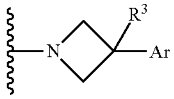

and Ar is

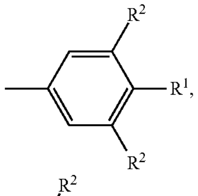

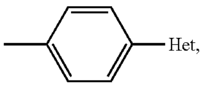

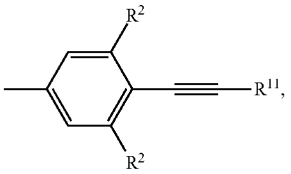

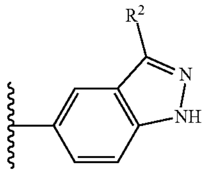

or

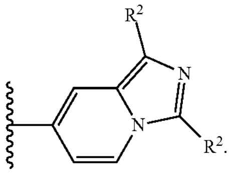

In some embodiments of Formula (XII), Ar is

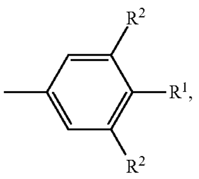

In some embodiments of Formula (XII), $R^1$ is halogen, —CN or $C_1$-$C_2$ haloalkyl.

In some embodiments of Formula (XII), $R^1$ is —CN.

In some embodiments of Formula (XII), $R^2$ is H.

In some embodiments of Formula (XII), $R^{21}$ is halogen, $C_1$-$C_4$ alkyl or $C_3$-$C_5$ cycloalkyl.

In some embodiments of Formula (XII), $R^{21}$ is $C_1$-$C_4$ alkyl or $C_3$-$C_5$ cycloalkyl.

In some embodiments of Formula (XII), $R^{21}$ is $C_1$-$C_2$ alkyl or $C_3$-$C_5$ cycloalkyl.

In some embodiments of Formula (XII), $R^{21}$ is $C_1$-$C_2$ alkyl.

In some embodiments of Formula (XII), $R^{21}$ is $—CH_3$.

In some embodiments of Formula (XII), $R^{22}$ is H or $C_1$-$C_2$ alkyl.

In some embodiments of Formula (XII), $R^{22}$ is H or $—CH_3$.

In some embodiments of Formula (XII), $R^{22}$ is $—CH_3$.

In some embodiments of Formula (XII), $R^{24}$ is H, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_6$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl).

In some embodiments of Formula (XII), $R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_6$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl).

In some embodiments of Formula (XII), $R^{24}$ is $C_1$-$C_4$ alkyl or —($C_1$-$C_4$ alkyl)-O—($C_1$-$C_4$ alkyl).

In some embodiments, the fatty acid synthase inhibitor is a compound of Formula (XII) wherein $R^{24}$ is —($C_1$-$C_2$ alkyl)-O—($C_1$-$C_2$ alkyl).

In some embodiments of Formula (XII), $R^{24}$ is $—CH_2—O—CH_3$.

In some embodiments of Formula (XII), $R^{24}$ is $C_1$-$C_2$ alkyl.

In some embodiments of Formula (XII), $R^{24}$ is $—CH_3$.

In some embodiments of Formula (XII), $R^{24}$ is $C_3$-$C_6$ cycloalkyl.

In some embodiments of Formula (XII), $R^{24}$ is —CN or —($C_1$-$C_2$ alkyl)-CN.

In some embodiments of Formula (XII), $R^{24}$ is —CN.

In some embodiments of Formula (XII), $R^{24}$ is —($C_1$-$C_2$ alkyl)-CN.

In some embodiments of Formula (XII), $R^{24}$ is H, $—CH_3$, $—CH_2OH$, $—CH_2OCH_3$, $—(CH_2)_2OH$, $—(CH_2)_2OCH_3$ or $—(CH_2)_2N(CH_3)_2$.

In some embodiments of Formula (XII), $R^{24}$ is methyl, isopropyl, cyclopropyl, —CN, or —($C_1$-$C_2$ alkyl)-CN.

In some embodiments of Formula (XII), $R^{24}$ is substituted with one or more substituents selected from $C_1$-$C_2$ alkyl, oxo, —CN, halogen, alkanoyl, alkoxycarbonyl, —OH and $C_1$-$C_2$ alkoxy.

In some embodiments of Formula (XII), $R^{24}$ is substituted with one or more substituents selected from methyl, —F, methoxy, —C(═O)$CH_3$ and —C(═O)—$OCH_3$.

In some embodiments of Formula (XII), $R^{24}$ is substituted with two substituents that are the same or different.

In some embodiments of Formula (XII), $R^{24}$ is substituted with three substituents that are the same or different.

In some embodiments of Formula (XII), $R^{25}$ is halogen, —CN, $C_1$-$C_2$ alkyl or cyclopropyl.

In some embodiments of Formula (XII), $R^{25}$ is halogen, $C_1$-$C_2$ alkyl or cyclopropyl.

In some embodiments of Formula (XII), $R^{25}$ is —CN, —$C_1$ or $—CH_3$.

In some embodiments of Formula (XII), $R^{25}$ is —$C_1$.

In some embodiments of Formula (XII), $R^{25}$ is $—CH_3$.

In some embodiments of Formula (XII), $R^{25}$ is substituted with one or more substituents selected from —OH, halogen, $C_1$-$C_2$ alkyl and alkylcarbonyloxy.

In some embodiments of Formula (XII), $R^{25}$ is substituted with one or more substituents selected from —F, methyl and —O—C(═O)—$CH_3$.

In some embodiments of Formula (XII), $R^{25}$ is substituted with two substituents that are the same or different.

In some embodiments of Formula (XII), $R^{25}$ is substituted with three substituents that are the same or different.

In some embodiments, the fatty acid synthase inhibitor is a compound of Formula (XII-1):

(XII-1)

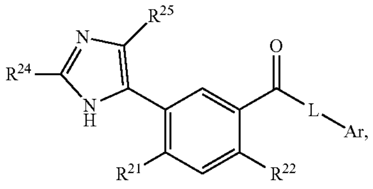

or pharmaceutically acceptable salts thereof, wherein:
L-Ar is

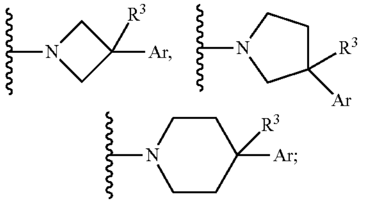

Ar is

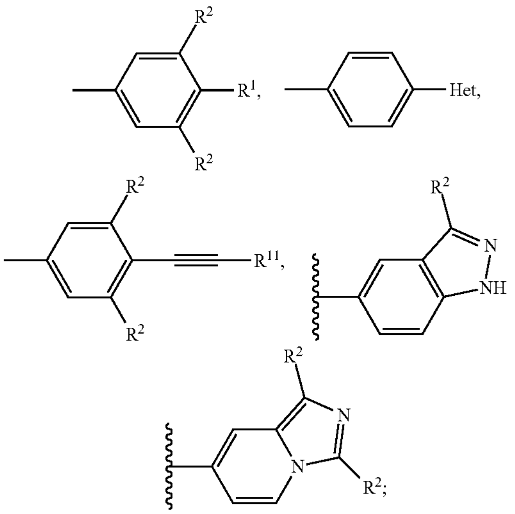

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently H, halogen or $C_1$-$C_4$ alkyl;

$R^3$ is H or F;

$R^{11}$ is H or $—CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl;

$R^{24}$ is H, —CN, —($C_1$-$C_4$ alkyl)-CN, $C_1$-$C_4$ alkyl, $C_1$-$C_4$ haloalkyl, —($C_1$-$C_4$ alkyl)-OH, —($C_1$-$C_4$ alkyl)-N $(R^{241})_2$, —$(C_1$-$C_4$ alkyl$)_t$-$O_u$—$(C_3$-$C_6$ cycloalkyl), —$(C_1$-$C_4$ alkyl$)_t$-$O_u$-(4- to 6-membered heterocycle) or —$(C_1$-$C_4$ alkyl)-O—$(C_1$-$C_4$ alkyl), wherein:

t is 0 or 1;

u is 0 or 1;

each $R^{241}$ is independently H or $C_1$-$C_2$ alkyl; and $R^{25}$ is halogen, —CN, —$(C_1$-$C_4$ alkyl)-CN, $C_1$-$C_2$ alkyl, $C_1$-$C_4$ haloalkyl, —$(C_1$-$C_4$ alkyl)-O—$(C_1$-$C_4$ alkyl), or cyclopropyl.

In some embodiments of Formula (XII-1), L-Ar is

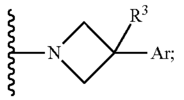

Ar is

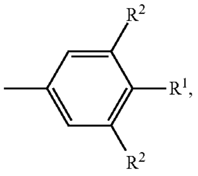

$R^1$ is H, —CN, halogen, or $C_1$-$C_4$ alkyl; each $R^2$ is independently H; $R^3$ is H or F; $R^{21}$ is H, halogen, or $C_1$-$C_4$ alkyl; $R^{22}$ is H, halogen, or $C_1$-$C_2$ alkyl; $R^{24}$ is $C_1$-$C_4$ alkyl, $C_1$-$C_4$ haloalkyl, —$(C_1$-$C_4$ alkyl$)_t$-$O_u$-(4- to 6-membered heterocycle), or —$(C_1$-$C_4$ alkyl)-O—$(C_1$-$C_4$ alkyl); $R^{25}$ is $C_1$-$C_2$ alkyl, $C_1$-$C_4$ haloalkyl, or —$(C_1$-$C_4$ alkyl)-O—$(C_1$-$C_4$ alkyl).

In some embodiments of Formula (XII-1), L-Ar is

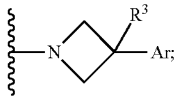

Ar is

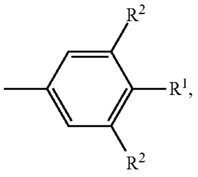

$R^1$ is —CN; each $R^2$ is independently H; $R^3$ is H; $R^{21}$ is $C_1$-$C_4$ alkyl; $R^{22}$ is H or $C_1$-$C_2$ alkyl; $R^{24}$ is $C_1$-$C_4$ haloalkyl, or —$(C_1$-$C_4$ alkyl$)_t$-$O_u$-(4- to 6-membered heterocycle), and $R^{25}$ is —$(C_1$-$C_4$ alkyl)-O—$(C_1$-$C_4$ alkyl).

In some embodiments, the compound of Formula (XII-1) has the following structure:

(Compound 002-386)

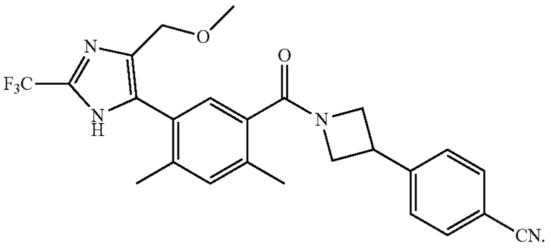

In some embodiments, the fatty acid synthase inhibitor is a compound of Formula (XIII):

(XIII)

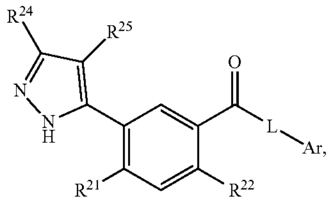

or pharmaceutically acceptable salts thereof, wherein: L-Ar is

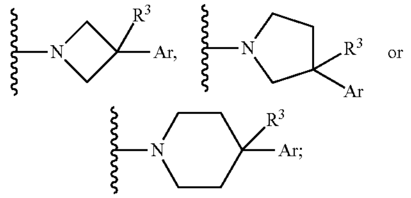

Ar is

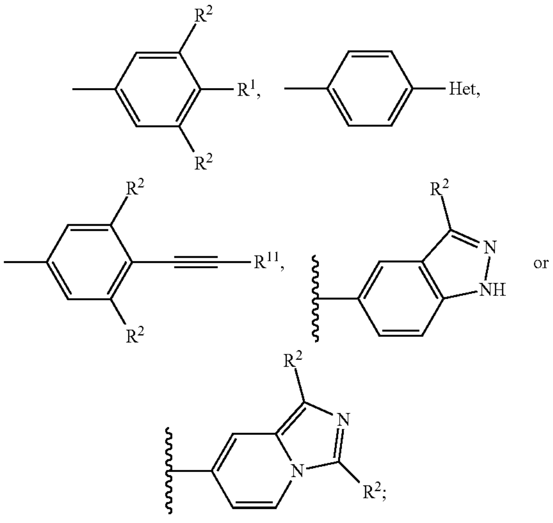

Het is a 5- to 6-membered heteroaryl;

$R^1$ is H, —CN, halogen, $C_1$-$C_4$ alkyl, —O—$(C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and each $R^{24}$ and $R^{25}$ is independently H, halogen, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_5$ cycloalkyl), —($C_1$-$C_4$ alkyl)$_t$-O$_u$-(4- to 6-membered heterocycle) or —($C_1$-$C_4$ alkyl)$_t$-O—($C_1$-$C_4$ alkyl), wherein:

each t is independently 0 or 1;

each u is independently 0 or 1; and each $R^{241}$ is independently H or $C_1$-$C_2$ alkyl.

In some embodiments of Formula (XIII), when L-Ar is

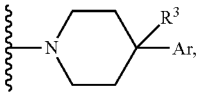

Ar is not

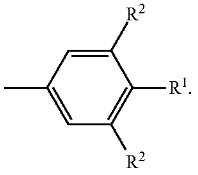

In some embodiments of Formula (XIII), L-Ar is

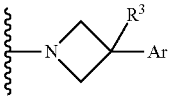
or
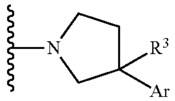

and Ar is

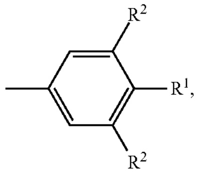
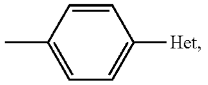
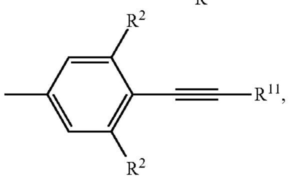
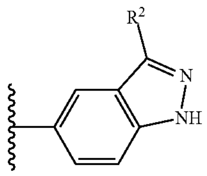
or

-continued

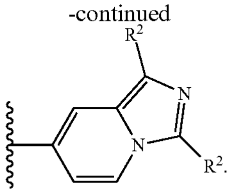

In some embodiments of Formula (XIII), L-Ar is

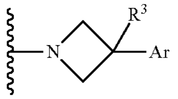

and Ar is

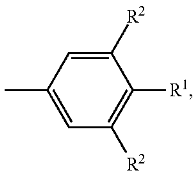
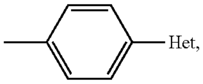
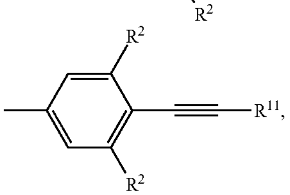
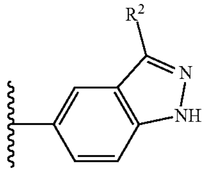
or
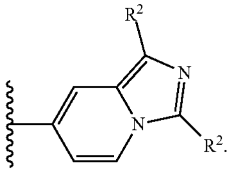

In some embodiments of Formula (XIII), Ar is

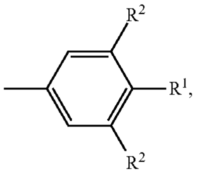

In some embodiments of Formula (XIII), $R^1$ is halogen, —CN or $C_1$-$C_2$ haloalkyl.

In some embodiments of Formula (XIII), $R^1$ is —CN.

In some embodiments of Formula (XIII), $R^2$ is H.

In some embodiments of Formula (XIII), $R^{21}$ is halogen, $C_1$-$C_4$ alkyl, $C_3$-$C_5$ cycloalkyl or 4- to 6-membered heterocycle.

In some embodiments of Formula (XIII), $R^{21}$ is $C_1$-$C_4$ alkyl, $C_3$-$C_5$ cycloalkyl or 4- to 6-membered heterocycle.

In some embodiments of Formula (XIII), $R^{21}$ is $C_1$-$C_2$ alkyl or $C_3$-$C_5$ cycloalkyl.

In some embodiments of Formula (XIII), $R^{21}$ is $C_1$-$C_2$ alkyl.

In some embodiments of Formula (XIII), $R^{21}$ is —$CH_3$.

In some embodiments of Formula (XIII), $R^{22}$ is H or $C_1$-$C_2$ alkyl.

In some embodiments of Formula (XIII), $R^{22}$ is H or $-CH_3$.

In some embodiments of Formula (XIII), $R^{22}$ is $-CH_3$.

In some embodiments of Formula (XIII), each $R^{24}$ and $R^{25}$ is independently H, —CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_5$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl).

In some embodiments of Formula (XIII), each $R^{24}$ and $R^{25}$ is independently H, $C_1$-$C_4$ alkyl, —($C_1$-$C_4$ alkyl)$_t$-$O_u$-(4- to 6-membered heterocycle) or —($C_1$-$C_4$ alkyl)-O—($C_1$-$C_4$ alkyl).

In some embodiments of Formula (XIII), $R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_5$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl).

In some embodiments of Formula (XIII), $R^{24}$ is —CN, —$C_1$, $C_1$-$C_4$ alkyl or —($C_1$-$C_4$ alkyl)-O—($C_1$-$C_4$ alkyl).

In some embodiments of Formula (XIII), $R^{24}$ is $C_1$-$C_4$ alkyl or —($C_1$-$C_4$ alkyl)-O—($C_1$-$C_4$ alkyl).

In some embodiments of Formula (XIII), $R^{24}$ is —($C_1$-$C_2$ alkyl)-O—($C_1$-$C_2$ alkyl).

In some embodiments of Formula (XIII), $R^{24}$ is $C_1$-$C_4$ alkyl.

In some embodiments of Formula (XIII), $R^{24}$ is $-CH_3$.

In some embodiments of Formula (XIII), $R^{24}$ is hydrogen.

In some embodiments of Formula (XIII), $R^{24}$ is substituted with one or more substituents selected from halogen, $C_3$-$C_5$ cycloalkyl and $C_1$-$C_2$ alkoxy.

In some embodiments of Formula (XIII), $R^{24}$ is substituted with one or more substituents selected from —F, cyclopropyl and $-OCH_3$.

In some embodiments of t Formula (XIII), $R^{24}$ is substituted with two substituents that are the same or different.

In some embodiments of Formula (XIII), $R^{24}$ is substituted with three substituents that are the same or different.

In some embodiments of Formula (XIII), $R^{25}$ is halogen, methyl, ethyl or cyclopropyl.

In some embodiments of Formula (XIII), $R^{25}$ is —CN, —$C_1$, $C_1$-$C_4$ alkyl, —($C_1$-$C_4$ alkyl)$_t$-O—($C_3$-$C_5$ cycloalkyl) or —($C_1$-$C_4$ alkyl)$_t$-O—($C_1$-$C_4$ alkyl).

In some embodiments of Formula (XIII), $R^{25}$ is —CN, —$C_1$, $-CH_3$, —O—($C_3$-$C_5$ cycloalkyl) or —O—($C_1$-$C_2$ alkyl).

In some embodiments of Formula (XIII), $R^{25}$ is —CN, —$C_1$ or $C_1$-$C_4$ alkyl.

In some embodiments of Formula (XIII), $R^{25}$ is $-CH_3$.

In some embodiments of Formula (XIII), $R^{25}$ is —$C_1$.

In some embodiments of Formula (XIII), $R^{25}$ is substituted with one or more halogen.

In some embodiments of Formula (XIII), $R^{25}$ is substituted with one or more —F.

In some embodiments of Formula (XIII), $R^{25}$ is substituted by two substituents.

In some embodiments of Formula (XIII), $R^{25}$ is substituted by three substituents.

In some embodiments, the fatty acid synthase inhibitor is a compound of Formula (XIII-1):

(XIII-1)

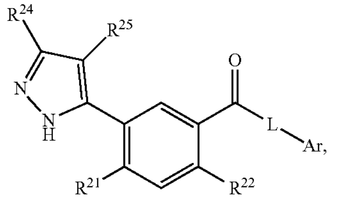

or pharmaceutically acceptable salts thereof, wherein:

L-Ar is

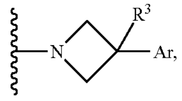

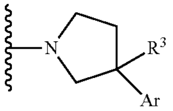

or

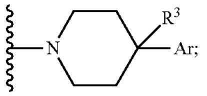

Ar is

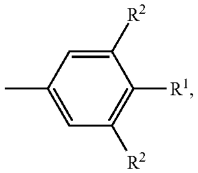

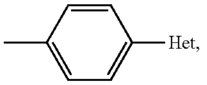

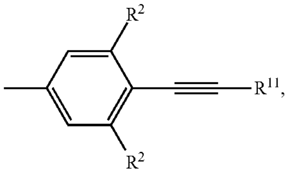

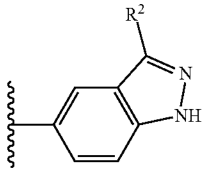

or

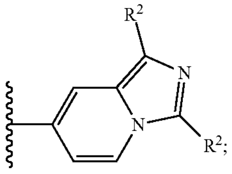

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or $-CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and each $R^{24}$ and $R^{25}$ is independently H, halogen, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_5$ cycloalkyl), —($C_1$-$C_4$ alkyl)$_t$-$O_u$-(4- to 6-membered heterocycle) or —($C_1$-$C_4$ alkyl)$_t$-O—($C_1$-$C_4$ alkyl), wherein:

each t is independently 0 or 1;

each u is independently 0 or 1; and each $R^{241}$ is independently H or $C_1$-$C_2$ alkyl.

In some embodiments of Formula (XIII-1), L-Ar is

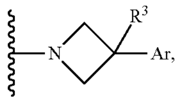

Ar is

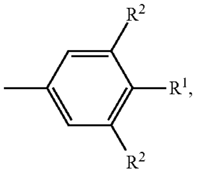

$R^1$ is H, —CN, halogen, or $C_1$-$C_4$ alkyl; each $R^2$ is independently H; $R^3$ is H or F; $R^{21}$ is H, halogen, or $C_1$-$C_4$ alkyl; $R^{22}$ is H, halogen, or $C_1$-$C_2$ alkyl; and each $R^{24}$ and $R^{25}$ is independently halogen, $C_1$-$C_4$ alkyl, or —($C_1$-$C_4$ alkyl)-O—($C_1$-$C_4$ alkyl).

In some embodiments of Formula (XIII-1), L-Ar is

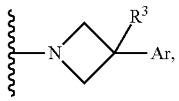

Ar is

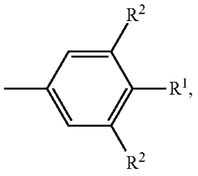

$R^1$ is —CN; each $R^2$ is independently H; $R^3$ is H; $R^{21}$ is $C_1$-$C_4$ alkyl; $R^{22}$ is H or $C_1$-$C_2$ alkyl; and each $R^{24}$ and $R^{25}$ is independently halogen, $C_1$-$C_4$ alkyl, or —($C_1$-$C_4$ alkyl)$_t$-O—($C_1$-$C_4$ alkyl).

In some embodiments, the fatty acid synthase inhibitor of Formula (XIII-1) has the following structure:

(Compound 002-242)

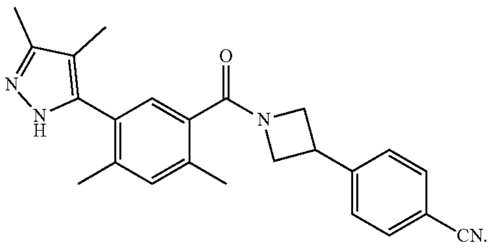

In some embodiments, the fatty acid synthase inhibitor is a compound of Formula (XIV):

(XIV)

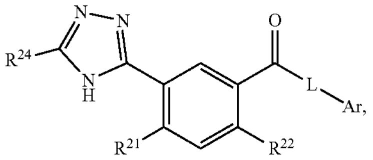

or pharmaceutically acceptable salts thereof, wherein:

L-Ar is

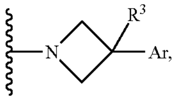

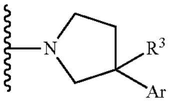

or

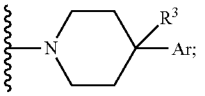

Ar is

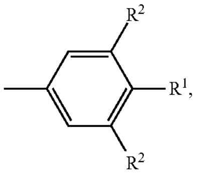

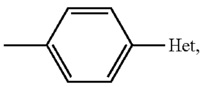

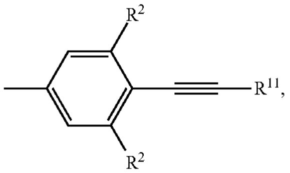

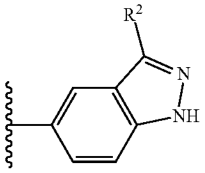

or

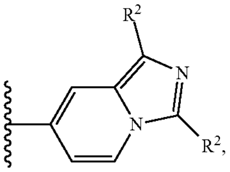

with the proviso that when L-Ar is

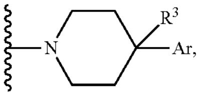

Ar is not

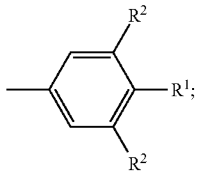

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl; and $R^{24}$ is H, $C_1$-$C_4$ alkyl, $C_1$-$C_4$ haloalkyl, —($C_1$-$C_4$ alkyl)-OH, —($C_1$-$C_4$ alkyl)-N($R^{241}$)$_2$, —($C_1$-$C_4$ alkyl)$_t$-O$_t$—($C_3$-$C_5$ cycloalkyl), —($C_1$-$C_4$ alkyl)$_t$-O$_t$-(4- to 6-membered heterocycle) or —($C_1$-$C_4$ alkyl)$_t$-O—($C_1$-$C_4$ alkyl), wherein:

each t is independently 0 or 1; and each $R^{241}$ is independently H or $C_1$-$C_2$ alkyl.

In some embodiments of Formula (XIV), L-Ar is

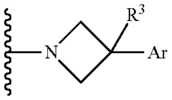 or 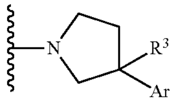

and Ar is

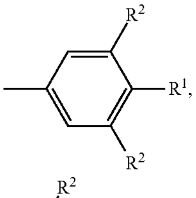 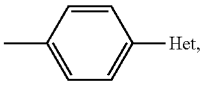

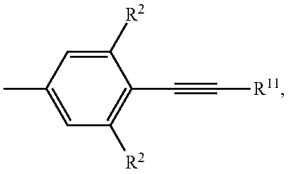 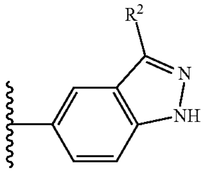 or

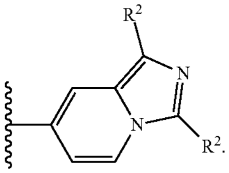

In some embodiments of Formula (XIV), L-Ar is

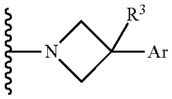

and Ar is

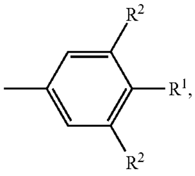 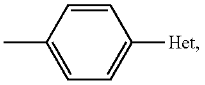

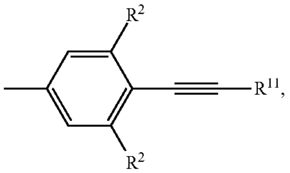 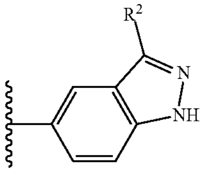 or

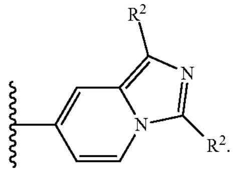

In some embodiments of Formula (XIV), Ar is

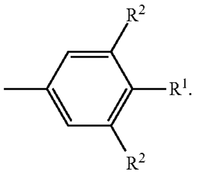

In some embodiments of Formula (XIV), $R^1$ is halogen, —CN or $C_1$-$C_2$ haloalkyl.

In some embodiments of Formula (XIV), $R^1$ is —CN.

In some embodiments of Formula (XIV), $R^2$ is H.

In some embodiments of Formula (XIV), $R^{21}$ is halogen, $C_1$-$C_4$ alkyl, $C_3$-$C_5$ cycloalkyl or 4- to 6-membered heterocycle.

In some embodiments of Formula (XIV), $R^{21}$ is H, $C_1$-$C_4$ alkyl, $C_3$-$C_5$ cycloalkyl or 4- to 6-membered heterocycle.

In some embodiments of Formula (XIV), $R^{21}$ is $C_1$-$C_2$ alkyl or $C_3$-$C_5$ cycloalkyl.

In some embodiments of Formula (XIV), $R^{21}$ is $C_1$-$C_2$ alkyl.

In some embodiments of Formula (XIV), $R^{21}$ is $C_3$-$C_5$ cycloalkyl.

In some embodiments of Formula (XIV), $R^{22}$ is H or $C_1$-$C_2$ alkyl.

In some embodiments of Formula (XIV), $R^{22}$ is H.

In some embodiments of Formula (XIV), $R^{22}$ is $C_1$-$C_2$ alkyl.

In some embodiments of Formula (XIV), $R^{22}$ is —$CH_3$.

In some embodiments of Formula (XIV), $R^{24}$ is $C_1$-$C_4$ alkyl or —($C_1$-$C_4$ alkyl)$_t$-O—($C_1$-$C_4$ alkyl).

In some embodiments of Formula (XIV), $R^{24}$ is —($C_1$-$C_2$ alkyl)$_t$-O—($C_1$-$C_2$ alkyl).

In some embodiments, the fatty acid synthase inhibitor is a compound of Formula (XV):

(XV)

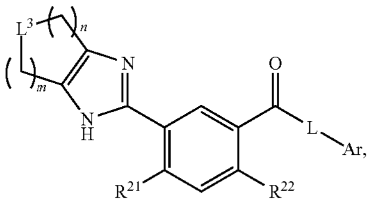

or pharmaceutically acceptable salts thereof, wherein:

$L^3$ is —$CH_2$—, —$CHR^{50}$—, —O—, —$NR^{50}$, —NC(O)$R^{50}$— or —NC(O)O$R^{50}$—, wherein $R^{50}$ is $C_1$-$C_6$ alkyl, $C_3$-$C_5$ cycloalkyl, or 4- to 6-membered heterocycle;

n is 1, 2, or 3;

m is 1 or 2 with the proviso that n+m≥3;

L-Ar is

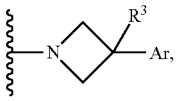 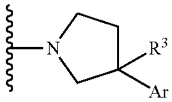 or

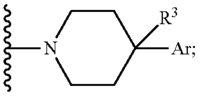

Ar is

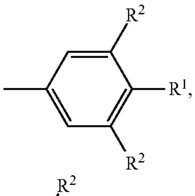 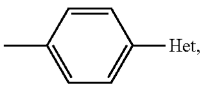

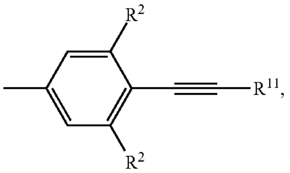 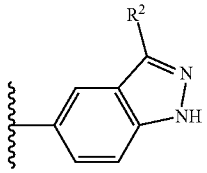 or

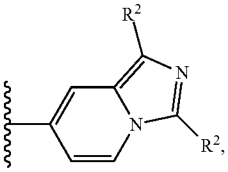

with the proviso that when L-Ar is

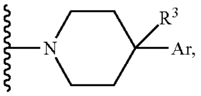

Ar is not

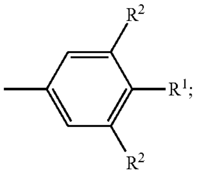

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle), or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl, or a 4- to 6-membered heterocycle; and $R^{22}$ is H, halogen, or $C_1$-$C_2$ alkyl.

In some embodiments of Formula (XV), L-Ar is

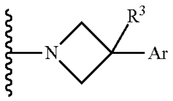 or 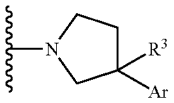

and Ar is

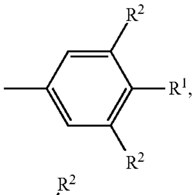 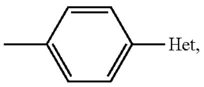

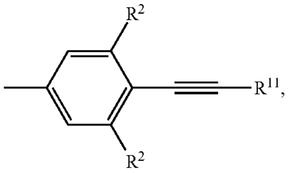 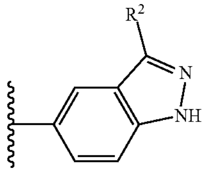 or

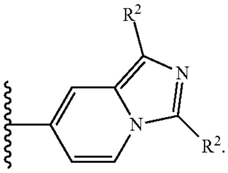

In some embodiments of Formula (XV), L-Ar is

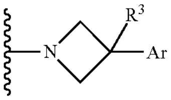

and Ar is

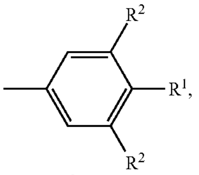
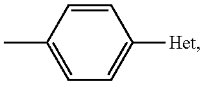
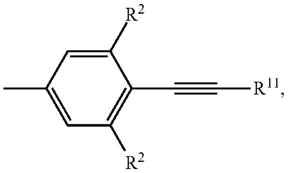
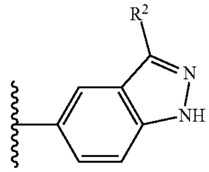
or
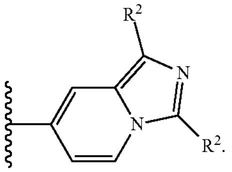

In some embodiments of Formula (XV), $R^1$ is H, —CN, —$C_1$-$C_4$ alkyl, —O—($C_3$-$C_5$ cycloalkyl), —O-(4- to 6-membered heterocycle) or —O—($C_1$-$C_4$ alkyl) wherein when $R^1$ is not H or —CN, $R^1$ is optionally substituted with one or more halogens.

In some embodiments of Formula (XV), $R^1$ is halogen, —CN or $C_1$-$C_2$ haloalkyl.

In some embodiments of Formula (XV), $R^1$ is —CN or $C_1$-$C_2$ haloalkyl.

In some embodiments of Formula (XV), $R^1$ is —CN.

In some embodiments of Formula (XV), $R^1$ is —$C_1$.

In some embodiments of Formula (XV), $R^2$ is H.

In some embodiments of Formula (XV), $R^{21}$ is halogen, $C_1$-$C_4$ alkyl, $C_3$-$C_5$ cycloalkyl or 4- to 6-membered heterocycle.

In some embodiments of Formula (XV), $R^{21}$ is $C_1$-$C_2$ alkyl or $C_3$-$C_5$ cycloalkyl.

In some embodiments of Formula (XV), $R^{21}$ is $C_3$-$C_5$ cycloalkyl.

In some embodiments of Formula (XV), $R^{22}$ is H or $C_1$-$C_2$ alkyl.

In some embodiments of Formula (XV), $R^{22}$ is H.

In some embodiments of Formula (XV), $R^{22}$ is $C_1$-$C_2$ alkyl.

In some embodiments of Formula (XV), $R^{22}$ is —$CH_3$.

In some embodiments of Formula (XV), $L^3$ is —$N(CH_3)$—.

In some embodiments of Formula (XV), n is 2 and m is 2.

In some embodiments of Formula (XV), n is 1 or 2.

In some embodiments of Formula (XV), n is 1 and m is 2.

In some embodiments, the fatty acid synthase inhibitor is a compound of Formula (XVI):

(XVI)

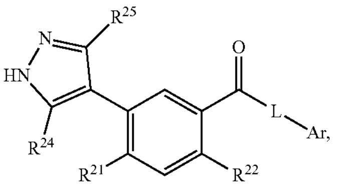

or pharmaceutically acceptable salts thereof, wherein:

L-Ar is

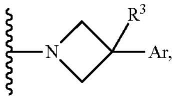
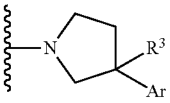
or
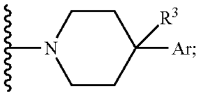

Ar is

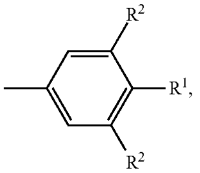
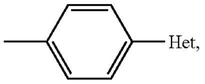
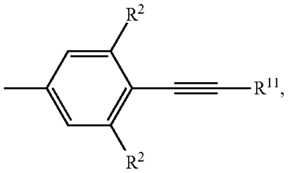
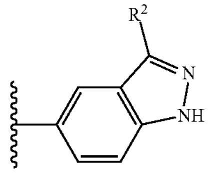
or
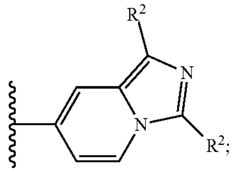

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and each of $R^{24}$ and $R^{25}$ is independently H, —$C_1$-$C_4$ alkyl, or halogen.

In some embodiments of Formula (XVI), L-Ar is

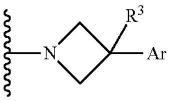
or
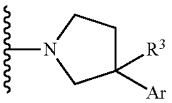

and Ar is

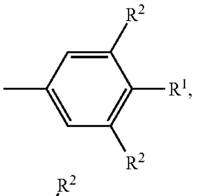
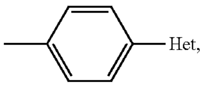
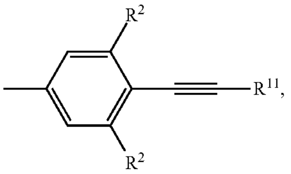
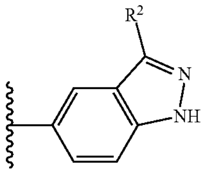
or
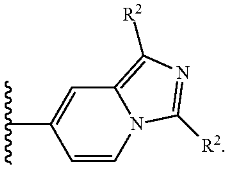

In some embodiments of Formula (XVI), L-Ar is

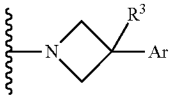

and Ar is

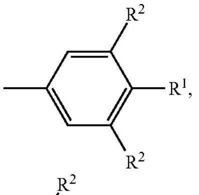
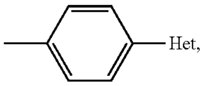
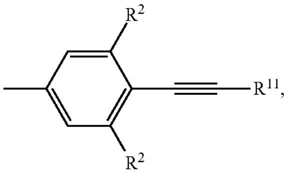
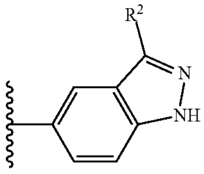
or
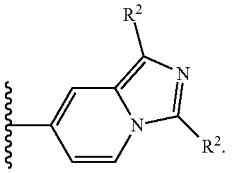

In some embodiments of Formula (XVI), $R^1$ is halogen, —CN or $C_1$-$C_2$ haloalkyl.

In some embodiments of Formula (XVI), $R^{21}$ is halogen, $C_1$-$C_4$ alkyl, $C_3$-$C_5$ cycloalkyl or 4- to 6-membered heterocycle.

In some embodiments of Formula (XVI), $R^{21}$ is —$CH_3$.

In some embodiments of Formula (XVI), $R^{22}$ is H.

In some embodiments, the fatty acid synthase inhibitor is a compound of Formula (XVII):

(XVII)

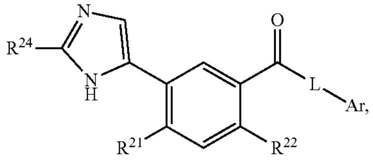

or pharmaceutically acceptable salts thereof, wherein:

L-Ar is

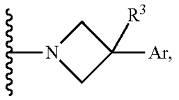
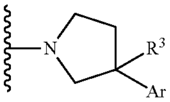
or
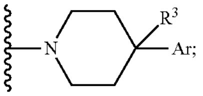

Ar is

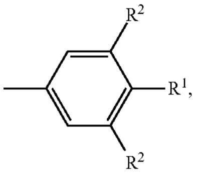
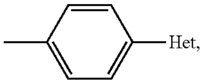
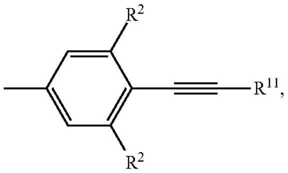
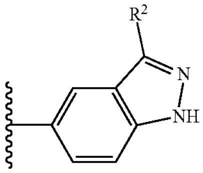
or
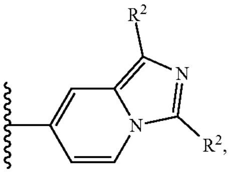

with the proviso that when L-Ar is

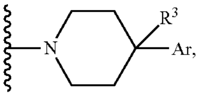

Ar is not

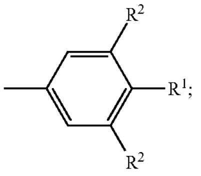

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle), or —O—($C_1$-$C_4$ alkyl), wherein when $R^1$ is not H, —CN or halogen, $R^1$ is optionally substituted with one or more halogens;

each $R^2$ is independently hydrogen, halogen, or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl, or 4- to 6-membered heterocycle;

$R^{22}$ is H, halogen, or $C_1$-$C_2$ alkyl; and $R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_5$ cycloalkyl), —($C_1$-$C_4$ alkyl)$_t$-O$_u$-(4- to 6-membered heterocycle), or —($C_1$-$C_4$ alkyl)-O—($C_1$-$C_4$ alkyl), wherein:

t is 0 or 1;

u is 0 or 1;

with the proviso that when u is 1, t is 1; and $R^{241}$ is H or $C_1$-$C_2$ alkyl.

In some embodiments of Formula (XVII), L-Ar is

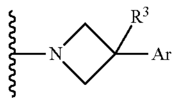
or
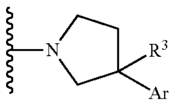

and Ar is

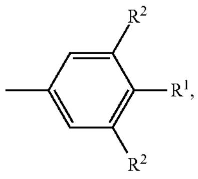
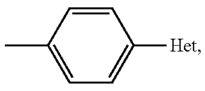
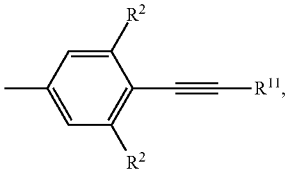
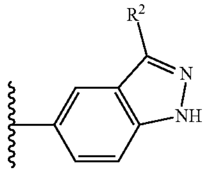
or
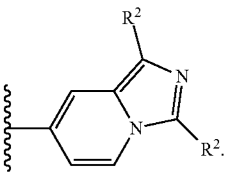

In some embodiments of Formula (XVII), $R^1$ is halogen, —CN or $C_1$-$C_2$ haloalkyl.

In some embodiments of Formula (XVII), $R^1$ is —CN.

In some embodiments of Formula (XVII), $R^2$ is H.

In some embodiments of Formula (XVII), $R^{21}$ is halogen, $C_1$-$C_4$ alkyl, $C_3$-$C_5$ cycloalkyl or 4- to 6-membered heterocycle.

In some embodiments of Formula (XVII), $R^{21}$ is $C_1$-$C_2$ alkyl or $C_3$-$C_5$ cycloalkyl.

In some embodiments of Formula (XVII), $R^{21}$ is $C_1$-$C_2$ alkyl.

In some embodiments of Formula (XVII), $R^{21}$ is $C_3$-$C_5$ cycloalkyl.

In some embodiments of Formula (XVII), $R^{22}$ is H or $C_1$-$C_2$ alkyl.

In some embodiments of Formula (XVII), $R^{22}$ is H.

In some embodiments of Formula (XVII), $R^{22}$ is $C_1$-$C_2$ alkyl.

In some embodiments of Formula (XVII), $R^{22}$ is —$CH_3$.

In some embodiments of Formula (XVII), $R^{24}$ is $C_1$-$C_4$ alkyl or —($C_1$-$C_4$ alkyl)-O—($C_1$-$C_4$ alkyl).

In some embodiments of Formula (XVII), $R^{24}$ is —($C_1$-$C_2$ alkyl)-O—($C_1$-$C_2$ alkyl).

In some embodiments, the fatty acid synthase inhibitor is a compound of Formula (XVIII):

(XVIII)

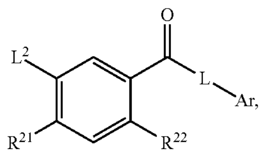

or pharmaceutically acceptable salts thereof, wherein:

L-Ar is

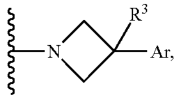
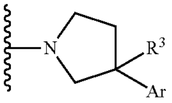
or
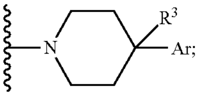

Ar is

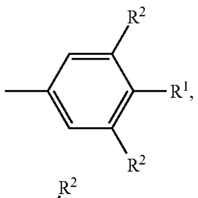
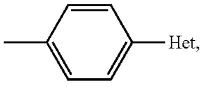
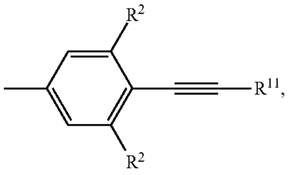
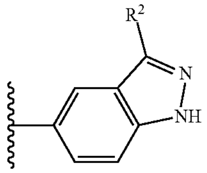
or
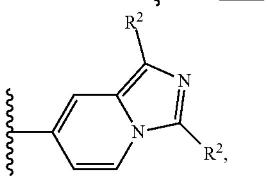

with the proviso that when L-Ar is

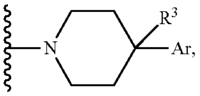

Ar is not

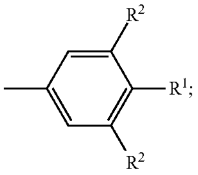

$L^2$ is —NHR$^{35}$ or —C(O)NHR$^{351}$, wherein $R^{351}$ is $C_1$-$C_6$ alkyl, $C_3$-$C_5$ cycloalkyl, 4- to 6-membered heterocycle, aryl, or heteroaryl;

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle), or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl; and $R^{35}$ is —C(O)$R^{351}$, —C(O)NHR$^{351}$, C(O)OR$^{351}$ or S(O)$_2R^{351}$, wherein $R^{351}$ is $C_1$-$C_6$ alkyl, $C_3$-$C_5$ cycloalkyl, 4- to 6-membered heterocycle, aryl, or heteroaryl.

In some embodiments, the fatty acid synthase inhibitor is a compound of Formula (XVIII) wherein L-Ar is

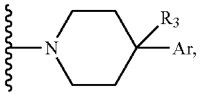

Ar is not

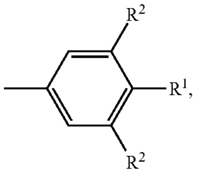

In some embodiments, the fatty acid synthase inhibitor is a compound of Formula (XVIII) wherein $L^2$ is —NHR$^{35}$.

In some embodiments, the fatty acid synthase inhibitor is a compound of Formula (XVIII) wherein $L^2$ is —C(O)NHR$^{351}$.

In some embodiments, the fatty acid synthase inhibitor is a compound of Formula (XIX):

(XIX)

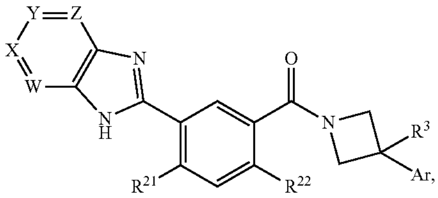

or pharmaceutically acceptable salts thereof, wherein:

each W, X, Y and Z is independently —N— or —CR$^{26}$— with the proviso that not more than 2 of W, X, Y and Z are —N—;

each $R^{26}$ is independently H, $C_1$-$C_4$ alkyl, —O—($C_1$-$C_4$ alkyl), —N($R^{27}$)$_2$, —S(O)$_2$—($C_1$-$C_4$ alkyl), or —C(O)—($C_1$-$C_4$ alkyl);

each $R^{27}$ is independently H or $C_1$-$C_4$ alkyl or both $R^{27}$ are $C_1$-$C_4$ alkyl and join to form a 3- to 6-membered ring together with the N to which they are attached and wherein the ring optionally includes one oxygen atom as one of the members of the ring;

Ar is

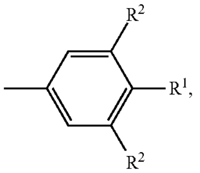 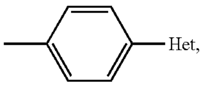

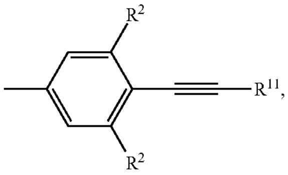 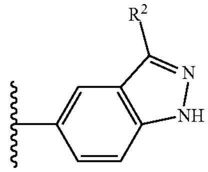 or

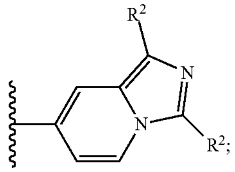

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle), or —O—($C_1$-$C_4$ alkyl) wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl, or a 4- to 6-membered heterocycle; and $R^{22}$ is H, halogen or $C_1$-$C_2$ alkyl.

In some embodiments of Formula (XIX), Ar is

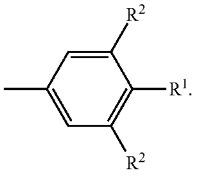

In some embodiments of Formula (XIX), Y is —CR$^{26}$— wherein $R^{26}$ is —N($R^{27}$)$_2$.

In some embodiments of Formula (XIX), X is —N—.

In some embodiments, the fatty acid synthase inhibitor is a compound of Formula (XX):

(XX)

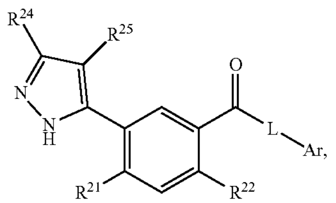

or a pharmaceutically acceptable salt thereof, wherein:

L-Ar is

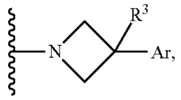

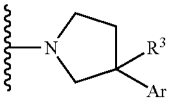

or

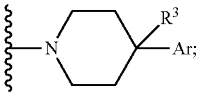

Ar is

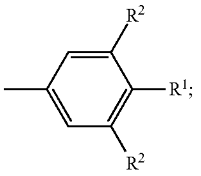

$R^1$ is H, —CN, halogen, $C_1$-$C_4$ alkyl, —O—($C_3$-$C_5$ cycloalkyl), —O-(4- to 6-membered heterocycle), or —O—($C_1$-$C_4$ alkyl), wherein when $R^1$ is not H, —CN or halogen, $R^1$ is optionally substituted with one or more halogen;

each $R^2$ is independently hydrogen, halogen or $C_1$-$C_4$ alkyl;

$R^3$ is H or F;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl;

$R^{24}$ is —O—($C_1$-$C_4$ alkyl), —O—($C_1$-$C_4$ alkyl)-O—($C_1$-$C_4$ alkyl), —O—($C_3$-$C_5$ cycloalkyl), or —O-(4- to 6-membered heterocycle), wherein $R^{24}$ is optionally substituted with one or more hydroxyl or halogen; and $R^{25}$ is H, halogen, $C_1$-$C_4$ alkyl or $C_3$-$C_5$ cycloalkyl, wherein $R^{25}$ is optionally substituted with one or more halogen.

In some embodiments of Formula (XX), L-Ar is

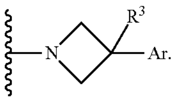

In some embodiments of Formula (XX), L-Ar is

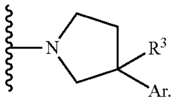

In some embodiments of Formula (XX), L-Ar is

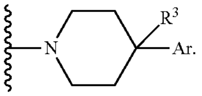

In some embodiments of Formula (XX), $R^3$ is H.

In some embodiments of t Formula (XX), $R^1$ is —CN or —O—($C_1$-$C_4$ alkyl), wherein when $R^1$ is not-CN, $R^1$ is optionally substituted with one or more halogen.

In some embodiments of Formula (XX), $R^1$ is —CN.

In some embodiments of Formula (XX), $R^1$ is —O—($C_1$-$C_4$ alkyl) optionally substituted with one or more halogen.

In some embodiments of Formula (XX), each $R^2$ is hydrogen.

In some embodiments of Formula (XX), $R^{21}$ is $C_1$-$C_4$ alkyl.

In some embodiments of Formula (XX), $R^{22}$ is H or $C_1$-$C_2$ alkyl.

In some embodiments of Formula (XX), $R^{24}$ is —O—($C_1$-$C_4$ alkyl) optionally substituted with one or more hydroxyl or halogen.

In some embodiments of Formula (XX), $R^{24}$ is —O—($C_1$-$C_4$ alkyl) optionally substituted with one or more hydroxyl.

In some embodiments of Formula (XX), $R^{25}$ is —$CH_3$.

In some embodiments, the fatty acid synthase inhibitor is a compound of Formula (XX-1):

(XX-1)

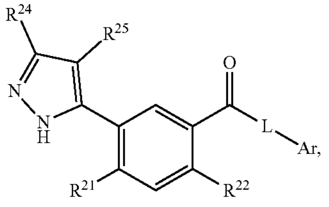

or a pharmaceutically acceptable salt thereof, wherein:

L-Ar is

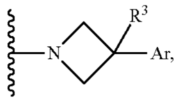

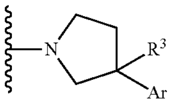

or

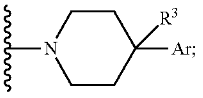

Ar is

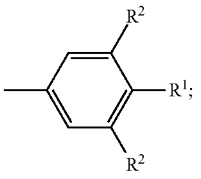

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogen;

each $R^2$ is independently hydrogen, halogen or $C_1$-$C_4$ alkyl;

$R^3$ is H or F;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl;

$R^{24}$ is —O—($C_1$-$C_4$ alkyl), —O—($C_1$-$C_4$ alkyl)-O—($C_1$-$C_4$ alkyl), —O—($C_3$-$C_5$ cycloalkyl), or —O-(4- to 6-membered heterocycle), wherein $R^{24}$ is optionally substituted with one or more hydroxyl or halogen; and $R^{25}$ is H, halogen, $C_1$-$C_4$ alkyl or $C_3$-$C_5$ cycloalkyl, wherein $R^{25}$ is optionally substituted with one or more halogen.

In some embodiments of Formula (XX-1), L-Ar is

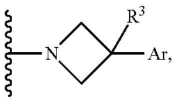

Ar is

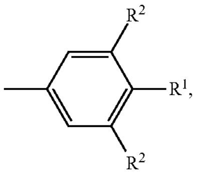

$R^1$ is —CN or —O—($C_1$-$C_4$ alkyl) optionally substituted with one or more halogen; each $R^2$ is independently H; $R^3$ is H or F; $R^{21}$ is H or $C_1$-$C_4$ alkyl; $R^{22}$ is H or $C_1$-$C_2$ alkyl; $R^{24}$ is —O—($C_1$-$C_4$ alkyl), —O—($C_1$-$C_4$ alkyl)-O—($C_1$-$C_4$ alkyl), or —O-(4- to 6-membered heterocycle), wherein $R^{24}$ is optionally substituted with one or more hydroxyl or halogen; and $R^{25}$ is H, halogen, or $C_1$-$C_4$ alkyl.

In some embodiments of Formula (XX-1), L-Ar is

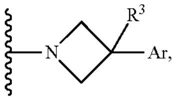

Ar is

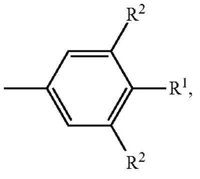

$R^1$ is —CN or —O—($C_1$-$C_4$ alkyl) optionally substituted with one or more halogen; each $R^2$ is independently H; $R^3$ is H or F; $R^{21}$ is H or $C_1$-$C_4$ alkyl; $R^{22}$ is H or $C_1$-$C_2$ alkyl; $R^{24}$ is —O—($C_1$-$C_4$ alkyl) substituted with one or more hydroxyl or halogen; and $R^{25}$ is $C_1$-$C_4$ alkyl.

In some embodiments, the compound of Formula (XX-1) has one of the following structures:

(Compound 005-2)

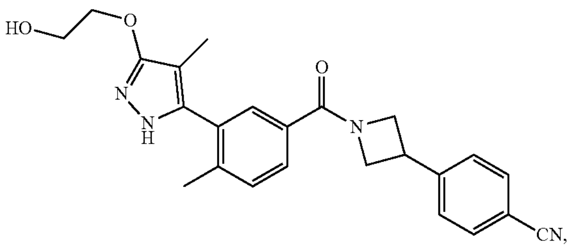

(Compound 005-5)

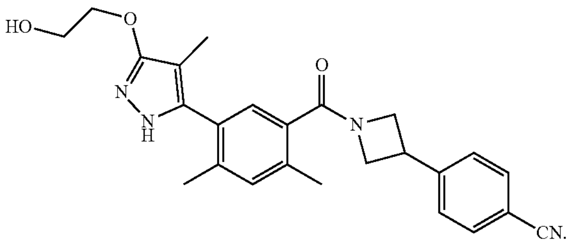

In some embodiments, the present disclosure provides pharmaceutical compositions comprising any one of the fatty acid synthase inhibitors of Formulae (IX-1), (XII-1), (XIII-1), (XX-1), (I), (II), (III), (IV), (V), (VI), (VII), (VIII), (IX), (X), (XI), (XII), (XIII), (XIV), (XV), (XVI), (XVII), (XVIII), (XIV), or (XX) and a pharmaceutically acceptable carrier, excipient, or diluent. In some embodiments, the fatty acid synthase inhibitor is a compound of Formula (IX-1), (XII-1), (XIII-1), or (XX-1), or a pharmaceutically acceptable salt thereof.

In some embodiments, the fatty acid synthase inhibitor is a compound selected from: Compound 001-152, Compound 002-386, Compound 002-242, Compound 005-2, and Compound 005-5, or a pharmaceutically acceptable salt thereof.

In some embodiments, the fatty acid synthase inhibitor is a compound selected from: Compound 001-152 and Compound 005-2, or a pharmaceutically acceptable salt thereof.

In some embodiments, the fatty acid synthase inhibitor is a compound selected from Table C-1, or a pharmaceutically acceptable salt thereof.

In some embodiments, the fatty acid synthase inhibitor is a compound selected from Table C-2, or a pharmaceutically acceptable salt thereof.

In some embodiments, the fatty acid synthase inhibitor is a compound selected from Table C-3, or a pharmaceutically acceptable salt thereof.

TABLE C-1
| Fatty Acid Synthase Inhibitors | | |
|---|---|---|
| Cmpd No. | Structure | FASN IC$_{50}$ (μM) |
| 001-1 | 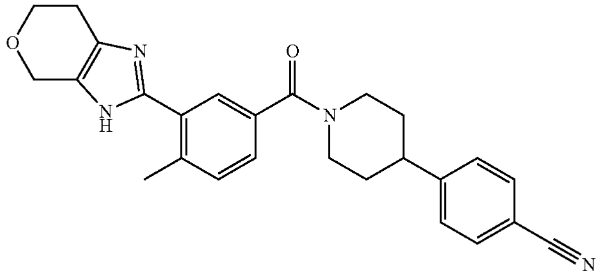 [SMILES: Cc1ccc(C(=O)N2CCC(c3ccc(C#N)cc3)CC2)cc1-c1nc2c([nH]1)COCC2] | 0.230 |
| 001-2 | 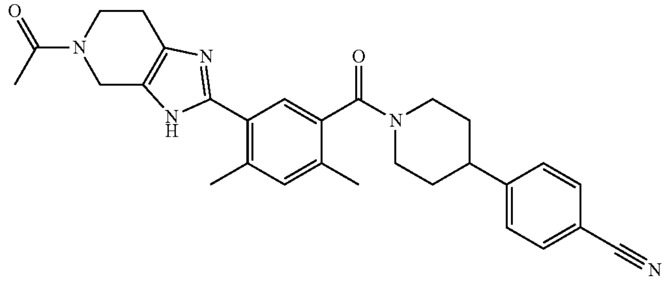 [SMILES: CC(=O)N1CCc2nc(-c3cc(C(=O)N4CCC(c5ccc(C#N)cc5)CC4)c(C)cc3C)[nH]c2C1] | 0.065 |
| 001-2.9 | 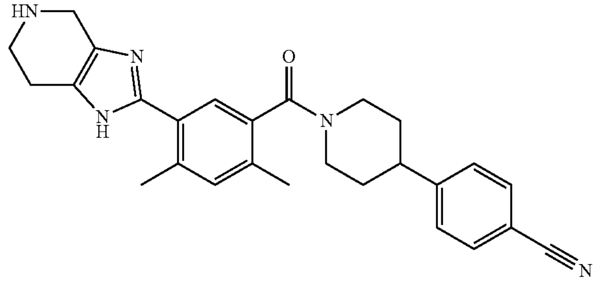 [SMILES: Cc1cc(C)c(-c2nc3c([nH]2)CCNC3)cc1C(=O)N1CCC(c2ccc(C#N)cc2)CC1] | 0.060 |
| 001-3 | 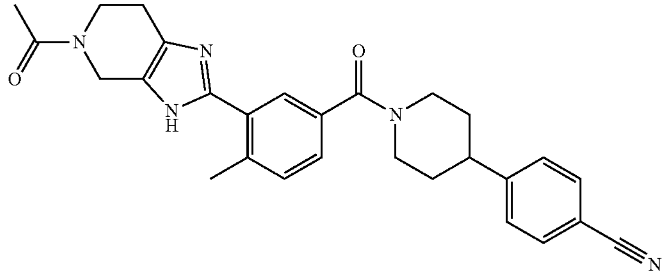 [SMILES: CC(=O)N1CCc2nc(-c3cc(C(=O)N4CCC(c5ccc(C#N)cc5)CC4)ccc3C)[nH]c2C1] | 0.146 |
| 001-4 | 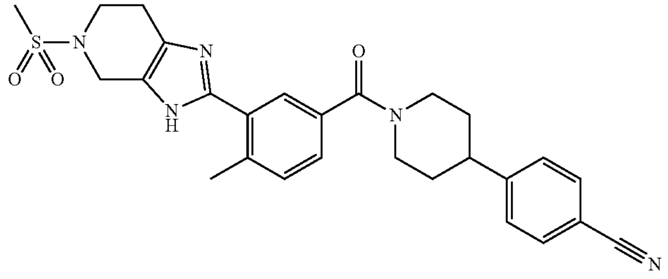 [SMILES: Cc1ccc(C(=O)N2CCC(c3ccc(C#N)cc3)CC2)cc1-c1nc2c([nH]1)CN(S(C)(=O)=O)CC2] | 0.200 |

TABLE C-1-continued
| Fatty Acid Synthase Inhibitors | | |
|---|---|---|
| Cmpd No. | Structure | FASN $IC_{50}$ (μM) |
| 001-5 | 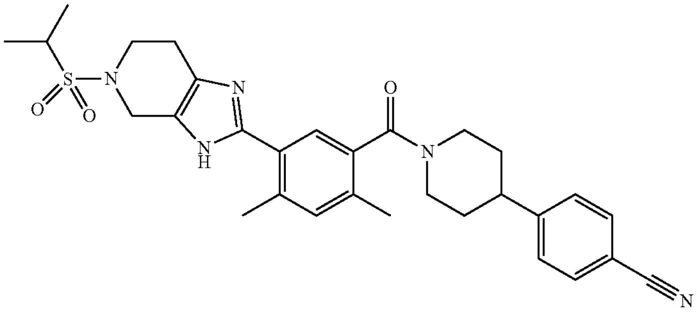 [SMILES: Cc1cc(C)c(-c2nc3c([nH]2)CN(S(=O)(=O)C(C)C)CC3)cc1C(=O)N1CCC(c2ccc(C#N)cc2)CC1] | 0.055 |
| 001-6 | 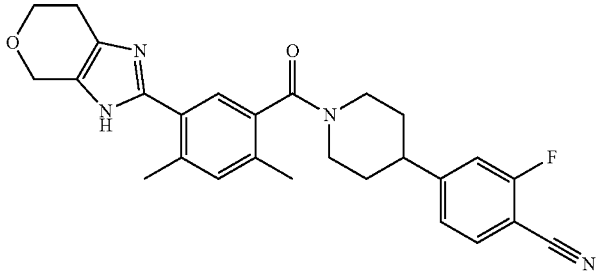 [SMILES: Cc1cc(C)c(-c2nc3c([nH]2)COCC3)cc1C(=O)N1CCC(c2ccc(C#N)c(F)c2)CC1] | 0.360 |
| 001-7 | 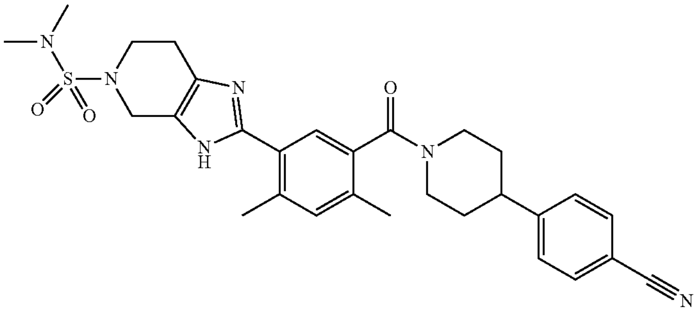 [SMILES: Cc1cc(C)c(-c2nc3c([nH]2)CN(S(=O)(=O)N(C)C)CC3)cc1C(=O)N1CCC(c2ccc(C#N)cc2)CC1] | 0.050 |
| 001-8 | 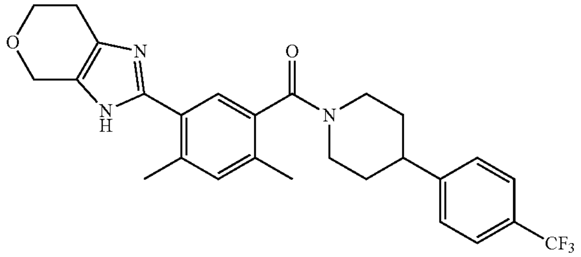 [SMILES: Cc1cc(C)c(-c2nc3c([nH]2)COCC3)cc1C(=O)N1CCC(c2ccc(C(F)(F)F)cc2)CC1] | 0.125 |
| 001-9 | 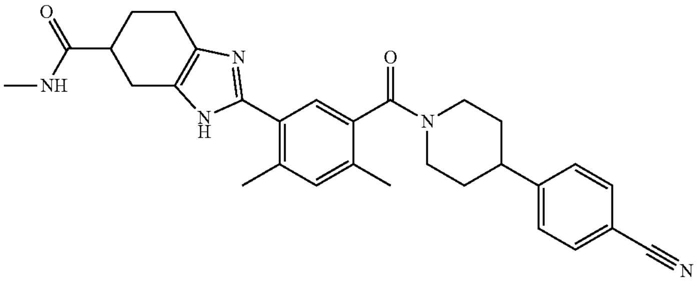 [SMILES: CNC(=O)C1CCc2nc(-c3cc(C(=O)N4CCC(c5ccc(C#N)cc5)CC4)c(C)cc3C)[nH]c2C1] | 0.040 |

TABLE C-1-continued
| Fatty Acid Synthase Inhibitors | | |
|---|---|---|
| Cmpd No. | Structure | FASN $IC_{50}$ (μM) |
| 001-11 | 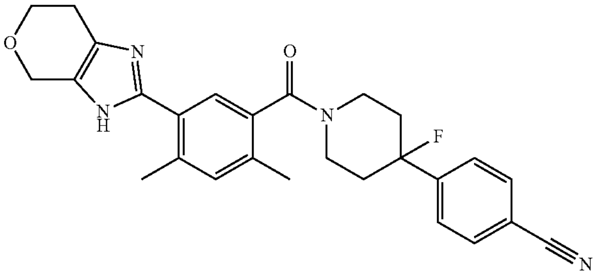 [SMILES: Cc1cc(C)c(-c2nc3c([nH]2)COCC3)cc1C(=O)N1CCC(F)(c2ccc(C#N)cc2)CC1] | 0.170 |
| 001-12 | 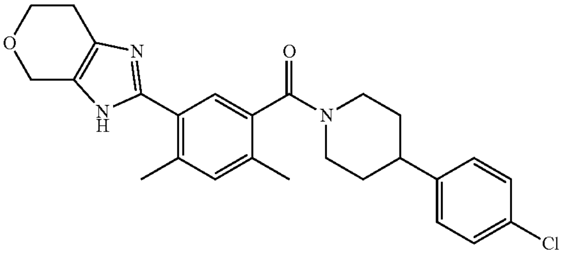 [SMILES: Cc1cc(C)c(-c2nc3c([nH]2)COCC3)cc1C(=O)N1CCC(c2ccc(Cl)cc2)CC1] | 0.370 |
| 001-13 | 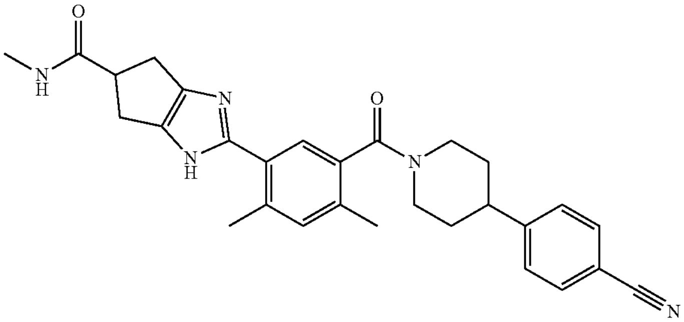 [SMILES: CNC(=O)C1Cc2nc(-c3cc(C(=O)N4CCC(c5ccc(C#N)cc5)CC4)c(C)cc3C)[nH]c2C1] | 0.260 |
| 001-14 | 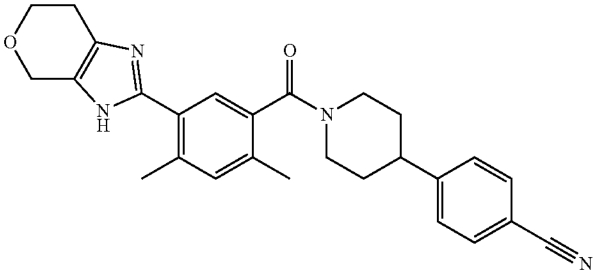 [SMILES: Cc1cc(C)c(-c2nc3c([nH]2)COCC3)cc1C(=O)N1CCC(c2ccc(C#N)cc2)CC1] | 0.263 |
| 001-15 | 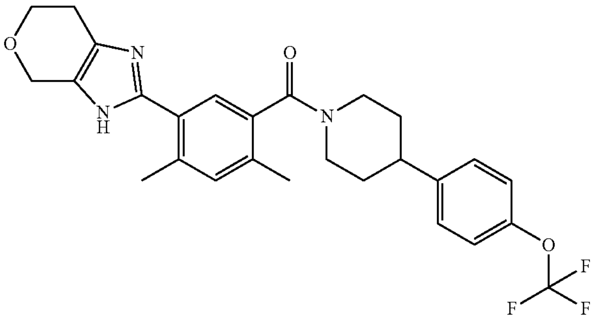 [SMILES: Cc1cc(C)c(-c2nc3c([nH]2)COCC3)cc1C(=O)N1CCC(c2ccc(OC(F)(F)F)cc2)CC1] | 0.180 |

TABLE C-1-continued
| Fatty Acid Synthase Inhibitors | | |
|---|---|---|
| Cmpd No. | Structure | FASN $IC_{50}$ (μM) |
| 001-16 | 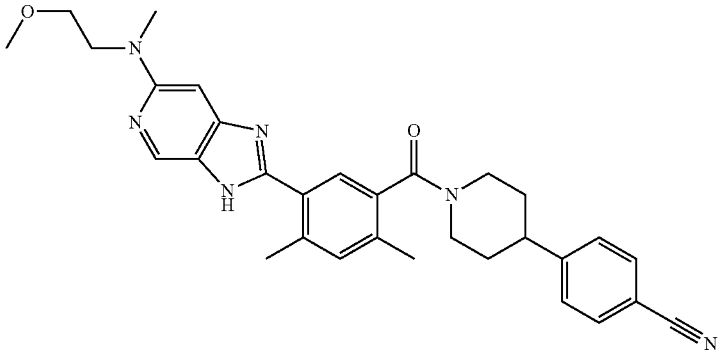 [SMILES: COCCN(C)c1cc2nc(-c3cc(C(=O)N4CCC(c5ccc(C#N)cc5)CC4)c(C)cc3C)[nH]c2cn1] | 0.058 |
| 001-17 | 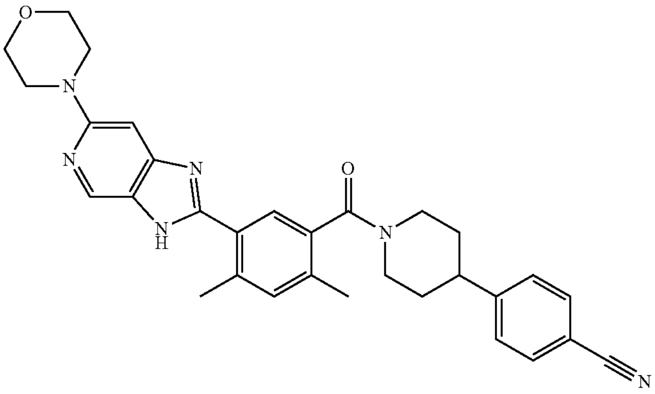 [SMILES: Cc1cc(C)c(-c2nc3cc(N4CCOCC4)ncc3[nH]2)cc1C(=O)N1CCC(c2ccc(C#N)cc2)CC1] | 0.073 |
| 001-18 | 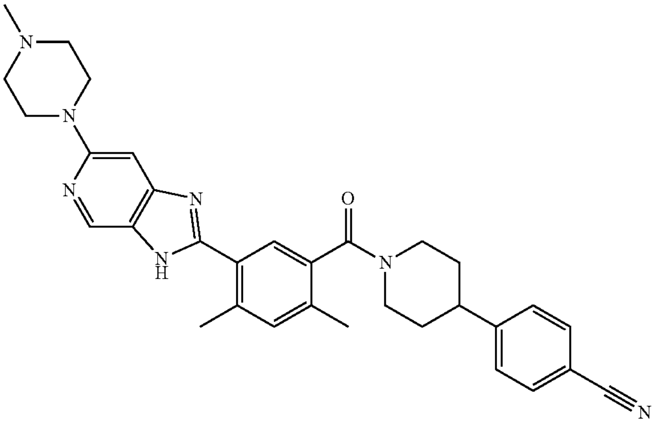 [SMILES: Cc1cc(C)c(-c2nc3cc(N4CCN(C)CC4)ncc3[nH]2)cc1C(=O)N1CCC(c2ccc(C#N)cc2)CC1] | 0.990 |

TABLE C-1-continued
Fatty Acid Synthase Inhibitors
| Cmpd No. | Structure | FASN $IC_{50}$ (μM) |
|---|---|---|
| 001-19 | 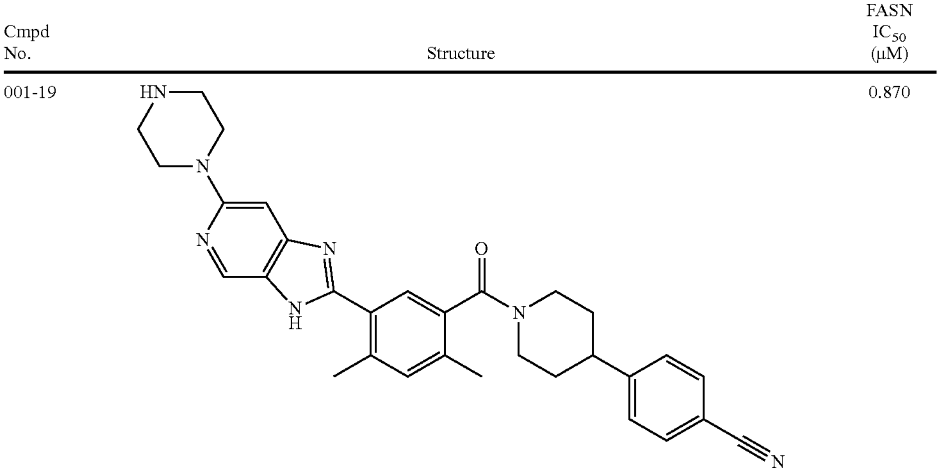 | 0.870 |
| 001-20 | 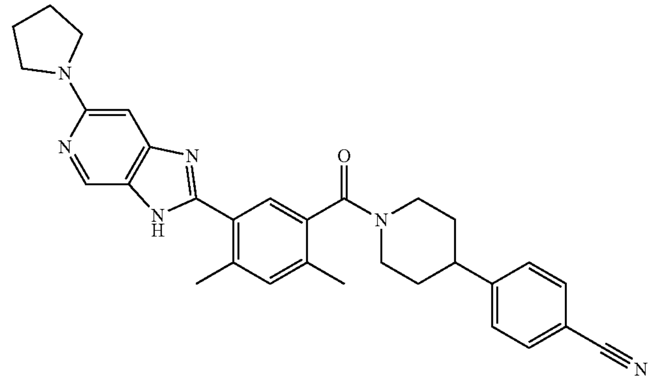 [SMILES: Cc1cc(C)c(-c2nc3cc(N4CCCC4)ncc3[nH]2)cc1C(=O)N1CCC(c2ccc(C#N)cc2)CC1] | 0.022 |
| 001-21 | 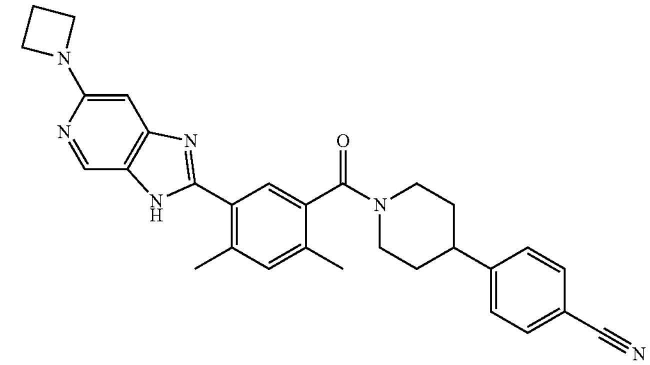 [SMILES: Cc1cc(C)c(-c2nc3cc(N4CCC4)ncc3[nH]2)cc1C(=O)N1CCC(c2ccc(C#N)cc2)CC1] | 0.045 |
| 001-22 | 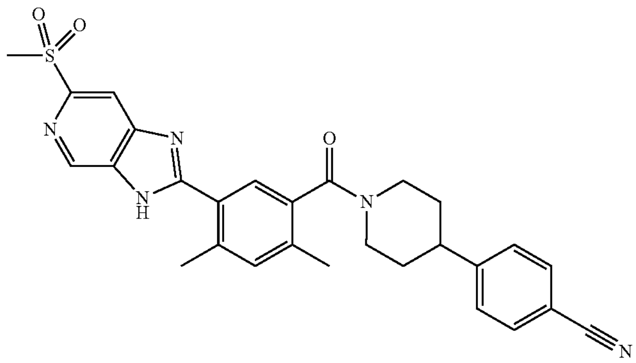 [SMILES: Cc1cc(C)c(-c2nc3cc(S(C)(=O)=O)ncc3[nH]2)cc1C(=O)N1CCC(c2ccc(C#N)cc2)CC1] | 0.085 |

TABLE C-1-continued
| Cmpd No. | Fatty Acid Synthase Inhibitors Structure | FASN $IC_{50}$ (μM) |
|---|---|---|
| 001-23 | 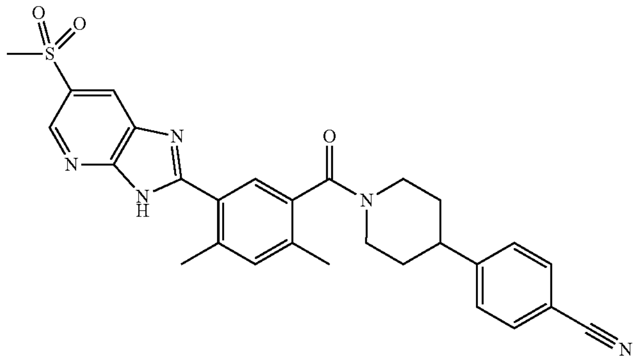 [SMILES: Cc1cc(C)c(-c2nc3cc(S(C)(=O)=O)cnc3[nH]2)cc1C(=O)N1CCC(c2ccc(C#N)cc2)CC1] | 0.070 |
| 001-24 | 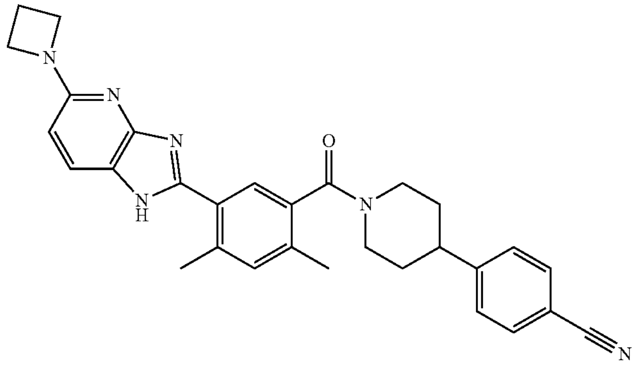 [SMILES: Cc1cc(C)c(-c2nc3nc(N4CCC4)ccc3[nH]2)cc1C(=O)N1CCC(c2ccc(C#N)cc2)CC1] | 0.070 |
| 001-25 | 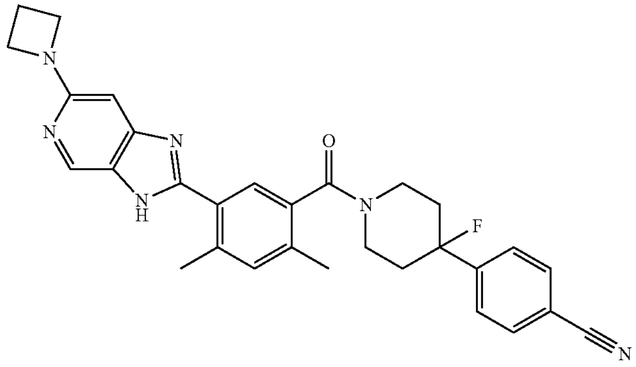 [SMILES: Cc1cc(C)c(-c2nc3cc(N4CCC4)ncc3[nH]2)cc1C(=O)N1CCC(F)(c2ccc(C#N)cc2)CC1] | 0.150 |
| 001-26 | 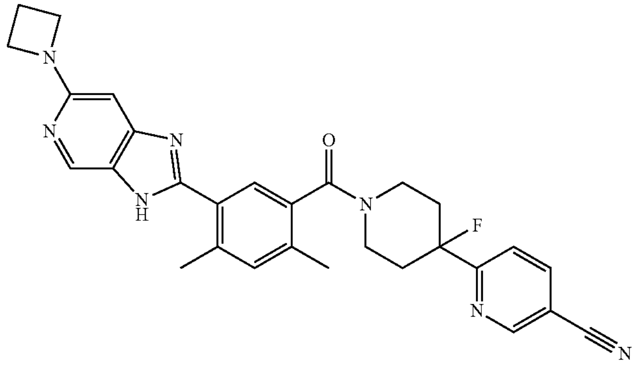 [SMILES: Cc1cc(C)c(-c2nc3cc(N4CCC4)ncc3[nH]2)cc1C(=O)N1CCC(F)(c2ccc(C#N)cn2)CC1] | 7.195 |

TABLE C-1-continued
| Cmpd No. | Structure | FASN $IC_{50}$ (μM) |
|---|---|---|
| 001-27 | 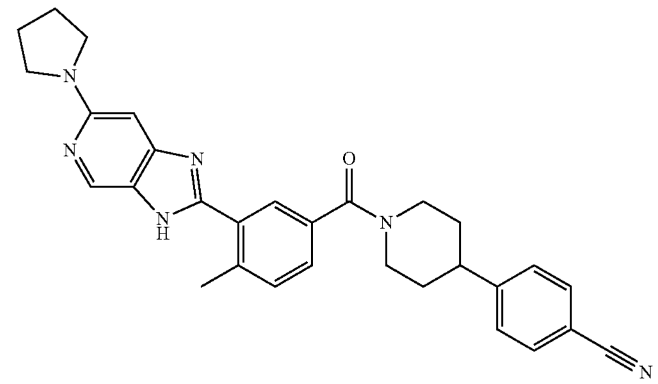 [SMILES: Cc1ccc(C(=O)N2CCC(c3ccc(C#N)cc3)CC2)cc1-c1nc2cc(N3CCCC3)ncc2[nH]1] | 0.107 |
| 001-28 | 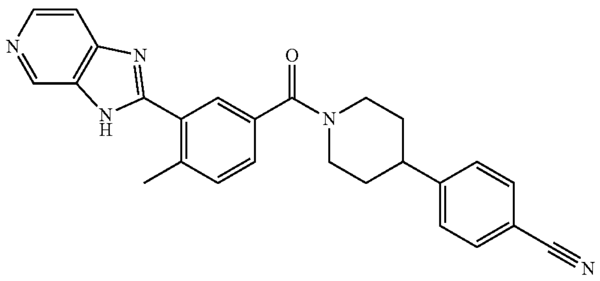 [SMILES: Cc1ccc(C(=O)N2CCC(c3ccc(C#N)cc3)CC2)cc1-c1nc2ccncc2[nH]1] | 0.490 |
| 001-29 | 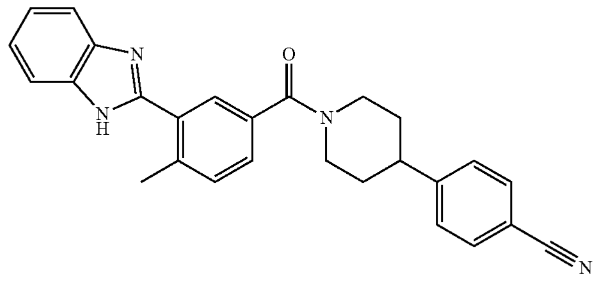 [SMILES: Cc1ccc(C(=O)N2CCC(c3ccc(C#N)cc3)CC2)cc1-c1nc2ccccc2[nH]1] | 0.980 |
| 001-30 | 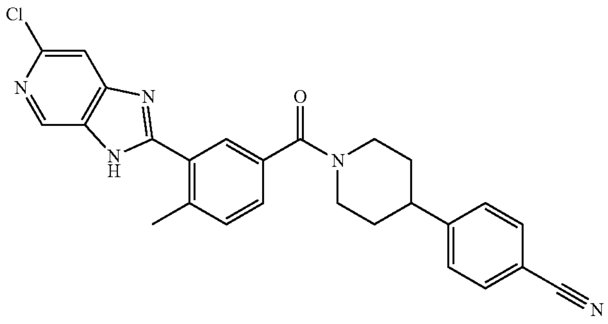 [SMILES: Cc1ccc(C(=O)N2CCC(c3ccc(C#N)cc3)CC2)cc1-c1nc2cc(Cl)ncc2[nH]1] | 0.320 |
Fatty Acid Synthase Inhibitors TABLE C-1-continued
| Cmpd No. | Structure | FASN $IC_{50}$ (μM) |
| --- | --- | --- |
| Fatty Acid Synthase Inhibitors | | |
| 001-31 | 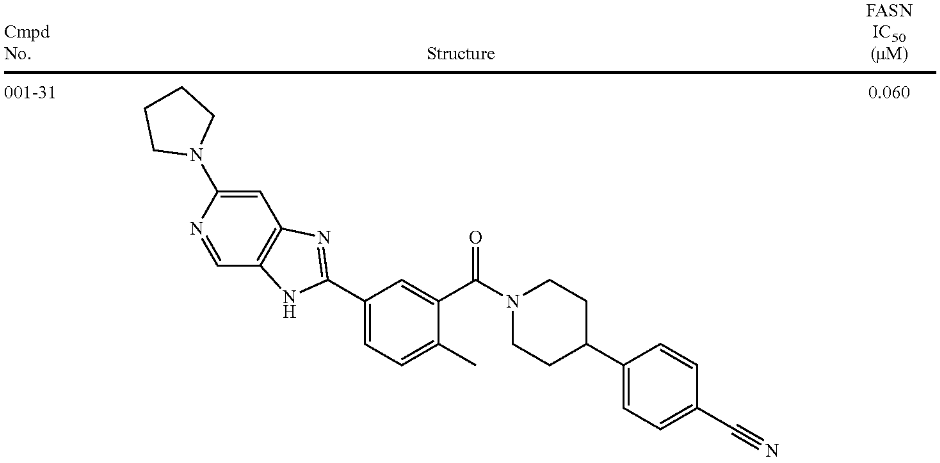 | 0.060 |
| 001-32 | 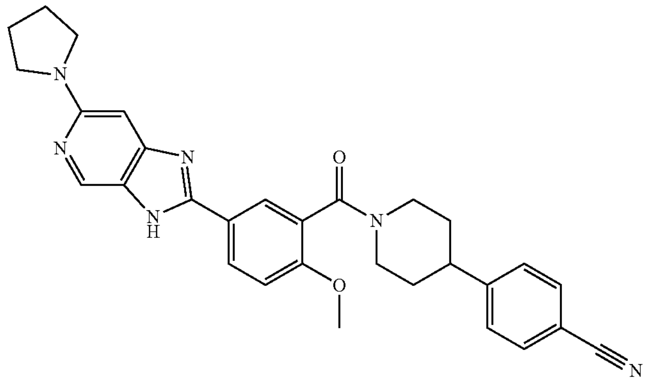 [SMILES: COc1ccc(-c2nc3cc(N4CCCC4)ncc3[nH]2)cc1C(=O)N1CCC(c2ccc(C#N)cc2)CC1] | 0.215 |
| 001-33 | 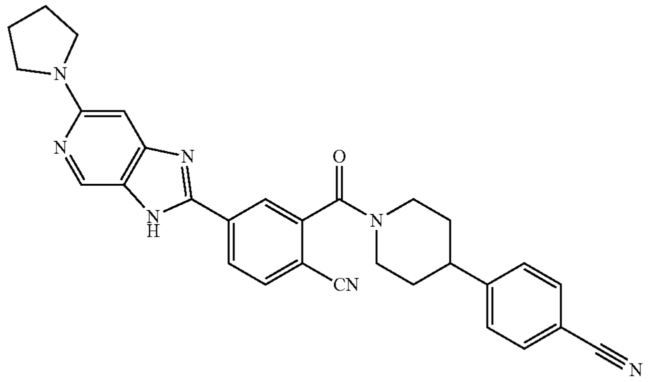 [SMILES: N#Cc1ccc(C2CCN(C(=O)c3cc(-c4nc5cc(N6CCCC6)ncc5[nH]4)ccc3C#N)CC2)cc1] | 7.500 |
| 001-34 | 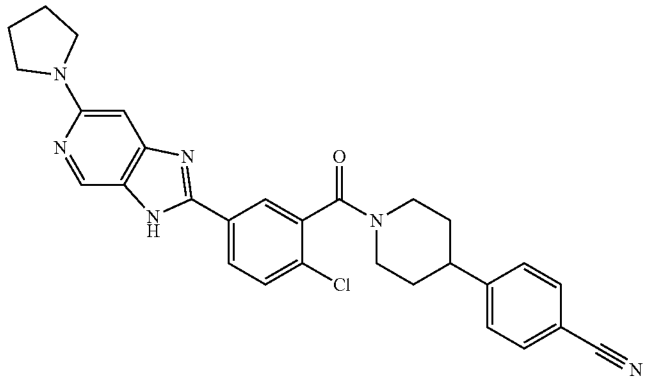 [SMILES: N#Cc1ccc(C2CCN(C(=O)c3cc(-c4nc5cc(N6CCCC6)ncc5[nH]4)ccc3Cl)CC2)cc1] | 0.080 |

TABLE C-1-continued
| Fatty Acid Synthase Inhibitors | | |
|---|---|---|
| Cmpd No. | Structure | FASN $IC_{50}$ (μM) |
| 001-35 | 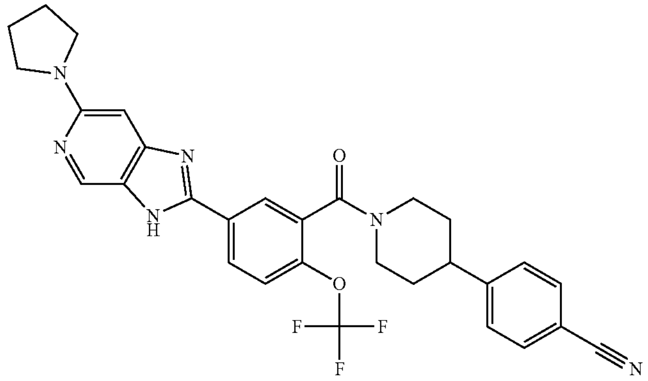 [SMILES: N#Cc1ccc(C2CCN(C(=O)c3cc(-c4nc5cc(N6CCCC6)ncc5[nH]4)ccc3OC(F)(F)F)CC2)cc1] | 25.083 |
| 001-36 | 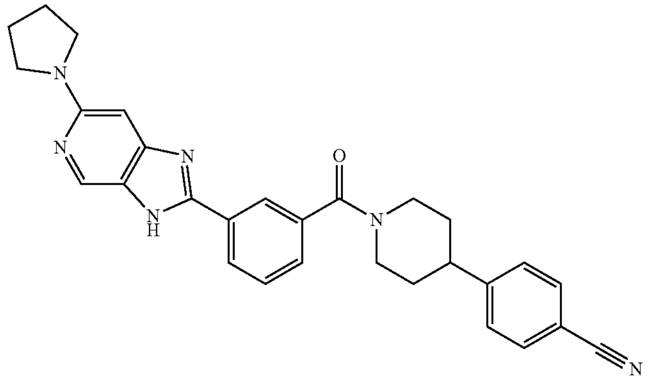 [SMILES: N#Cc1ccc(C2CCN(C(=O)c3cccc(-c4nc5cc(N6CCCC6)ncc5[nH]4)c3)CC2)cc1] | 0.130 |
| 001-37 | 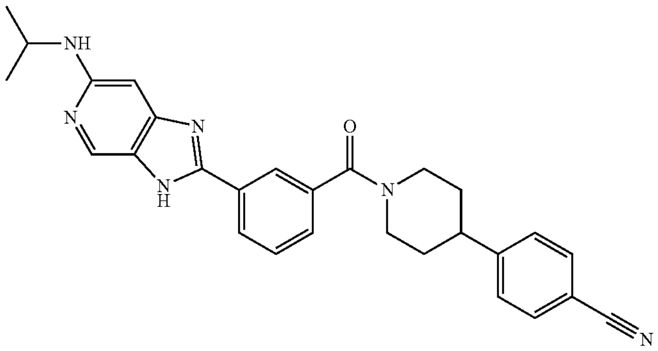 [SMILES: CC(C)Nc1cc2nc(-c3cccc(C(=O)N4CCC(c5ccc(C#N)cc5)CC4)c3)[nH]c2cn1] | 0.675 |
| 001-38 | 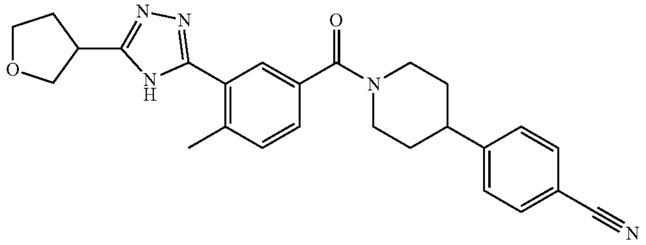 [SMILES: Cc1ccc(C(=O)N2CCC(c3ccc(C#N)cc3)CC2)cc1-c1nnc(C2CCOC2)[nH]1] | 2.345 |

TABLE C-1-continued
| Fatty Acid Synthase Inhibitors | | |
|---|---|---|
| Cmpd No. | Structure | FASN $IC_{50}$ (μM) |
| 001-39 | 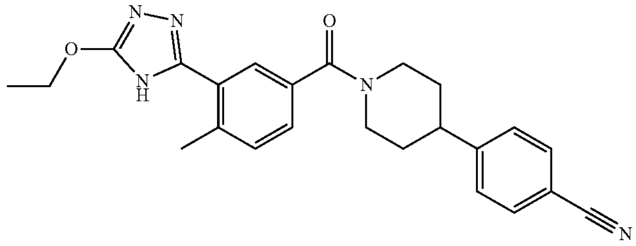 [SMILES: CCOc1nnc(-c2cc(C(=O)N3CCC(c4ccc(C#N)cc4)CC3)ccc2C)[nH]1] | 1.710 |
| 001-40 | 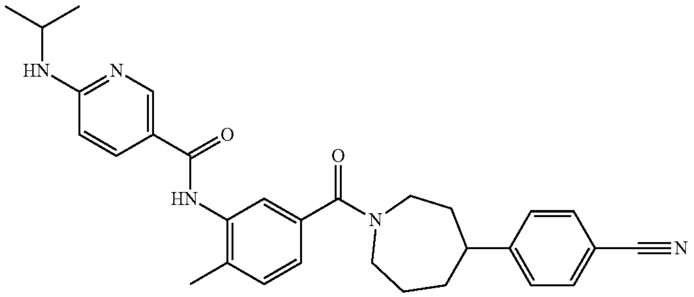 [SMILES: Cc1ccc(C(=O)N2CCCC(c3ccc(C#N)cc3)CC2)cc1NC(=O)c1ccc(NC(C)C)nc1] | 0.050 |
| 001-41 | 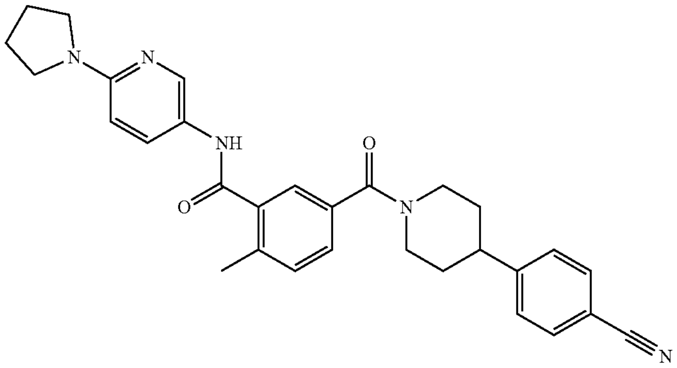 [SMILES: Cc1ccc(C(=O)N2CCC(c3ccc(C#N)cc3)CC2)cc1C(=O)Nc1ccc(N2CCCC2)nc1] | 0.035 |
| 001-42 | 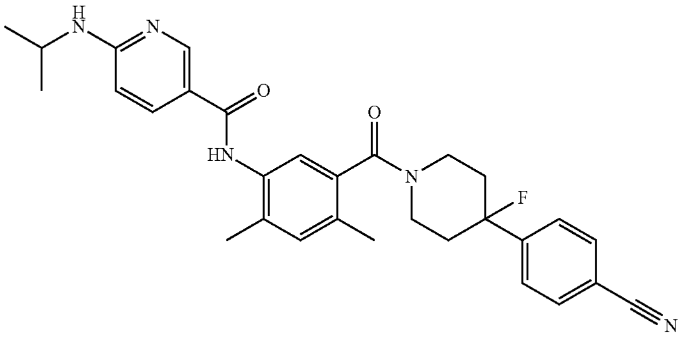 [SMILES: Cc1cc(C)c(C(=O)N2CCC(F)(c3ccc(C#N)cc3)CC2)cc1NC(=O)c1ccc(NC(C)C)nc1] | 0.067 |

TABLE C-1-continued
| Fatty Acid Synthase Inhibitors | | |
|---|---|---|
| Cmpd No. | Structure | FASN $IC_{50}$ (μM) |
| 001-43 | 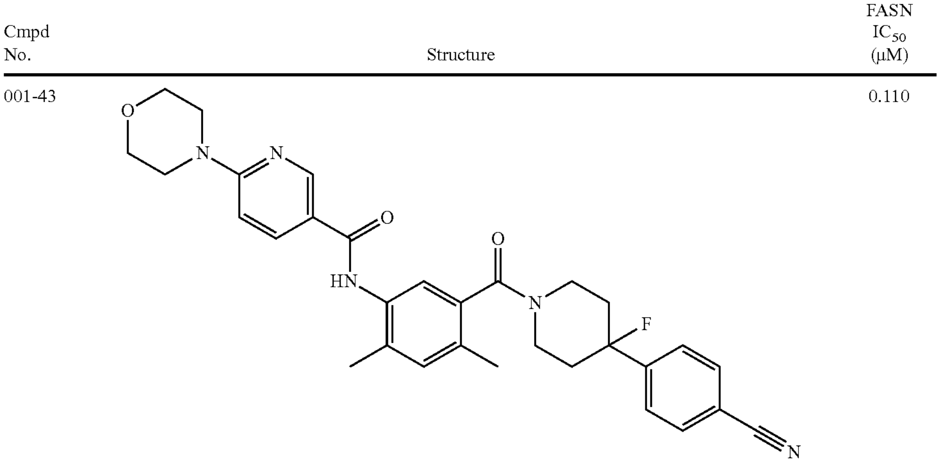 | 0.110 |
| 001-44 | 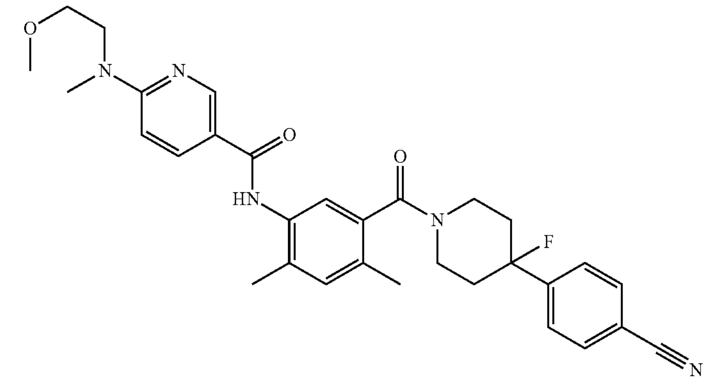 [SMILES: COCCN(C)c1ccc(C(=O)Nc2cc(C(=O)N3CCC(F)(c4ccc(C#N)cc4)CC3)c(C)cc2C)cn1] | 0.180 |
| 001-45 | 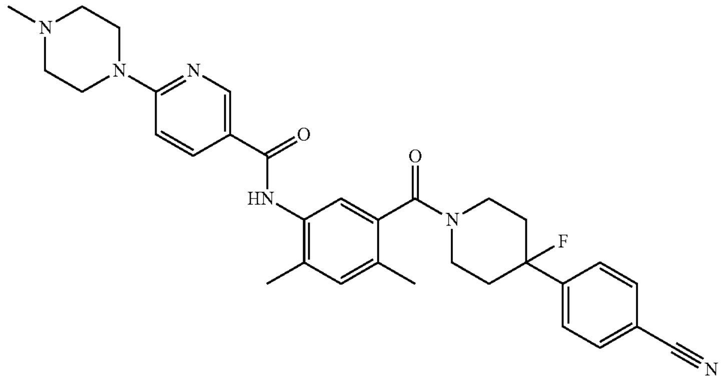 [SMILES: Cc1cc(C)c(C(=O)N2CCC(F)(c3ccc(C#N)cc3)CC2)cc1NC(=O)c1ccc(N2CCN(C)CC2)nc1] | 0.147 |
| 001-46 | 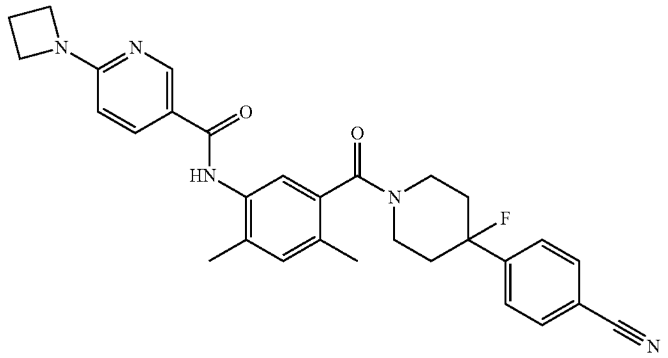 [SMILES: Cc1cc(C)c(C(=O)N2CCC(F)(c3ccc(C#N)cc3)CC2)cc1NC(=O)c1ccc(N2CCC2)nc1] | 0.050 |

TABLE C-1-continued
| Fatty Acid Synthase Inhibitors | | |
|---|---|---|
| Cmpd No. | Structure | FASN $IC_{50}$ (μM) |
| 001-47 | 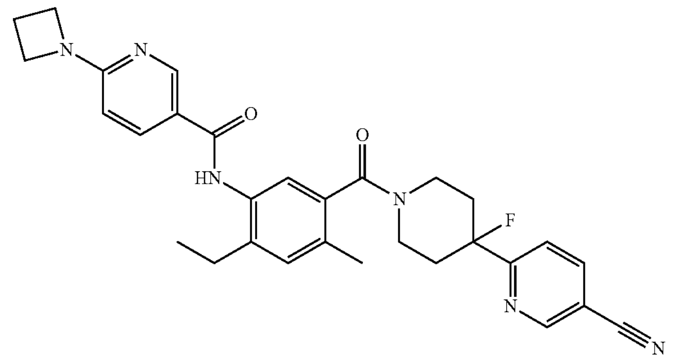 [SMILES: CCc1cc(C)c(C(=O)N2CCC(F)(c3ccc(C#N)cn3)CC2)cc1NC(=O)c1ccc(N2CCC2)nc1] | 0.230 |
| 001-48 | 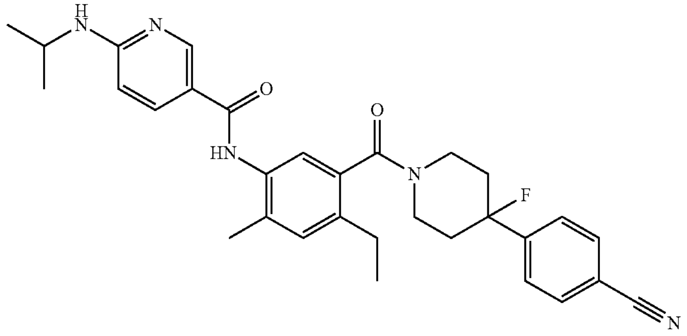 [SMILES: CCc1cc(C)c(NC(=O)c2ccc(NC(C)C)nc2)cc1C(=O)N1CCC(F)(c2ccc(C#N)cc2)CC1] | 0.170 |
| 001-49 | 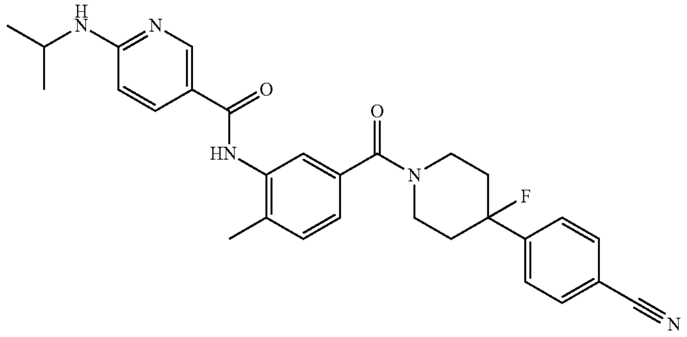 | 0.040 |
| 001-50 | 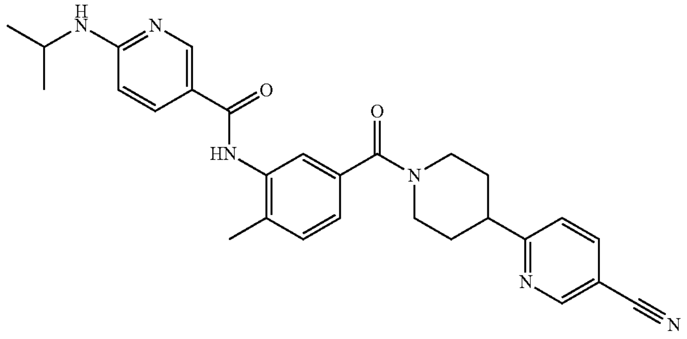 [SMILES: Cc1ccc(C(=O)N2CCC(c3ccc(C#N)cn3)CC2)cc1NC(=O)c1ccc(NC(C)C)nc1] | 0.520 |

TABLE C-1-continued
| Fatty Acid Synthase Inhibitors | | |
|---|---|---|
| Cmpd No. | Structure | FASN $IC_{50}$ (μM) |
| 001-51 | 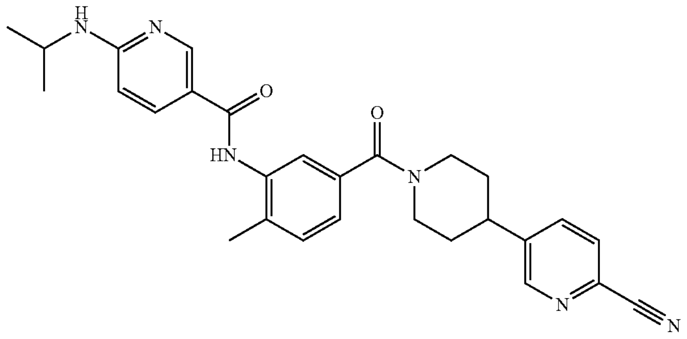 [SMILES: Cc1ccc(C(=O)N2CCC(c3ccc(C#N)nc3)CC2)cc1NC(=O)c1ccc(NC(C)C)nc1] | 1.700 |
| 001-52 | 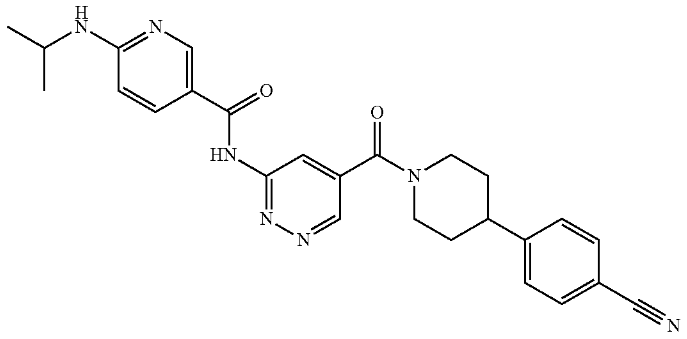 [SMILES: CC(C)Nc1ccc(C(=O)Nc2cc(C(=O)N3CCC(c4ccc(C#N)cc4)CC3)cnn2)cn1] | 31.650 |
| 001-53 | 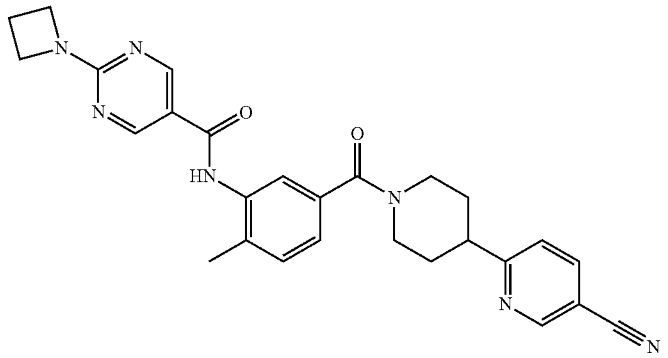 [SMILES: Cc1ccc(C(=O)N2CCC(c3ccc(C#N)cn3)CC2)cc1NC(=O)c1cnc(N2CCC2)nc1] | 1.970 |
| 001-54 | 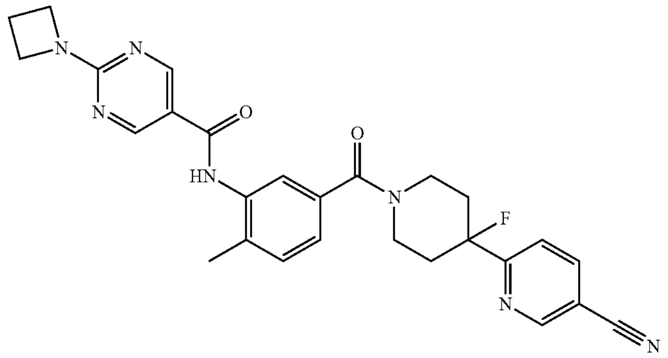 [SMILES: Cc1ccc(C(=O)N2CCC(F)(c3ccc(C#N)cn3)CC2)cc1NC(=O)c1cnc(N2CCC2)nc1] | 0.310 |

TABLE C-1-continued
| Fatty Acid Synthase Inhibitors | | |
|---|---|---|
| Cmpd No. | Structure | FASN $IC_{50}$ (μM) |
| 001-55 | 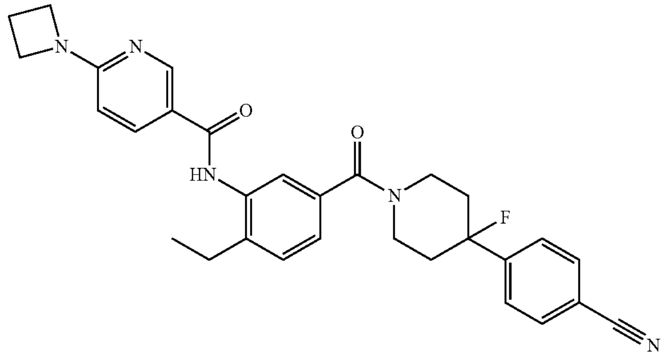 | 0.035 |
| 001-56 | 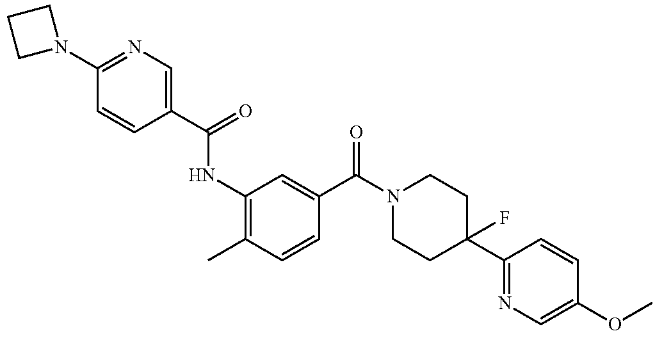 [SMILES: COc1ccc(C2(F)CCN(C(=O)c3ccc(C)c(NC(=O)c4ccc(N5CCC5)nc4)c3)CC2)nc1] | 2.800 |
| 001-57 | 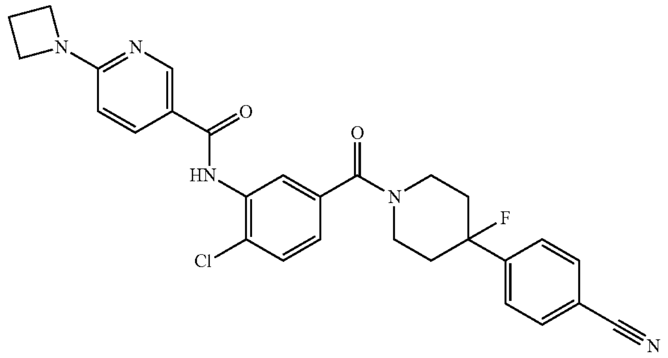 | 0.030 |
| 001-58 | 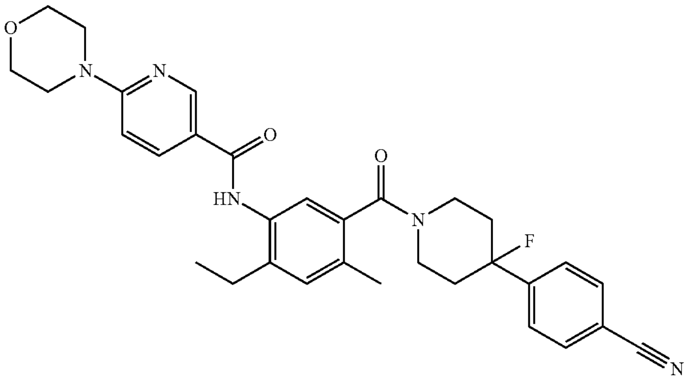 | 0.025 |

TABLE C-1-continued
| Fatty Acid Synthase Inhibitors | | |
|---|---|---|
| Cmpd No. | Structure | FASN $IC_{50}$ (μM) |
| 001-60 | 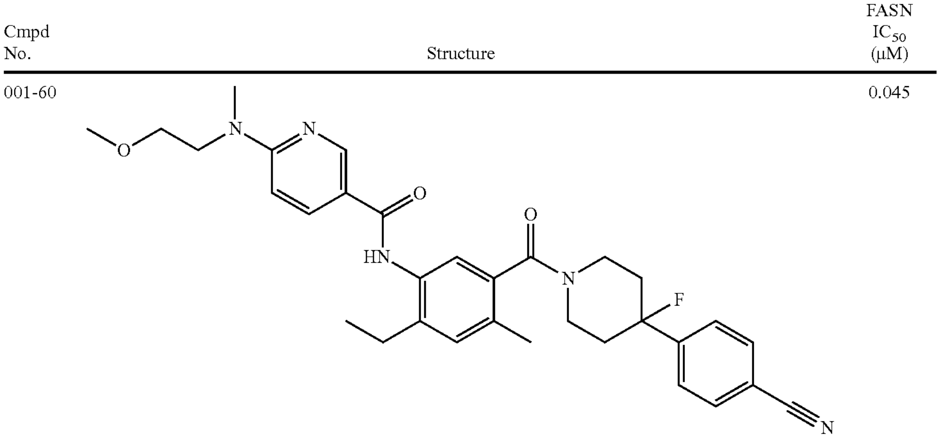 | 0.045 |
| 001-61 | 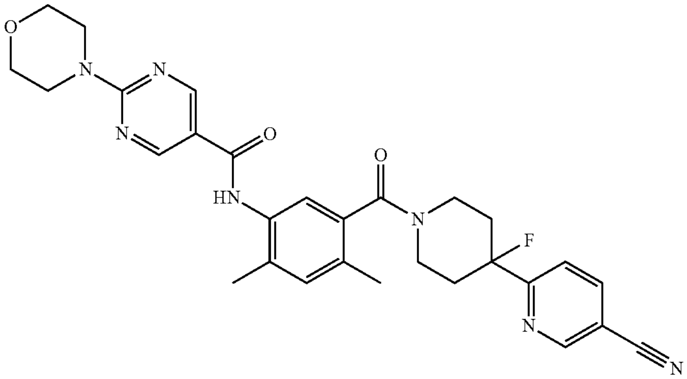 [SMILES: Cc1cc(C)c(C(=O)N2CCC(F)(c3ccc(C#N)cn3)CC2)cc1NC(=O)c1cnc(N2CCOCC2)nc1] | 0.230 |
| 001-62 | 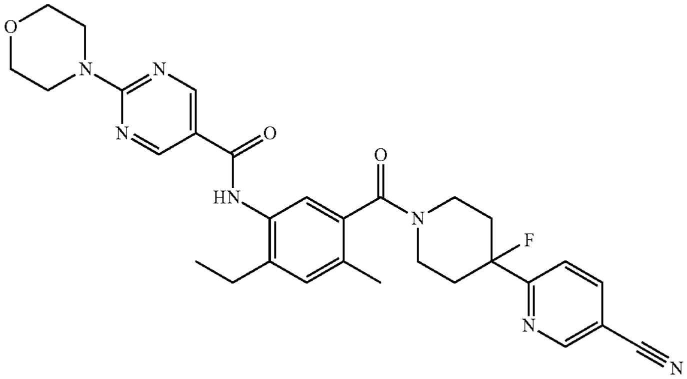 [SMILES: CCc1cc(C)c(C(=O)N2CCC(F)(c3ccc(C#N)cn3)CC2)cc1NC(=O)c1cnc(N2CCOCC2)nc1] | 0.093 |
| 001-63 | 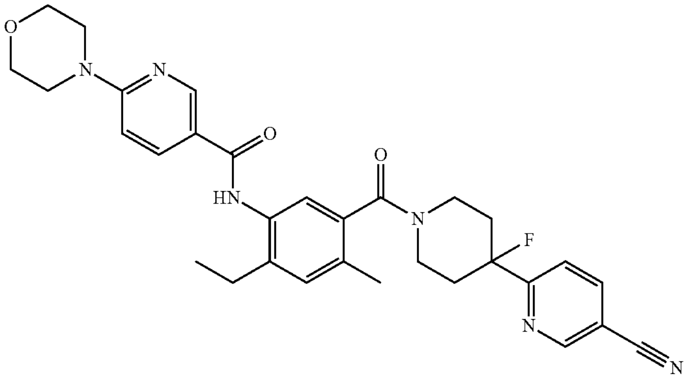 [SMILES: CCc1cc(C)c(C(=O)N2CCC(F)(c3ccc(C#N)cn3)CC2)cc1NC(=O)c1ccc(N2CCOCC2)nc1] | 0.510 |

TABLE C-1-continued
| Cmpd No. | Structure | FASN $IC_{50}$ (μM) |
| --- | --- | --- |
| | Fatty Acid Synthase Inhibitors | |
| 001-64 | 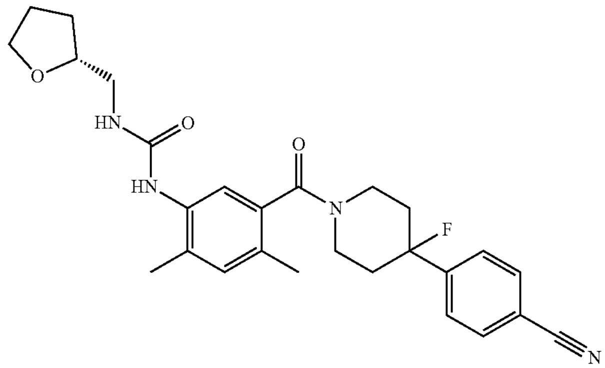 [SMILES: Cc1cc(C)c(C(=O)N2CCC(F)(c3ccc(C#N)cc3)CC2)cc1NC(=O)NC[C@H]1CCCO1] | 0.170 |
| 001-65 | 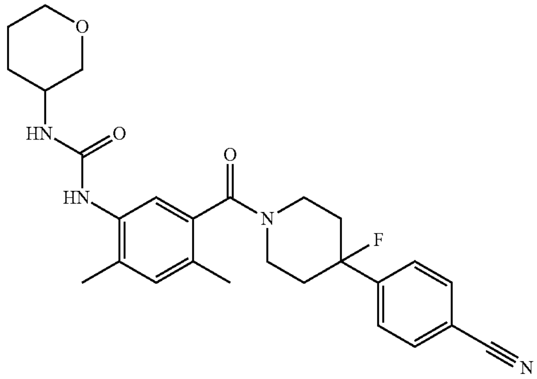 [SMILES: Cc1cc(C)c(C(=O)N2CCC(F)(c3ccc(C#N)cc3)CC2)cc1NC(=O)NC1CCCOC1] | 0.090 |
| 001-66 | 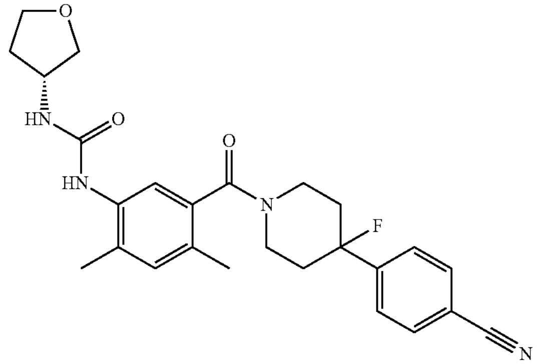 [SMILES: Cc1cc(C)c(C(=O)N2CCC(F)(c3ccc(C#N)cc3)CC2)cc1NC(=O)N[C@@H]1CCOC1] | 0.230 |
| 001-67 | 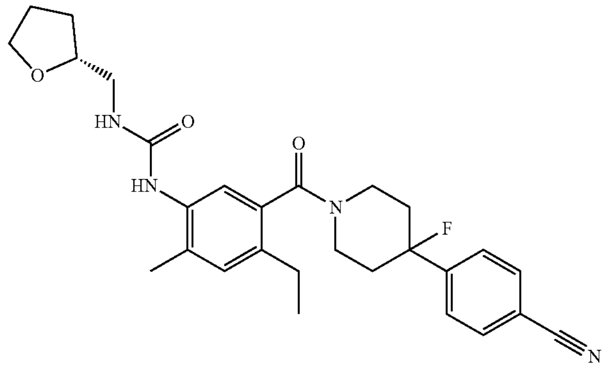 [SMILES: CCc1cc(C)c(NC(=O)NC[C@H]2CCCO2)cc1C(=O)N1CCC(F)(c2ccc(C#N)cc2)CC1] | 0.090 |

TABLE C-1-continued
| Fatty Acid Synthase Inhibitors | | |
|---|---|---|
| Cmpd No. | Structure | FASN $IC_{50}$ (μM) |
| 001-68 | 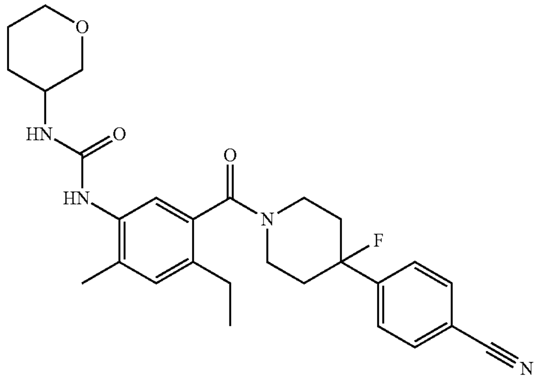 [SMILES: CCc1cc(C)c(NC(=O)NC2CCCOC2)cc1C(=O)N1CCC(F)(c2ccc(C#N)cc2)CC1] | 0.100 |
| 001-69 | 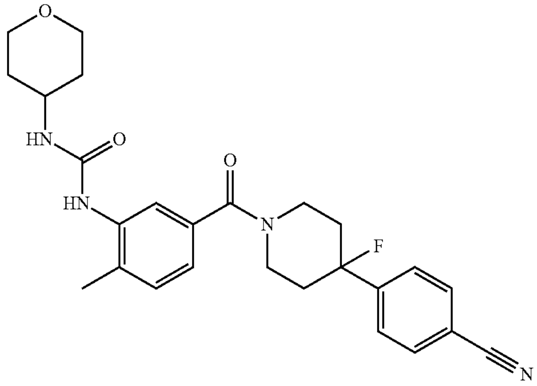 [SMILES: Cc1ccc(C(=O)N2CCC(F)(c3ccc(C#N)cc3)CC2)cc1NC(=O)NC1CCOCC1] | 0.065 |
| 001-70 | 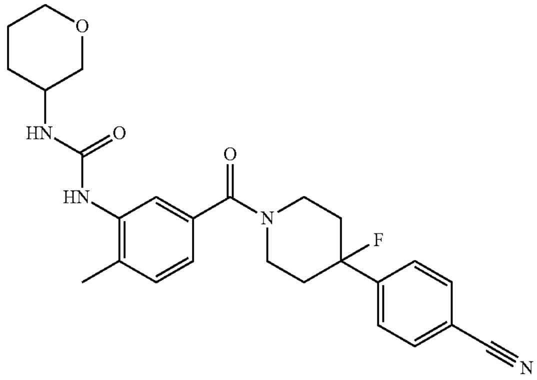 [SMILES: Cc1ccc(C(=O)N2CCC(F)(c3ccc(C#N)cc3)CC2)cc1NC(=O)NC1CCCOC1] | 0.037 |
| 001-71 | 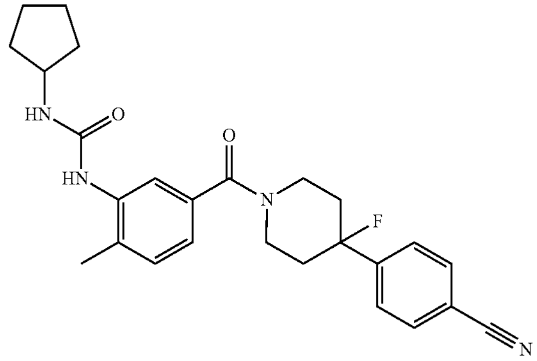 [SMILES: Cc1ccc(C(=O)N2CCC(F)(c3ccc(C#N)cc3)CC2)cc1NC(=O)NC1CCCC1] | 0.030 |

TABLE C-1-continued
| Fatty Acid Synthase Inhibitors | | |
|---|---|---|
| Cmpd No. | Structure | FASN $IC_{50}$ (μM) |
| 001-72 | 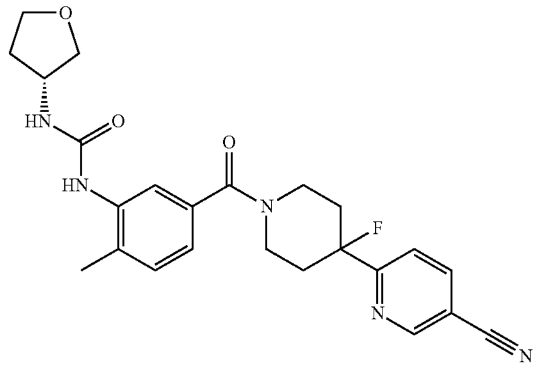 [SMILES: Cc1ccc(C(=O)N2CCC(F)(c3ccc(C#N)cn3)CC2)cc1NC(=O)N[C@@H]1CCOC1] | 0.200 |
| 001-73 | 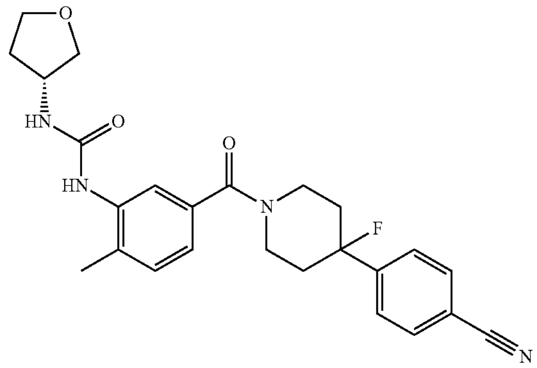 [SMILES: Cc1ccc(C(=O)N2CCC(F)(c3ccc(C#N)cc3)CC2)cc1NC(=O)N[C@@H]1CCOC1] | 0.040 |
| 001-74 | 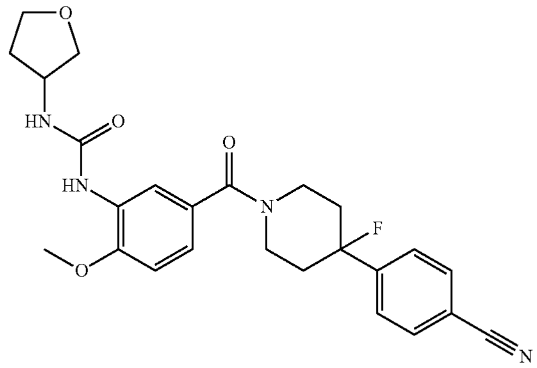 [SMILES: COc1ccc(C(=O)N2CCC(F)(c3ccc(C#N)cc3)CC2)cc1NC(=O)NC1CCOC1] | 0.120 |
| 001-75 | 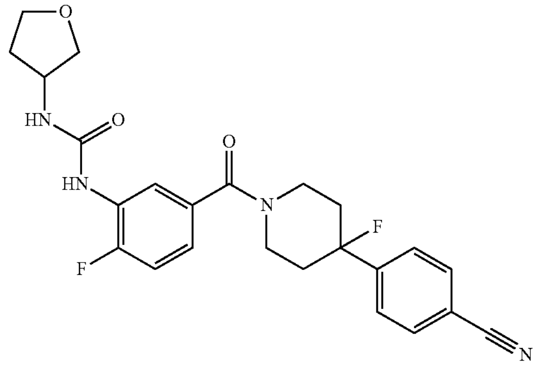 [SMILES: N#Cc1ccc(C2(F)CCN(C(=O)c3ccc(F)c(NC(=O)NC4CCOC4)c3)CC2)cc1] | 0.130 |

TABLE C-1-continued
| Fatty Acid Synthase Inhibitors | | |
|---|---|---|
| Cmpd No. | Structure | FASN $IC_{50}$ (μM) |
| 001-76 | 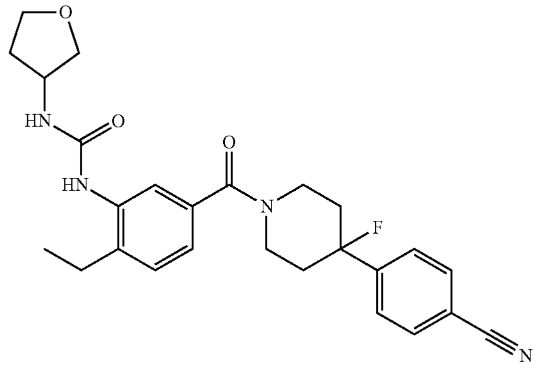 [SMILES: CCc1ccc(C(=O)N2CCC(F)(c3ccc(C#N)cc3)CC2)cc1NC(=O)NC1CCOC1] | 0.035 |
| 001-77 | 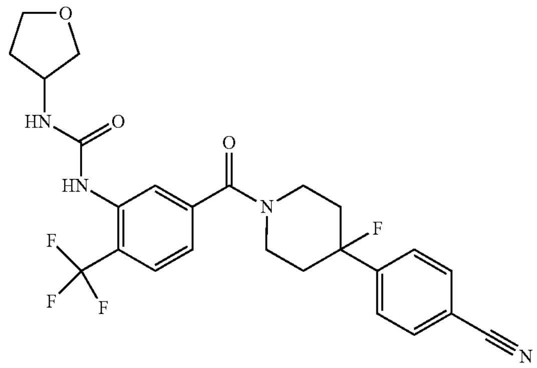 [SMILES: N#Cc1ccc(C2(F)CCN(C(=O)c3ccc(C(F)(F)F)c(NC(=O)NC4CCOC4)c3)CC2)cc1] | 0.080 |
| 001-78 | 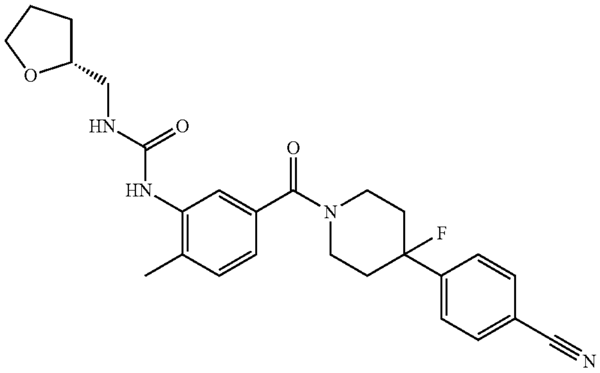 [SMILES: Cc1ccc(C(=O)N2CCC(F)(c3ccc(C#N)cc3)CC2)cc1NC(=O)NC[C@H]1CCCO1] | 0.035 |
| 001-79 | 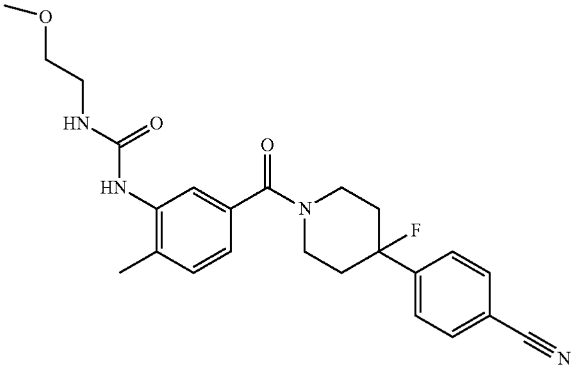 [SMILES: COCCNC(=O)Nc1cc(C(=O)N2CCC(F)(c3ccc(C#N)cc3)CC2)ccc1C] | 0.045 |

TABLE C-1-continued
| Fatty Acid Synthase Inhibitors | | |
|---|---|---|
| Cmpd No. | Structure | FASN $IC_{50}$ (μM) |
| 001-80 | 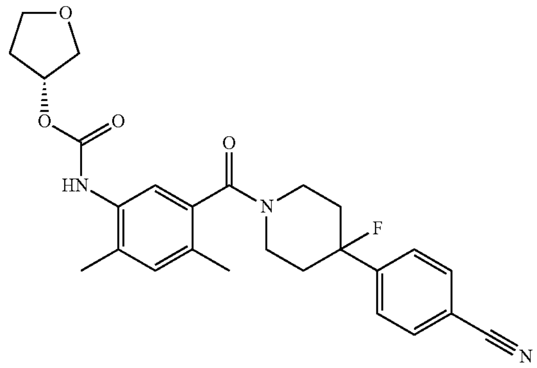 [SMILES: Cc1cc(C)c(C(=O)N2CCC(F)(c3ccc(C#N)cc3)CC2)cc1NC(=O)O[C@@H]1CCOC1] | 0.400 |
| 001-81 | 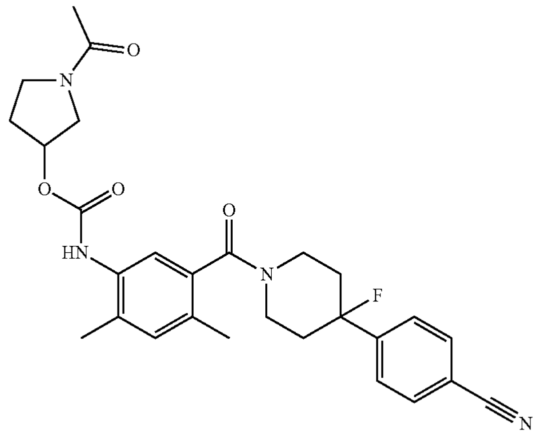 [SMILES: CC(=O)N1CCC(OC(=O)Nc2cc(C(=O)N3CCC(F)(c4ccc(C#N)cc4)CC3)c(C)cc2C)C1] | 0.200 |
| 001-82 | 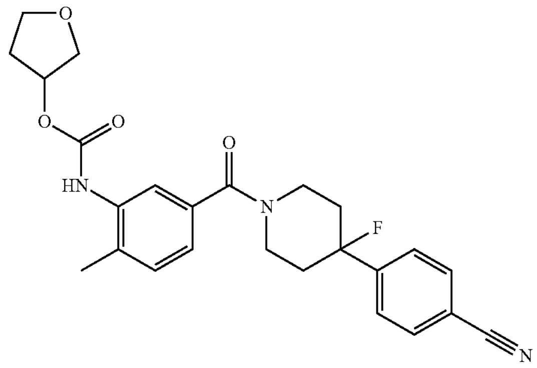 [SMILES: Cc1ccc(C(=O)N2CCC(F)(c3ccc(C#N)cc3)CC2)cc1NC(=O)OC1CCOC1] | 0.077 |
| 001-83 | 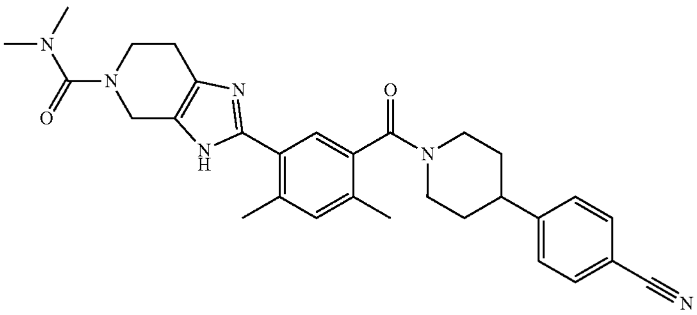 [SMILES: Cc1cc(C)c(-c2nc3c([nH]2)CN(C(=O)N(C)C)CC3)cc1C(=O)N1CCC(c2ccc(C#N)cc2)CC1] | 0.090 |

TABLE C-1-continued
| Fatty Acid Synthase Inhibitors | | |
|---|---|---|
| Cmpd No. | Structure | FASN $IC_{50}$ (μM) |
| 001-84 | 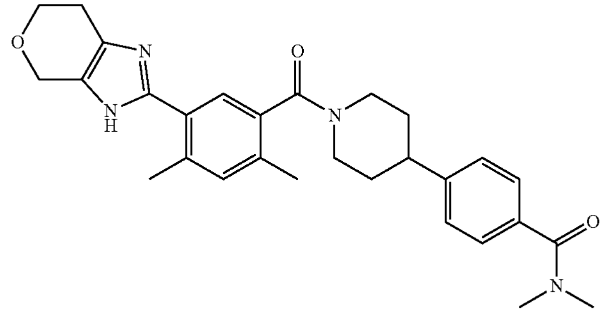 [SMILES: Cc1cc(C)c(-c2nc3c([nH]2)COCC3)cc1C(=O)N1CCC(c2ccc(C(=O)N(C)C)cc2)CC1] | 5.320 |
| 001-85 | 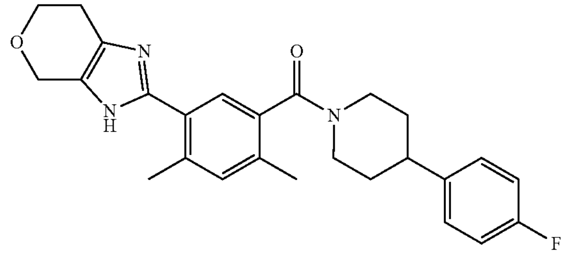 [SMILES: Cc1cc(C)c(-c2nc3c([nH]2)COCC3)cc1C(=O)N1CCC(c2ccc(F)cc2)CC1] | 1.450 |
| 001-86 | 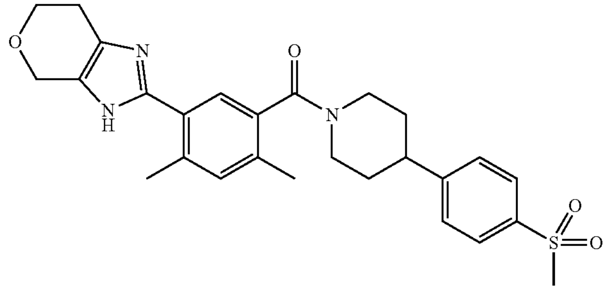 [SMILES: Cc1cc(C)c(-c2nc3c([nH]2)COCC3)cc1C(=O)N1CCC(c2ccc(S(C)(=O)=O)cc2)CC1] | 5.420 |
| 001-87 | 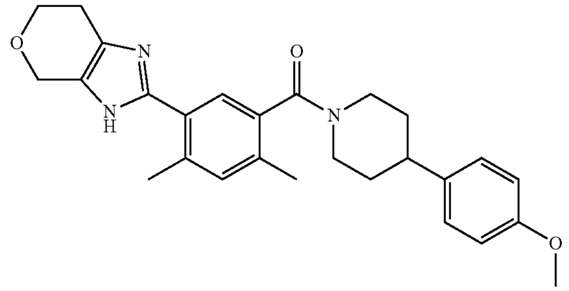 [SMILES: COc1ccc(C2CCN(C(=O)c3cc(-c4nc5c([nH]4)COCC5)c(C)cc3C)CC2)cc1] | 0.310 |
| 001-88 | 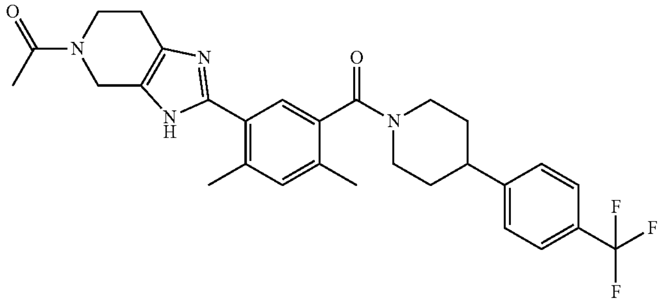 [SMILES: CC(=O)N1CCc2nc(-c3cc(C(=O)N4CCC(c5ccc(C(F)(F)F)cc5)CC4)c(C)cc3C)[nH]c2C1] | 0.040 |

TABLE C-1-continued
| Fatty Acid Synthase Inhibitors | | |
|---|---|---|
| Cmpd No. | Structure | FASN $IC_{50}$ (μM) |
| 001-89 | 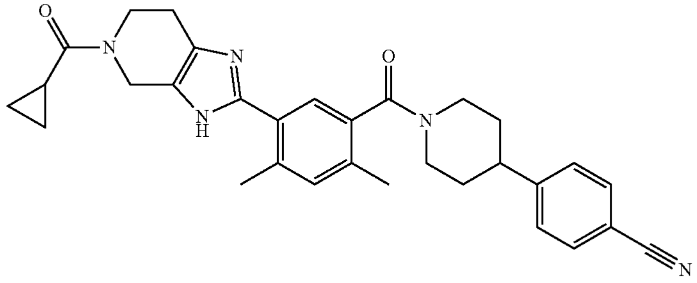 [SMILES: Cc1cc(C)c(-c2nc3c([nH]2)CN(C(=O)C2CC2)CC3)cc1C(=O)N1CCC(c2ccc(C#N)cc2)CC1] | 0.030 |
| 001-90 | 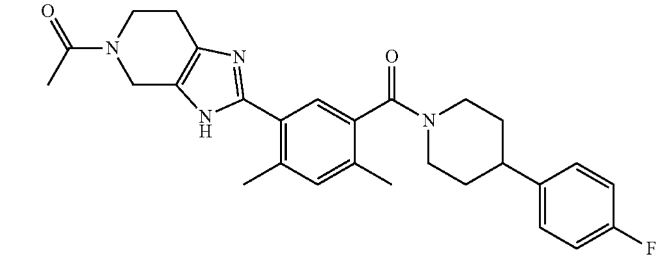 [SMILES: CC(=O)N1CCc2nc(-c3cc(C(=O)N4CCC(c5ccc(F)cc5)CC4)c(C)cc3C)[nH]c2C1] | 0.380 |
| 001-91 | 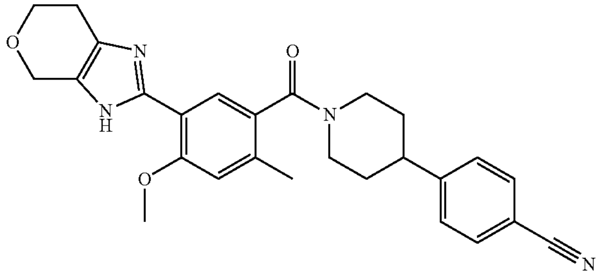 [SMILES: COc1cc(C)c(C(=O)N2CCC(c3ccc(C#N)cc3)CC2)cc1-c1nc2c([nH]1)COCC2] | 2.210 |
| 001-92 | 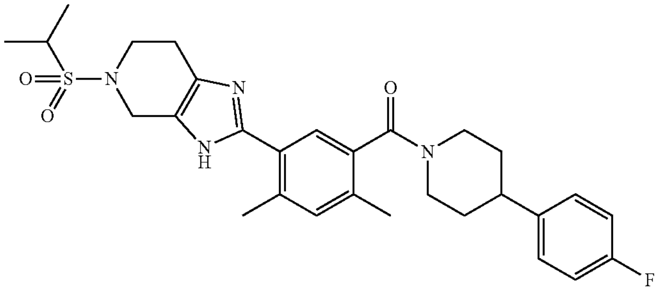 [SMILES: Cc1cc(C)c(-c2nc3c([nH]2)CN(S(=O)(=O)C(C)C)CC3)cc1C(=O)N1CCC(c2ccc(F)cc2)CC1] | 0.940 |
| 001-93 | 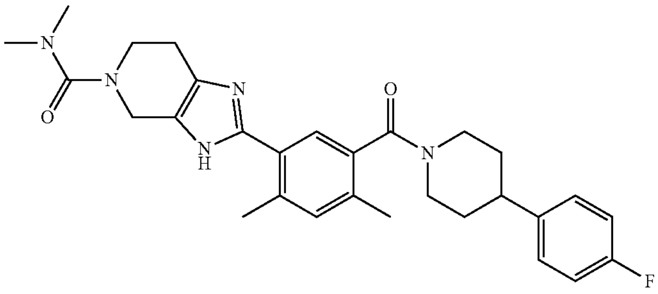 [SMILES: Cc1cc(C)c(-c2nc3c([nH]2)CN(C(=O)N(C)C)CC3)cc1C(=O)N1CCC(c2ccc(F)cc2)CC1] | 0.550 |

TABLE C-1-continued
| Fatty Acid Synthase Inhibitors | | |
|---|---|---|
| Cmpd No. | Structure | FASN $IC_{50}$ (μM) |
| 001-94 | 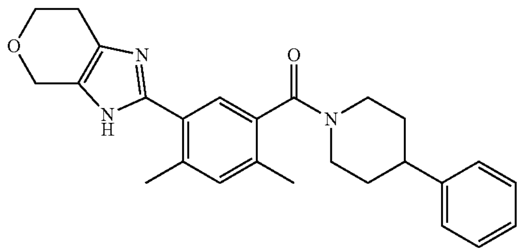 [SMILES: Cc1cc(C)c(-c2nc3c([nH]2)COCC3)cc1C(=O)N1CCC(c2ccccc2)CC1] | 5.260 |
| 001-95 | 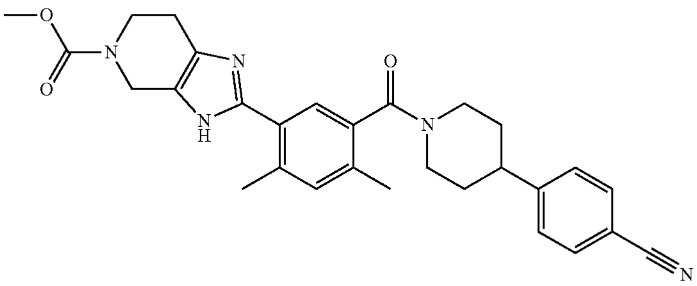 [SMILES: COC(=O)N1CCc2nc(-c3cc(C(=O)N4CCC(c5ccc(C#N)cc5)CC4)c(C)cc3C)[nH]c2C1] | 0.030 |
| 001-96 | 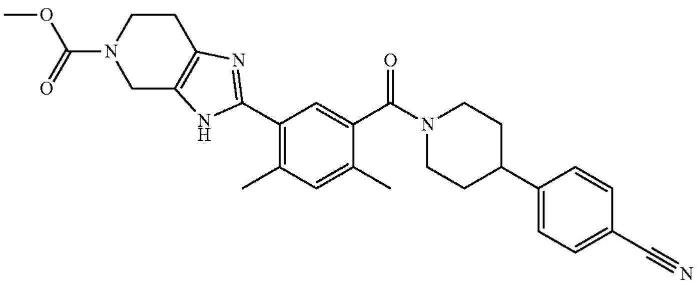 [SMILES: COC(=O)N1CCc2nc(-c3cc(C(=O)N4CCC(c5ccc(C#N)cc5)CC4)c(C)cc3C)[nH]c2C1] | 0.030 |
| 001-97 | 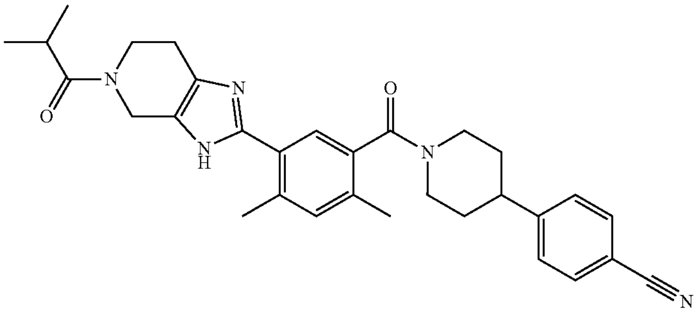 | 0.025 |
| 001-98 | 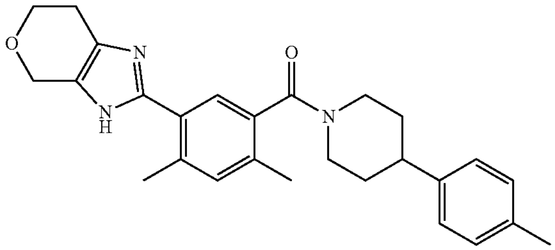 [SMILES: Cc1ccc(C2CCN(C(=O)c3cc(-c4nc5c([nH]4)COCC5)c(C)cc3C)CC2)cc1] | 0.900 |

TABLE C-1-continued
| Fatty Acid Synthase Inhibitors | | |
|---|---|---|
| Cmpd No. | Structure | FASN $IC_{50}$ (μM) |
| 001-99 | 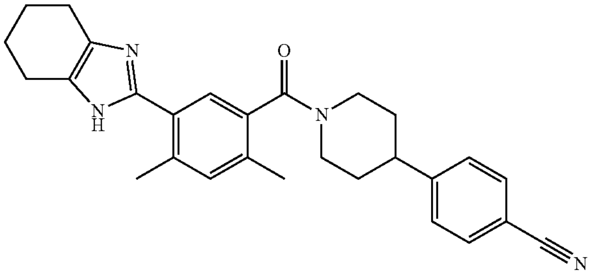 [SMILES: Cc1cc(C)c(-c2nc3c([nH]2)CCCC3)cc1C(=O)N1CCC(c2ccc(C#N)cc2)CC1] | 0.220 |
| 001-100 | 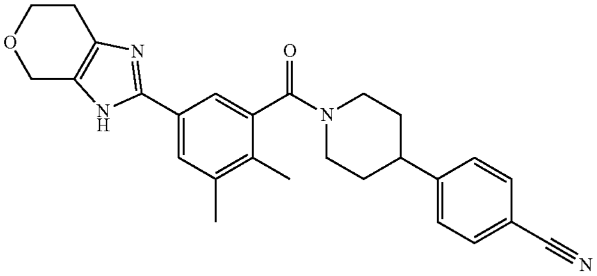 [SMILES: Cc1cc(-c2nc3c([nH]2)COCC3)cc(C(=O)N2CCC(c3ccc(C#N)cc3)CC2)c1C] | >50 |
| 001-101 | 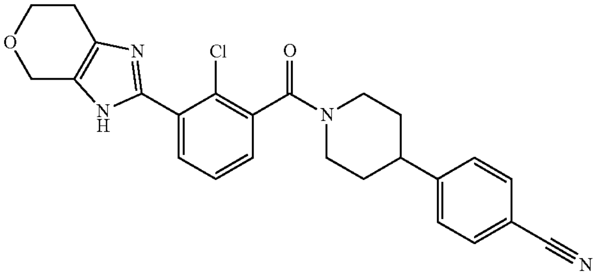 [SMILES: N#Cc1ccc(C2CCN(C(=O)c3cccc(-c4nc5c([nH]4)COCC5)c3Cl)CC2)cc1] | >50 |
| 001-102 | 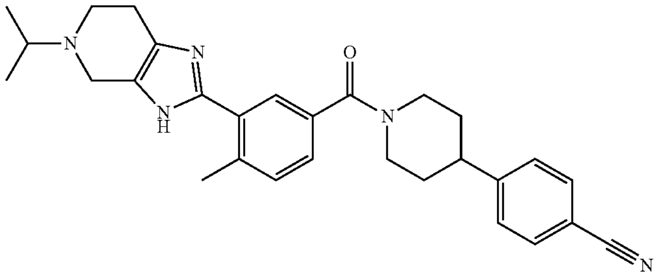 [SMILES: Cc1ccc(C(=O)N2CCC(c3ccc(C#N)cc3)CC2)cc1-c1nc2c([nH]1)CN(C(C)C)CC2] | 0.085 |
| 001-103 | 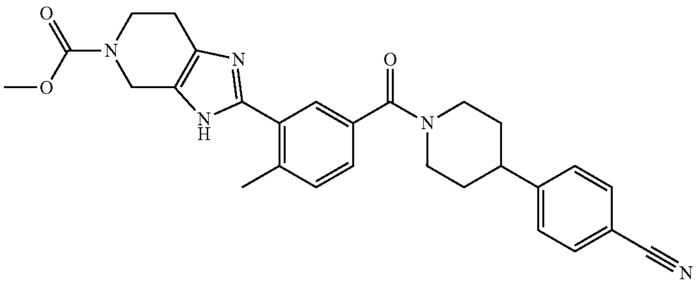 [SMILES: COC(=O)N1CCc2nc(-c3cc(C(=O)N4CCC(c5ccc(C#N)cc5)CC4)ccc3C)[nH]c2C1] | 0.035 |

TABLE C-1-continued
| Fatty Acid Synthase Inhibitors | | |
|---|---|---|
| Cmpd No. | Structure | FASN $IC_{50}$ (μM) |
| 001-104 | 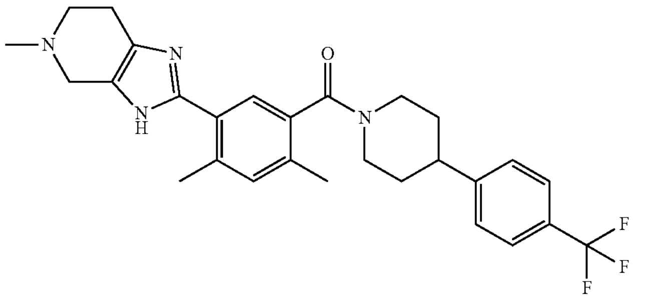 [SMILES: Cc1cc(C)c(-c2nc3c([nH]2)CN(C)CC3)cc1C(=O)N1CCC(c2ccc(C(F)(F)F)cc2)CC1] | 0.130 |
| 001-105 | 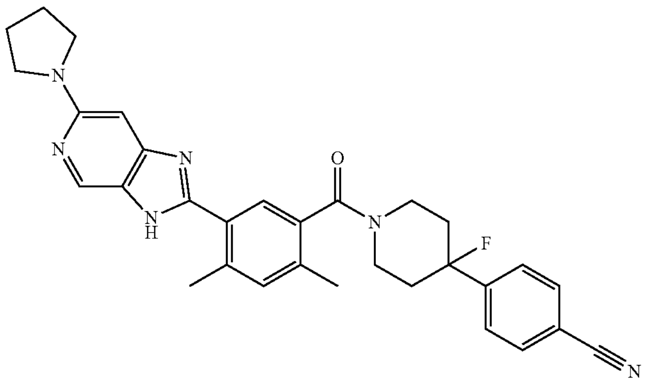 [SMILES: Cc1cc(C)c(-c2nc3cc(N4CCCC4)ncc3[nH]2)cc1C(=O)N1CCC(F)(c2ccc(C#N)cc2)CC1] | 0.015 |
| 001-106 | 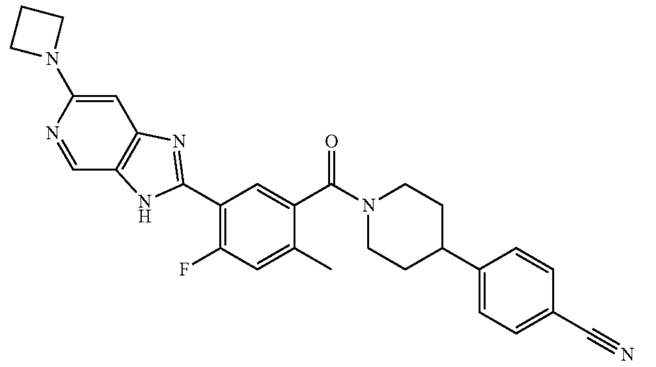 [SMILES: Cc1cc(F)c(-c2nc3cc(N4CCC4)ncc3[nH]2)cc1C(=O)N1CCC(c2ccc(C#N)cc2)CC1] | 0.900 |
| 001-107 | 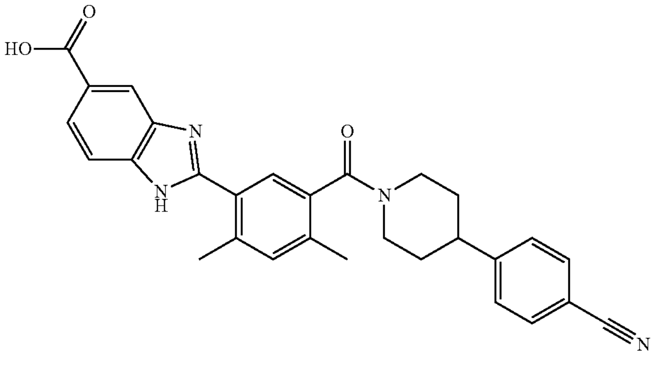 [SMILES: Cc1cc(C)c(-c2nc3cc(C(=O)O)ccc3[nH]2)cc1C(=O)N1CCC(c2ccc(C#N)cc2)CC1] | 1.490 |

TABLE C-1-continued
| Fatty Acid Synthase Inhibitors | | |
|---|---|---|
| Cmpd No. | Structure | FASN $IC_{50}$ (μM) |
| 001-108 | 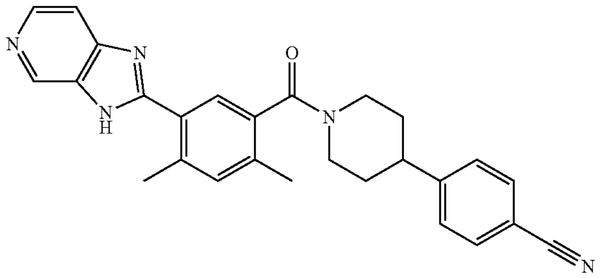 [SMILES: Cc1cc(C)c(-c2nc3ccncc3[nH]2)cc1C(=O)N1CCC(c2ccc(C#N)cc2)CC1] | 1.050 |
| 001-109 | 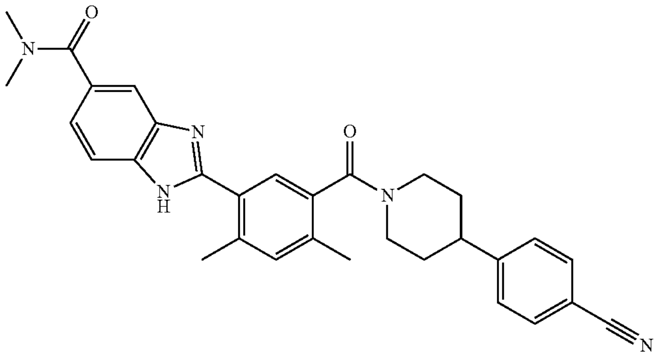 [SMILES: Cc1cc(C)c(-c2nc3cc(C(=O)N(C)C)ccc3[nH]2)cc1C(=O)N1CCC(c2ccc(C#N)cc2)CC1] | 0.250 |
| 001-110 | 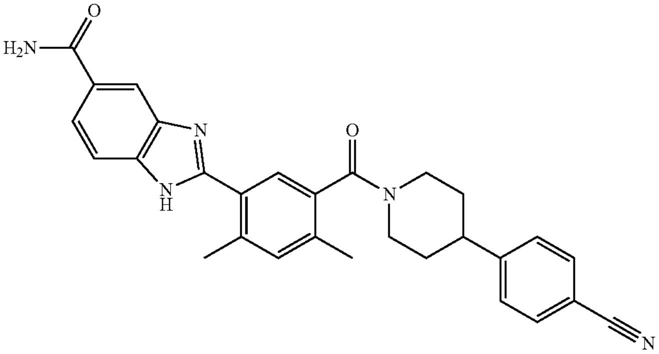 [SMILES: Cc1cc(C)c(-c2nc3cc(C(N)=O)ccc3[nH]2)cc1C(=O)N1CCC(c2ccc(C#N)cc2)CC1] | 0.280 |
| 001-111 | 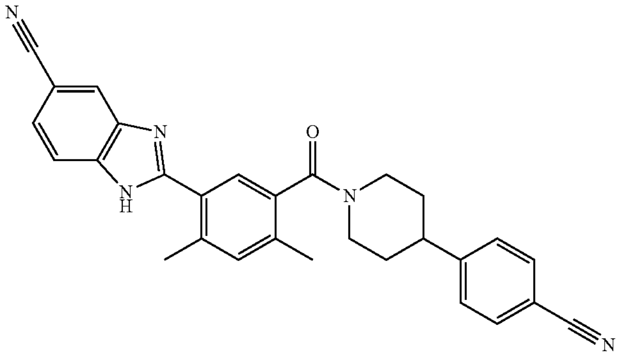 [SMILES: Cc1cc(C)c(-c2nc3cc(C#N)ccc3[nH]2)cc1C(=O)N1CCC(c2ccc(C#N)cc2)CC1] | 0.135 |

TABLE C-1-continued
| Cmpd No. | Structure | FASN IC$_{50}$ (μM) |
|---|---|---|
| | Fatty Acid Synthase Inhibitors | |
| 001-112 | 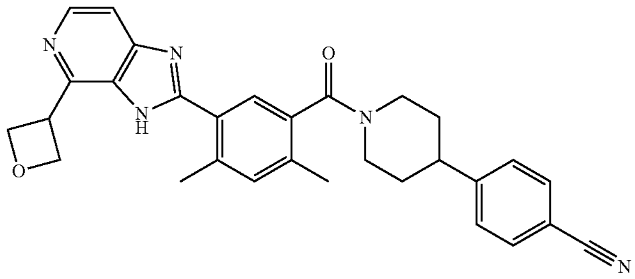 [SMILES: Cc1cc(C)c(-c2nc3ccnc(C4COC4)c3[nH]2)cc1C(=O)N1CCC(c2ccc(C#N)cc2)CC1] | 1.295 |
| 001-113 | 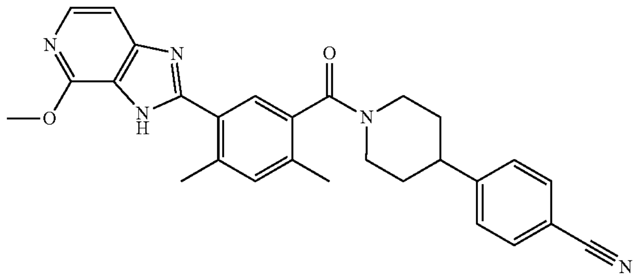 [SMILES: COc1nccc2nc(-c3cc(C(=O)N4CCC(c5ccc(C#N)cc5)CC4)c(C)cc3C)[nH]c12] | 0.130 |
| 001-114 | 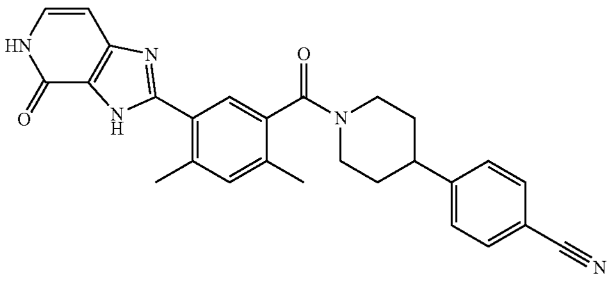 [SMILES: Cc1cc(C)c(-c2nc3cc[nH]c(=O)c3[nH]2)cc1C(=O)N1CCC(c2ccc(C#N)cc2)CC1] | 0.245 |
| 001-115 | 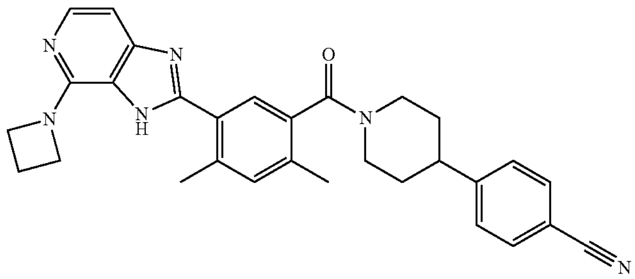 [SMILES: Cc1cc(C)c(-c2nc3ccnc(N4CCC4)c3[nH]2)cc1C(=O)N1CCC(c2ccc(C#N)cc2)CC1] | 0.480 |
| 001-116 | 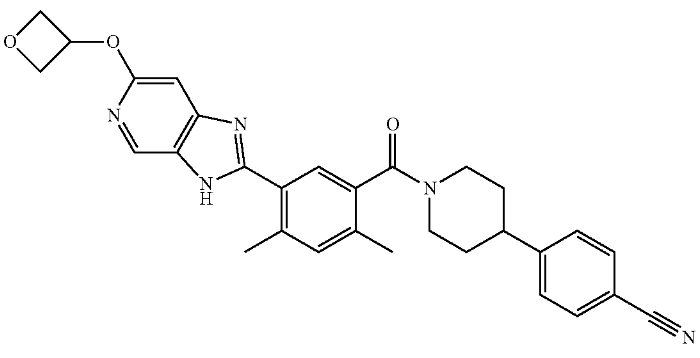 [SMILES: Cc1cc(C)c(-c2nc3cc(OC4COC4)ncc3[nH]2)cc1C(=O)N1CCC(c2ccc(C#N)cc2)CC1] | 0.090 |

TABLE C-1-continued
| Fatty Acid Synthase Inhibitors | | |
|---|---|---|
| Cmpd No. | Structure | FASN $IC_{50}$ (μM) |
| 001-117 | 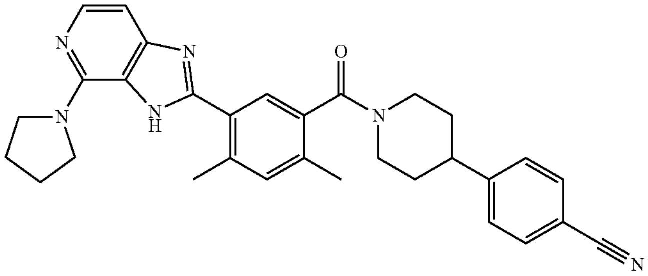 [SMILES: Cc1cc(C)c(-c2nc3ccnc(N4CCCC4)c3[nH]2)cc1C(=O)N1CCC(c2ccc(C#N)cc2)CC1] | 0.090 |
| 001-118 | 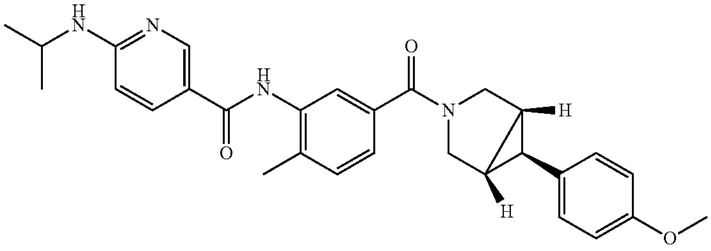 [SMILES: COc1ccc([C@H]2[C@@H]3CN(C(=O)c4ccc(C)c(NC(=O)c5ccc(NC(C)C)nc5)c4)C[C@@H]32)cc1] | 0.350 |
| 001-119 | 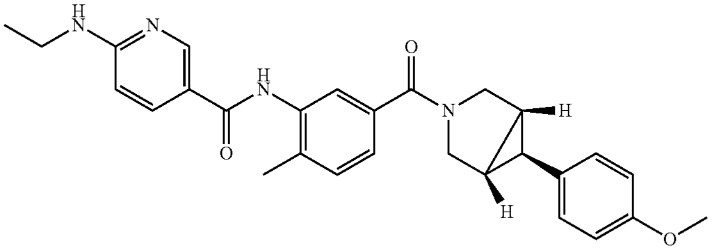 [SMILES: CCNc1ccc(C(=O)Nc2cc(C(=O)N3C[C@@H]4[C@H](C3)[C@H]4c3ccc(OC)cc3)ccc2C)cn1] | |
| 001-120 | 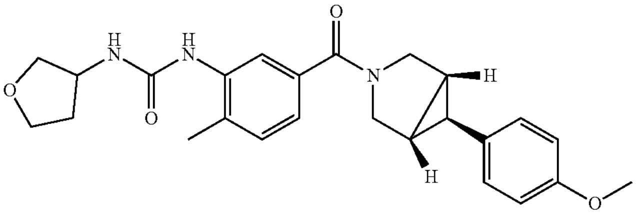 [SMILES: COc1ccc([C@H]2[C@@H]3CN(C(=O)c4ccc(C)c(NC(=O)NC5CCOC5)c4)C[C@@H]32)cc1] | 0.460 |
| 001-121 | 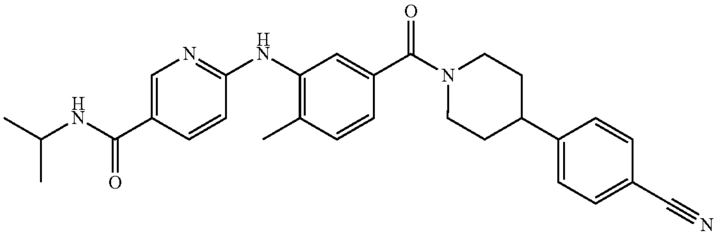 [SMILES: Cc1ccc(C(=O)N2CCC(c3ccc(C#N)cc3)CC2)cc1Nc1ccc(C(=O)NC(C)C)cn1] | 2.300 |
| 001-122 | 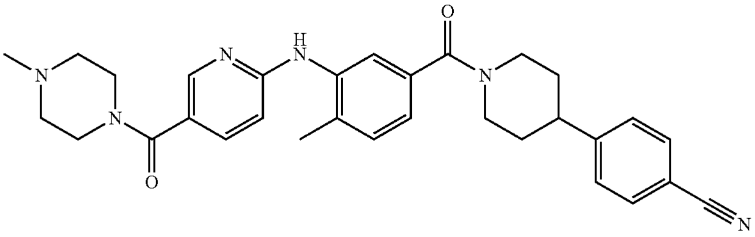 [SMILES: Cc1ccc(C(=O)N2CCC(c3ccc(C#N)cc3)CC2)cc1Nc1ccc(C(=O)N2CCN(C)CC2)cn1] | 0.890 |

TABLE C-1-continued
| Fatty Acid Synthase Inhibitors | | |
|---|---|---|
| Cmpd No. | Structure | FASN $IC_{50}$ (μM) |
| 001-123 | 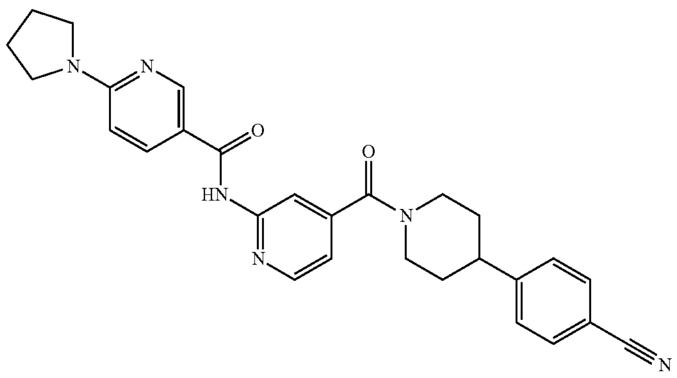 [SMILES: N#Cc1ccc(C2CCN(C(=O)c3ccnc(NC(=O)c4ccc(N5CCCC5)nc4)c3)CC2)cc1] | 0.690 |
| 001-124 | 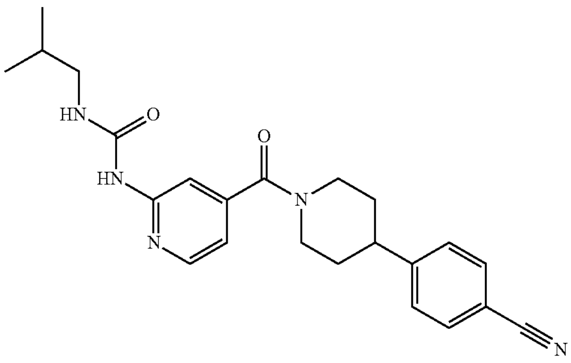 [SMILES: CC(C)CNC(=O)Nc1cc(C(=O)N2CCC(c3ccc(C#N)cc3)CC2)ccn1] | 32.880 |
| 001-125 | 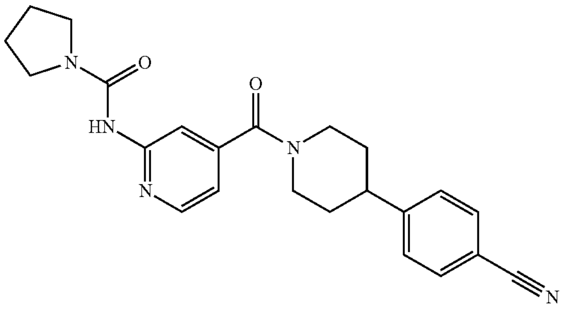 [SMILES: N#Cc1ccc(C2CCN(C(=O)c3ccnc(NC(=O)N4CCCC4)c3)CC2)cc1] | >50 |
| 001-126 | 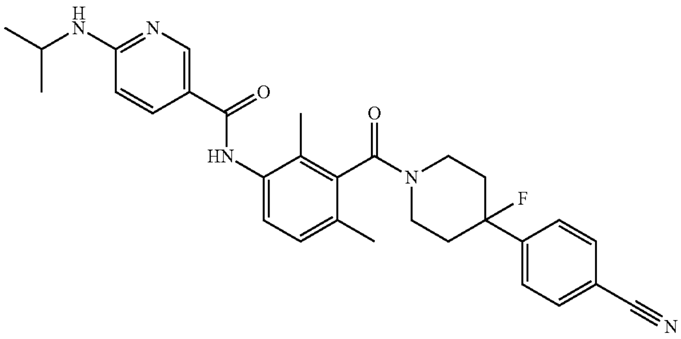 [SMILES: Cc1ccc(NC(=O)c2ccc(NC(C)C)nc2)c(C)c1C(=O)N1CCC(F)(c2ccc(C#N)cc2)CC1] | >50 |

TABLE C-1-continued
| Fatty Acid Synthase Inhibitors | | |
|---|---|---|
| Cmpd No. | Structure | FASN $IC_{50}$ (μM) |
| 001-127 | 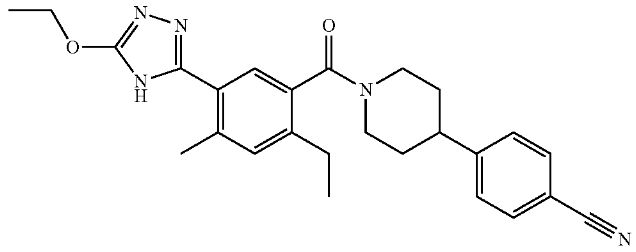 [SMILES: CCOc1nnc(-c2cc(C(=O)N3CCC(c4ccc(C#N)cc4)CC3)c(CC)cc2C)[nH]1] | 0.730 |
| 001-128 | 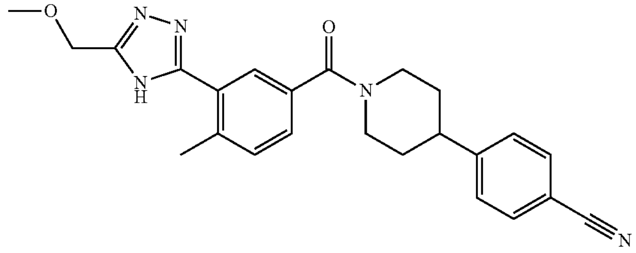 [SMILES: COCc1nnc(-c2cc(C(=O)N3CCC(c4ccc(C#N)cc4)CC3)ccc2C)[nH]1] | 2.260 |
| 001-129 | 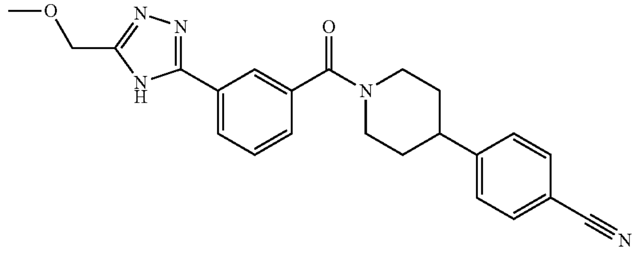 [SMILES: COCc1nnc(-c2cccc(C(=O)N3CCC(c4ccc(C#N)cc4)CC3)c2)[nH]1] | >50 |
| 001-130 | 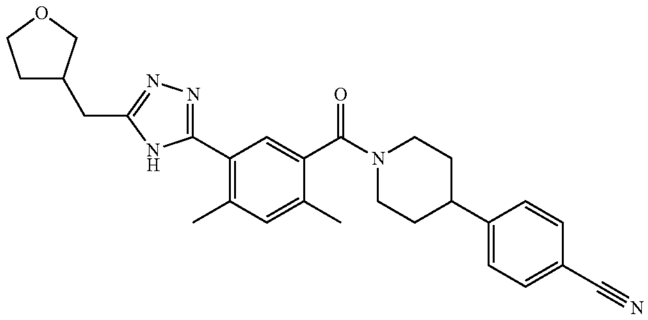 [SMILES: Cc1cc(C)c(-c2nnc(CC3CCOC3)[nH]2)cc1C(=O)N1CCC(c2ccc(C#N)cc2)CC1] | 0.300 |
| 001-131 | 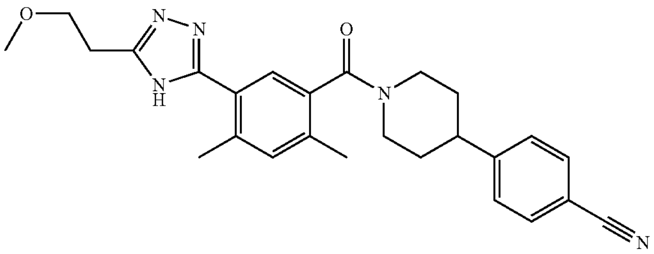 [SMILES: COCCc1nnc(-c2cc(C(=O)N3CCC(c4ccc(C#N)cc4)CC3)c(C)cc2C)[nH]1] | 0.220 |

TABLE C-1-continued
| Fatty Acid Synthase Inhibitors | | |
|---|---|---|
| Cmpd No. | Structure | FASN $IC_{50}$ (μM) |
| 001-132 | 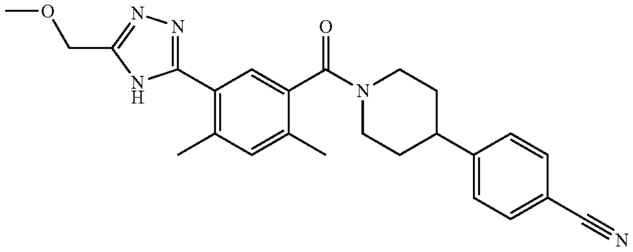 [SMILES: COCc1nnc(-c2cc(C(=O)N3CCC(c4ccc(C#N)cc4)CC3)c(C)cc2C)[nH]1] | 0.450 |
| 001-133 | 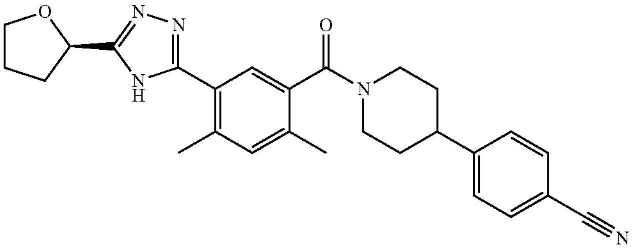 [SMILES: Cc1cc(C)c(-c2nnc([C@H]3CCCO3)[nH]2)cc1C(=O)N1CCC(c2ccc(C#N)cc2)CC1] | 0.790 |
| 001-134 | 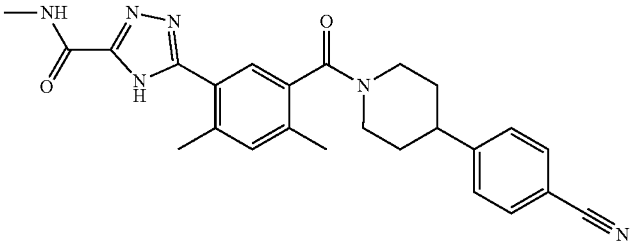 [SMILES: CNC(=O)c1nnc(-c2cc(C(=O)N3CCC(c4ccc(C#N)cc4)CC3)c(C)cc2C)[nH]1] | 1.330 |
| 001-135 | 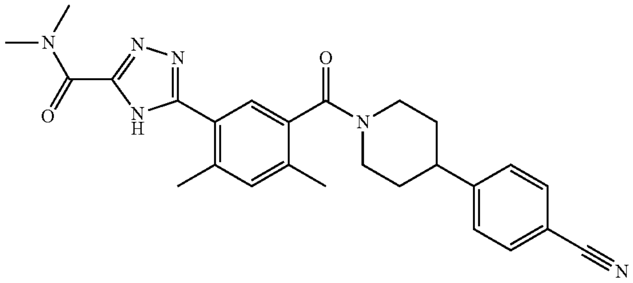 [SMILES: Cc1cc(C)c(-c2nnc(C(=O)N(C)C)[nH]2)cc1C(=O)N1CCC(c2ccc(C#N)cc2)CC1] | 2.040 |
| 001-136 | 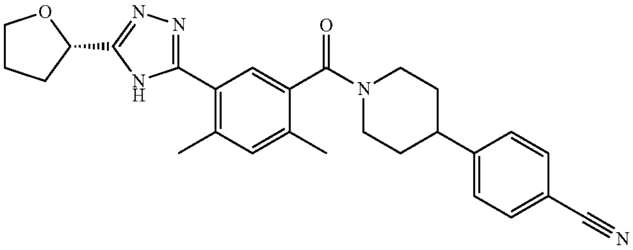 [SMILES: Cc1cc(C)c(-c2nnc([C@@H]3CCCO3)[nH]2)cc1C(=O)N1CCC(c2ccc(C#N)cc2)CC1] | 0.240 |

TABLE C-1-continued
| Fatty Acid Synthase Inhibitors | | |
|---|---|---|
| Cmpd No. | Structure | FASN $IC_{50}$ (μM) |
| 001-137 | 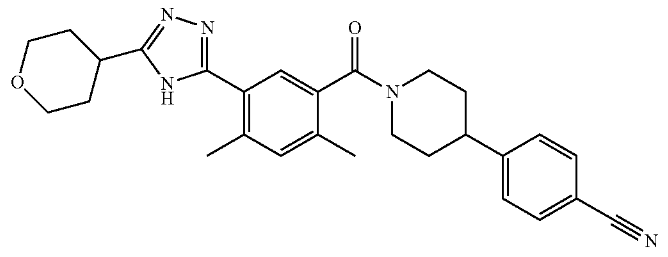 [SMILES: Cc1cc(C)c(-c2nnc(C3CCOCC3)[nH]2)cc1C(=O)N1CCC(c2ccc(C#N)cc2)CC1] | 0.500 |
| 001-138 | 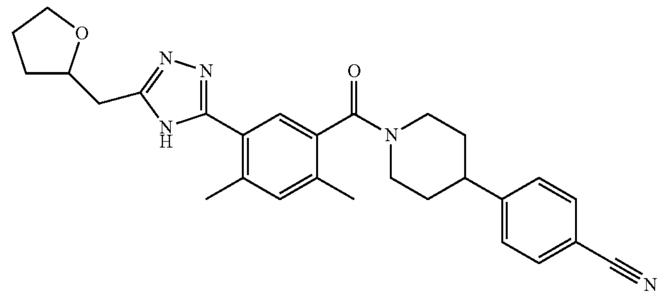 [SMILES: Cc1cc(C)c(-c2nnc(CC3CCCO3)[nH]2)cc1C(=O)N1CCC(c2ccc(C#N)cc2)CC1] | 0.640 |
| 001-139 | 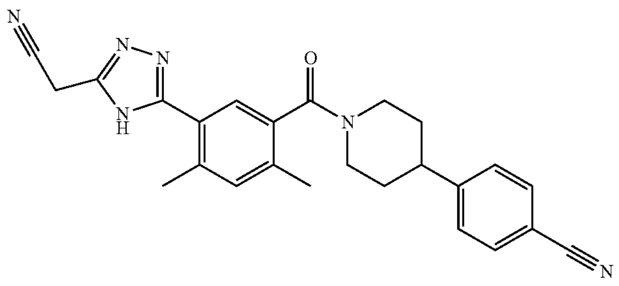 [SMILES: Cc1cc(C)c(-c2nnc(CC#N)[nH]2)cc1C(=O)N1CCC(c2ccc(C#N)cc2)CC1] | 1.210 |
| 001-140 | 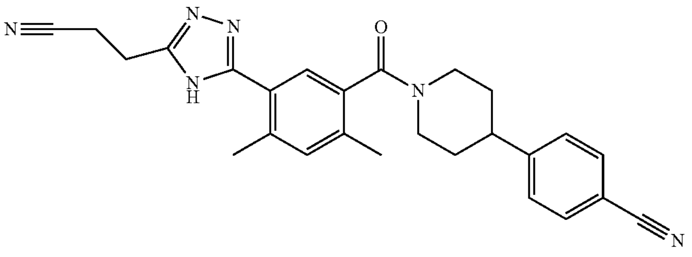 [SMILES: Cc1cc(C)c(-c2nnc(CCC#N)[nH]2)cc1C(=O)N1CCC(c2ccc(C#N)cc2)CC1] | 0.380 |
| 001-141 | 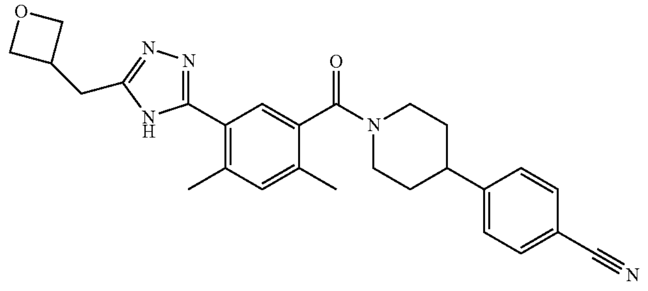 [SMILES: Cc1cc(C)c(-c2nnc(CC3COC3)[nH]2)cc1C(=O)N1CCC(c2ccc(C#N)cc2)CC1] | >50 |

TABLE C-1-continued
| Fatty Acid Synthase Inhibitors | | |
|---|---|---|
| Cmpd No. | Structure | FASN $IC_{50}$ (μM) |
| 001-142 | 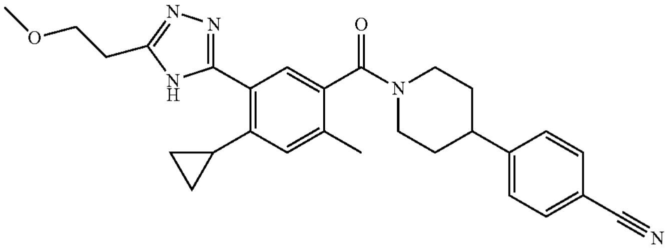 [SMILES: COCCc1nnc(-c2cc(C(=O)N3CCC(c4ccc(C#N)cc4)CC3)c(C)cc2C2CC2)[nH]1] | 0.140 |
| 001-143 | 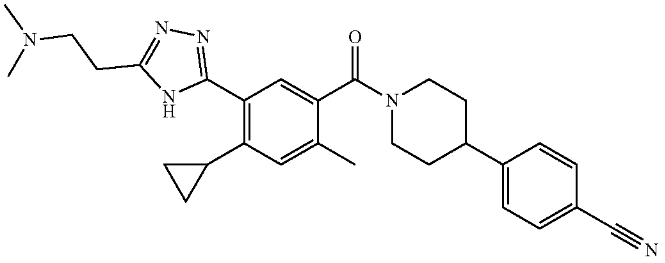 [SMILES: Cc1cc(C2CC2)c(-c2nnc(CCN(C)C)[nH]2)cc1C(=O)N1CCC(c2ccc(C#N)cc2)CC1] | 0.175 |
| 001-144 | 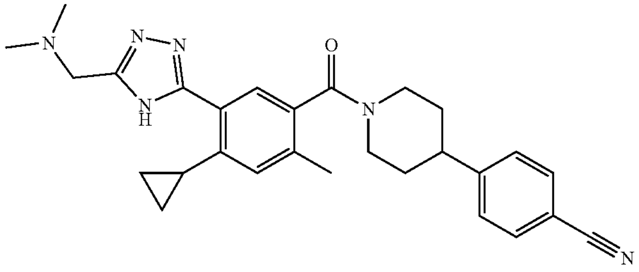 [SMILES: Cc1cc(C2CC2)c(-c2nnc(CN(C)C)[nH]2)cc1C(=O)N1CCC(c2ccc(C#N)cc2)CC1] | 0.320 |
| 001-145 | 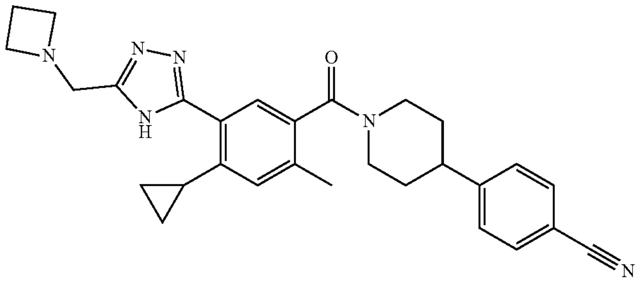 [SMILES: Cc1cc(C2CC2)c(-c2nnc(CN3CCC3)[nH]2)cc1C(=O)N1CCC(c2ccc(C#N)cc2)CC1] | 0.820 |
| 001-146 | 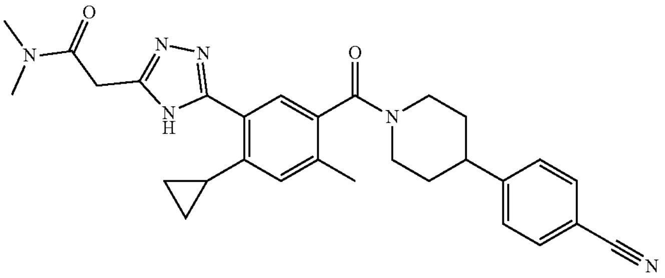 [SMILES: Cc1cc(C2CC2)c(-c2nnc(CC(=O)N(C)C)[nH]2)cc1C(=O)N1CCC(c2ccc(C#N)cc2)CC1] | 0.260 |

TABLE C-1-continued
| Fatty Acid Synthase Inhibitors | | |
|---|---|---|
| Cmpd No. | Structure | FASN $IC_{50}$ (μM) |
| 001-147 | 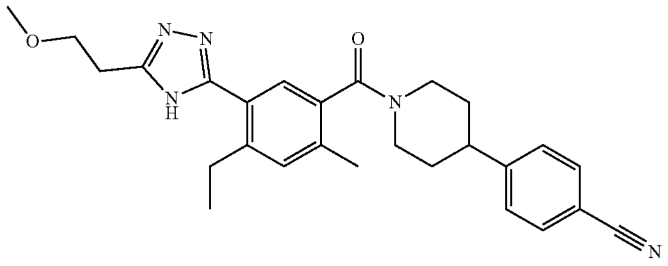 [SMILES: CCc1cc(C)c(C(=O)N2CCC(c3ccc(C#N)cc3)CC2)cc1-c1nnc(CCOC)[nH]1] | 0.250 |
| 001-148 | 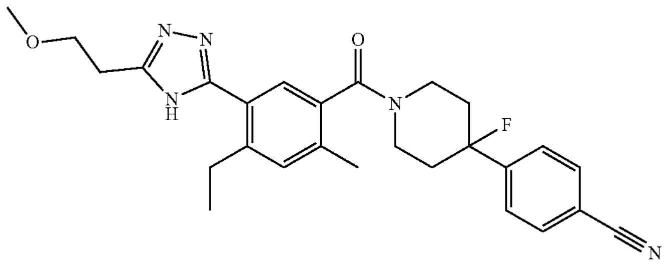 [SMILES: CCc1cc(C)c(C(=O)N2CCC(F)(c3ccc(C#N)cc3)CC2)cc1-c1nnc(CCOC)[nH]1] | 0.180 |
| 001-149 | 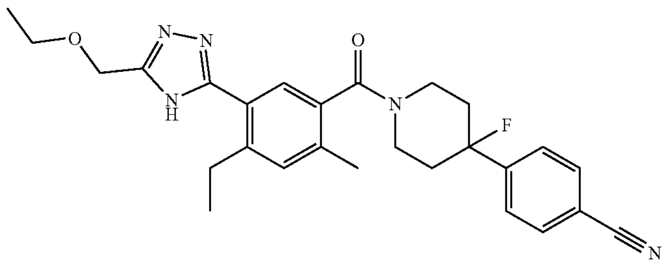 [SMILES: CCOCc1nnc(-c2cc(C(=O)N3CCC(F)(c4ccc(C#N)cc4)CC3)c(C)cc2CC)[nH]1] | 0.240 |
| 001-150 | 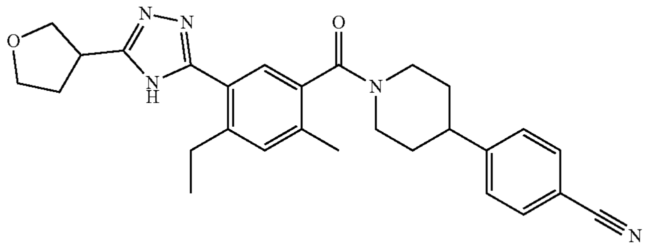 [SMILES: CCc1cc(C)c(C(=O)N2CCC(c3ccc(C#N)cc3)CC2)cc1-c1nnc(C2CCOC2)[nH]1] | 0.300 |
| 001-151 | 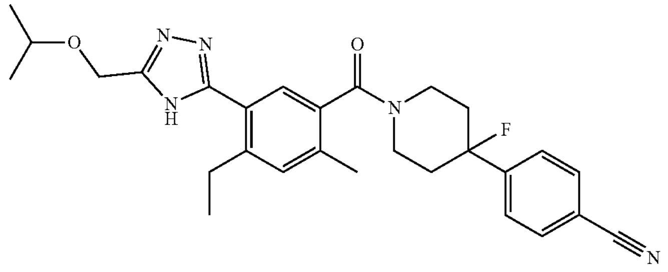 [SMILES: CCc1cc(C)c(C(=O)N2CCC(F)(c3ccc(C#N)cc3)CC2)cc1-c1nnc(COC(C)C)[nH]1] | 0.420 |

TABLE C-1-continued
| Cmpd No. | Structure | FASN $IC_{50}$ (μM) |
|---|---|---|
| | Fatty Acid Synthase Inhibitors | |
| 001-152 | 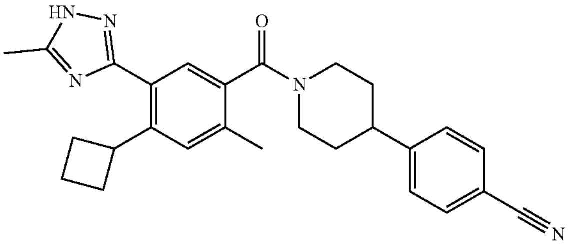 [SMILES: Cc1nc(-c2cc(C(=O)N3CCC(c4ccc(C#N)cc4)CC3)c(C)cc2C2CCC2)n[nH]1] | 0.052 |
| 001-153 | 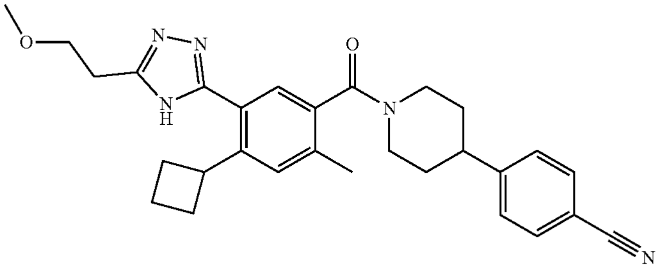 [SMILES: COCCc1nnc(-c2cc(C(=O)N3CCC(c4ccc(C#N)cc4)CC3)c(C)cc2C2CCC2)[nH]1] | 0.055 |
| 001-154 | 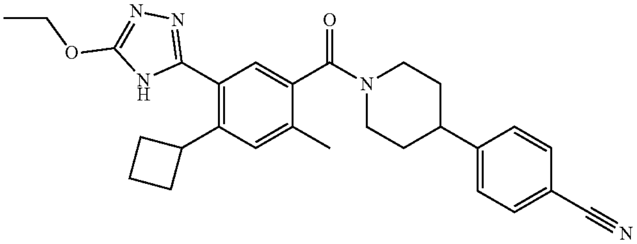 [SMILES: CCOc1nnc(-c2cc(C(=O)N3CCC(c4ccc(C#N)cc4)CC3)c(C)cc2C2CCC2)[nH]1] | 0.105 |
| 001-155 | 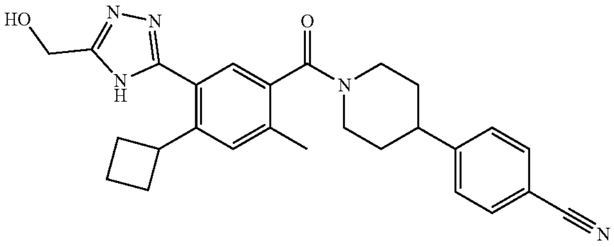 [SMILES: Cc1cc(C2CCC2)c(-c2nnc(CO)[nH]2)cc1C(=O)N1CCC(c2ccc(C#N)cc2)CC1] | 0.20 |
| 001-156 | 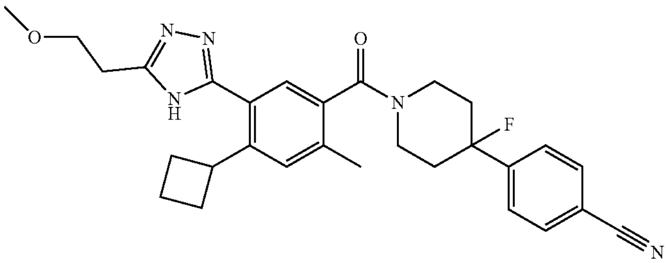 [SMILES: COCCc1nnc(-c2cc(C(=O)N3CCC(F)(c4ccc(C#N)cc4)CC3)c(C)cc2C2CCC2)[nH]1] | 0.030 |

TABLE C-1-continued
| Fatty Acid Synthase Inhibitors | | |
|---|---|---|
| Cmpd No. | Structure | FASN $IC_{50}$ (μM) |
| 001-157 | 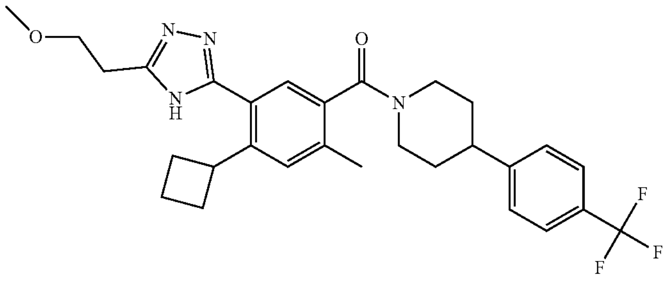 [SMILES: COCCc1nnc(-c2cc(C(=O)N3CCC(c4ccc(C(F)(F)F)cc4)CC3)c(C)cc2C2CCC2)[nH]1] | 0.090 |
| 001-158 | 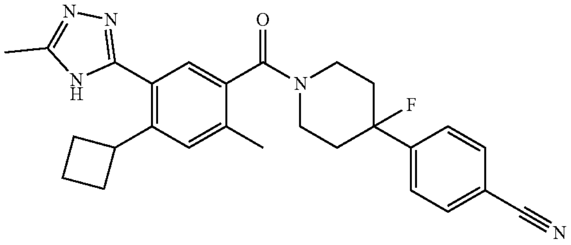 [SMILES: Cc1nnc(-c2cc(C(=O)N3CCC(F)(c4ccc(C#N)cc4)CC3)c(C)cc2C2CCC2)[nH]1] | 0.057 |
| 001-159 | 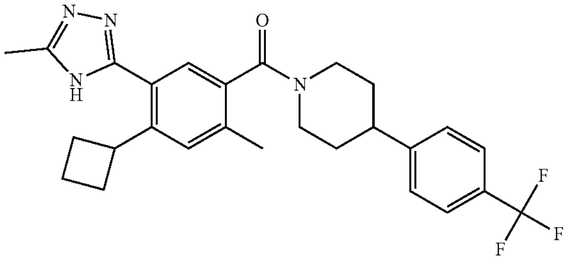 [SMILES: Cc1nnc(-c2cc(C(=O)N3CCC(c4ccc(C(F)(F)F)cc4)CC3)c(C)cc2C2CCC2)[nH]1] | 0.070 |
| 001-160 | 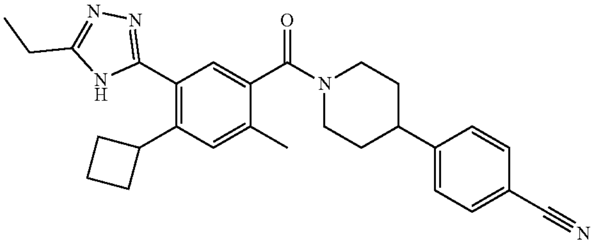 [SMILES: CCc1nnc(-c2cc(C(=O)N3CCC(c4ccc(C#N)cc4)CC3)c(C)cc2C2CCC2)[nH]1] | 0.055 |
| 001-161 | 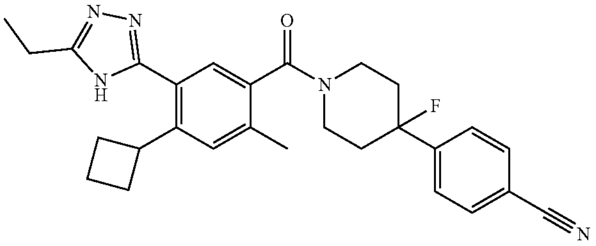 [SMILES: CCc1nnc(-c2cc(C(=O)N3CCC(F)(c4ccc(C#N)cc4)CC3)c(C)cc2C2CCC2)[nH]1] | 0.040 |

TABLE C-1-continued
| Cmpd No. | Fatty Acid Synthase Inhibitors Structure | FASN $IC_{50}$ (μM) |
|---|---|---|
| 001-162 | 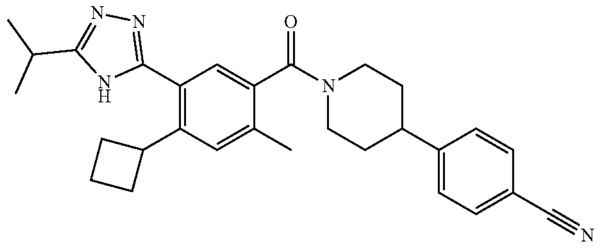 [SMILES: Cc1cc(C2CCC2)c(-c2nnc(C(C)C)[nH]2)cc1C(=O)N1CCC(c2ccc(C#N)cc2)CC1] | 0.115 |
| 001-163 | 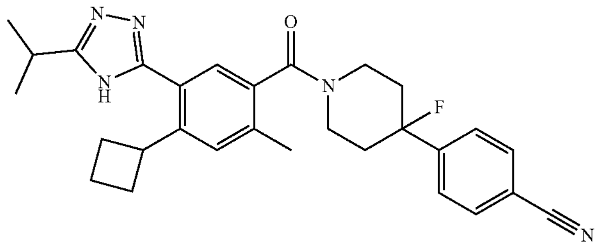 [SMILES: Cc1cc(C2CCC2)c(-c2nnc(C(C)C)[nH]2)cc1C(=O)N1CCC(F)(c2ccc(C#N)cc2)CC1] | 0.135 |
| 001-164 | 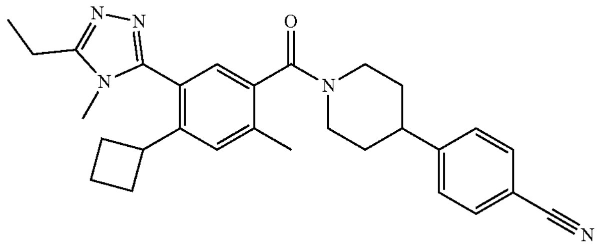 [SMILES: CCc1nnc(-c2cc(C(=O)N3CCC(c4ccc(C#N)cc4)CC3)c(C)cc2C2CCC2)n1C] | >50 |
| 001-165 | 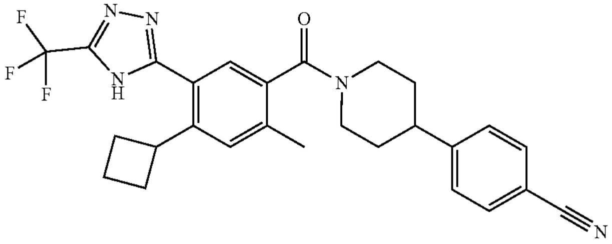 [SMILES: Cc1cc(C2CCC2)c(-c2nnc(C(F)(F)F)[nH]2)cc1C(=O)N1CCC(c2ccc(C#N)cc2)CC1] | 1.000 |
| 001-166 | 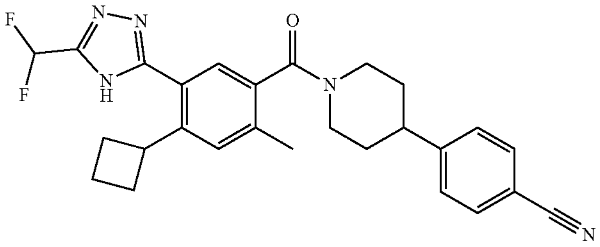 [SMILES: Cc1cc(C2CCC2)c(-c2nnc(C(F)F)[nH]2)cc1C(=O)N1CCC(c2ccc(C#N)cc2)CC1] | 0.160 |
| 001-167 | 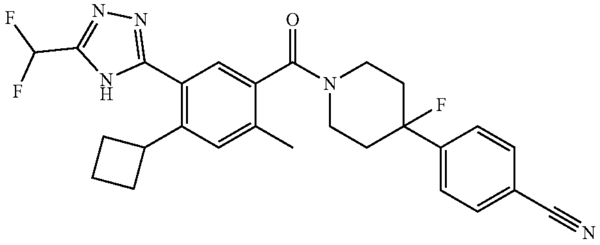 [SMILES: Cc1cc(C2CCC2)c(-c2nnc(C(F)F)[nH]2)cc1C(=O)N1CCC(F)(c2ccc(C#N)cc2)CC1] | 0.125 |

TABLE C-1-continued
Fatty Acid Synthase Inhibitors
| Cmpd No. | Structure | FASN $IC_{50}$ (μM) |
| --- | --- | --- |
| 001-168 | 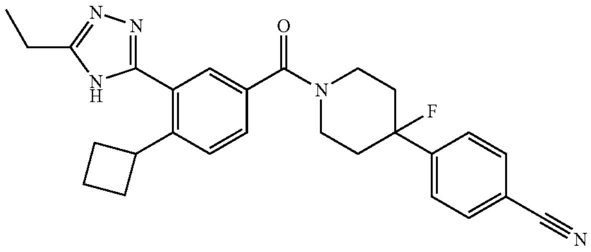 [SMILES: CCc1nnc(-c2cc(C(=O)N3CCC(F)(c4ccc(C#N)cc4)CC3)ccc2C2CCC2)[nH]1] | 0.060 |
| 001-169 | 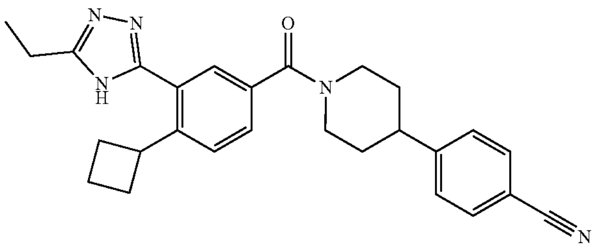 [SMILES: CCc1nnc(-c2cc(C(=O)N3CCC(c4ccc(C#N)cc4)CC3)ccc2C2CCC2)[nH]1] | 0.090 |
| 001-170 | 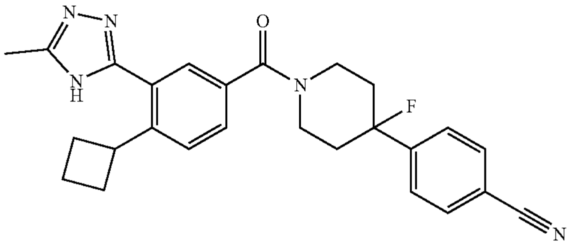 [SMILES: Cc1nnc(-c2cc(C(=O)N3CCC(F)(c4ccc(C#N)cc4)CC3)ccc2C2CCC2)[nH]1] | 0.090 |
| 001-171 | 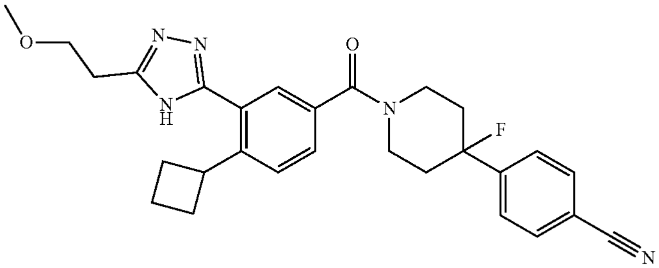 [SMILES: COCCc1nnc(-c2cc(C(=O)N3CCC(F)(c4ccc(C#N)cc4)CC3)ccc2C2CCC2)[nH]1] | 0.070 |
| 001-172 | 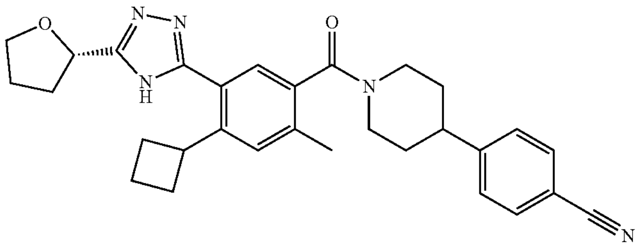 [SMILES: Cc1cc(C2CCC2)c(-c2nnc([C@@H]3CCCO3)[nH]2)cc1C(=O)N1CCC(c2ccc(C#N)cc2)CC1] | 0.140 |

TABLE C-1-continued
| Fatty Acid Synthase Inhibitors | | |
|---|---|---|
| Cmpd No. | Structure | FASN $IC_{50}$ (μM) |
| 001-173 | 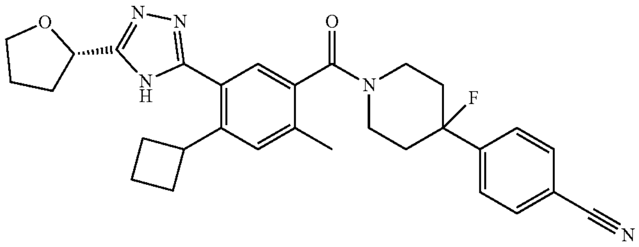 [SMILES: Cc1cc(C2CCC2)c(-c2nnc([C@@H]3CCCO3)[nH]2)cc1C(=O)N1CCC(F)(c2ccc(C#N)cc2)CC1] | 0.240 |
| 001-174 | 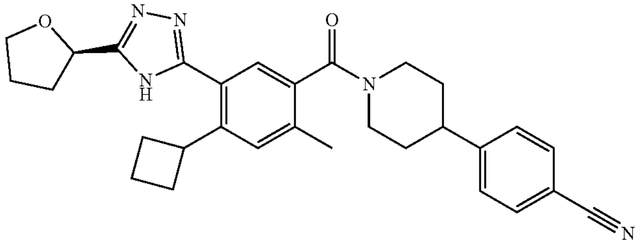 [SMILES: Cc1cc(C2CCC2)c(-c2nnc([C@H]3CCCO3)[nH]2)cc1C(=O)N1CCC(c2ccc(C#N)cc2)CC1] | 0.200 |
| 001-175 | 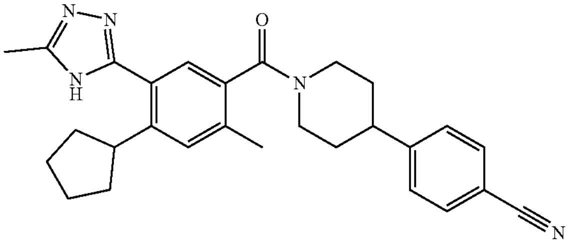 [SMILES: Cc1nnc(-c2cc(C(=O)N3CCC(c4ccc(C#N)cc4)CC3)c(C)cc2C2CCCC2)[nH]1] | 0.310 |
| 001-176 | 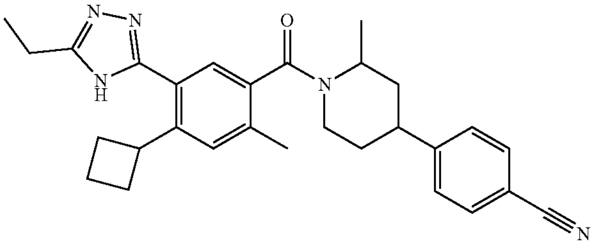 [SMILES: CCc1nnc(-c2cc(C(=O)N3CCC(c4ccc(C#N)cc4)CC3C)c(C)cc2C2CCC2)[nH]1] | 5.990 |
| 001-177 | 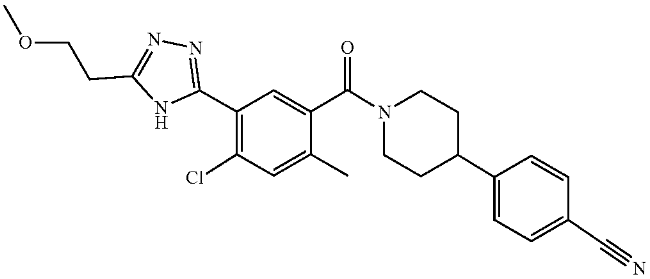 | 2.110 |

TABLE C-1-continued
| Fatty Acid Synthase Inhibitors | | |
|---|---|---|
| Cmpd No. | Structure | FASN $IC_{50}$ (μM) |
| 001-178 | 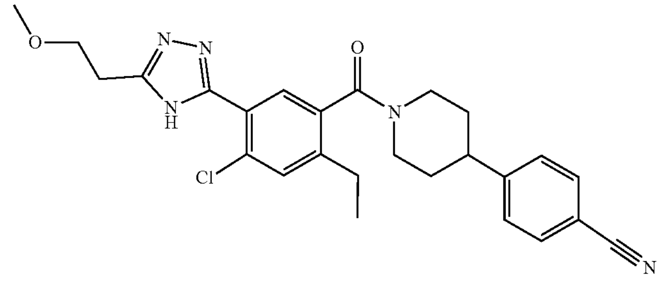 [SMILES: CCc1cc(Cl)c(-c2nnc(CCOC)[nH]2)cc1C(=O)N1CCC(c2ccc(C#N)cc2)CC1] | 0.555 |
| 001-179 | 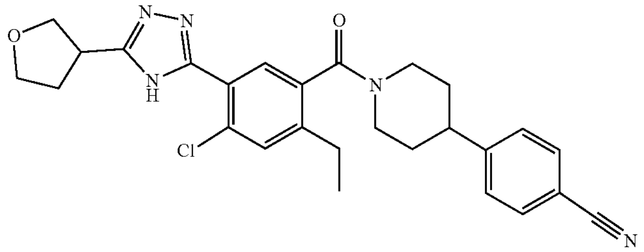 [SMILES: CCc1cc(Cl)c(-c2nnc(C3CCOC3)[nH]2)cc1C(=O)N1CCC(c2ccc(C#N)cc2)CC1] | 1.260 |
| 001-180 | 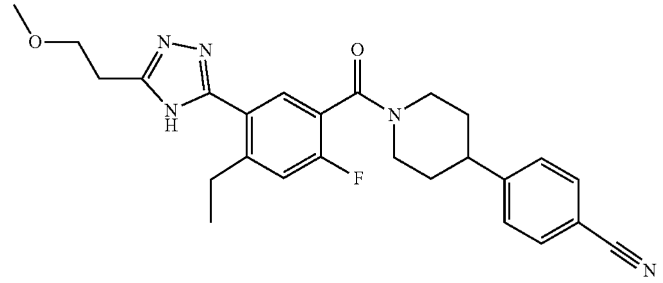 [SMILES: CCc1cc(F)c(C(=O)N2CCC(c3ccc(C#N)cc3)CC2)cc1-c1nnc(CCOC)[nH]1] | 8.230 |
| 001-181 | 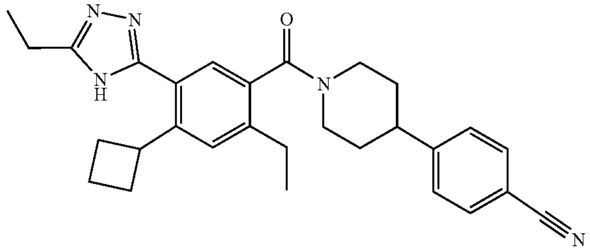 [SMILES: CCc1nnc(-c2cc(C(=O)N3CCC(c4ccc(C#N)cc4)CC3)c(CC)cc2C2CCC2)[nH]1] | 0.115 |
| 001-182 | 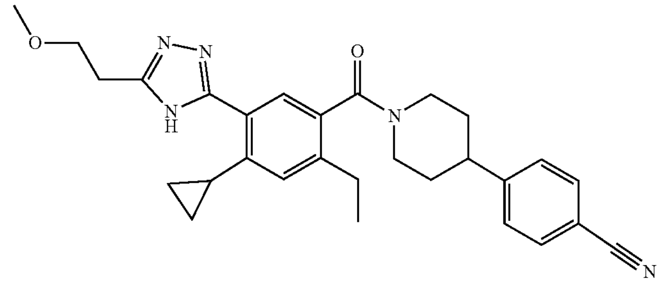 [SMILES: CCc1cc(C2CC2)c(-c2nnc(CCOC)[nH]2)cc1C(=O)N1CCC(c2ccc(C#N)cc2)CC1] | 0.145 |

TABLE C-1-continued
| Cmpd No. | Structure | FASN $IC_{50}$ (μM) |
| --- | --- | --- |
| | Fatty Acid Synthase Inhibitors | |
| 001-183 | 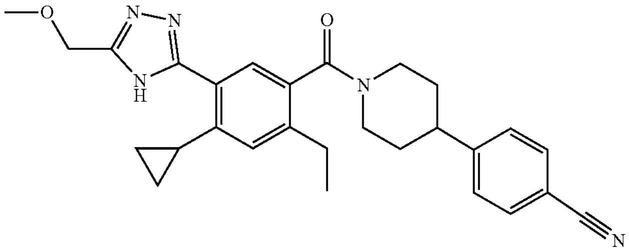 [SMILES: CCc1cc(C2CC2)c(-c2nnc(COC)[nH]2)cc1C(=O)N1CCC(c2ccc(C#N)cc2)CC1] | 0.170 |
| 001-184 | 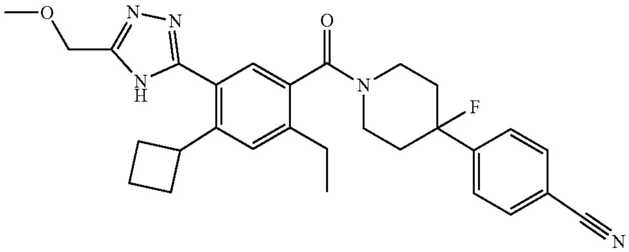 [SMILES: CCc1cc(C2CCC2)c(-c2nnc(COC)[nH]2)cc1C(=O)N1CCC(F)(c2ccc(C#N)cc2)CC1] | 0.085 |
| 001-185 | 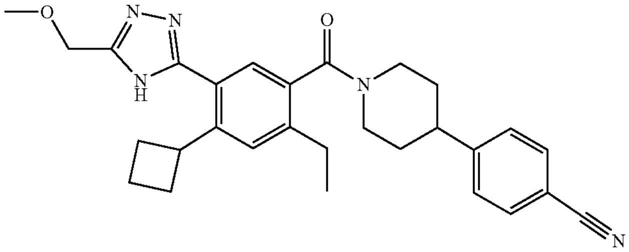 [SMILES: CCc1cc(C2CCC2)c(-c2nnc(COC)[nH]2)cc1C(=O)N1CCC(c2ccc(C#N)cc2)CC1] | 0.080 |
| 001-186 | 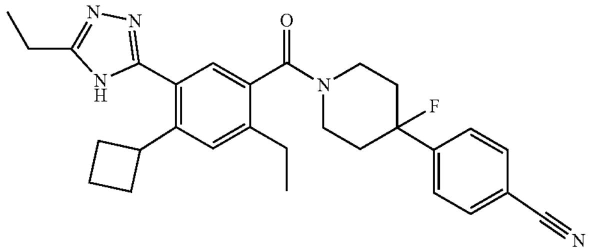 [SMILES: CCc1nnc(-c2cc(C(=O)N3CCC(F)(c4ccc(C#N)cc4)CC3)c(CC)cc2C2CCC2)[nH]1] | 0.055 |
| 001-187 | 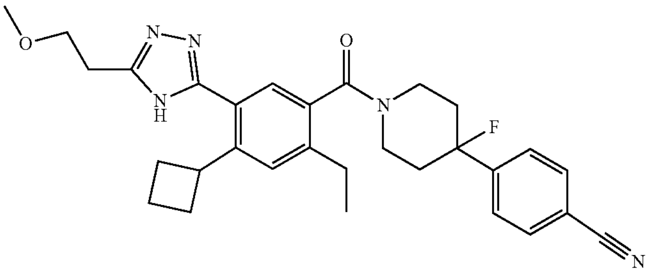 [SMILES: CCc1cc(C2CCC2)c(-c2nnc(CCOC)[nH]2)cc1C(=O)N1CCC(F)(c2ccc(C#N)cc2)CC1] | 0.065 |

TABLE C-1-continued
| Fatty Acid Synthase Inhibitors | | |
|---|---|---|
| Cmpd No. | Structure | FASN $IC_{50}$ (μM) |
| 001-188 | 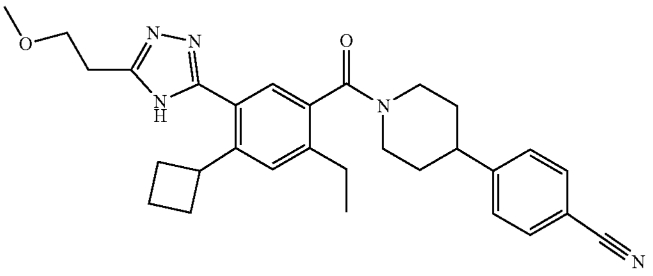 [SMILES: CCc1cc(C2CCC2)c(-c2nnc(CCOC)[nH]2)cc1C(=O)N1CCC(c2ccc(C#N)cc2)CC1] | 0.070 |
| 001-189 | 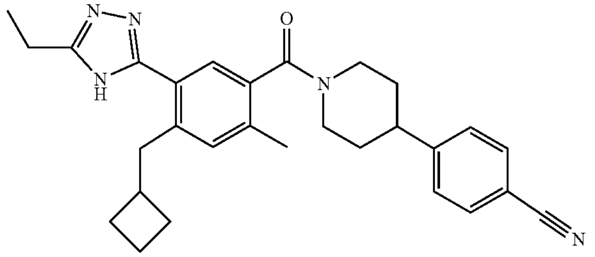 [SMILES: CCc1nnc(-c2cc(C(=O)N3CCC(c4ccc(C#N)cc4)CC3)c(C)cc2CC2CCC2)[nH]1] | 0.270 |
| 001-190 | 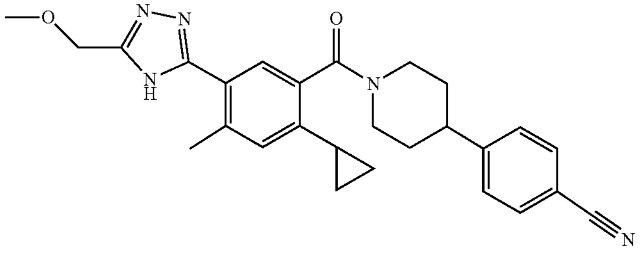 [SMILES: COCc1nnc(-c2cc(C(=O)N3CCC(c4ccc(C#N)cc4)CC3)c(C3CC3)cc2C)[nH]1] | 5.060 |
| 001-191 | 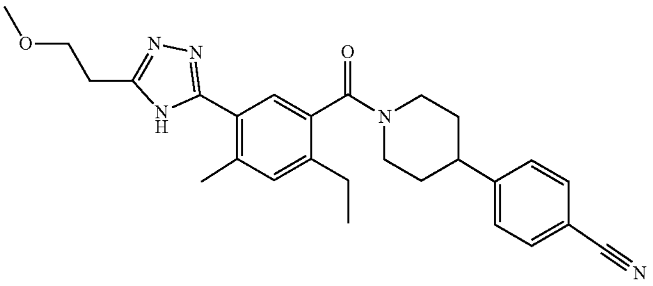 [SMILES: CCc1cc(C)c(-c2nnc(CCOC)[nH]2)cc1C(=O)N1CCC(c2ccc(C#N)cc2)CC1] | 0.200 |
| 001-192 | 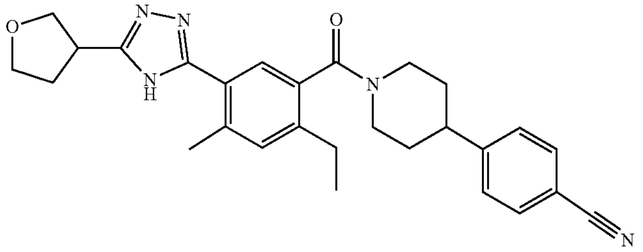 [SMILES: CCc1cc(C)c(-c2nnc(C3CCOC3)[nH]2)cc1C(=O)N1CCC(c2ccc(C#N)cc2)CC1] | 0.300 |

TABLE C-1-continued
| Fatty Acid Synthase Inhibitors | | |
|---|---|---|
| Cmpd No. | Structure | FASN $IC_{50}$ (μM) |
| 001-193 | 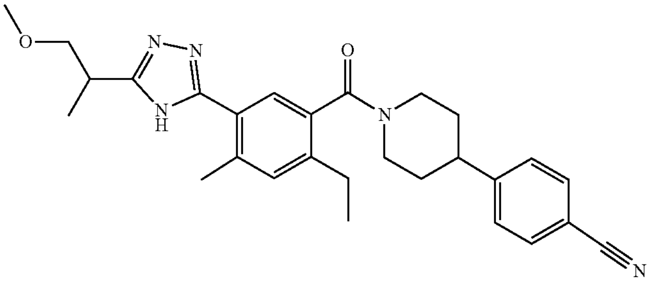 [SMILES: CCc1cc(C)c(-c2nnc(C(C)COC)[nH]2)cc1C(=O)N1CCC(c2ccc(C#N)cc2)CC1] | 0.440 |
| 001-194 | 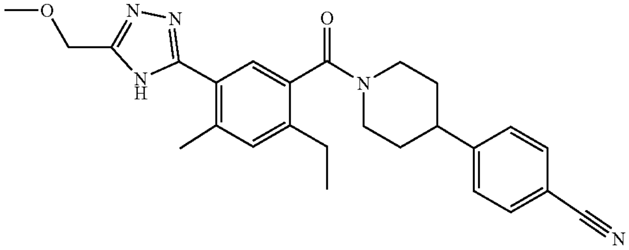 [SMILES: CCc1cc(C)c(-c2nnc(COC)[nH]2)cc1C(=O)N1CCC(c2ccc(C#N)cc2)CC1] | 0.400 |
| 001-195 | 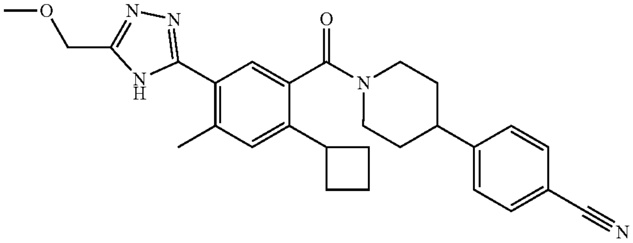 [SMILES: COCc1nnc(-c2cc(C(=O)N3CCC(c4ccc(C#N)cc4)CC3)c(C3CCC3)cc2C)[nH]1] | >50 |
| 001-196 | 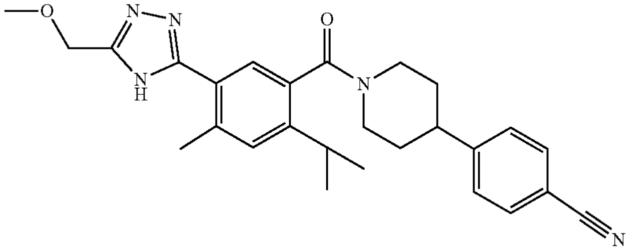 [SMILES: COCc1nnc(-c2cc(C(=O)N3CCC(c4ccc(C#N)cc4)CC3)c(C(C)C)cc2C)[nH]1] | >50 |
| 001-197 | 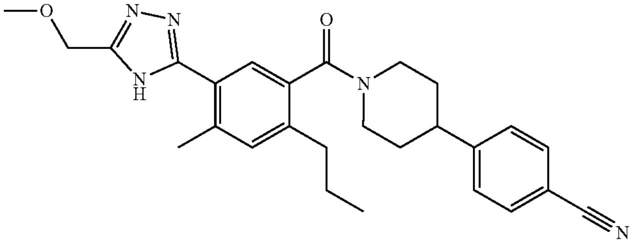 [SMILES: CCCc1cc(C)c(-c2nnc(COC)[nH]2)cc1C(=O)N1CCC(c2ccc(C#N)cc2)CC1] | 11.105 |

TABLE C-1-continued
Fatty Acid Synthase Inhibitors
| Cmpd No. | Structure | FASN $IC_{50}$ (μM) |
| --- | --- | --- |
| 001-198 | 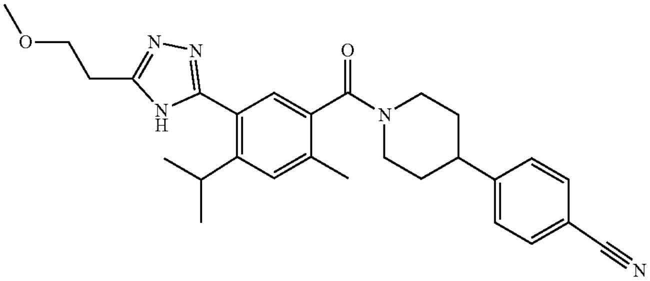 [SMILES: COCCc1nnc(-c2cc(C(=O)N3CCC(c4ccc(C#N)cc4)CC3)c(C)cc2C(C)C)[nH]1] | 0.705 |
| 001-199 | 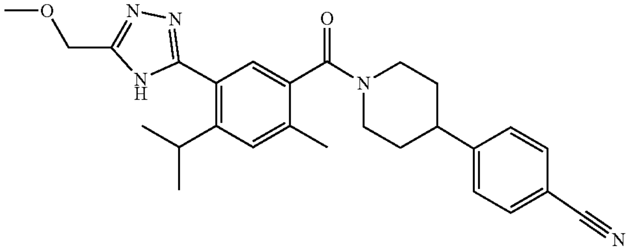 [SMILES: COCc1nnc(-c2cc(C(=O)N3CCC(c4ccc(C#N)cc4)CC3)c(C)cc2C(C)C)[nH]1] | 1.060 |
| 001-200 | 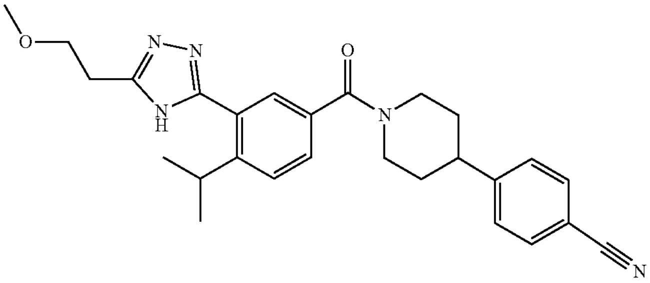 [SMILES: COCCc1nnc(-c2cc(C(=O)N3CCC(c4ccc(C#N)cc4)CC3)ccc2C(C)C)[nH]1] | 13.520 |
| 001-201 | 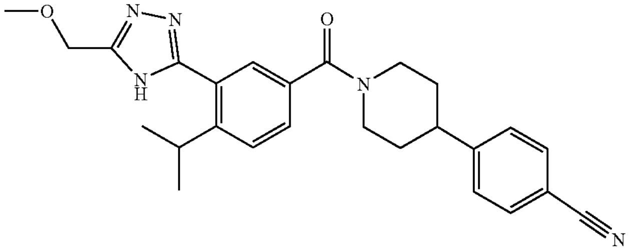 [SMILES: COCc1nnc(-c2cc(C(=O)N3CCC(c4ccc(C#N)cc4)CC3)ccc2C(C)C)[nH]1] | 23.140 |
| 001-202 | 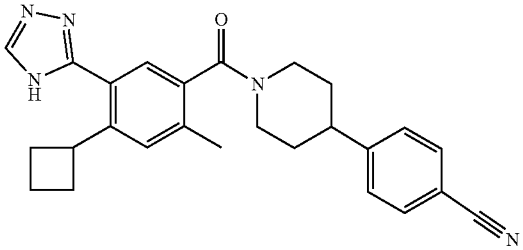 [SMILES: Cc1cc(C2CCC2)c(-c2nnc[nH]2)cc1C(=O)N1CCC(c2ccc(C#N)cc2)CC1] | 0.055 |

TABLE C-1-continued
| Fatty Acid Synthase Inhibitors | | |
|---|---|---|
| Cmpd No. | Structure | FASN $IC_{50}$ (μM) |
| 001-203 | 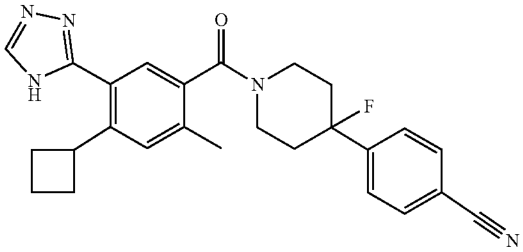 [SMILES: Cc1cc(C2CCC2)c(-c2nnc[nH]2)cc1C(=O)N1CCC(F)(c2ccc(C#N)cc2)CC1] | 0.045 |
| 001-204 | 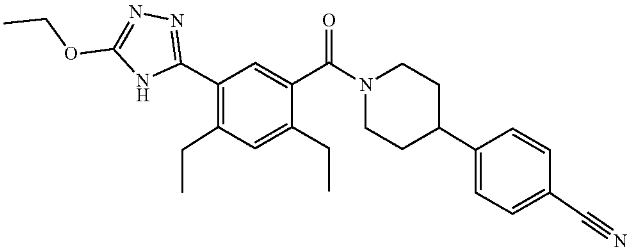 [SMILES: CCOc1nnc(-c2cc(C(=O)N3CCC(c4ccc(C#N)cc4)CC3)c(CC)cc2CC)[nH]1] | 0.195 |
| 001-205 | 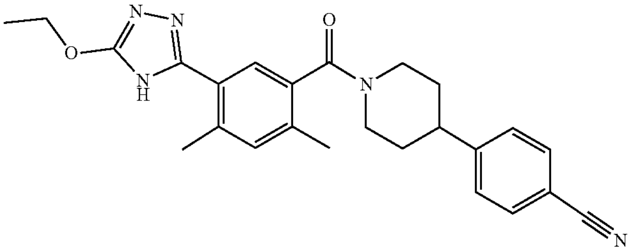 [SMILES: CCOc1nnc(-c2cc(C(=O)N3CCC(c4ccc(C#N)cc4)CC3)c(C)cc2C)[nH]1] | 0.220 |
| 001-206 | 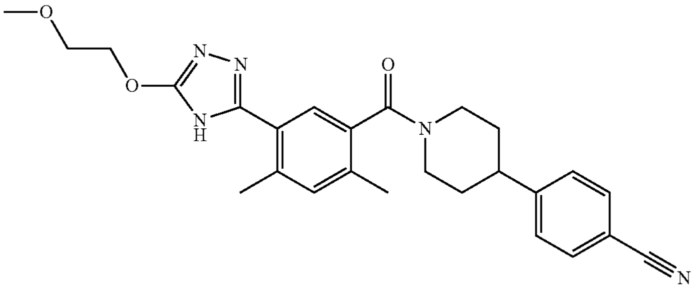 [SMILES: COCCOc1nnc(-c2cc(C(=O)N3CCC(c4ccc(C#N)cc4)CC3)c(C)cc2C)[nH]1] | 0.320 |
| 001-207 | 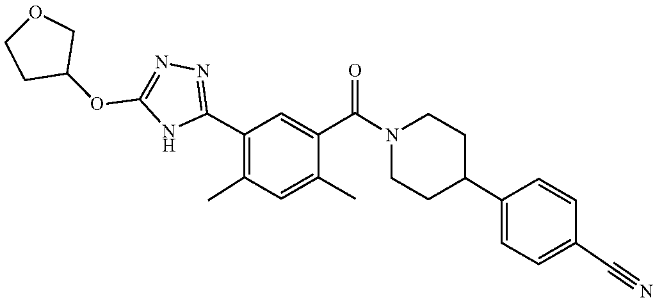 [SMILES: Cc1cc(C)c(-c2nnc(OC3CCOC3)[nH]2)cc1C(=O)N1CCC(c2ccc(C#N)cc2)CC1] | 0.300 |

TABLE C-1-continued
| Fatty Acid Synthase Inhibitors | | |
|---|---|---|
| Cmpd No. | Structure | FASN $IC_{50}$ (μM) |
| 001-208 | 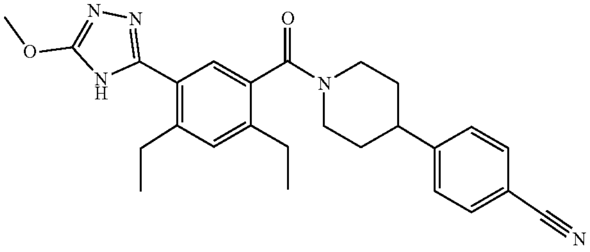 [SMILES: CCc1cc(CC)c(-c2nnc(OC)[nH]2)cc1C(=O)N1CCC(c2ccc(C#N)cc2)CC1] | 0.100 |
| 001-209 | 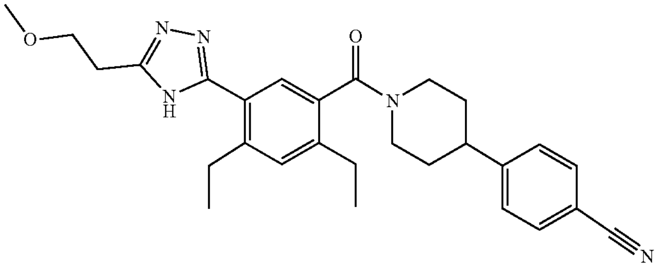 [SMILES: CCc1cc(CC)c(-c2nnc(CCOC)[nH]2)cc1C(=O)N1CCC(c2ccc(C#N)cc2)CC1] | 0.105 |
| 001-210 | 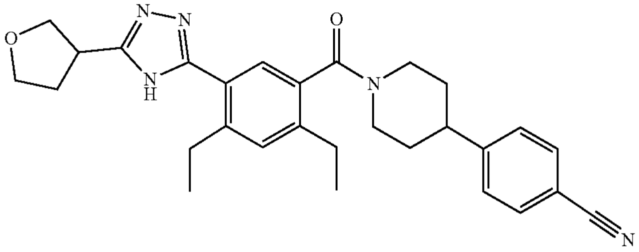 [SMILES: CCc1cc(CC)c(-c2nnc(C3CCOC3)[nH]2)cc1C(=O)N1CCC(c2ccc(C#N)cc2)CC1] | 0.310 |
| 001-211 | 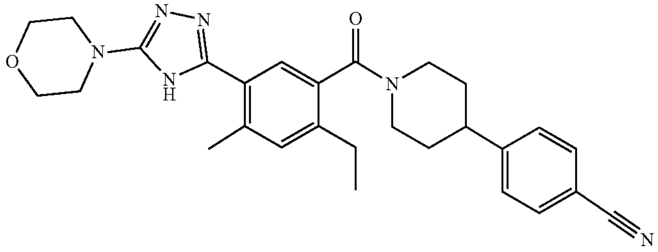 [SMILES: CCc1cc(C)c(-c2nnc(N3CCOCC3)[nH]2)cc1C(=O)N1CCC(c2ccc(C#N)cc2)CC1] | 0.830 |
| 001-212 | 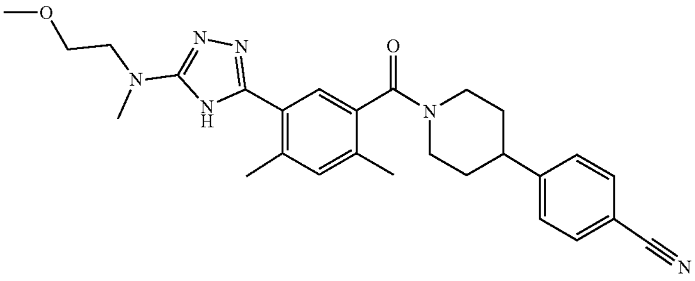 [SMILES: COCCN(C)c1nnc(-c2cc(C(=O)N3CCC(c4ccc(C#N)cc4)CC3)c(C)cc2C)[nH]1] | 7.190 |

TABLE C-1-continued
| Fatty Acid Synthase Inhibitors | | |
|---|---|---|
| Cmpd No. | Structure | FASN $IC_{50}$ (μM) |
| 001-213 | 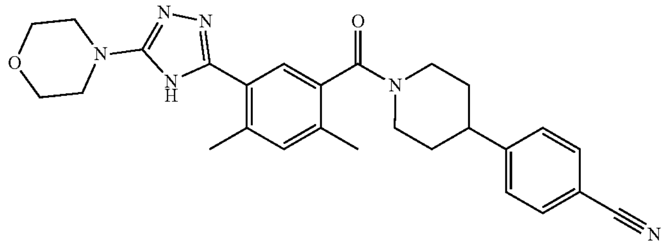 [SMILES: Cc1cc(C)c(-c2nnc(N3CCOCC3)[nH]2)cc1C(=O)N1CCC(c2ccc(C#N)cc2)CC1] | 0.790 |
| 001-214 | 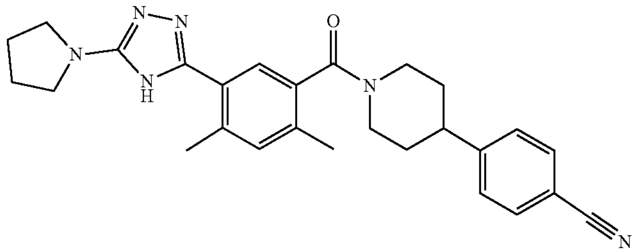 [SMILES: Cc1cc(C)c(-c2nnc(N3CCCC3)[nH]2)cc1C(=O)N1CCC(c2ccc(C#N)cc2)CC1] | 28.760 |
| 001-215 | 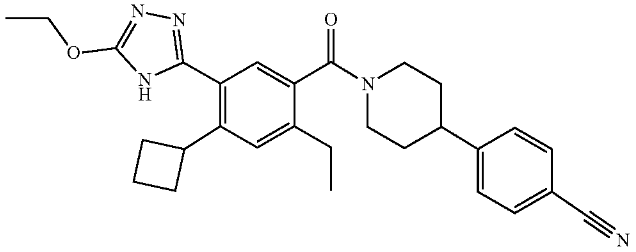 [SMILES: CCOc1nnc(-c2cc(C(=O)N3CCC(c4ccc(C#N)cc4)CC3)c(CC)cc2C2CCC2)[nH]1] | 0.080 |
| 001-216 | 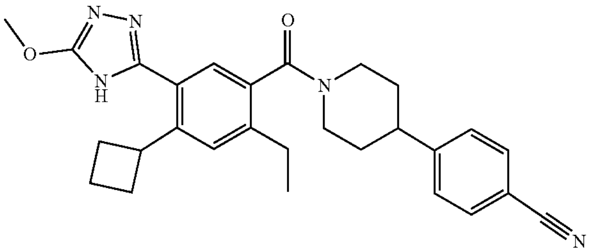 [SMILES: CCc1cc(C2CCC2)c(-c2nnc(OC)[nH]2)cc1C(=O)N1CCC(c2ccc(C#N)cc2)CC1] | 0.090 |
| 001-217 | 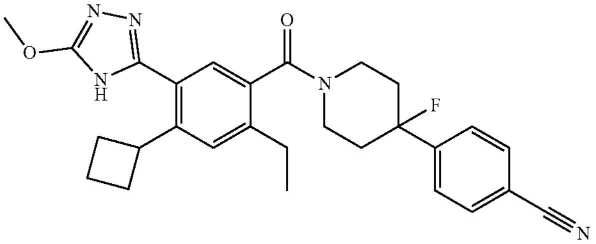 [SMILES: CCc1cc(C2CCC2)c(-c2nnc(OC)[nH]2)cc1C(=O)N1CCC(F)(c2ccc(C#N)cc2)CC1] | 0.100 |

TABLE C-1-continued
Fatty Acid Synthase Inhibitors
| Cmpd No. | Structure | FASN $IC_{50}$ (μM) |
|---|---|---|
| 001-218 | 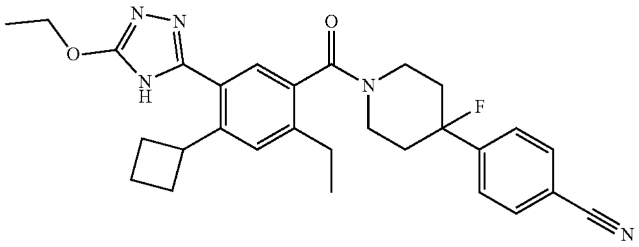 [SMILES: CCOc1nnc(-c2cc(C(=O)N3CCC(F)(c4ccc(C#N)cc4)CC3)c(CC)cc2C2CCC2)[nH]1] | 0.170 |
| 001-219 | 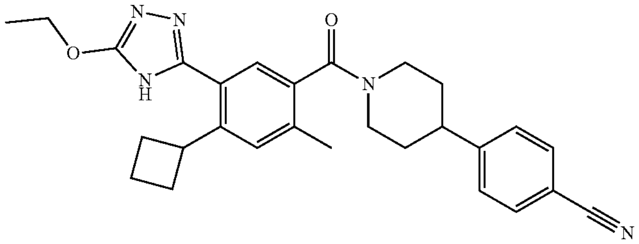 [SMILES: CCOc1nnc(-c2cc(C(=O)N3CCC(c4ccc(C#N)cc4)CC3)c(C)cc2C2CCC2)[nH]1] | 0.085 |
| 001-220 | 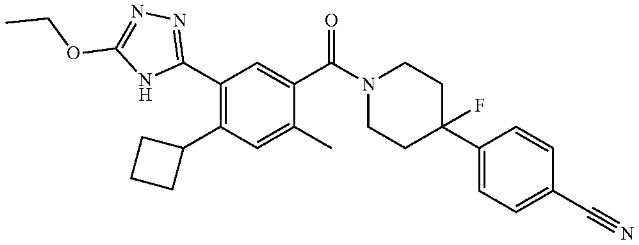 [SMILES: CCOc1nnc(-c2cc(C(=O)N3CCC(F)(c4ccc(C#N)cc4)CC3)c(C)cc2C2CCC2)[nH]1] | 0.055 |
| 001-221 | 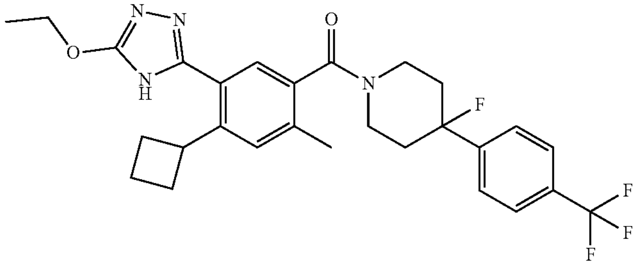 [SMILES: CCOc1nnc(-c2cc(C(=O)N3CCC(F)(c4ccc(C(F)(F)F)cc4)CC3)c(C)cc2C2CCC2)[nH]1] | 0.250 |
| 001-222 | 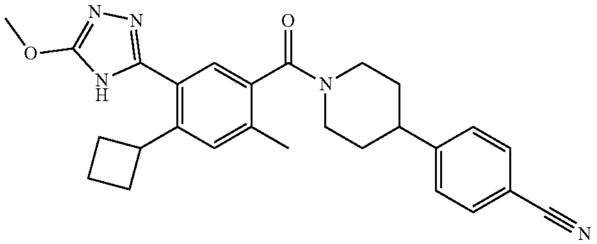 [SMILES: COc1nnc(-c2cc(C(=O)N3CCC(c4ccc(C#N)cc4)CC3)c(C)cc2C2CCC2)[nH]1] | 0.065 |
| 001-223 | 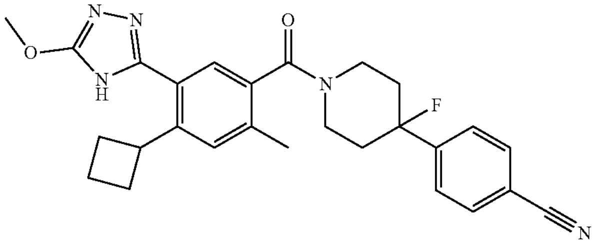 [SMILES: COc1nnc(-c2cc(C(=O)N3CCC(F)(c4ccc(C#N)cc4)CC3)c(C)cc2C2CCC2)[nH]1] | 0.030 |

TABLE C-1-continued
| Fatty Acid Synthase Inhibitors | | |
|---|---|---|
| Cmpd No. | Structure | FASN $IC_{50}$ (μM) |
| 001-224 | 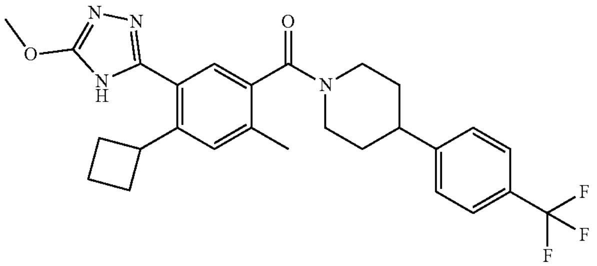 [SMILES: COc1nnc(-c2cc(C(=O)N3CCC(c4ccc(C(F)(F)F)cc4)CC3)c(C)cc2C2CCC2)[nH]1] | 0.160 |
| 001-225 | 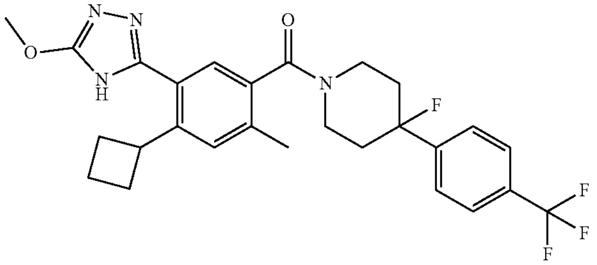 [SMILES: COc1nnc(-c2cc(C(=O)N3CCC(F)(c4ccc(C(F)(F)F)cc4)CC3)c(C)cc2C2CCC2)[nH]1] | 0.140 |
| 001-226 | 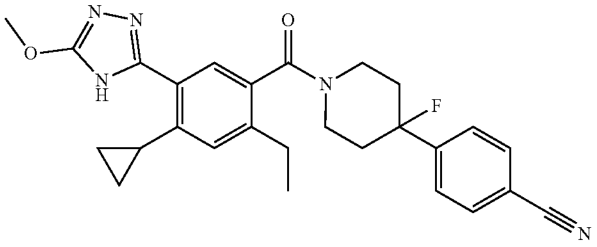 [SMILES: CCc1cc(C2CC2)c(-c2nnc(OC)[nH]2)cc1C(=O)N1CCC(F)(c2ccc(C#N)cc2)CC1] | 0.055 |
| 001-227 | 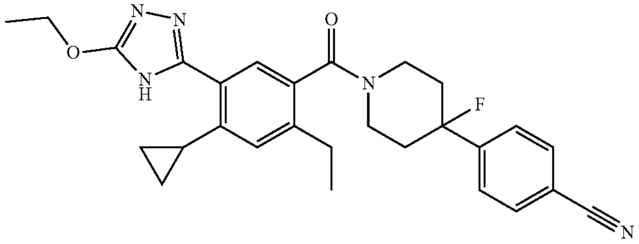 [SMILES: CCOc1nnc(-c2cc(C(=O)N3CCC(F)(c4ccc(C#N)cc4)CC3)c(CC)cc2C2CC2)[nH]1] | 0.070 |
| 001-228 | 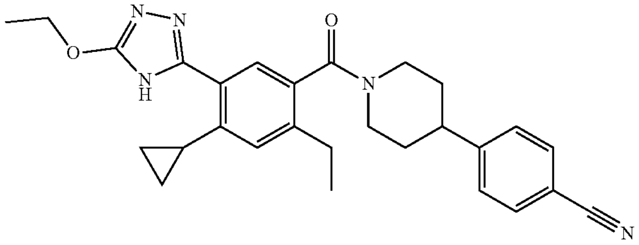 [SMILES: CCOc1nnc(-c2cc(C(=O)N3CCC(c4ccc(C#N)cc4)CC3)c(CC)cc2C2CC2)[nH]1] | 0.110 |

TABLE C-1-continued
| Fatty Acid Synthase Inhibitors | | |
|---|---|---|
| Cmpd No. | Structure | FASN $IC_{50}$ (μM) |
| 001-229 | 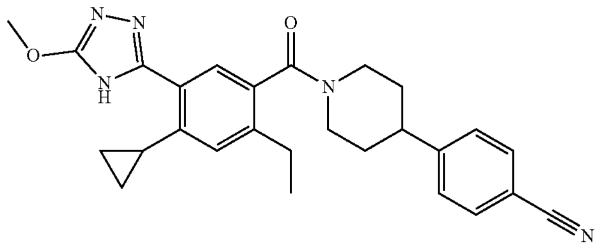 | 0.090 |
| 001-230 | 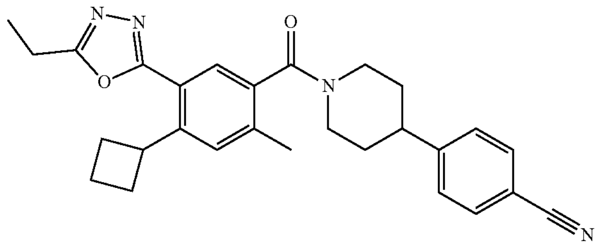 [SMILES: CCc1nnc(-c2cc(C(=O)N3CCC(c4ccc(C#N)cc4)CC3)c(C)cc2C2CCC2)o1] | 30.990 |
| 001-231 | 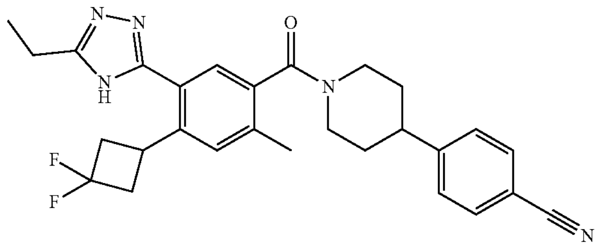 [SMILES: CCc1nnc(-c2cc(C(=O)N3CCC(c4ccc(C#N)cc4)CC3)c(C)cc2C2CC(F)(F)C2)[nH]1] | 0.300 |
| 001-232 | 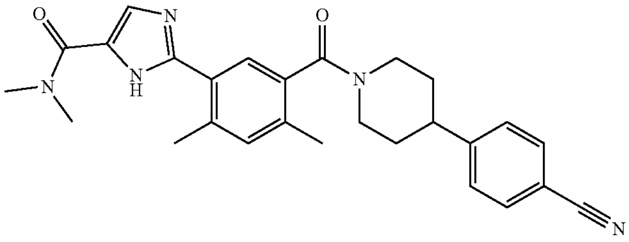 [SMILES: Cc1cc(C)c(-c2ncc(C(=O)N(C)C)[nH]2)cc1C(=O)N1CCC(c2ccc(C#N)cc2)CC1] | 0.650 |
| 001-233 | 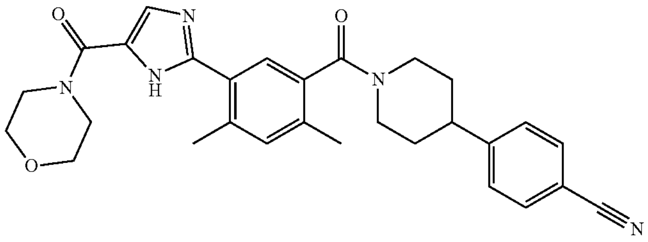 [SMILES: Cc1cc(C)c(-c2ncc(C(=O)N3CCOCC3)[nH]2)cc1C(=O)N1CCC(c2ccc(C#N)cc2)CC1] | 1.630 |
| 001-234 | 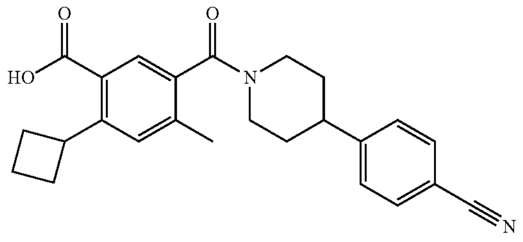 [SMILES: Cc1cc(C2CCC2)c(C(=O)O)cc1C(=O)N1CCC(c2ccc(C#N)cc2)CC1] | >50 |

TABLE C-1-continued
| Cmpd No. | Structure | FASN $IC_{50}$ (μM) |
|---|---|---|
| Fatty Acid Synthase Inhibitors | | |
| 001-235 | 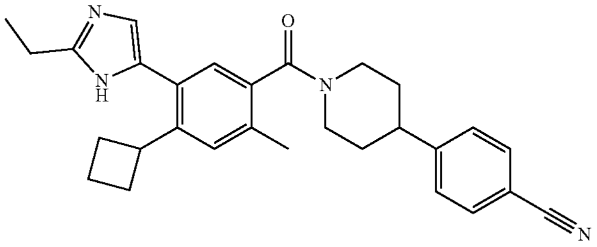 [SMILES: CCc1ncc(-c2cc(C(=O)N3CCC(c4ccc(C#N)cc4)CC3)c(C)cc2C2CCC2)[nH]1] | 0.030 |
| 001-236 | 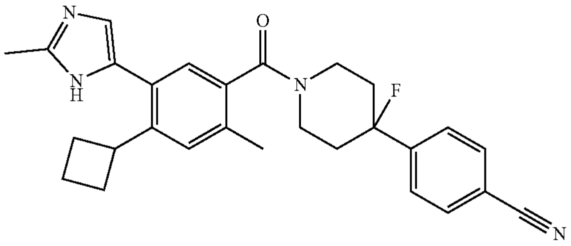 [SMILES: Cc1ncc(-c2cc(C(=O)N3CCC(F)(c4ccc(C#N)cc4)CC3)c(C)cc2C2CCC2)[nH]1] | 0.060 |
| 001-237 | 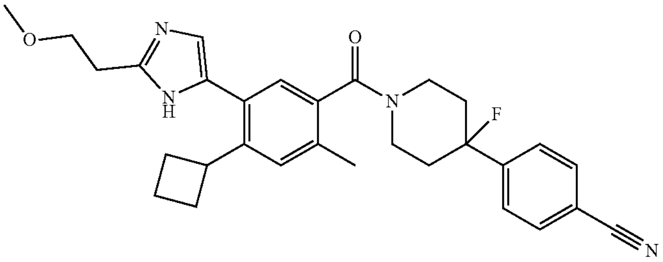 [SMILES: COCCc1ncc(-c2cc(C(=O)N3CCC(F)(c4ccc(C#N)cc4)CC3)c(C)cc2C2CCC2)[nH]1] | 0.080 |
| 001-238 | 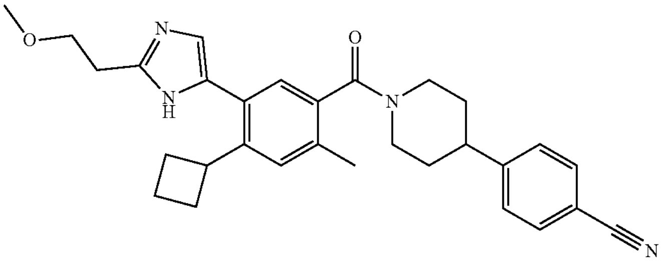 [SMILES: COCCc1ncc(-c2cc(C(=O)N3CCC(c4ccc(C#N)cc4)CC3)c(C)cc2C2CCC2)[nH]1] | 0.100 |
| 001-239 | 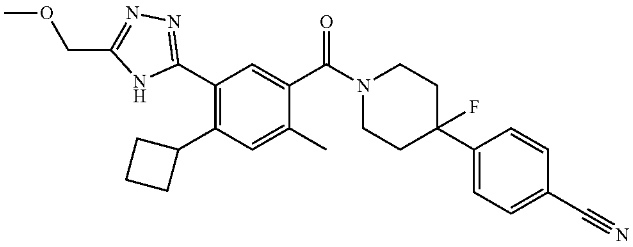 [SMILES: COCc1nnc(-c2cc(C(=O)N3CCC(F)(c4ccc(C#N)cc4)CC3)c(C)cc2C2CCC2)[nH]1] | 0.050 |

TABLE C-1-continued
| Fatty Acid Synthase Inhibitors | | |
|---|---|---|
| Cmpd No. | Structure | FASN $IC_{50}$ (μM) |
| 001-240 | 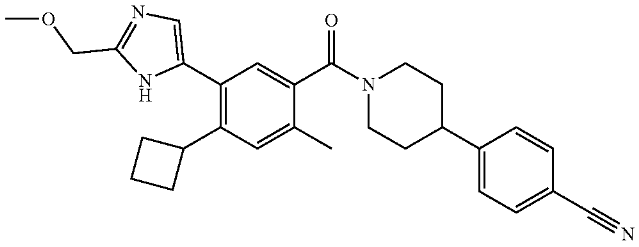 [SMILES: COCc1ncc(-c2cc(C(=O)N3CCC(c4ccc(C#N)cc4)CC3)c(C)cc2C2CCC2)[nH]1] | 0.050 |
| 001-241 | 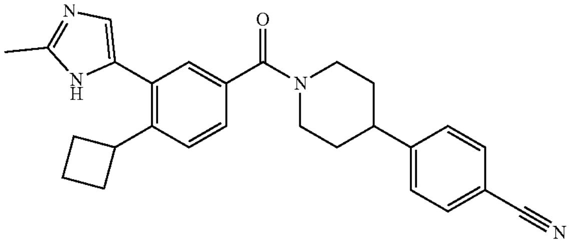 [SMILES: Cc1ncc(-c2cc(C(=O)N3CCC(c4ccc(C#N)cc4)CC3)ccc2C2CCC2)[nH]1] | 0.120 |
| 001-242 | 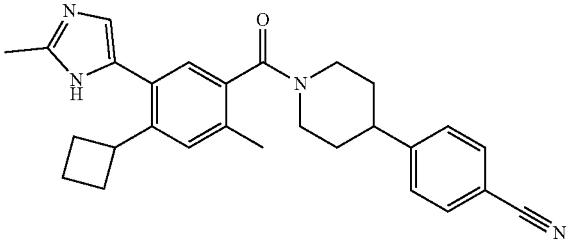 | 0.050 |
| 001-243 | 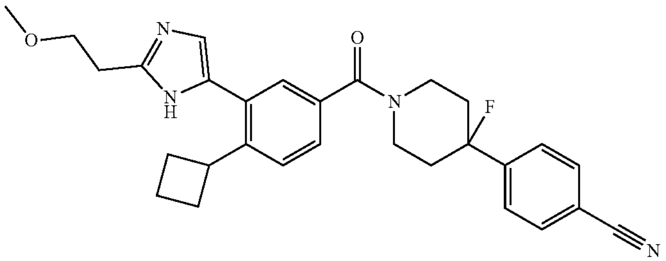 [SMILES: COCCc1ncc(-c2cc(C(=O)N3CCC(F)(c4ccc(C#N)cc4)CC3)ccc2C2CCC2)[nH]1] | 0.120 |
| 001-244 | 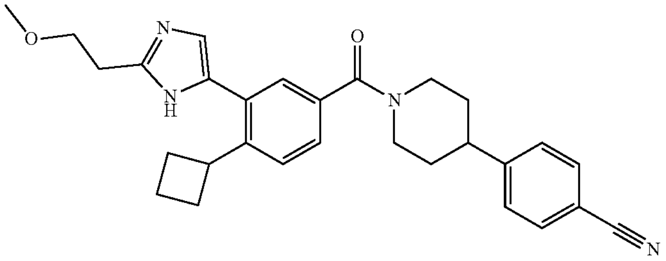 [SMILES: COCCc1ncc(-c2cc(C(=O)N3CCC(c4ccc(C#N)cc4)CC3)ccc2C2CCC2)[nH]1] | 0.220 |

TABLE C-1-continued
| Cmpd No. | Structure | FASN $IC_{50}$ (μM) |
| --- | --- | --- |
| | Fatty Acid Synthase Inhibitors | |
| 001-245 | 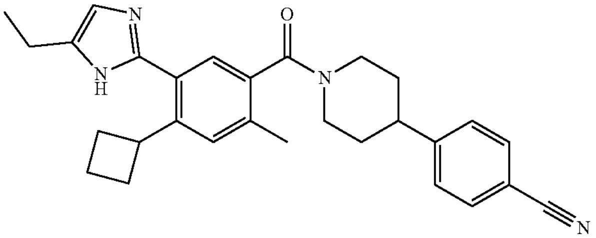 [SMILES: CCc1cnc(-c2cc(C(=O)N3CCC(c4ccc(C#N)cc4)CC3)c(C)cc2C2CCC2)[nH]1] | 0.020 |
| 001-246 | 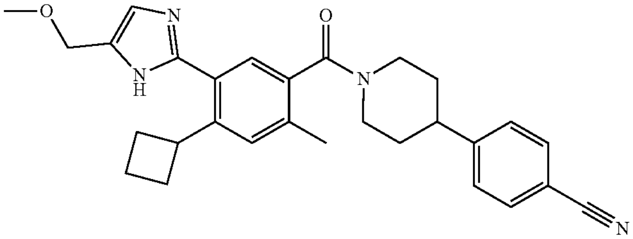 [SMILES: COCc1cnc(-c2cc(C(=O)N3CCC(c4ccc(C#N)cc4)CC3)c(C)cc2C2CCC2)[nH]1] | 0.050 |
| 001-247 | 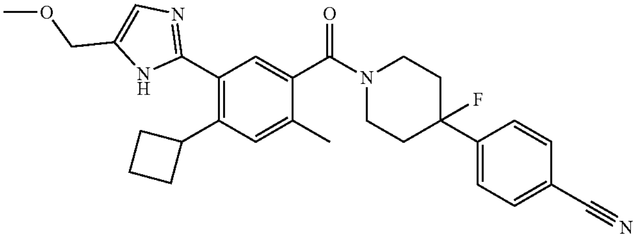 [SMILES: COCc1cnc(-c2cc(C(=O)N3CCC(F)(c4ccc(C#N)cc4)CC3)c(C)cc2C2CCC2)[nH]1] | 0.020 |
| 001-248 | 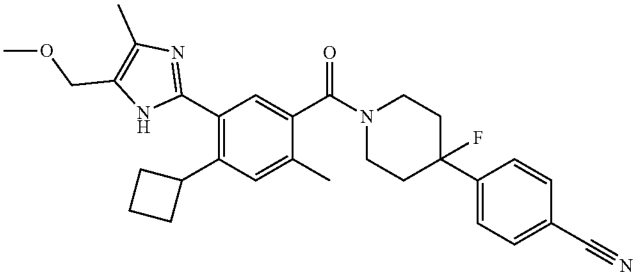 [SMILES: COCc1[nH]c(-c2cc(C(=O)N3CCC(F)(c4ccc(C#N)cc4)CC3)c(C)cc2C2CCC2)nc1C] | 0.060 |
| 001-249 | 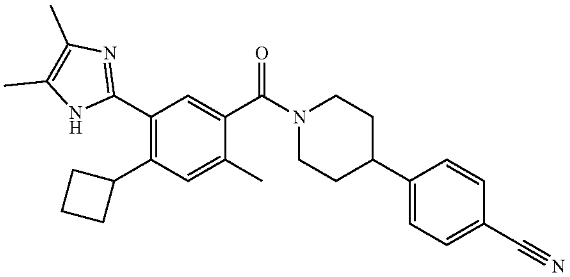 [SMILES: Cc1cc(C2CCC2)c(-c2nc(C)c(C)[nH]2)cc1C(=O)N1CCC(c2ccc(C#N)cc2)CC1] | 0.070 |

TABLE C-1-continued
| Fatty Acid Synthase Inhibitors | | |
|---|---|---|
| Cmpd No. | Structure | FASN $IC_{50}$ (μM) |
| 001-250 | 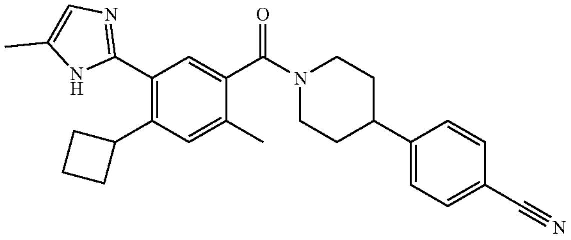 [SMILES: Cc1cnc(-c2cc(C(=O)N3CCC(c4ccc(C#N)cc4)CC3)c(C)cc2C2CCC2)[nH]1] | 0.030 |
| 001-251 | 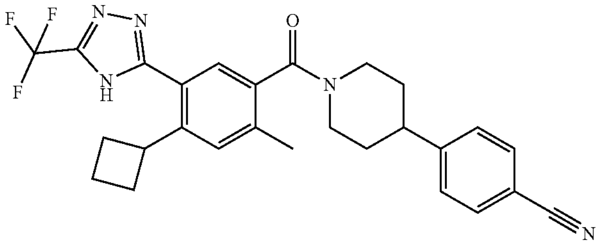 [SMILES: Cc1cc(C2CCC2)c(-c2nnc(C(F)(F)F)[nH]2)cc1C(=O)N1CCC(c2ccc(C#N)cc2)CC1] | 0.580 |
| 001-252 | 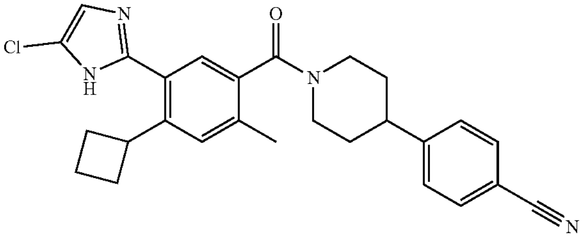 [SMILES: Cc1cc(C2CCC2)c(-c2ncc(Cl)[nH]2)cc1C(=O)N1CCC(c2ccc(C#N)cc2)CC1] | 0.180 |
| 001-253 | 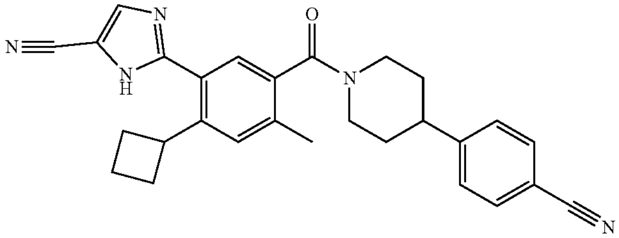 [SMILES: Cc1cc(C2CCC2)c(-c2ncc(C#N)[nH]2)cc1C(=O)N1CCC(c2ccc(C#N)cc2)CC1] | 0.090 |
| 001-254 | 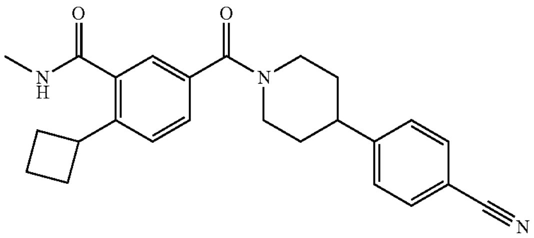 [SMILES: CNC(=O)c1cc(C(=O)N2CCC(c3ccc(C#N)cc3)CC2)ccc1C1CCC1] | 0.090 |
| 001-255 | 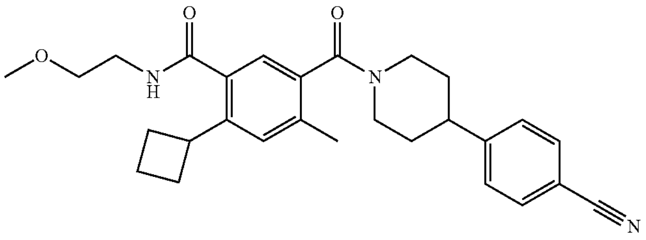 [SMILES: COCCNC(=O)c1cc(C(=O)N2CCC(c3ccc(C#N)cc3)CC2)c(C)cc1C1CCC1] | 0.410 |

TABLE C-1-continued
| Cmpd No. | Fatty Acid Synthase Inhibitors<br>Structure | FASN $IC_{50}$ (μM) |
|---|---|---|
| 001-256 | 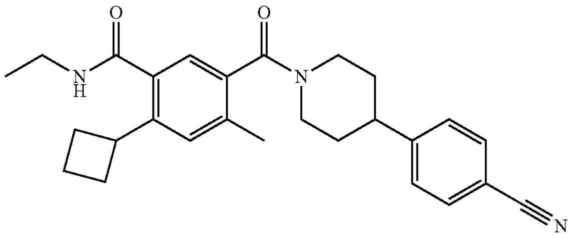 [SMILES: CCNC(=O)c1cc(C(=O)N2CCC(c3ccc(C#N)cc3)CC2)c(C)cc1C1CCC1] | 0.090 |
| 001-257 | 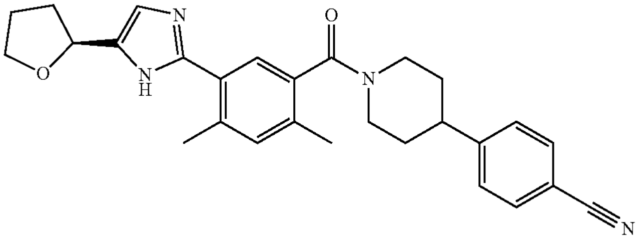 [SMILES: Cc1cc(C)c(-c2ncc([C@@H]3CCCO3)[nH]2)cc1C(=O)N1CCC(c2ccc(C#N)cc2)CC1] | 0.580 |
| 001-258 | 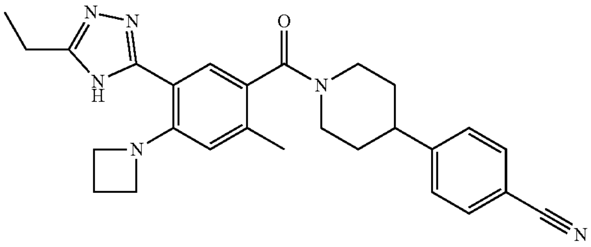 [SMILES: CCc1nnc(-c2cc(C(=O)N3CCC(c4ccc(C#N)cc4)CC3)c(C)cc2N2CCC2)[nH]1] | 0.150 |
| 001-259 | 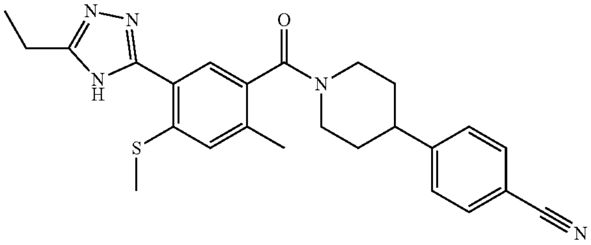 [SMILES: CCc1nnc(-c2cc(C(=O)N3CCC(c4ccc(C#N)cc4)CC3)c(C)cc2SC)[nH]1] | 1.330 |
| 001-260 | 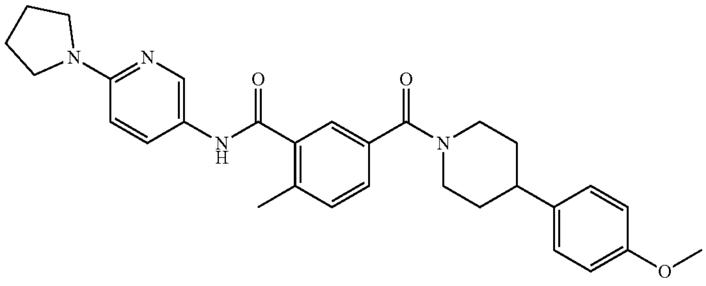 [SMILES: COc1ccc(C2CCN(C(=O)c3ccc(C)c(C(=O)Nc4ccc(N5CCCC5)nc4)c3)CC2)cc1] | 3.500 |
| 001-261 | 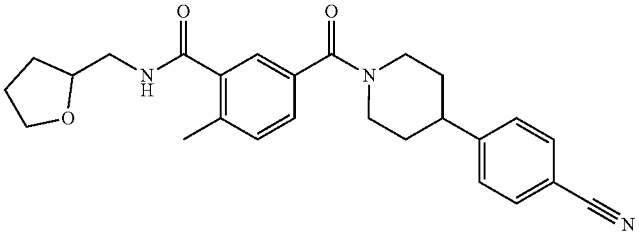 [SMILES: Cc1ccc(C(=O)N2CCC(c3ccc(C#N)cc3)CC2)cc1C(=O)NCC1CCCO1] | 21.750 |

TABLE C-1-continued
| Fatty Acid Synthase Inhibitors | | |
|---|---|---|
| Cmpd No. | Structure | FASN $IC_{50}$ (μM) |
| 001-262 | 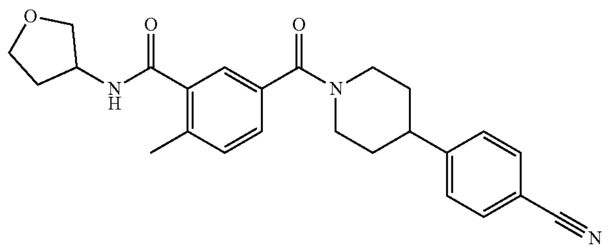 [SMILES: Cc1ccc(C(=O)N2CCC(c3ccc(C#N)cc3)CC2)cc1C(=O)NC1CCOC1] | 5.343 |
| 001-263 | 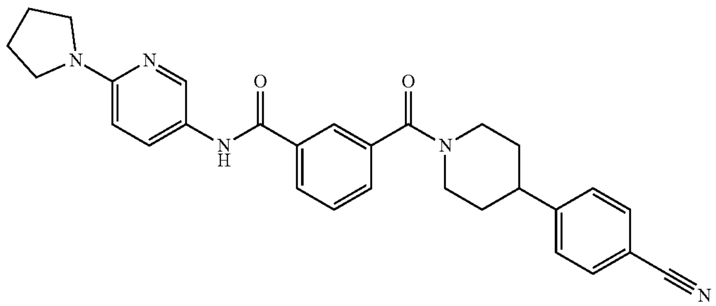 [SMILES: N#Cc1ccc(C2CCN(C(=O)c3cccc(C(=O)Nc4ccc(N5CCCC5)nc4)c3)CC2)cc1] | 0.250 |
| 001-264 | 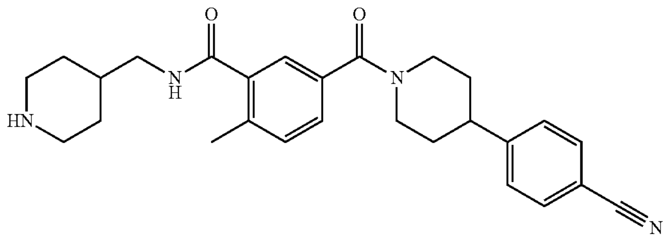 [SMILES: Cc1ccc(C(=O)N2CCC(c3ccc(C#N)cc3)CC2)cc1C(=O)NCC1CCNCC1] | >50 |
| 001-265 | 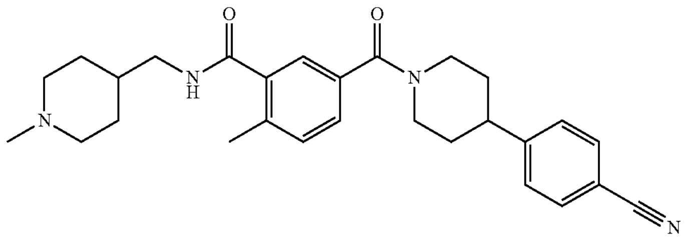 [SMILES: Cc1ccc(C(=O)N2CCC(c3ccc(C#N)cc3)CC2)cc1C(=O)NCC1CCN(C)CC1] | >50 |
| 001-266 | 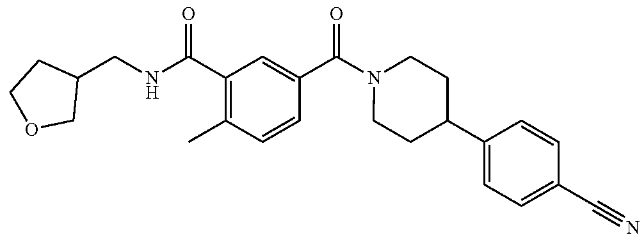 [SMILES: Cc1ccc(C(=O)N2CCC(c3ccc(C#N)cc3)CC2)cc1C(=O)NCC1CCOC1] | >50 |

TABLE C-1-continued
| Fatty Acid Synthase Inhibitors | | |
|---|---|---|
| Cmpd No. | Structure | FASN $IC_{50}$ (μM) |
| 001-267 | 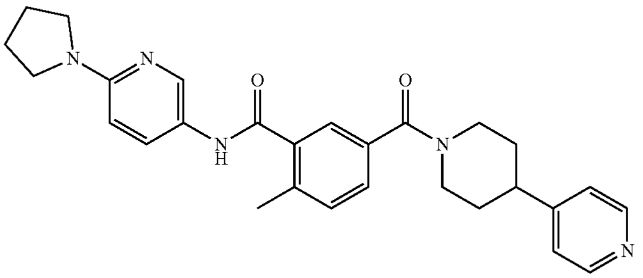 [SMILES: Cc1ccc(C(=O)N2CCC(c3ccncc3)CC2)cc1C(=O)Nc1ccc(N2CCCC2)nc1] | 30.260 |
| 001-268 | 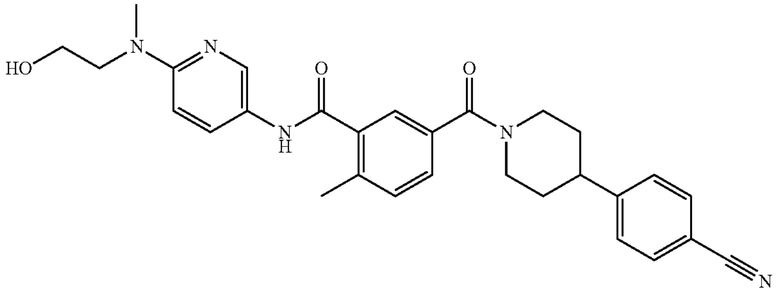 [SMILES: Cc1ccc(C(=O)N2CCC(c3ccc(C#N)cc3)CC2)cc1C(=O)Nc1ccc(N(C)CCO)nc1] | 0.390 |
| 001-269 | 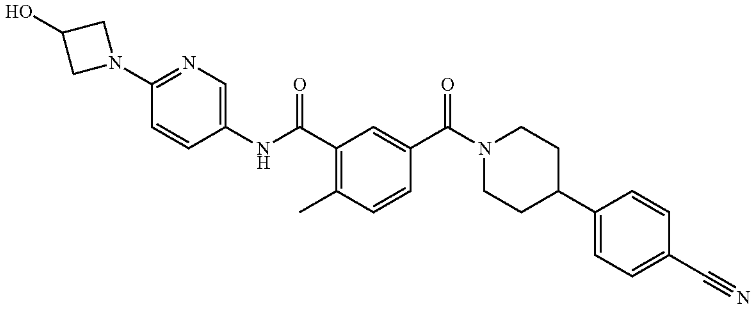 [SMILES: Cc1ccc(C(=O)N2CCC(c3ccc(C#N)cc3)CC2)cc1C(=O)Nc1ccc(N2CC(O)C2)nc1] | 1.350 |
| 001-270 | 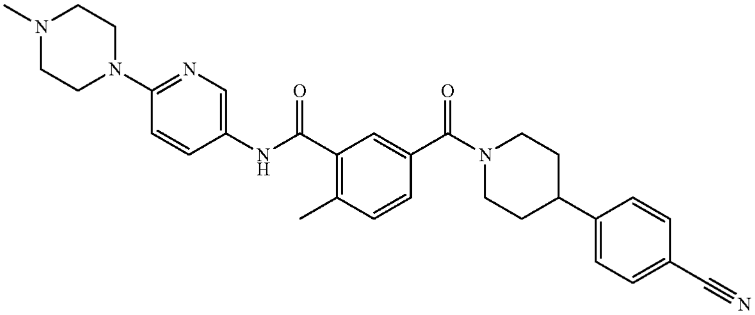 [SMILES: Cc1ccc(C(=O)N2CCC(c3ccc(C#N)cc3)CC2)cc1C(=O)Nc1ccc(N2CCN(C)CC2)nc1] | 1.980 |

TABLE C-1-continued
Fatty Acid Synthase Inhibitors
| Cmpd No. | Structure | FASN $IC_{50}$ (μM) |
|---|---|---|
| 001-271 | 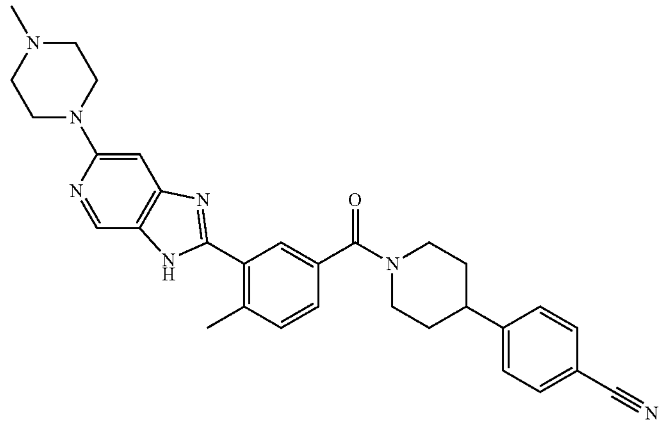 [SMILES: Cc1ccc(C(=O)N2CCC(c3ccc(C#N)cc3)CC2)cc1-c1nc2cc(N3CCN(C)CC3)ncc2[nH]1] | 0.520 |
| 001-272 | 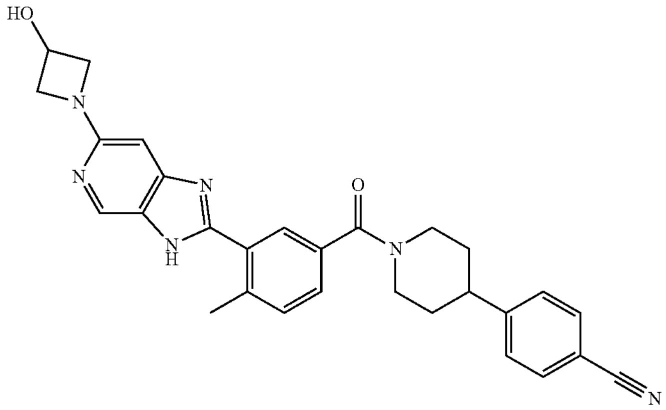 [SMILES: Cc1ccc(C(=O)N2CCC(c3ccc(C#N)cc3)CC2)cc1-c1nc2cc(N3CC(O)C3)ncc2[nH]1] | 0.300 |
| 001-273 | 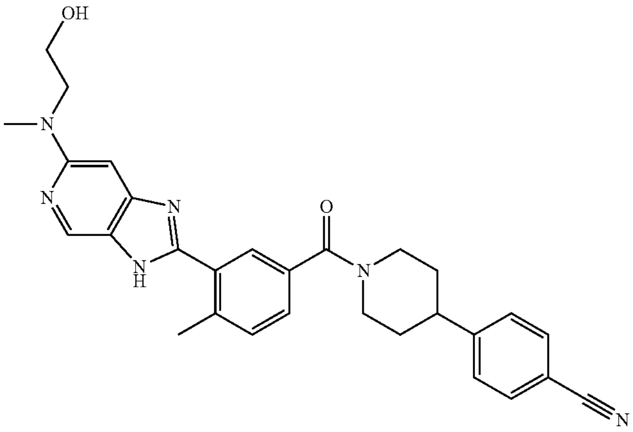 [SMILES: Cc1ccc(C(=O)N2CCC(c3ccc(C#N)cc3)CC2)cc1-c1nc2cc(N(C)CCO)ncc2[nH]1] | 0.060 |
| 001-274 | 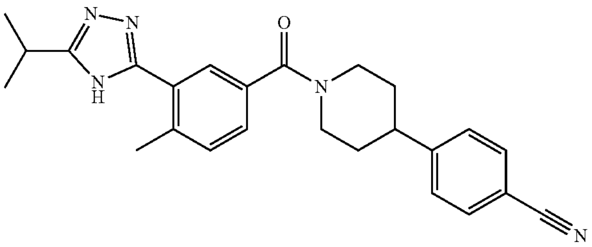 [SMILES: Cc1ccc(C(=O)N2CCC(c3ccc(C#N)cc3)CC2)cc1-c1nnc(C(C)C)[nH]1] | 2.345 |

TABLE C-1-continued
| Fatty Acid Synthase Inhibitors | | |
|---|---|---|
| Cmpd No. | Structure | FASN $IC_{50}$ (μM) |
| 001-275 | 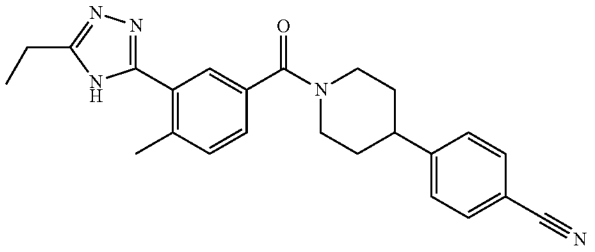 [SMILES: CCc1nnc(-c2cc(C(=O)N3CCC(c4ccc(C#N)cc4)CC3)ccc2C)[nH]1] | 2.245 |
| 001-276 | 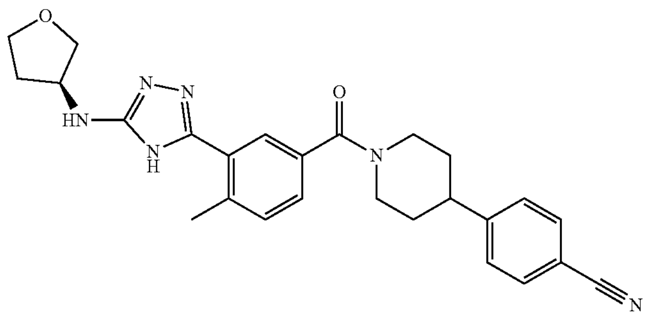 [SMILES: Cc1ccc(C(=O)N2CCC(c3ccc(C#N)cc3)CC2)cc1-c1nnc(N[C@H]2CCOC2)[nH]1] | 9.060 |
| 001-277 | 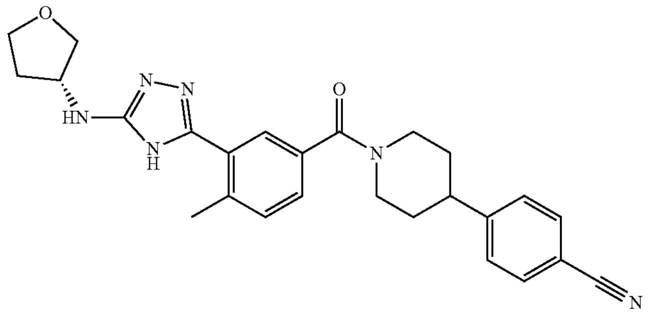 [SMILES: Cc1ccc(C(=O)N2CCC(c3ccc(C#N)cc3)CC2)cc1-c1nnc(N[C@@H]2CCOC2)[nH]1] | 11.680 |
| 001-278 | 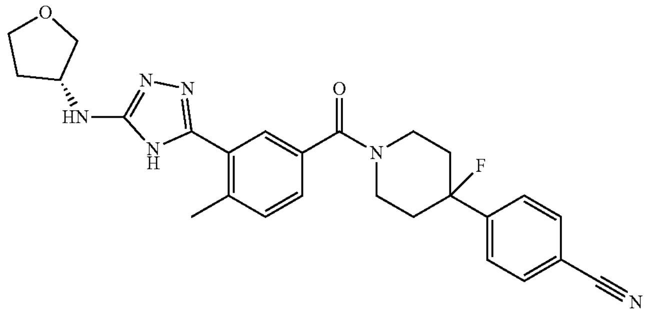 [SMILES: Cc1ccc(C(=O)N2CCC(F)(c3ccc(C#N)cc3)CC2)cc1-c1nnc(N[C@@H]2CCOC2)[nH]1] | 1.750 |

TABLE C-1-continued
| Cmpd No. | Fatty Acid Synthase Inhibitors<br>Structure | FASN $IC_{50}$ (μM) |
|---|---|---|
| 001-279 | 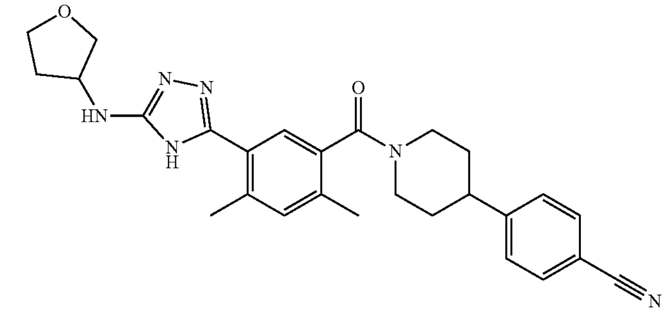 [SMILES: Cc1cc(C)c(-c2nnc(NC3CCOC3)[nH]2)cc1C(=O)N1CCC(c2ccc(C#N)cc2)CC1] | 0.330 |
| 001-280 | 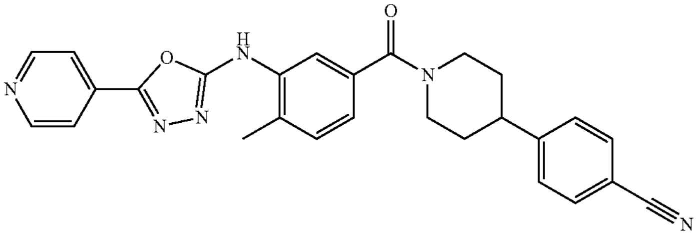 [SMILES: Cc1ccc(C(=O)N2CCC(c3ccc(C#N)cc3)CC2)cc1Nc1nnc(-c2ccncc2)o1] | 0.700 |
| 001-281 | 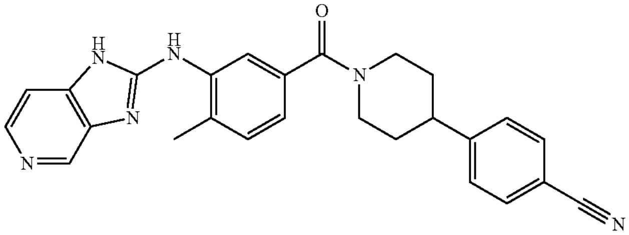 [SMILES: Cc1ccc(C(=O)N2CCC(c3ccc(C#N)cc3)CC2)cc1Nc1nc2cnccc2[nH]1] | 42.300 |
| 001-282 | 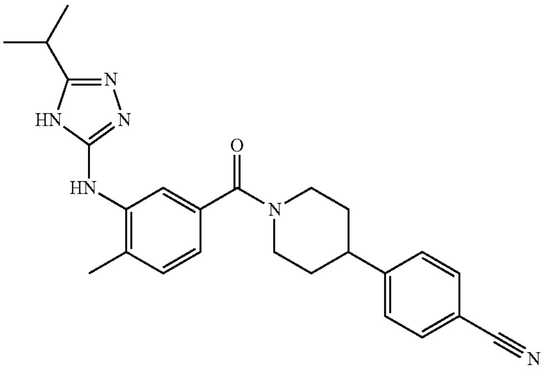 [SMILES: Cc1ccc(C(=O)N2CCC(c3ccc(C#N)cc3)CC2)cc1Nc1nnc(C(C)C)[nH]1] | 30.090 |
| 001-283 | 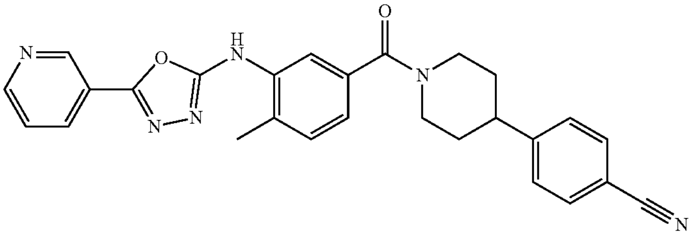 [SMILES: Cc1ccc(C(=O)N2CCC(c3ccc(C#N)cc3)CC2)cc1Nc1nnc(-c2cccnc2)o1] | 1.000 |

TABLE C-1-continued
| Cmpd No. | Structure | FASN $IC_{50}$ (μM) |
|---|---|---|
| Fatty Acid Synthase Inhibitors | | |
| 001-284 | 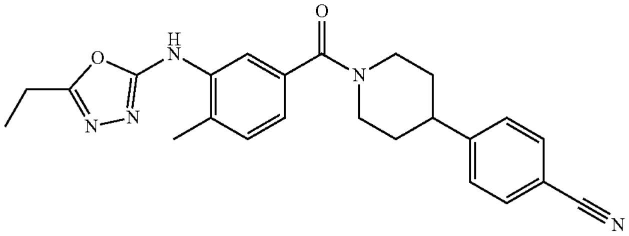 [SMILES: CCc1nnc(Nc2cc(C(=O)N3CCC(c4ccc(C#N)cc4)CC3)ccc2C)o1] | 1.005 |
| 001-285 | 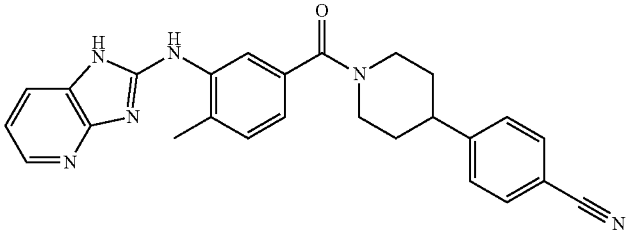 [SMILES: Cc1ccc(C(=O)N2CCC(c3ccc(C#N)cc3)CC2)cc1Nc1nc2ncccc2[nH]1] | >50 |
| 001-286 | 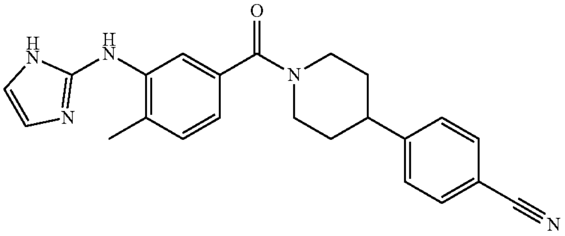 [SMILES: Cc1ccc(C(=O)N2CCC(c3ccc(C#N)cc3)CC2)cc1Nc1ncc[nH]1] | >50 |
| 001-287 | 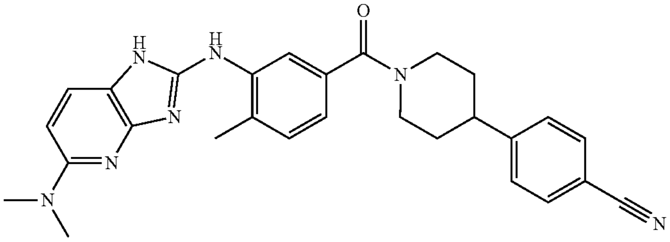 [SMILES: Cc1ccc(C(=O)N2CCC(c3ccc(C#N)cc3)CC2)cc1Nc1nc2nc(N(C)C)ccc2[nH]1] | >40 |
| 001-288 | 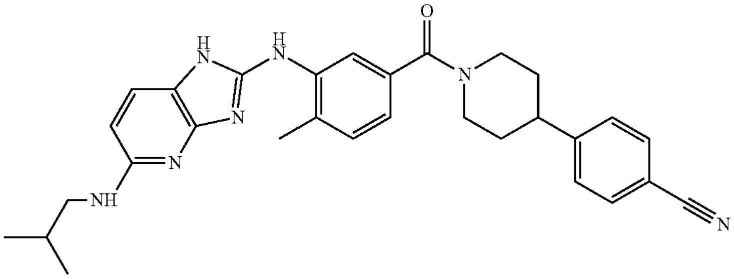 [SMILES: Cc1ccc(C(=O)N2CCC(c3ccc(C#N)cc3)CC2)cc1Nc1nc2nc(NCC(C)C)ccc2[nH]1] | |
| 001-289 | 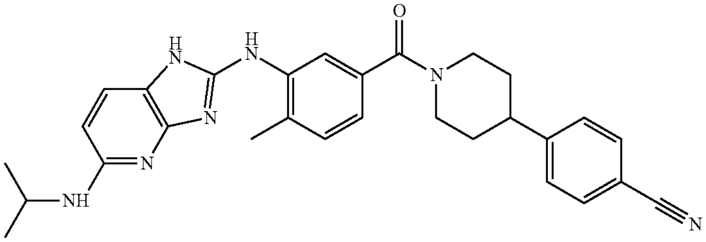 [SMILES: Cc1ccc(C(=O)N2CCC(c3ccc(C#N)cc3)CC2)cc1Nc1nc2nc(NC(C)C)ccc2[nH]1] | 32.733 |

TABLE C-1-continued
| Cmpd No. | Structure | FASN $IC_{50}$ (μM) |
|---|---|---|
| Fatty Acid Synthase Inhibitors | | |
| 001-290 | 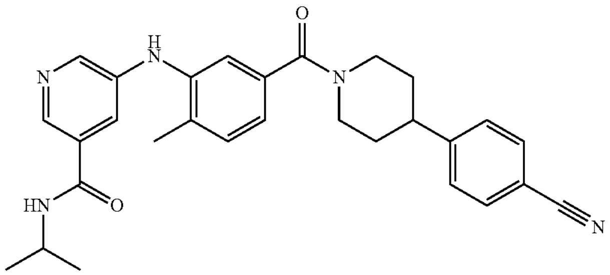 [SMILES: Cc1ccc(C(=O)N2CCC(c3ccc(C#N)cc3)CC2)cc1Nc1cncc(C(=O)NC(C)C)c1] | 0.470 |
| 001-291 | 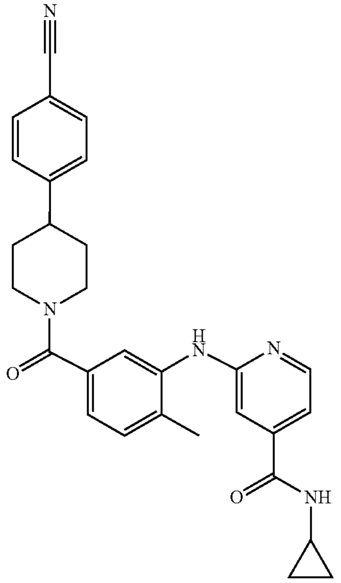 [SMILES: Cc1ccc(C(=O)N2CCC(c3ccc(C#N)cc3)CC2)cc1Nc1cc(C(=O)NC2CC2)ccn1] | 0.370 |
| 001-292 | 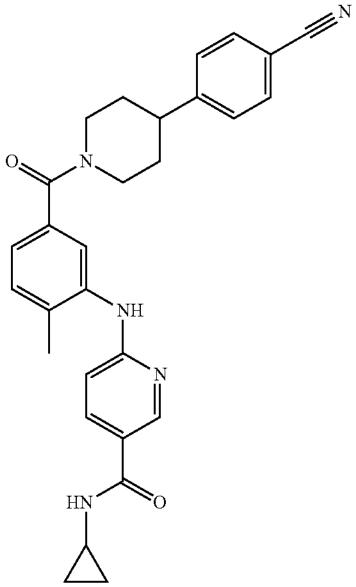 [SMILES: Cc1ccc(C(=O)N2CCC(c3ccc(C#N)cc3)CC2)cc1Nc1ccc(C(=O)NC2CC2)cn1] | 0.270 |

TABLE C-1-continued
| Fatty Acid Synthase Inhibitors | | |
|---|---|---|
| Cmpd No. | Structure | FASN $IC_{50}$ (μM) |
| 001-293 | 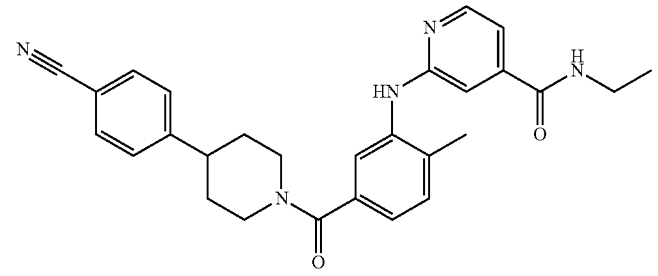 [SMILES: CCNC(=O)c1ccnc(Nc2cc(C(=O)N3CCC(c4ccc(C#N)cc4)CC3)ccc2C)c1] | 1.080 |
| 001-294 | 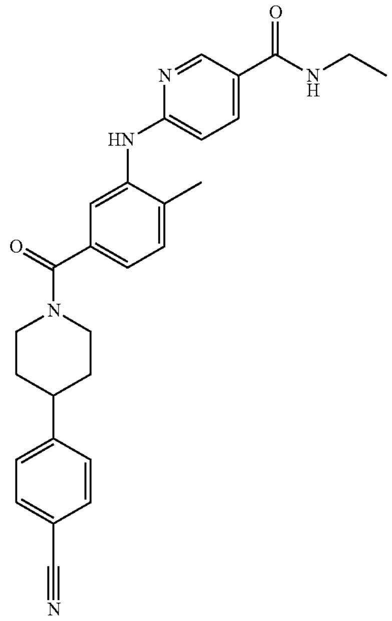 [SMILES: CCNC(=O)c1ccc(Nc2cc(C(=O)N3CCC(c4ccc(C#N)cc4)CC3)ccc2C)nc1] | |
| 001-295 | 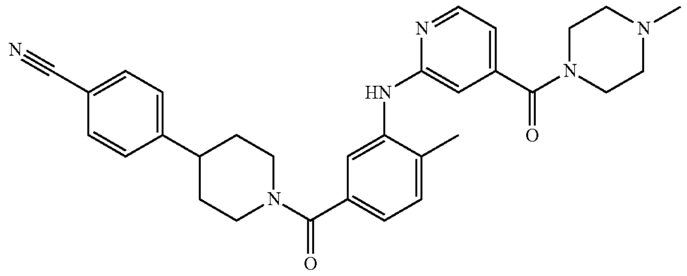 [SMILES: Cc1ccc(C(=O)N2CCC(c3ccc(C#N)cc3)CC2)cc1Nc1cc(C(=O)N2CCN(C)CC2)ccn1] | 3.820 |
| 001-296 | 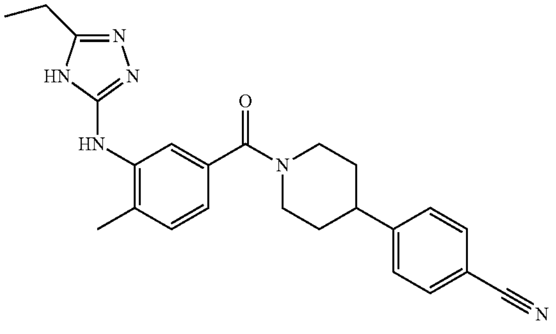 [SMILES: CCc1nnc(Nc2cc(C(=O)N3CCC(c4ccc(C#N)cc4)CC3)ccc2C)[nH]1] | 3.250 |

TABLE C-1-continued
| Fatty Acid Synthase Inhibitors | | |
|---|---|---|
| Cmpd No. | Structure | FASN $IC_{50}$ (μM) |
| 001-297 | 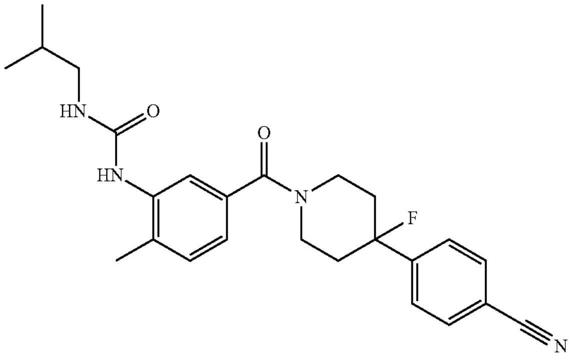 [SMILES: Cc1ccc(C(=O)N2CCC(F)(c3ccc(C#N)cc3)CC2)cc1NC(=O)NCC(C)C] | 0.025 |
| 001-298 | 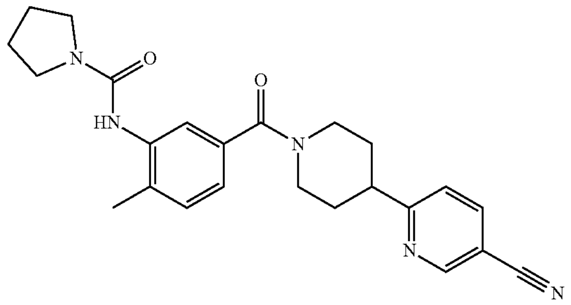 [SMILES: Cc1ccc(C(=O)N2CCC(c3ccc(C#N)cn3)CC2)cc1NC(=O)N1CCCC1] | |
| 001-299 | 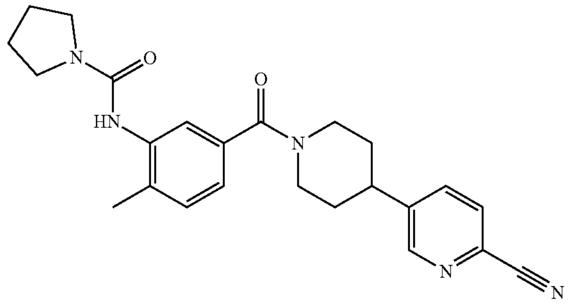 [SMILES: Cc1ccc(C(=O)N2CCC(c3ccc(C#N)nc3)CC2)cc1NC(=O)N1CCCC1] | |
| 001-300 | 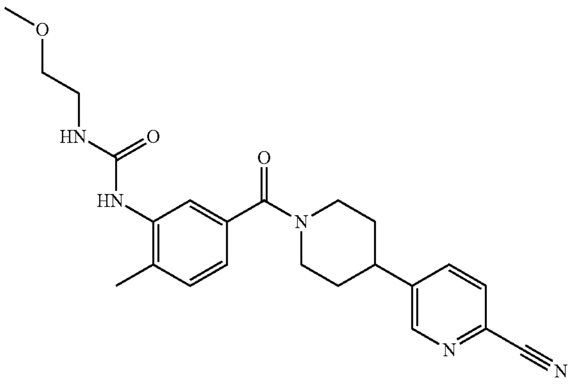 [SMILES: COCCNC(=O)Nc1cc(C(=O)N2CCC(c3ccc(C#N)nc3)CC2)ccc1C] | |

TABLE C-1-continued
| Fatty Acid Synthase Inhibitors | | |
|---|---|---|
| Cmpd No. | Structure | FASN $IC_{50}$ (μM) |
| 001-301 | 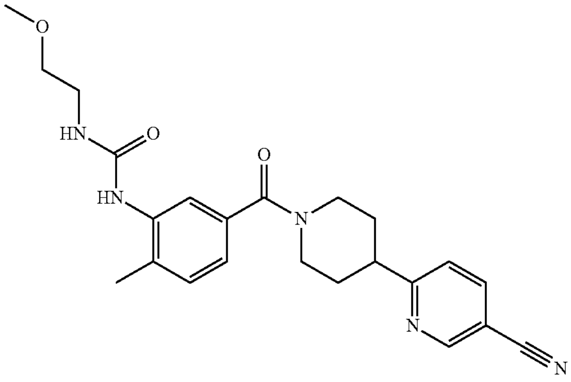 [SMILES: COCCNC(=O)Nc1cc(C(=O)N2CCC(c3ccc(C#N)cn3)CC2)ccc1C] | |
| 001-302 | 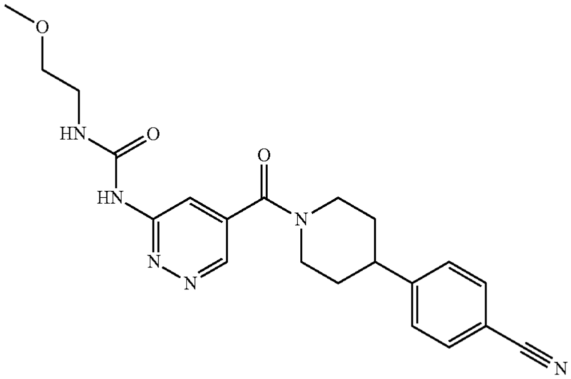 [SMILES: COCCNC(=O)Nc1cc(C(=O)N2CCC(c3ccc(C#N)cc3)CC2)cnn1] | >50 |
| 001-303 | 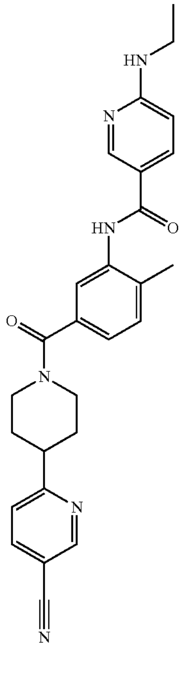 [SMILES: CCNc1ccc(C(=O)Nc2cc(C(=O)N3CCC(c4ccc(C#N)cn4)CC3)ccc2C)cn1] | |

TABLE C-1-continued
| Fatty Acid Synthase Inhibitors | | |
|---|---|---|
| Cmpd No. | Structure | FASN $IC_{50}$ (μM) |
| 001-304 | 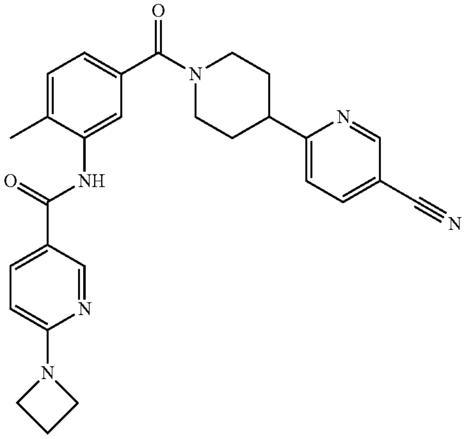 [SMILES: Cc1ccc(C(=O)N2CCC(c3ccc(C#N)cn3)CC2)cc1NC(=O)c1ccc(N2CCC2)nc1] | 0.680 |
| 001-305 | 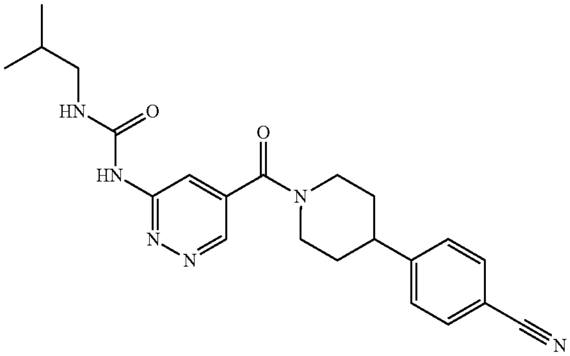 | >50 |
| 001-306 | 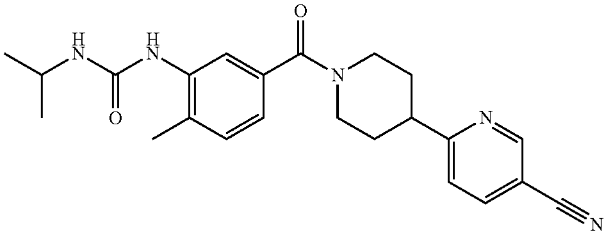 [SMILES: Cc1ccc(C(=O)N2CCC(c3ccc(C#N)cn3)CC2)cc1NC(=O)NC(C)C] | 2.900 |
| 001-307 | 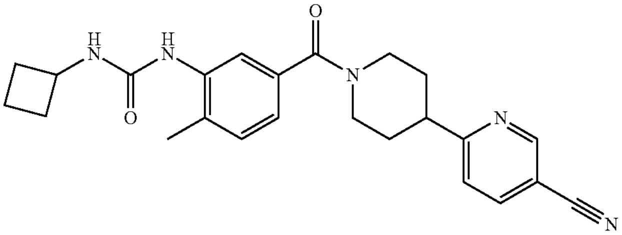 [SMILES: Cc1ccc(C(=O)N2CCC(c3ccc(C#N)cn3)CC2)cc1NC(=O)NC1CCC1] | 5.360 |
| 001-308 | 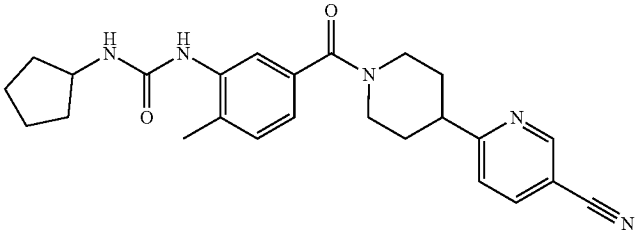 [SMILES: Cc1ccc(C(=O)N2CCC(c3ccc(C#N)cn3)CC2)cc1NC(=O)NC1CCCC1] | 2.750 |

TABLE C-1-continued
| Fatty Acid Synthase Inhibitors | | |
|---|---|---|
| Cmpd No. | Structure | FASN $IC_{50}$ (μM) |
| 001-309 | 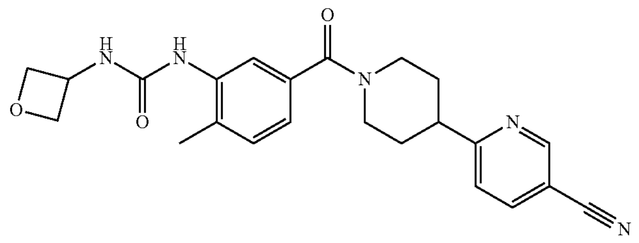 [SMILES: Cc1ccc(C(=O)N2CCC(c3ccc(C#N)cn3)CC2)cc1NC(=O)NC1COC1] | |
| 001-310 | 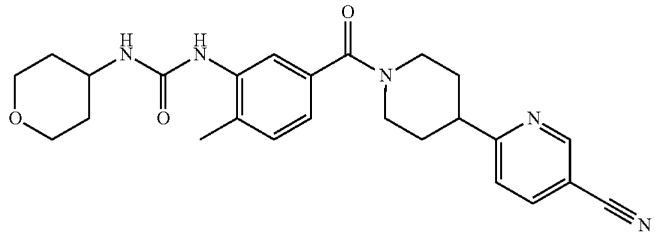 [SMILES: Cc1ccc(C(=O)N2CCC(c3ccc(C#N)cn3)CC2)cc1NC(=O)NC1CCOCC1] | 8.780 |
| 001-311 | 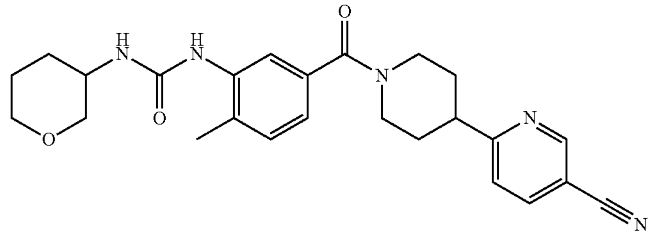 [SMILES: Cc1ccc(C(=O)N2CCC(c3ccc(C#N)cn3)CC2)cc1NC(=O)NC1CCCOC1] | |
| 001-312 | 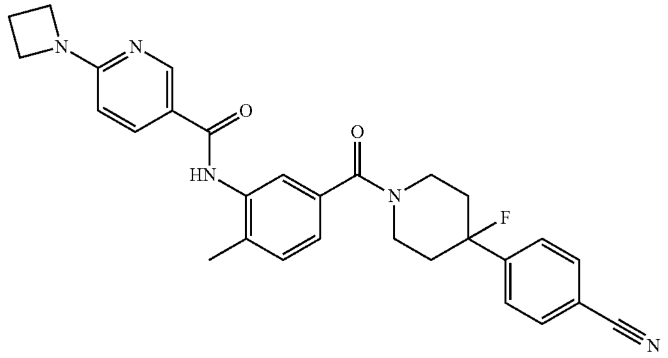 | 0.025 |
| 001-313 | 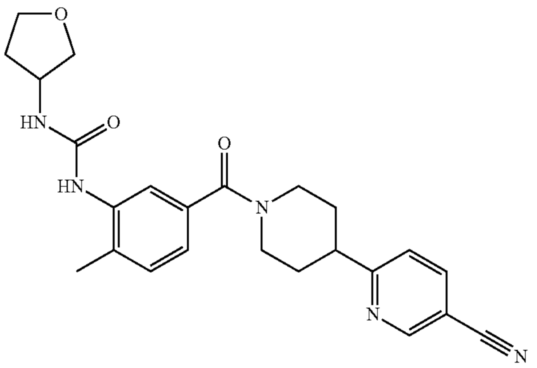 [SMILES: Cc1ccc(C(=O)N2CCC(c3ccc(C#N)cn3)CC2)cc1NC(=O)NC1CCOC1] | 1.630 |

TABLE C-1-continued
| Cmpd No. | Structure | FASN IC$_{50}$ (μM) |
| --- | --- | --- |
| | Fatty Acid Synthase Inhibitors | |
| 001-314 | 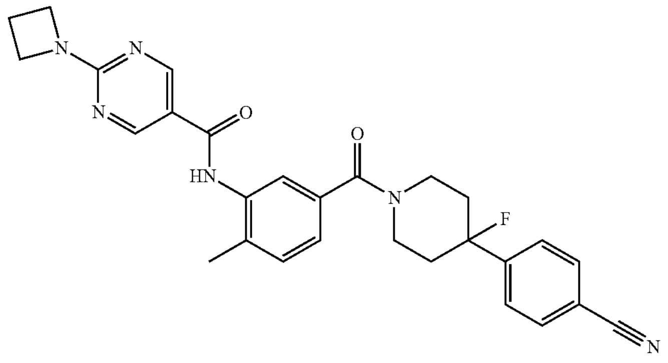 [SMILES: Cc1ccc(C(=O)N2CCC(F)(c3ccc(C#N)cc3)CC2)cc1NC(=O)c1cnc(N2CCC2)nc1] | 0.047 |
| 001-315 | 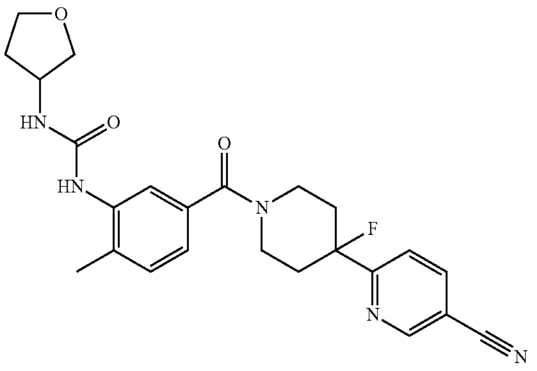 [SMILES: Cc1ccc(C(=O)N2CCC(F)(c3ccc(C#N)cn3)CC2)cc1NC(=O)NC1CCOC1] | 0.267 |
| 001-316 | 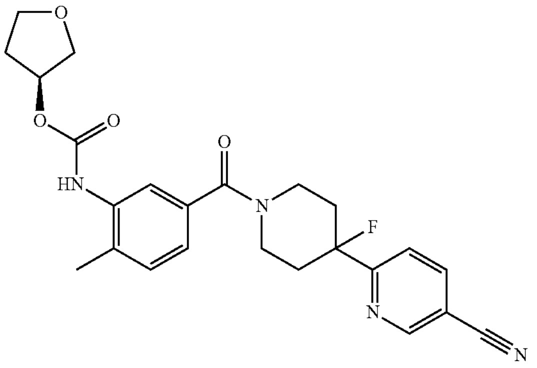 [SMILES: Cc1ccc(C(=O)N2CCC(F)(c3ccc(C#N)cn3)CC2)cc1NC(=O)O[C@H]1CCOC1] | 0.690 |
| 001-317 | 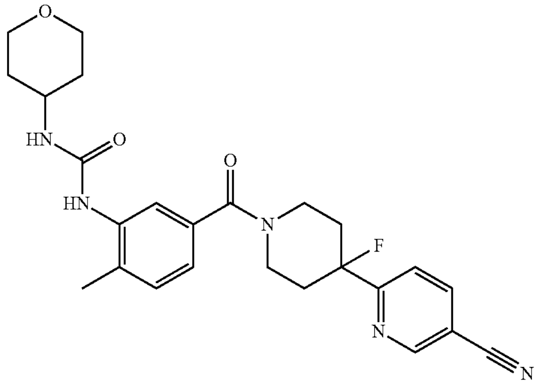 [SMILES: Cc1ccc(C(=O)N2CCC(F)(c3ccc(C#N)cn3)CC2)cc1NC(=O)NC1CCOCC1] | 1.170 |

TABLE C-1-continued
| Fatty Acid Synthase Inhibitors | | |
|---|---|---|
| Cmpd No. | Structure | FASN $IC_{50}$ (μM) |
| 001-318 | 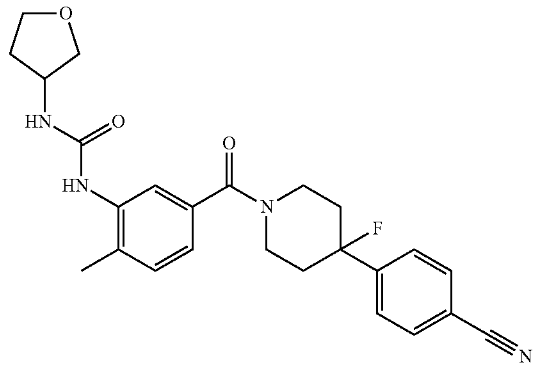 [SMILES: Cc1ccc(C(=O)N2CCC(F)(c3ccc(C#N)cc3)CC2)cc1NC(=O)NC1CCOC1] | 0.037 |
| 001-319 | 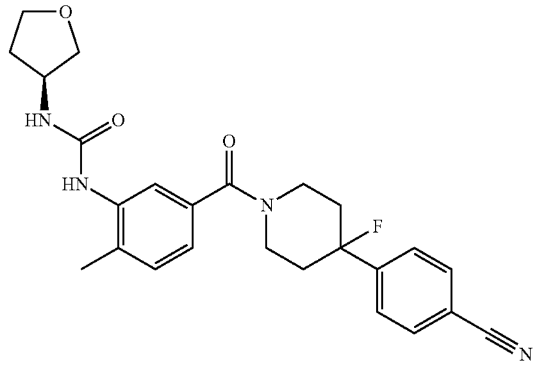 [SMILES: Cc1ccc(C(=O)N2CCC(F)(c3ccc(C#N)cc3)CC2)cc1NC(=O)N[C@H]1CCOC1] | 0.195 |
| 001-320 | 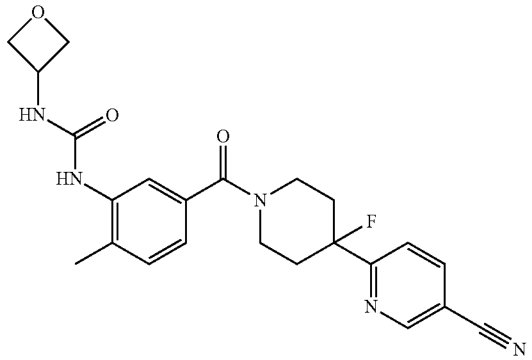 [SMILES: Cc1ccc(C(=O)N2CCC(F)(c3ccc(C#N)cn3)CC2)cc1NC(=O)NC1COC1] | 1.020 |
| 001-321 | 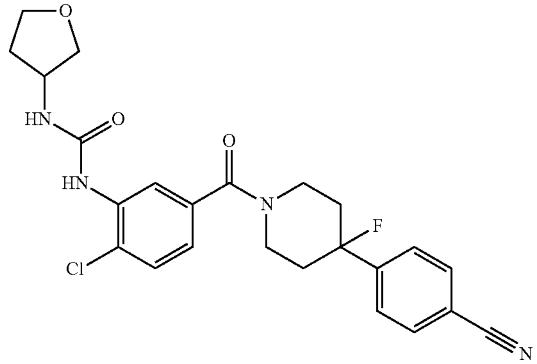 [SMILES: N#Cc1ccc(C2(F)CCN(C(=O)c3ccc(Cl)c(NC(=O)NC4CCOC4)c3)CC2)cc1] | 0.030 |

TABLE C-1-continued
| Fatty Acid Synthase Inhibitors | | |
|---|---|---|
| Cmpd No. | Structure | FASN $IC_{50}$ (μM) |
| 001-322 | 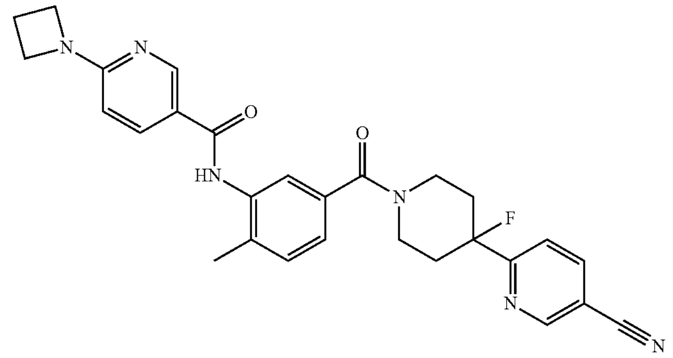 [SMILES: Cc1ccc(C(=O)N2CCC(F)(c3ccc(C#N)cn3)CC2)cc1NC(=O)c1ccc(N2CCC2)nc1] | 0.180 |
| 001-323 | 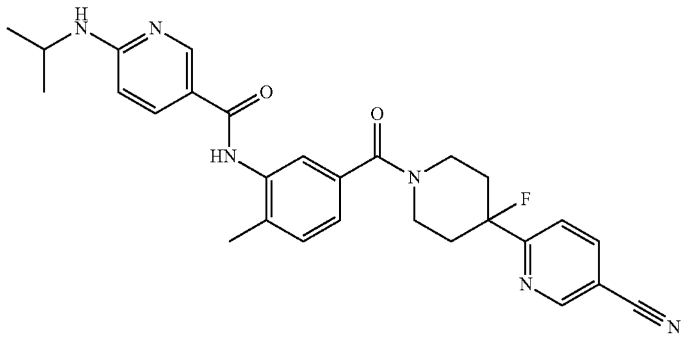 [SMILES: Cc1ccc(C(=O)N2CCC(F)(c3ccc(C#N)cn3)CC2)cc1NC(=O)c1ccc(NC(C)C)nc1] | 0.360 |
| 001-324 | 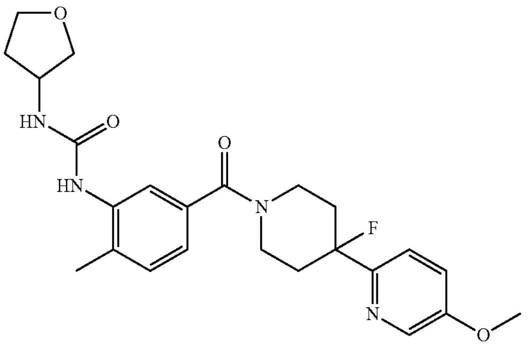 [SMILES: COc1ccc(C2(F)CCN(C(=O)c3ccc(C)c(NC(=O)NC4CCOC4)c3)CC2)nc1] | 1.175 |
| 001-325 | 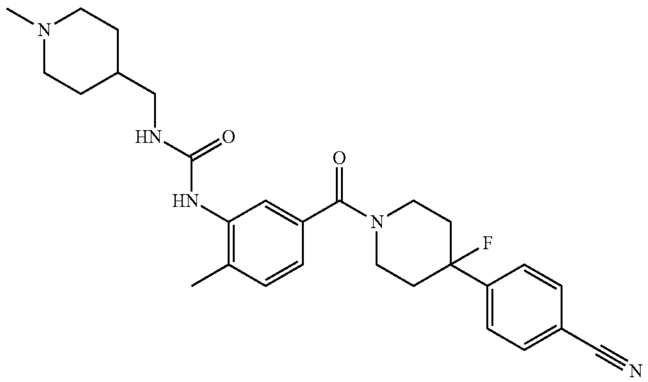 [SMILES: Cc1ccc(C(=O)N2CCC(F)(c3ccc(C#N)cc3)CC2)cc1NC(=O)NCC1CCN(C)CC1] | 0.340 |

TABLE C-1-continued
| Fatty Acid Synthase Inhibitors | | |
|---|---|---|
| Cmpd No. | Structure | FASN $IC_{50}$ (μM) |
| 001-326 | 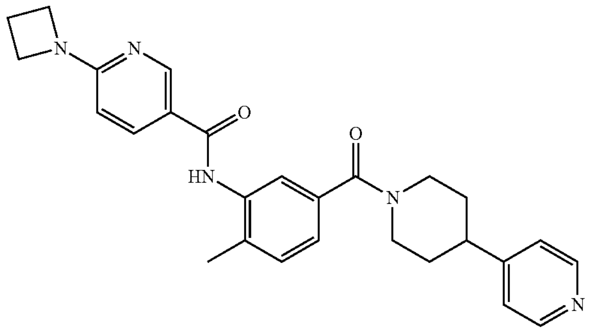 [SMILES: Cc1ccc(C(=O)N2CCC(c3ccncc3)CC2)cc1NC(=O)c1ccc(N2CCC2)nc1] | 2.750 |
| 001-327 | 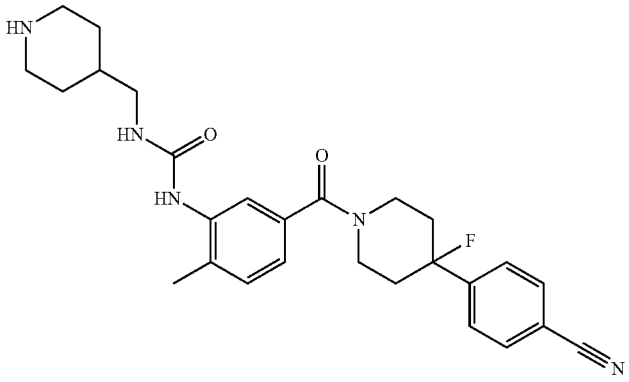 [SMILES: Cc1ccc(C(=O)N2CCC(F)(c3ccc(C#N)cc3)CC2)cc1NC(=O)NCC1CCNCC1] | 0.610 |
| 001-328 | 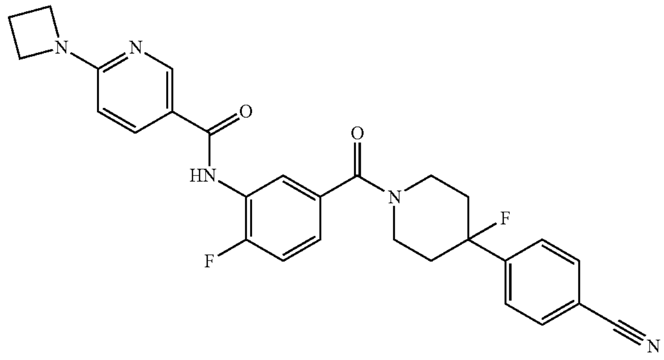 [SMILES: N#Cc1ccc(C2(F)CCN(C(=O)c3ccc(F)c(NC(=O)c4ccc(N5CCC5)nc4)c3)CC2)cc1] | 0.220 |
| 001-329 | 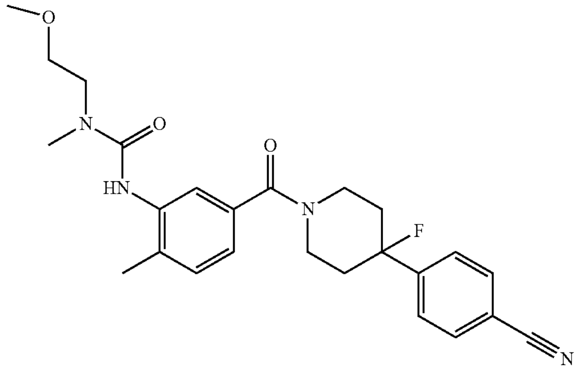 [SMILES: COCCN(C)C(=O)Nc1cc(C(=O)N2CCC(F)(c3ccc(C#N)cc3)CC2)ccc1C] | 8.870 |

TABLE C-1-continued
| Fatty Acid Synthase Inhibitors | | |
|---|---|---|
| Cmpd No. | Structure | FASN $IC_{50}$ (μM) |
| 001-330 | 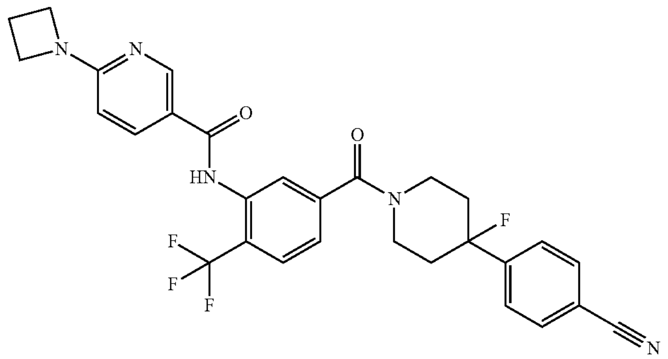 [SMILES: N#Cc1ccc(C2(F)CCN(C(=O)c3ccc(C(F)(F)F)c(NC(=O)c4ccc(N5CCC5)nc4)c3)CC2)cc1] | 0.120 |
| 001-331 | 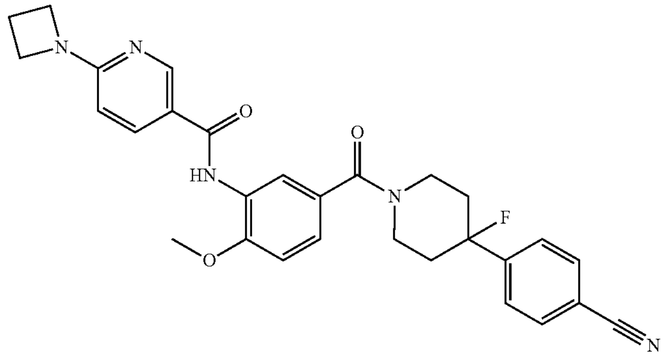 [SMILES: COc1ccc(C(=O)N2CCC(F)(c3ccc(C#N)cc3)CC2)cc1NC(=O)c1ccc(N2CCC2)nc1] | 0.085 |
| 001-332 | 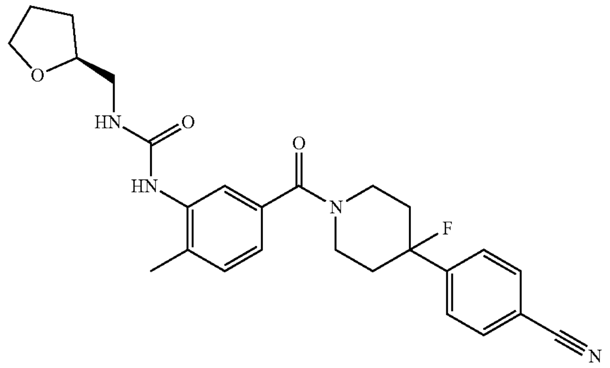 [SMILES: Cc1ccc(C(=O)N2CCC(F)(c3ccc(C#N)cc3)CC2)cc1NC(=O)NC[C@@H]1CCCO1] | 0.050 |
| 001-333 | 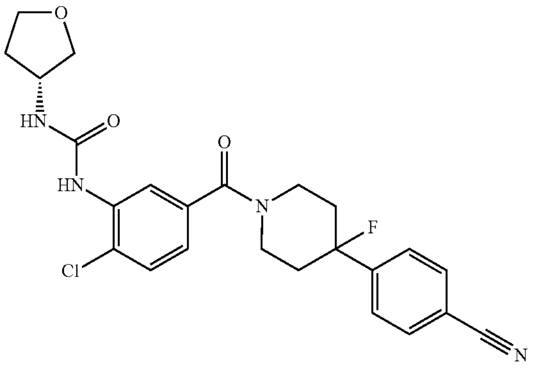 [SMILES: N#Cc1ccc(C2(F)CCN(C(=O)c3ccc(Cl)c(NC(=O)N[C@@H]4CCOC4)c3)CC2)cc1] | |

TABLE C-1-continued
| Fatty Acid Synthase Inhibitors | | |
|---|---|---|
| Cmpd No. | Structure | FASN $IC_{50}$ (μM) |
| 001-334 | 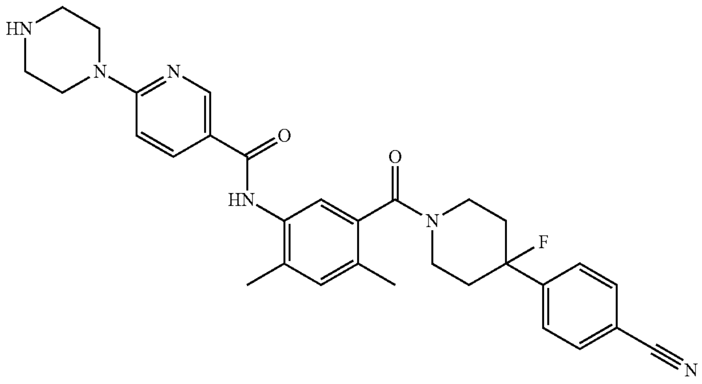 [SMILES: Cc1cc(C)c(C(=O)N2CCC(F)(c3ccc(C#N)cc3)CC2)cc1NC(=O)c1ccc(N2CCNCC2)nc1] | 0.140 |
| 001-335 | 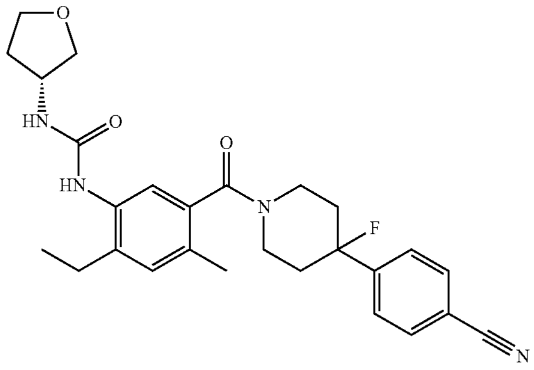 [SMILES: CCc1cc(C)c(C(=O)N2CCC(F)(c3ccc(C#N)cc3)CC2)cc1NC(=O)N[C@@H]1CCOC1] | 0.490 |
| 001-336 | 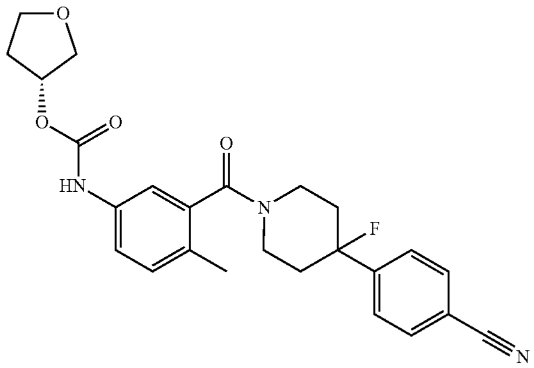 [SMILES: Cc1ccc(NC(=O)O[C@@H]2CCOC2)cc1C(=O)N1CCC(F)(c2ccc(C#N)cc2)CC1] | 0.420 |

TABLE C-1-continued
| Fatty Acid Synthase Inhibitors | | |
|---|---|---|
| Cmpd No. | Structure | FASN $IC_{50}$ (μM) |
| 001-337 | 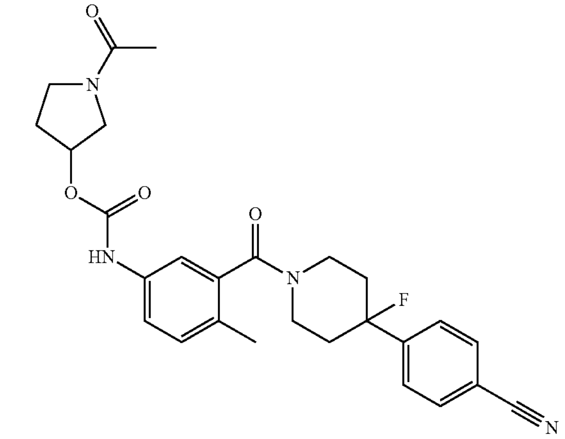 [SMILES: CC(=O)N1CCC(OC(=O)Nc2ccc(C)c(C(=O)N3CCC(F)(c4ccc(C#N)cc4)CC3)c2)C1] | 0.165 |
| 001-338 | 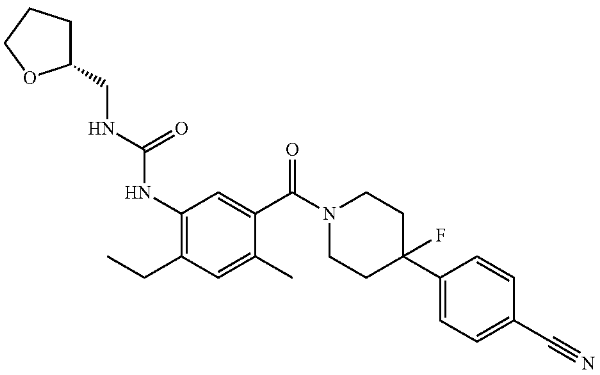 [SMILES: CCc1cc(C)c(C(=O)N2CCC(F)(c3ccc(C#N)cc3)CC2)cc1NC(=O)NC[C@H]1CCCO1] | 0.035 |
| 001-339 | 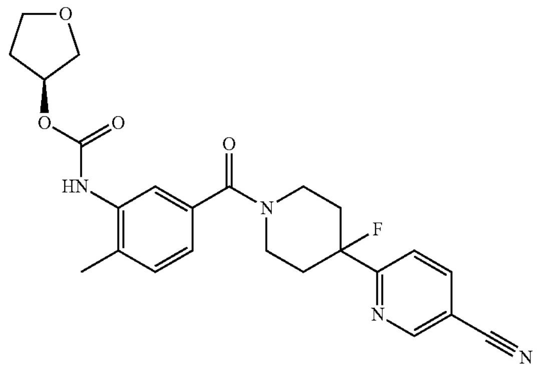 [SMILES: Cc1ccc(C(=O)N2CCC(F)(c3ccc(C#N)cn3)CC2)cc1NC(=O)O[C@H]1CCOC1] | 0.093 |

TABLE C-1-continued
| Fatty Acid Synthase Inhibitors | | |
|---|---|---|
| Cmpd No. | Structure | FASN $IC_{50}$ (μM) |
| 001-340 | 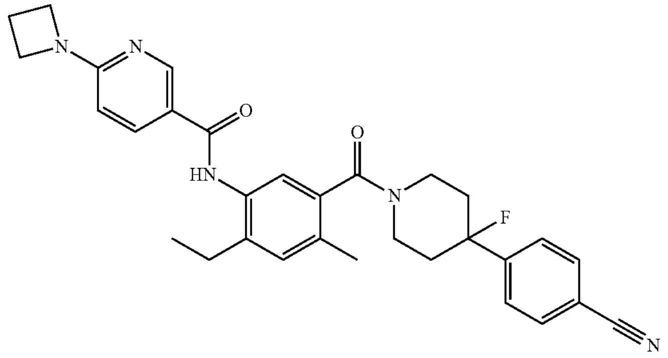 | 0.080 |
| 001-341 | 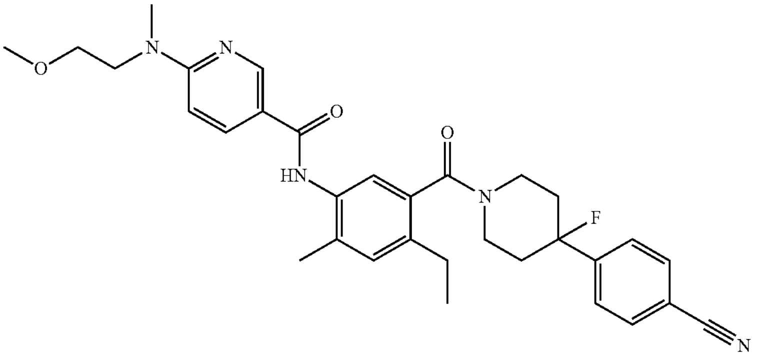 [SMILES: CCc1cc(C)c(NC(=O)c2ccc(N(C)CCOC)nc2)cc1C(=O)N1CCC(F)(c2ccc(C#N)cc2)CC1] | 0.085 |
| 001-342 | 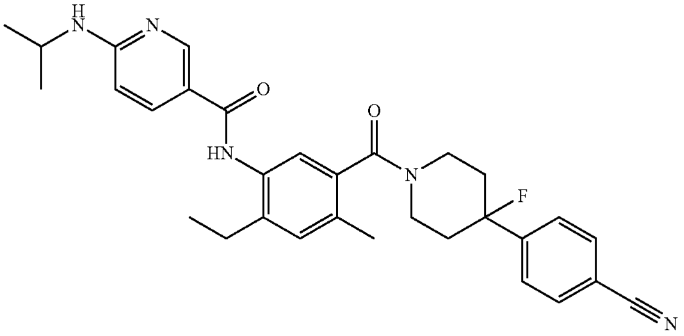 [SMILES: CCc1cc(C)c(C(=O)N2CCC(F)(c3ccc(C#N)cc3)CC2)cc1NC(=O)c1ccc(NC(C)C)nc1] | 0.090 |
| 001-343 | 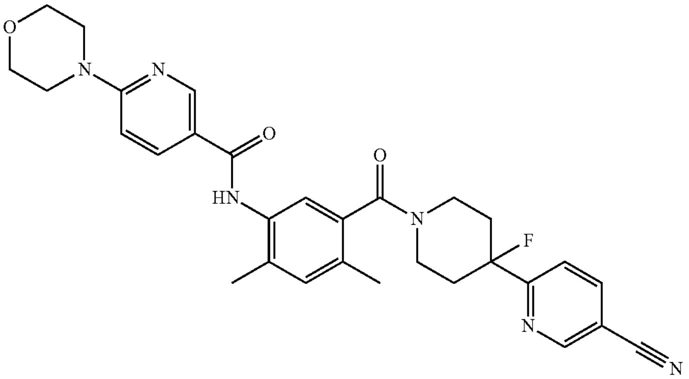 [SMILES: Cc1cc(C)c(C(=O)N2CCC(F)(c3ccc(C#N)cn3)CC2)cc1NC(=O)c1ccc(N2CCOCC2)nc1] | 0.600 |

TABLE C-1-continued
| Fatty Acid Synthase Inhibitors | | |
|---|---|---|
| Cmpd No. | Structure | FASN $IC_{50}$ (μM) |
| 001-344 | 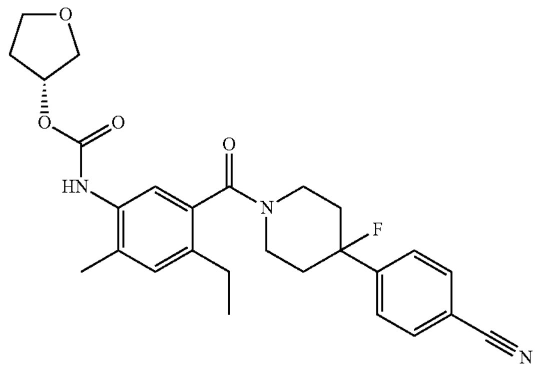 | 0.250 |
| 001-345 | 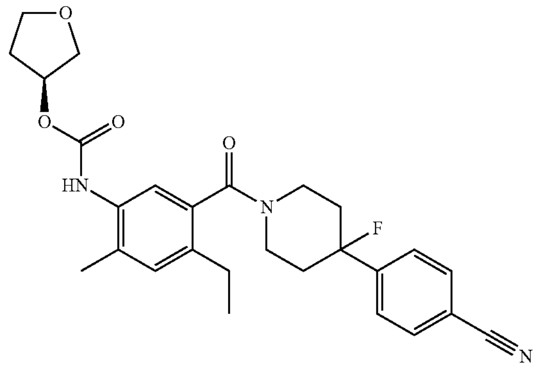 [SMILES: CCc1cc(C)c(NC(=O)O[C@H]2CCOC2)cc1C(=O)N1CCC(F)(c2ccc(C#N)cc2)CC1] | 0.140 |
| 001-346 | 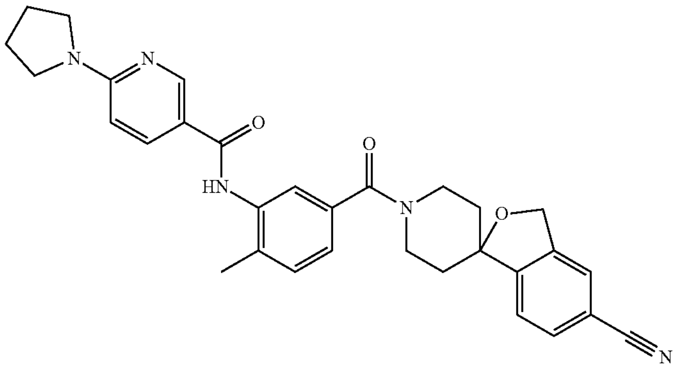 [SMILES: Cc1ccc(C(=O)N2CCC3(CC2)OCc2cc(C#N)ccc23)cc1NC(=O)c1ccc(N2CCCC2)nc1] | 0.330 |
| 001-347 | 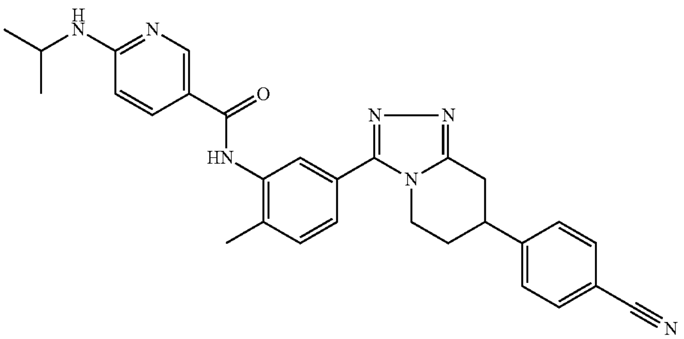 [SMILES: Cc1ccc(-c2nnc3n2CCC(c2ccc(C#N)cc2)C3)cc1NC(=O)c1ccc(NC(C)C)nc1] | 0.300 |

TABLE C-1-continued
| Fatty Acid Synthase Inhibitors | | |
|---|---|---|
| Cmpd No. | Structure | FASN $IC_{50}$ (μM) |
| 001-348 | 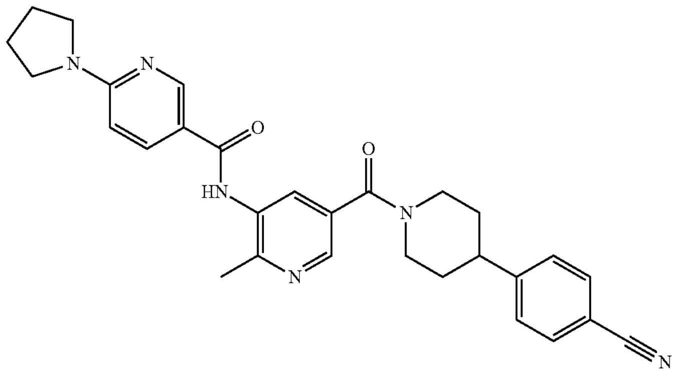 [SMILES: Cc1ncc(C(=O)N2CCC(c3ccc(C#N)cc3)CC2)cc1NC(=O)c1ccc(N2CCCC2)nc1] | 0.455 |
| 001-349 | 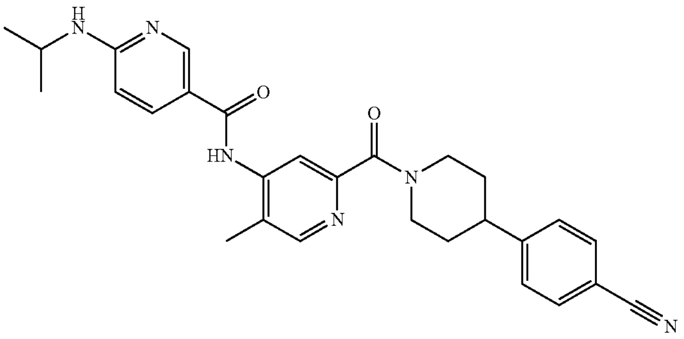 [SMILES: Cc1cnc(C(=O)N2CCC(c3ccc(C#N)cc3)CC2)cc1NC(=O)c1ccc(NC(C)C)nc1] | >50 |
| 001-350 | 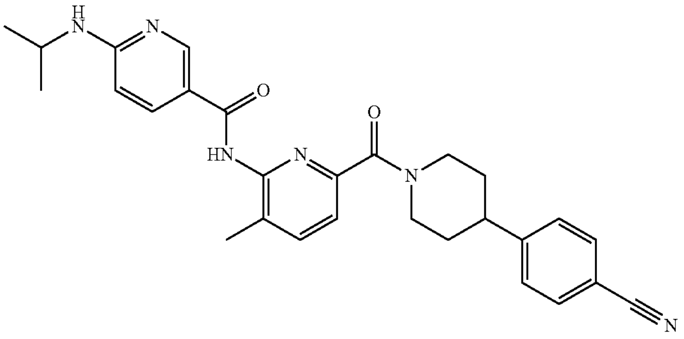 [SMILES: Cc1ccc(C(=O)N2CCC(c3ccc(C#N)cc3)CC2)nc1NC(=O)c1ccc(NC(C)C)nc1] | 32.600 |
| 001-351 | 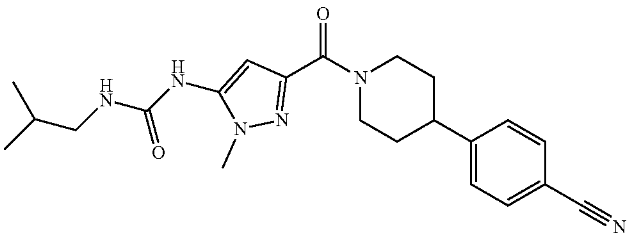 [SMILES: CC(C)CNC(=O)Nc1cc(C(=O)N2CCC(c3ccc(C#N)cc3)CC2)nn1C] | >50 |

TABLE C-1-continued
| Fatty Acid Synthase Inhibitors | | |
|---|---|---|
| Cmpd No. | Structure | FASN $IC_{50}$ (μM) |
| 001-352 | 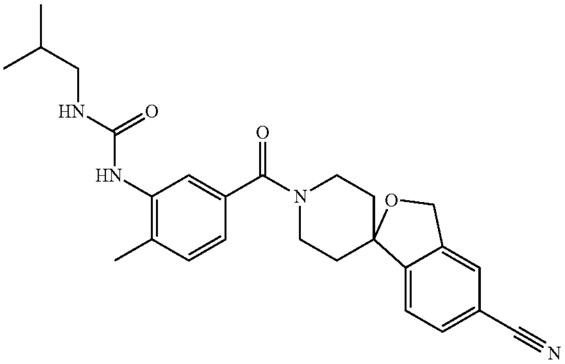 [SMILES: Cc1ccc(C(=O)N2CCC3(CC2)OCc2cc(C#N)ccc23)cc1NC(=O)NCC(C)C] | 0.880 |
| 001-353 | 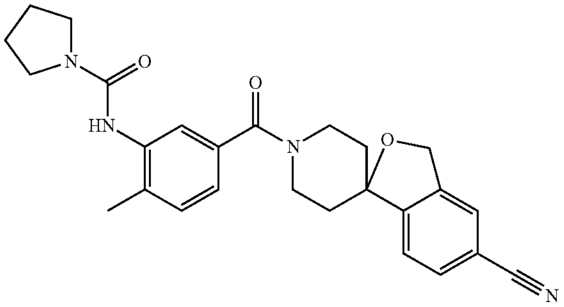 [SMILES: Cc1ccc(C(=O)N2CCC3(CC2)OCc2cc(C#N)ccc23)cc1NC(=O)N1CCCC1] | 18.500 |
| 001-354 | 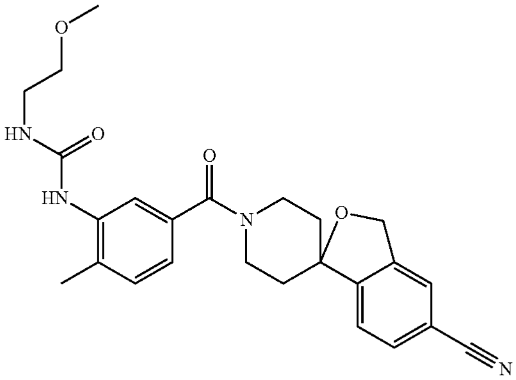 [SMILES: COCCNC(=O)Nc1cc(C(=O)N2CCC3(CC2)OCc2cc(C#N)ccc23)ccc1C] | 0.380 |
| 001-355 | 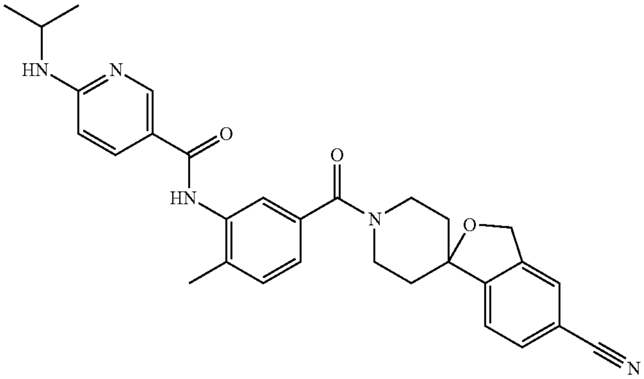 [SMILES: Cc1ccc(C(=O)N2CCC3(CC2)OCc2cc(C#N)ccc23)cc1NC(=O)c1ccc(NC(C)C)nc1] | 0.140 |

TABLE C-1-continued
| Fatty Acid Synthase Inhibitors | | |
|---|---|---|
| Cmpd No. | Structure | FASN $IC_{50}$ (μM) |
| 001-356 | 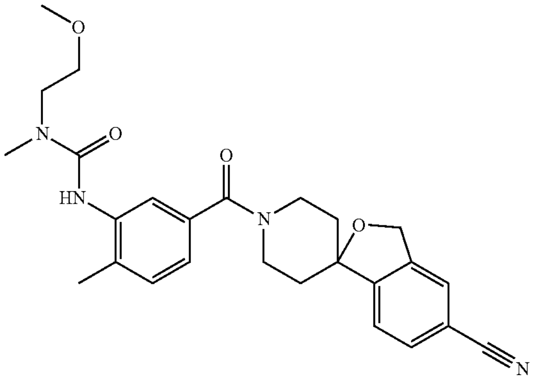 [SMILES: COCCN(C)C(=O)Nc1cc(C(=O)N2CCC3(CC2)OCc2cc(C#N)ccc23)ccc1C] | >50 |
| 001-357 | 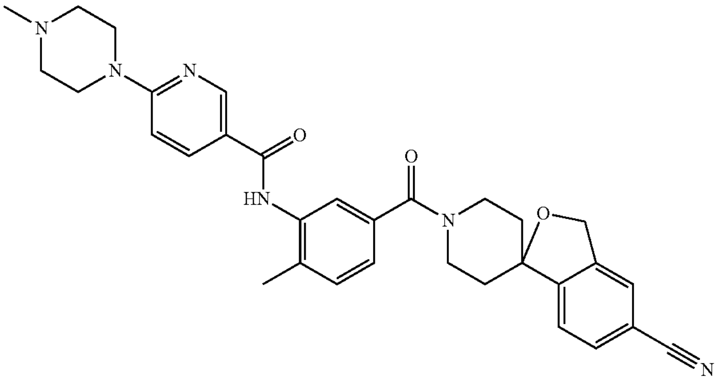 [SMILES: Cc1ccc(C(=O)N2CCC3(CC2)OCc2cc(C#N)ccc23)cc1NC(=O)c1ccc(N2CCN(C)CC2)nc1] | 0.230 |
| 358 | 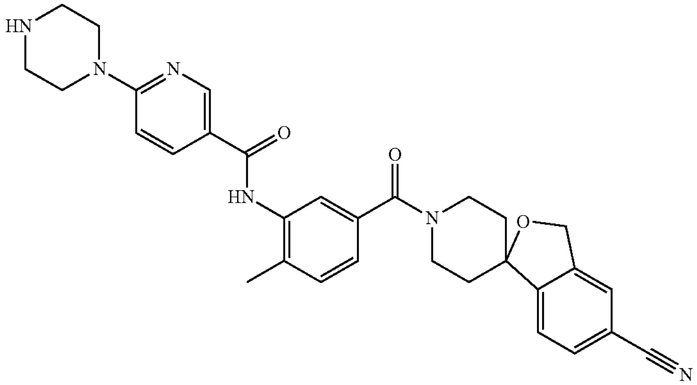 [SMILES: Cc1ccc(C(=O)N2CCC3(CC2)OCc2cc(C#N)ccc23)cc1NC(=O)c1ccc(N2CCNCC2)nc1] | 0.805 |
| 001-359 | 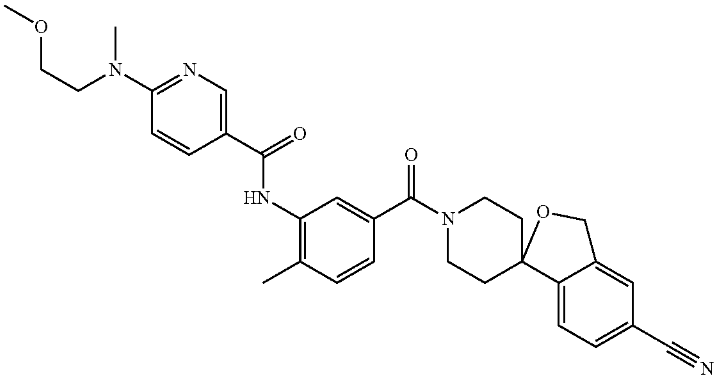 [SMILES: COCCN(C)c1ccc(C(=O)Nc2cc(C(=O)N3CCC4(CC3)OCc3cc(C#N)ccc34)ccc2C)cn1] | 0.105 |

TABLE C-1-continued
| Fatty Acid Synthase Inhibitors | | |
|---|---|---|
| Cmpd No. | Structure | FASN $IC_{50}$ (μM) |
| 001-360 | 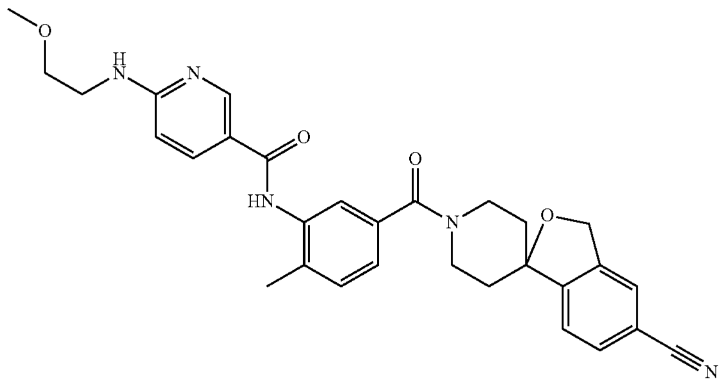 [SMILES: COCCNc1ccc(C(=O)Nc2cc(C(=O)N3CCC4(CC3)OCc3cc(C#N)ccc34)ccc2C)cn1] | 0.280 |
| 001-361 | 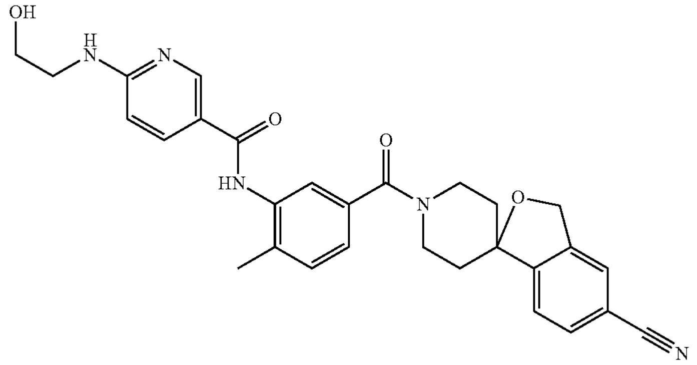 [SMILES: Cc1ccc(C(=O)N2CCC3(CC2)OCc2cc(C#N)ccc23)cc1NC(=O)c1ccc(NCCO)nc1] | 0.360 |
| 001-362 | 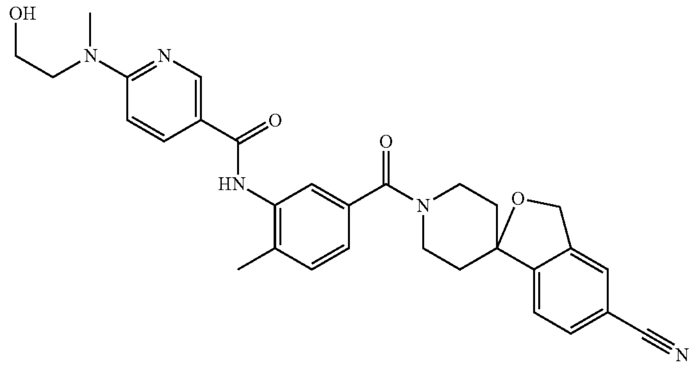 [SMILES: Cc1ccc(C(=O)N2CCC3(CC2)OCc2cc(C#N)ccc23)cc1NC(=O)c1ccc(N(C)CCO)nc1] | 0.247 |
| 001-363 | 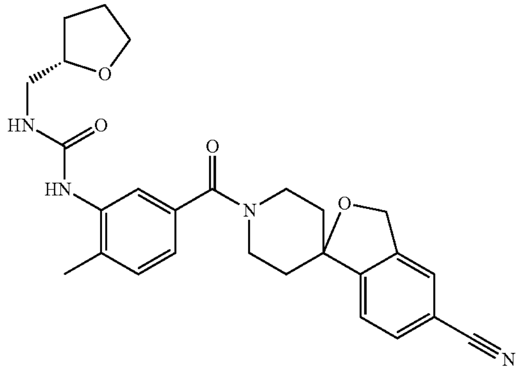 [SMILES: Cc1ccc(C(=O)N2CCC3(CC2)OCc2cc(C#N)ccc23)cc1NC(=O)NC[C@@H]1CCCO1] | 0.050 |

TABLE C-1-continued
| Fatty Acid Synthase Inhibitors | | |
|---|---|---|
| Cmpd No. | Structure | FASN $IC_{50}$ (μM) |
| 001-364 | 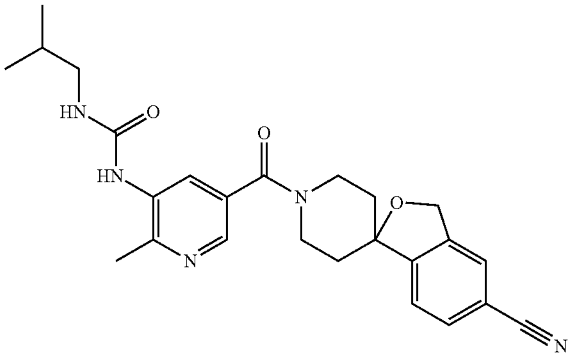 [SMILES: Cc1ncc(C(=O)N2CCC3(CC2)OCc2cc(C#N)ccc23)cc1NC(=O)NCC(C)C] | 37.000 |
| 001-365 | 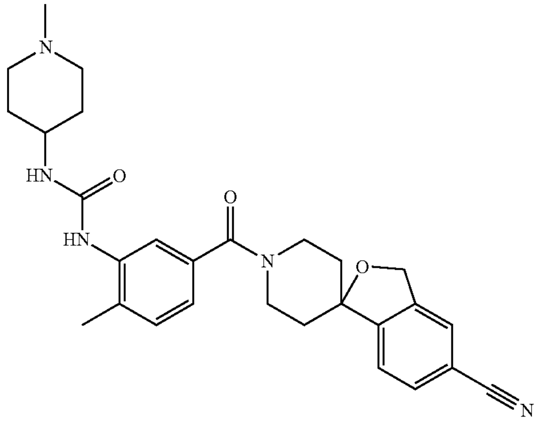 [SMILES: Cc1ccc(C(=O)N2CCC3(CC2)OCc2cc(C#N)ccc23)cc1NC(=O)NC1CCN(C)CC1] | 0.310 |
| 001-366 | 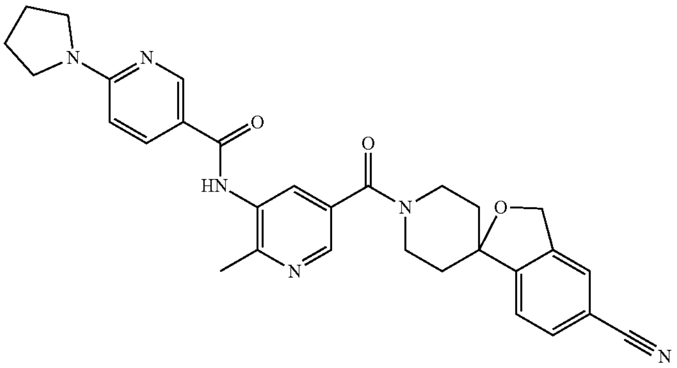 [SMILES: Cc1ncc(C(=O)N2CCC3(CC2)OCc2cc(C#N)ccc23)cc1NC(=O)c1ccc(N2CCCC2)nc1] | 1.100 |
| 001-367 | 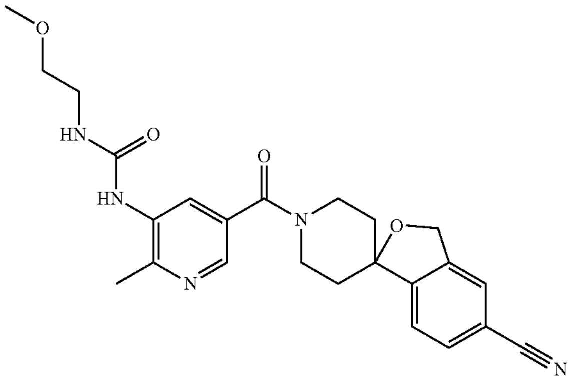 [SMILES: COCCNC(=O)Nc1cc(C(=O)N2CCC3(CC2)OCc2cc(C#N)ccc23)cnc1C] | |

TABLE C-1-continued
| Cmpd No. | Structure | FASN $IC_{50}$ (μM) |
|---|---|---|
| | Fatty Acid Synthase Inhibitors | |
| 001-368 | 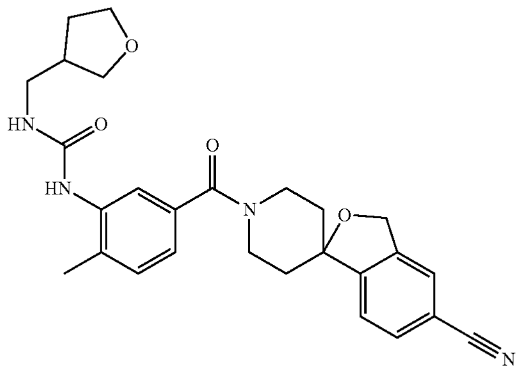 [SMILES: Cc1ccc(C(=O)N2CCC3(CC2)OCc2cc(C#N)ccc23)cc1NC(=O)NCC1CCOC1] | 0.310 |
| 001-369 | 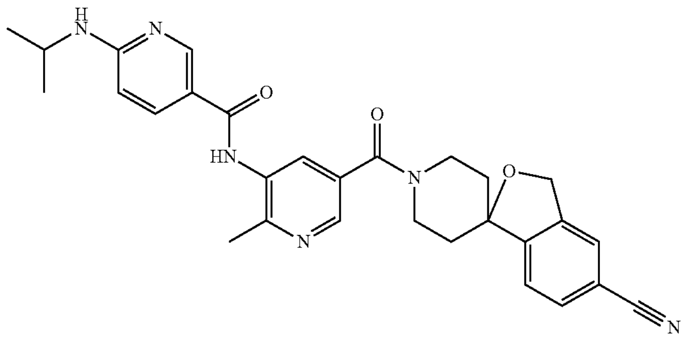 [SMILES: Cc1ncc(C(=O)N2CCC3(CC2)OCc2cc(C#N)ccc23)cc1NC(=O)c1ccc(NC(C)C)nc1] | 7.150 |
| 001-370 | 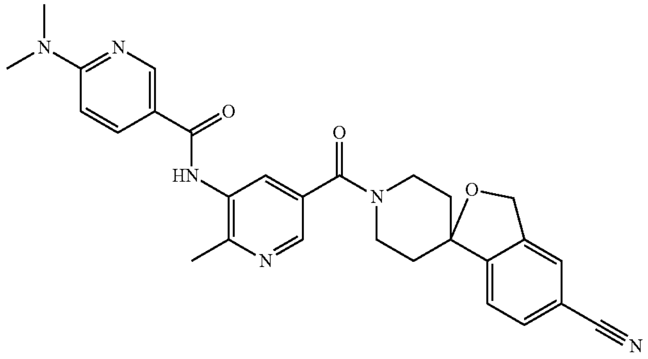 [SMILES: Cc1ncc(C(=O)N2CCC3(CC2)OCc2cc(C#N)ccc23)cc1NC(=O)c1ccc(N(C)C)nc1] | |
| 001-371 | 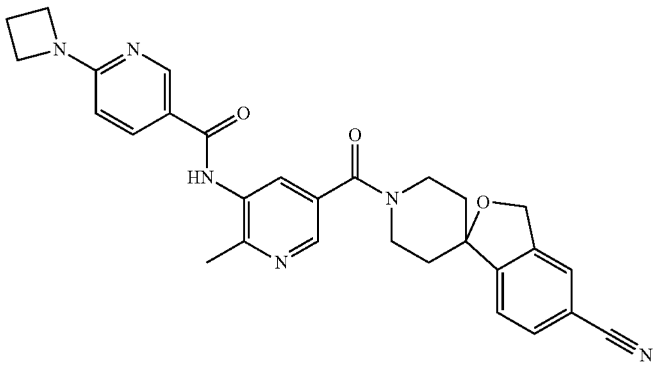 [SMILES: Cc1ncc(C(=O)N2CCC3(CC2)OCc2cc(C#N)ccc23)cc1NC(=O)c1ccc(N2CCC2)nc1] | |

TABLE C-1-continued
| Fatty Acid Synthase Inhibitors | | |
|---|---|---|
| Cmpd No. | Structure | FASN $IC_{50}$ (μM) |
| 001-372 | 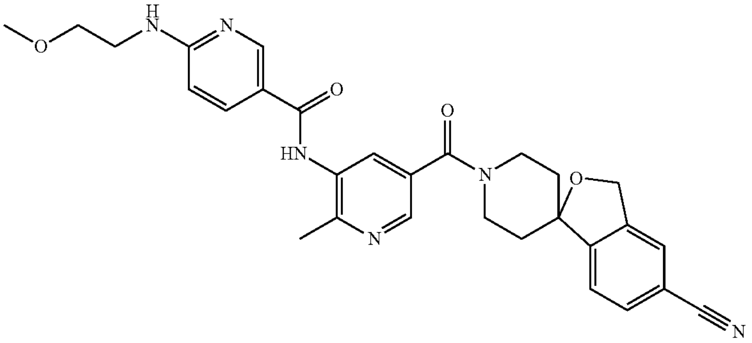 [SMILES: COCCNc1ccc(C(=O)Nc2cc(C(=O)N3CCC4(CC3)OCc3cc(C#N)ccc34)cnc2C)cn1] | |
| 001-373 | 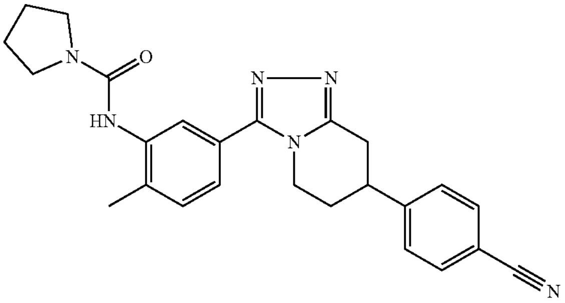 [SMILES: Cc1ccc(-c2nnc3n2CCC(c2ccc(C#N)cc2)C3)cc1NC(=O)N1CCCC1] | >50 |
| 001-374 | 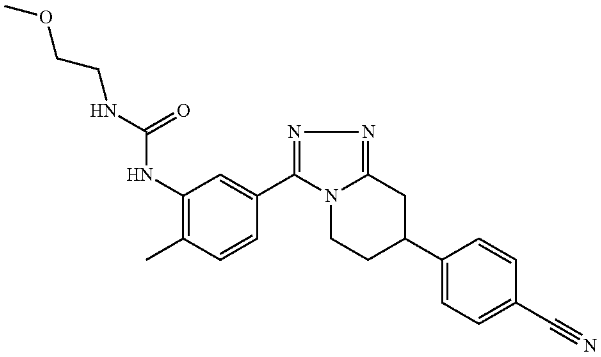 [SMILES: COCCNC(=O)Nc1cc(-c2nnc3n2CCC(c2ccc(C#N)cc2)C3)ccc1C] | 3.580 |
| 001-375 | 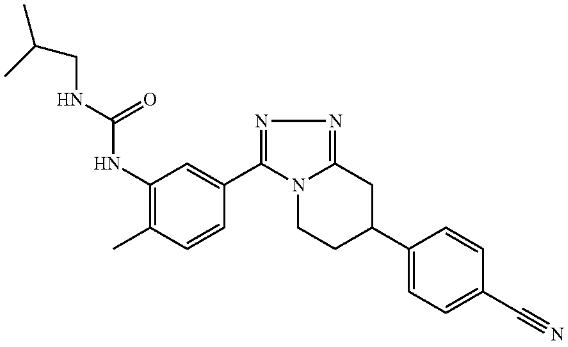 [SMILES: Cc1ccc(-c2nnc3n2CCC(c2ccc(C#N)cc2)C3)cc1NC(=O)NCC(C)C] | 6.360 |

TABLE C-1-continued
| Cmpd No. | Structure | FASN $IC_{50}$ (μM) |
|---|---|---|
| | Fatty Acid Synthase Inhibitors | |
| 001-376 | 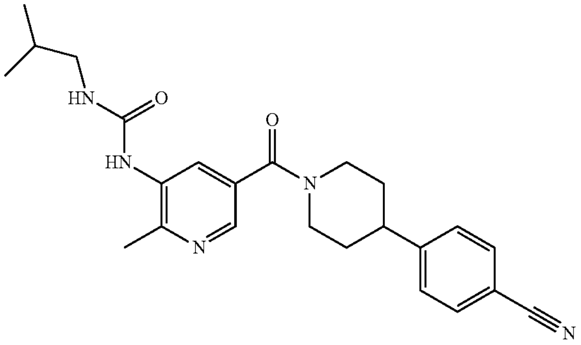 [SMILES: Cc1ncc(C(=O)N2CCC(c3ccc(C#N)cc3)CC2)cc1NC(=O)NCC(C)C] | 6.070 |
| 001-377 | 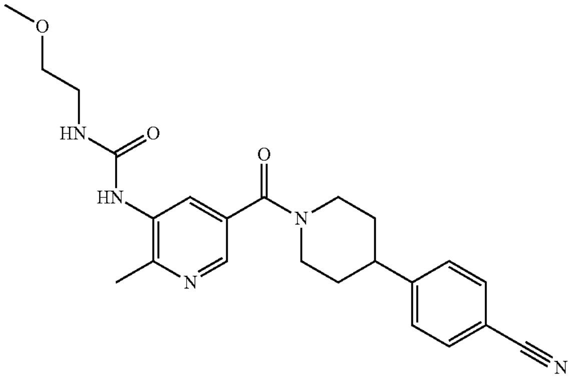 [SMILES: COCCNC(=O)Nc1cc(C(=O)N2CCC(c3ccc(C#N)cc3)CC2)cnc1C] | 2.550 |
| 001-378 | 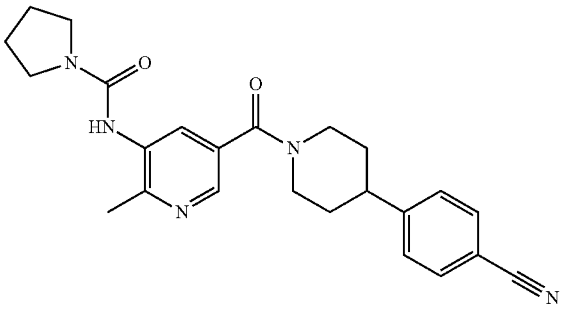 [SMILES: Cc1ncc(C(=O)N2CCC(c3ccc(C#N)cc3)CC2)cc1NC(=O)N1CCCC1] | |
| 001-379 | 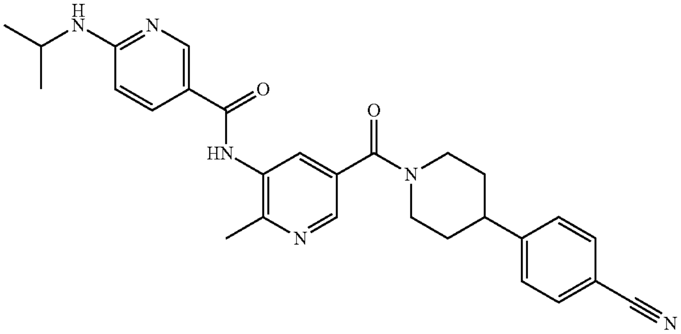 [SMILES: Cc1ncc(C(=O)N2CCC(c3ccc(C#N)cc3)CC2)cc1NC(=O)c1ccc(NC(C)C)nc1] | 0.705 |

TABLE C-1-continued
| Fatty Acid Synthase Inhibitors | | |
|---|---|---|
| Cmpd No. | Structure | FASN $IC_{50}$ (μM) |
| 001-380 | 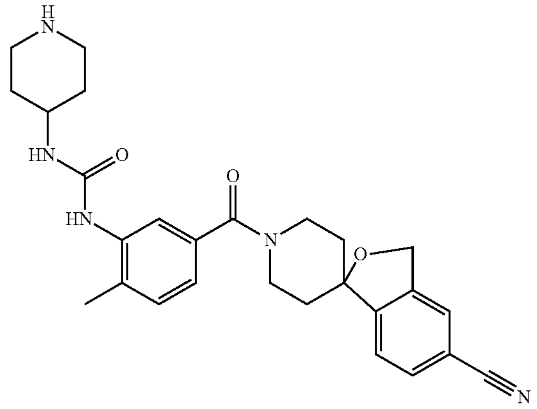 [SMILES: Cc1ccc(C(=O)N2CCC3(CC2)OCc2cc(C#N)ccc23)cc1NC(=O)NC1CCNCC1] | 0.420 |
| 001-381 | 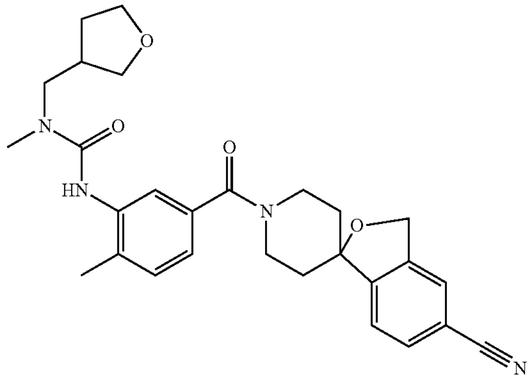 [SMILES: Cc1ccc(C(=O)N2CCC3(CC2)OCc2cc(C#N)ccc23)cc1NC(=O)N(C)CC1CCOC1] | >50 |
| 001-382 | 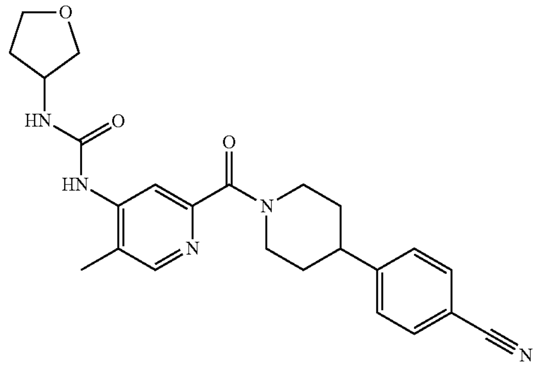 [SMILES: Cc1cnc(C(=O)N2CCC(c3ccc(C#N)cc3)CC2)cc1NC(=O)NC1CCOC1] | >50 |
| 001-383 | 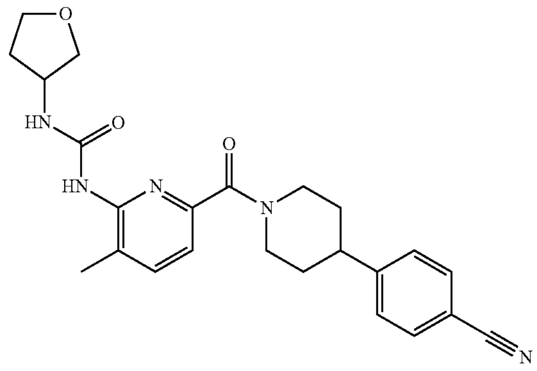 [SMILES: Cc1ccc(C(=O)N2CCC(c3ccc(C#N)cc3)CC2)nc1NC(=O)NC1CCOC1] | >50 |

TABLE C-1-continued
| Fatty Acid Synthase Inhibitors | | |
|---|---|---|
| Cmpd No. | Structure | FASN IC50 (μM) |
| 001-384 | 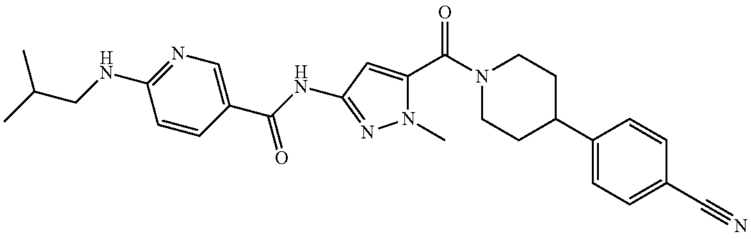 [SMILES: CC(C)CNc1ccc(C(=O)Nc2cc(C(=O)N3CCC(c4ccc(C#N)cc4)CC3)n(C)n2)cn1] | >50 |
| 001-385 | 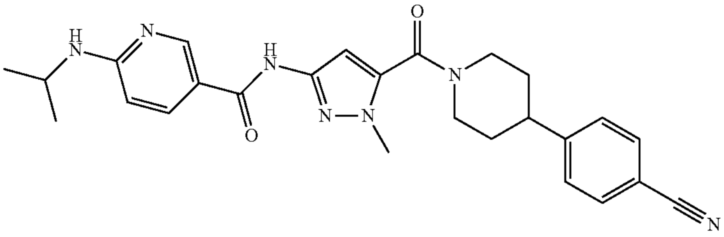 [SMILES: CC(C)Nc1ccc(C(=O)Nc2cc(C(=O)N3CCC(c4ccc(C#N)cc4)CC3)n(C)n2)cn1] | 8.867 |
| 001-386 | 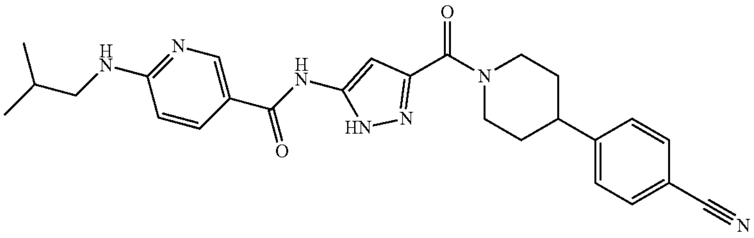 [SMILES: CC(C)CNc1ccc(C(=O)Nc2cc(C(=O)N3CCC(c4ccc(C#N)cc4)CC3)n[nH]2)cn1] | |
| 001-387 | 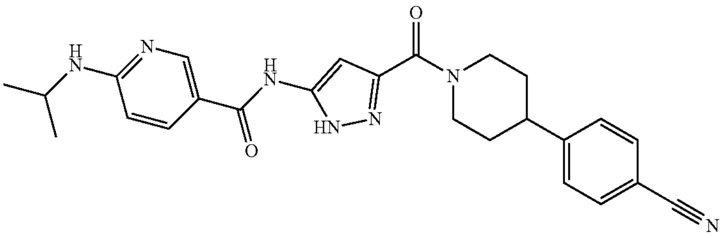 [SMILES: CC(C)Nc1ccc(C(=O)Nc2cc(C(=O)N3CCC(c4ccc(C#N)cc4)CC3)n[nH]2)cn1] | >50 |
| 001-388 | 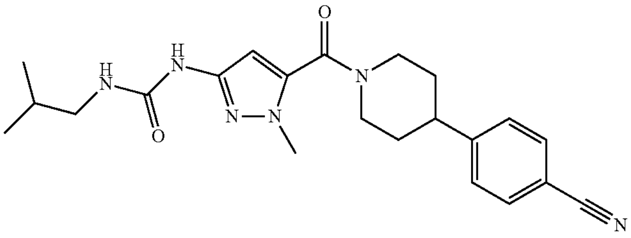 [SMILES: CC(C)CNC(=O)Nc1cc(C(=O)N2CCC(c3ccc(C#N)cc3)CC2)n(C)n1] | 13.380 |
| 001-389 | 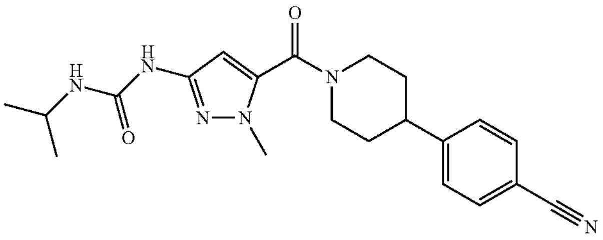 [SMILES: CC(C)NC(=O)Nc1cc(C(=O)N2CCC(c3ccc(C#N)cc3)CC2)n(C)n1] | 16.600 |

TABLE C-1-continued
Fatty Acid Synthase Inhibitors
| Cmpd No. | Structure | FASN $IC_{50}$ (μM) |
|---|---|---|
| 001-390 | 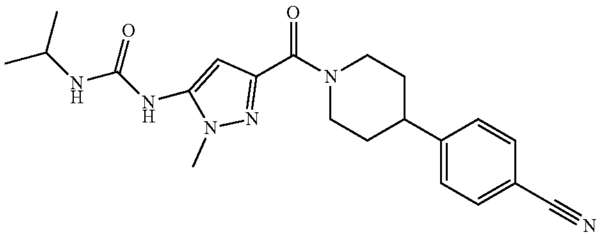 [SMILES: CC(C)NC(=O)Nc1cc(C(=O)N2CCC(c3ccc(C#N)cc3)CC2)nn1C] | >50 |
| 001-391 | 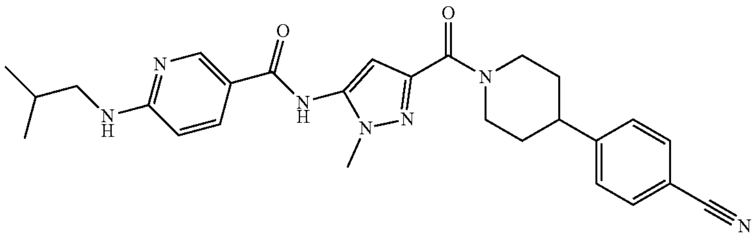 [SMILES: CC(C)CNc1ccc(C(=O)Nc2cc(C(=O)N3CCC(c4ccc(C#N)cc4)CC3)nn2C)cn1] | >50 |
| 001-392 | 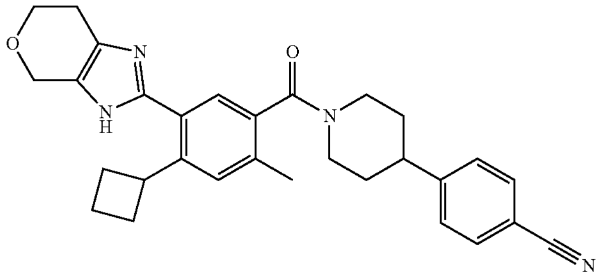 [SMILES: Cc1cc(C2CCC2)c(-c2nc3c([nH]2)COCC3)cc1C(=O)N1CCC(c2ccc(C#N)cc2)CC1] | 0.025 |
| 001-393 | 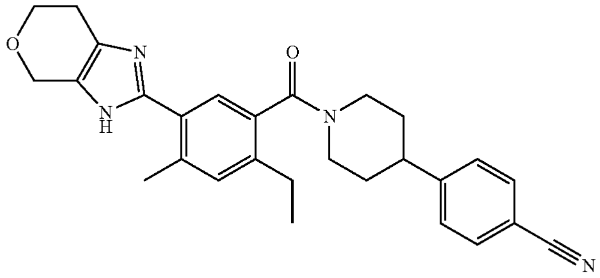 [SMILES: CCc1cc(C)c(-c2nc3c([nH]2)COCC3)cc1C(=O)N1CCC(c2ccc(C#N)cc2)CC1] | 0.065 |
| 001-394 | 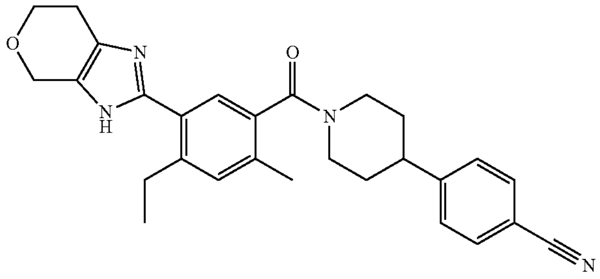 [SMILES: CCc1cc(C)c(C(=O)N2CCC(c3ccc(C#N)cc3)CC2)cc1-c1nc2c([nH]1)COCC2] | 0.135 |

TABLE C-1-continued
| Cmpd No. | Structure | FASN $IC_{50}$ (μM) |
|---|---|---|
| | Fatty Acid Synthase Inhibitors | |
| 001-395 | 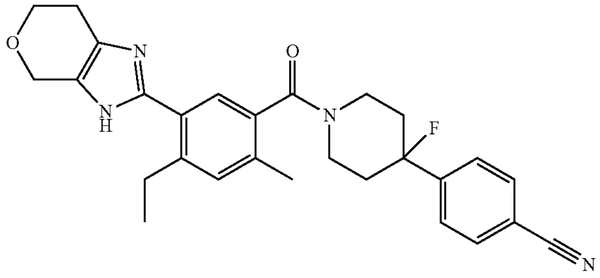 [SMILES: CCc1cc(C)c(C(=O)N2CCC(F)(c3ccc(C#N)cc3)CC2)cc1-c1nc2c([nH]1)COCC2] | 0.260 |
| 001-396 | 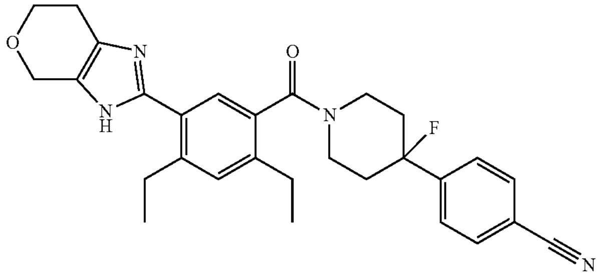 [SMILES: CCc1cc(CC)c(-c2nc3c([nH]2)COCC3)cc1C(=O)N1CCC(F)(c2ccc(C#N)cc2)CC1] | 0.050 |
| 001-397 | 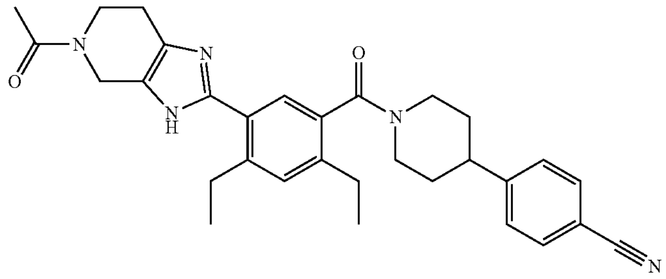 | 0.040 |
| 001-398 | 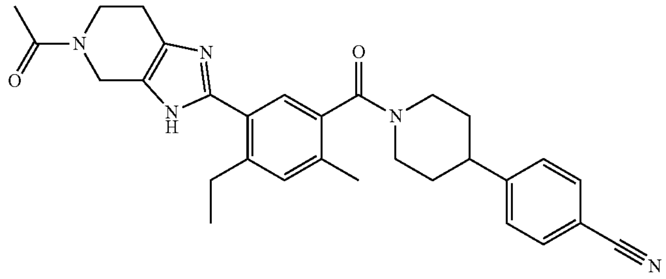 [SMILES: CCc1cc(C)c(C(=O)N2CCC(c3ccc(C#N)cc3)CC2)cc1-c1nc2c([nH]1)CN(C(C)=O)CC2] | 0.035 |
| 001-399 | 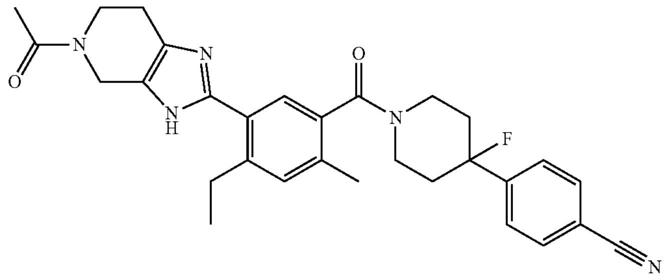 [SMILES: CCc1cc(C)c(C(=O)N2CCC(F)(c3ccc(C#N)cc3)CC2)cc1-c1nc2c([nH]1)CN(C(C)=O)CC2] | 0.030 |

TABLE C-1-continued
| Fatty Acid Synthase Inhibitors | | |
|---|---|---|
| Cmpd No. | Structure | FASN $IC_{50}$ (μM) |
| 001-400 | 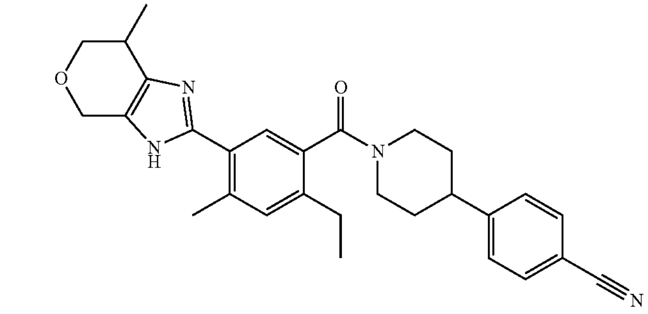 [SMILES: CCc1cc(C)c(-c2nc3c([nH]2)COCC3C)cc1C(=O)N1CCC(c2ccc(C#N)cc2)CC1] | 0.260 |
| 001-401 | 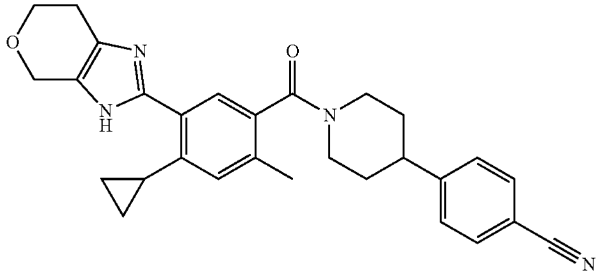 [SMILES: Cc1cc(C2CC2)c(-c2nc3c([nH]2)COCC3)cc1C(=O)N1CCC(c2ccc(C#N)cc2)CC1] | 0.065 |
| 001-402 | 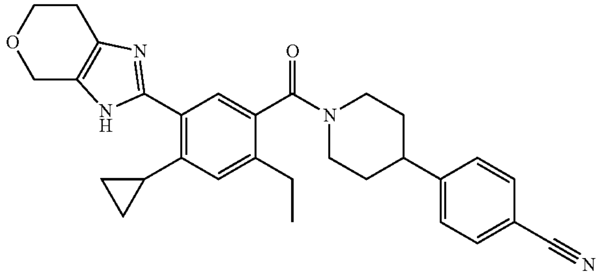 [SMILES: CCc1cc(C2CC2)c(-c2nc3c([nH]2)COCC3)cc1C(=O)N1CCC(c2ccc(C#N)cc2)CC1] | 0.077 |
| 001-403 | 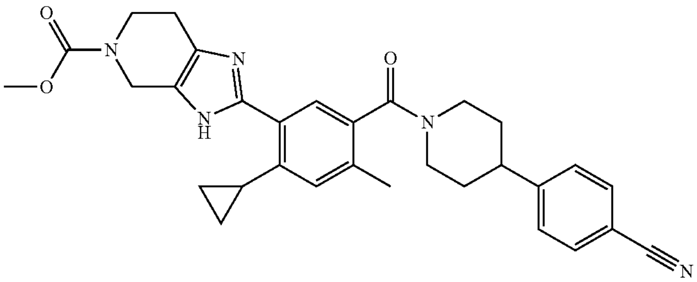 [SMILES: COC(=O)N1CCc2nc(-c3cc(C(=O)N4CCC(c5ccc(C#N)cc5)CC4)c(C)cc3C3CC3)[nH]c2C1] | 0.045 |
| 001-404 | 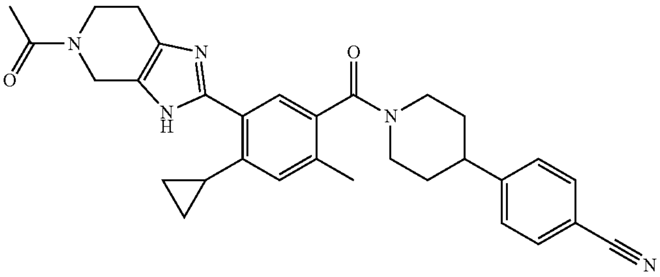 [SMILES: CC(=O)N1CCc2nc(-c3cc(C(=O)N4CCC(c5ccc(C#N)cc5)CC4)c(C)cc3C3CC3)[nH]c2C1] | 0.040 |

TABLE C-1-continued
| Fatty Acid Synthase Inhibitors | | |
|---|---|---|
| Cmpd No. | Structure | FASN $IC_{50}$ (μM) |
| 001-405 | 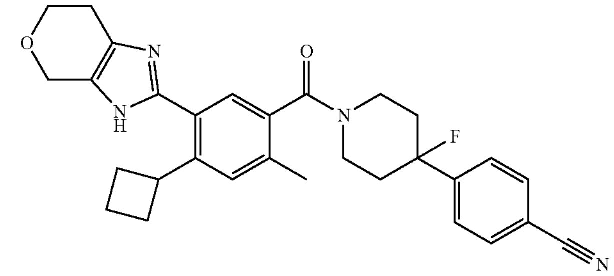 | 0.010 |
| 001-406 | 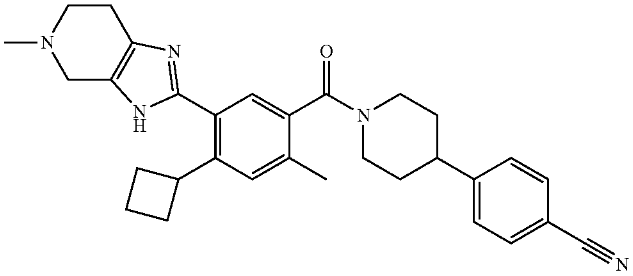 [SMILES: Cc1cc(C2CCC2)c(-c2nc3c([nH]2)CN(C)CC3)cc1C(=O)N1CCC(c2ccc(C#N)cc2)CC1] | 0.020 |
| 001-407 | 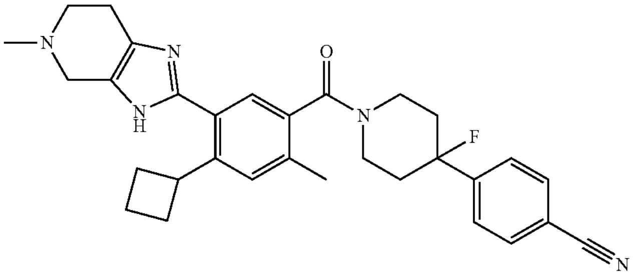 [SMILES: Cc1cc(C2CCC2)c(-c2nc3c([nH]2)CN(C)CC3)cc1C(=O)N1CCC(F)(c2ccc(C#N)cc2)CC1] | 0.040 |
| 001-408 | 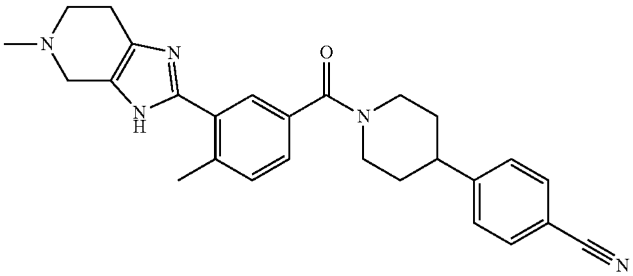 [SMILES: Cc1ccc(C(=O)N2CCC(c3ccc(C#N)cc3)CC2)cc1-c1nc2c([nH]1)CN(C)CC2] | 0.145 |
| 001-409 | 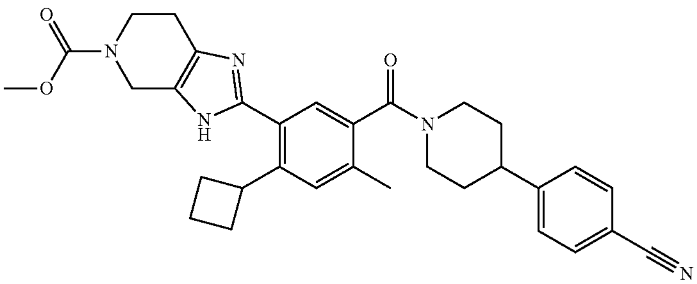 [SMILES: COC(=O)N1CCc2nc(-c3cc(C(=O)N4CCC(c5ccc(C#N)cc5)CC4)c(C)cc3C3CCC3)[nH]c2C1] | 0.020 |

TABLE C-1-continued
| Fatty Acid Synthase Inhibitors | | |
|---|---|---|
| Cmpd No. | Structure | FASN $IC_{50}$ (μM) |
| 001-410 | 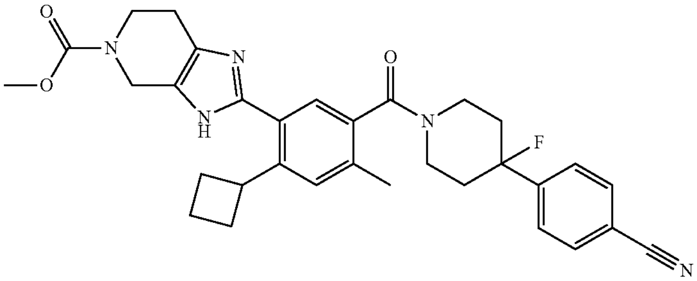 [SMILES: COC(=O)N1CCc2nc(-c3cc(C(=O)N4CCC(F)(c5ccc(C#N)cc5)CC4)c(C)cc3C3CCC3)[nH]c2C1] | 0.010 |
| 001-411 | 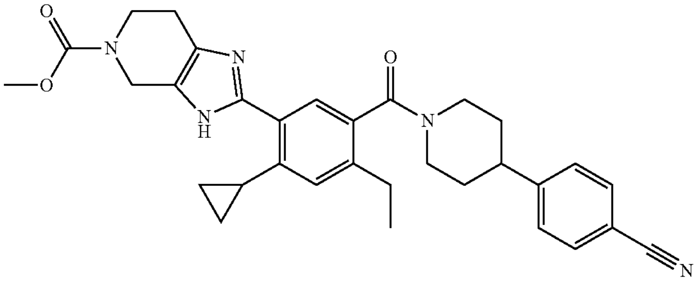 [SMILES: CCc1cc(C2CC2)c(-c2nc3c([nH]2)CN(C(=O)OC)CC3)cc1C(=O)N1CCC(c2ccc(C#N)cc2)CC1] | 0.035 |
| 001-412 | 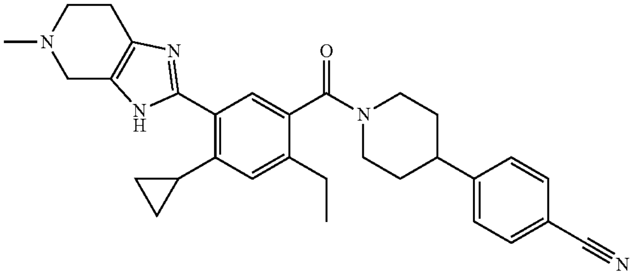 [SMILES: CCc1cc(C2CC2)c(-c2nc3c([nH]2)CN(C)CC3)cc1C(=O)N1CCC(c2ccc(C#N)cc2)CC1] | 0.035 |
| 001-413 | 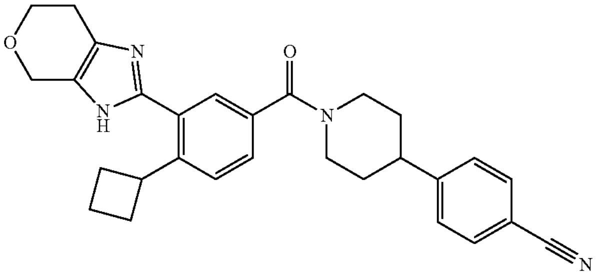 [SMILES: N#Cc1ccc(C2CCN(C(=O)c3ccc(C4CCC4)c(-c4nc5c([nH]4)COCC5)c3)CC2)cc1] | 0.065 |
| 001-414 | 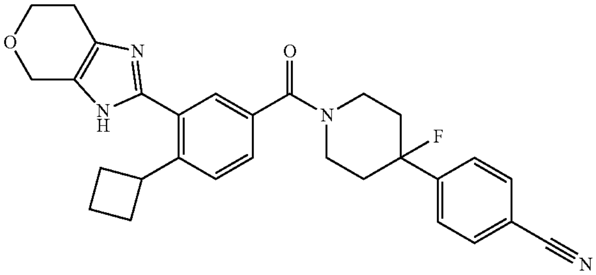 [SMILES: N#Cc1ccc(C2(F)CCN(C(=O)c3ccc(C4CCC4)c(-c4nc5c([nH]4)COCC5)c3)CC2)cc1] | 0.033 |

TABLE C-1-continued
| Fatty Acid Synthase Inhibitors | | |
|---|---|---|
| Cmpd No. | Structure | FASN $IC_{50}$ (μM) |
| 001-415 | 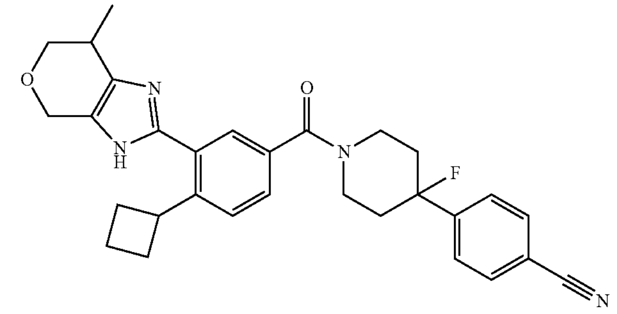 [SMILES: CC1COCc2[nH]c(-c3cc(C(=O)N4CCC(F)(c5ccc(C#N)cc5)CC4)ccc3C3CCC3)nc21] | 0.040 |
| 001-416 | 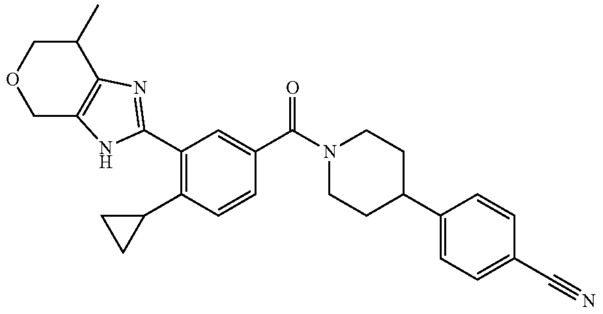 [SMILES: CC1COCc2[nH]c(-c3cc(C(=O)N4CCC(c5ccc(C#N)cc5)CC4)ccc3C3CC3)nc21] | 0.055 |
| 001-417 | 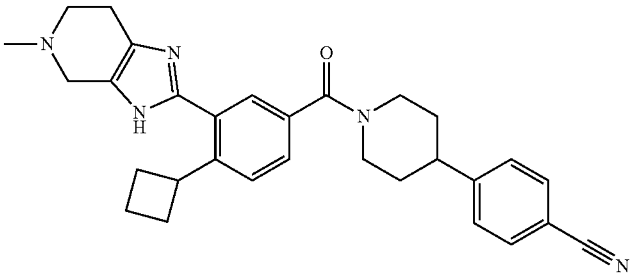 [SMILES: CN1CCc2nc(-c3cc(C(=O)N4CCC(c5ccc(C#N)cc5)CC4)ccc3C3CCC3)[nH]c2C1] | 0.020 |
| 001-418 | 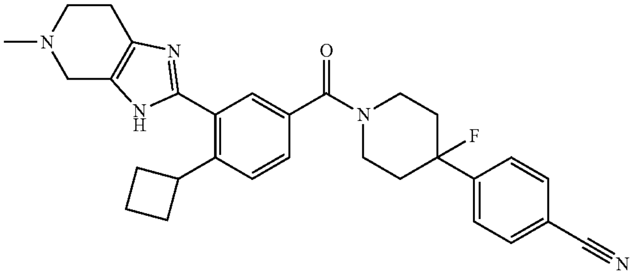 [SMILES: CN1CCc2nc(-c3cc(C(=O)N4CCC(F)(c5ccc(C#N)cc5)CC4)ccc3C3CCC3)[nH]c2C1] | 0.050 |
| 001-419 | 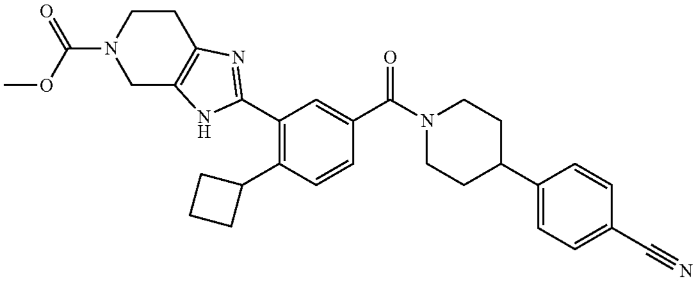 [SMILES: COC(=O)N1CCc2nc(-c3cc(C(=O)N4CCC(c5ccc(C#N)cc5)CC4)ccc3C3CCC3)[nH]c2C1] | 0.010 |

TABLE C-1-continued
| Fatty Acid Synthase Inhibitors | | |
|---|---|---|
| Cmpd No. | Structure | FASN $IC_{50}$ (μM) |
| 001-420 | 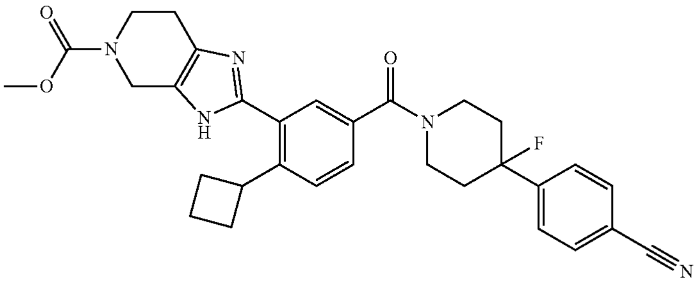 [SMILES: COC(=O)N1CCc2nc(-c3cc(C(=O)N4CCC(F)(c5ccc(C#N)cc5)CC4)ccc3C3CCC3)[nH]c2C1] | 0.020 |
| 001-421 | 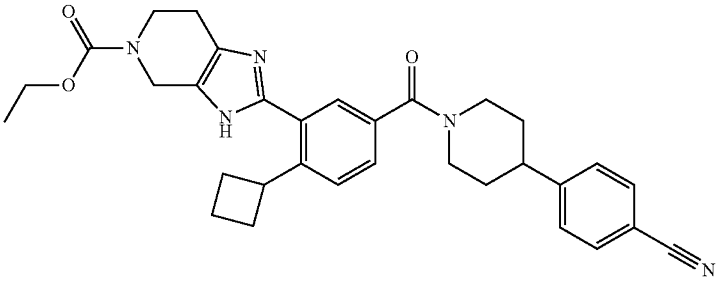 [SMILES: CCOC(=O)N1CCc2nc(-c3cc(C(=O)N4CCC(c5ccc(C#N)cc5)CC4)ccc3C3CCC3)[nH]c2C1] | 0.050 |
| 001-422 | 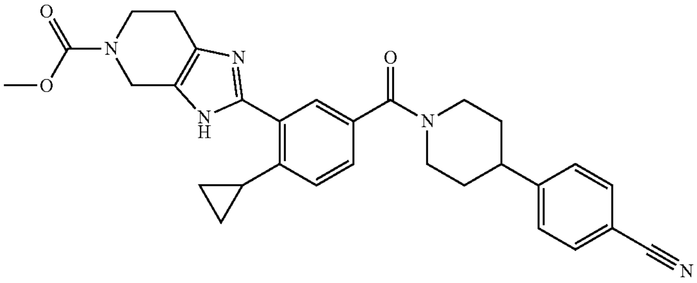 [SMILES: COC(=O)N1CCc2nc(-c3cc(C(=O)N4CCC(c5ccc(C#N)cc5)CC4)ccc3C3CC3)[nH]c2C1] | 0.020 |
| 001-423 | 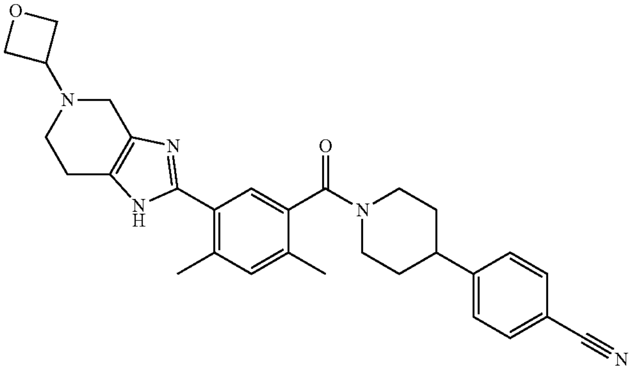 [SMILES: Cc1cc(C)c(-c2nc3c([nH]2)CCN(C2COC2)C3)cc1C(=O)N1CCC(c2ccc(C#N)cc2)CC1] | 0.175 |

TABLE C-1-continued
| Fatty Acid Synthase Inhibitors | | |
|---|---|---|
| Cmpd No. | Structure | FASN $IC_{50}$ (μM) |
| 001-424 | 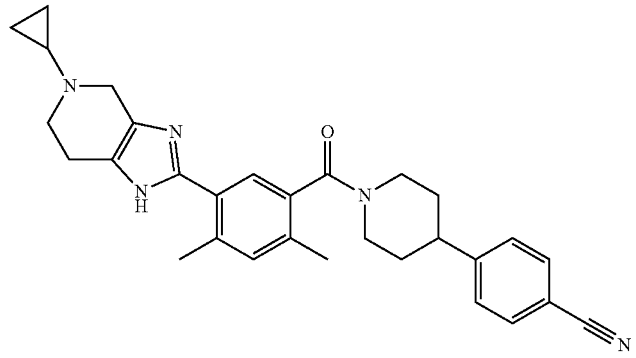 [SMILES: Cc1cc(C)c(-c2nc3c([nH]2)CCN(C2CC2)C3)cc1C(=O)N1CCC(c2ccc(C#N)cc2)CC1] | 0.165 |
| 001-425 | 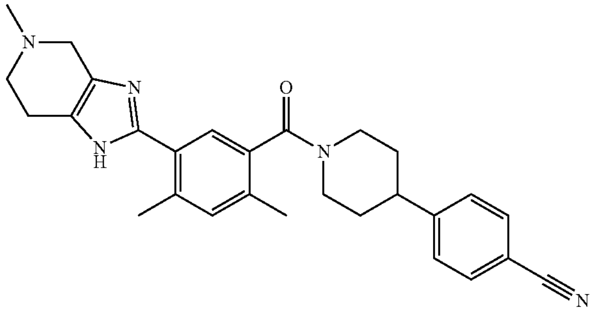 [SMILES: Cc1cc(C)c(-c2nc3c([nH]2)CCN(C)C3)cc1C(=O)N1CCC(c2ccc(C#N)cc2)CC1] | 0.075 |
| 001-426 | 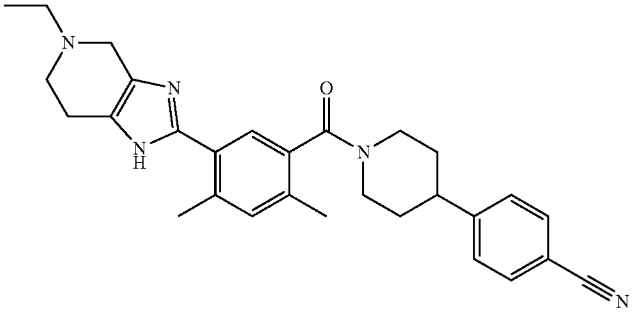 [SMILES: CCN1CCc2[nH]c(-c3cc(C(=O)N4CCC(c5ccc(C#N)cc5)CC4)c(C)cc3C)nc2C1] | 0.060 |
| 001-427 | 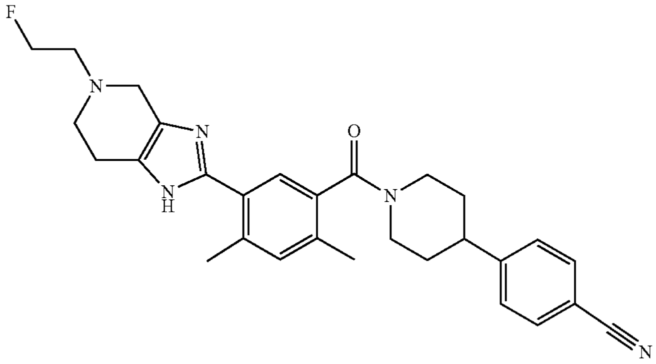 [SMILES: Cc1cc(C)c(-c2nc3c([nH]2)CCN(CCF)C3)cc1C(=O)N1CCC(c2ccc(C#N)cc2)CC1] | 0.080 |

TABLE C-1-continued
| Fatty Acid Synthase Inhibitors | | |
|---|---|---|
| Cmpd No. | Structure | FASN $IC_{50}$ (μM) |
| 001-428 | 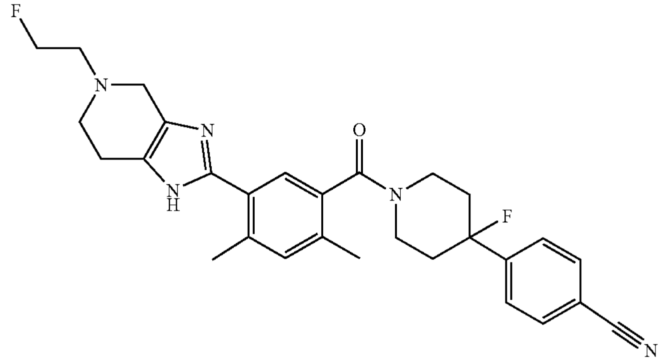 [SMILES: Cc1cc(C)c(-c2nc3c([nH]2)CCN(CCF)C3)cc1C(=O)N1CCC(F)(c2ccc(C#N)cc2)CC1] | 0.040 |
| 001-429 | 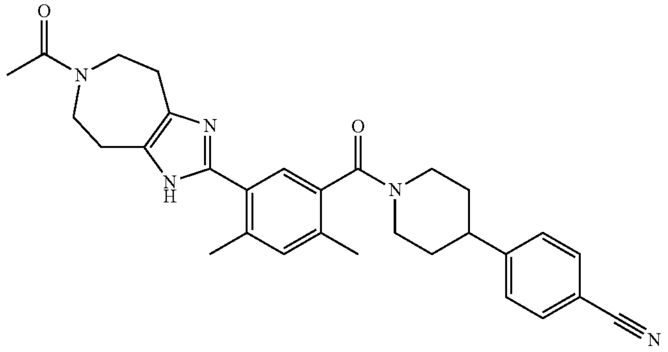 [SMILES: CC(=O)N1CCc2nc(-c3cc(C(=O)N4CCC(c5ccc(C#N)cc5)CC4)c(C)cc3C)[nH]c2CC1] | 0.060 |
| 001-430 | 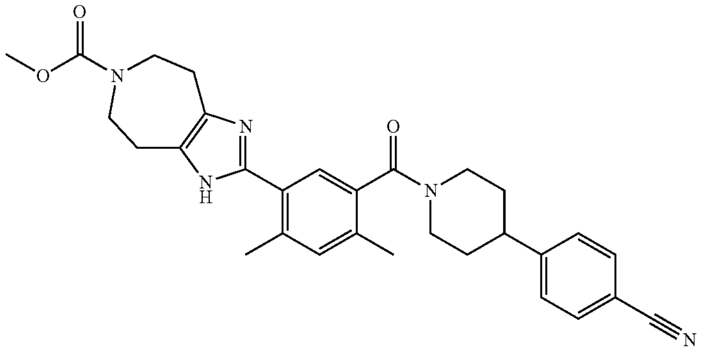 [SMILES: COC(=O)N1CCc2nc(-c3cc(C(=O)N4CCC(c5ccc(C#N)cc5)CC4)c(C)cc3C)[nH]c2CC1] | 0.035 |
| 001-431 | 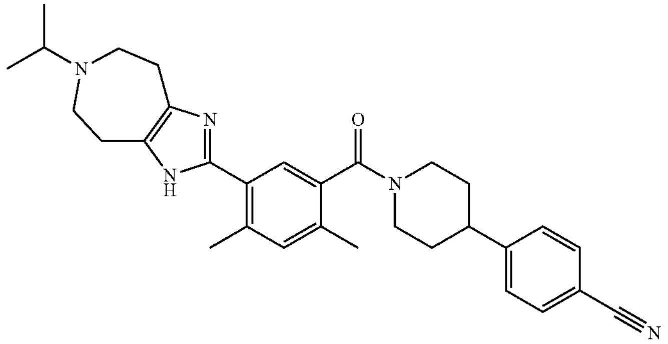 [SMILES: Cc1cc(C)c(-c2nc3c([nH]2)CCN(C(C)C)CC3)cc1C(=O)N1CCC(c2ccc(C#N)cc2)CC1] | 0.025 |

TABLE C-1-continued
| Fatty Acid Synthase Inhibitors | | |
|---|---|---|
| Cmpd No. | Structure | FASN $IC_{50}$ (μM) |
| 001-432 | 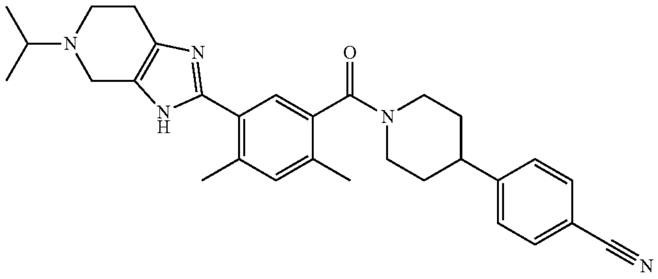 [SMILES: Cc1cc(C)c(-c2nc3c([nH]2)CN(C(C)C)CC3)cc1C(=O)N1CCC(c2ccc(C#N)cc2)CC1] | 0.065 |
| 001-433 | 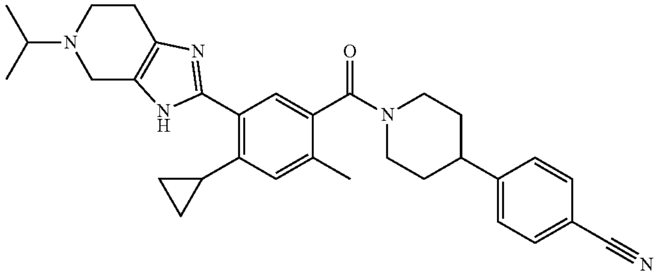 [SMILES: Cc1cc(C2CC2)c(-c2nc3c([nH]2)CN(C(C)C)CC3)cc1C(=O)N1CCC(c2ccc(C#N)cc2)CC1] | 0.040 |
| 001-434 | 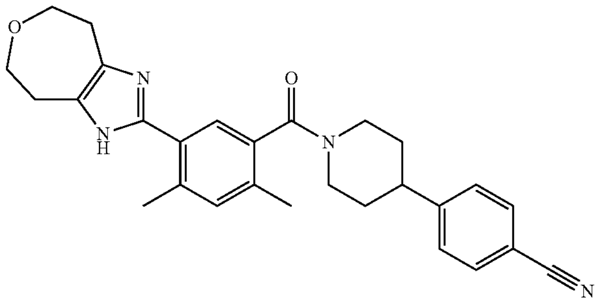 [SMILES: Cc1cc(C)c(-c2nc3c([nH]2)CCOCC3)cc1C(=O)N1CCC(c2ccc(C#N)cc2)CC1] | 0.470 |
| 001-435 | 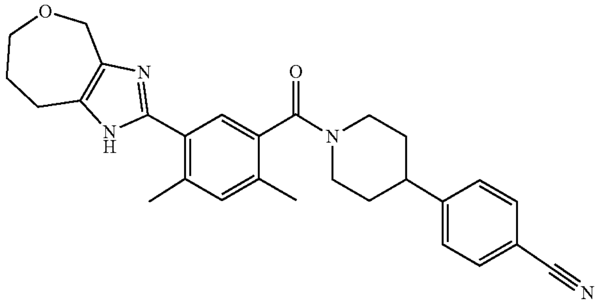 [SMILES: Cc1cc(C)c(-c2nc3c([nH]2)CCCOC3)cc1C(=O)N1CCC(c2ccc(C#N)cc2)CC1] | 0.365 |
| 001-436 | 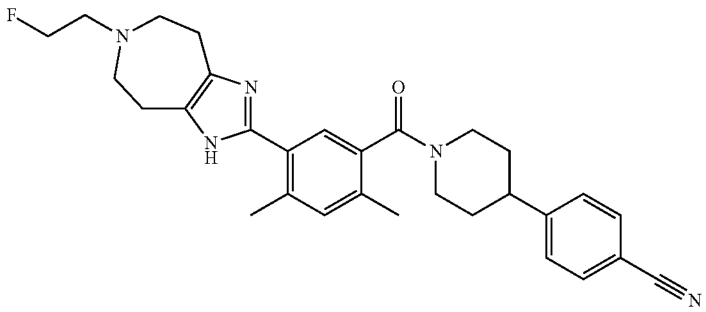 [SMILES: Cc1cc(C)c(-c2nc3c([nH]2)CCN(CCF)CC3)cc1C(=O)N1CCC(c2ccc(C#N)cc2)CC1] | 0.040 |

TABLE C-1-continued
| Cmpd No. | Structure | FASN $IC_{50}$ (μM) |
| --- | --- | --- |
| Fatty Acid Synthase Inhibitors | | |
| 001-437 | 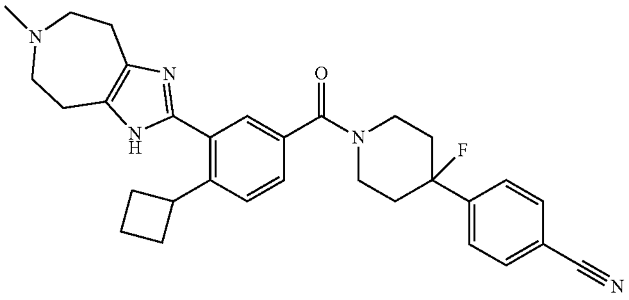 [SMILES: CN1CCc2nc(-c3cc(C(=O)N4CCC(F)(c5ccc(C#N)cc5)CC4)ccc3C3CCC3)[nH]c2CC1] | 0.050 |
| 001-438 | 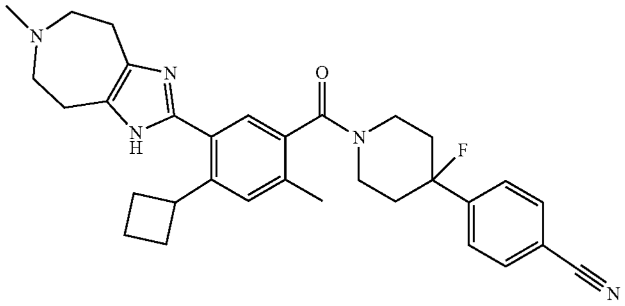 [SMILES: Cc1cc(C2CCC2)c(-c2nc3c([nH]2)CCN(C)CC3)cc1C(=O)N1CCC(F)(c2ccc(C#N)cc2)CC1] | 0.060 |
| 001-439 | 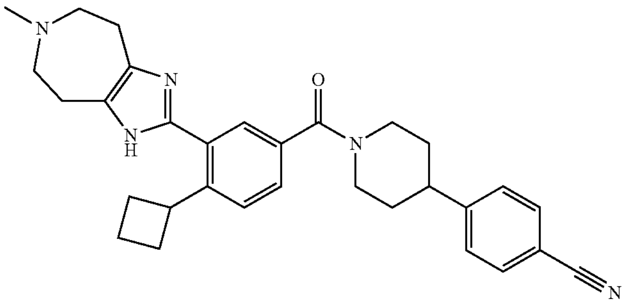 [SMILES: CN1CCc2nc(-c3cc(C(=O)N4CCC(c5ccc(C#N)cc5)CC4)ccc3C3CCC3)[nH]c2CC1] | 0.110 |
| 001-440 | 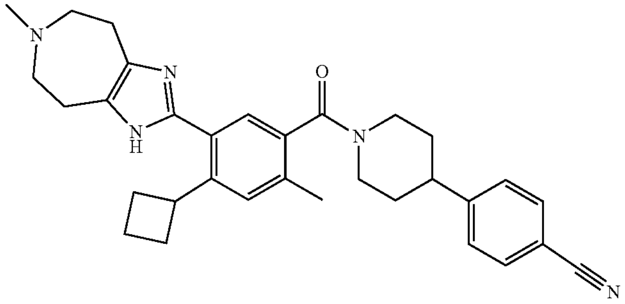 [SMILES: Cc1cc(C2CCC2)c(-c2nc3c([nH]2)CCN(C)CC3)cc1C(=O)N1CCC(c2ccc(C#N)cc2)CC1] | 0.050 |

TABLE C-1-continued
| Fatty Acid Synthase Inhibitors | | |
|---|---|---|
| Cmpd No. | Structure | FASN $IC_{50}$ (μM) |
| 001-441 | 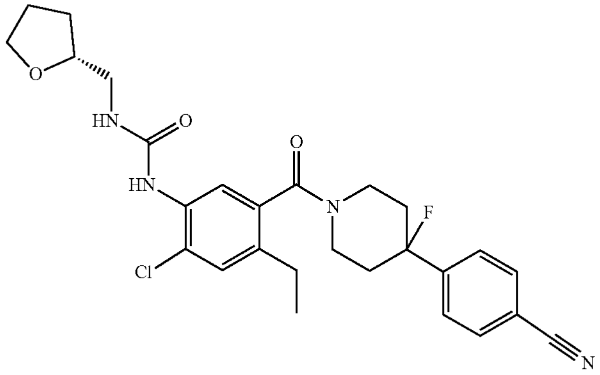 [SMILES: CCc1cc(Cl)c(NC(=O)NC[C@H]2CCCO2)cc1C(=O)N1CCC(F)(c2ccc(C#N)cc2)CC1] | 0.140 |
| 001-442 | 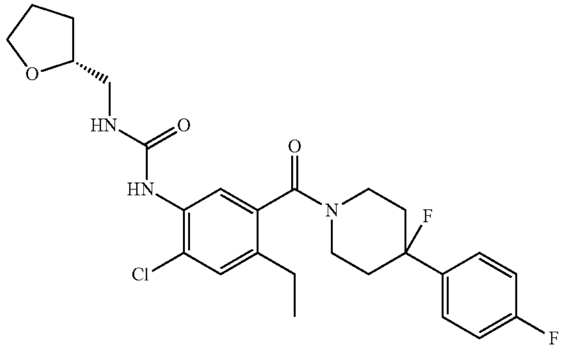 [SMILES: CCc1cc(Cl)c(NC(=O)NC[C@H]2CCCO2)cc1C(=O)N1CCC(F)(c2ccc(F)cc2)CC1] | 12.480 |
| 001-443 | 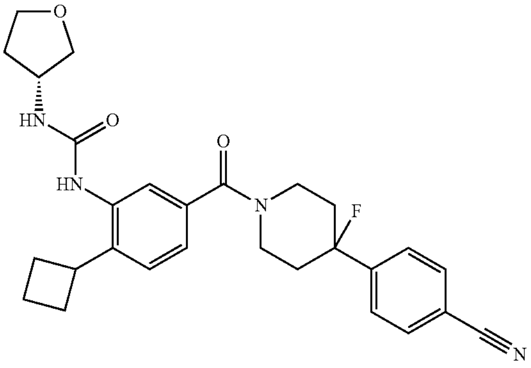 [SMILES: N#Cc1ccc(C2(F)CCN(C(=O)c3ccc(C4CCC4)c(NC(=O)N[C@@H]4CCOC4)c3)CC2)cc1] | 0.060 |
| 001-444 | 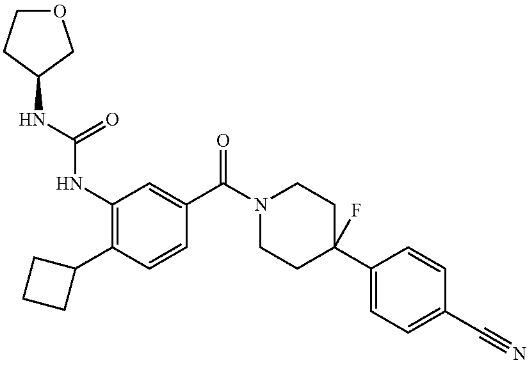 [SMILES: N#Cc1ccc(C2(F)CCN(C(=O)c3ccc(C4CCC4)c(NC(=O)N[C@H]4CCOC4)c3)CC2)cc1] | 0.040 |

TABLE C-1-continued
| Fatty Acid Synthase Inhibitors | | |
|---|---|---|
| Cmpd No. | Structure | FASN $IC_{50}$ (μM) |
| 001-445 | 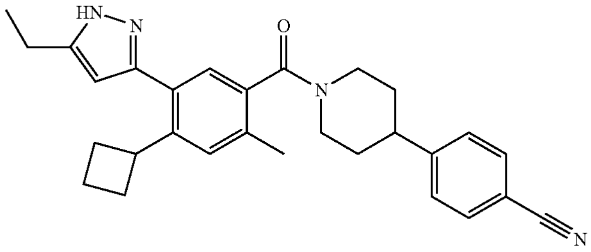 [SMILES: CCc1cc(-c2cc(C(=O)N3CCC(c4ccc(C#N)cc4)CC3)c(C)cc2C2CCC2)n[nH]1] | 0.490 |
| 001-446 | 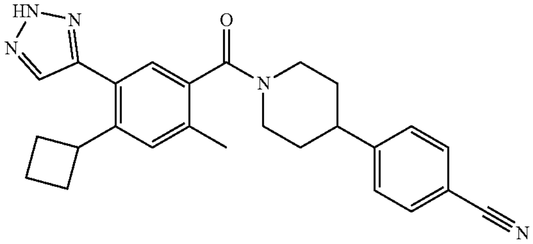 [SMILES: Cc1cc(C2CCC2)c(-c2cn[nH]n2)cc1C(=O)N1CCC(c2ccc(C#N)cc2)CC1] | 0.390 |
| 001-447 | 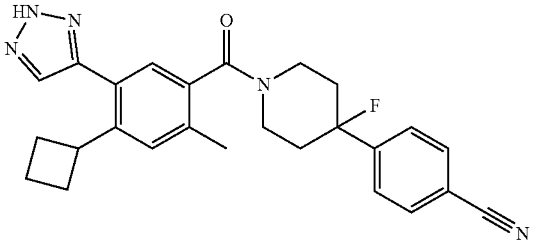 [SMILES: Cc1cc(C2CCC2)c(-c2cn[nH]n2)cc1C(=O)N1CCC(F)(c2ccc(C#N)cc2)CC1] | |
| 001-448 | 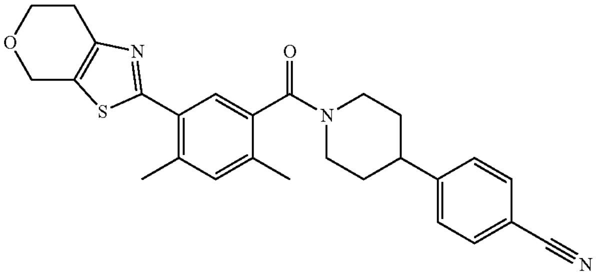 | 10.610 |
| 001-449 | 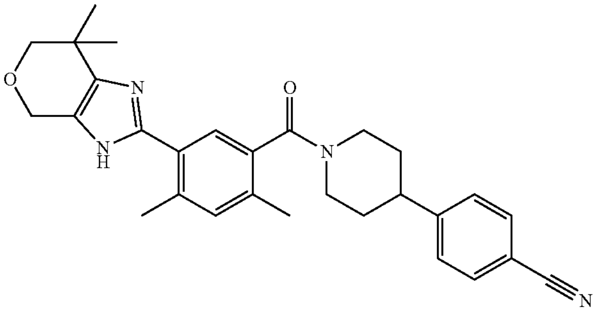 [SMILES: Cc1cc(C)c(-c2nc3c([nH]2)COCC3(C)C)cc1C(=O)N1CCC(c2ccc(C#N)cc2)CC1] | 0.135 |

TABLE C-1-continued
| Fatty Acid Synthase Inhibitors | | |
|---|---|---|
| Cmpd No. | Structure | FASN IC50 (μM) |
| 001-450 | 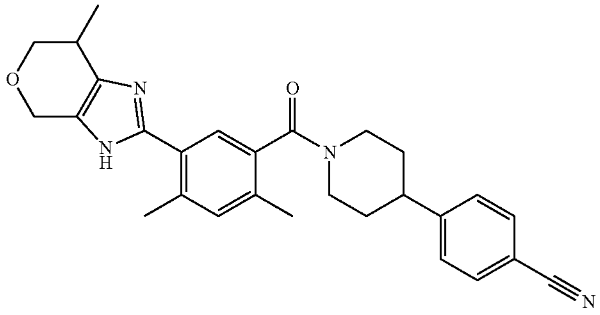 [SMILES: Cc1cc(C)c(-c2nc3c([nH]2)COCC3C)cc1C(=O)N1CCC(c2ccc(C#N)cc2)CC1] | 0.105 |
| 001-451 | 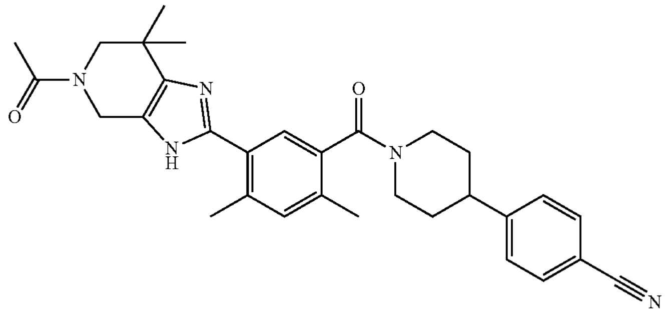 [SMILES: CC(=O)N1Cc2[nH]c(-c3cc(C(=O)N4CCC(c5ccc(C#N)cc5)CC4)c(C)cc3C)nc2C(C)(C)C1] | 0.070 |
| 001-452 | 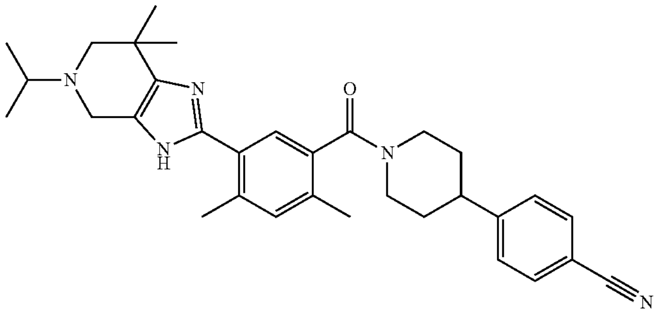 [SMILES: Cc1cc(C)c(-c2nc3c([nH]2)CN(C(C)C)CC3(C)C)cc1C(=O)N1CCC(c2ccc(C#N)cc2)CC1] | 0.130 |
| 001-453 | 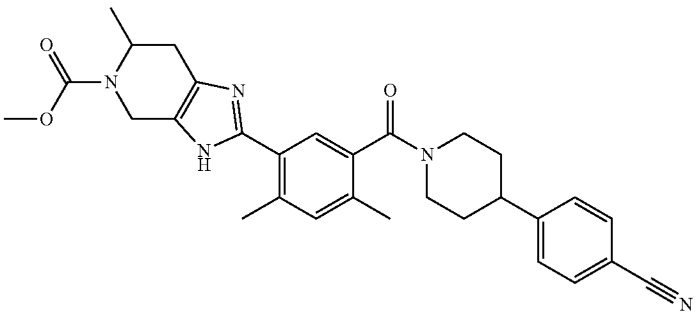 [SMILES: COC(=O)N1Cc2[nH]c(-c3cc(C(=O)N4CCC(c5ccc(C#N)cc5)CC4)c(C)cc3C)nc2CC1C] | 0.070 |

TABLE C-1-continued
| Fatty Acid Synthase Inhibitors | | |
|---|---|---|
| Cmpd No. | Structure | FASN $IC_{50}$ (μM) |
| 001-454 | 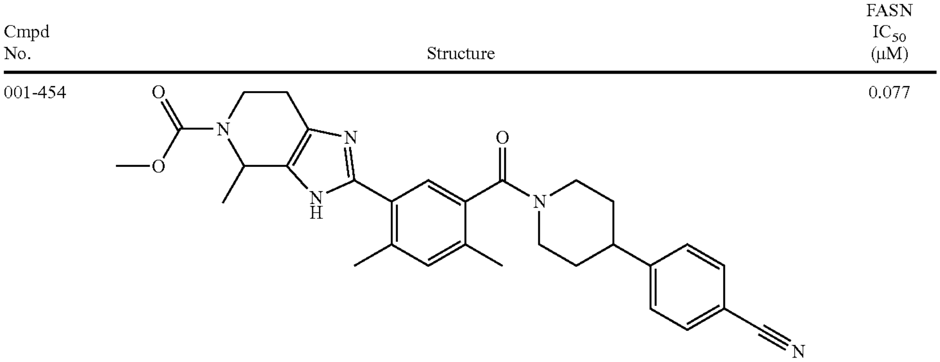 | 0.077 |
| 001-455 | 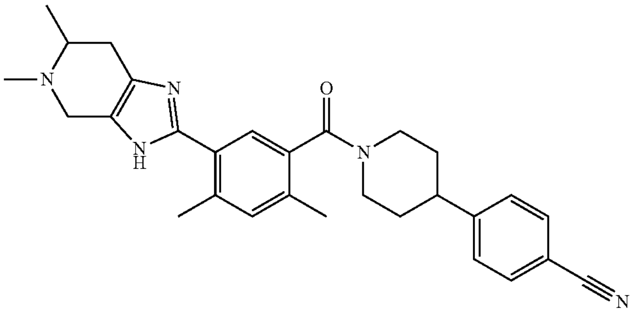 [SMILES: Cc1cc(C)c(-c2nc3c([nH]2)CN(C)C(C)C3)cc1C(=O)N1CCC(c2ccc(C#N)cc2)CC1] | 0.130 |
| 001-456 | 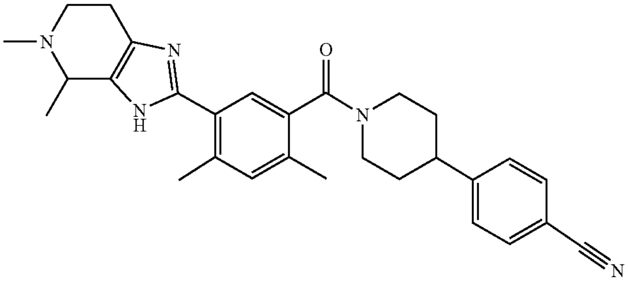 [SMILES: Cc1cc(C)c(-c2nc3c([nH]2)C(C)N(C)CC3)cc1C(=O)N1CCC(c2ccc(C#N)cc2)CC1] | 0.135 |
| 001-457 | 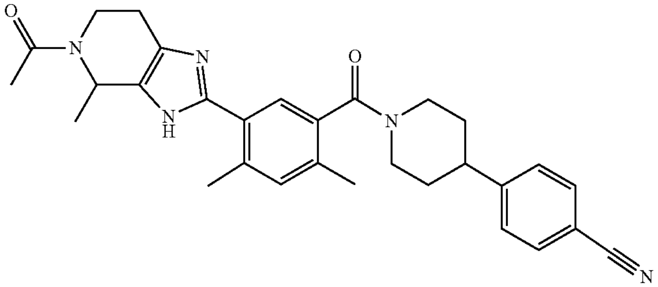 [SMILES: CC(=O)N1CCc2nc(-c3cc(C(=O)N4CCC(c5ccc(C#N)cc5)CC4)c(C)cc3C)[nH]c2C1C] | 0.080 |
| 001-458 | 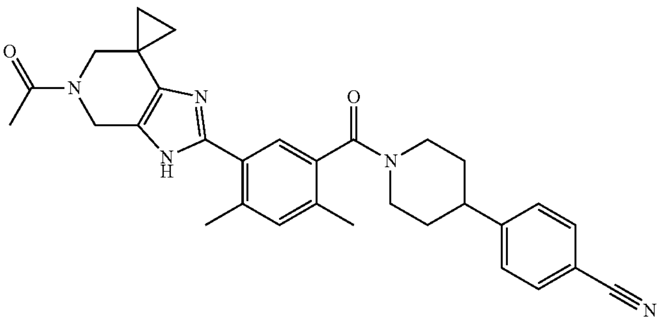 [SMILES: CC(=O)N1Cc2[nH]c(-c3cc(C(=O)N4CCC(c5ccc(C#N)cc5)CC4)c(C)cc3C)nc2C2(CC2)C1] | 0.130 |

TABLE C-1-continued
| Cmpd No. | Structure | FASN IC$_{50}$ (μM) |
|---|---|---|
| Fatty Acid Synthase Inhibitors | | |
| 001-459 | 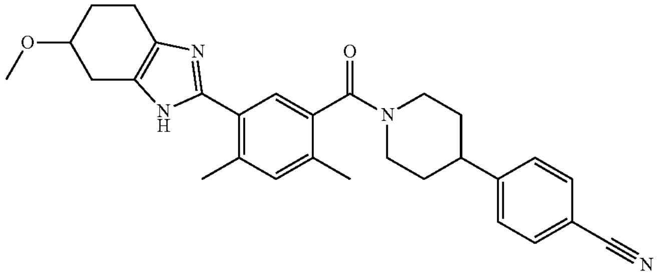 [SMILES: COC1CCc2nc(-c3cc(C(=O)N4CCC(c5ccc(C#N)cc5)CC4)c(C)cc3C)[nH]c2C1] | 0.310 |
| 001-460 | 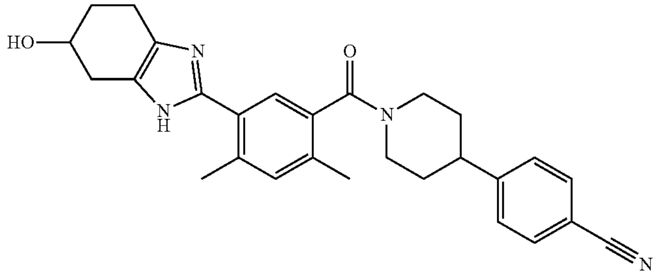 [SMILES: Cc1cc(C)c(-c2nc3c([nH]2)CC(O)CC3)cc1C(=O)N1CCC(c2ccc(C#N)cc2)CC1] | 0.090 |
| 001-461 | 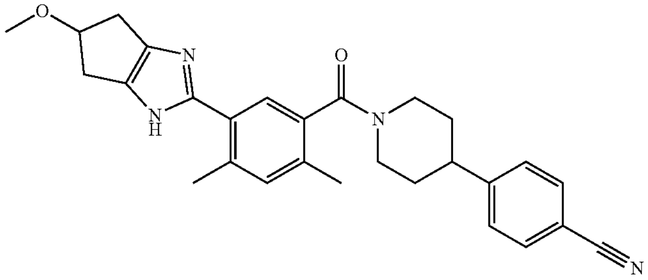 [SMILES: COC1Cc2nc(-c3cc(C(=O)N4CCC(c5ccc(C#N)cc5)CC4)c(C)cc3C)[nH]c2C1] | 0.105 |
| 001-462 | 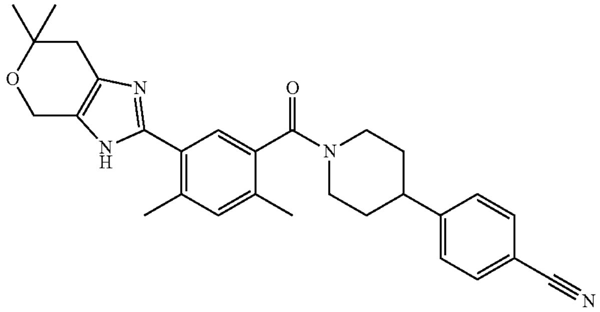 [SMILES: Cc1cc(C)c(-c2nc3c([nH]2)COC(C)(C)C3)cc1C(=O)N1CCC(c2ccc(C#N)cc2)CC1] | 0.780 |
| 001-463 | 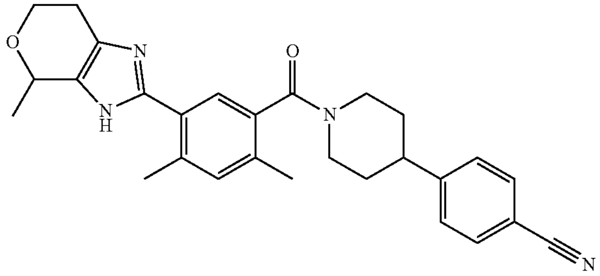 [SMILES: Cc1cc(C)c(-c2nc3c([nH]2)C(C)OCC3)cc1C(=O)N1CCC(c2ccc(C#N)cc2)CC1] | 0.440 |

TABLE C-1-continued
Fatty Acid Synthase Inhibitors
| Cmpd No. | Structure | FASN $IC_{50}$ (μM) |
| --- | --- | --- |
| 001-464 | 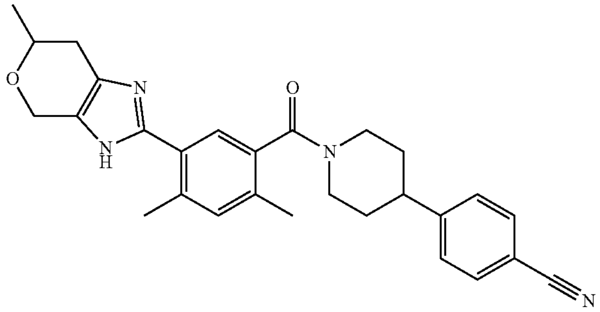 [SMILES: Cc1cc(C)c(-c2nc3c([nH]2)COC(C)C3)cc1C(=O)N1CCC(c2ccc(C#N)cc2)CC1] | 0.065 |
| 001-465 | 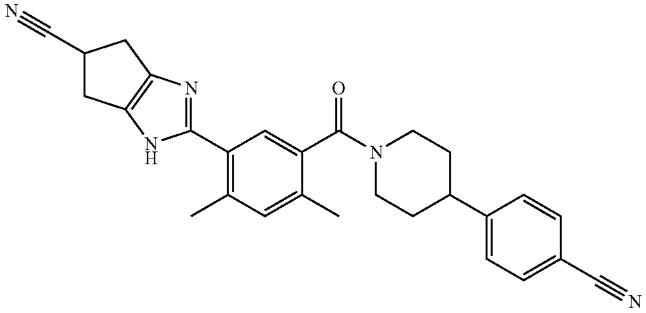 [SMILES: Cc1cc(C)c(-c2nc3c([nH]2)CC(C#N)C3)cc1C(=O)N1CCC(c2ccc(C#N)cc2)CC1] | 0.050 |
| 001-466 | 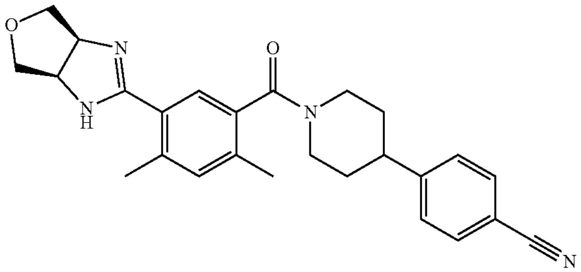 [SMILES: Cc1cc(C)c(C2=N[C@@H]3COC[C@@H]3N2)cc1C(=O)N1CCC(c2ccc(C#N)cc2)CC1] | 34.670 |
| 001-467 | 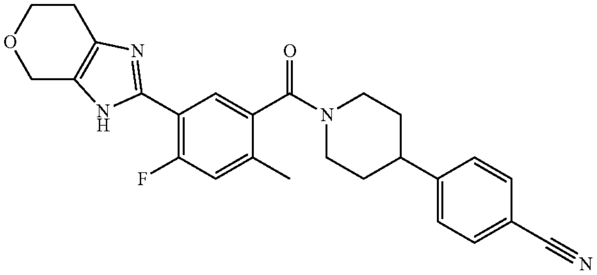 [SMILES: Cc1cc(F)c(-c2nc3c([nH]2)COCC3)cc1C(=O)N1CCC(c2ccc(C#N)cc2)CC1] | 1.810 |
| 001-468 | 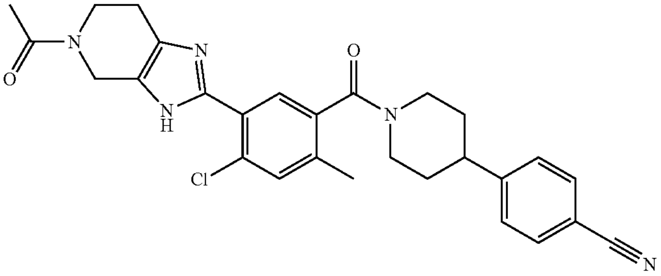 [SMILES: CC(=O)N1CCc2nc(-c3cc(C(=O)N4CCC(c5ccc(C#N)cc5)CC4)c(C)cc3Cl)[nH]c2C1] | 0.170 |

TABLE C-1-continued
| Fatty Acid Synthase Inhibitors | | |
|---|---|---|
| Cmpd No. | Structure | FASN $IC_{50}$ (μM) |
| 001-469 | 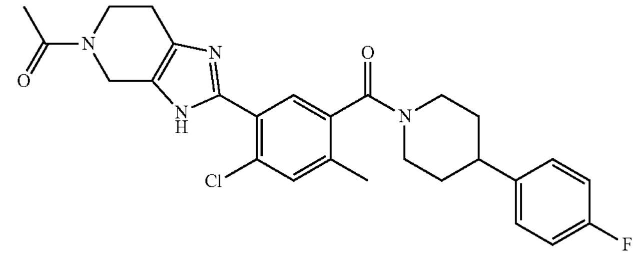 [SMILES: CC(=O)N1CCc2nc(-c3cc(C(=O)N4CCC(c5ccc(F)cc5)CC4)c(C)cc3Cl)[nH]c2C1] | 2.100 |
| 001-470 | 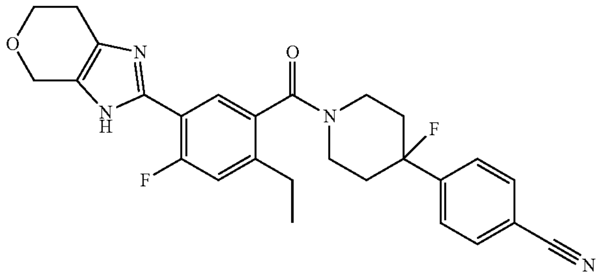 | 1.130 |
| 001-471 | 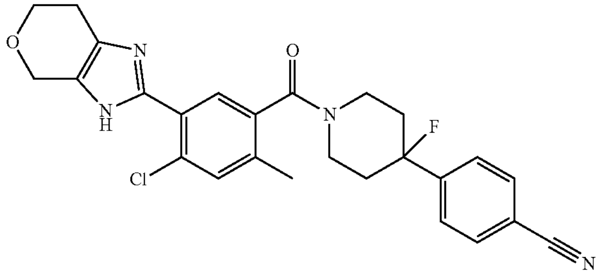 [SMILES: Cc1cc(Cl)c(-c2nc3c([nH]2)COCC3)cc1C(=O)N1CCC(F)(c2ccc(C#N)cc2)CC1] | 0.450 |
| 001-472 | 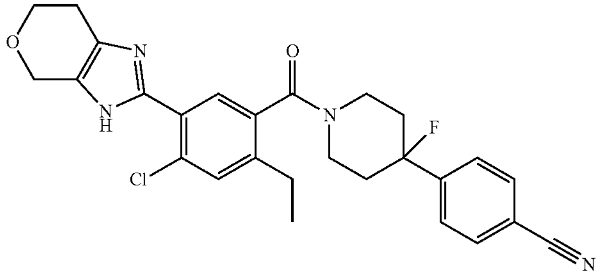 [SMILES: CCc1cc(Cl)c(-c2nc3c([nH]2)COCC3)cc1C(=O)N1CCC(F)(c2ccc(C#N)cc2)CC1] | 0.230 |
| 001-473 | 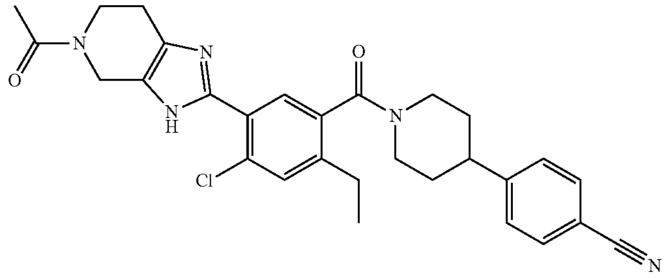 [SMILES: CCc1cc(Cl)c(-c2nc3c([nH]2)CN(C(C)=O)CC3)cc1C(=O)N1CCC(c2ccc(C#N)cc2)CC1] | 0.110 |

TABLE C-1-continued
| Fatty Acid Synthase Inhibitors | | |
|---|---|---|
| Cmpd No. | Structure | FASN $IC_{50}$ (μM) |
| 001-474 | 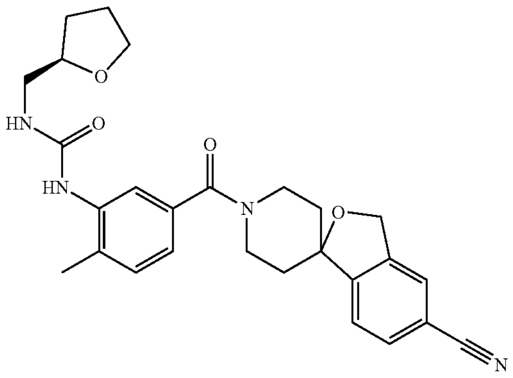 [SMILES: Cc1ccc(C(=O)N2CCC3(CC2)OCc2cc(C#N)ccc23)cc1NC(=O)NC[C@H]1CCCO1] | 0.180 |
| 001-475 | 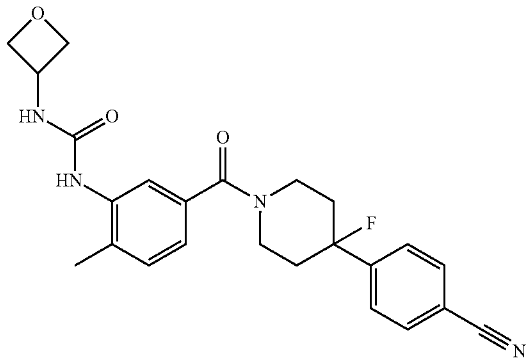 | 0.050 |
| 001-476 | 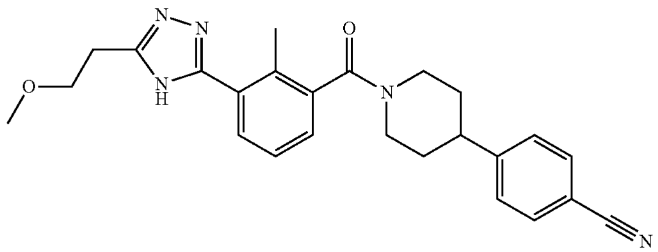 [SMILES: COCCc1nnc(-c2cccc(C(=O)N3CCC(c4ccc(C#N)cc4)CC3)c2C)[nH]1] | >50 |
| 001-477 | 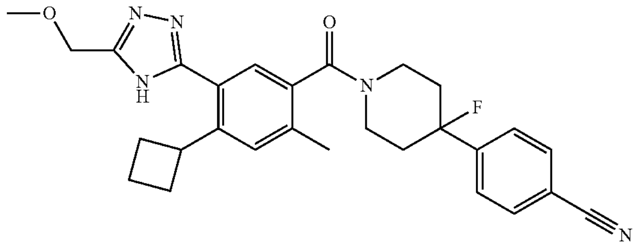 [SMILES: COCc1nnc(-c2cc(C(=O)N3CCC(F)(c4ccc(C#N)cc4)CC3)c(C)cc2C2CCC2)[nH]1] | 0.130 |
| 001-478 | 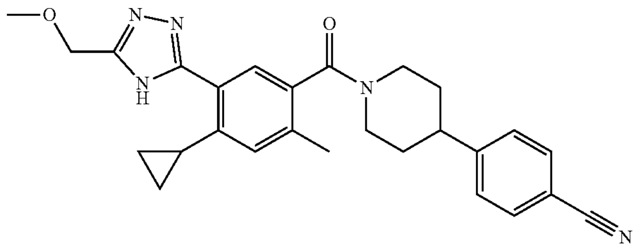 [SMILES: COCc1nnc(-c2cc(C(=O)N3CCC(c4ccc(C#N)cc4)CC3)c(C)cc2C2CC2)[nH]1] | 0.420 |

TABLE C-1-continued
Fatty Acid Synthase Inhibitors
| Cmpd No. | Structure | FASN IC50 (μM) |
| --- | --- | --- |
| 001-479 | 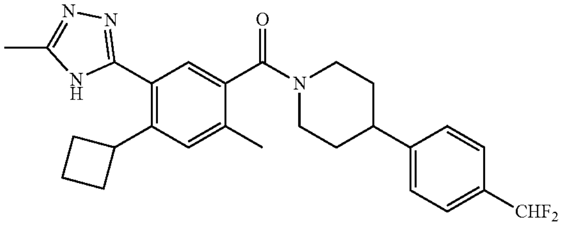 [SMILES: Cc1nnc(-c2cc(C(=O)N3CCC(c4ccc(C(F)F)cc4)CC3)c(C)cc2C2CCC2)[nH]1] | 0.110 |
| 001-480 | 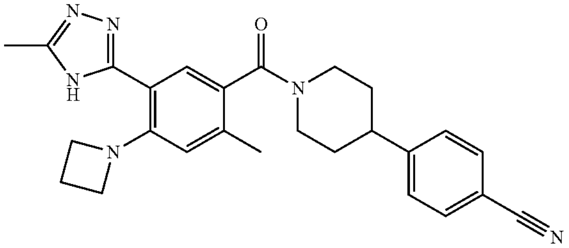 [SMILES: Cc1nnc(-c2cc(C(=O)N3CCC(c4ccc(C#N)cc4)CC3)c(C)cc2N2CCC2)[nH]1] | 0.180 |
| 001-481 | 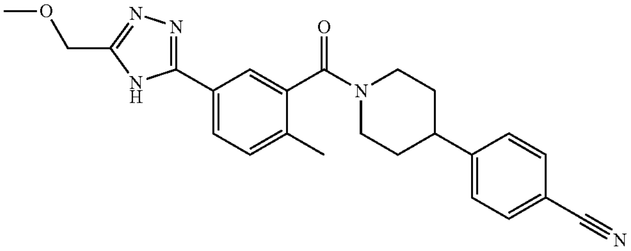 [SMILES: COCc1nnc(-c2ccc(C)c(C(=O)N3CCC(c4ccc(C#N)cc4)CC3)c2)[nH]1] | 21.240 |
| 001-482 | 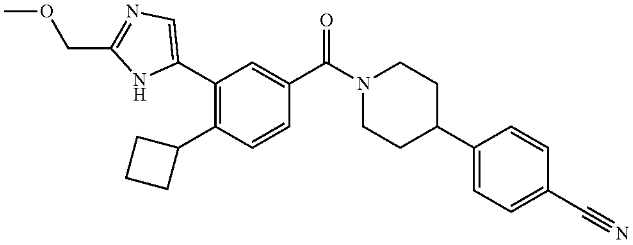 [SMILES: COCc1ncc(-c2cc(C(=O)N3CCC(c4ccc(C#N)cc4)CC3)ccc2C2CCC2)[nH]1] | 0.240 |
| 001-483 | 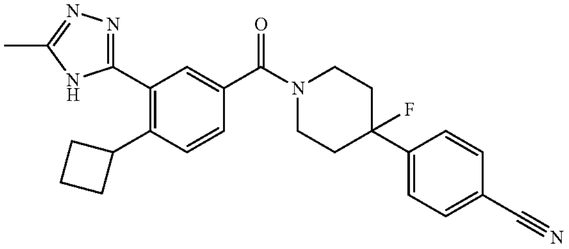 [SMILES: Cc1nnc(-c2cc(C(=O)N3CCC(F)(c4ccc(C#N)cc4)CC3)ccc2C2CCC2)[nH]1] | 0.100 |
| 001-484 | 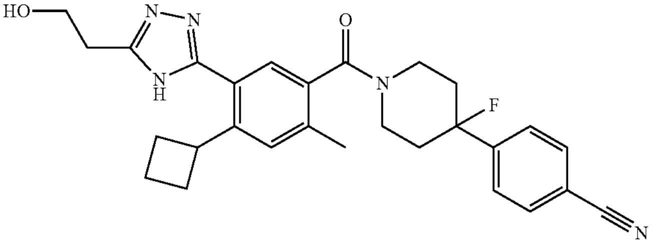 [SMILES: Cc1cc(C2CCC2)c(-c2nnc(CCO)[nH]2)cc1C(=O)N1CCC(F)(c2ccc(C#N)cc2)CC1] | 0.070 |

TABLE C-1-continued
| Fatty Acid Synthase Inhibitors | | |
|---|---|---|
| Cmpd No. | Structure | FASN $IC_{50}$ (μM) |
| 001-485 | 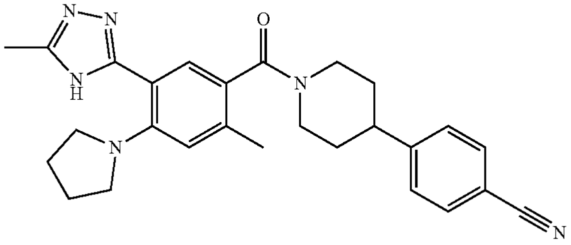 [SMILES: Cc1nnc(-c2cc(C(=O)N3CCC(c4ccc(C#N)cc4)CC3)c(C)cc2N2CCCC2)[nH]1] | 0.130 |
| 001-486 | 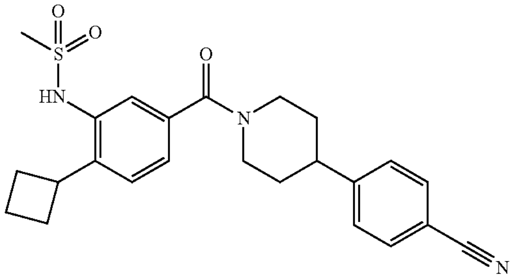 [SMILES: CS(=O)(=O)Nc1cc(C(=O)N2CCC(c3ccc(C#N)cc3)CC2)ccc1C1CCC1] | 0.540 |
| 001-487 | 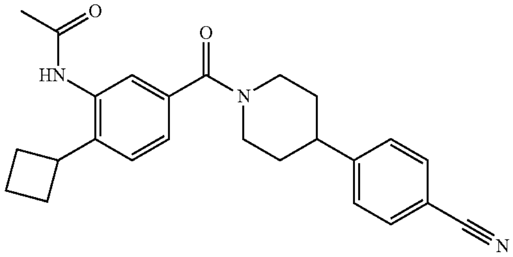 [SMILES: CC(=O)Nc1cc(C(=O)N2CCC(c3ccc(C#N)cc3)CC2)ccc1C1CCC1] | 0.380 |
| 001-488 | 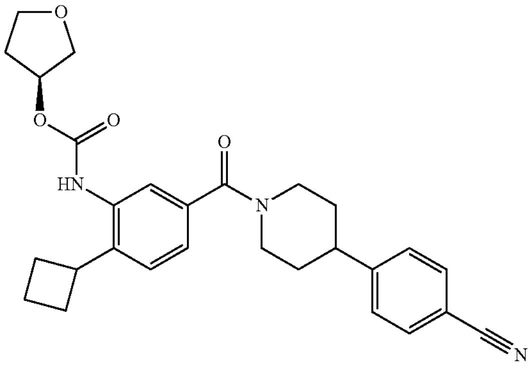 [SMILES: N#Cc1ccc(C2CCN(C(=O)c3ccc(C4CCC4)c(NC(=O)O[C@H]4CCOC4)c3)CC2)cc1] | 0.030 |
| 001-489 | 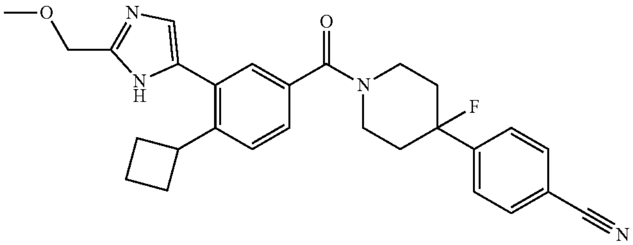 [SMILES: COCc1ncc(-c2cc(C(=O)N3CCC(F)(c4ccc(C#N)cc4)CC3)ccc2C2CCC2)[nH]1] | 0.180 |

TABLE C-1-continued
| Fatty Acid Synthase Inhibitors | | |
|---|---|---|
| Cmpd No. | Structure | FASN $IC_{50}$ (μM) |
| 001-490 | 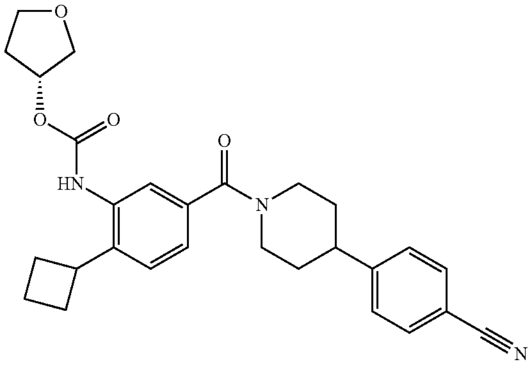 [SMILES: N#Cc1ccc(C2CCN(C(=O)c3ccc(C4CCC4)c(NC(=O)O[C@@H]4CCOC4)c3)CC2)cc1] | 0.090 |
| 001-491 | 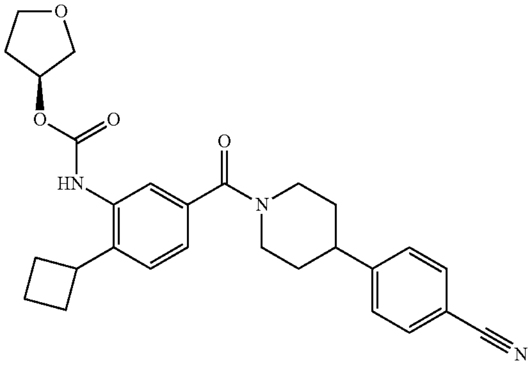 [SMILES: N#Cc1ccc(C2CCN(C(=O)c3ccc(C4CCC4)c(NC(=O)O[C@H]4CCOC4)c3)CC2)cc1] | 0.070 |
| 001-492 | 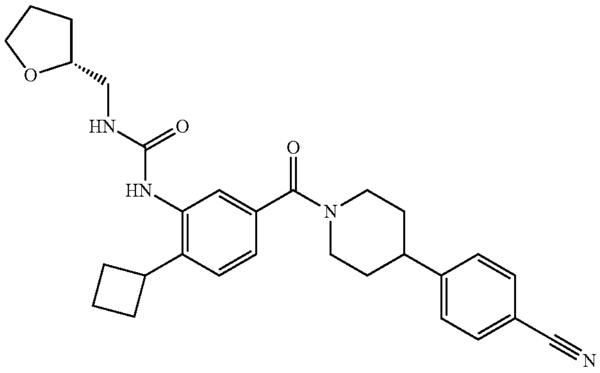 [SMILES: N#Cc1ccc(C2CCN(C(=O)c3ccc(C4CCC4)c(NC(=O)NC[C@H]4CCCO4)c3)CC2)cc1] | 0.030 |
| 001-493 | 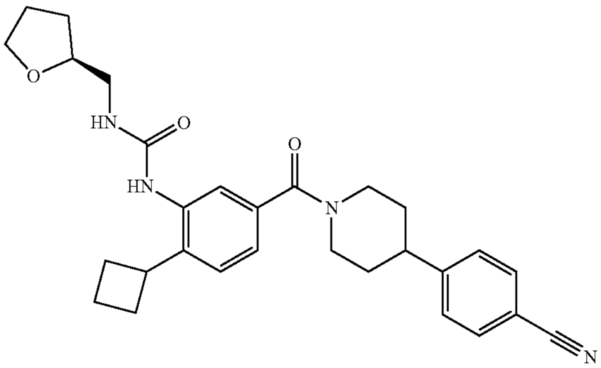 [SMILES: N#Cc1ccc(C2CCN(C(=O)c3ccc(C4CCC4)c(NC(=O)NC[C@@H]4CCCO4)c3)CC2)cc1] | 0.090 |

TABLE C-1-continued
| Fatty Acid Synthase Inhibitors | | |
|---|---|---|
| Cmpd No. | Structure | FASN IC50 (μM) |
| 001-494 | 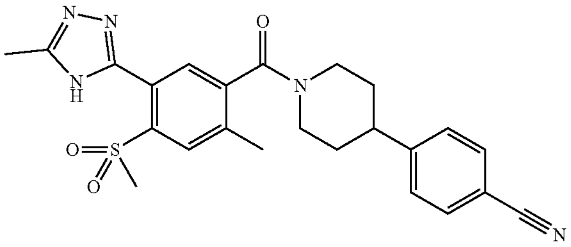 [SMILES: Cc1nnc(-c2cc(C(=O)N3CCC(c4ccc(C#N)cc4)CC3)c(C)cc2S(C)(=O)=O)[nH]1] | >50 |
| 001-495 | 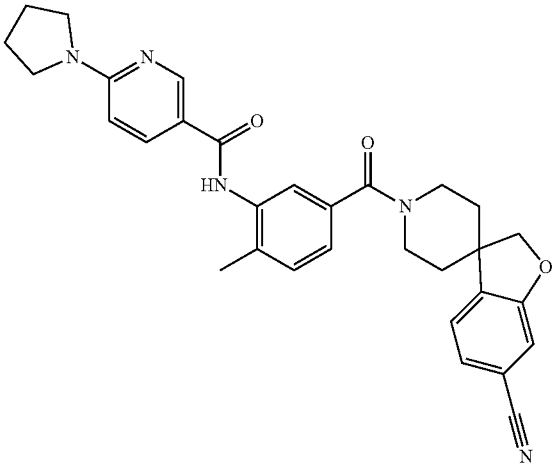 [SMILES: Cc1ccc(C(=O)N2CCC3(CC2)COc2cc(C#N)ccc23)cc1NC(=O)c1ccc(N2CCCC2)nc1] | |
| 001-496 | 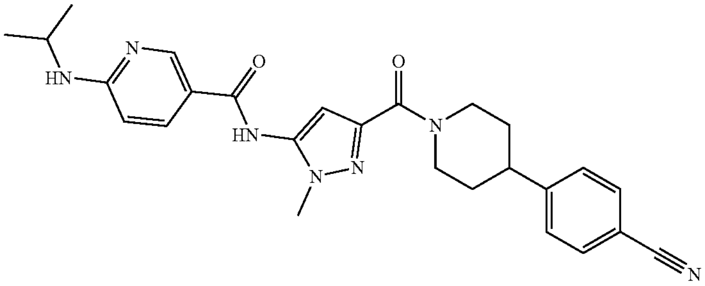 [SMILES: CC(C)Nc1ccc(C(=O)Nc2cc(C(=O)N3CCC(c4ccc(C#N)cc4)CC3)nn2C)cn1] | |
| 001-497 | 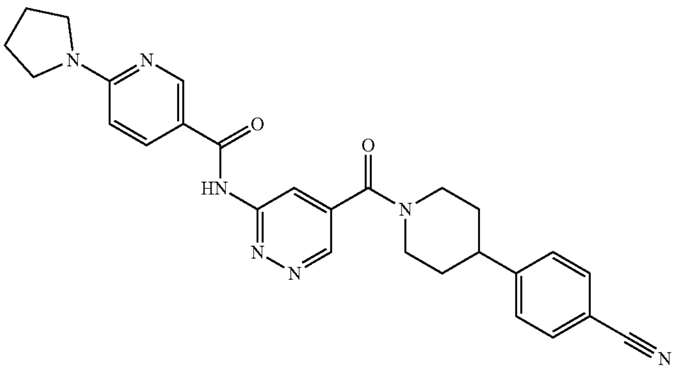 [SMILES: N#Cc1ccc(C2CCN(C(=O)c3cnnc(NC(=O)c4ccc(N5CCCC5)nc4)c3)CC2)cc1] | |

TABLE C-1-continued
| Fatty Acid Synthase Inhibitors | | |
|---|---|---|
| Cmpd No. | Structure | FASN $IC_{50}$ (μM) |
| 001-498 | 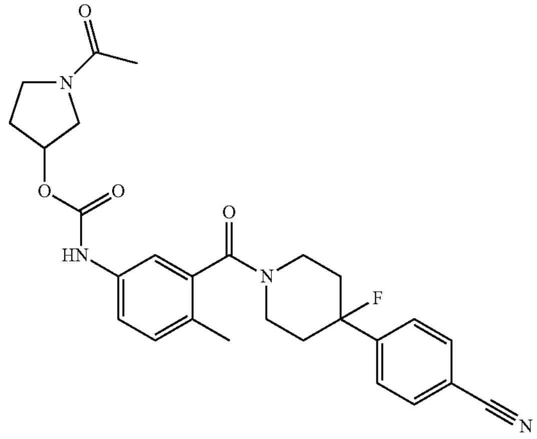 [SMILES: CC(=O)N1CCC(OC(=O)Nc2ccc(C)c(C(=O)N3CCC(F)(c4ccc(C#N)cc4)CC3)c2)C1] | |
| 001-498 | 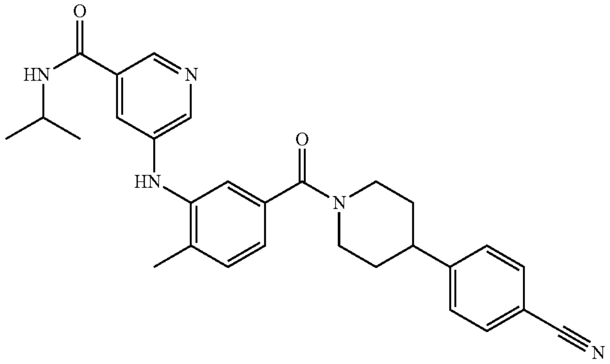 [SMILES: Cc1ccc(C(=O)N2CCC(c3ccc(C#N)cc3)CC2)cc1Nc1cncc(C(=O)NC(C)C)c1] | |
| 001-499 | 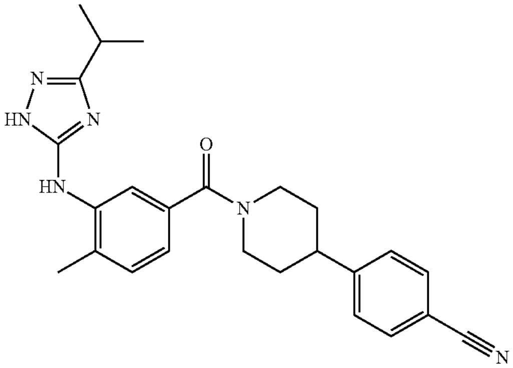 [SMILES: Cc1ccc(C(=O)N2CCC(c3ccc(C#N)cc3)CC2)cc1Nc1nc(C(C)C)n[nH]1] | |

TABLE C-1-continued
| Fatty Acid Synthase Inhibitors | | |
|---|---|---|
| Cmpd No. | Structure | FASN $IC_{50}$ (μM) |
| 001-500 | 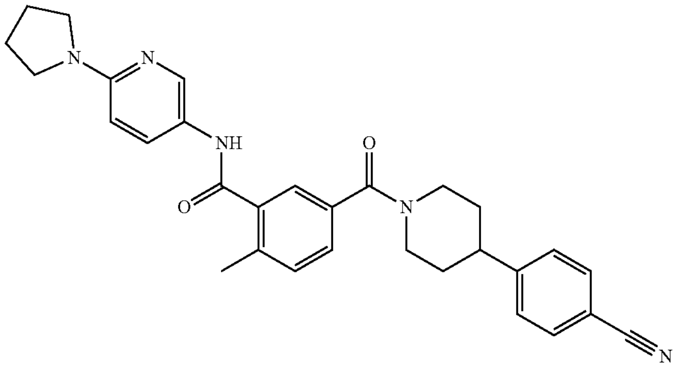 [SMILES: Cc1ccc(C(=O)N2CCC(c3ccc(C#N)cc3)CC2)cc1C(=O)Nc1ccc(N2CCCC2)nc1] | |
TABLE C-2
| Fatty Acid Synthase Inhibitors | | |
|---|---|---|
| Cmpd No. | Structure | Hu FASN IC50 (μM) |
| 002-1 | 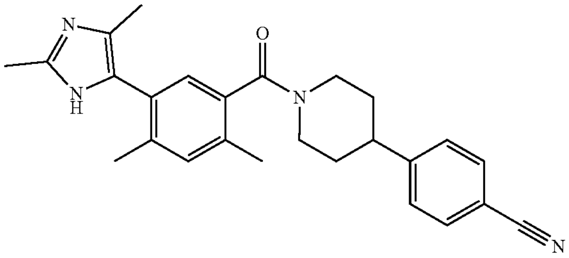 [SMILES: Cc1nc(C)c(-c2cc(C(=O)N3CCC(c4ccc(C#N)cc4)CC3)c(C)cc2C)[nH]1] | 0.024 |
| 002-2 | 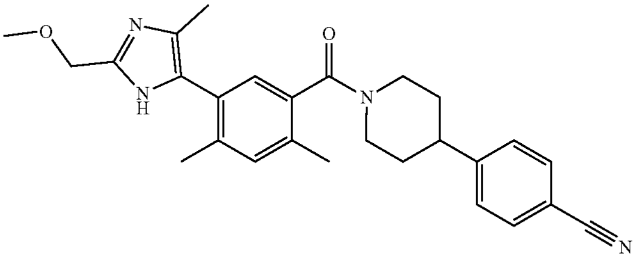 [SMILES: COCc1nc(C)c(-c2cc(C(=O)N3CCC(c4ccc(C#N)cc4)CC3)c(C)cc2C)[nH]1] | 0.041 |
| 002-3 | 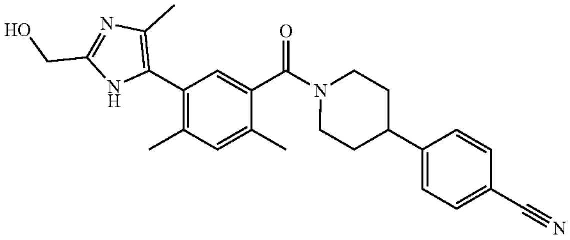 [SMILES: Cc1cc(C)c(-c2[nH]c(CO)nc2C)cc1C(=O)N1CCC(c2ccc(C#N)cc2)CC1] | 0.032 |

TABLE C-2-continued
Fatty Acid Synthase Inhibitors
| Cmpd No. | Structure | Hu FASN IC50 (μM) |
| --- | --- | --- |
| 002-4 | 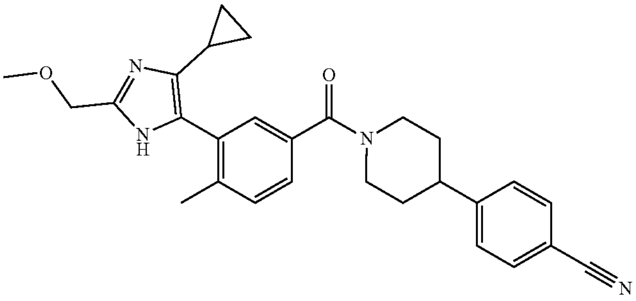 [SMILES: COCc1nc(C2CC2)c(-c2cc(C(=O)N3CCC(c4ccc(C#N)cc4)CC3)ccc2C)[nH]1] | 0.053 |
| 002-5 | 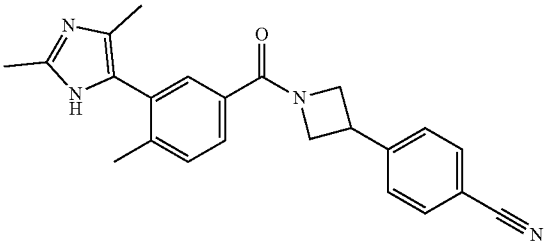 [SMILES: Cc1nc(C)c(-c2cc(C(=O)N3CC(c4ccc(C#N)cc4)C3)ccc2C)[nH]1] | 0.010 |
| 002-6 | 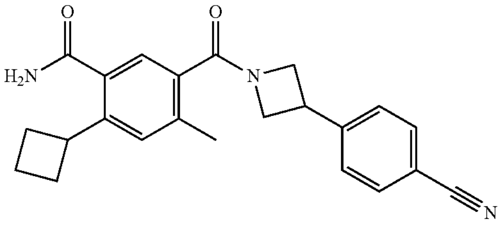 [SMILES: Cc1cc(C2CCC2)c(C(N)=O)cc1C(=O)N1CC(c2ccc(C#N)cc2)C1] | 0.105 |
| 002-7 | 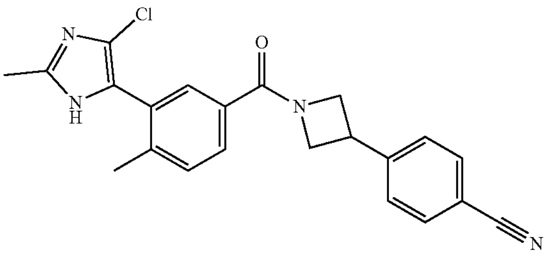 [SMILES: Cc1nc(Cl)c(-c2cc(C(=O)N3CC(c4ccc(C#N)cc4)C3)ccc2C)[nH]1] | 0.006 |
| 002-8 | 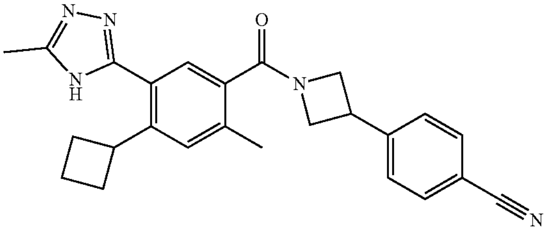 [SMILES: Cc1nnc(-c2cc(C(=O)N3CC(c4ccc(C#N)cc4)C3)c(C)cc2C2CCC2)[nH]1] | 0.040 |

TABLE C-2-continued
| Fatty Acid Synthase Inhibitors | | |
|---|---|---|
| Cmpd No. | Structure | Hu FASN IC50 (μM) |
| 002-9 | 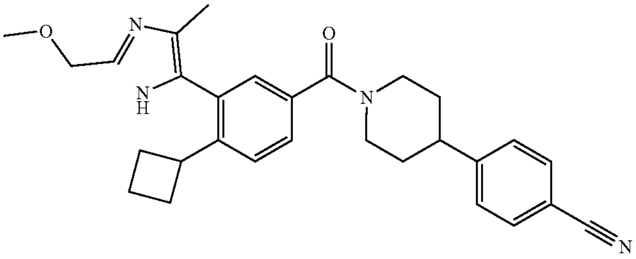 [SMILES: COC/C=N/C(C)=C(\N)c1cc(C(=O)N2CCC(c3ccc(C#N)cc3)CC2)ccc1C1CCC1] | 0.025 |
| 002-10 | 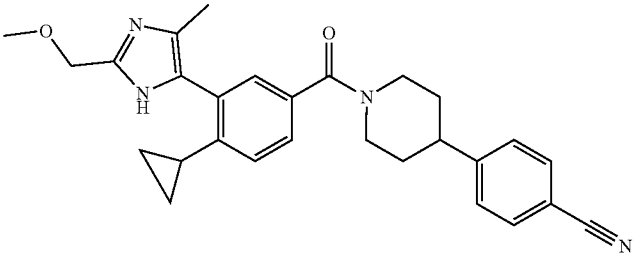 [SMILES: COCc1nc(C)c(-c2cc(C(=O)N3CCC(c4ccc(C#N)cc4)CC3)ccc2C2CC2)[nH]1] | 0.027 |
| 002-11 | 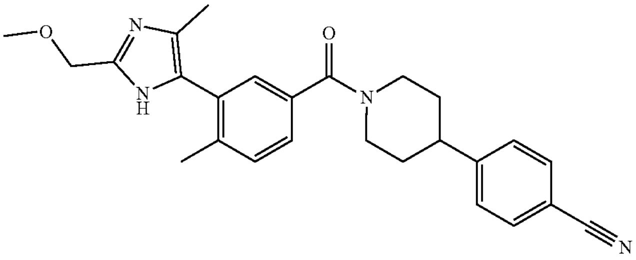 [SMILES: COCc1nc(C)c(-c2cc(C(=O)N3CCC(c4ccc(C#N)cc4)CC3)ccc2C)[nH]1] | 0.036 |
| 002-12 | 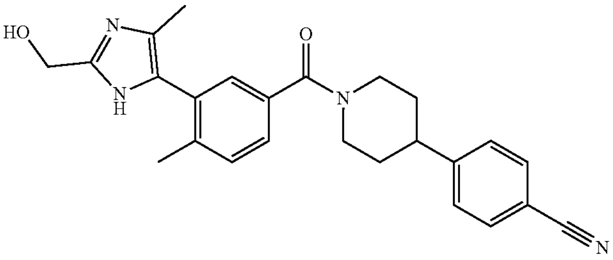 [SMILES: Cc1ccc(C(=O)N2CCC(c3ccc(C#N)cc3)CC2)cc1-c1[nH]c(CO)nc1C] | 0.036 |
| 002-13 | 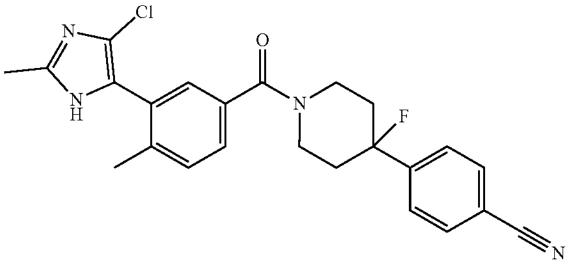 [SMILES: Cc1nc(Cl)c(-c2cc(C(=O)N3CCC(F)(c4ccc(C#N)cc4)CC3)ccc2C)[nH]1] | 0.006 |

TABLE C-2-continued
| Fatty Acid Synthase Inhibitors | | |
|---|---|---|
| Cmpd No. | Structure | Hu FASN IC50 (μM) |
| 002-14 | 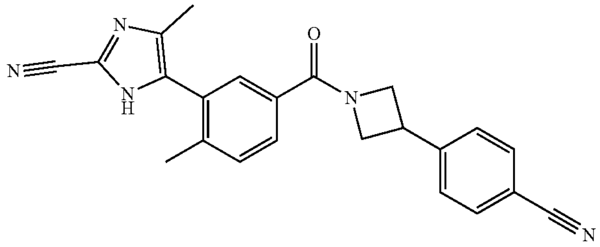 [SMILES: Cc1ccc(C(=O)N2CC(c3ccc(C#N)cc3)C2)cc1-c1[nH]c(C#N)nc1C] | 0.027 |
| 002-15 | 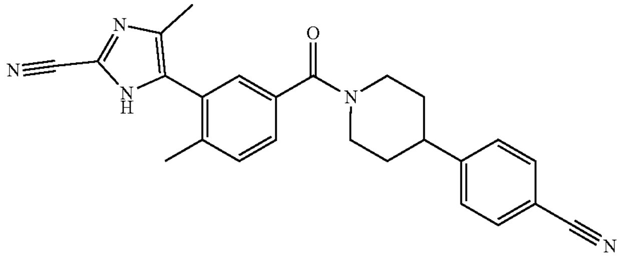 [SMILES: Cc1ccc(C(=O)N2CCC(c3ccc(C#N)cc3)CC2)cc1-c1[nH]c(C#N)nc1C] | 0.026 |
| 002-16 | 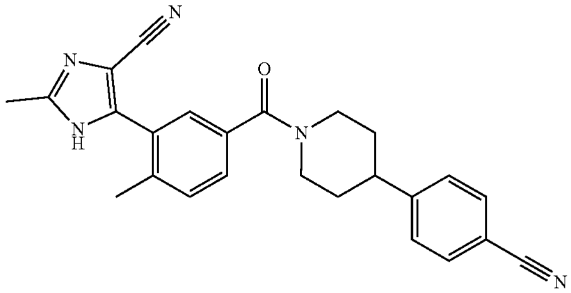 [SMILES: Cc1nc(C#N)c(-c2cc(C(=O)N3CCC(c4ccc(C#N)cc4)CC3)ccc2C)[nH]1] | 0.018 |
| 002-17 | 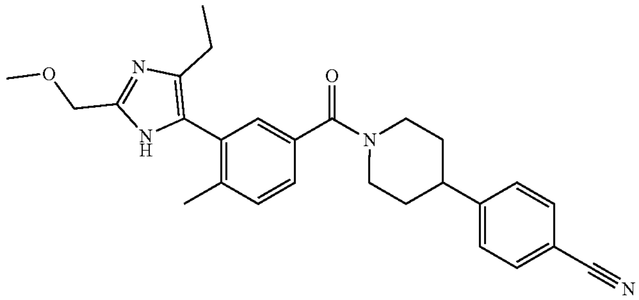 [SMILES: CCc1nc(COC)[nH]c1-c1cc(C(=O)N2CCC(c3ccc(C#N)cc3)CC2)ccc1C] | 0.045 |
| 002-18 | 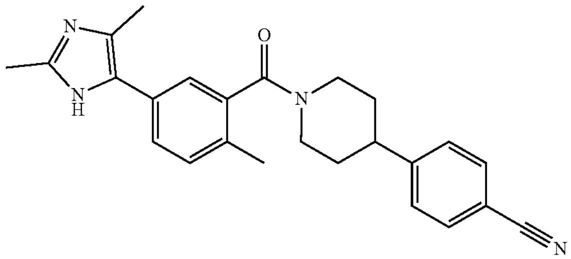 [SMILES: Cc1nc(C)c(-c2ccc(C)c(C(=O)N3CCC(c4ccc(C#N)cc4)CC3)c2)[nH]1] | 0.540 |

TABLE C-2-continued
| Fatty Acid Synthase Inhibitors | | |
|---|---|---|
| Cmpd No. | Structure | Hu FASN IC50 (μM) |
| 002-19 | 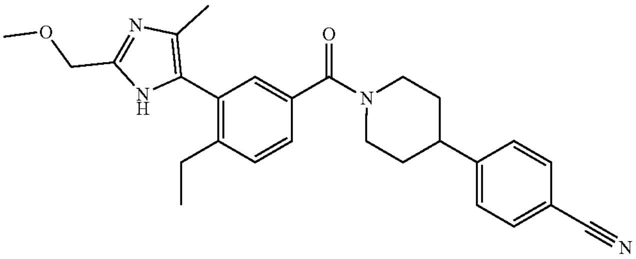 [SMILES: CCc1ccc(C(=O)N2CCC(c3ccc(C#N)cc3)CC2)cc1-c1[nH]c(COC)nc1C] | 0.030 |
| 002-20 | 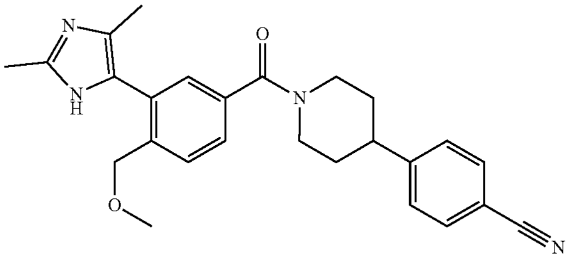 [SMILES: COCc1ccc(C(=O)N2CCC(c3ccc(C#N)cc3)CC2)cc1-c1[nH]c(C)nc1C] | 0.165 |
| 002-21 | 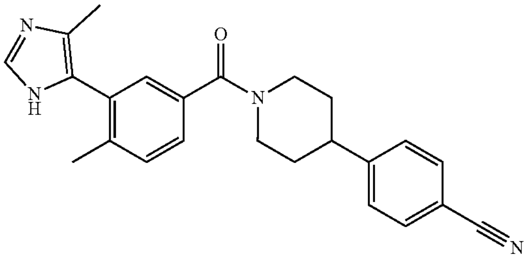 [SMILES: Cc1ccc(C(=O)N2CCC(c3ccc(C#N)cc3)CC2)cc1-c1[nH]cnc1C] | 0.207 |
| 002-22 | 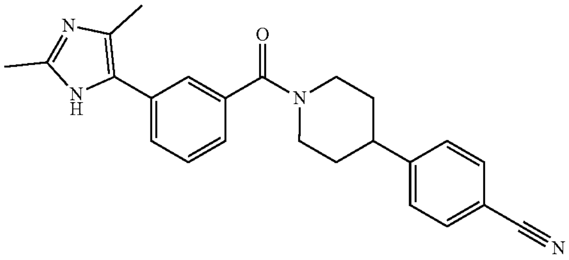 [SMILES: Cc1nc(C)c(-c2cccc(C(=O)N3CCC(c4ccc(C#N)cc4)CC3)c2)[nH]1] | 1.690 |
| 002-23 | 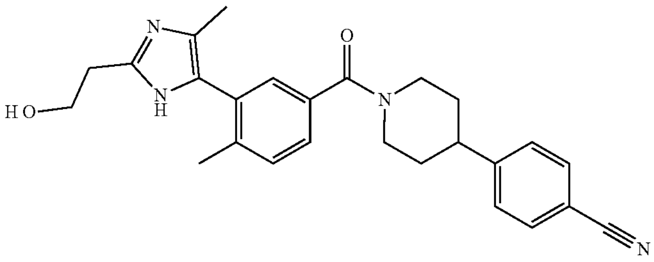 | 0.209 |

TABLE C-2-continued
| Fatty Acid Synthase Inhibitors | | |
|---|---|---|
| Cmpd No. | Structure | Hu FASN IC50 (μM) |
| 002-24 | 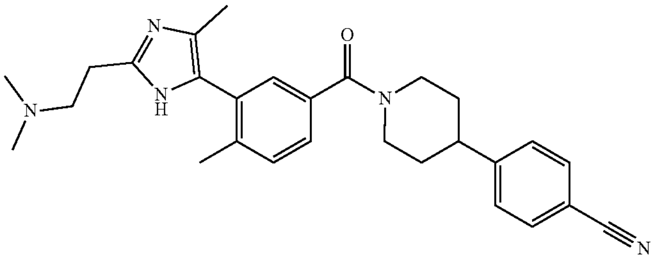 [SMILES: Cc1ccc(C(=O)N2CCC(c3ccc(C#N)cc3)CC2)cc1-c1[nH]c(CCN(C)C)nc1C] | 0.041 |
| 002-25 | 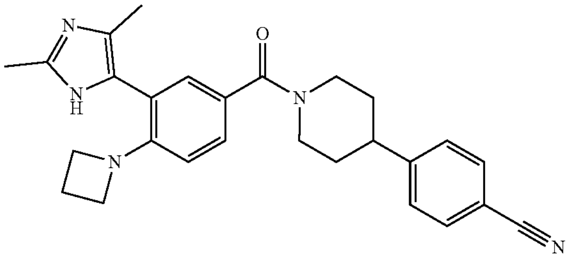 [SMILES: Cc1nc(C)c(-c2cc(C(=O)N3CCC(c4ccc(C#N)cc4)CC3)ccc2N2CCC2)[nH]1] | |
| 002-26 | 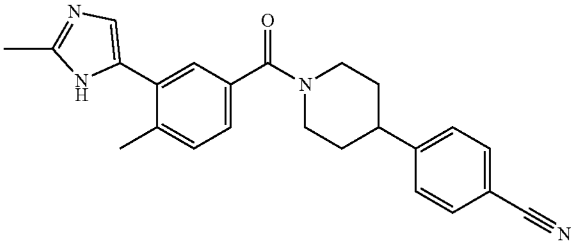 [SMILES: Cc1ncc(-c2cc(C(=O)N3CCC(c4ccc(C#N)cc4)CC3)ccc2C)[nH]1] | 0.245 |
| 002-27 | 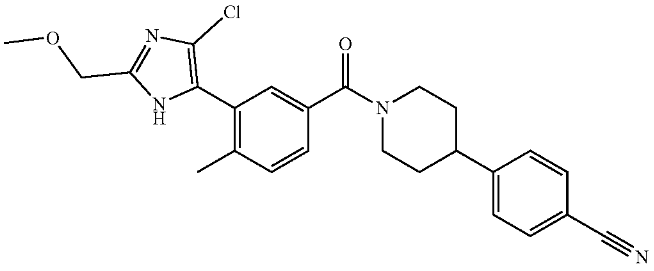 [SMILES: COCc1nc(Cl)c(-c2cc(C(=O)N3CCC(c4ccc(C#N)cc4)CC3)ccc2C)[nH]1] | 0.009 |
| 002-28 | 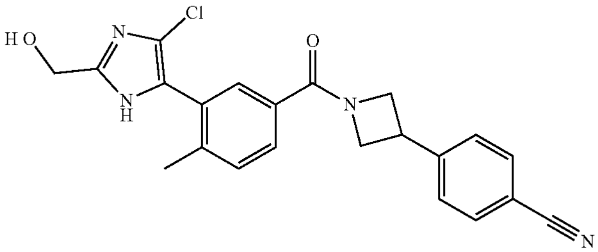 | 0.048 |

TABLE C-2-continued
| Fatty Acid Synthase Inhibitors | | |
|---|---|---|
| Cmpd No. | Structure | Hu FASN IC50 (μM) |
| 002-29 | 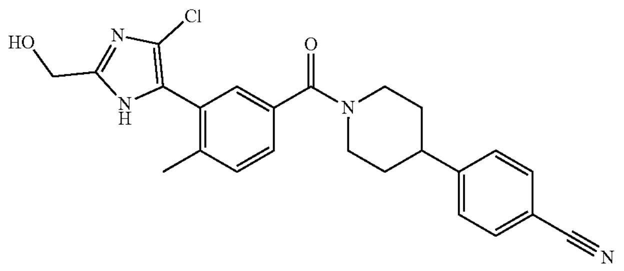 [SMILES: Cc1ccc(C(=O)N2CCC(c3ccc(C#N)cc3)CC2)cc1-c1[nH]c(CO)nc1Cl] | 0.024 |
| 002-30 | 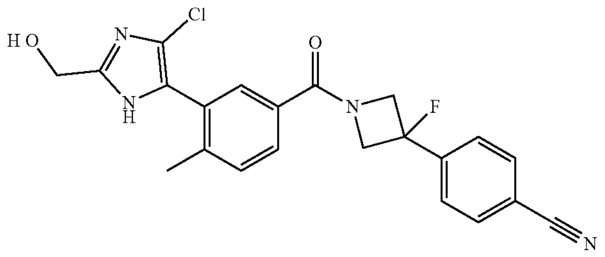 | 0.016 |
| 002-31 | 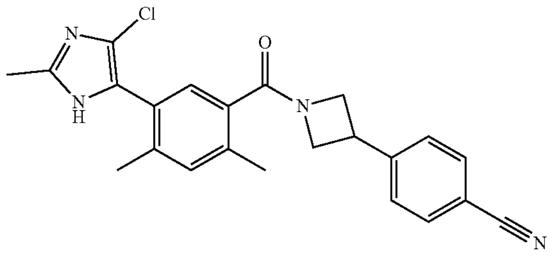 [SMILES: Cc1nc(Cl)c(-c2cc(C(=O)N3CC(c4ccc(C#N)cc4)C3)c(C)cc2C)[nH]1] | 0.011 |
| 002-32 | 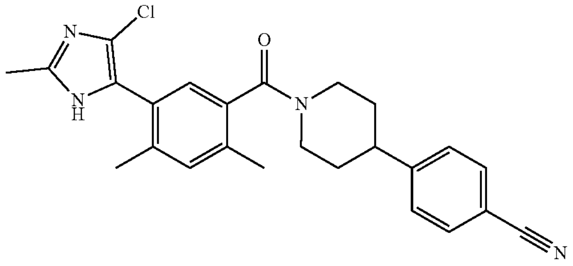 [SMILES: Cc1nc(Cl)c(-c2cc(C(=O)N3CCC(c4ccc(C#N)cc4)CC3)c(C)cc2C)[nH]1] | 0.012 |
| 002-33 | 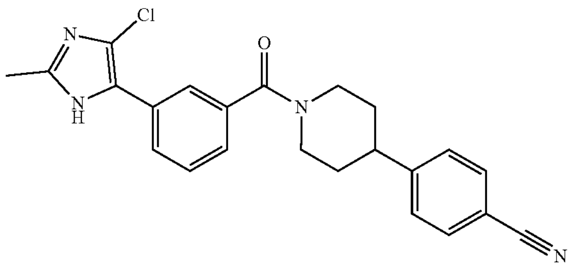 [SMILES: Cc1nc(Cl)c(-c2cccc(C(=O)N3CCC(c4ccc(C#N)cc4)CC3)c2)[nH]1] | 0.080 |

TABLE C-2-continued
| Fatty Acid Synthase Inhibitors | | |
|---|---|---|
| Cmpd No. | Structure | Hu FASN IC50 (µM) |
| 002-34 | 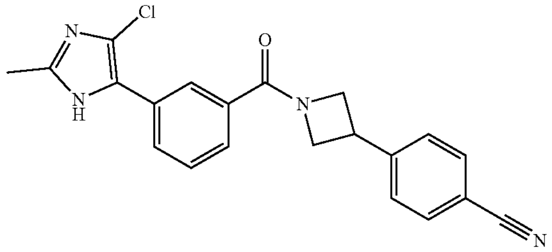 [SMILES: Cc1nc(Cl)c(-c2cccc(C(=O)N3CC(c4ccc(C#N)cc4)C3)c2)[nH]1] | 0.048 |
| 002-35 | 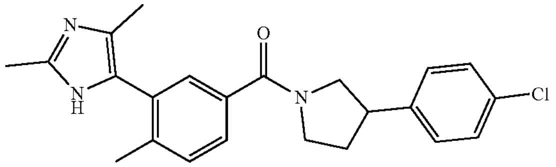 [SMILES: Cc1nc(C)c(-c2cc(C(=O)N3CCC(c4ccc(Cl)cc4)C3)ccc2C)[nH]1] | 2.870 |
| 002-36 | 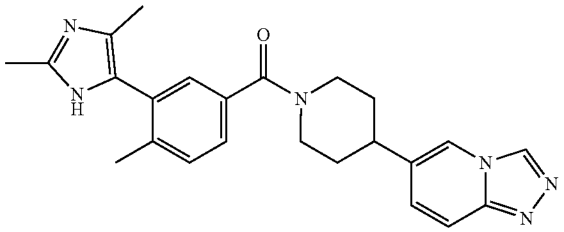 [SMILES: Cc1nc(C)c(-c2cc(C(=O)N3CCC(c4ccc5nncn5c4)CC3)ccc2C)[nH]1] | 9.190 |
| 002-37 | 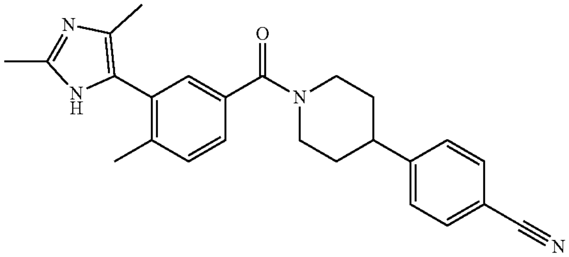 [SMILES: Cc1nc(C)c(-c2cc(C(=O)N3CCC(c4ccc(C#N)cc4)CC3)ccc2C)[nH]1] | 0.032 |
| 002-38 | 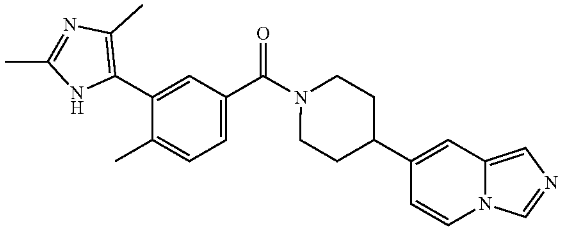 | 0.104 |
| 002-39 | 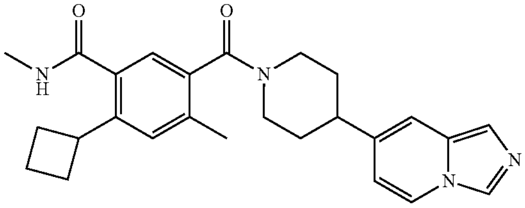 [SMILES: CNC(=O)c1cc(C(=O)N2CCC(c3ccn4cncc4c3)CC2)c(C)cc1C1CCC1] | 0.420 |

TABLE C-2-continued
| Fatty Acid Synthase Inhibitors | | |
|---|---|---|
| Cmpd No. | Structure | Hu FASN IC50 (μM) |
| 002-40 | 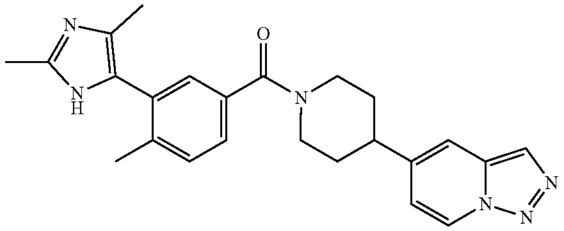 [SMILES: Cc1nc(C)c(-c2cc(C(=O)N3CCC(c4ccn5nncc5c4)CC3)ccc2C)[nH]1] | 0.620 |
| 002-41 | 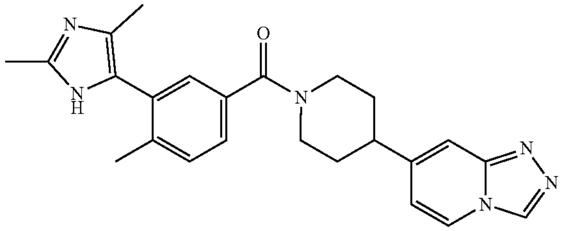 [SMILES: Cc1nc(C)c(-c2cc(C(=O)N3CCC(c4ccn5cnnc5c4)CC3)ccc2C)[nH]1] | 50.000 |
| 002-42 | 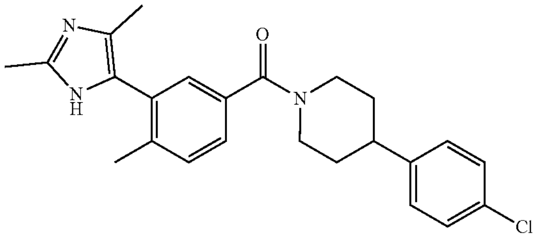 [SMILES: Cc1nc(C)c(-c2cc(C(=O)N3CCC(c4ccc(Cl)cc4)CC3)ccc2C)[nH]1] | 0.032 |
| 002-43 | 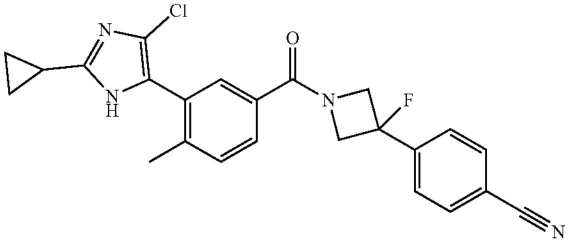 [SMILES: Cc1ccc(C(=O)N2CC(F)(c3ccc(C#N)cc3)C2)cc1-c1[nH]c(C2CC2)nc1Cl] | 0.012 |
| 002-44 | 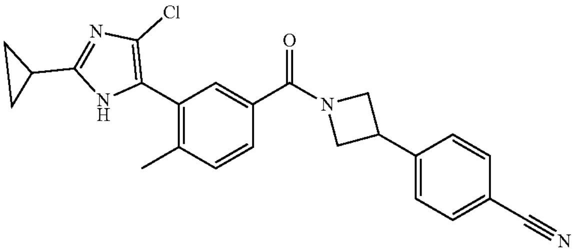 [SMILES: Cc1ccc(C(=O)N2CC(c3ccc(C#N)cc3)C2)cc1-c1[nH]c(C2CC2)nc1Cl] | 0.007 |
| 002-45 | 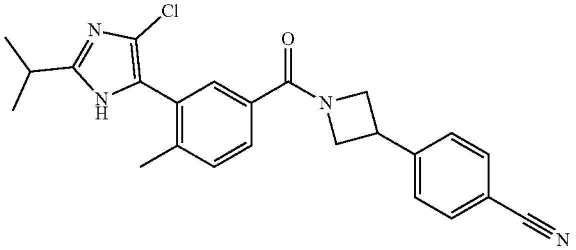 [SMILES: Cc1ccc(C(=O)N2CC(c3ccc(C#N)cc3)C2)cc1-c1[nH]c(C(C)C)nc1Cl] | 0.009 |

TABLE C-2-continued
| Fatty Acid Synthase Inhibitors | | |
|---|---|---|
| Cmpd No. | Structure | Hu FASN IC50 (μM) |
| 002-46 | 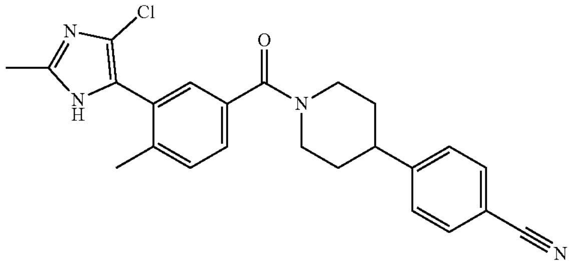 [SMILES: Cc1nc(Cl)c(-c2cc(C(=O)N3CCC(c4ccc(C#N)cc4)CC3)ccc2C)[nH]1] | 0.005 |
| 002-47 | 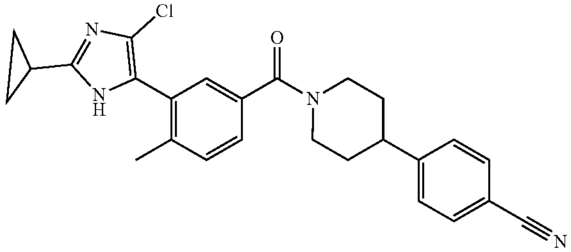 [SMILES: Cc1ccc(C(=O)N2CCC(c3ccc(C#N)cc3)CC2)cc1-c1[nH]c(C2CC2)nc1Cl] | 0.007 |
| 002-48 | 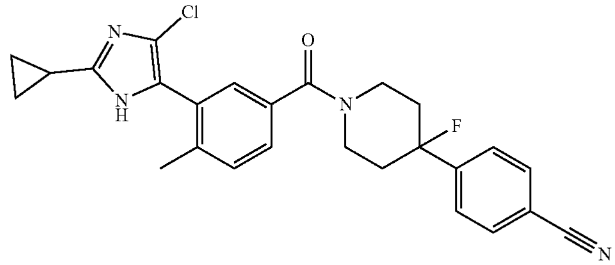 [SMILES: Cc1ccc(C(=O)N2CCC(F)(c3ccc(C#N)cc3)CC2)cc1-c1[nH]c(C2CC2)nc1Cl] | 0.009 |
| 002-49 | 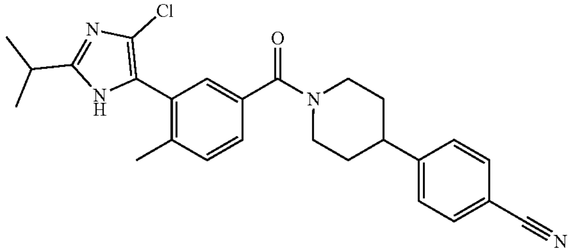 [SMILES: Cc1ccc(C(=O)N2CCC(c3ccc(C#N)cc3)CC2)cc1-c1[nH]c(C(C)C)nc1Cl] | 0.009 |
| 002-50 | 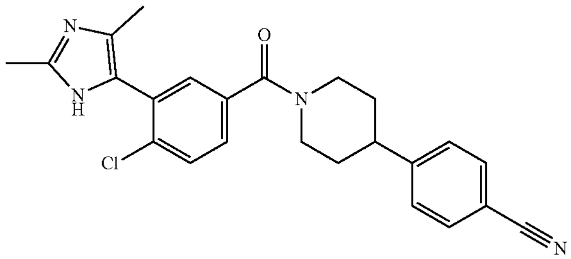 [SMILES: Cc1nc(C)c(-c2cc(C(=O)N3CCC(c4ccc(C#N)cc4)CC3)ccc2Cl)[nH]1] | 0.145 |

TABLE C-2-continued
| Fatty Acid Synthase Inhibitors | | |
|---|---|---|
| Cmpd No. | Structure | Hu FASN IC50 (μM) |
| 002-51 | 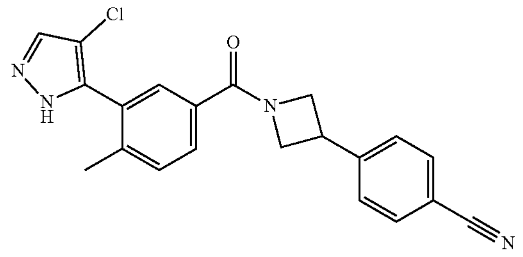 [SMILES: Cc1ccc(C(=O)N2CC(c3ccc(C#N)cc3)C2)cc1-c1[nH]ncc1Cl] | 0.019 |
| 002-52 | 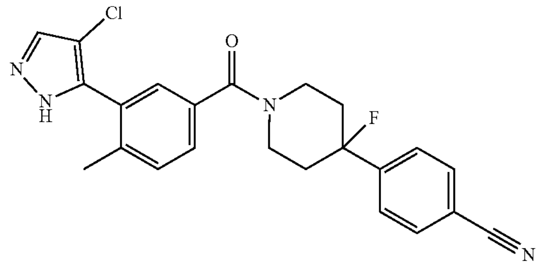 [SMILES: Cc1ccc(C(=O)N2CCC(F)(c3ccc(C#N)cc3)CC2)cc1-c1[nH]ncc1Cl] | 0.046 |
| 002-53 | 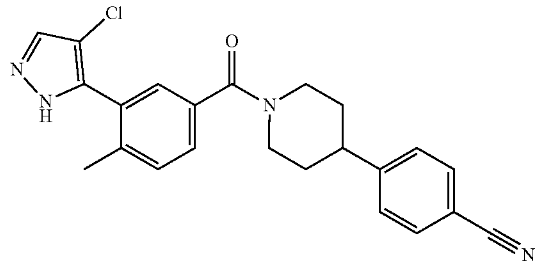 [SMILES: Cc1ccc(C(=O)N2CCC(c3ccc(C#N)cc3)CC2)cc1-c1[nH]ncc1Cl] | 0.033 |
| 002-54 | 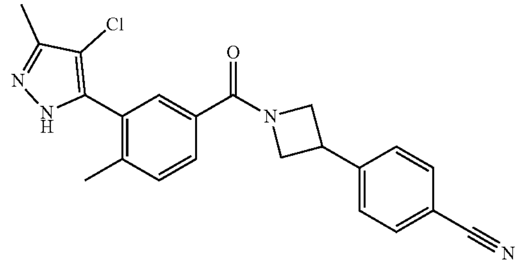 [SMILES: Cc1ccc(C(=O)N2CC(c3ccc(C#N)cc3)C2)cc1-c1[nH]nc(C)c1Cl] | 0.020 |
| 002-55 | 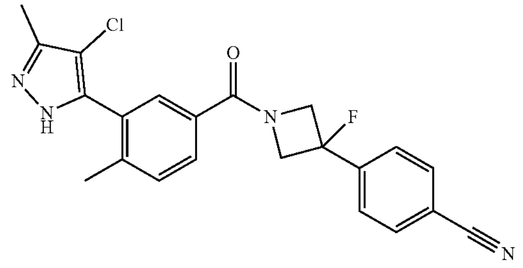 [SMILES: Cc1ccc(C(=O)N2CC(F)(c3ccc(C#N)cc3)C2)cc1-c1[nH]nc(C)c1Cl] | 0.086 |

TABLE C-2-continued
| Fatty Acid Synthase Inhibitors | | |
|---|---|---|
| Cmpd No. | Structure | Hu FASN IC50 (μM) |
| 002-56 | 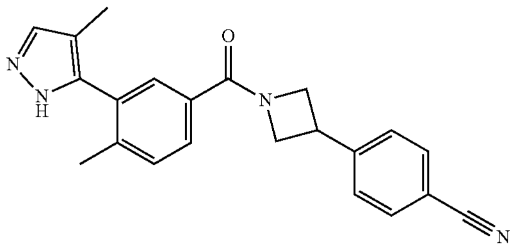 [SMILES: Cc1ccc(C(=O)N2CC(c3ccc(C#N)cc3)C2)cc1-c1[nH]ncc1C] | 0.021 |
| 002-57 | 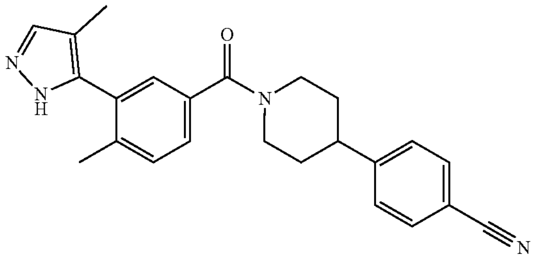 [SMILES: Cc1ccc(C(=O)N2CCC(c3ccc(C#N)cc3)CC2)cc1-c1[nH]ncc1C] | 0.097 |
| 002-58 | 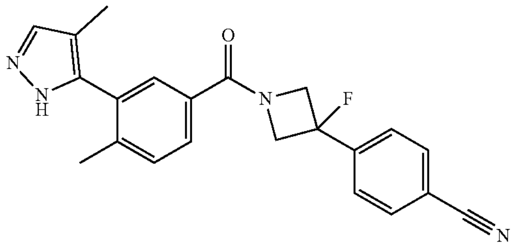 [SMILES: Cc1ccc(C(=O)N2CC(F)(c3ccc(C#N)cc3)C2)cc1-c1[nH]ncc1C] | 0.102 |
| 002-59 | 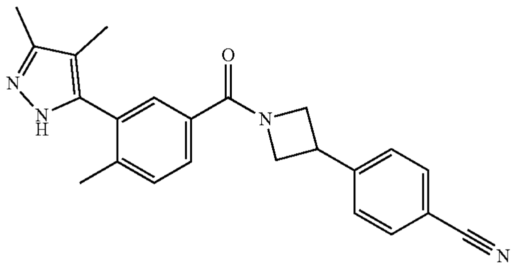 [SMILES: Cc1ccc(C(=O)N2CC(c3ccc(C#N)cc3)C2)cc1-c1[nH]nc(C)c1C] | 0.033 |
| 002-60 | 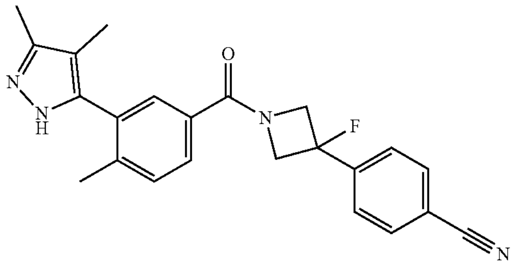 [SMILES: Cc1ccc(C(=O)N2CC(F)(c3ccc(C#N)cc3)C2)cc1-c1[nH]nc(C)c1C] | 0.110 |

TABLE C-2-continued
| Cmpd No. | Structure | Hu FASN IC50 (μM) |
|---|---|---|
| 002-61 | 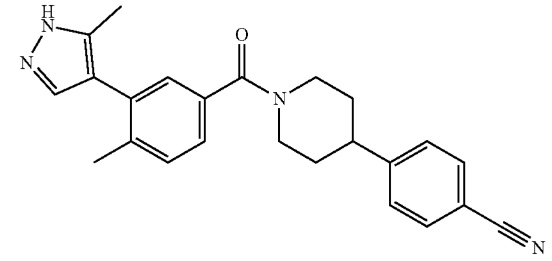 [SMILES: Cc1ccc(C(=O)N2CCC(c3ccc(C#N)cc3)CC2)cc1-c1cn[nH]c1C] | 0.310 |
| 002-62 | 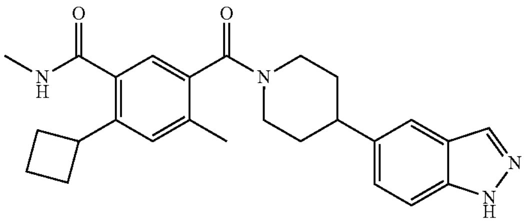 [SMILES: CNC(=O)c1cc(C(=O)N2CCC(c3ccc4[nH]ncc4c3)CC2)c(C)cc1C1CCC1] | 0.650 |
| 002-63 | 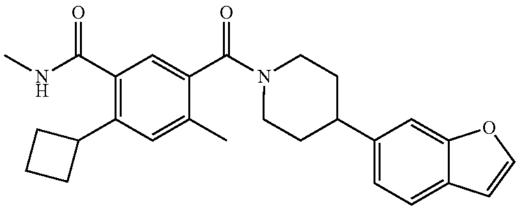 [SMILES: CNC(=O)c1cc(C(=O)N2CCC(c3ccc4ccoc4c3)CC2)c(C)cc1C1CCC1] | 1.180 |
| 002-64 | 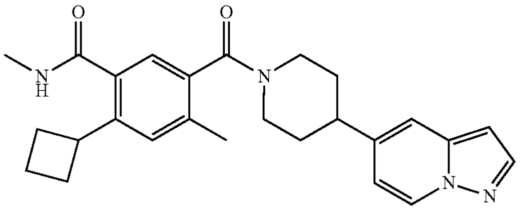 [SMILES: CNC(=O)c1cc(C(=O)N2CCC(c3ccn4nccc4c3)CC2)c(C)cc1C1CCC1] | 1.550 |
| 002-65 | 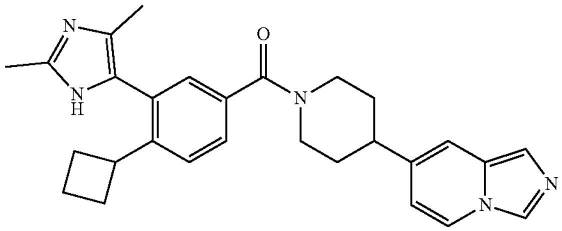 [SMILES: Cc1nc(C)c(-c2cc(C(=O)N3CCC(c4ccn5cncc5c4)CC3)ccc2C2CCC2)[nH]1] | 0.050 |
| 002-66 | 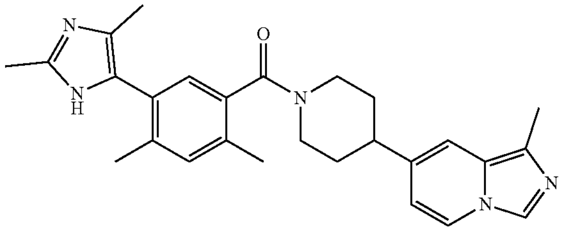 [SMILES: Cc1nc(C)c(-c2cc(C(=O)N3CCC(c4ccn5cnc(C)c5c4)CC3)c(C)cc2C)[nH]1] | 2.370 |
Fatty Acid Synthase Inhibitors TABLE C-2-continued
| Fatty Acid Synthase Inhibitors | | |
|---|---|---|
| Cmpd No. | Structure | Hu FASN IC50 (μM) |
| 002-67 | 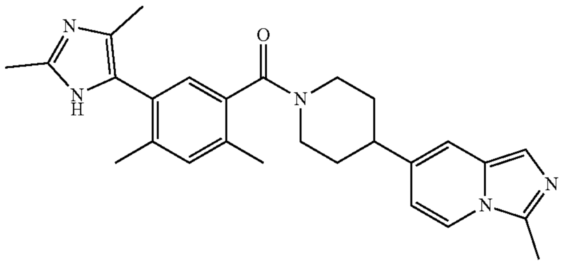 [SMILES: Cc1nc(C)c(-c2cc(C(=O)N3CCC(c4ccn5c(C)ncc5c4)CC3)c(C)cc2C)[nH]1] | 2.490 |
| 002-68 | 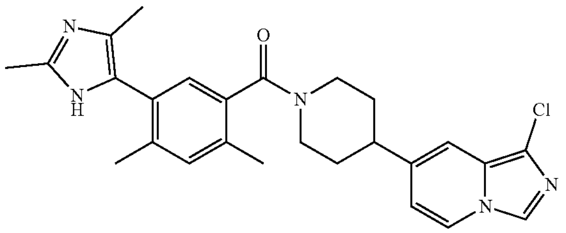 [SMILES: Cc1nc(C)c(-c2cc(C(=O)N3CCC(c4ccn5cnc(Cl)c5c4)CC3)c(C)cc2C)[nH]1] | 0.150 |
| 002-69 | 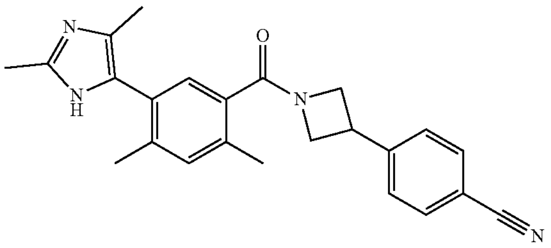 [SMILES: Cc1nc(C)c(-c2cc(C(=O)N3CC(c4ccc(C#N)cc4)C3)c(C)cc2C)[nH]1] | 0.018 |
| 002-70 | 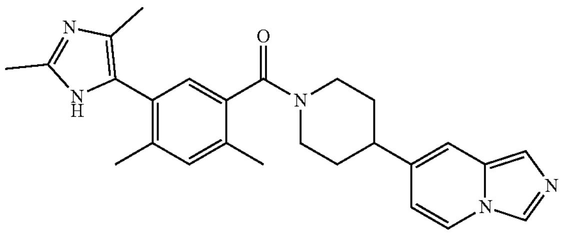 | 0.205 |
| lp;2p 002-71 | 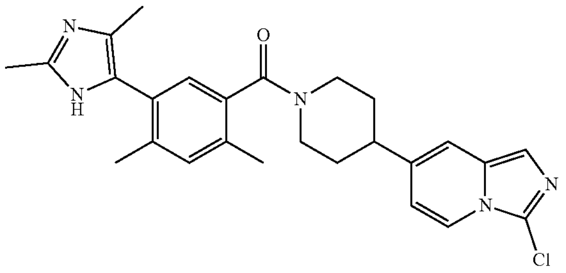 [SMILES: Cc1nc(C)c(-c2cc(C(=O)N3CCC(c4ccn5c(Cl)ncc5c4)CC3)c(C)cc2C)[nH]1] | 0.300 |

TABLE C-2-continued
| Fatty Acid Synthase Inhibitors | | |
|---|---|---|
| Cmpd No. | Structure | Hu FASN IC50 (μM) |
| 002-72 | 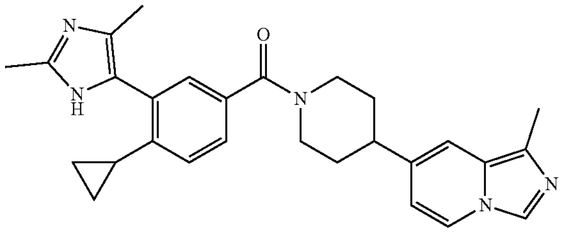 [SMILES: Cc1nc(C)c(-c2cc(C(=O)N3CCC(c4ccn5cnc(C)c5c4)CC3)ccc2C2CC2)[nH]1] | 0.420 |
| 002-73 | 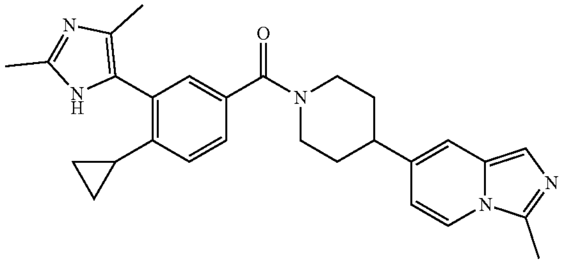 [SMILES: Cc1nc(C)c(-c2cc(C(=O)N3CCC(c4ccn5c(C)ncc5c4)CC3)ccc2C2CC2)[nH]1] | 1.000 |
| 002-74 | 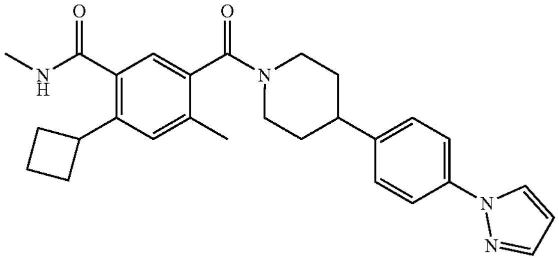 [SMILES: CNC(=O)c1cc(C(=O)N2CCC(c3ccc(-n4cccn4)cc3)CC2)c(C)cc1C1CCC1] | 0.460 |
| 002-75 | 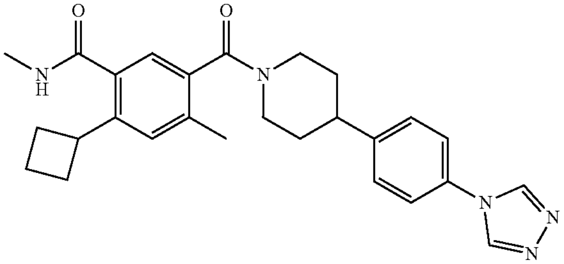 [SMILES: CNC(=O)c1cc(C(=O)N2CCC(c3ccc(-n4cnnc4)cc3)CC2)c(C)cc1C1CCC1] | 0.073 |
| 002-76 | 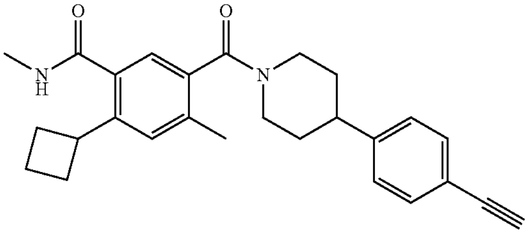 [SMILES: C#Cc1ccc(C2CCN(C(=O)c3cc(C(=O)NC)c(C4CCC4)cc3C)CC2)cc1] | 0.069 |

TABLE C-2-continued
| Fatty Acid Synthase Inhibitors | | |
|---|---|---|
| Cmpd No. | Structure | Hu FASN IC50 (μM) |
| 002-77 | 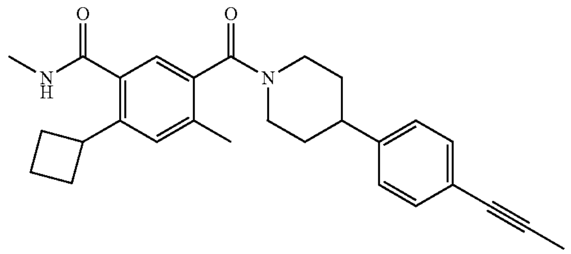 [SMILES: CC#Cc1ccc(C2CCN(C(=O)c3cc(C(=O)NC)c(C4CCC4)cc3C)CC2)cc1] | 0.125 |
| 002-78 | 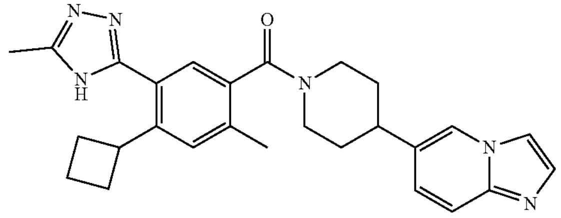 [SMILES: Cc1nnc(-c2cc(C(=O)N3CCC(c4ccc5nccn5c4)CC3)c(C)cc2C2CCC2)[nH]1] | 3.670 |
| 002-79 | 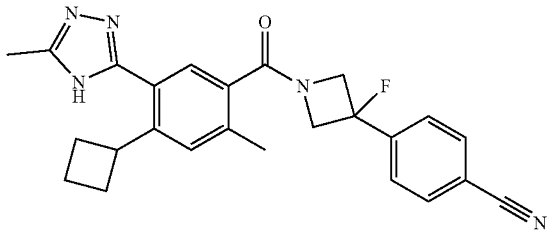 [SMILES: Cc1nnc(-c2cc(C(=O)N3CC(F)(c4ccc(C#N)cc4)C3)c(C)cc2C2CCC2)[nH]1] | 0.059 |
| 002-80 | 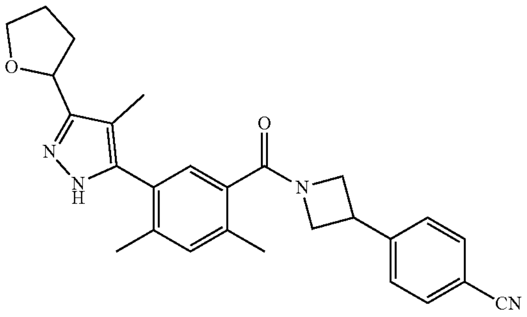 [SMILES: Cc1cc(C)c(-c2[nH]nc(C3CCCO3)c2C)cc1C(=O)N1CC(c2ccc(C#N)cc2)C1] | 0.057 |
| 002-81 | 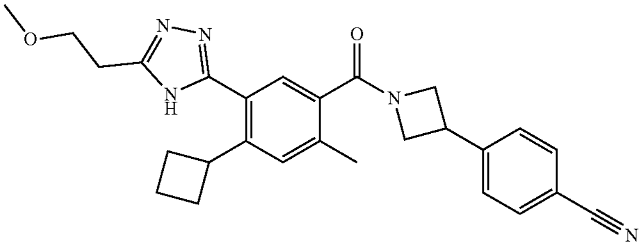 [SMILES: COCCc1nnc(-c2cc(C(=O)N3CC(c4ccc(C#N)cc4)C3)c(C)cc2C2CCC2)[nH]1] | 0.054 |

TABLE C-2-continued
| Cmpd No. | Fatty Acid Synthase Inhibitors<br>Structure | Hu FASN IC50 (μM) |
|---|---|---|
| 002-82 | 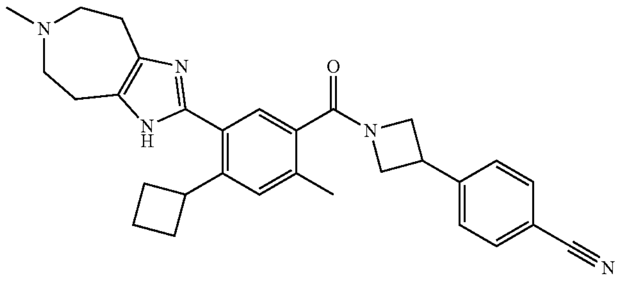 [SMILES: Cc1cc(C2CCC2)c(-c2nc3c([nH]2)CCN(C)CC3)cc1C(=O)N1CC(c2ccc(C#N)cc2)C1] | 0.020 |
| 002-83 | 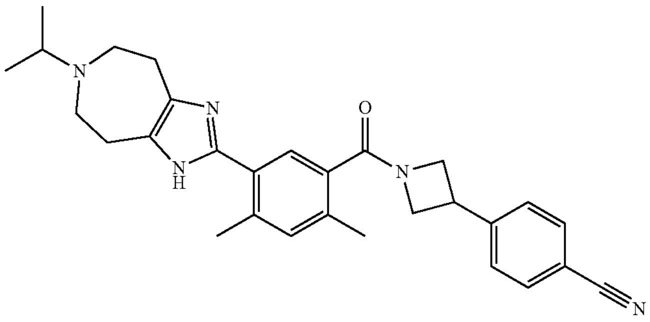 [SMILES: Cc1cc(C)c(-c2nc3c([nH]2)CCN(C(C)C)CC3)cc1C(=O)N1CC(c2ccc(C#N)cc2)C1] | 0.062 |
| 002-84 | 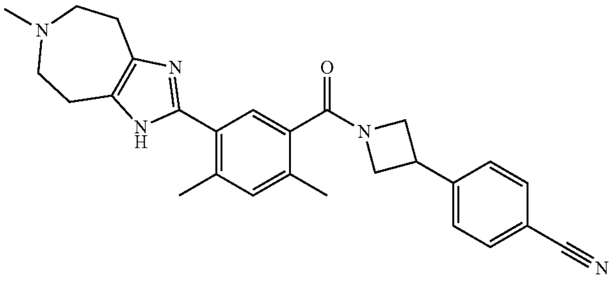 [SMILES: Cc1cc(C)c(-c2nc3c([nH]2)CCN(C)CC3)cc1C(=O)N1CC(c2ccc(C#N)cc2)C1] | 0.112 |
| 002-85 | 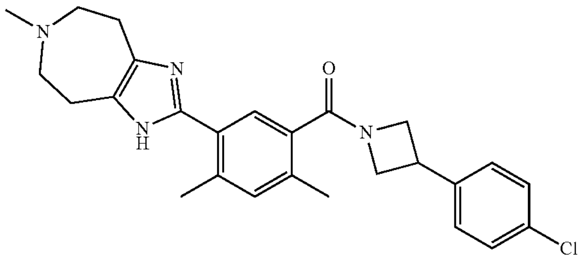 [SMILES: Cc1cc(C)c(-c2nc3c([nH]2)CCN(C)CC3)cc1C(=O)N1CC(c2ccc(Cl)cc2)C1] | 0.057 |
| 002-86 | 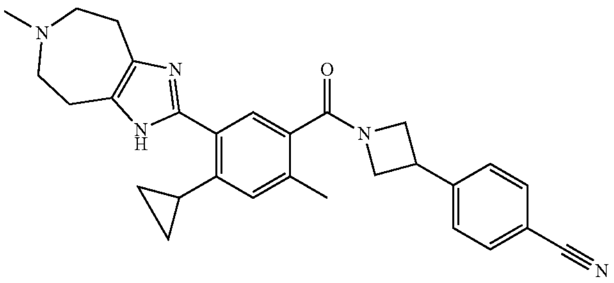 [SMILES: Cc1cc(C2CC2)c(-c2nc3c([nH]2)CCN(C)CC3)cc1C(=O)N1CC(c2ccc(C#N)cc2)C1] | 0.086 |

TABLE C-2-continued
| Cmpd No. | Fatty Acid Synthase Inhibitors<br>Structure | Hu FASN IC50 (μM) |
|---|---|---|
| 002-87 | 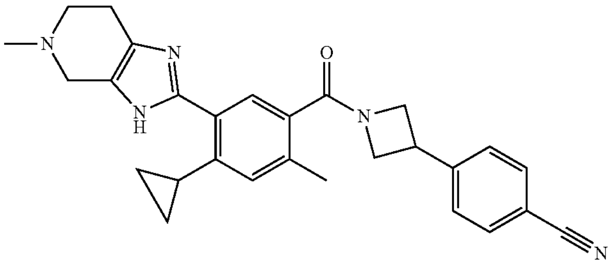 [SMILES: Cc1cc(C2CC2)c(-c2nc3c([nH]2)CN(C)CC3)cc1C(=O)N1CC(c2ccc(C#N)cc2)C1] | 0.040 |
| 002-88 | 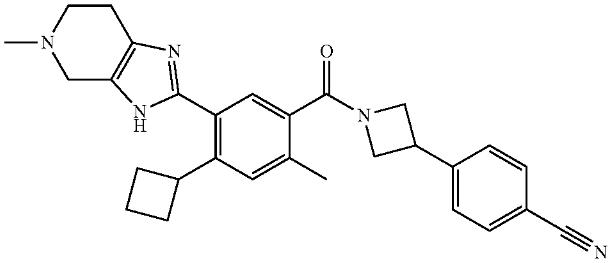 [SMILES: Cc1cc(C2CCC2)c(-c2nc3c([nH]2)CN(C)CC3)cc1C(=O)N1CC(c2ccc(C#N)cc2)C1] | 0.021 |
| 002-89 | 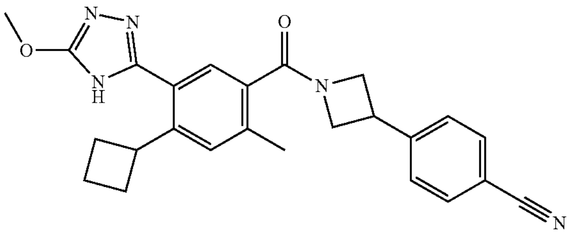 [SMILES: COc1nnc(-c2cc(C(=O)N3CC(c4ccc(C#N)cc4)C3)c(C)cc2C2CCC2)[nH]1] | 0.049 |
| 002-90 | 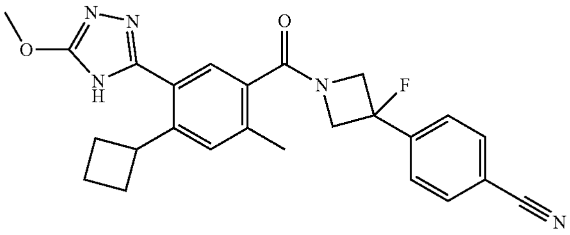 [SMILES: COc1nnc(-c2cc(C(=O)N3CC(F)(c4ccc(C#N)cc4)C3)c(C)cc2C2CCC2)[nH]1] | 0.071 |
| 002-91 | 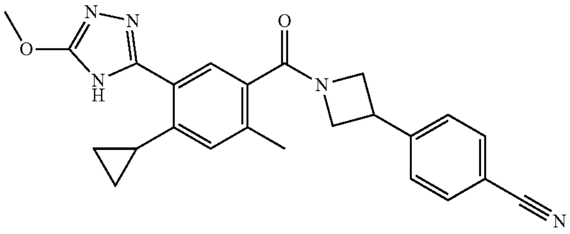 [SMILES: COc1nnc(-c2cc(C(=O)N3CC(c4ccc(C#N)cc4)C3)c(C)cc2C2CC2)[nH]1] | 0.140 |
| 002-92 | 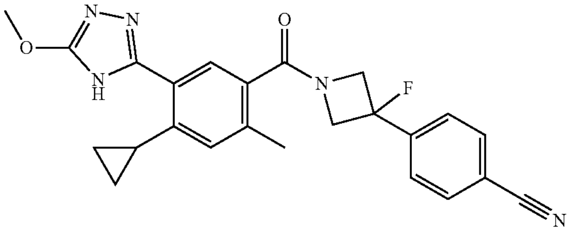 [SMILES: COc1nnc(-c2cc(C(=O)N3CC(F)(c4ccc(C#N)cc4)C3)c(C)cc2C2CC2)[nH]1] | 0.140 |

TABLE C-2-continued
| Fatty Acid Synthase Inhibitors | | |
|---|---|---|
| Cmpd No. | Structure | Hu FASN IC50 (μM) |
| 002-93 | 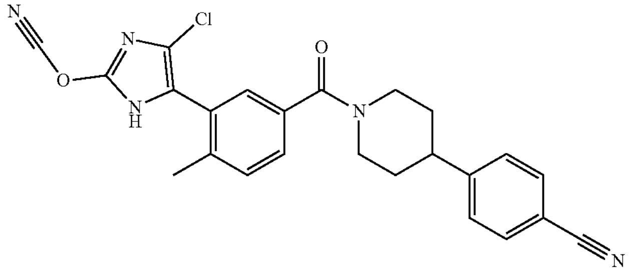 [SMILES: Cc1ccc(C(=O)N2CCC(c3ccc(C#N)cc3)CC2)cc1-c1[nH]c(OC#N)nc1Cl] | 0.034 |
| 002-94 | 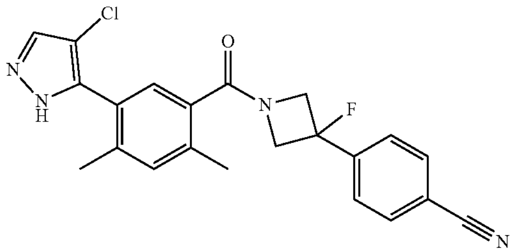 [SMILES: Cc1cc(C)c(-c2[nH]ncc2Cl)cc1C(=O)N1CC(F)(c2ccc(C#N)cc2)C1] | 0.029 |
| 002-95 | 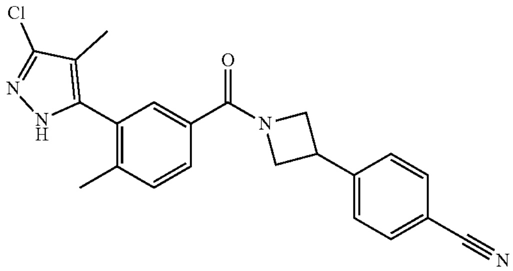 [SMILES: Cc1ccc(C(=O)N2CC(c3ccc(C#N)cc3)C2)cc1-c1[nH]nc(Cl)c1C] | 0.030 |
| 002-96 | 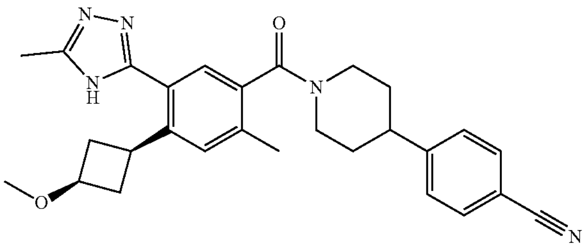 [SMILES: CO[C@H]1C[C@@H](c2cc(C)c(C(=O)N3CCC(c4ccc(C#N)cc4)CC3)cc2-c2nnc(C)[nH]2)C1] | 0.270 |
| 002-97 | 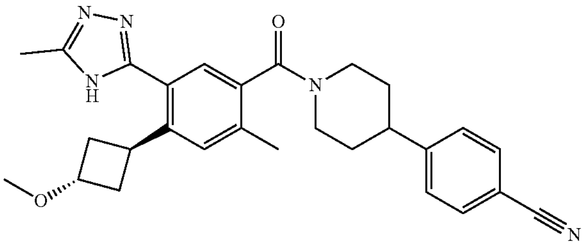 [SMILES: CO[C@H]1C[C@H](c2cc(C)c(C(=O)N3CCC(c4ccc(C#N)cc4)CC3)cc2-c2nnc(C)[nH]2)C1] | 0.190 |

TABLE C-2-continued
| Fatty Acid Synthase Inhibitors | | |
|---|---|---|
| Cmpd No. | Structure | Hu FASN IC50 (μM) |
| 002-98 | 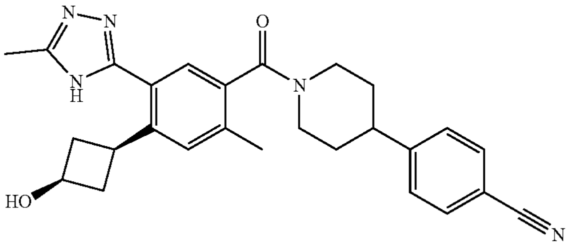 [SMILES: Cc1nnc(-c2cc(C(=O)N3CCC(c4ccc(C#N)cc4)CC3)c(C)cc2[C@H]2C[C@@H](O)C2)[nH]1] | 0.240 |
| 002-99 | 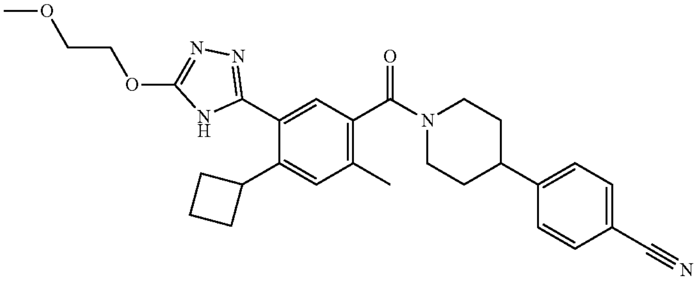 [SMILES: COCCOc1nnc(-c2cc(C(=O)N3CCC(c4ccc(C#N)cc4)CC3)c(C)cc2C2CCC2)[nH]1] | 0.045 |
| 002-100 | 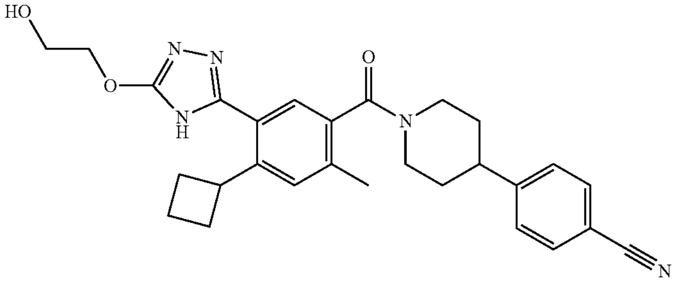 [SMILES: Cc1cc(C2CCC2)c(-c2nnc(OCCO)[nH]2)cc1C(=O)N1CCC(c2ccc(C#N)cc2)CC1] | 0.055 |
| 002-101 | 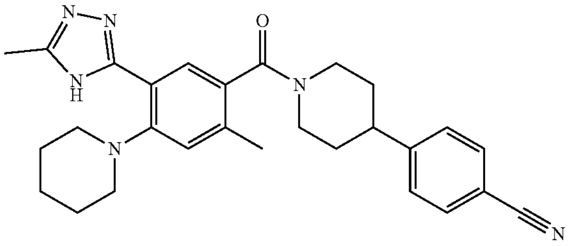 [SMILES: Cc1nnc(-c2cc(C(=O)N3CCC(c4ccc(C#N)cc4)CC3)c(C)cc2N2CCCCC2)[nH]1] | 0.530 |
| 002-102 | 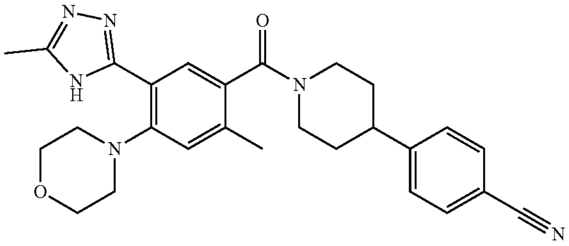 [SMILES: Cc1nnc(-c2cc(C(=O)N3CCC(c4ccc(C#N)cc4)CC3)c(C)cc2N2CCOCC2)[nH]1] | 0.890 |

TABLE C-2-continued
| Fatty Acid Synthase Inhibitors | | |
|---|---|---|
| Cmpd No. | Structure | Hu FASN IC50 (μM) |
| 002-103 | 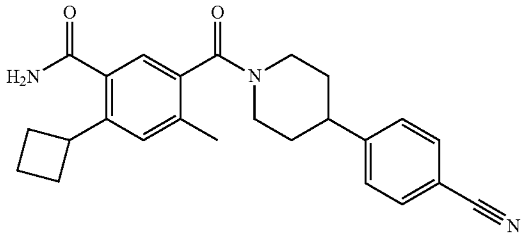 [SMILES: Cc1cc(C2CCC2)c(C(N)=O)cc1C(=O)N1CCC(c2ccc(C#N)cc2)CC1] | 0.135 |
| 002-104 | 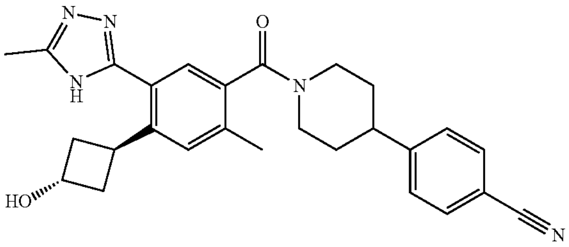 [SMILES: Cc1nnc(-c2cc(C(=O)N3CCC(c4ccc(C#N)cc4)CC3)c(C)cc2[C@H]2C[C@H](O)C2)[nH]1] | 0.070 |
| 002-105 | 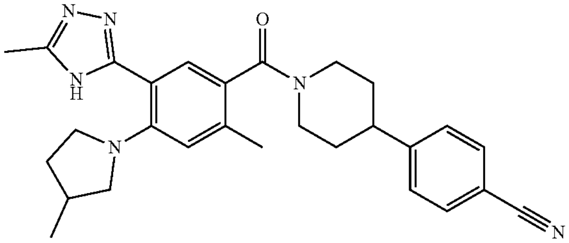 [SMILES: Cc1nnc(-c2cc(C(=O)N3CCC(c4ccc(C#N)cc4)CC3)c(C)cc2N2CCC(C)C2)[nH]1] | 0.070 |
| 002-106 | 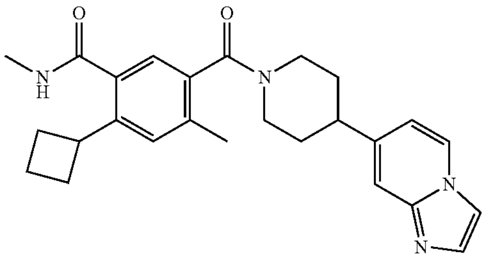 [SMILES: CNC(=O)c1cc(C(=O)N2CCC(c3ccn4ccnc4c3)CC2)c(C)cc1C1CCC1] | 50.000 |
| 002-107 | 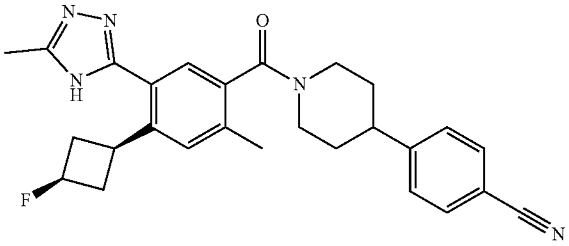 [SMILES: Cc1nnc(-c2cc(C(=O)N3CCC(c4ccc(C#N)cc4)CC3)c(C)cc2[C@H]2C[C@@H](F)C2)[nH]1] | 5.580 |

TABLE C-2-continued
| Cmpd No. | Structure | Hu FASN IC50 (μM) |
|---|---|---|
| | Fatty Acid Synthase Inhibitors | |
| 002-108 | 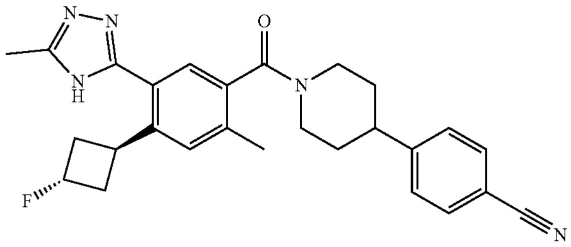 [SMILES: Cc1nnc(-c2cc(C(=O)N3CCC(c4ccc(C#N)cc4)CC3)c(C)cc2[C@H]2C[C@H](F)C2)[nH]1] | 2.250 |
| 002-109 | 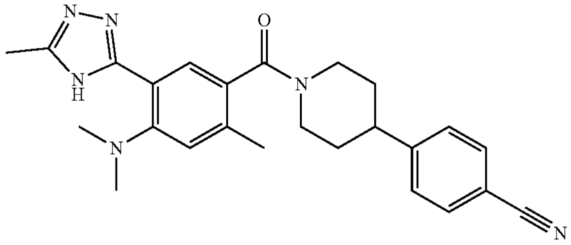 [SMILES: Cc1nnc(-c2cc(C(=O)N3CCC(c4ccc(C#N)cc4)CC3)c(C)cc2N(C)C)[nH]1] | 0.280 |
| 002-110 | 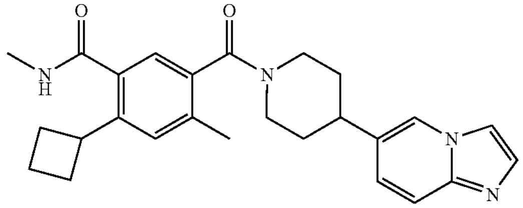 [SMILES: CNC(=O)c1cc(C(=O)N2CCC(c3ccc4nccn4c3)CC2)c(C)cc1C1CCC1] | 11.020 |
| 002-111 | 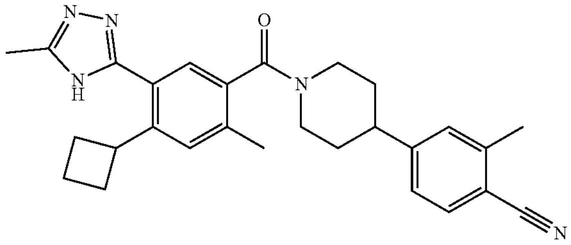 [SMILES: Cc1nnc(-c2cc(C(=O)N3CCC(c4ccc(C#N)c(C)c4)CC3)c(C)cc2C2CCC2)[nH]1] | 0.230 |
| 002-112 | 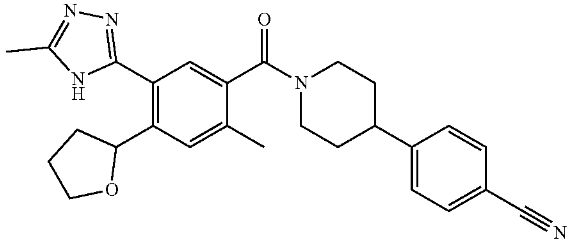 | 0.840 |
| 002-113 | 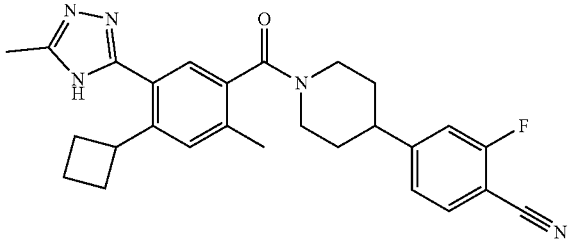 [SMILES: Cc1nnc(-c2cc(C(=O)N3CCC(c4ccc(C#N)c(F)c4)CC3)c(C)cc2C2CCC2)[nH]1] | 0.145 |

TABLE C-2-continued
Fatty Acid Synthase Inhibitors
| Cmpd No. | Structure | Hu FASN IC50 (μM) |
|---|---|---|
| 002-114 | 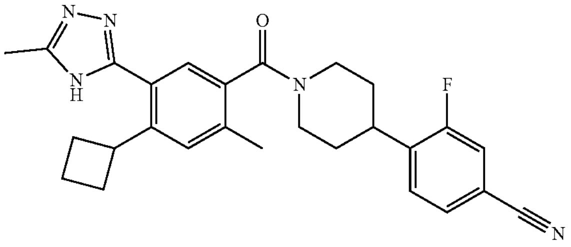 [SMILES: Cc1nnc(-c2cc(C(=O)N3CCC(c4ccc(C#N)cc4F)CC3)c(C)cc2C2CCC2)[nH]1] | 0.200 |
| 002-115 | 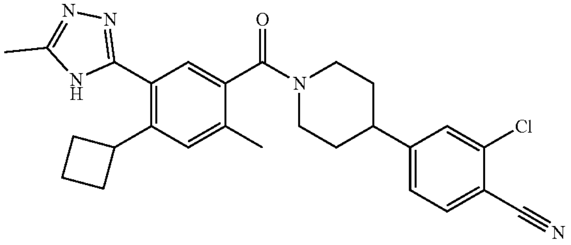 [SMILES: Cc1nnc(-c2cc(C(=O)N3CCC(c4ccc(C#N)c(Cl)c4)CC3)c(C)cc2C2CCC2)[nH]1] | 0.320 |
| 002-116 | 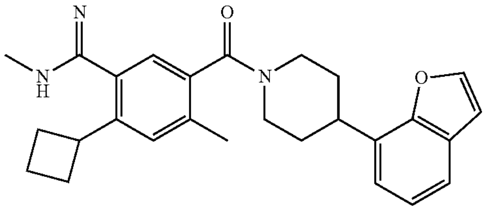 [SMILES: CNC(=N)c1cc(C(=O)N2CCC(c3cccc4ccoc34)CC2)c(C)cc1C1CCC1] | 50.000 |
| 002-117 | 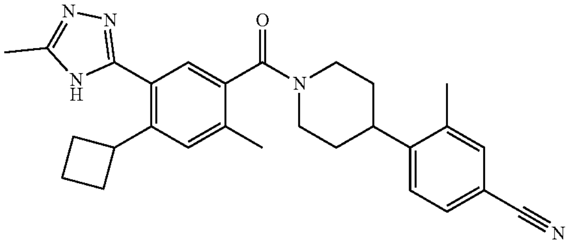 [SMILES: Cc1nnc(-c2cc(C(=O)N3CCC(c4ccc(C#N)cc4C)CC3)c(C)cc2C2CCC2)[nH]1] | 0.980 |
| 002-118 | 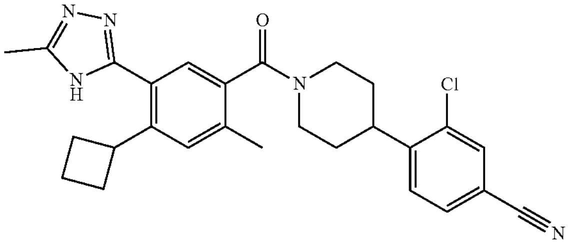 [SMILES: Cc1nnc(-c2cc(C(=O)N3CCC(c4ccc(C#N)cc4Cl)CC3)c(C)cc2C2CCC2)[nH]1] | 0.680 |
| 002-119 | 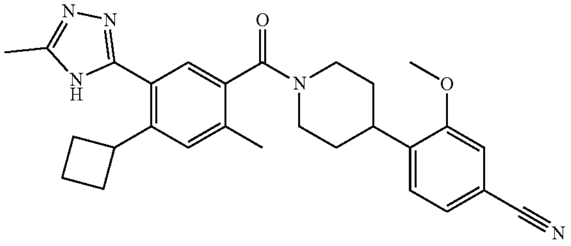 [SMILES: COc1cc(C#N)ccc1C1CCN(C(=O)c2cc(-c3nnc(C)[nH]3)c(C3CCC3)cc2C)CC1] | 4.480 |

TABLE C-2-continued
| Fatty Acid Synthase Inhibitors | | |
|---|---|---|
| Cmpd No. | Structure | Hu FASN IC50 (μM) |
| 002-120 | 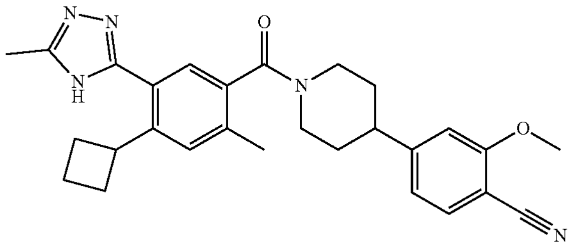 | 1.300 |
| 002-121 | 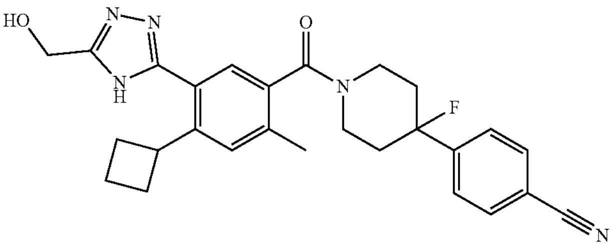 [SMILES: Cc1cc(C2CCC2)c(-c2nnc(CO)[nH]2)cc1C(=O)N1CCC(F)(c2ccc(C#N)cc2)CC1] | 0.030 |
| 002-122 | 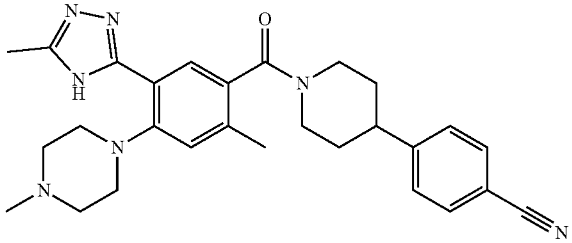 [SMILES: Cc1nnc(-c2cc(C(=O)N3CCC(c4ccc(C#N)cc4)CC3)c(C)cc2N2CCN(C)CC2)[nH]1] | 3.440 |
| 002-123 | 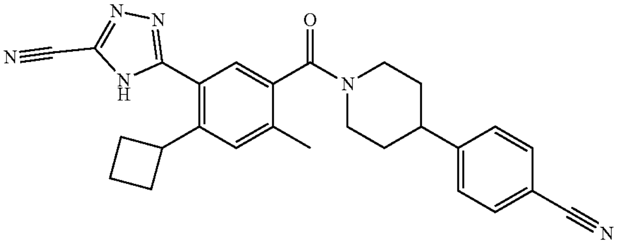 [SMILES: Cc1cc(C2CCC2)c(-c2nnc(C#N)[nH]2)cc1C(=O)N1CCC(c2ccc(C#N)cc2)CC1] | 3.710 |
| 002-124 | 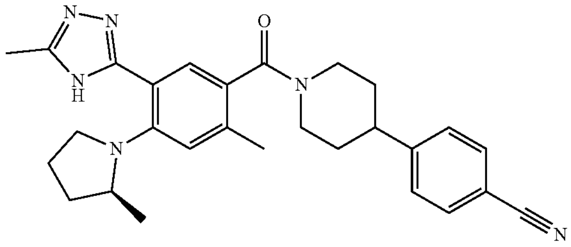 [SMILES: Cc1nnc(-c2cc(C(=O)N3CCC(c4ccc(C#N)cc4)CC3)c(C)cc2N2CCC[C@@H]2C)[nH]1] | 0.140 |

TABLE C-2-continued
| Fatty Acid Synthase Inhibitors | | |
|---|---|---|
| Cmpd No. | Structure | Hu FASN IC50 (μM) |
| 002-125 | 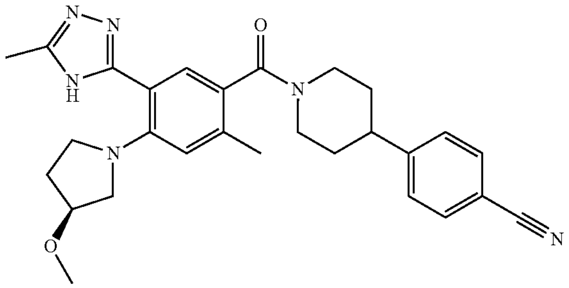 [SMILES: CO[C@H]1CCN(c2cc(C)c(C(=O)N3CCC(c4ccc(C#N)cc4)CC3)cc2-c2nnc(C)[nH]2)C1] | 0.110 |
| 002-126 | 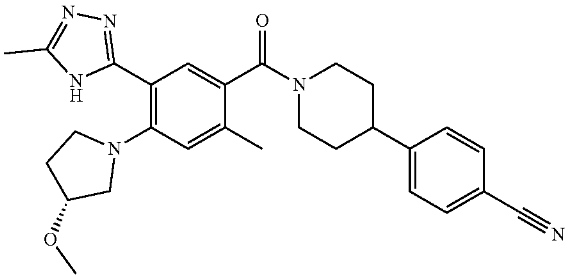 [SMILES: CO[C@@H]1CCN(c2cc(C)c(C(=O)N3CCC(c4ccc(C#N)cc4)CC3)cc2-c2nnc(C)[nH]2)C1] | 1.130 |
| 002-127 | 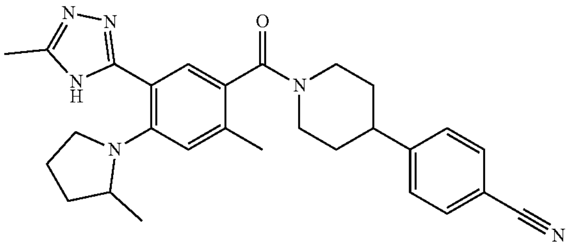 [SMILES: Cc1nnc(-c2cc(C(=O)N3CCC(c4ccc(C#N)cc4)CC3)c(C)cc2N2CCCC2C)[nH]1] | 3.270 |
| 002-128 | 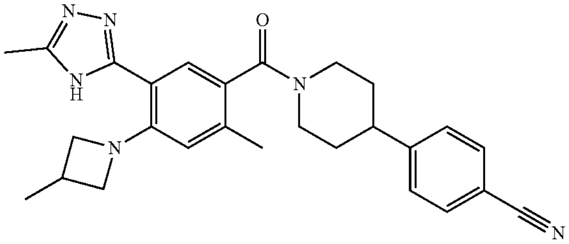 [SMILES: Cc1nnc(-c2cc(C(=O)N3CCC(c4ccc(C#N)cc4)CC3)c(C)cc2N2CC(C)C2)[nH]1] | 0.098 |
| 002-129 | 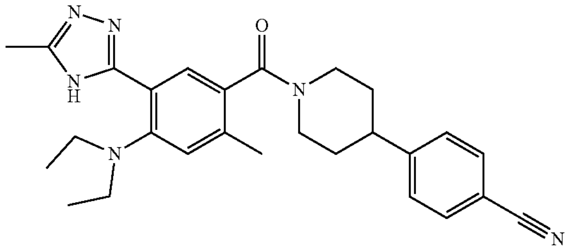 [SMILES: CCN(CC)c1cc(C)c(C(=O)N2CCC(c3ccc(C#N)cc3)CC2)cc1-c1nnc(C)[nH]1] | 1.210 |

TABLE C-2-continued
| Fatty Acid Synthase Inhibitors | | |
|---|---|---|
| Cmpd No. | Structure | Hu FASN IC50 (μM) |
| 002-130 | 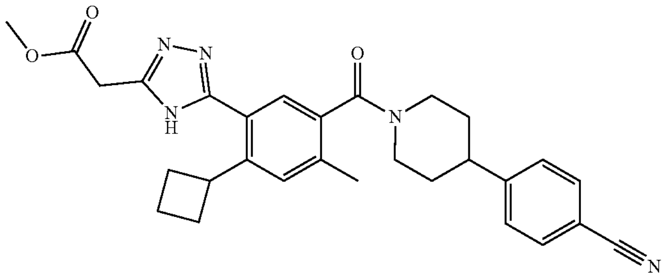 [SMILES: COC(=O)Cc1nnc(-c2cc(C(=O)N3CCC(c4ccc(C#N)cc4)CC3)c(C)cc2C2CCC2)[nH]1] | 0.082 |
| 002-131 | 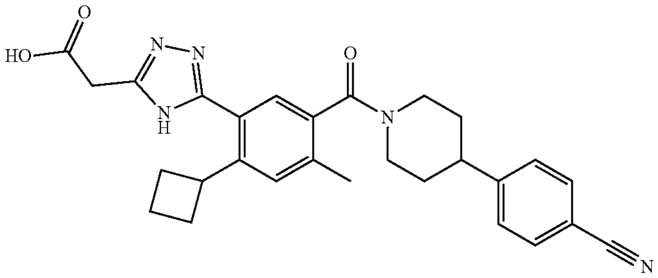 [SMILES: Cc1cc(C2CCC2)c(-c2nnc(CC(=O)O)[nH]2)cc1C(=O)N1CCC(c2ccc(C#N)cc2)CC1] | 0.185 |
| 002-132 | 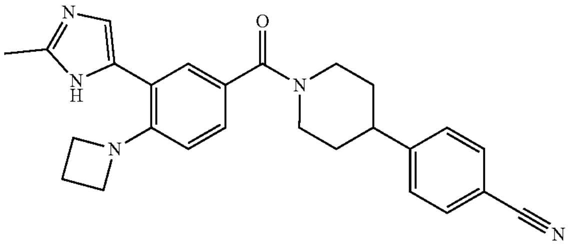 [SMILES: Cc1ncc(-c2cc(C(=O)N3CCC(c4ccc(C#N)cc4)CC3)ccc2N2CCC2)[nH]1] | 0.210 |
| 002-133 | 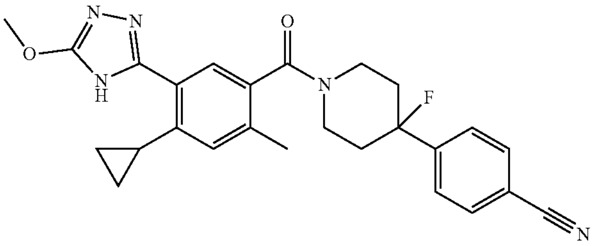 [SMILES: COc1nnc(-c2cc(C(=O)N3CCC(F)(c4ccc(C#N)cc4)CC3)c(C)cc2C2CC2)[nH]1] | 0.065 |
| 002-134 | 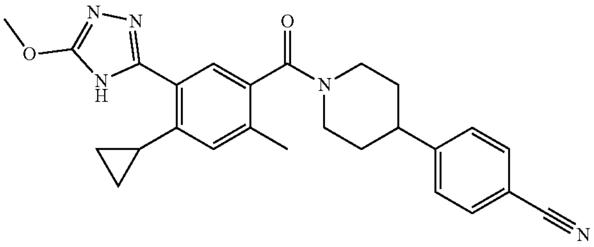 [SMILES: COc1nnc(-c2cc(C(=O)N3CCC(c4ccc(C#N)cc4)CC3)c(C)cc2C2CC2)[nH]1] | 0.099 |

TABLE C-2-continued
| Fatty Acid Synthase Inhibitors | | |
|---|---|---|
| Cmpd No. | Structure | Hu FASN IC50 (μM) |
| 002-135 | 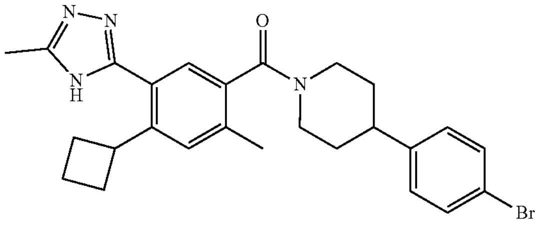 [SMILES: Cc1nnc(-c2cc(C(=O)N3CCC(c4ccc(Br)cc4)CC3)c(C)cc2C2CCC2)[nH]1] | |
| 002-136 | 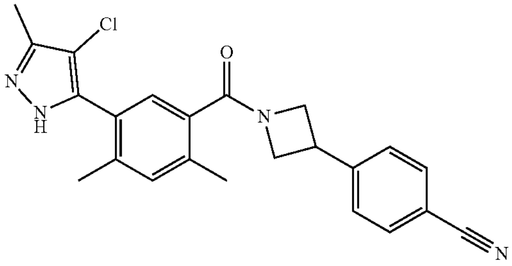 [SMILES: Cc1cc(C)c(-c2[nH]nc(C)c2Cl)cc1C(=O)N1CC(c2ccc(C#N)cc2)C1] | 0.026 |
| 002-137 | 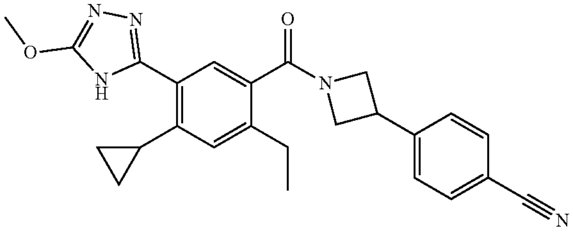 [SMILES: CCc1cc(C2CC2)c(-c2nnc(OC)[nH]2)cc1C(=O)N1CC(c2ccc(C#N)cc2)C1] | 0.105 |
| 002-138 | 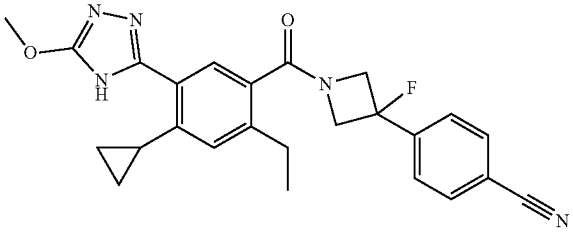 [SMILES: CCc1cc(C2CC2)c(-c2nnc(OC)[nH]2)cc1C(=O)N1CC(F)(c2ccc(C#N)cc2)C1] | 0.120 |
| 002-139 | 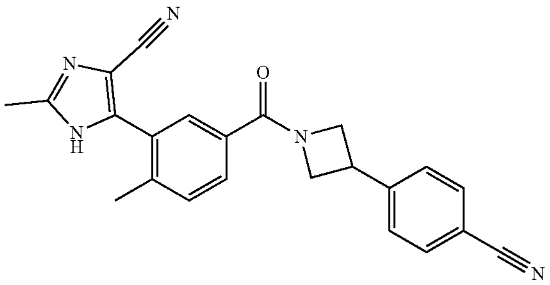 [SMILES: Cc1nc(C#N)c(-c2cc(C(=O)N3CC(c4ccc(C#N)cc4)C3)ccc2C)[nH]1] | 0.017 |

TABLE C-2-continued
| Fatty Acid Synthase Inhibitors | | |
|---|---|---|
| Cmpd No. | Structure | Hu FASN IC50 (μM) |
| 002-140 | 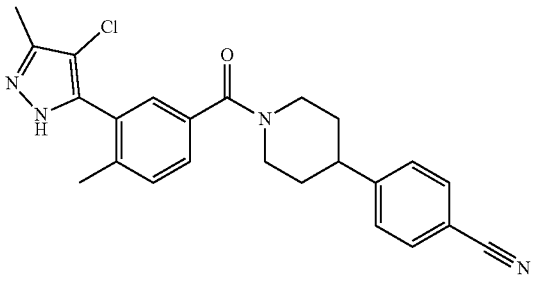 [SMILES: Cc1ccc(C(=O)N2CCC(c3ccc(C#N)cc3)CC2)cc1-c1[nH]nc(C)c1Cl] | 0.080 |
| 002-141 | 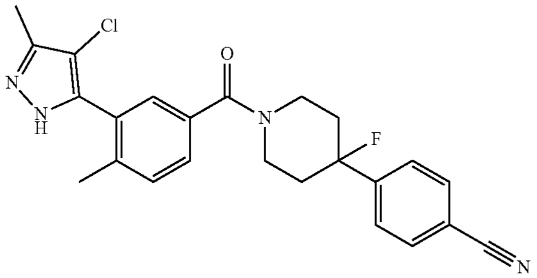 [SMILES: Cc1ccc(C(=O)N2CCC(F)(c3ccc(C#N)cc3)CC2)cc1-c1[nH]nc(C)c1Cl] | 0.099 |
| 002-142 | 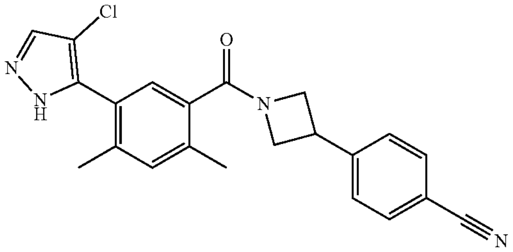 [SMILES: Cc1cc(C)c(-c2[nH]ncc2Cl)cc1C(=O)N1CC(c2ccc(C#N)cc2)C1] | 0.024 |
| 002-143 | 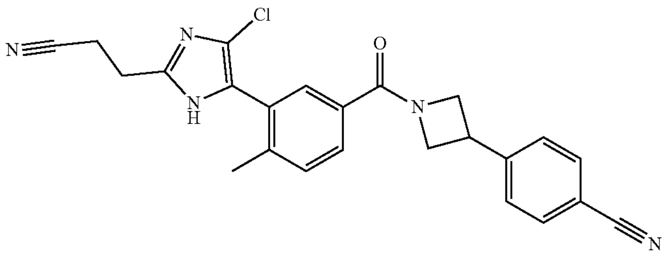 [SMILES: Cc1ccc(C(=O)N2CC(c3ccc(C#N)cc3)C2)cc1-c1[nH]c(CCC#N)nc1Cl] | 0.018 |
| 002-144 | 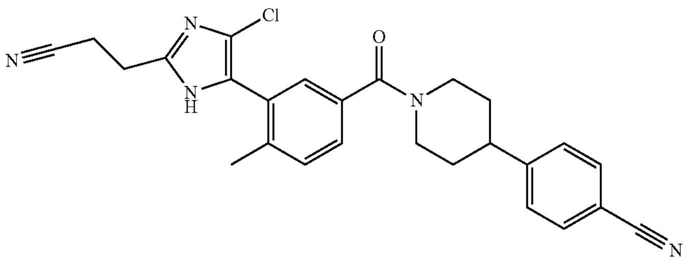 [SMILES: Cc1ccc(C(=O)N2CCC(c3ccc(C#N)cc3)CC2)cc1-c1[nH]c(CCC#N)nc1Cl] | 0.020 |

TABLE C-2-continued
| Fatty Acid Synthase Inhibitors | | |
|---|---|---|
| Cmpd No. | Structure | Hu FASN IC50 (μM) |
| 002-145 | 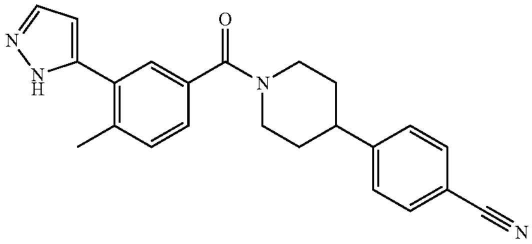 [SMILES: Cc1ccc(C(=O)N2CCC(c3ccc(C#N)cc3)CC2)cc1-c1ccn[nH]1] | 2.170 |
| 002-146 | 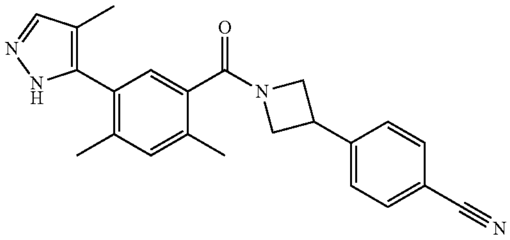 [SMILES: Cc1cc(C)c(-c2[nH]ncc2C)cc1C(=O)N1CC(c2ccc(C#N)cc2)C1] | 0.062 |
| 002-147 | 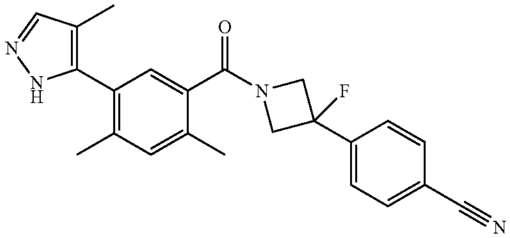 [SMILES: Cc1cc(C)c(-c2[nH]ncc2C)cc1C(=O)N1CC(F)(c2ccc(C#N)cc2)C1] | 0.120 |
| 002-148 | 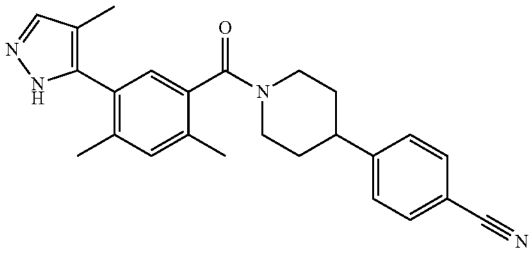 [SMILES: Cc1cc(C)c(-c2[nH]ncc2C)cc1C(=O)N1CCC(c2ccc(C#N)cc2)CC1] | 0.084 |
| 002-149 | 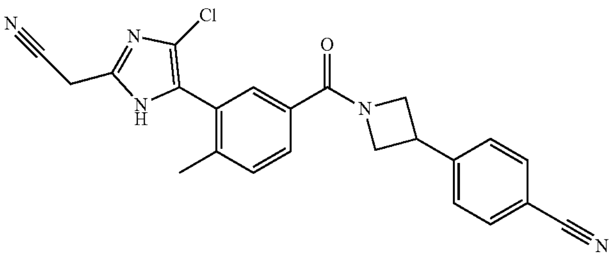 [SMILES: Cc1ccc(C(=O)N2CC(c3ccc(C#N)cc3)C2)cc1-c1[nH]c(CC#N)nc1Cl] | 0.021 |

TABLE C-2-continued
| Fatty Acid Synthase Inhibitors | | |
|---|---|---|
| Cmpd No. | Structure | Hu FASN IC50 (μM) |
| 002-150 | 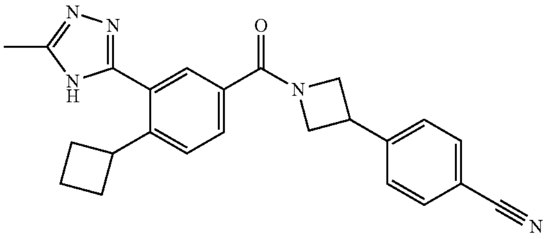 [SMILES: Cc1nnc(-c2cc(C(=O)N3CC(c4ccc(C#N)cc4)C3)ccc2C2CCC2)[nH]1] | 0.097 |
| 002-151 | 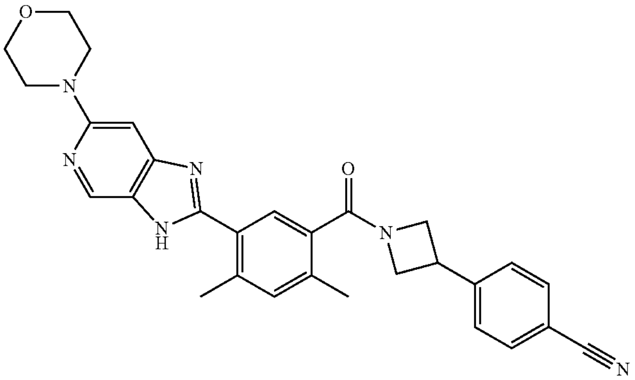 | 0.057 |
| 002-152 | 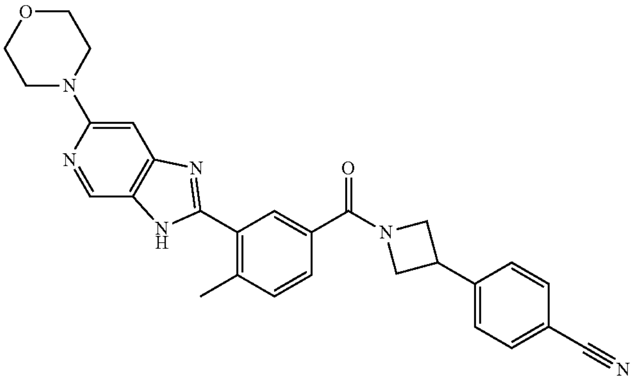 [SMILES: Cc1ccc(C(=O)N2CC(c3ccc(C#N)cc3)C2)cc1-c1nc2cc(N3CCOCC3)ncc2[nH]1] | 0.290 |
| 002-153 | 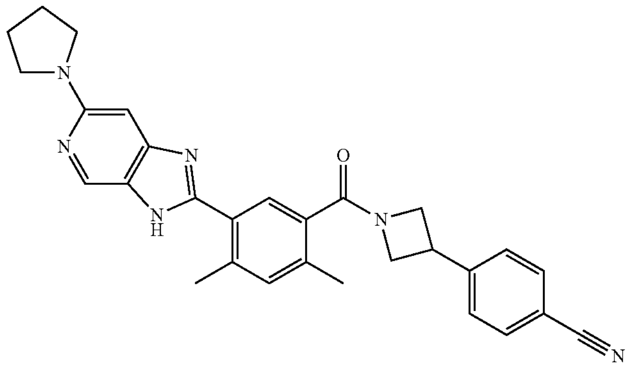 [SMILES: Cc1cc(C)c(-c2nc3cc(N4CCCC4)ncc3[nH]2)cc1C(=O)N1CC(c2ccc(C#N)cc2)C1] | 0.036 |

TABLE C-2-continued
| Fatty Acid Synthase Inhibitors | | |
|---|---|---|
| Cmpd No. | Structure | Hu FASN IC50 (μM) |
| 002-154 | 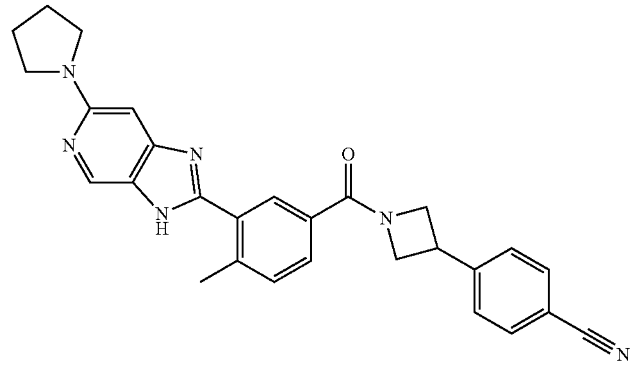 [SMILES: Cc1ccc(C(=O)N2CC(c3ccc(C#N)cc3)C2)cc1-c1nc2cc(N3CCCC3)ncc2[nH]1] | 0.094 |
| 002-155 | 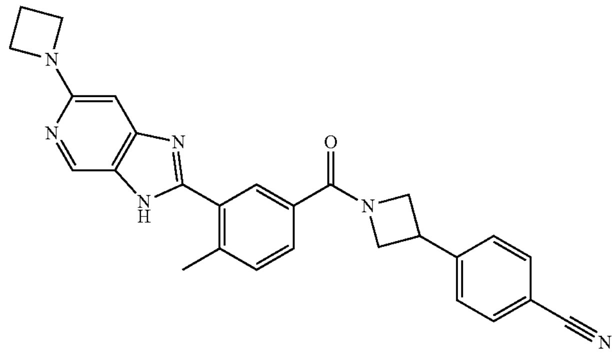 [SMILES: Cc1ccc(C(=O)N2CC(c3ccc(C#N)cc3)C2)cc1-c1nc2cc(N3CCC3)ncc2[nH]1] | 0.590 |
| 002-156 | 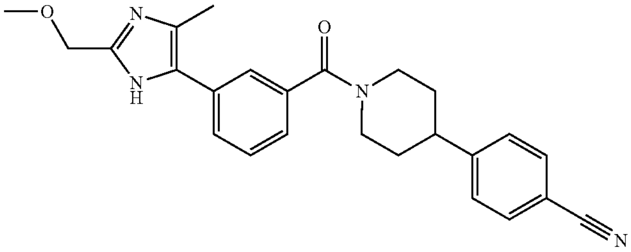 [SMILES: COCc1nc(C)c(-c2cccc(C(=O)N3CCC(c4ccc(C#N)cc4)CC3)c2)[nH]1] | 1.495 |
| 002-157 | 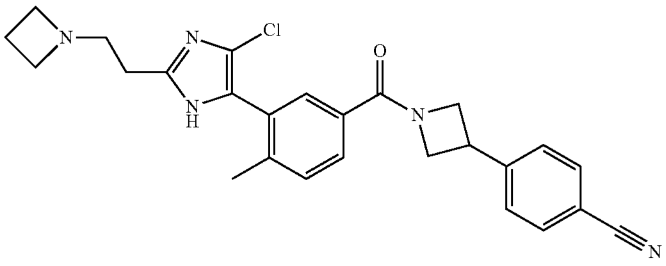 [SMILES: Cc1ccc(C(=O)N2CC(c3ccc(C#N)cc3)C2)cc1-c1[nH]c(CCN2CCC2)nc1Cl] | 0.210 |

TABLE C-2-continued
| Fatty Acid Synthase Inhibitors | | |
|---|---|---|
| Cmpd No. | Structure | Hu FASN IC50 (μM) |
| 002-158 | 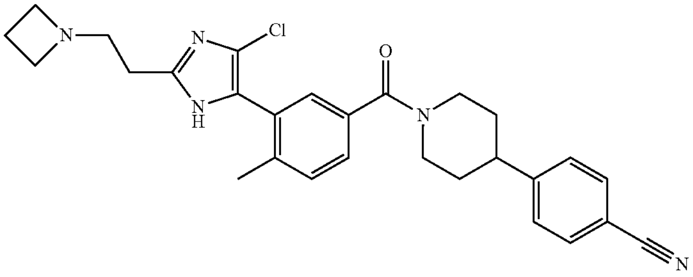 [SMILES: Cc1ccc(C(=O)N2CCC(c3ccc(C#N)cc3)CC2)cc1-c1[nH]c(CCN2CCC2)nc1Cl] | |
| 002-159 | 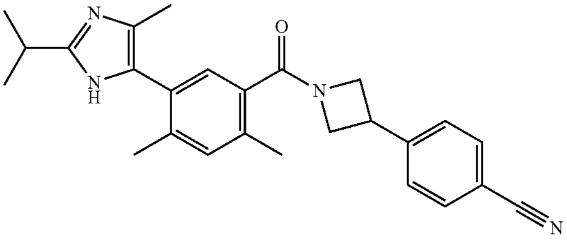 [SMILES: Cc1cc(C)c(-c2[nH]c(C(C)C)nc2C)cc1C(=O)N1CC(c2ccc(C#N)cc2)C1] | 0.021 |
| 002-160 | 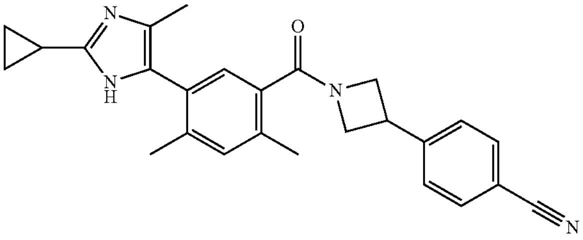 [SMILES: Cc1cc(C)c(-c2[nH]c(C3CC3)nc2C)cc1C(=O)N1CC(c2ccc(C#N)cc2)C1] | 0.017 |
| 002-161 | 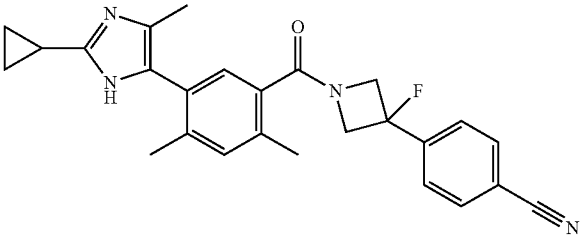 [SMILES: Cc1cc(C)c(-c2[nH]c(C3CC3)nc2C)cc1C(=O)N1CC(F)(c2ccc(C#N)cc2)C1] | 0.026 |
| 002-162 | 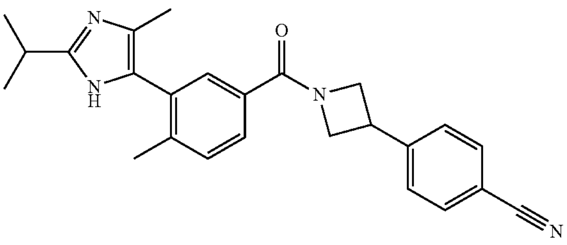 [SMILES: Cc1ccc(C(=O)N2CC(c3ccc(C#N)cc3)C2)cc1-c1[nH]c(C(C)C)nc1C] | 0.019 |

TABLE C-2-continued
| Fatty Acid Synthase Inhibitors | | |
|---|---|---|
| Cmpd No. | Structure | Hu FASN IC50 (μM) |
| 002-163 | 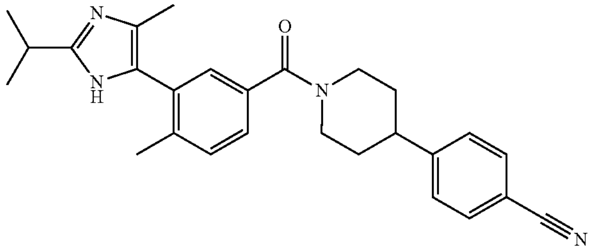 [SMILES: Cc1ccc(C(=O)N2CCC(c3ccc(C#N)cc3)CC2)cc1-c1[nH]c(C(C)C)nc1C] | 0.037 |
| 002-164 | 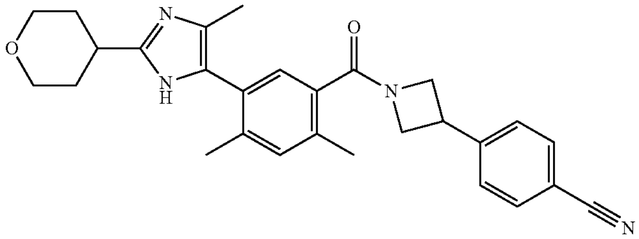 [SMILES: Cc1cc(C)c(-c2[nH]c(C3CCOCC3)nc2C)cc1C(=O)N1CC(c2ccc(C#N)cc2)C1] | 0.019 |
| 002-165 | 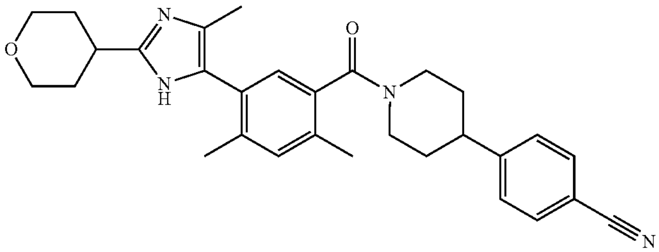 [SMILES: Cc1cc(C)c(-c2[nH]c(C3CCOCC3)nc2C)cc1C(=O)N1CCC(c2ccc(C#N)cc2)CC1] | 0.038 |
| 002-166 | 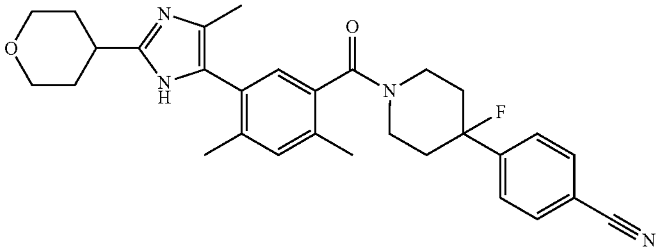 [SMILES: Cc1cc(C)c(-c2[nH]c(C3CCOCC3)nc2C)cc1C(=O)N1CCC(F)(c2ccc(C#N)cc2)CC1] | 0.040 |
| 002-167 | 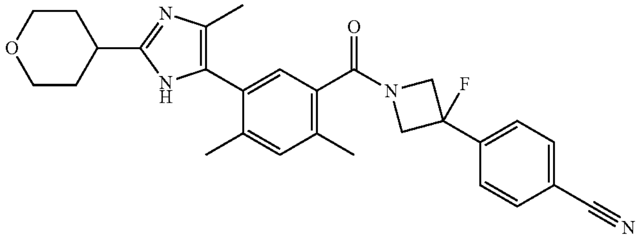 [SMILES: Cc1cc(C)c(-c2[nH]c(C3CCOCC3)nc2C)cc1C(=O)N1CC(F)(c2ccc(C#N)cc2)C1] | 0.061 |

TABLE C-2-continued
| Fatty Acid Synthase Inhibitors | | |
|---|---|---|
| Cmpd No. | Structure | Hu FASN IC50 (μM) |
| 002-168 | 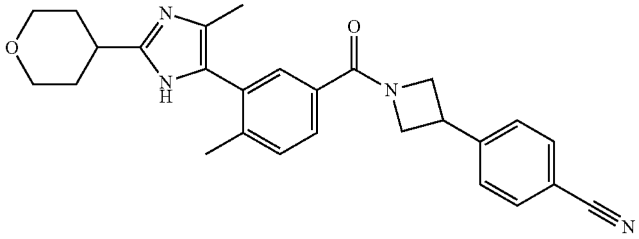 [SMILES: Cc1ccc(C(=O)N2CC(c3ccc(C#N)cc3)C2)cc1-c1[nH]c(C2CCOCC2)nc1C] | 0.011 |
| 002-169 | 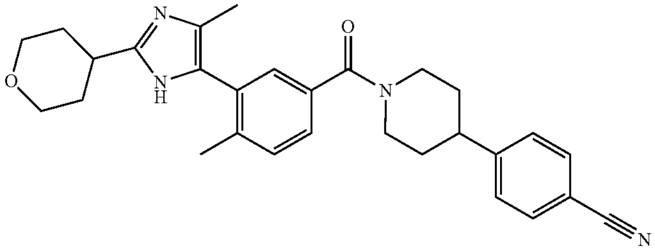 [SMILES: Cc1ccc(C(=O)N2CCC(c3ccc(C#N)cc3)CC2)cc1-c1[nH]c(C2CCOCC2)nc1C] | 0.035 |
| 002-170 | 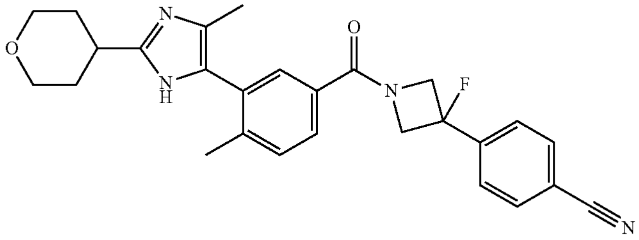 [SMILES: Cc1ccc(C(=O)N2CC(F)(c3ccc(C#N)cc3)C2)cc1-c1[nH]c(C2CCOCC2)nc1C] | 0.040 |
| 002-171 | 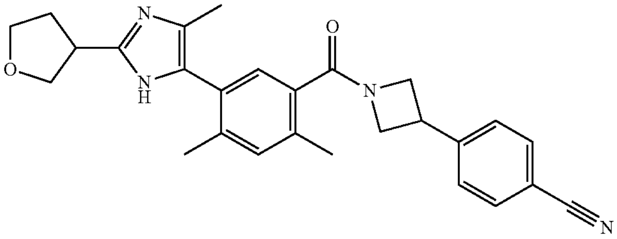 [SMILES: Cc1cc(C)c(-c2[nH]c(C3CCOC3)nc2C)cc1C(=O)N1CC(c2ccc(C#N)cc2)C1] | 0.021 |
| 002-172 | 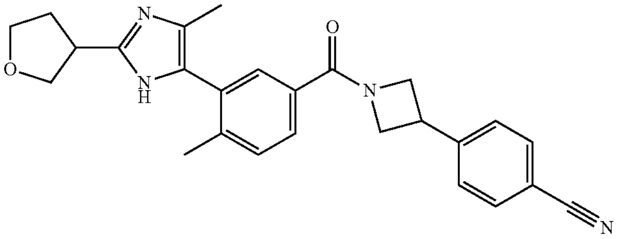 [SMILES: Cc1ccc(C(=O)N2CC(c3ccc(C#N)cc3)C2)cc1-c1[nH]c(C2CCOC2)nc1C] | 0.011 |
| 002-173 | 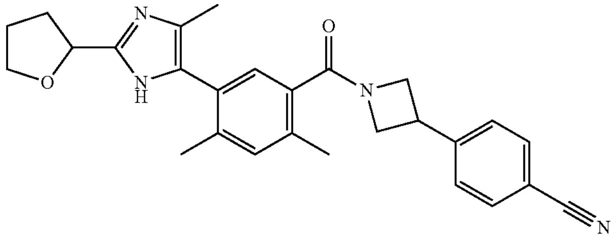 [SMILES: Cc1cc(C)c(-c2[nH]c(C3CCCO3)nc2C)cc1C(=O)N1CC(c2ccc(C#N)cc2)C1] | 0.035 |

TABLE C-2-continued
| Fatty Acid Synthase Inhibitors | | |
|---|---|---|
| Cmpd No. | Structure | Hu FASN IC50 (μM) |
| 002-174 | 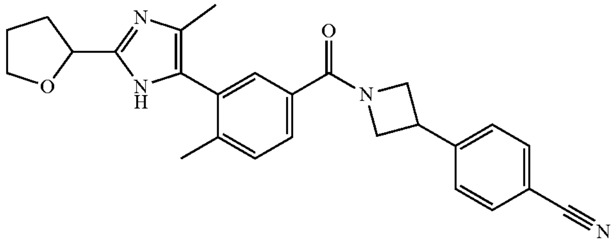 [SMILES: Cc1ccc(C(=O)N2CC(c3ccc(C#N)cc3)C2)cc1-c1[nH]c(C2CCCO2)nc1C] | 0.037 |
| 002-175 | 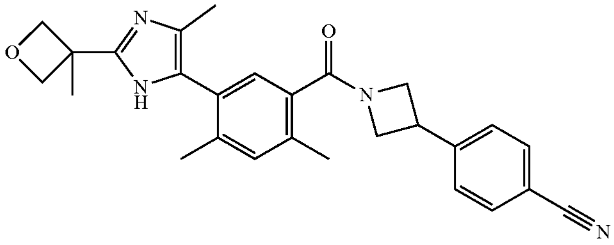 [SMILES: Cc1cc(C)c(-c2[nH]c(C3(C)COC3)nc2C)cc1C(=O)N1CC(c2ccc(C#N)cc2)C1] | 0.020 |
| 002-176 | 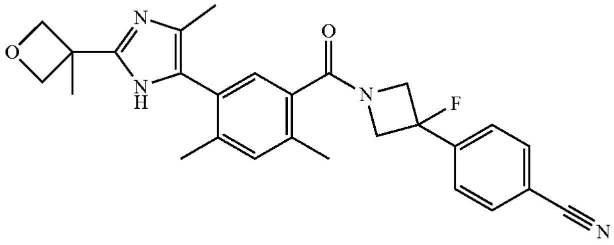 [SMILES: Cc1cc(C)c(-c2[nH]c(C3(C)COC3)nc2C)cc1C(=O)N1CC(F)(c2ccc(C#N)cc2)C1] | 0.024 |
| 002-177 | 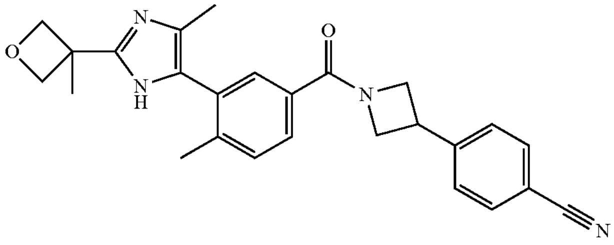 [SMILES: Cc1ccc(C(=O)N2CC(c3ccc(C#N)cc3)C2)cc1-c1[nH]c(C2(C)COC2)nc1C] | 0.011 |
| 002-178 | 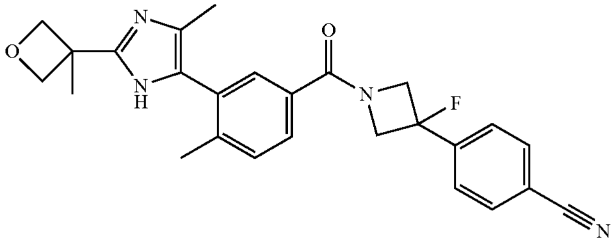 [SMILES: Cc1ccc(C(=O)N2CC(F)(c3ccc(C#N)cc3)C2)cc1-c1[nH]c(C2(C)COC2)nc1C] | 0.027 |

TABLE C-2-continued
| Fatty Acid Synthase Inhibitors | | |
|---|---|---|
| Cmpd No. | Structure | Hu FASN IC50 (μM) |
| 002-179 | 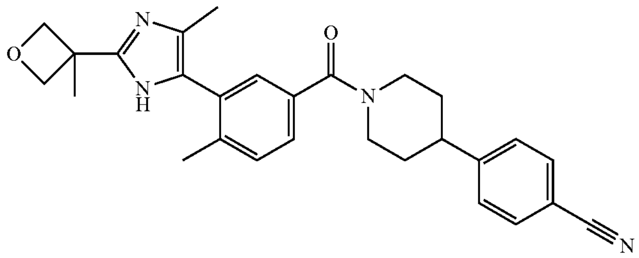 [SMILES: Cc1ccc(C(=O)N2CCC(c3ccc(C#N)cc3)CC2)cc1-c1[nH]c(C2(C)COC2)nc1C] | 0.025 |
| 002-180 | 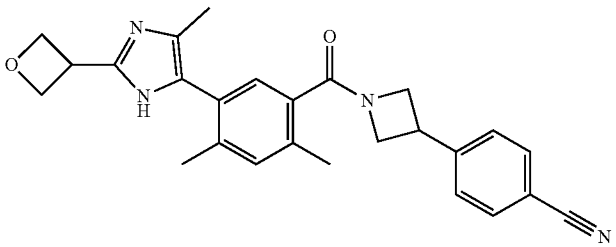 [SMILES: Cc1cc(C)c(-c2[nH]c(C3COC3)nc2C)cc1C(=O)N1CC(c2ccc(C#N)cc2)C1] | 0.034 |
| 002-181 | 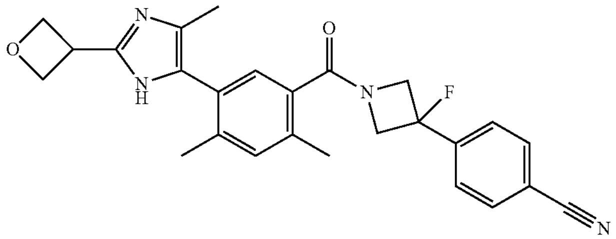 [SMILES: Cc1cc(C)c(-c2[nH]c(C3COC3)nc2C)cc1C(=O)N1CC(F)(c2ccc(C#N)cc2)C1] | 0.068 |
| 002-182 | 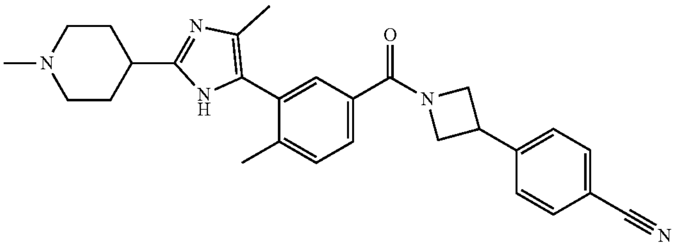 [SMILES: Cc1ccc(C(=O)N2CC(c3ccc(C#N)cc3)C2)cc1-c1[nH]c(C2CCN(C)CC2)nc1C] | 0.038 |
| 002-183 | 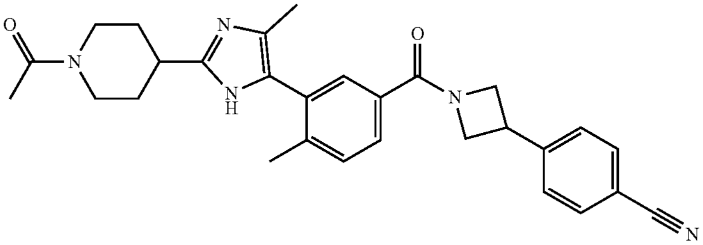 [SMILES: CC(=O)N1CCC(c2nc(C)c(-c3cc(C(=O)N4CC(c5ccc(C#N)cc5)C4)ccc3C)[nH]2)CC1] | 0.029 |

TABLE C-2-continued
| Fatty Acid Synthase Inhibitors | | |
|---|---|---|
| Cmpd No. | Structure | Hu FASN IC50 (μM) |
| 002-184 | 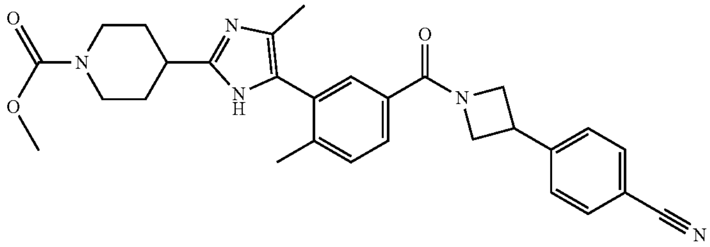 [SMILES: COC(=O)N1CCC(c2nc(C)c(-c3cc(C(=O)N4CC(c5ccc(C#N)cc5)C4)ccc3C)[nH]2)CC1] | 0.009 |
| 002-185 | 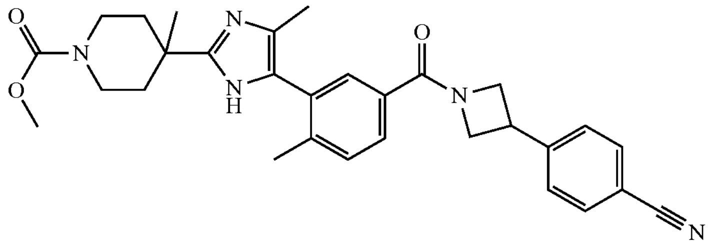 [SMILES: COC(=O)N1CCC(C)(c2nc(C)c(-c3cc(C(=O)N4CC(c5ccc(C#N)cc5)C4)ccc3C)[nH]2)CC1] | 0.033 |
| 002-186 | 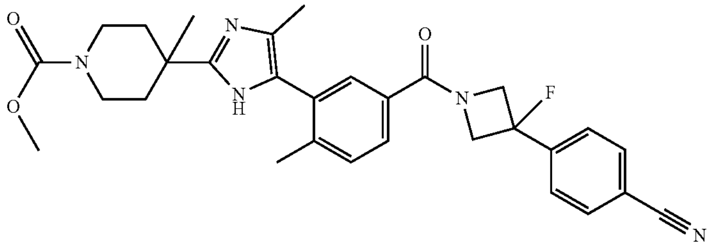 [SMILES: COC(=O)N1CCC(C)(c2nc(C)c(-c3cc(C(=O)N4CC(F)(c5ccc(C#N)cc5)C4)ccc3C)[nH]2)CC1] | 0.066 |
| 002-187 | 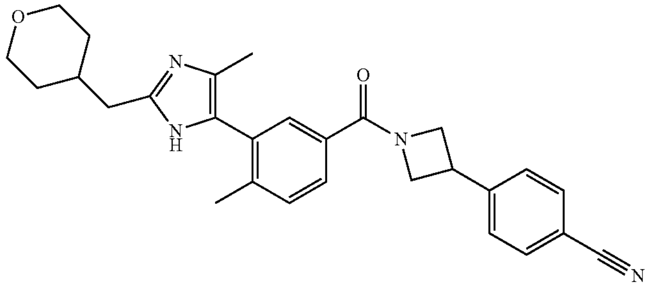 [SMILES: Cc1ccc(C(=O)N2CC(c3ccc(C#N)cc3)C2)cc1-c1[nH]c(CC2CCOCC2)nc1C] | 0.063 |
| 002-188 | 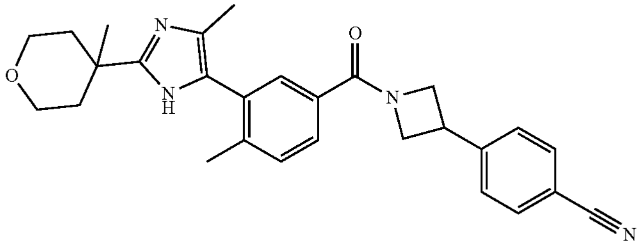 [SMILES: Cc1ccc(C(=O)N2CC(c3ccc(C#N)cc3)C2)cc1-c1[nH]c(C2(C)CCOCC2)nc1C] | 0.052 |

TABLE C-2-continued
| Cmpd No. | Fatty Acid Synthase Inhibitors Structure | Hu FASN IC50 (μM) |
|---|---|---|
| 002-189 | 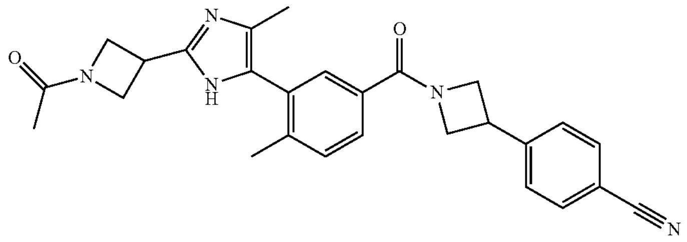 [SMILES: CC(=O)N1CC(c2nc(C)c(-c3cc(C(=O)N4CC(c5ccc(C#N)cc5)C4)ccc3C)[nH]2)C1] | 0.020 |
| 002-190 | 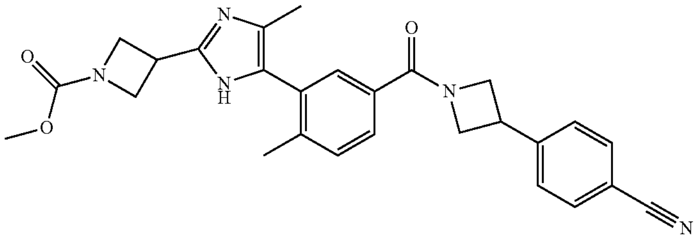 [SMILES: COC(=O)N1CC(c2nc(C)c(-c3cc(C(=O)N4CC(c5ccc(C#N)cc5)C4)ccc3C)[nH]2)C1] | 0.008 |
| 002-191 | 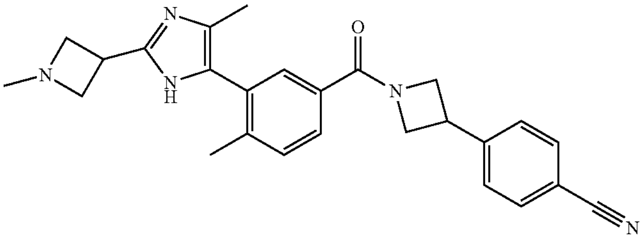 [SMILES: Cc1ccc(C(=O)N2CC(c3ccc(C#N)cc3)C2)cc1-c1[nH]c(C2CN(C)C2)nc1C] | 0.065 |
| 002-192 | 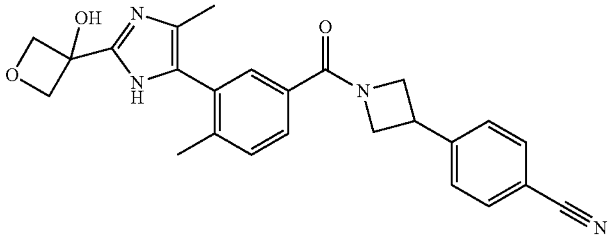 [SMILES: Cc1ccc(C(=O)N2CC(c3ccc(C#N)cc3)C2)cc1-c1[nH]c(C2(O)COC2)nc1C] | 0.024 |
| 002-193 | 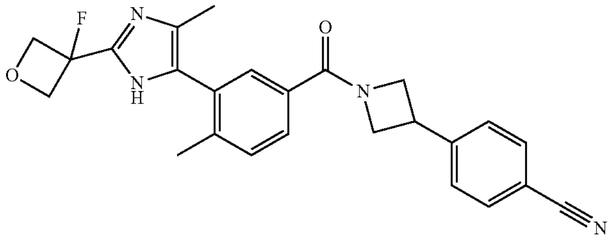 [SMILES: Cc1ccc(C(=O)N2CC(c3ccc(C#N)cc3)C2)cc1-c1[nH]c(C2(F)COC2)nc1C] | 0.065 |
| 002-194 | 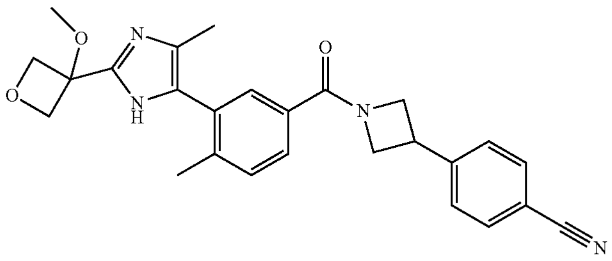 [SMILES: COC1(c2nc(C)c(-c3cc(C(=O)N4CC(c5ccc(C#N)cc5)C4)ccc3C)[nH]2)COC1] | 0.025 |

TABLE C-2-continued
| Cmpd No. | Structure | Hu FASN IC50 (μM) |
|---|---|---|
| Fatty Acid Synthase Inhibitors | | |
| 002-195 | 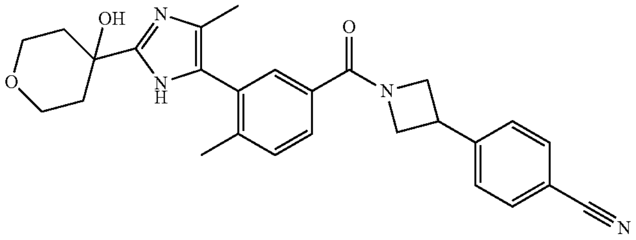 [SMILES: Cc1ccc(C(=O)N2CC(c3ccc(C#N)cc3)C2)cc1-c1[nH]c(C2(O)CCOCC2)nc1C] | 0.013 |
| 002-196 | 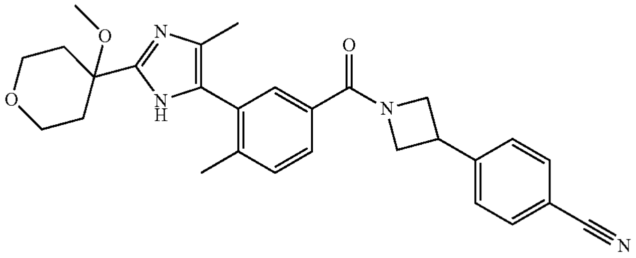 [SMILES: COC1(c2nc(C)c(-c3cc(C(=O)N4CC(c5ccc(C#N)cc5)C4)ccc3C)[nH]2)CCOCC1] | 0.015 |
| 002-197 | 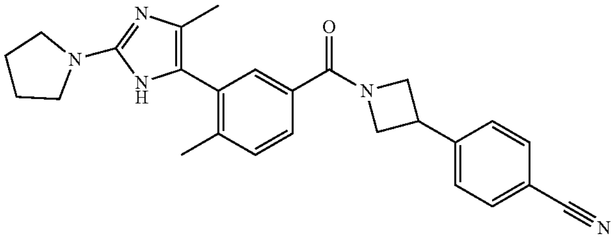 [SMILES: Cc1ccc(C(=O)N2CC(c3ccc(C#N)cc3)C2)cc1-c1[nH]c(N2CCCC2)nc1C] | 0.870 |
| 002-198 | 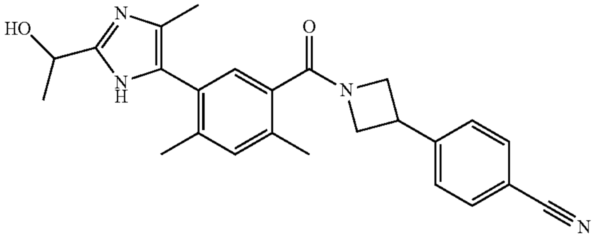 | 0.054 |
| 002-199 | 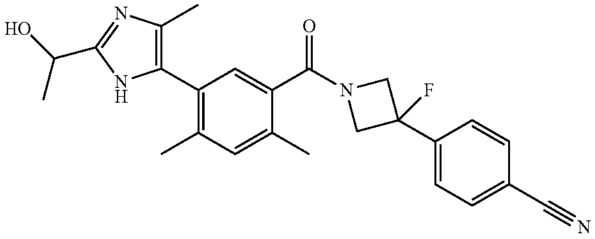 [SMILES: Cc1cc(C)c(-c2[nH]c(C(C)O)nc2C)cc1C(=O)N1CC(F)(c2ccc(C#N)cc2)C1] | 0.110 |
| 002-200 | 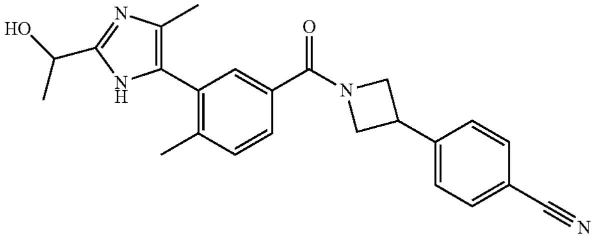 [SMILES: Cc1ccc(C(=O)N2CC(c3ccc(C#N)cc3)C2)cc1-c1[nH]c(C(C)O)nc1C] | 0.027 |

TABLE C-2-continued
| Fatty Acid Synthase Inhibitors | | |
|---|---|---|
| Cmpd No. | Structure | Hu FASN IC50 (μM) |
| 002-201 | 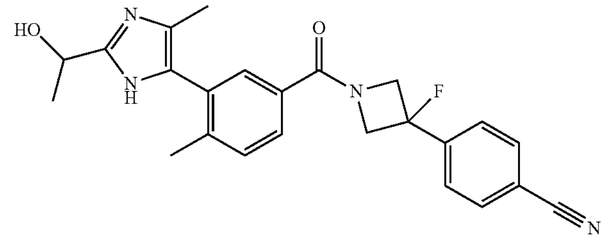 [SMILES: Cc1ccc(C(=O)N2CC(F)(c3ccc(C#N)cc3)C2)cc1-c1[nH]c(C(C)O)nc1C] | 0.130 |
| 002-202 | 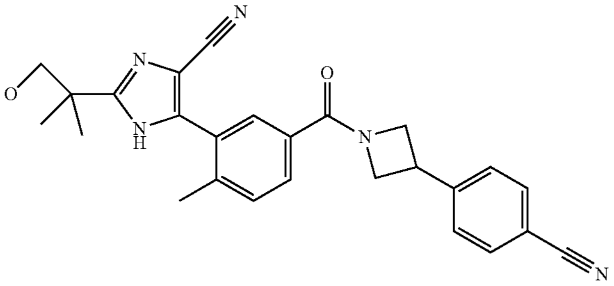 [SMILES: Cc1ccc(C(=O)N2CC(c3ccc(C#N)cc3)C2)cc1-c1[nH]c(C(C)(C)CO)nc1C#N] | 0.020 |
| 002-203 | 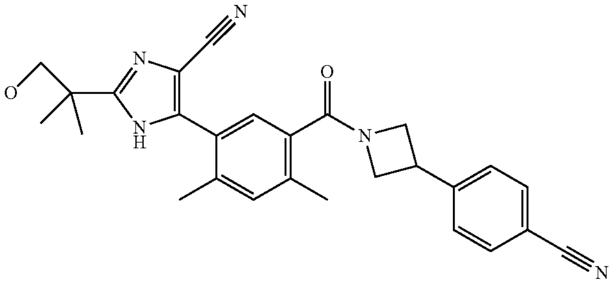 [SMILES: Cc1cc(C)c(-c2[nH]c(C(C)(C)CO)nc2C#N)cc1C(=O)N1CC(c2ccc(C#N)cc2)C1] | 0.035 |
| 002-204 | 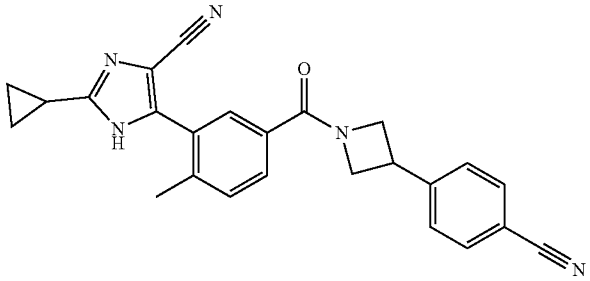 [SMILES: Cc1ccc(C(=O)N2CC(c3ccc(C#N)cc3)C2)cc1-c1[nH]c(C2CC2)nc1C#N] | 0.010 |
| 002-205 | 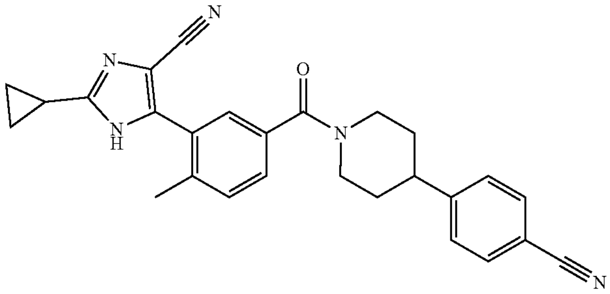 [SMILES: Cc1ccc(C(=O)N2CCC(c3ccc(C#N)cc3)CC2)cc1-c1[nH]c(C2CC2)nc1C#N] | 0.016 |

TABLE C-2-continued
| Fatty Acid Synthase Inhibitors | | |
|---|---|---|
| Cmpd No. | Structure | Hu FASN IC50 (μM) |
| 002-206 | 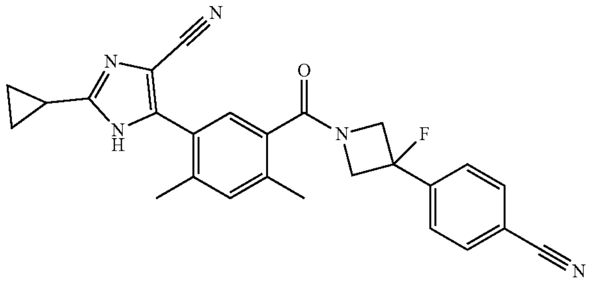 [SMILES: Cc1cc(C)c(-c2[nH]c(C3CC3)nc2C#N)cc1C(=O)N1CC(F)(c2ccc(C#N)cc2)C1] | 0.024 |
| 002-207 | 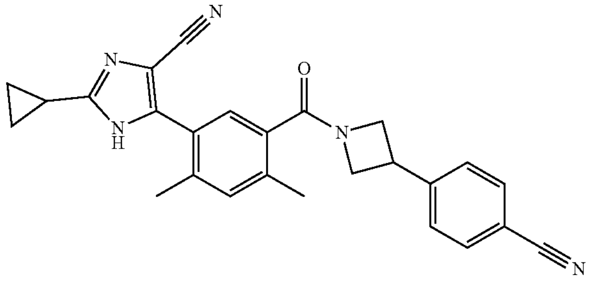 [SMILES: Cc1cc(C)c(-c2[nH]c(C3CC3)nc2C#N)cc1C(=O)N1CC(c2ccc(C#N)cc2)C1] | 0.035 |
| 002-208 | 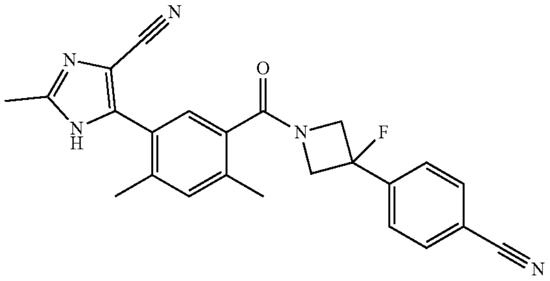 [SMILES: Cc1nc(C#N)c(-c2cc(C(=O)N3CC(F)(c4ccc(C#N)cc4)C3)c(C)cc2C)[nH]1] | 0.036 |
| 002-209 | 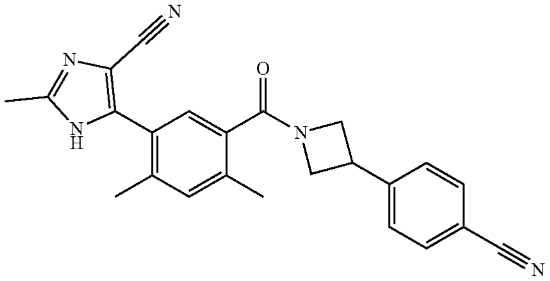 [SMILES: Cc1nc(C#N)c(-c2cc(C(=O)N3CC(c4ccc(C#N)cc4)C3)c(C)cc2C)[nH]1] | 0.024 |
| 002-210 | 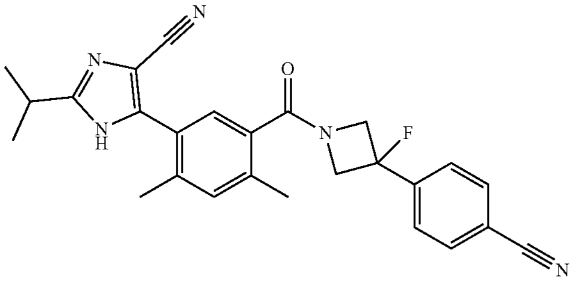 [SMILES: Cc1cc(C)c(-c2[nH]c(C(C)C)nc2C#N)cc1C(=O)N1CC(F)(c2ccc(C#N)cc2)C1] | 0.020 |

TABLE C-2-continued
| Fatty Acid Synthase Inhibitors | | |
|---|---|---|
| Cmpd No. | Structure | Hu FASN IC50 (μM) |
| 002-211 | 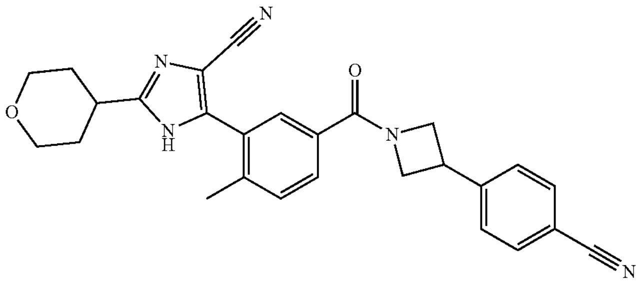 [SMILES: Cc1ccc(C(=O)N2CC(c3ccc(C#N)cc3)C2)cc1-c1[nH]c(C2CCOCC2)nc1C#N] | 0.011 |
| 002-212 | 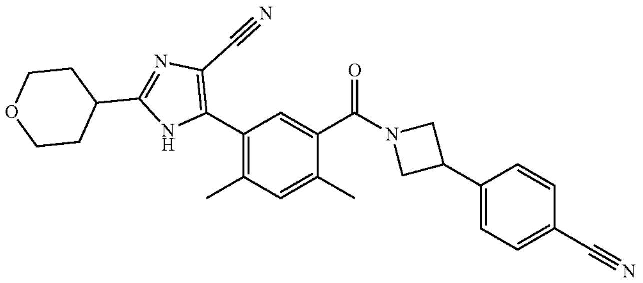 [SMILES: Cc1cc(C)c(-c2[nH]c(C3CCOCC3)nc2C#N)cc1C(=O)N1CC(c2ccc(C#N)cc2)C1] | 0.018 |
| 002-213 | 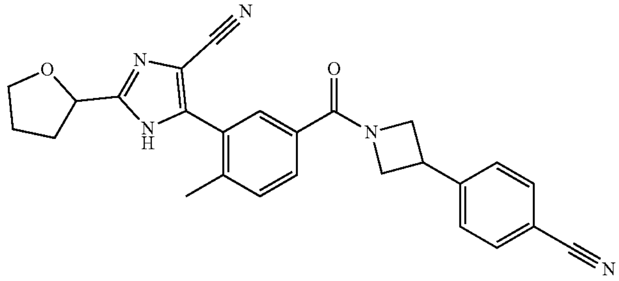 [SMILES: Cc1ccc(C(=O)N2CC(c3ccc(C#N)cc3)C2)cc1-c1[nH]c(C2CCCO2)nc1C#N] | 0.065 |
| 002-214 | 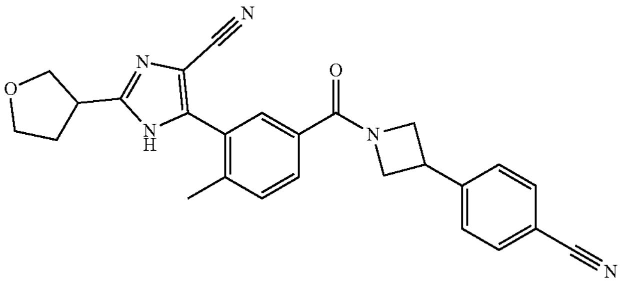 [SMILES: Cc1ccc(C(=O)N2CC(c3ccc(C#N)cc3)C2)cc1-c1[nH]c(C2CCOC2)nc1C#N] | 0.014 |
| 002-215 | 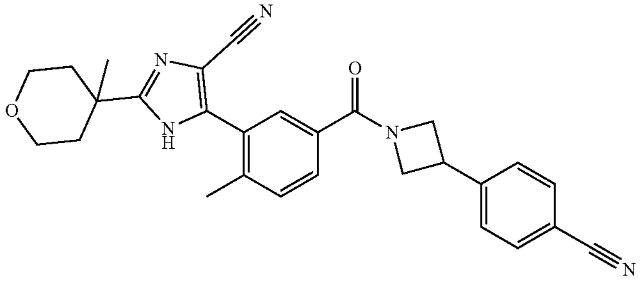 [SMILES: Cc1ccc(C(=O)N2CC(c3ccc(C#N)cc3)C2)cc1-c1[nH]c(C2(C)CCOCC2)nc1C#N] | 0.048 |

TABLE C-2-continued
| Fatty Acid Synthase Inhibitors | | |
|---|---|---|
| Cmpd No. | Structure | Hu FASN IC50 (μM) |
| 002-216 | 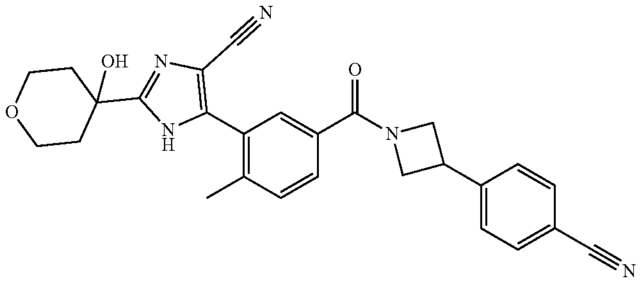 [SMILES: Cc1ccc(C(=O)N2CC(c3ccc(C#N)cc3)C2)cc1-c1[nH]c(C2(O)CCOCC2)nc1C#N] | 0.079 |
| 002-217 | 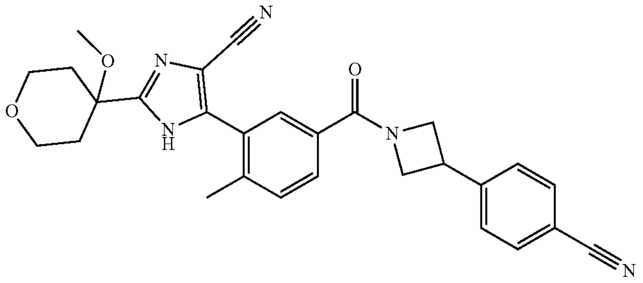 [SMILES: COC1(c2nc(C#N)c(-c3cc(C(=O)N4CC(c5ccc(C#N)cc5)C4)ccc3C)[nH]2)CCOCC1] | 0.052 |
| 002-218 | 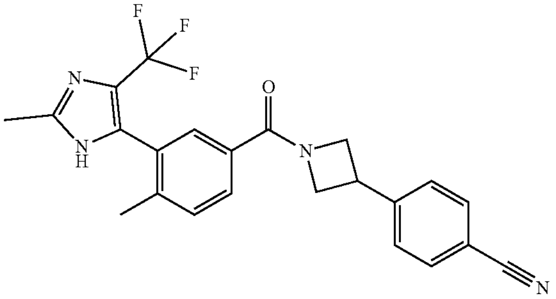 [SMILES: Cc1nc(C(F)(F)F)c(-c2cc(C(=O)N3CC(c4ccc(C#N)cc4)C3)ccc2C)[nH]1] | 0.015 |
| 002-219 | 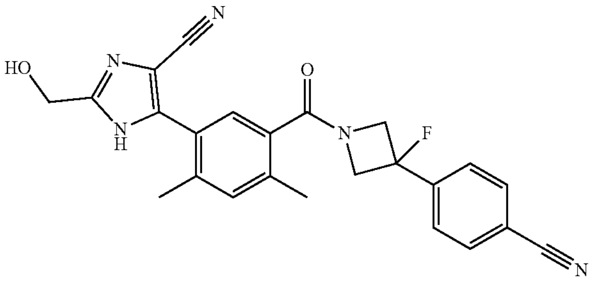 [SMILES: Cc1cc(C)c(-c2[nH]c(CO)nc2C#N)cc1C(=O)N1CC(F)(c2ccc(C#N)cc2)C1] | 0.059 |
| 002-220 | 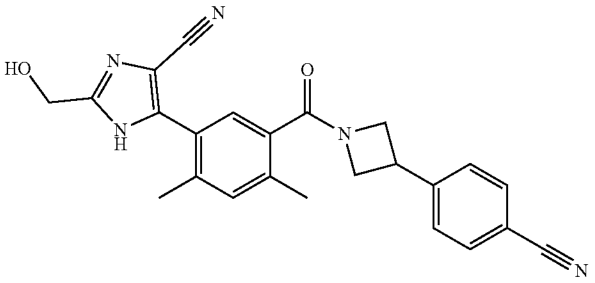 [SMILES: Cc1cc(C)c(-c2[nH]c(CO)nc2C#N)cc1C(=O)N1CC(c2ccc(C#N)cc2)C1] | 0.050 |

TABLE C-2-continued
| Fatty Acid Synthase Inhibitors | | |
|---|---|---|
| Cmpd No. | Structure | Hu FASN IC50 (μM) |
| 002-221 | 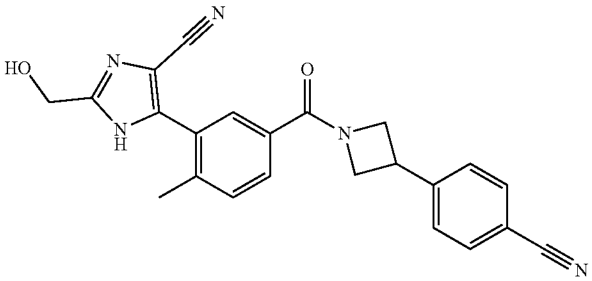 [SMILES: Cc1ccc(C(=O)N2CC(c3ccc(C#N)cc3)C2)cc1-c1[nH]c(CO)nc1C#N] | 0.043 |
| 002-222 | 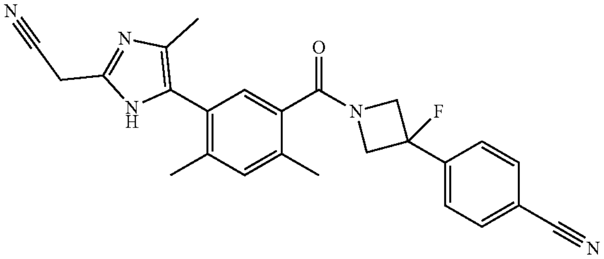 [SMILES: Cc1cc(C)c(-c2[nH]c(CC#N)nc2C)cc1C(=O)N1CC(F)(c2ccc(C#N)cc2)C1] | 0.053 |
| 002-223 | 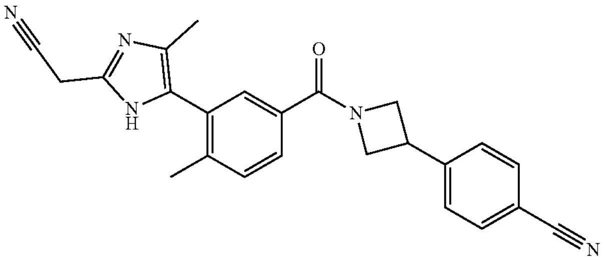 [SMILES: Cc1ccc(C(=O)N2CC(c3ccc(C#N)cc3)C2)cc1-c1[nH]c(CC#N)nc1C] | 0.023 |
| 002-224 | 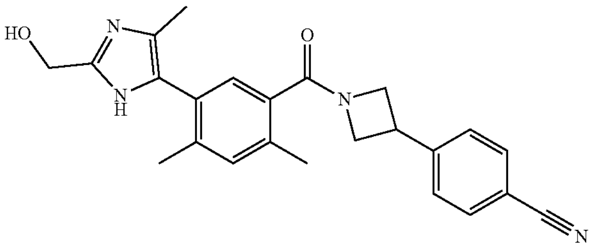 [SMILES: Cc1cc(C)c(-c2[nH]c(CO)nc2C)cc1C(=O)N1CC(c2ccc(C#N)cc2)C1] | 0.031 |
| 002-225 | 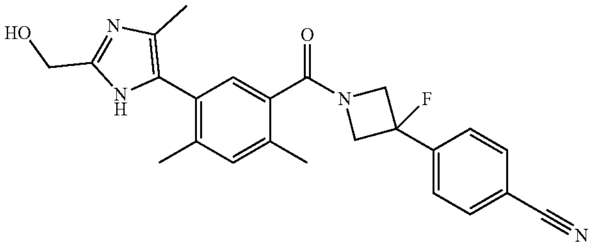 [SMILES: Cc1cc(C)c(-c2[nH]c(CO)nc2C)cc1C(=O)N1CC(F)(c2ccc(C#N)cc2)C1] | 0.059 |

TABLE C-2-continued
| Cmpd No. | Structure | Hu FASN IC50 (μM) |
| --- | --- | --- |
| Fatty Acid Synthase Inhibitors | | |
| 002-226 | 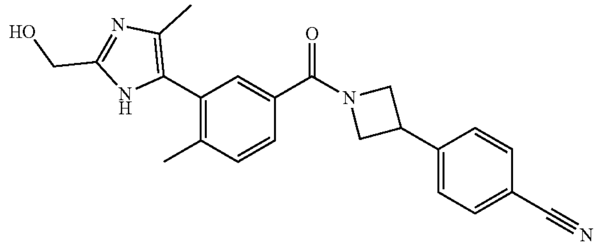 [SMILES: Cc1ccc(C(=O)N2CC(c3ccc(C#N)cc3)C2)cc1-c1[nH]c(CO)nc1C] | 0.088 |
| 002-227 | 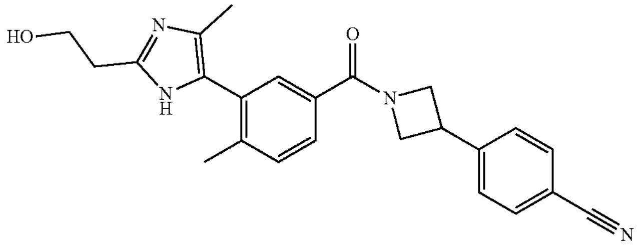 [SMILES: Cc1ccc(C(=O)N2CC(c3ccc(C#N)cc3)C2)cc1-c1[nH]c(CCO)nc1C] | 0.012 |
| 002-228 | 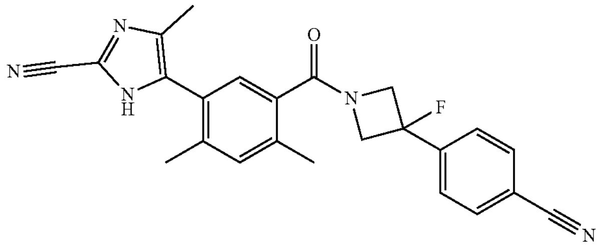 [SMILES: Cc1cc(C)c(-c2[nH]c(C#N)nc2C)cc1C(=O)N1CC(F)(c2ccc(C#N)cc2)C1] | 0.027 |
| 002-229 | 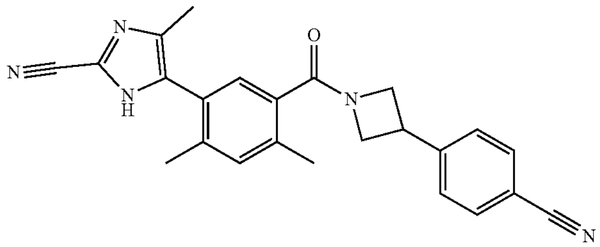 [SMILES: Cc1cc(C)c(-c2[nH]c(C#N)nc2C)cc1C(=O)N1CC(c2ccc(C#N)cc2)C1] | 0.042 |
| 002-230 | 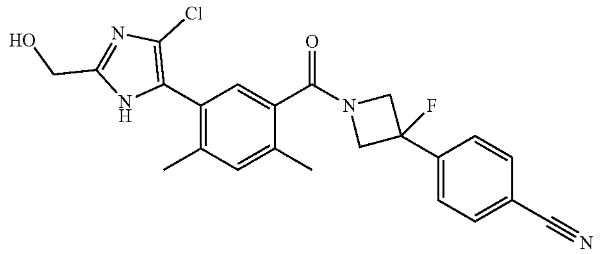 [SMILES: Cc1cc(C)c(-c2[nH]c(CO)nc2Cl)cc1C(=O)N1CC(F)(c2ccc(C#N)cc2)C1] | 0.017 |

TABLE C-2-continued
| Fatty Acid Synthase Inhibitors | | |
|---|---|---|
| Cmpd No. | Structure | Hu FASN IC50 (μM) |
| 002-231 | 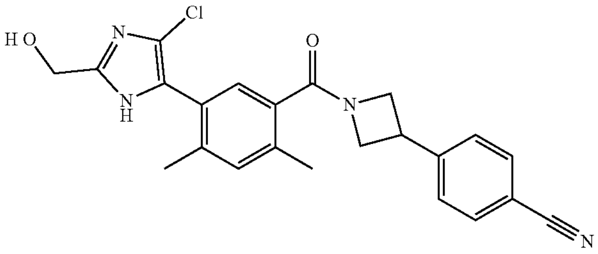 | 0.019 |
| 002-232 | 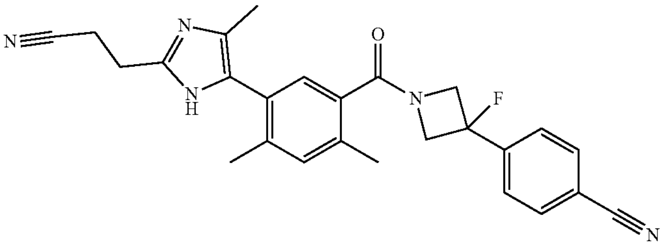 [SMILES: Cc1cc(C)c(-c2[nH]c(CCC#N)nc2C)cc1C(=O)N1CC(F)(c2ccc(C#N)cc2)C1] | 0.020 |
| 002-233 | 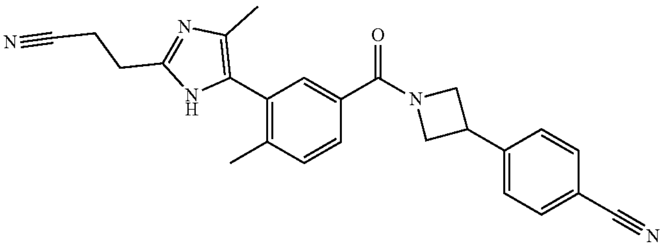 [SMILES: Cc1ccc(C(=O)N2CC(c3ccc(C#N)cc3)C2)cc1-c1[nH]c(CCC#N)nc1C] | 0.011 |
| 002-234 | 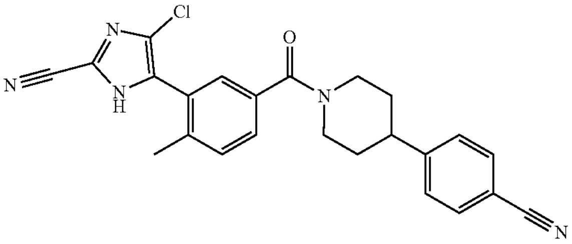 [SMILES: Cc1ccc(C(=O)N2CCC(c3ccc(C#N)cc3)CC2)cc1-c1[nH]c(C#N)nc1Cl] | 0.053 |
| 002-235 | 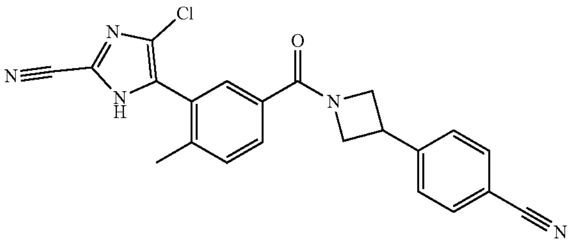 [SMILES: Cc1ccc(C(=O)N2CC(c3ccc(C#N)cc3)C2)cc1-c1[nH]c(C#N)nc1Cl] | 0.039 |

TABLE C-2-continued
Fatty Acid Synthase Inhibitors
| Cmpd No. | Structure | Hu FASN IC50 (μM) |
|---|---|---|
| 002-236 | 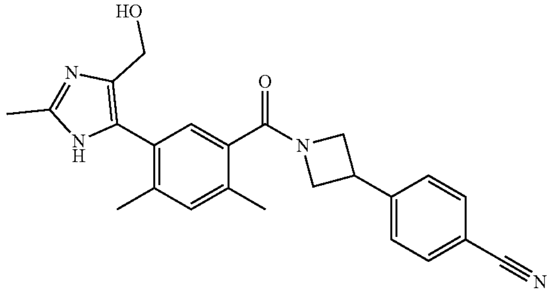 [SMILES: Cc1nc(CO)c(-c2cc(C(=O)N3CC(c4ccc(C#N)cc4)C3)c(C)cc2C)[nH]1] | 0.019 |
| 002-237 | 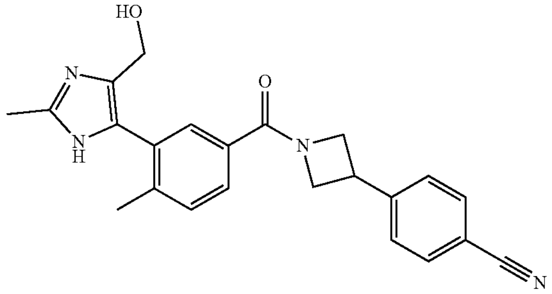 [SMILES: Cc1nc(CO)c(-c2cc(C(=O)N3CC(c4ccc(C#N)cc4)C3)ccc2C)[nH]1] | 0.016 |
| 002-238 | 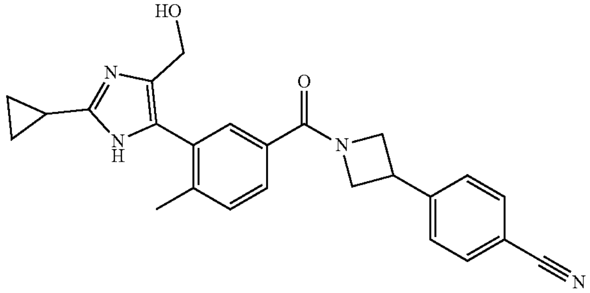 [SMILES: Cc1ccc(C(=O)N2CC(c3ccc(C#N)cc3)C2)cc1-c1[nH]c(C2CC2)nc1CO] | 0.0001-10 |
| 002-239 | 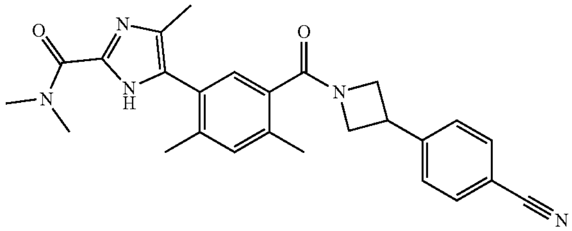 [SMILES: Cc1cc(C)c(-c2[nH]c(C(=O)N(C)C)nc2C)cc1C(=O)N1CC(c2ccc(C#N)cc2)C1] | 0.440 |
| 002-240 | 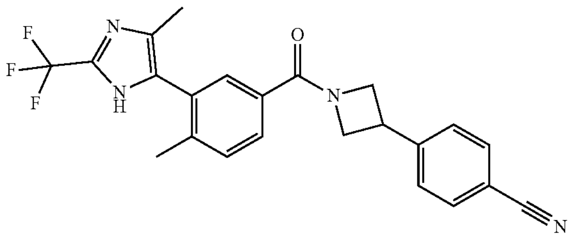 [SMILES: Cc1ccc(C(=O)N2CC(c3ccc(C#N)cc3)C2)cc1-c1[nH]c(C(F)(F)F)nc1C] | 0.053 |

TABLE C-2-continued
| Cmpd No. | Fatty Acid Synthase Inhibitors Structure | Hu FASN IC50 (μM) |
|---|---|---|
| 002-241 | 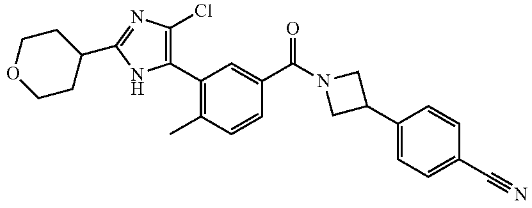 [SMILES: Cc1ccc(C(=O)N2CC(c3ccc(C#N)cc3)C2)cc1-c1[nH]c(C2CCOCC2)nc1Cl] | 0.009 |
| 002-242 | 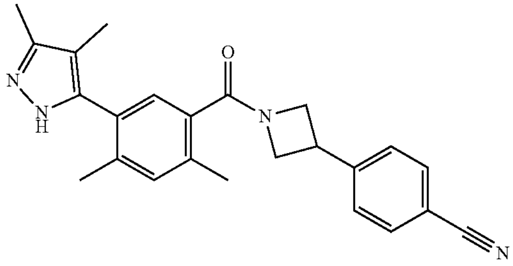 [SMILES: Cc1cc(C)c(-c2[nH]nc(C)c2C)cc1C(=O)N1CC(c2ccc(C#N)cc2)C1] | 0.060 |
| 002-243 | 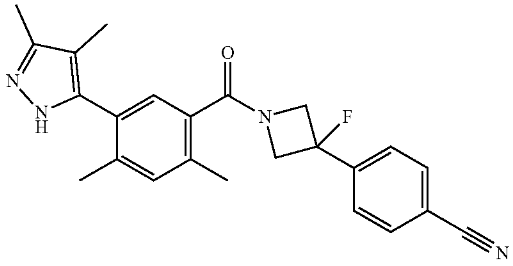 [SMILES: Cc1cc(C)c(-c2[nH]nc(C)c2C)cc1C(=O)N1CC(F)(c2ccc(C#N)cc2)C1] | 0.170 |
| 002-244 | 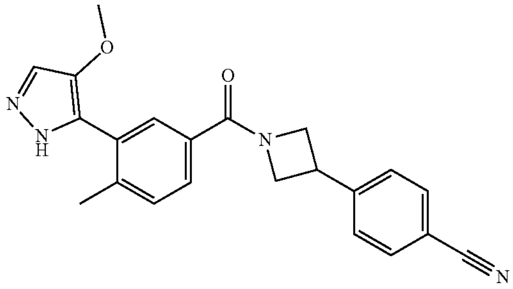 [SMILES: COc1cn[nH]c1-c1cc(C(=O)N2CC(c3ccc(C#N)cc3)C2)ccc1C] | 0.150 |
| 002-245 | 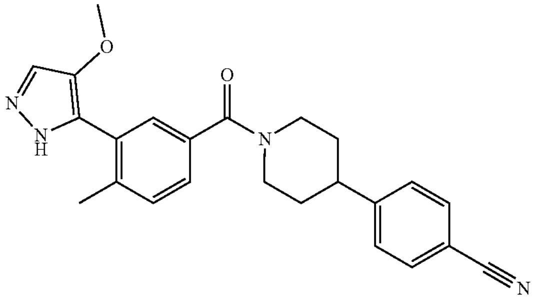 [SMILES: COc1cn[nH]c1-c1cc(C(=O)N2CCC(c3ccc(C#N)cc3)CC2)ccc1C] | 0.109 |

TABLE C-2-continued
| Fatty Acid Synthase Inhibitors | | |
|---|---|---|
| Cmpd No. | Structure | Hu FASN IC50 (μM) |
| 002-246 | 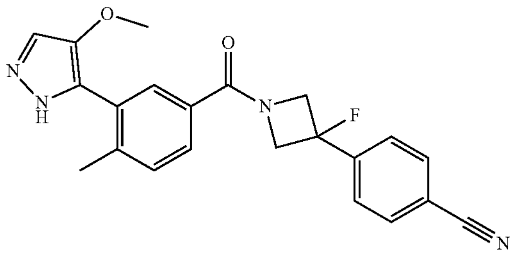 [SMILES: COc1cn[nH]c1-c1cc(C(=O)N2CC(F)(c3ccc(C#N)cc3)C2)ccc1C] | 0.340 |
| 002-247 | 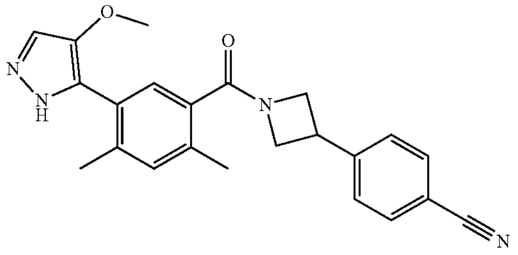 | 0.110 |
| 002-248 | 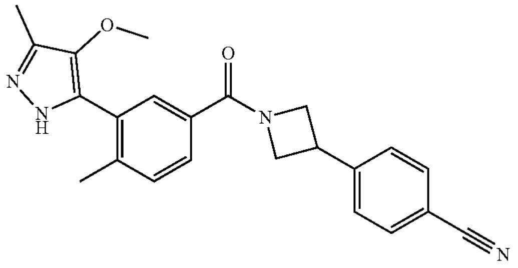 [SMILES: COc1c(C)n[nH]c1-c1cc(C(=O)N2CC(c3ccc(C#N)cc3)C2)ccc1C] | 0.075 |
| 002-249 | 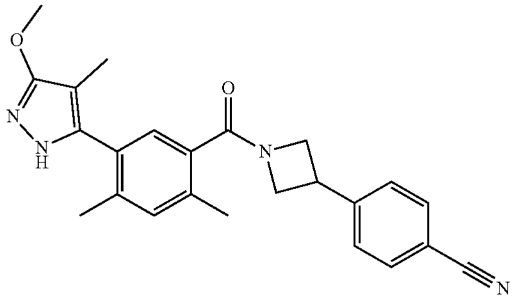 [SMILES: COc1n[nH]c(-c2cc(C(=O)N3CC(c4ccc(C#N)cc4)C3)c(C)cc2C)c1C] | 0.043 |
| 002-250 | 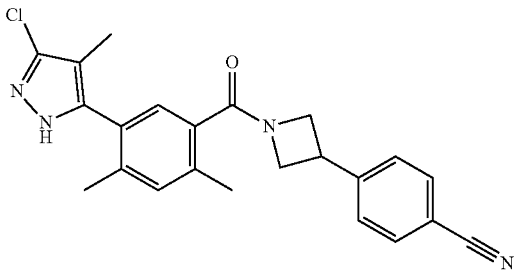 [SMILES: Cc1cc(C)c(-c2[nH]nc(Cl)c2C)cc1C(=O)N1CC(c2ccc(C#N)cc2)C1] | 0.051 |

TABLE C-2-continued
| Fatty Acid Synthase Inhibitors | | |
|---|---|---|
| Cmpd No. | Structure | Hu FASN IC50 (μM) |
| 002-251 | 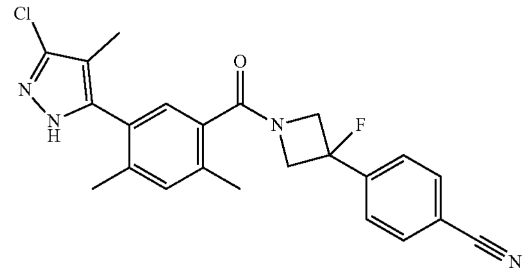 [SMILES: Cc1cc(C)c(-c2[nH]nc(Cl)c2C)cc1C(=O)N1CC(F)(c2ccc(C#N)cc2)C1] | 0.178 |
| 002-252 | 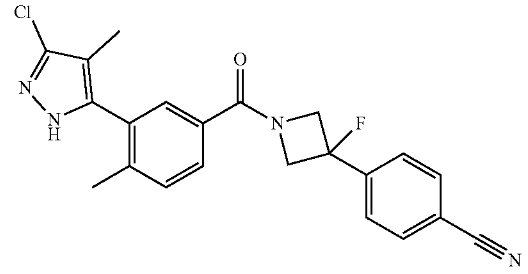 [SMILES: Cc1ccc(C(=O)N2CC(F)(c3ccc(C#N)cc3)C2)cc1-c1[nH]nc(Cl)c1C] | 0.095 |
| 002-253 | 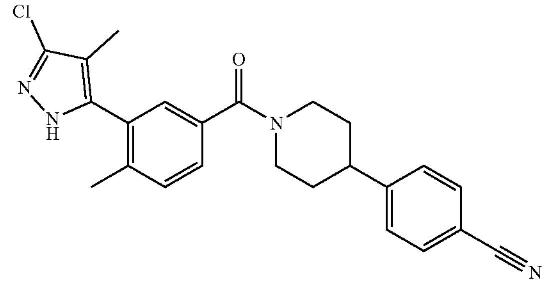 [SMILES: Cc1ccc(C(=O)N2CCC(c3ccc(C#N)cc3)CC2)cc1-c1[nH]nc(Cl)c1C] | 0.080 |
| 002-255 | 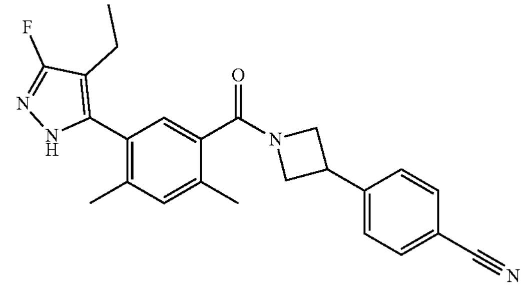 [SMILES: CCc1c(F)n[nH]c1-c1cc(C(=O)N2CC(c3ccc(C#N)cc3)C2)c(C)cc1C] | 0.063 |
| 002-256 | 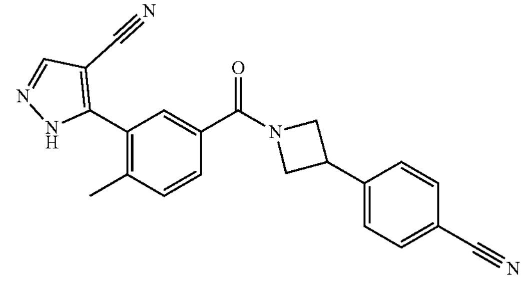 [SMILES: Cc1ccc(C(=O)N2CC(c3ccc(C#N)cc3)C2)cc1-c1[nH]ncc1C#N] | 0.210 |

TABLE C-2-continued
| Cmpd No. | Structure | Hu FASN IC50 (μM) |
|---|---|---|
| Fatty Acid Synthase Inhibitors | | |
| 002-257 | 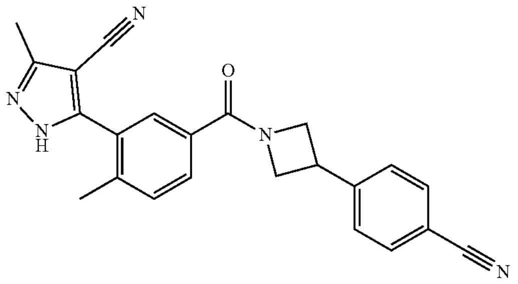 [SMILES: Cc1ccc(C(=O)N2CC(c3ccc(C#N)cc3)C2)cc1-c1[nH]nc(C)c1C#N] | 0.440 |
| 002-258 | 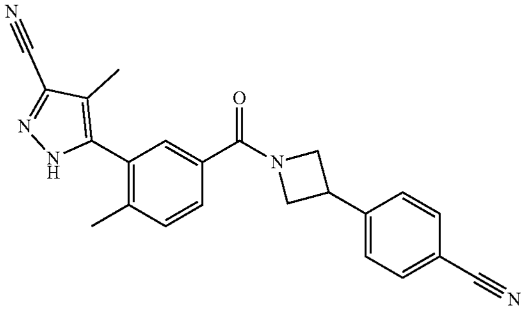 [SMILES: Cc1ccc(C(=O)N2CC(c3ccc(C#N)cc3)C2)cc1-c1[nH]nc(C#N)c1C] | 0.058 |
| 002-259 | 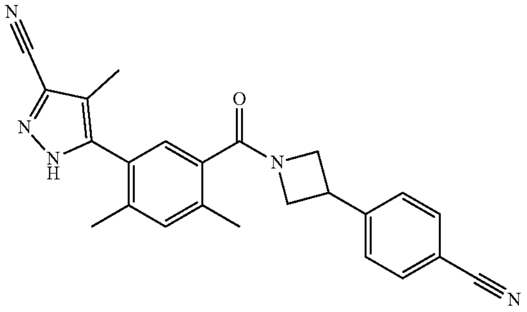 [SMILES: Cc1cc(C)c(-c2[nH]nc(C#N)c2C)cc1C(=O)N1CC(c2ccc(C#N)cc2)C1] | 0.140 |
| 002-260 | 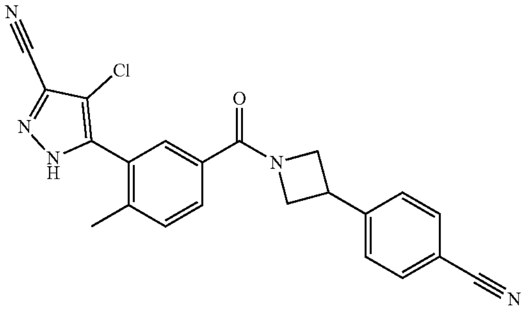 | 0.067 |

TABLE C-2-continued
| Fatty Acid Synthase Inhibitors | | |
|---|---|---|
| Cmpd No. | Structure | Hu FASN IC50 (μM) |
| 002-261 | 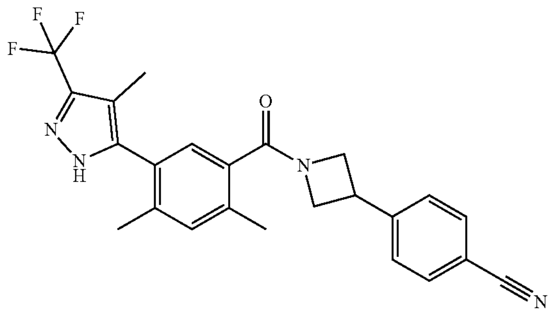 [SMILES: Cc1cc(C)c(-c2[nH]nc(C(F)(F)F)c2C)cc1C(=O)N1CC(c2ccc(C#N)cc2)C1] | 0.190 |
| 002-262 | 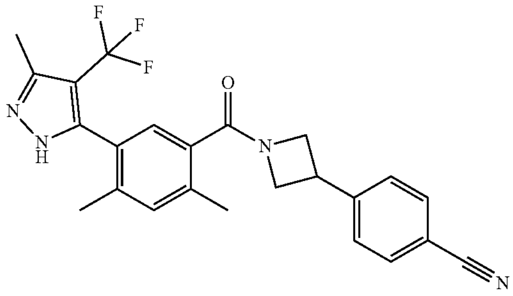 [SMILES: Cc1cc(C)c(-c2[nH]nc(C)c2C(F)(F)F)cc1C(=O)N1CC(c2ccc(C#N)cc2)C1] | 0.140 |
| 002-263 | 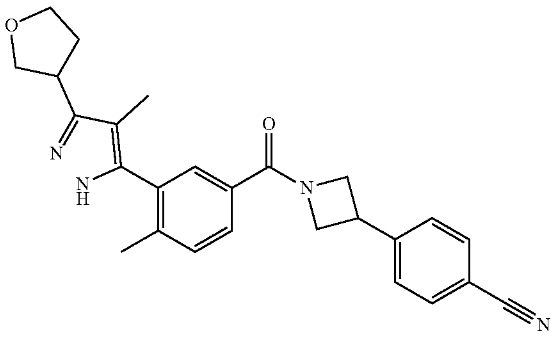 [SMILES: C/C(C(=N)C1CCOC1)=C(/N)c1cc(C(=O)N2CC(c3ccc(C#N)cc3)C2)ccc1C] | 0.094 |
| 002-264 | 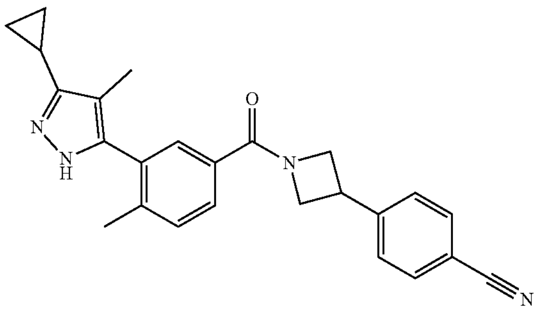 [SMILES: Cc1ccc(C(=O)N2CC(c3ccc(C#N)cc3)C2)cc1-c1[nH]nc(C2CC2)c1C] | 0.056 |

TABLE C-2-continued
| Fatty Acid Synthase Inhibitors | | |
|---|---|---|
| Cmpd No. | Structure | Hu FASN IC50 (μM) |
| 002-265 | 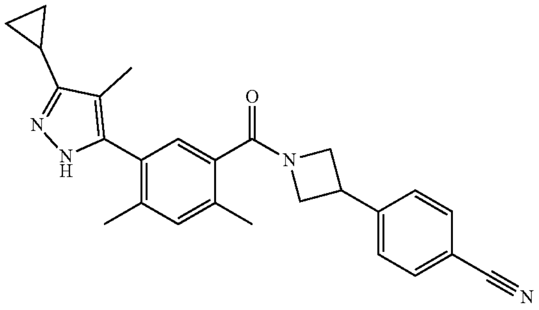 [SMILES: Cc1cc(C)c(-c2[nH]nc(C3CC3)c2C)cc1C(=O)N1CC(c2ccc(C#N)cc2)C1] | 0.110 |
| 002-266 | 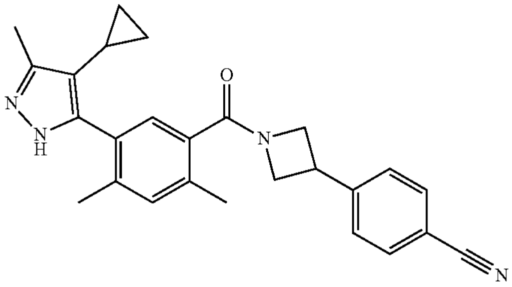 [SMILES: Cc1cc(C)c(-c2[nH]nc(C)c2C2CC2)cc1C(=O)N1CC(c2ccc(C#N)cc2)C1] | 0.200 |
| 002-267 | 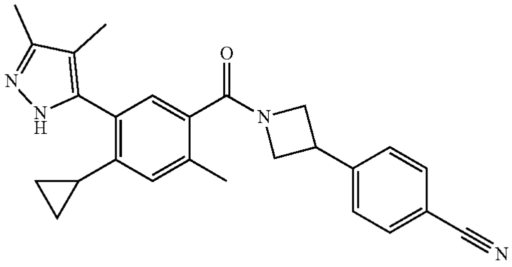 [SMILES: Cc1cc(C2CC2)c(-c2[nH]nc(C)c2C)cc1C(=O)N1CC(c2ccc(C#N)cc2)C1] | 0.100 |
| 002-268 | 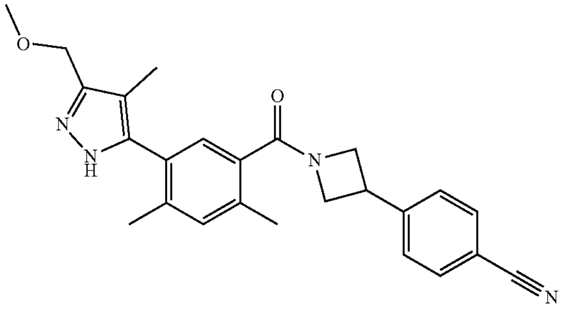 [SMILES: COCc1n[nH]c(-c2cc(C(=O)N3CC(c4ccc(C#N)cc4)C3)c(C)cc2C)c1C] | 0.059 |
| 002-269 | 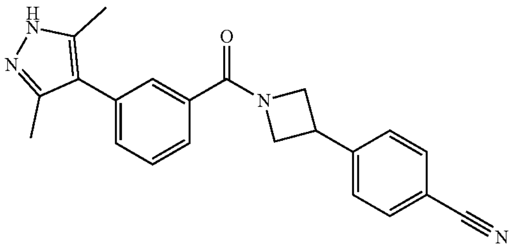 [SMILES: Cc1n[nH]c(C)c1-c1cccc(C(=O)N2CC(c3ccc(C#N)cc3)C2)c1] | 50.000 |

TABLE C-2-continued
| Fatty Acid Synthase Inhibitors | | |
|---|---|---|
| Cmpd No. | Structure | Hu FASN IC50 (μM) |
| 002-270 | 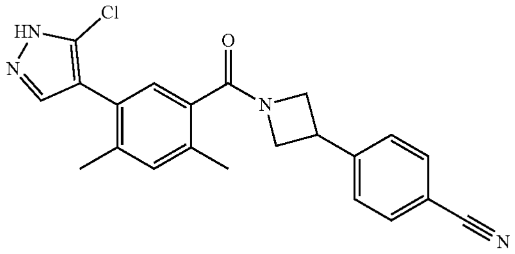 [SMILES: Cc1cc(C)c(-c2cn[nH]c2Cl)cc1C(=O)N1CC(c2ccc(C#N)cc2)C1] | |
| 002-271 | 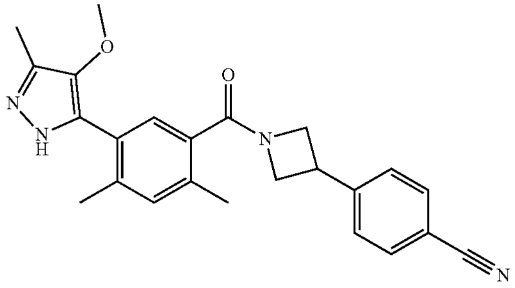 [SMILES: COc1c(C)n[nH]c1-c1cc(C(=O)N2CC(c3ccc(C#N)cc3)C2)c(C)cc1C] | |
| 002-272 | 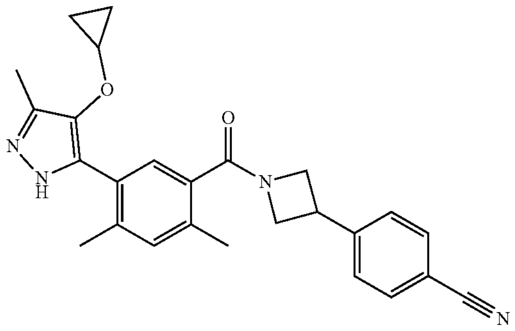 [SMILES: Cc1cc(C)c(-c2[nH]nc(C)c2OC2CC2)cc1C(=O)N1CC(c2ccc(C#N)cc2)C1] | |
| 002-273 | 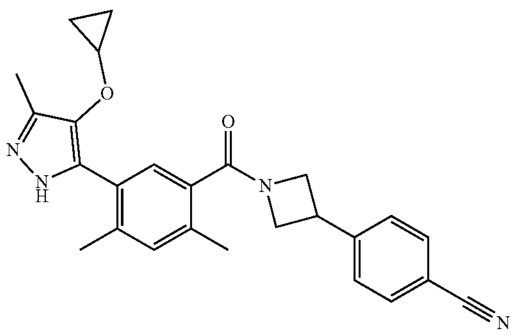 [SMILES: Cc1cc(C)c(-c2[nH]nc(C)c2OC2CC2)cc1C(=O)N1CC(c2ccc(C#N)cc2)C1] | |

TABLE C-2-continued
| Fatty Acid Synthase Inhibitors | | |
|---|---|---|
| Cmpd No. | Structure | Hu FASN IC50 (μM) |
| 002-274 | 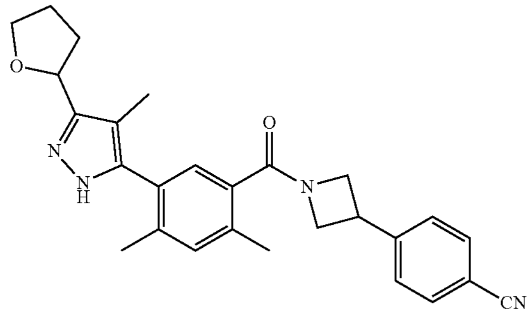 [SMILES: Cc1cc(C)c(-c2[nH]nc(C3CCCO3)c2C)cc1C(=O)N1CC(c2ccc(C#N)cc2)C1] | 0.051 |
| 002-275 | 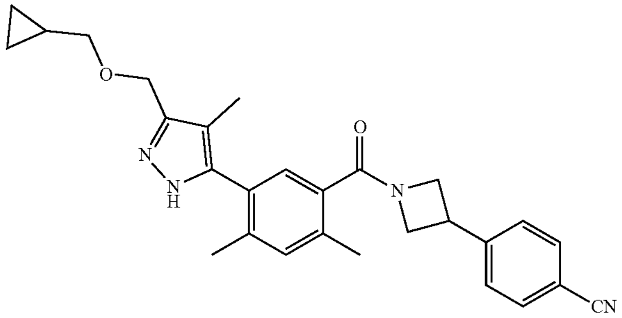 [SMILES: Cc1cc(C)c(-c2[nH]nc(COCC3CC3)c2C)cc1C(=O)N1CC(c2ccc(C#N)cc2)C1] | 0.057 |
| 002-276 | 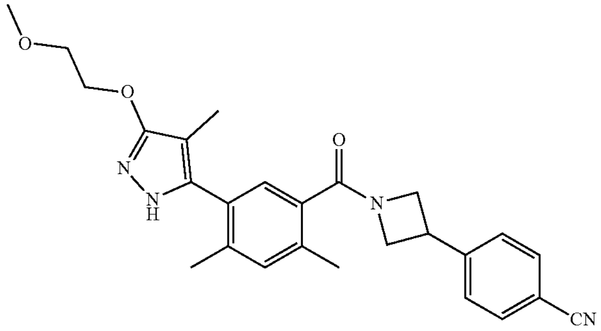 [SMILES: COCCOc1n[nH]c(-c2cc(C(=O)N3CC(c4ccc(C#N)cc4)C3)c(C)cc2C)c1C] | 50 |
| 002-277 | 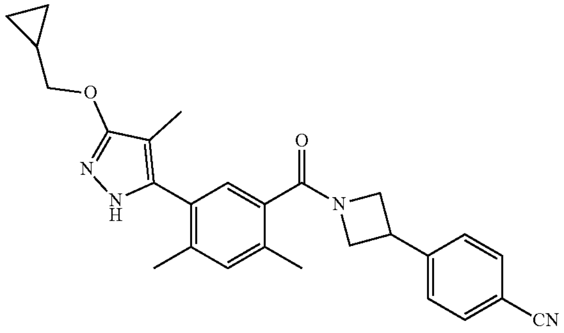 [SMILES: Cc1cc(C)c(-c2[nH]nc(OCC3CC3)c2C)cc1C(=O)N1CC(c2ccc(C#N)cc2)C1] | 50 |

TABLE C-2-continued
| Fatty Acid Synthase Inhibitors | | |
|---|---|---|
| Cmpd No. | Structure | Hu FASN IC50 (μM) |
| 002-278 | 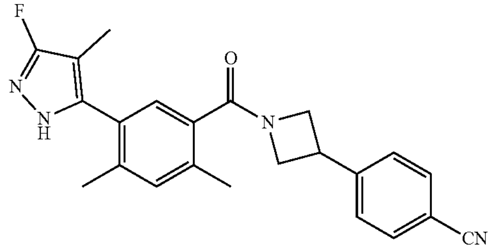 [SMILES: Cc1cc(C)c(-c2[nH]nc(F)c2C)cc1C(=O)N1CC(c2ccc(C#N)cc2)C1] | |
| 002-279 | 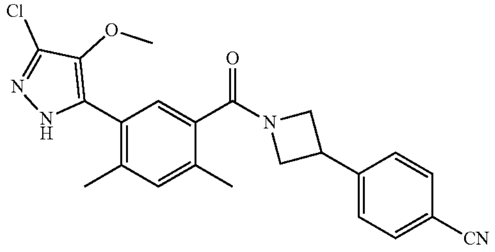 [SMILES: COc1c(Cl)n[nH]c1-c1cc(C(=O)N2CC(c3ccc(C#N)cc3)C2)c(C)cc1C] | 0.11 |
| 002-280 | 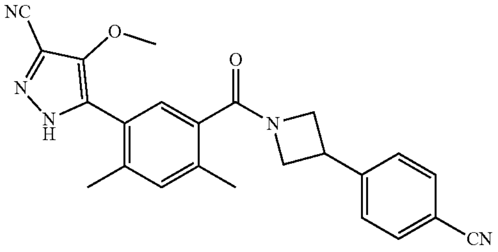 [SMILES: COc1c(C#N)n[nH]c1-c1cc(C(=O)N2CC(c3ccc(C#N)cc3)C2)c(C)cc1C] | 0.089 |
| 002-281 | 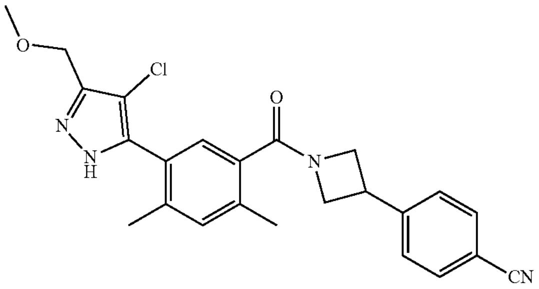 [SMILES: COCc1n[nH]c(-c2cc(C(=O)N3CC(c4ccc(C#N)cc4)C3)c(C)cc2C)c1Cl] | 0.072 |
| 002-282 | 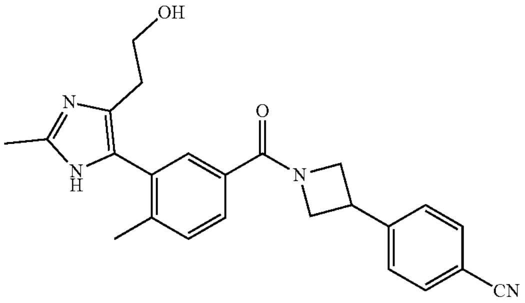 [SMILES: Cc1nc(CCO)c(-c2cc(C(=O)N3CC(c4ccc(C#N)cc4)C3)ccc2C)[nH]1] | 0.091 |

TABLE C-2-continued
| Fatty Acid Synthase Inhibitors | | |
|---|---|---|
| Cmpd No. | Structure | Hu FASN IC50 (μM) |
| 002-283 | 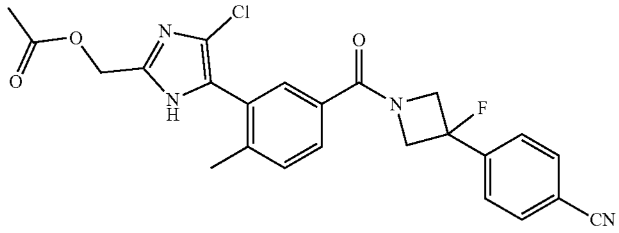 [SMILES: CC(=O)OCc1nc(Cl)c(-c2cc(C(=O)N3CC(F)(c4ccc(C#N)cc4)C3)ccc2C)[nH]1] | 0.064 |
| 002-284 | 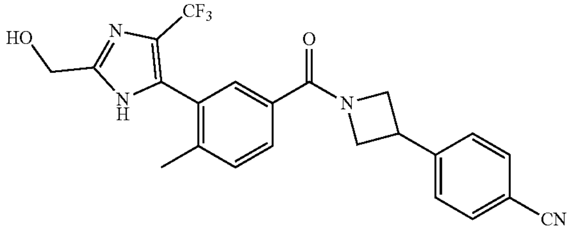 [SMILES: Cc1ccc(C(=O)N2CC(c3ccc(C#N)cc3)C2)cc1-c1[nH]c(CO)nc1C(F)(F)F] | 0.044 |
| 002-285 | 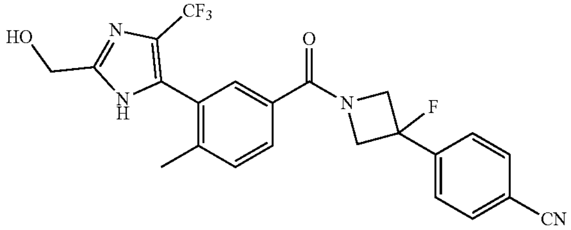 [SMILES: Cc1ccc(C(=O)N2CC(F)(c3ccc(C#N)cc3)C2)cc1-c1[nH]c(CO)nc1C(F)(F)F] | 0.048 |
| 002-286 | 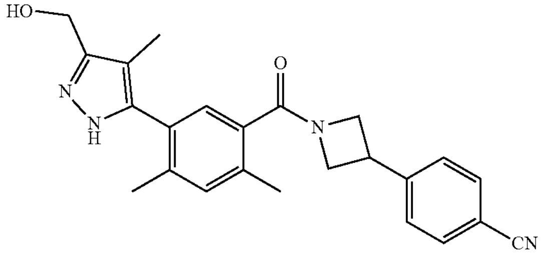 [SMILES: Cc1cc(C)c(-c2[nH]nc(CO)c2C)cc1C(=O)N1CC(c2ccc(C#N)cc2)C1] | 0.061 |
| 002-287 | 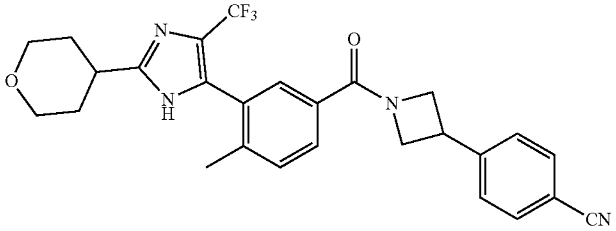 [SMILES: Cc1ccc(C(=O)N2CC(c3ccc(C#N)cc3)C2)cc1-c1[nH]c(C2CCOCC2)nc1C(F)(F)F] | 0.029 |
| 002-288 | 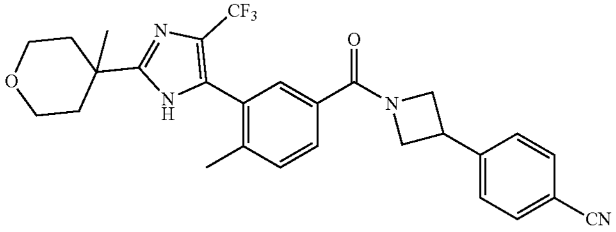 [SMILES: Cc1ccc(C(=O)N2CC(c3ccc(C#N)cc3)C2)cc1-c1[nH]c(C2(C)CCOCC2)nc1C(F)(F)F] | 0.026 |

TABLE C-2-continued
| Fatty Acid Synthase Inhibitors | | |
|---|---|---|
| Cmpd No. | Structure | Hu FASN IC50 (μM) |
| 002-289 | 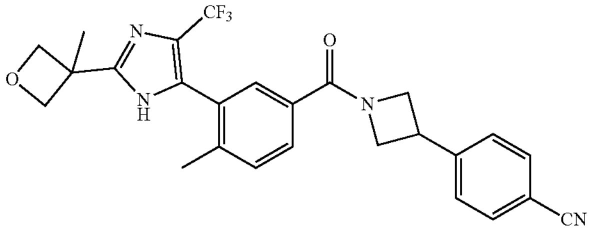 [SMILES: Cc1ccc(C(=O)N2CC(c3ccc(C#N)cc3)C2)cc1-c1[nH]c(C2(C)COC2)nc1C(F)(F)F] | 0.018 |
| 002-290 | 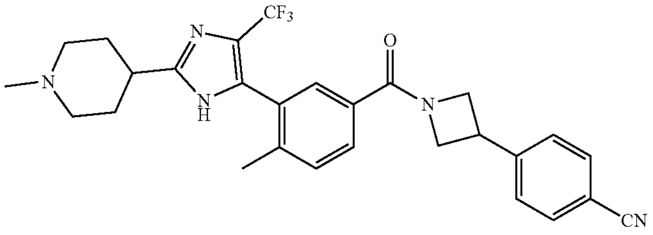 [SMILES: Cc1ccc(C(=O)N2CC(c3ccc(C#N)cc3)C2)cc1-c1[nH]c(C2CCN(C)CC2)nc1C(F)(F)F] | 0.021 |
| 002-291 | 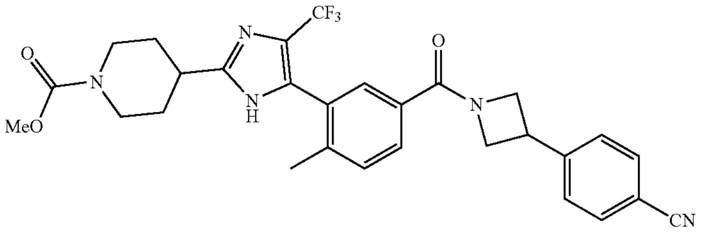 [SMILES: COC(=O)N1CCC(c2nc(C(F)(F)F)c(-c3cc(C(=O)N4CC(c5ccc(C#N)cc5)C4)ccc3C)[nH]2)CC1] | 0.02 |
| 002-292 | 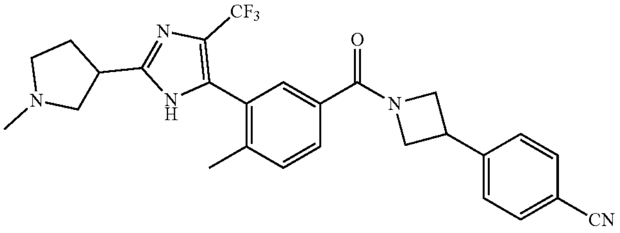 [SMILES: Cc1ccc(C(=O)N2CC(c3ccc(C#N)cc3)C2)cc1-c1[nH]c(C2CCN(C)C2)nc1C(F)(F)F] | 0.044 |
| 002-293 | 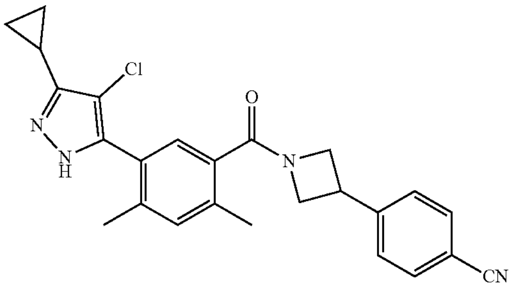 [SMILES: Cc1cc(C)c(-c2[nH]nc(C3CC3)c2Cl)cc1C(=O)N1CC(c2ccc(C#N)cc2)C1] | 0.064 |

TABLE C-2-continued
| Fatty Acid Synthase Inhibitors | | |
|---|---|---|
| Cmpd No. | Structure | Hu FASN IC50 (μM) |
| 002-294 | 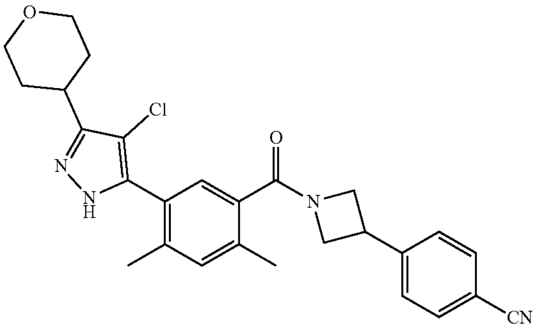 [SMILES: Cc1cc(C)c(-c2[nH]nc(C3CCOCC3)c2Cl)cc1C(=O)N1CC(c2ccc(C#N)cc2)C1] | 0.049 |
| 002-295 | 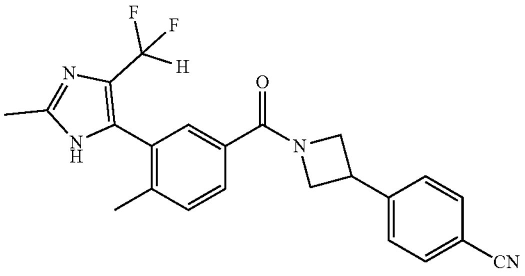 [SMILES: Cc1nc(C(F)F)c(-c2cc(C(=O)N3CC(c4ccc(C#N)cc4)C3)ccc2C)[nH]1] | 0.031 |
| 002-296 | 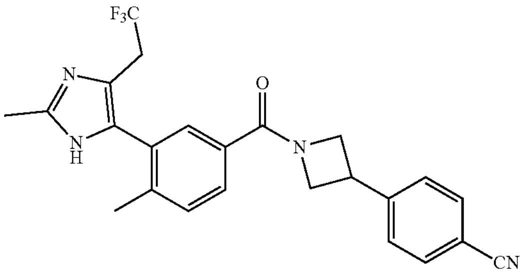 [SMILES: Cc1nc(CC(F)(F)F)c(-c2cc(C(=O)N3CC(c4ccc(C#N)cc4)C3)ccc2C)[nH]1] | 0.024 |
| 002-297 | 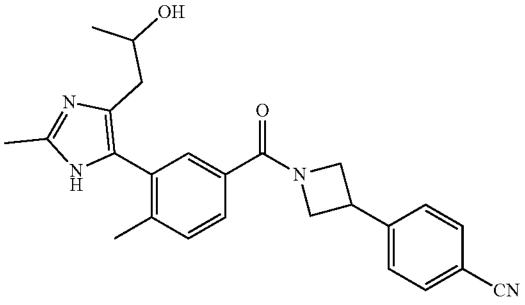 [SMILES: Cc1nc(CC(C)O)c(-c2cc(C(=O)N3CC(c4ccc(C#N)cc4)C3)ccc2C)[nH]1] | |
| 002-298 | 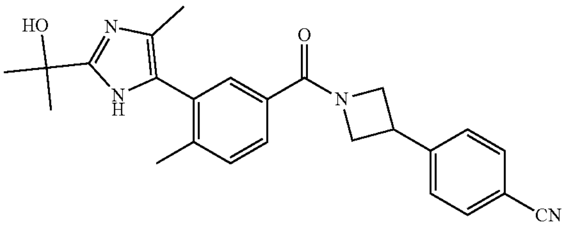 [SMILES: Cc1ccc(C(=O)N2CC(c3ccc(C#N)cc3)C2)cc1-c1[nH]c(C(C)(C)O)nc1C] | |

TABLE C-2-continued
| Fatty Acid Synthase Inhibitors | | |
|---|---|---|
| Cmpd No. | Structure | Hu FASN IC50 (μM) |
| 002-299 | 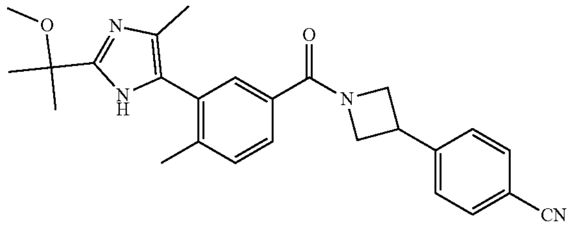 [SMILES: COC(C)(C)c1nc(C)c(-c2cc(C(=O)N3CC(c4ccc(C#N)cc4)C3)ccc2C)[nH]1] | |
| 002-300A | 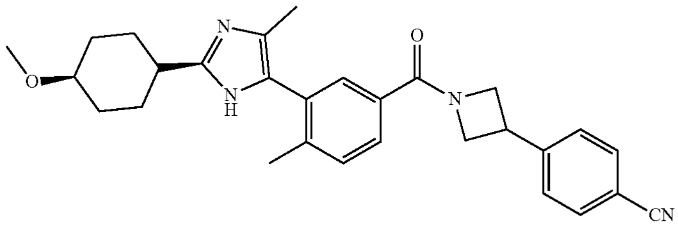 | 0.026 |
| 002-300B | 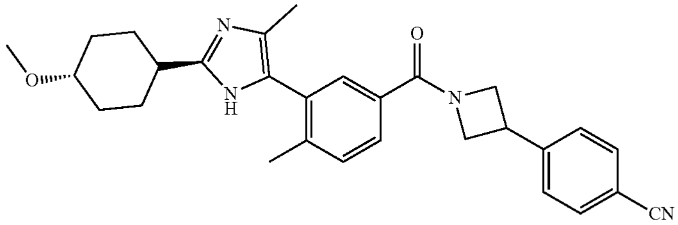 | 0.024 |
| 002-301 | 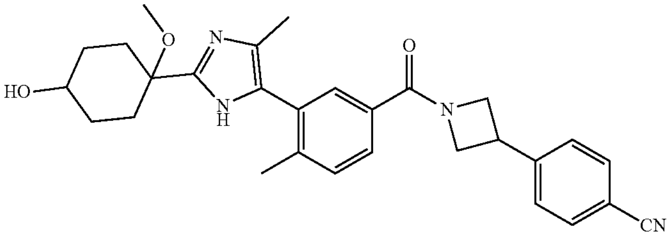 [SMILES: COC1(c2nc(C)c(-c3cc(C(=O)N4CC(c5ccc(C#N)cc5)C4)ccc3C)[nH]2)CCC(O)CC1] | |
| 002-302 | 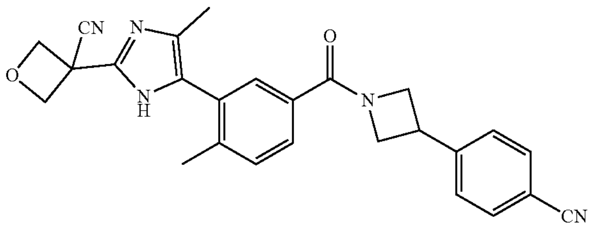 [SMILES: Cc1ccc(C(=O)N2CC(c3ccc(C#N)cc3)C2)cc1-c1[nH]c(C2(C#N)COC2)nc1C] | |
| 002-203 | 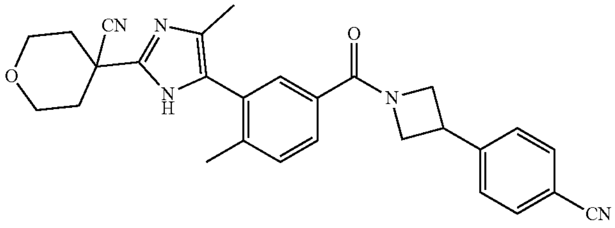 [SMILES: Cc1ccc(C(=O)N2CC(c3ccc(C#N)cc3)C2)cc1-c1[nH]c(C2(C#N)CCOCC2)nc1C] | |

TABLE C-2-continued
| Fatty Acid Synthase Inhibitors | | |
|---|---|---|
| Cmpd No. | Structure | Hu FASN IC50 (μM) |
| 002-304 | 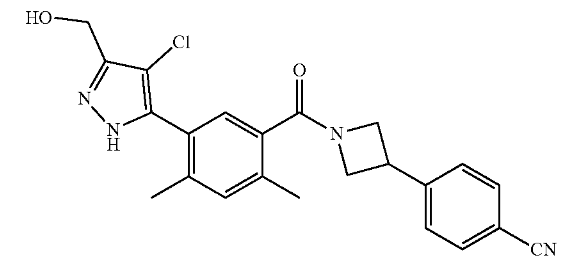 [SMILES: Cc1cc(C)c(-c2[nH]nc(CO)c2Cl)cc1C(=O)N1CC(c2ccc(C#N)cc2)C1] | 0.021 |
| 002-305 | 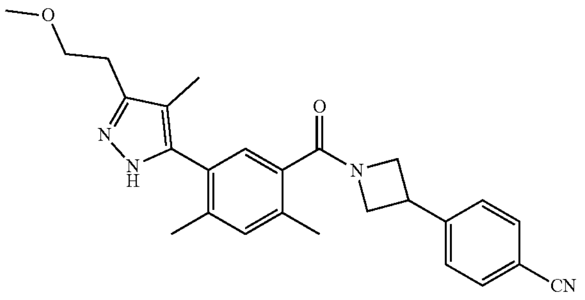 [SMILES: COCCc1n[nH]c(-c2cc(C(=O)N3CC(c4ccc(C#N)cc4)C3)c(C)cc2C)c1C] | 0.078 |
| 002-306 | 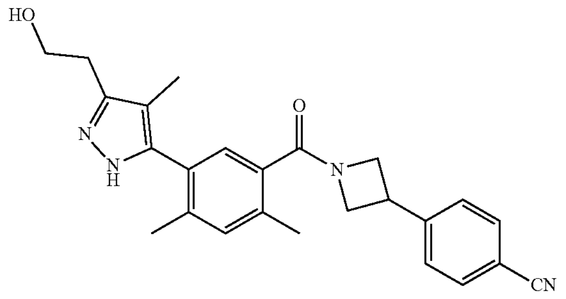 [SMILES: Cc1cc(C)c(-c2[nH]nc(CCO)c2C)cc1C(=O)N1CC(c2ccc(C#N)cc2)C1] | |
| 002-307 | 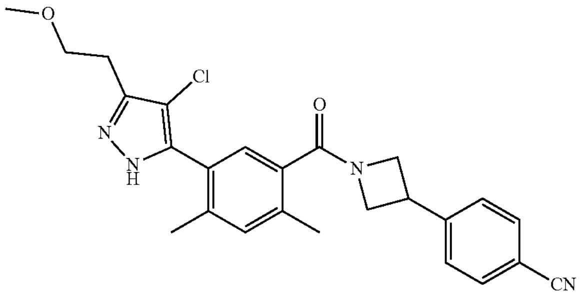 [SMILES: COCCc1n[nH]c(-c2cc(C(=O)N3CC(c4ccc(C#N)cc4)C3)c(C)cc2C)c1Cl] | 0.056 |
| 002-308 | 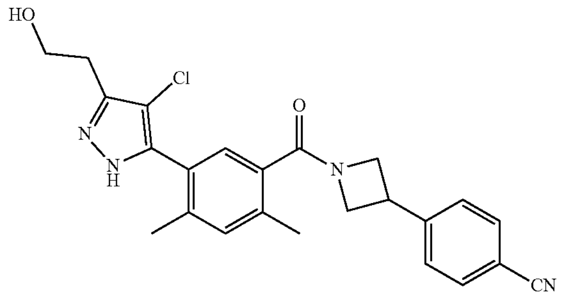 [SMILES: Cc1cc(C)c(-c2[nH]nc(CCO)c2Cl)cc1C(=O)N1CC(c2ccc(C#N)cc2)C1] | |

TABLE C-2-continued
| Cmpd No. | Structure | Hu FASN IC50 (μM) |
|---|---|---|
| | Fatty Acid Synthase Inhibitors | |
| 002-309 | 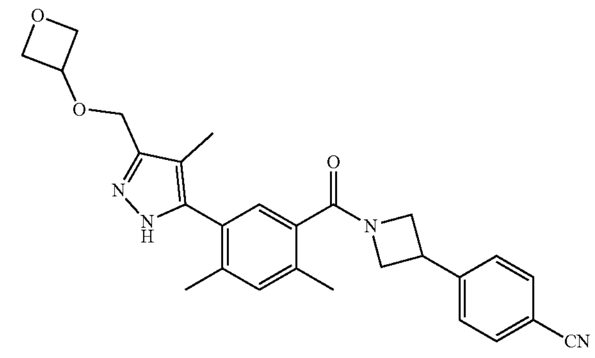 [SMILES: Cc1cc(C)c(-c2[nH]nc(COC3COC3)c2C)cc1C(=O)N1CC(c2ccc(C#N)cc2)C1] | 0.037 |
| 002-310 | 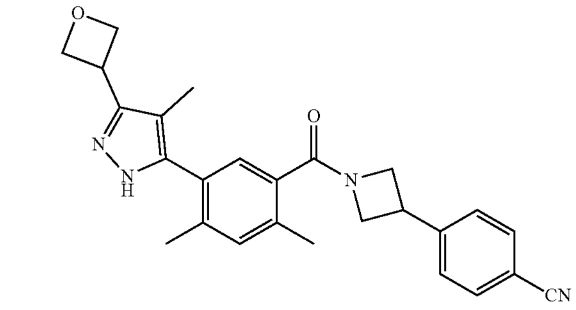 [SMILES: Cc1cc(C)c(-c2[nH]nc(C3COC3)c2C)cc1C(=O)N1CC(c2ccc(C#N)cc2)C1] | |
| 002-311 | 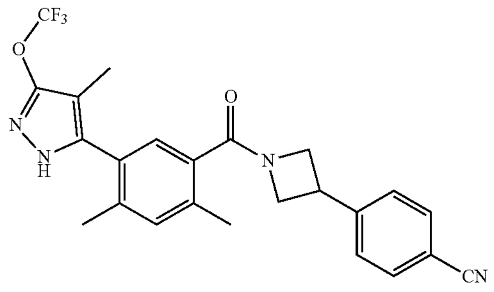 [SMILES: Cc1cc(C)c(-c2[nH]nc(OC(F)(F)F)c2C)cc1C(=O)N1CC(c2ccc(C#N)cc2)C1] | |
| 002-312 | 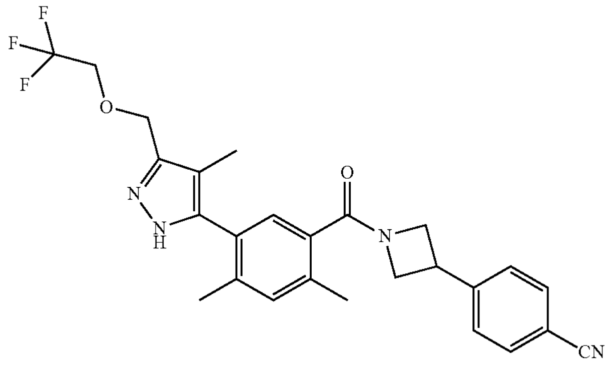 [SMILES: Cc1cc(C)c(-c2[nH]nc(COCC(F)(F)F)c2C)cc1C(=O)N1CC(c2ccc(C#N)cc2)C1] | 0.037 |

TABLE C-2-continued
| Fatty Acid Synthase Inhibitors | | |
|---|---|---|
| Cmpd No. | Structure | Hu FASN IC50 (μM) |
| 002-313 | 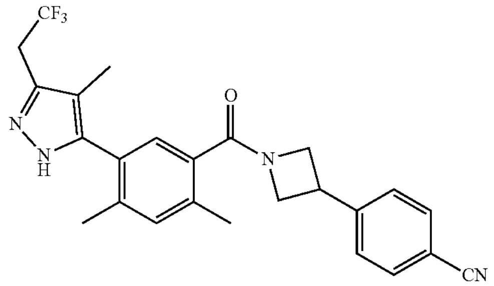 [SMILES: Cc1cc(C)c(-c2[nH]nc(CC(F)(F)F)c2C)cc1C(=O)N1CC(c2ccc(C#N)cc2)C1] | 0.1 |
| 002-314 | 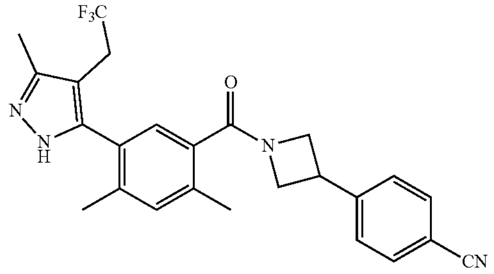 [SMILES: Cc1cc(C)c(-c2[nH]nc(C)c2CC(F)(F)F)cc1C(=O)N1CC(c2ccc(C#N)cc2)C1] | 0.46 |
| 002-315 | 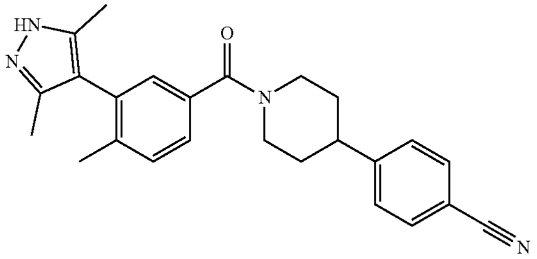 [SMILES: Cc1ccc(C(=O)N2CCC(c3ccc(C#N)cc3)CC2)cc1-c1c(C)n[nH]c1C] | |
| 002-316 | 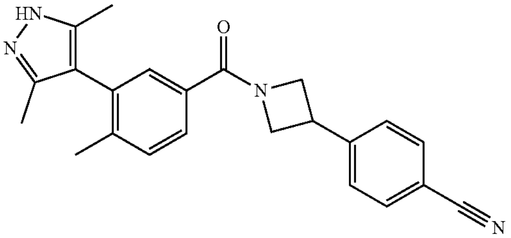 [SMILES: Cc1ccc(C(=O)N2CC(c3ccc(C#N)cc3)C2)cc1-c1c(C)n[nH]c1C] | |
| 002-317 | 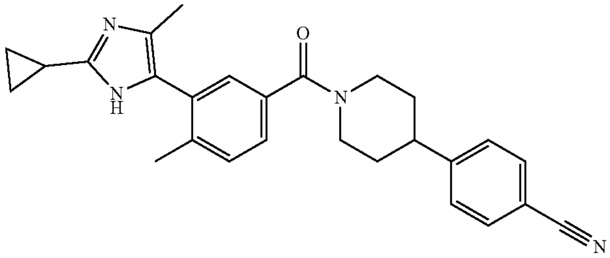 [SMILES: Cc1ccc(C(=O)N2CCC(c3ccc(C#N)cc3)CC2)cc1-c1[nH]c(C2CC2)nc1C] | |

TABLE C-2-continued
| Fatty Acid Synthase Inhibitors | | |
|---|---|---|
| Cmpd No. | Structure | Hu FASN IC50 (μM) |
| 002-318 | 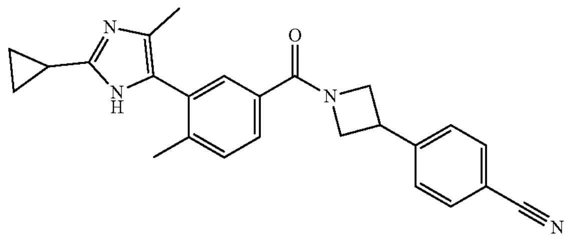 [SMILES: Cc1ccc(C(=O)N2CC(c3ccc(C#N)cc3)C2)cc1-c1[nH]c(C2CC2)nc1C] | |
| 002-320 | 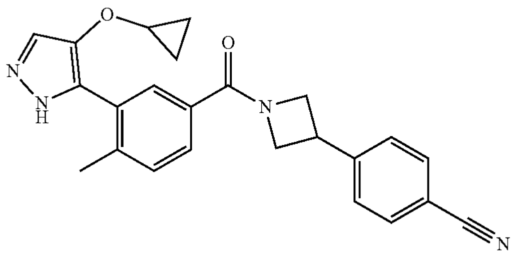 [SMILES: Cc1ccc(C(=O)N2CC(c3ccc(C#N)cc3)C2)cc1-c1[nH]ncc1OC1CC1] | |
| 002-321 | 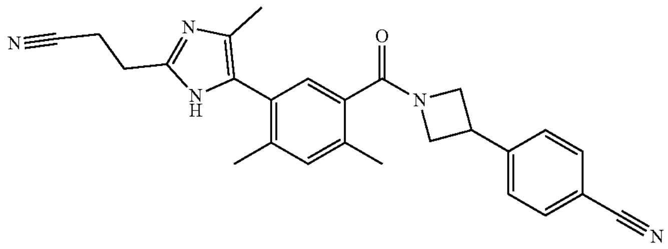 [SMILES: Cc1cc(C)c(-c2[nH]c(CCC#N)nc2C)cc1C(=O)N1CC(c2ccc(C#N)cc2)C1] | |
| 002-322 | 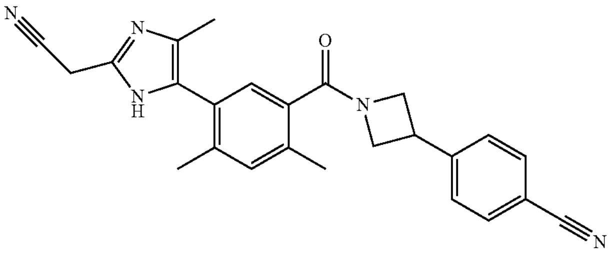 [SMILES: Cc1cc(C)c(-c2[nH]c(CC#N)nc2C)cc1C(=O)N1CC(c2ccc(C#N)cc2)C1] | |
| 002-323 | 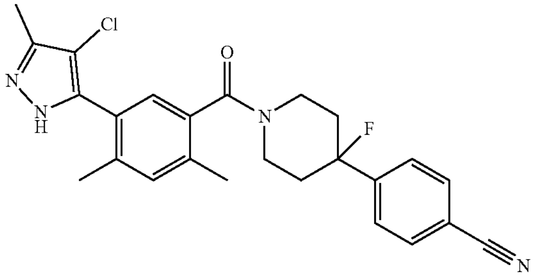 [SMILES: Cc1cc(C)c(-c2[nH]nc(C)c2Cl)cc1C(=O)N1CCC(F)(c2ccc(C#N)cc2)CC1] | |

TABLE C-2-continued
| Cmpd No. | Structure | Hu FASN IC50 (μM) |
|---|---|---|
| Fatty Acid Synthase Inhibitors | | |
| 002-324 | 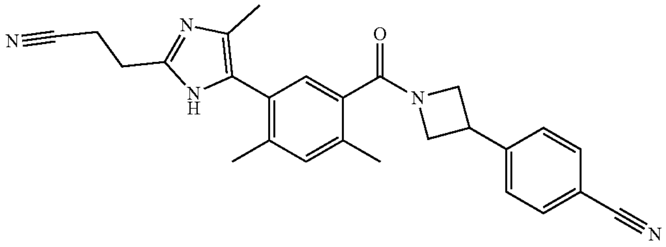 [SMILES: Cc1cc(C)c(-c2[nH]c(CCC#N)nc2C)cc1C(=O)N1CC(c2ccc(C#N)cc2)C1] | |
| 002-325 | 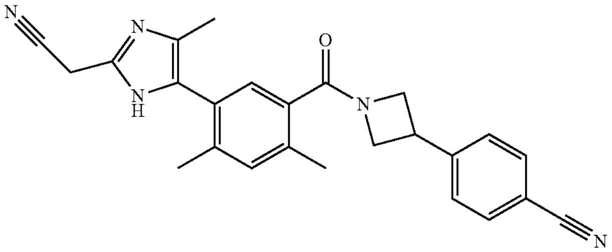 [SMILES: Cc1cc(C)c(-c2[nH]c(CC#N)nc2C)cc1C(=O)N1CC(c2ccc(C#N)cc2)C1] | |
| 002-326 | 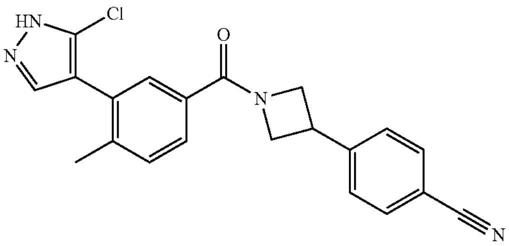 [SMILES: Cc1ccc(C(=O)N2CC(c3ccc(C#N)cc3)C2)cc1-c1cn[nH]c1Cl] | |
| 002-327 | 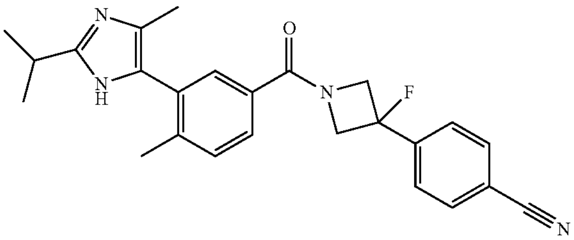 [SMILES: Cc1ccc(C(=O)N2CC(F)(c3ccc(C#N)cc3)C2)cc1-c1[nH]c(C(C)C)nc1C] | |
| 002-328 | 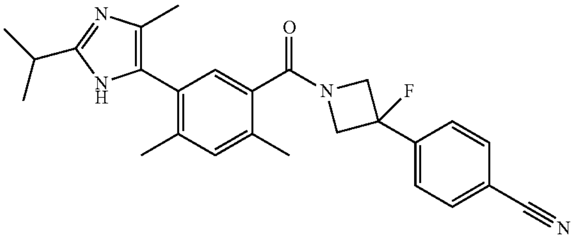 [SMILES: Cc1cc(C)c(-c2[nH]c(C(C)C)nc2C)cc1C(=O)N1CC(F)(c2ccc(C#N)cc2)C1] | |
| 002-329 | 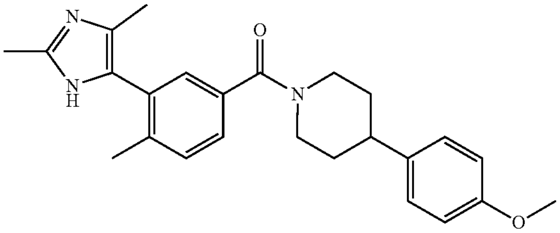 | 0.089 |

TABLE C-2-continued
| Fatty Acid Synthase Inhibitors | | |
|---|---|---|
| Cmpd No. | Structure | Hu FASN IC50 (μM) |
| 002-330 | 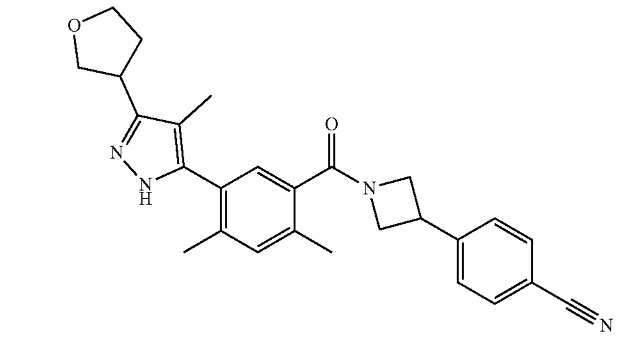 [SMILES: Cc1cc(C)c(-c2[nH]nc(C3CCOC3)c2C)cc1C(=O)N1CC(c2ccc(C#N)cc2)C1] | 0.1 |
| 002-331 | 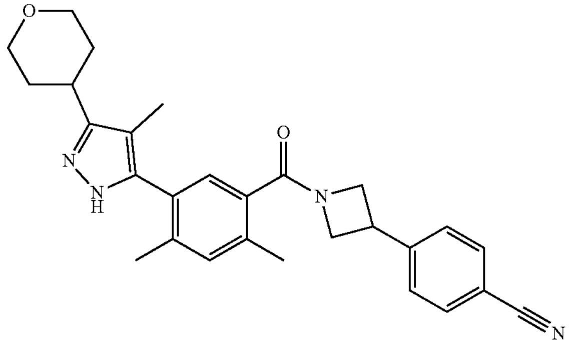 [SMILES: Cc1cc(C)c(-c2[nH]nc(C3CCOCC3)c2C)cc1C(=O)N1CC(c2ccc(C#N)cc2)C1] | 0.11 |
| 002-332 | 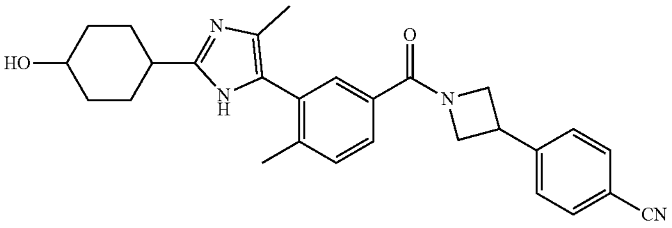 [SMILES: Cc1ccc(C(=O)N2CC(c3ccc(C#N)cc3)C2)cc1-c1[nH]c(C2CCC(O)CC2)nc1C] | 0.01 |
| 002-233 | 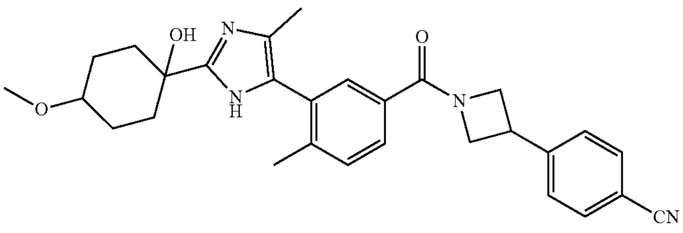 [SMILES: COC1CCC(O)(c2nc(C)c(-c3cc(C(=O)N4CC(c5ccc(C#N)cc5)C4)ccc3C)[nH]2)CC1] | |
| 002-334 | 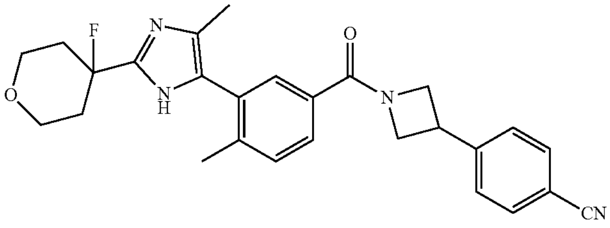 [SMILES: Cc1ccc(C(=O)N2CC(c3ccc(C#N)cc3)C2)cc1-c1[nH]c(C2(F)CCOCC2)nc1C] | |

TABLE C-2-continued
| Fatty Acid Synthase Inhibitors | | |
|---|---|---|
| Cmpd No. | Structure | Hu FASN IC50 (μM) |
| 002-335 | 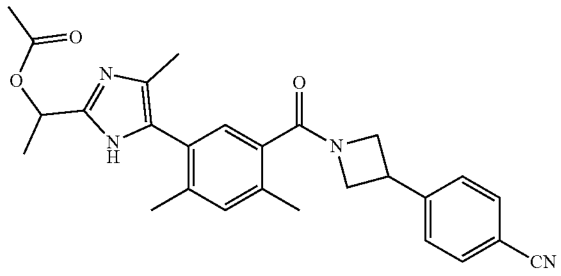 [SMILES: CC(=O)OC(C)c1nc(C)c(-c2cc(C(=O)N3CC(c4ccc(C#N)cc4)C3)c(C)cc2C)[nH]1] | |
| 002-336 | 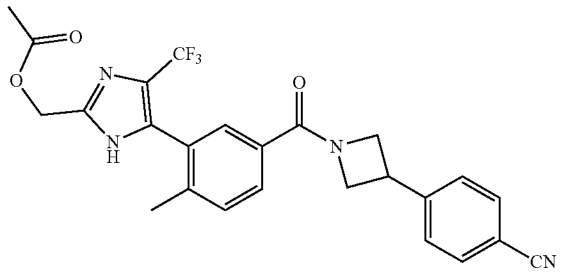 [SMILES: CC(=O)OCc1nc(C(F)(F)F)c(-c2cc(C(=O)N3CC(c4ccc(C#N)cc4)C3)ccc2C)[nH]1] | |
| 002-337 | 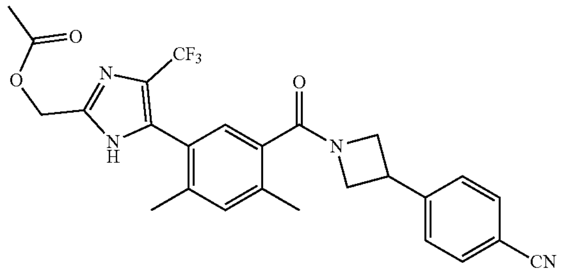 [SMILES: CC(=O)OCc1nc(C(F)(F)F)c(-c2cc(C(=O)N3CC(c4ccc(C#N)cc4)C3)c(C)cc2C)[nH]1] | |
| 002-338 | 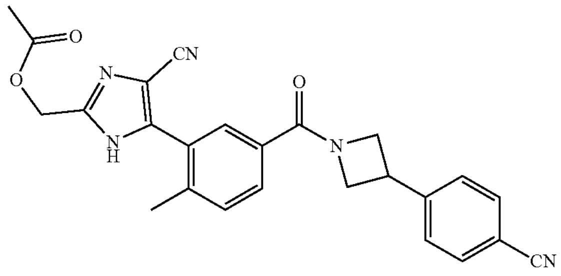 [SMILES: CC(=O)OCc1nc(C#N)c(-c2cc(C(=O)N3CC(c4ccc(C#N)cc4)C3)ccc2C)[nH]1] | |
| 002-339 | 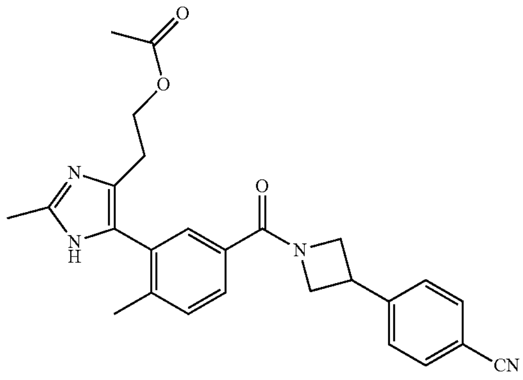 [SMILES: CC(=O)OCCc1nc(C)[nH]c1-c1cc(C(=O)N2CC(c3ccc(C#N)cc3)C2)ccc1C] | |

TABLE C-2-continued
| Fatty Acid Synthase Inhibitors | | |
|---|---|---|
| Cmpd No. | Structure | Hu FASN IC50 (μM) |
| 002-340 | 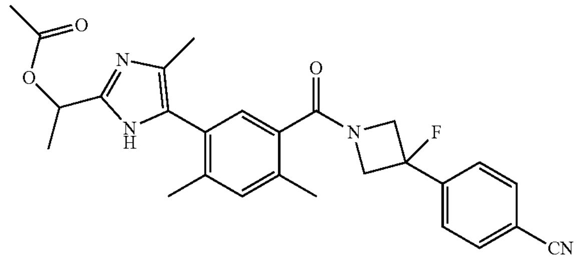 [SMILES: CC(=O)OC(C)c1nc(C)c(-c2cc(C(=O)N3CC(F)(c4ccc(C#N)cc4)C3)c(C)cc2C)[nH]1] | |
| 002-341 | 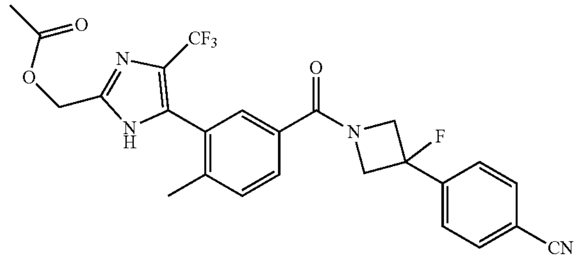 [SMILES: CC(=O)OCc1nc(C(F)(F)F)c(-c2cc(C(=O)N3CC(F)(c4ccc(C#N)cc4)C3)ccc2C)[nH]1] | |
| 002-342 | 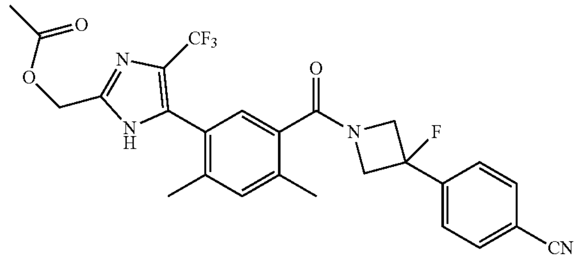 [SMILES: CC(=O)OCc1nc(C(F)(F)F)c(-c2cc(C(=O)N3CC(F)(c4ccc(C#N)cc4)C3)c(C)cc2C)[nH]1] | |
| 002-343 | 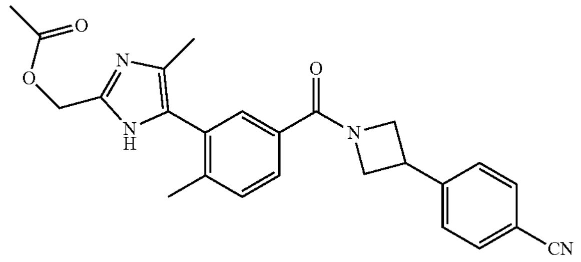 [SMILES: CC(=O)OCc1nc(C)c(-c2cc(C(=O)N3CC(c4ccc(C#N)cc4)C3)ccc2C)[nH]1] | |
| 002-344 | 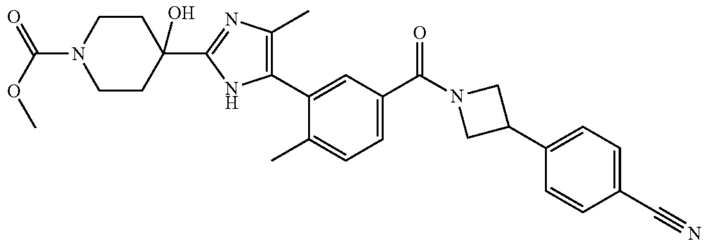 [SMILES: COC(=O)N1CCC(O)(c2nc(C)c(-c3cc(C(=O)N4CC(c5ccc(C#N)cc5)C4)ccc3C)[nH]2)CC1] | 0.024 |

TABLE C-2-continued
| Fatty Acid Synthase Inhibitors | | |
|---|---|---|
| Cmpd No. | Structure | Hu FASN IC50 (μM) |
| 002-345 | 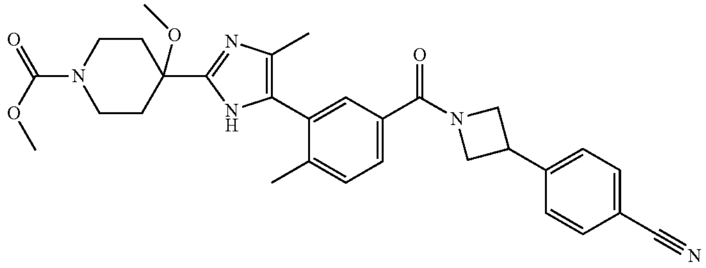 [SMILES: COC(=O)N1CCC(OC)(c2nc(C)c(-c3cc(C(=O)N4CC(c5ccc(C#N)cc5)C4)ccc3C)[nH]2)CC1] | 0.035 |
| 002-346 | 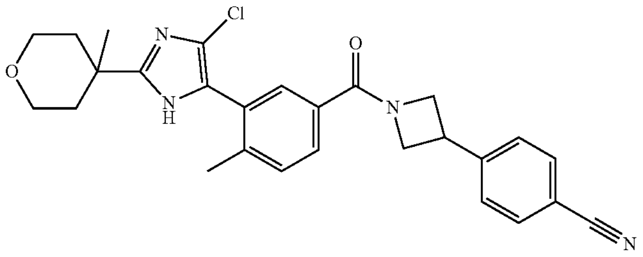 [SMILES: Cc1ccc(C(=O)N2CC(c3ccc(C#N)cc3)C2)cc1-c1[nH]c(C2(C)CCOCC2)nc1Cl] | 0.018 |
| 002-347 | 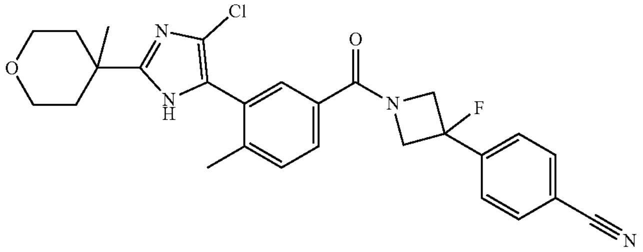 [SMILES: Cc1ccc(C(=O)N2CC(F)(c3ccc(C#N)cc3)C2)cc1-c1[nH]c(C2(C)CCOCC2)nc1Cl] | 0.016 |
| 002-348 | 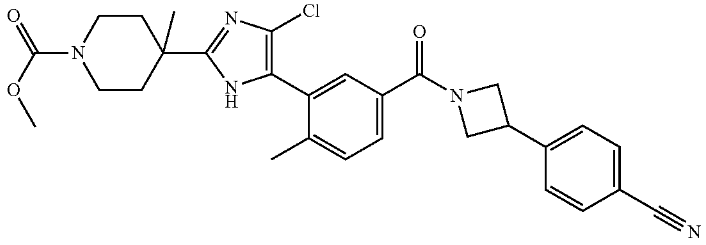 [SMILES: COC(=O)N1CCC(C)(c2nc(Cl)c(-c3cc(C(=O)N4CC(c5ccc(C#N)cc5)C4)ccc3C)[nH]2)CC1] | 0.014 |
| 002-349 | 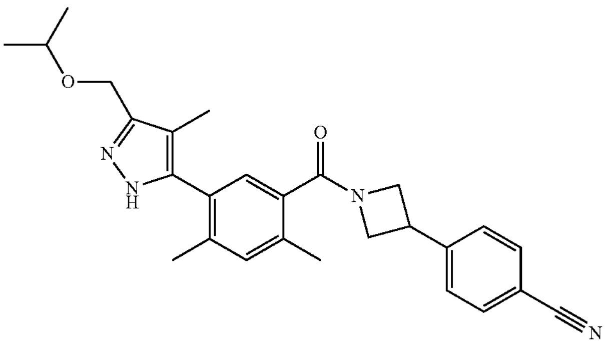 [SMILES: Cc1cc(C)c(-c2[nH]nc(COC(C)C)c2C)cc1C(=O)N1CC(c2ccc(C#N)cc2)C1] | 0.019 |

TABLE C-2-continued
| Fatty Acid Synthase Inhibitors | | |
|---|---|---|
| Cmpd No. | Structure | Hu FASN IC50 (μM) |
| 002-350 | 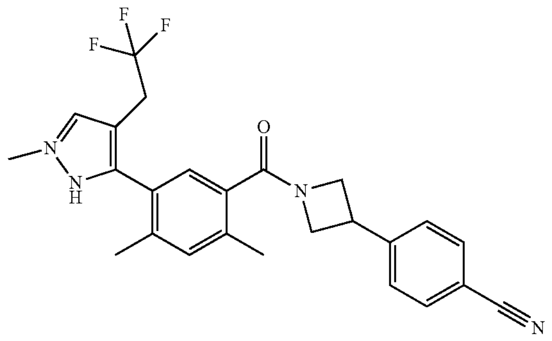 | 0.055 |
| 002-351 | 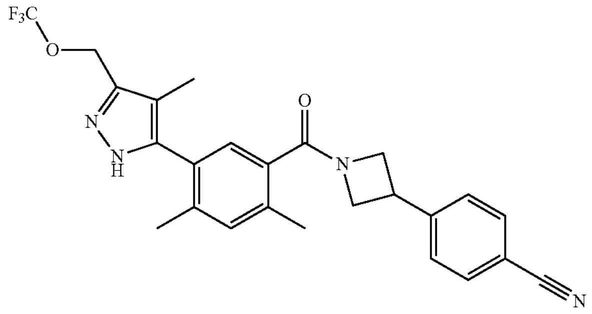 [SMILES: Cc1cc(C)c(-c2[nH]nc(COC(F)(F)F)c2C)cc1C(=O)N1CC(c2ccc(C#N)cc2)C1] | |
| 002-352 | 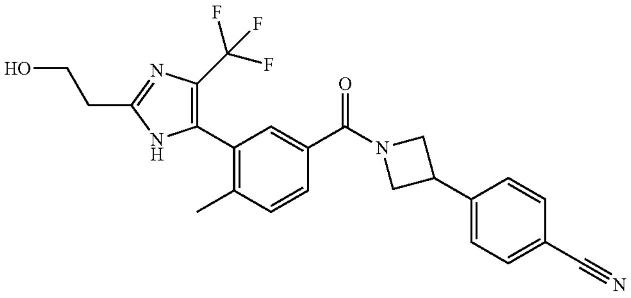 [SMILES: Cc1ccc(C(=O)N2CC(c3ccc(C#N)cc3)C2)cc1-c1[nH]c(CCO)nc1C(F)(F)F] | 0.011 |
| 002-353 | 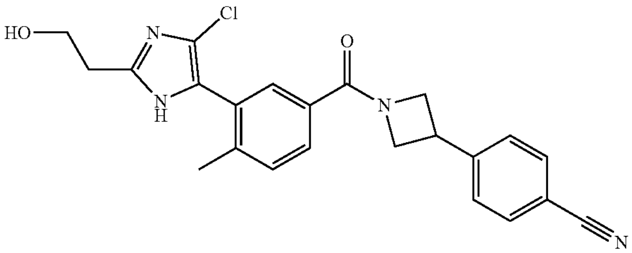 [SMILES: Cc1ccc(C(=O)N2CC(c3ccc(C#N)cc3)C2)cc1-c1[nH]c(CCO)nc1Cl] | 0.009 |
| 002-354 | 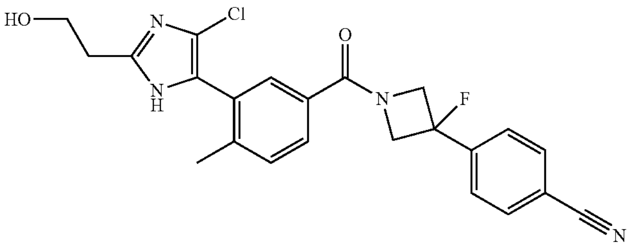 [SMILES: Cc1ccc(C(=O)N2CC(F)(c3ccc(C#N)cc3)C2)cc1-c1[nH]c(CCO)nc1Cl] | 0.018 |

TABLE C-2-continued
| Fatty Acid Synthase Inhibitors | | |
|---|---|---|
| Cmpd No. | Structure | Hu FASN IC50 (μM) |
| 002-355 | 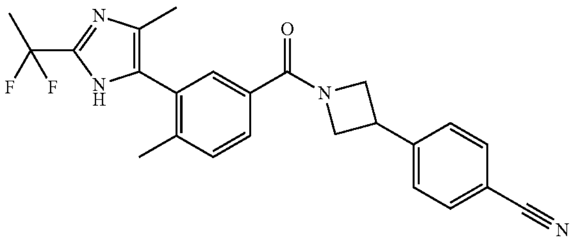 [SMILES: Cc1ccc(C(=O)N2CC(c3ccc(C#N)cc3)C2)cc1-c1[nH]c(C(C)(F)F)nc1C] | 0.082 |
| 002-356 | 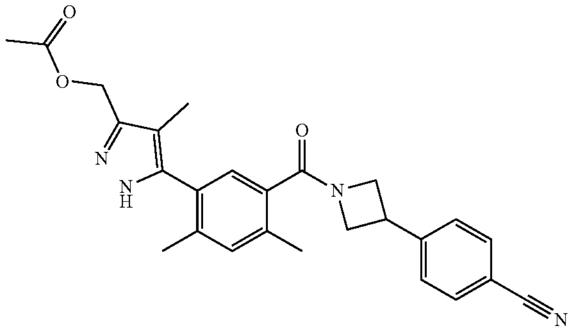 [SMILES: CC(=O)OCC(=N)/C(C)=C(\N)c1cc(C(=O)N2CC(c3ccc(C#N)cc3)C2)c(C)cc1C] | 0.851 |
| 002-357 | 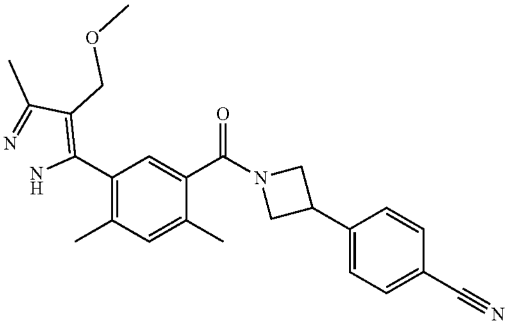 [SMILES: COC/C(C(C)=N)=C(/N)c1cc(C(=O)N2CC(c3ccc(C#N)cc3)C2)c(C)cc1C] | 0.087 |
| 002-358 | 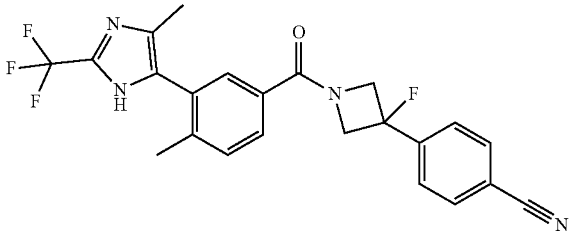 [SMILES: Cc1ccc(C(=O)N2CC(F)(c3ccc(C#N)cc3)C2)cc1-c1[nH]c(C(F)(F)F)nc1C] | 0.1001-10 |
| 002-359 | 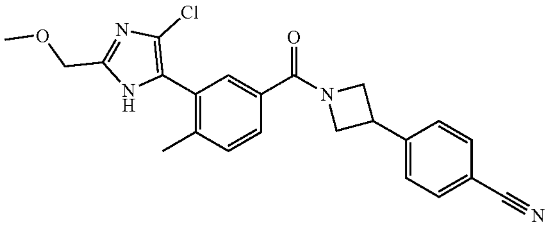 [SMILES: COCc1nc(Cl)c(-c2cc(C(=O)N3CC(c4ccc(C#N)cc4)C3)ccc2C)[nH]1] | 0.014 |

TABLE C-2-continued
| Fatty Acid Synthase Inhibitors | | |
|---|---|---|
| Cmpd No. | Structure | Hu FASN IC50 (μM) |
| 002-360 | 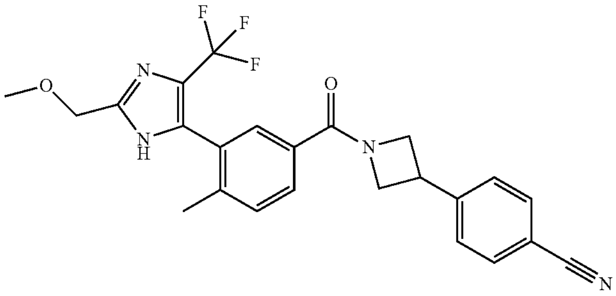 [SMILES: COCc1nc(C(F)(F)F)c(-c2cc(C(=O)N3CC(c4ccc(C#N)cc4)C3)ccc2C)[nH]1] | 0.012 |
| 002-361 | 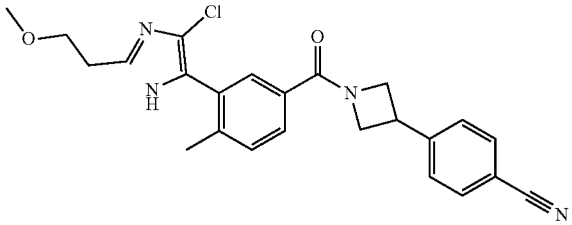 [SMILES: COCC/C=N/C(Cl)=C(\N)c1cc(C(=O)N2CC(c3ccc(C#N)cc3)C2)ccc1C] | 0.013 |
| 002-362 | 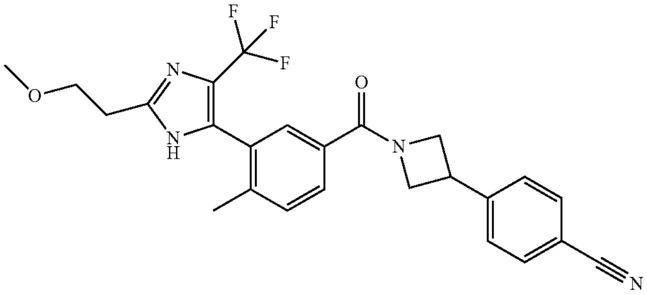 [SMILES: COCCc1nc(C(F)(F)F)c(-c2cc(C(=O)N3CC(c4ccc(C#N)cc4)C3)ccc2C)[nH]1] | 0.011 |
| 002-363 | 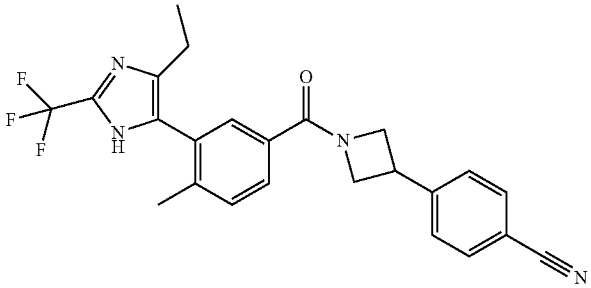 [SMILES: CCc1nc(C(F)(F)F)[nH]c1-c1cc(C(=O)N2CC(c3ccc(C#N)cc3)C2)ccc1C] | 0.021 |
| 002-364 | 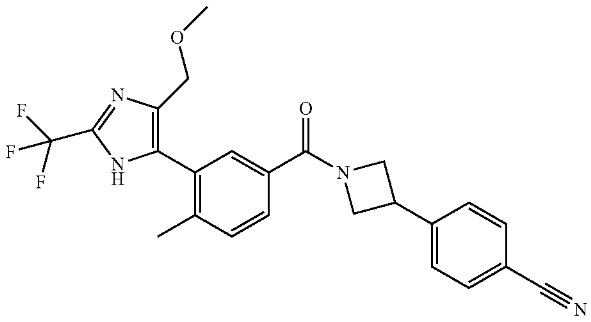 [SMILES: COCc1nc(C(F)(F)F)[nH]c1-c1cc(C(=O)N2CC(c3ccc(C#N)cc3)C2)ccc1C] | 0.040 |

TABLE C-2-continued
| Fatty Acid Synthase Inhibitors | | |
|---|---|---|
| Cmpd No. | Structure | Hu FASN IC50 (µM) |
| 002-365 | 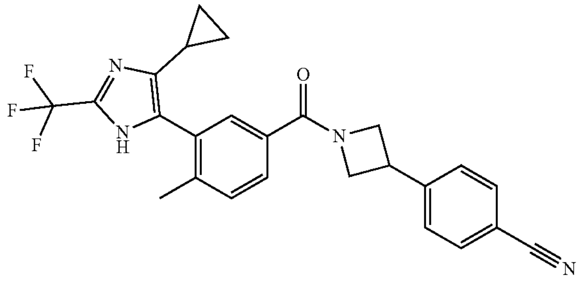 [SMILES: Cc1ccc(C(=O)N2CC(c3ccc(C#N)cc3)C2)cc1-c1[nH]c(C(F)(F)F)nc1C1CC1] | 0.023 |
| 002-366 | 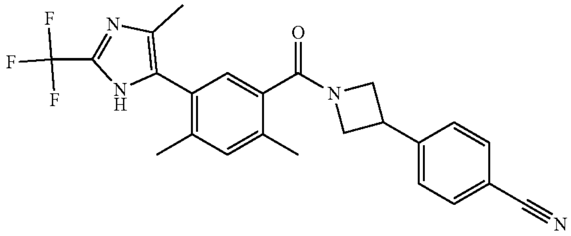 [SMILES: Cc1cc(C)c(-c2[nH]c(C(F)(F)F)nc2C)cc1C(=O)N1CC(c2ccc(C#N)cc2)C1] | 0.022 |
| 002-367 | 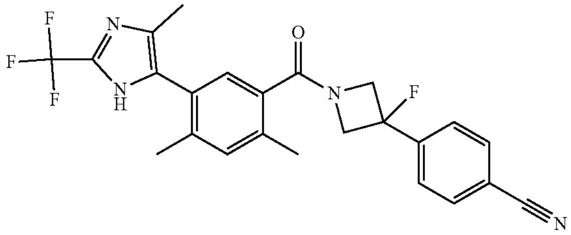 [SMILES: Cc1cc(C)c(-c2[nH]c(C(F)(F)F)nc2C)cc1C(=O)N1CC(F)(c2ccc(C#N)cc2)C1] | 0.040 |
| 002-368 | 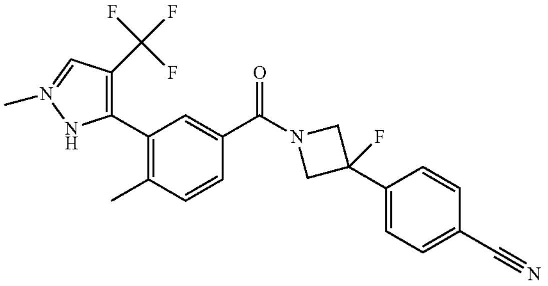 | 0.012 |
| 002-369 | 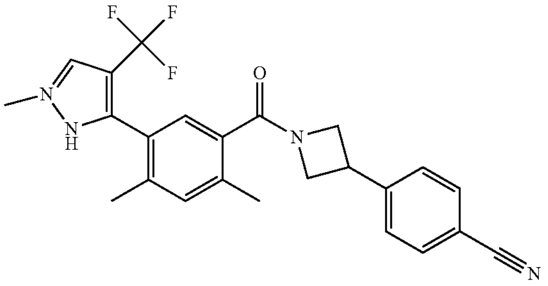 | 0.014 |

TABLE C-2-continued
| Fatty Acid Synthase Inhibitors | | |
|---|---|---|
| Cmpd No. | Structure | Hu FASN IC50 (μM) |
| 002-370 | 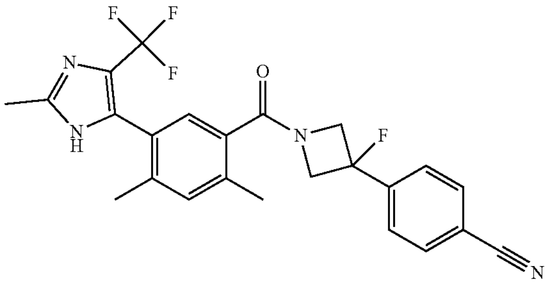 [SMILES: Cc1nc(C(F)(F)F)c(-c2cc(C(=O)N3CC(F)(c4ccc(C#N)cc4)C3)c(C)cc2C)[nH]1] | 0.012 |
| 002-371 | 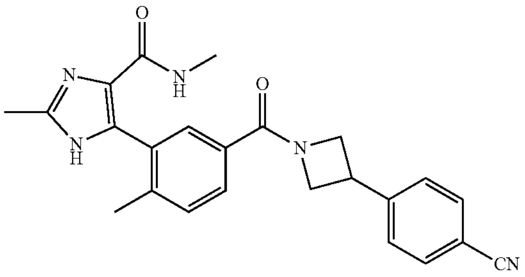 [SMILES: CNC(=O)c1nc(C)[nH]c1-c1cc(C(=O)N2CC(c3ccc(C#N)cc3)C2)ccc1C] | 0.82 |
| 002-374 | 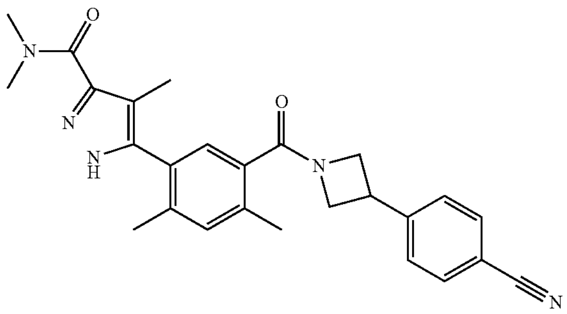 [SMILES: C/C(C(=N)C(=O)N(C)C)=C(/N)c1cc(C(=O)N2CC(c3ccc(C#N)cc3)C2)c(C)cc1C] | 0.024 |
| 002-375 | 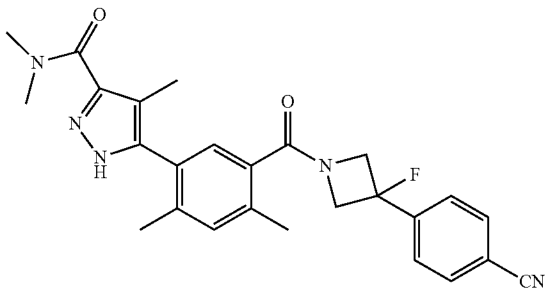 [SMILES: Cc1cc(C)c(-c2[nH]nc(C(=O)N(C)C)c2C)cc1C(=O)N1CC(F)(c2ccc(C#N)cc2)C1] | |
| 002-376 | 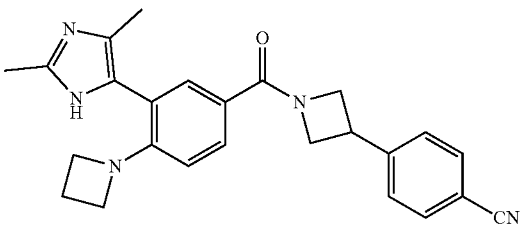 [SMILES: Cc1nc(C)c(-c2cc(C(=O)N3CC(c4ccc(C#N)cc4)C3)ccc2N2CCC2)[nH]1] | 0.029 |

TABLE C-2-continued
| Fatty Acid Synthase Inhibitors | | |
|---|---|---|
| Cmpd No. | Structure | Hu FASN IC50 (μM) |
| 002-377 | 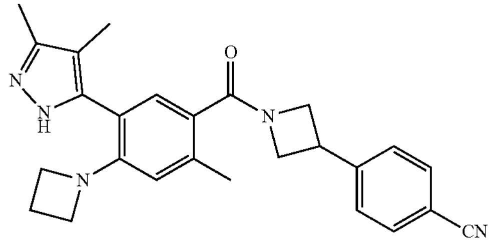 [SMILES: Cc1cc(N2CCC2)c(-c2[nH]nc(C)c2C)cc1C(=O)N1CC(c2ccc(C#N)cc2)C1] | 0.029 |
| 002-378 | 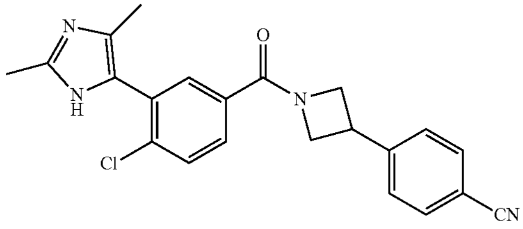 [SMILES: Cc1nc(C)c(-c2cc(C(=O)N3CC(c4ccc(C#N)cc4)C3)ccc2Cl)[nH]1] | 0.072 |
| 002-379 | 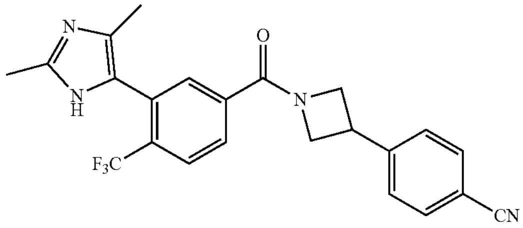 [SMILES: Cc1nc(C)c(-c2cc(C(=O)N3CC(c4ccc(C#N)cc4)C3)ccc2C(F)(F)F)[nH]1] | 0.059 |
| 002-380 | 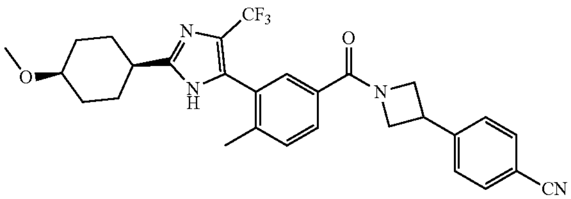 [SMILES: CO[C@H]1CC[C@@H](c2nc(C(F)(F)F)c(-c3cc(C(=O)N4CC(c5ccc(C#N)cc5)C4)ccc3C)[nH]2)CC1] | 0.013 |
| 002-381 | 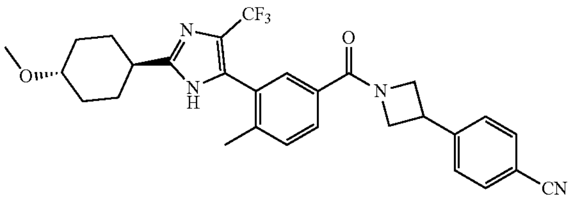 [SMILES: CO[C@H]1CC[C@H](c2nc(C(F)(F)F)c(-c3cc(C(=O)N4CC(c5ccc(C#N)cc5)C4)ccc3C)[nH]2)CC1] | 0.009 |
| 002-382 | 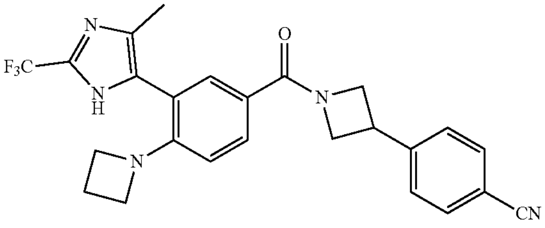 [SMILES: Cc1nc(C(F)(F)F)[nH]c1-c1cc(C(=O)N2CC(c3ccc(C#N)cc3)C2)ccc1N1CCC1] | 0.018 |

TABLE C-2-continued
| Fatty Acid Synthase Inhibitors | | |
|---|---|---|
| Cmpd No. | Structure | Hu FASN IC50 (μM) |
| 002-383 | 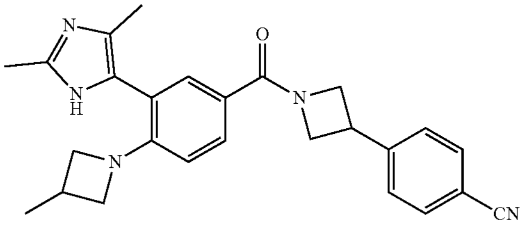 [SMILES: Cc1nc(C)c(-c2cc(C(=O)N3CC(c4ccc(C#N)cc4)C3)ccc2N2CC(C)C2)[nH]1] | 0.024 |
| 002-384 | 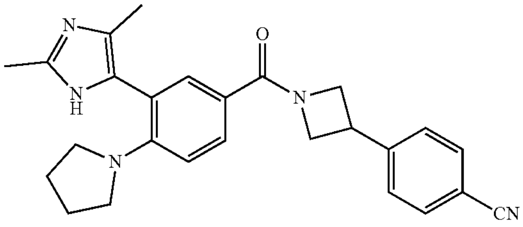 [SMILES: Cc1nc(C)c(-c2cc(C(=O)N3CC(c4ccc(C#N)cc4)C3)ccc2N2CCCC2)[nH]1] | 0.012 |
| 002-385 | 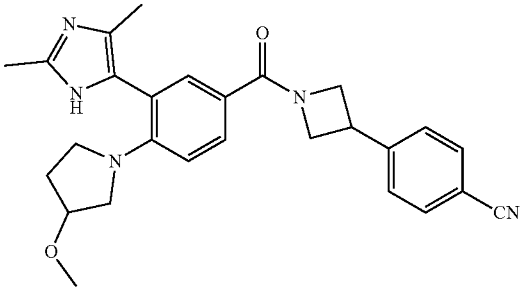 [SMILES: COC1CCN(c2ccc(C(=O)N3CC(c4ccc(C#N)cc4)C3)cc2-c2[nH]c(C)nc2C)C1] | 0.04 |
| 002-386 | 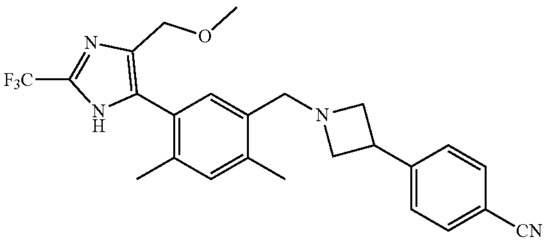 [SMILES: COCc1nc(C(F)(F)F)[nH]c1-c1cc(CN2CC(c3ccc(C#N)cc3)C2)c(C)cc1C] | |

TABLE C-3
| Fatty Acid Synthase Inhibitors | | |
|---|---|---|
| Cmpd No. | Structure | FASN (human) IC50 (μM) |
| 005-1 | 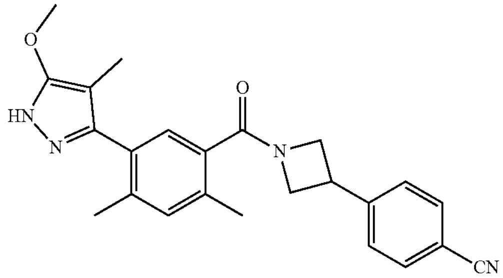 [SMILES: COc1[nH]nc(-c2cc(C(=O)N3CC(c4ccc(C#N)cc4)C3)c(C)cc2C)c1C] | 0.039 |
| 005-2 | 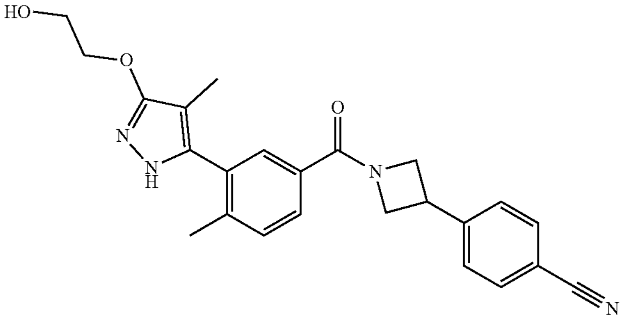 [SMILES: Cc1ccc(C(=O)N2CC(c3ccc(C#N)cc3)C2)cc1-c1[nH]nc(OCCO)c1C] | 0.023 |
| 005-3 | 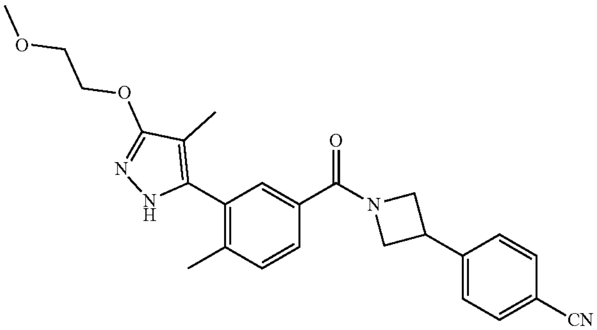 [SMILES: COCCOc1n[nH]c(-c2cc(C(=O)N3CC(c4ccc(C#N)cc4)C3)ccc2C)c1C] | 0.015 |
| 005-4 | 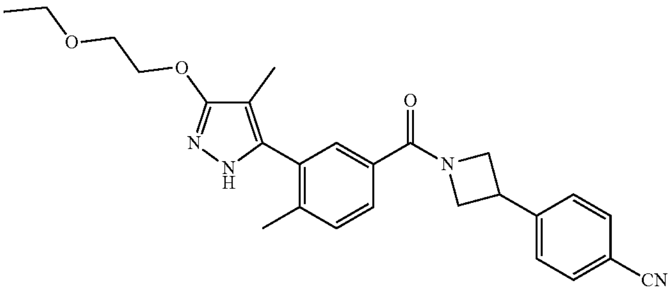 [SMILES: CCOCCOc1n[nH]c(-c2cc(C(=O)N3CC(c4ccc(C#N)cc4)C3)ccc2C)c1C] | 0.02 |
| 005-5 | 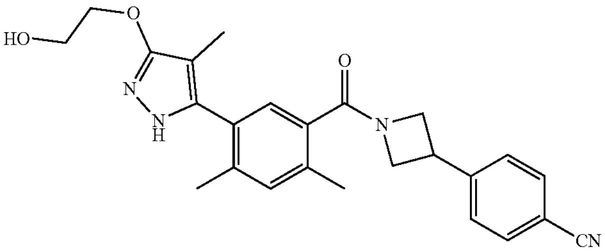 [SMILES: Cc1cc(C)c(-c2[nH]nc(OCCO)c2C)cc1C(=O)N1CC(c2ccc(C#N)cc2)C1] | 0.019 |

TABLE C-3-continued
| Fatty Acid Synthase Inhibitors | | |
|---|---|---|
| Cmpd No. | Structure | FASN (human) IC50 (μM) |
| 005-6 | 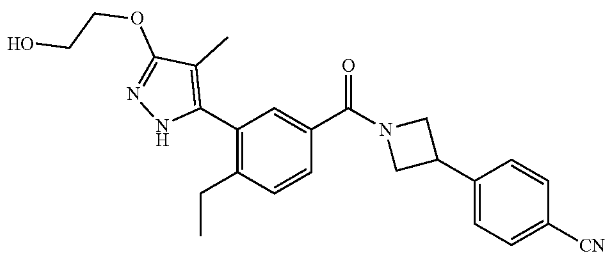 [SMILES: CCc1ccc(C(=O)N2CC(c3ccc(C#N)cc3)C2)cc1-c1[nH]nc(OCCO)c1C] | 0.016 |
| 005-7 | 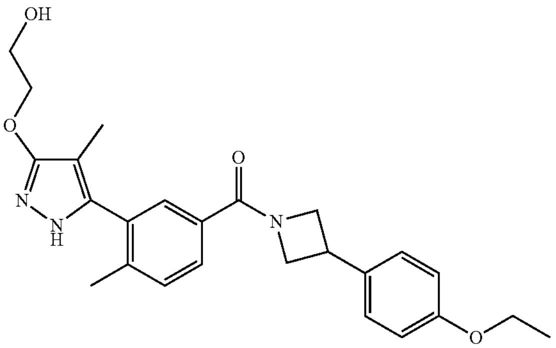 [SMILES: CCOc1ccc(C2CN(C(=O)c3ccc(C)c(-c4[nH]nc(OCCO)c4C)c3)C2)cc1] | 0.022 |
| 005-8 | 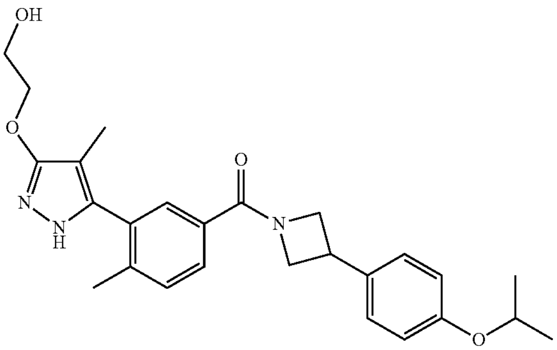 [SMILES: Cc1ccc(C(=O)N2CC(c3ccc(OC(C)C)cc3)C2)cc1-c1[nH]nc(OCCO)c1C] | 0.035 |
| 005-9 | 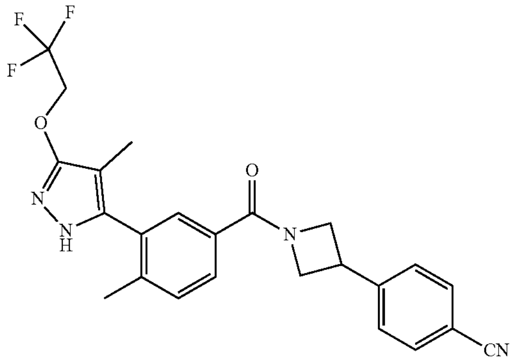 [SMILES: Cc1ccc(C(=O)N2CC(c3ccc(C#N)cc3)C2)cc1-c1[nH]nc(OCC(F)(F)F)c1C] | |

TABLE C-3-continued
| Fatty Acid Synthase Inhibitors | | |
|---|---|---|
| Cmpd No. | Structure | FASN (human) IC50 (μM) |
| 005-10 | 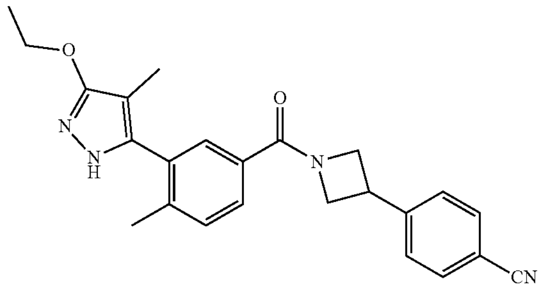 [SMILES: CCOc1n[nH]c(-c2cc(C(=O)N3CC(c4ccc(C#N)cc4)C3)ccc2C)c1C] | |
| 005-11 | 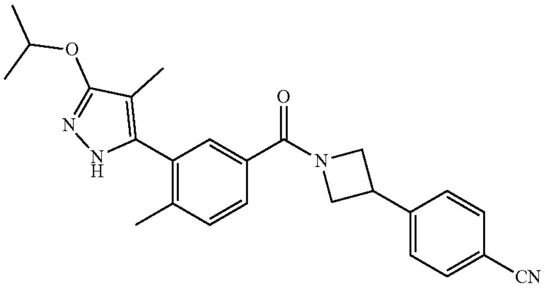 [SMILES: Cc1ccc(C(=O)N2CC(c3ccc(C#N)cc3)C2)cc1-c1[nH]nc(OC(C)C)c1C] | |
| 005-12 | 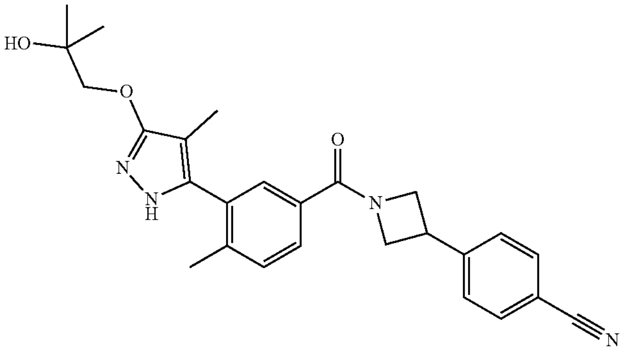 [SMILES: Cc1ccc(C(=O)N2CC(c3ccc(C#N)cc3)C2)cc1-c1[nH]nc(OCC(C)(C)O)c1C] | 0.01 |
| 005-13 | 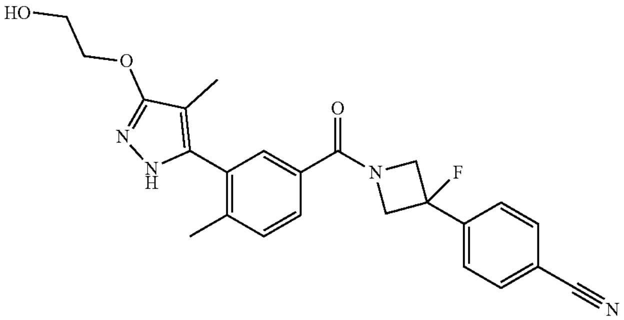 [SMILES: Cc1ccc(C(=O)N2CC(F)(c3ccc(C#N)cc3)C2)cc1-c1[nH]nc(OCCO)c1C] | 0.19 |

TABLE C-3-continued
| Fatty Acid Synthase Inhibitors | | |
|---|---|---|
| Cmpd No. | Structure | FASN (human) IC50 (μM) |
| 005-14 | 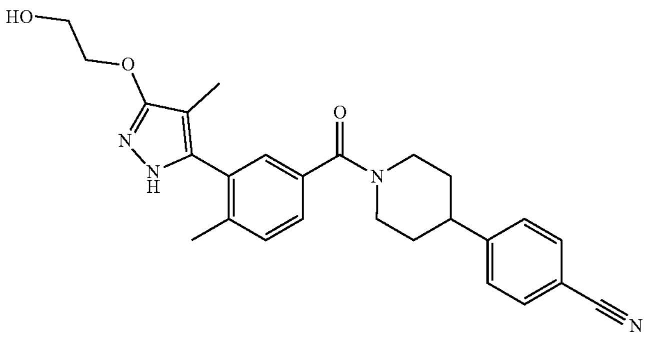 [SMILES: Cc1ccc(C(=O)N2CCC(c3ccc(C#N)cc3)CC2)cc1-c1[nH]nc(OCCO)c1C] | 0.084 |
| 005-15 | 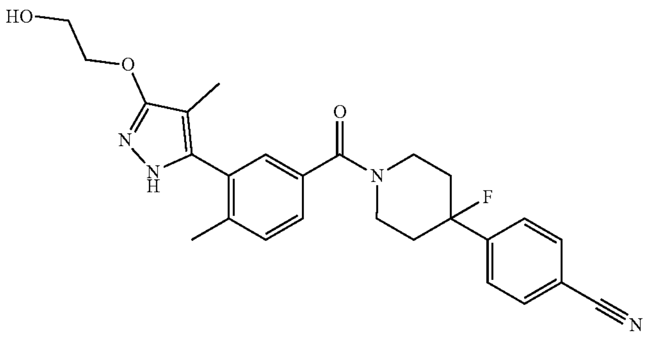 [SMILES: Cc1ccc(C(=O)N2CCC(F)(c3ccc(C#N)cc3)CC2)cc1-c1[nH]nc(OCCO)c1C] | 0.23 |
| 005-16 | 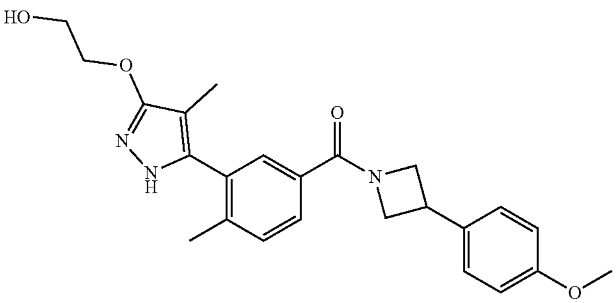 [SMILES: COc1ccc(C2CN(C(=O)c3ccc(C)c(-c4[nH]nc(OCCO)c4C)c3)C2)cc1] | 0.039 |
| 005-17 | 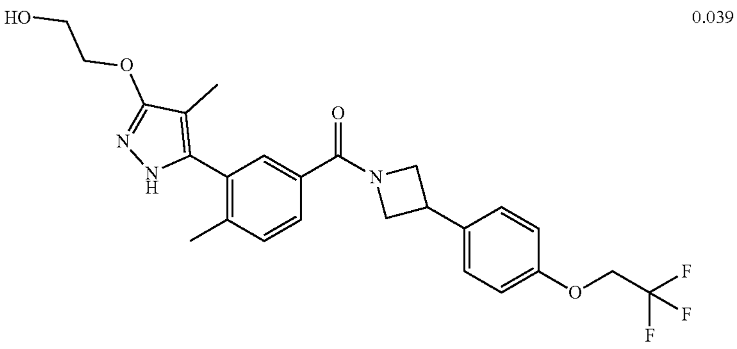 | 0.039 |

TABLE C-3-continued

| Fatty Acid Synthase Inhibitors | | |
|---|---|---|
| Cmpd No. | Structure | FASN (human) IC50 (μM) |
| 005-18 | 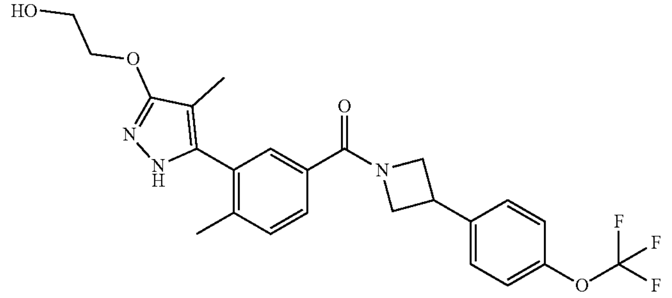 [SMILES: Cc1ccc(C(=O)N2CC(c3ccc(OC(F)(F)F)cc3)C2)cc1-c1[nH]nc(OCCO)c1C] | 0.037 |
| 005-19 | 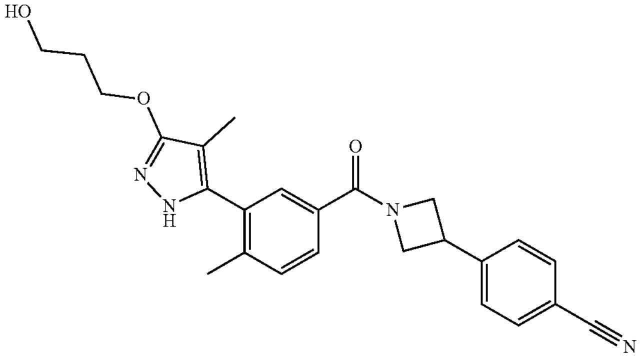 [SMILES: Cc1ccc(C(=O)N2CC(c3ccc(C#N)cc3)C2)cc1-c1[nH]nc(OCCCO)c1C] | 0.066 |
| 005-20 | 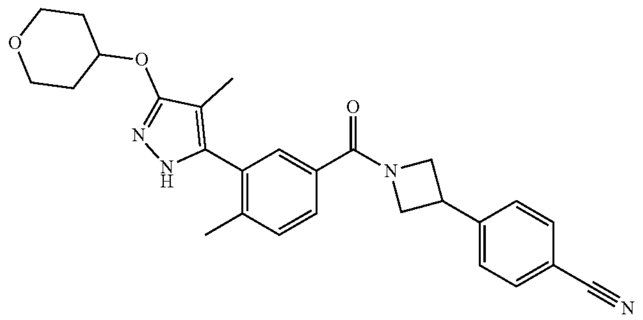 [SMILES: Cc1ccc(C(=O)N2CC(c3ccc(C#N)cc3)C2)cc1-c1[nH]nc(OC2CCOCC2)c1C] | 0.058 |

Thyroid Hormone Receptor Agonists

Examples of thyroid hormone receptor agonists that can be used in the methods and compositions of the present disclosure are described below.

In some embodiments, the thyroid hormone receptor (THR) agonist (e.g., THHβ agonist) is selected from:

VK2809

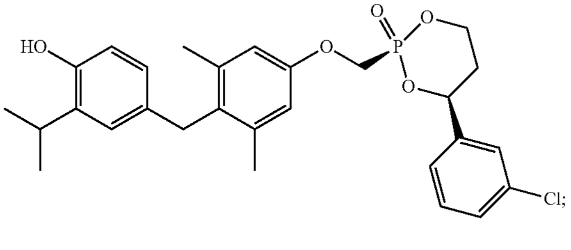

-continued

TERN-501

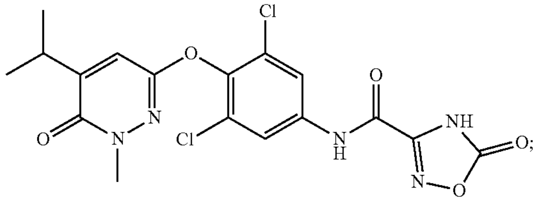

and ALG-055009.

In some embodiments, the thyroid hormone receptor agonist is a compound of Formula (XXI):

(XXI)

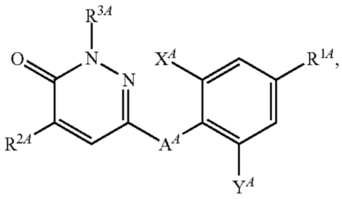

or a pharmaceutically acceptable salt thereof, wherein:

$A^A$ is O, $CH_2$, S, SO or $SO_2$;

$X^A$ and $Y^A$ are each independently selected from the group consisting of Br, Cl and $CH_3$;

$R^{1A}$ is selected from the group consisting of: $—(CH_2)_n COOH$, $—OCH_2COOH$, —NHC(═O)COOH, $—NHCH_2COOH$,

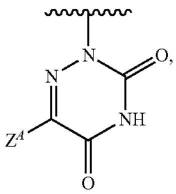

and

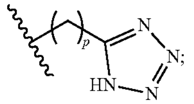

;

$Z^A$ is H, or —C≡N;

$R^{2A}$ is lower alkyl having from 1 to 4 C atoms;

$R^3$ is H or lower alkyl;

n is 1 or 2; and p is 1 or 2.

In some embodiments, the thyroid hormone receptor agonist is a compound of Formula (XXI-1):

(XXI-1)

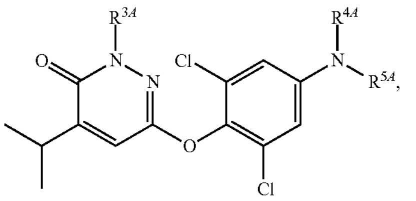

or a pharmaceutically acceptable salt thereof, wherein:

$R^{3A}$ is H or $CH_2R^{3B}$;

$R^{3B}$ is hydroxyl, O-linked amino acid, $—OP(O)(OH)_2$ or $—OC(O)R^{3C}$, wherein $R^{3C}$ is lower alkyl, alkoxy, alkyl acid, cycloalkyl, aryl, heteroaryl, or $—(CH_2)_n$-heteroaryl, wherein n is 0 or 1;

$R^{4A}$ is H, and $R^{5A}$ is $CH_2COOH$, $C(O)CO_2H$, or an ester or amide thereof, or $R^{4A}$ and $R^5$ together are —N═C($R^{4B}$)—C(O)—NH—C(O)—; wherein $R^{4B}$ is H or cyano.

In some embodiments, the thyroid hormone receptor agonist of Formula (XXI) has the following structure:

(Compound A)

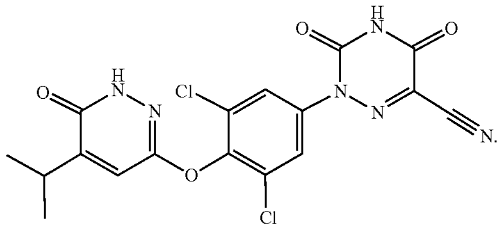

In some embodiments, the thyroid hormone receptor agonist of Formula (XXI) has the following structure:

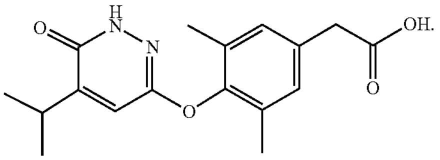 [SMILES: Cc1cc(CC(=O)O)cc(C)c1Oc1cc(C(C)C)c(=O)[nH]n1]

In some embodiments, the thyroid hormone receptor agonist of Formula (XXI) has the following structure:

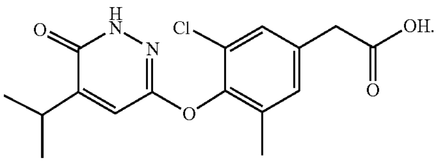 [SMILES: Cc1cc(CC(=O)O)cc(Cl)c1Oc1cc(C(C)C)c(=O)[nH]n1]

In some embodiments, the thyroid hormone receptor agonist of Formula (XXI) has the following structure:

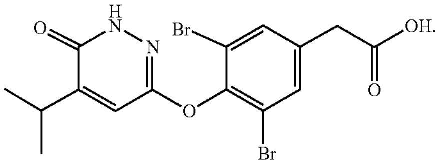 [SMILES: CC(C)c1cc(Oc2c(Br)cc(CC(=O)O)cc2Br)n[nH]c1=O]

In some embodiments, the thyroid hormone receptor agonist of Formula (XXI) has the following structure:

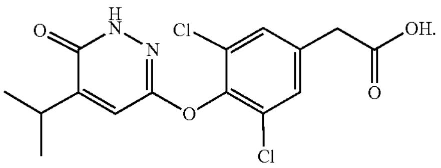 [SMILES: CC(C)c1cc(Oc2c(Cl)cc(CC(=O)O)cc2Cl)n[nH]c1=O]

In some embodiments, the thyroid hormone receptor agonist of Formula (XXI) has the following structure:

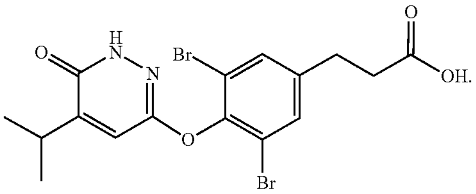 [SMILES: CC(C)c1cc(Oc2c(Br)cc(CCC(=O)O)cc2Br)n[nH]c1=O]

In some embodiments, the thyroid hormone receptor agonist of Formula (XXI) has the following structure:

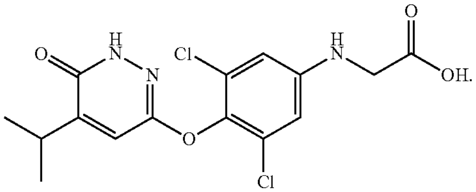 [SMILES: CC(C)c1cc(Oc2c(Cl)cc(NCC(=O)O)cc2Cl)n[nH]c1=O]

In some embodiments, the thyroid hormone receptor agonist of Formula (XXI) has the following structure:

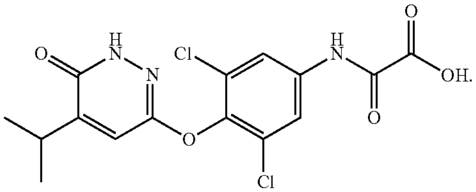 [SMILES: CC(C)c1cc(Oc2c(Cl)cc(NC(=O)C(=O)O)cc2Cl)n[nH]c1=O]

In some embodiments, the thyroid hormone receptor agonist of Formula (XXI) has the following structure:

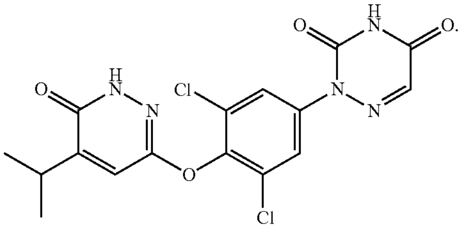 [SMILES: CC(C)c1cc(Oc2c(Cl)cc(-n3ncc(=O)[nH]c3=O)cc2Cl)n[nH]c1=O]

In some embodiments, the thyroid hormone receptor agonist of Formula (XXI) has the following structure:

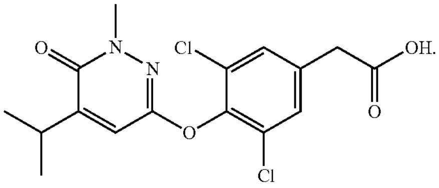 [SMILES: CC(C)c1cc(Oc2c(Cl)cc(CC(=O)O)cc2Cl)nn(C)c1=O]

In some embodiments, the thyroid hormone receptor agonist of Formula (XXI) has the following structure:

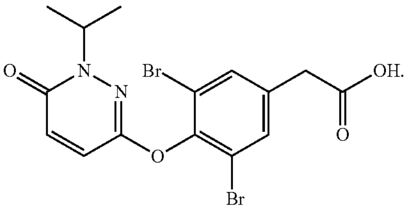 [SMILES: CC(C)n1nc(Oc2c(Br)cc(CC(=O)O)cc2Br)ccc1=O]

In some embodiments, the thyroid hormone receptor agonist of Formula (XXI) has the following structure:

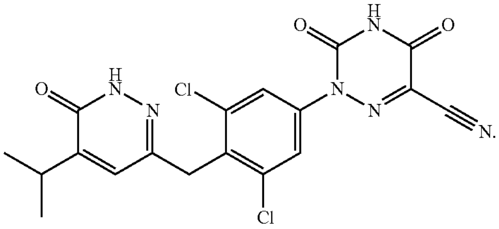 [SMILES: CC(C)c1cc(Cc2c(Cl)cc(-n3nc(C#N)c(=O)[nH]c3=O)cc2Cl)n[nH]c1=O]

In some embodiments, the thyroid hormone receptor agonist of Formula (XXI) has the following structure:

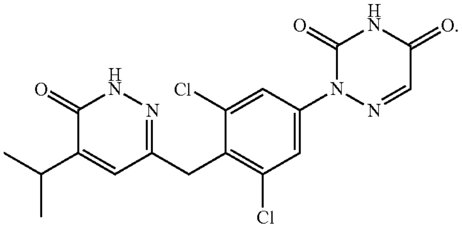 [SMILES: CC(C)c1cc(Cc2c(Cl)cc(-n3ncc(=O)[nH]c3=O)cc2Cl)n[nH]c1=O]

In some embodiments, the thyroid hormone receptor agonist of Formula (XXI) has the following structure:

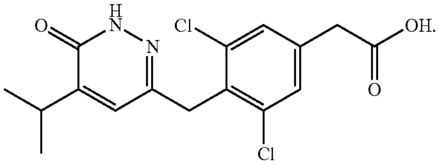 [SMILES: CC(C)c1cc(Cc2c(Cl)cc(CC(=O)O)cc2Cl)n[nH]c1=O]

In some embodiments, the thyroid hormone receptor agonist of Formula (XXI) has the following structure:

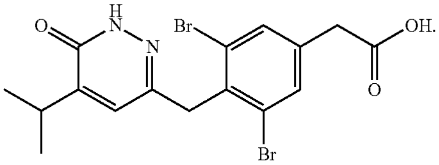

In some embodiments, the thyroid hormone receptor agonist of Formula (XXI) has the following structure:

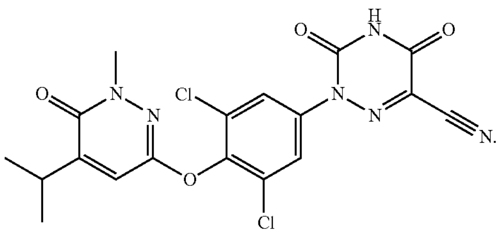 [SMILES: CC(C)c1cc(Oc2c(Cl)cc(-n3nc(C#N)c(=O)[nH]c3=O)cc2Cl)nn(C)c1=O]

In some embodiments, the thyroid hormone receptor agonist of Formula (XXI) has the following structure:

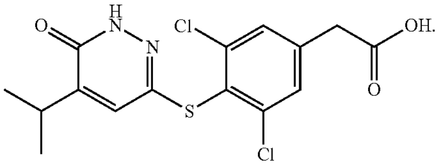 [SMILES: CC(C)c1cc(Sc2c(Cl)cc(CC(=O)O)cc2Cl)n[nH]c1=O]

In some embodiments, the thyroid hormone receptor agonist of Formula (XXI) has the following structure:

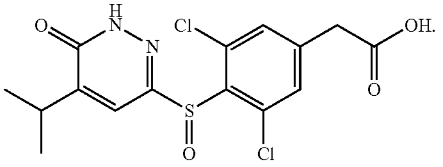 [SMILES: CC(C)c1cc(S(=O)c2c(Cl)cc(CC(=O)O)cc2Cl)n[nH]c1=O]

In some embodiments, the thyroid hormone receptor agonist of Formula (XXI) has the following structure:

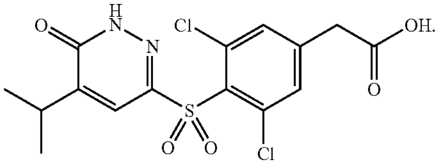 [SMILES: CC(C)c1cc(S(=O)(=O)c2c(Cl)cc(CC(=O)O)cc2Cl)n[nH]c1=O]

In some embodiments, the thyroid hormone receptor agonist of Formula (XXI) has the following structure:

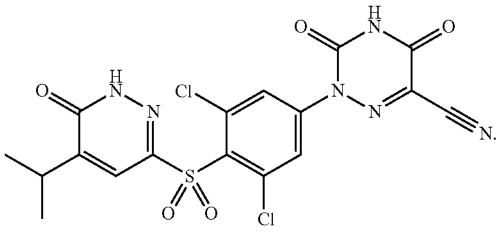 [SMILES: CC(C)c1cc(S(=O)(=O)c2c(Cl)cc(-n3nc(C#N)c(=O)[nH]c3=O)cc2Cl)n[nH]c1=O]

In some embodiments, the thyroid hormone receptor agonist of Formula (XXI) has the following structure:

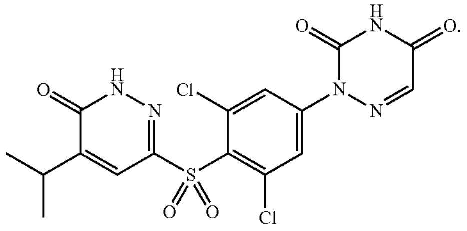 [SMILES: CC(C)c1cc(S(=O)(=O)c2c(Cl)cc(-n3ncc(=O)[nH]c3=O)cc2Cl)n[nH]c1=O]

In some embodiments, the thyroid hormone receptor agonist of Formula (XXI) has the following structure:

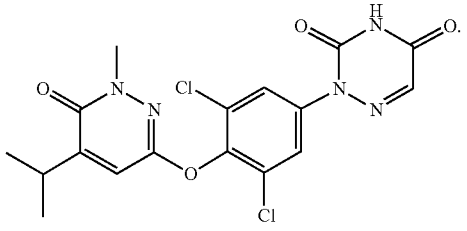 [SMILES: CC(C)c1cc(Oc2c(Cl)cc(-n3ncc(=O)[nH]c3=O)cc2Cl)nn(C)c1=O]

In some embodiments, the thyroid hormone receptor agonist of Formula (XXI) has the following structure:

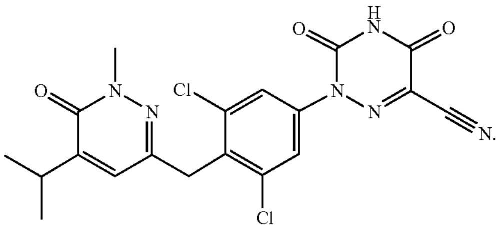 [SMILES: CC(C)c1cc(Cc2c(Cl)cc(-n3nc(C#N)c(=O)[nH]c3=O)cc2Cl)nn(C)c1=O]

In some embodiments, the thyroid hormone receptor agonist of Formula (XXI) has the following structure:

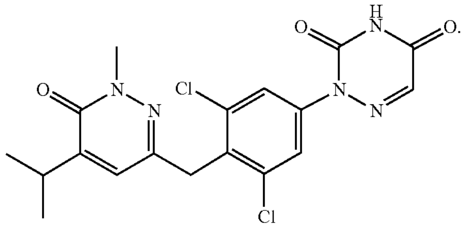 [SMILES: CC(C)c1cc(Cc2c(Cl)cc(-n3ncc(=O)[nH]c3=O)cc2Cl)nn(C)c1=O]

In some embodiments, the thyroid hormone receptor agonist of Formula (XXI) has the following structure:

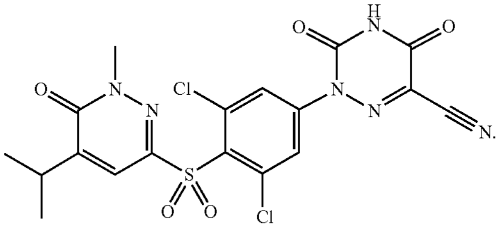 [SMILES: CC(C)c1cc(S(=O)(=O)c2c(Cl)cc(-n3nc(C#N)c(=O)[nH]c3=O)cc2Cl)nn(C)c1=O]

In some embodiments, the thyroid hormone receptor agonist of Formula (XXI) has the following structure:

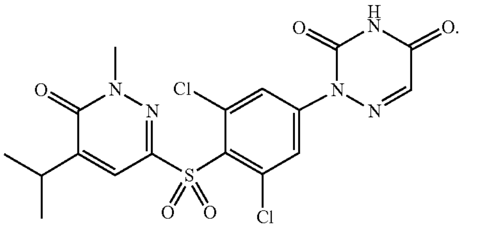 [SMILES: CC(C)c1cc(S(=O)(=O)c2c(Cl)cc(-n3ncc(=O)[nH]c3=O)cc2Cl)nn(C)c1=O]

In some embodiments, the thyroid hormone receptor agonist of Formula (XXI) has the following structure:

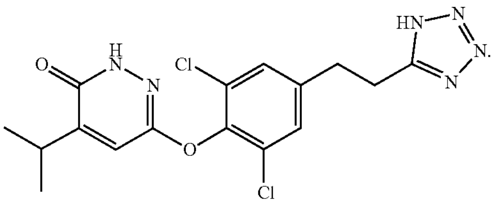

In some embodiments, the thyroid hormone receptor agonist of Formula (XXI) has the following structure:

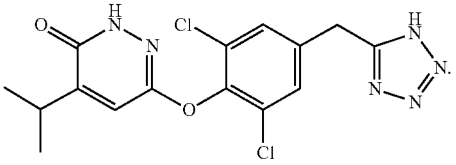

In some embodiments, the thyroid hormone receptor agonist of Formula (XXI) has the following structure:

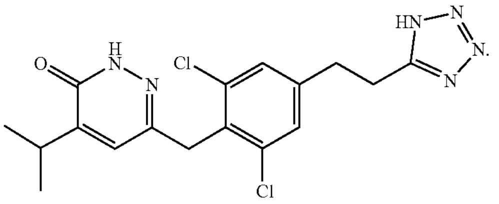

In some embodiments, the thyroid hormone receptor agonist of Formula (XXI) has the following structure:

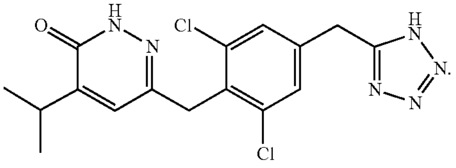 [SMILES: CC(C)c1cc(Cc2c(Cl)cc(Cc3nnn[nH]3)cc2Cl)n[nH]c1=O]

In some embodiments, the thyroid hormone receptor agonist of Formula (XXI) has the following structure:

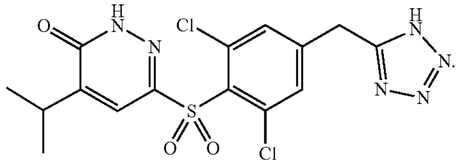 [SMILES: CC(C)c1cc(S(=O)(=O)c2c(Cl)cc(Cc3nnn[nH]3)cc2Cl)n[nH]c1=O]

In some embodiments, the thyroid hormone receptor agonist of Formula (XXI) has the following structure:

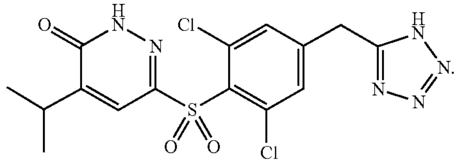 [SMILES: CC(C)c1cc(S(=O)(=O)c2c(Cl)cc(Cc3nnn[nH]3)cc2Cl)n[nH]c1=O]

Figure 6:
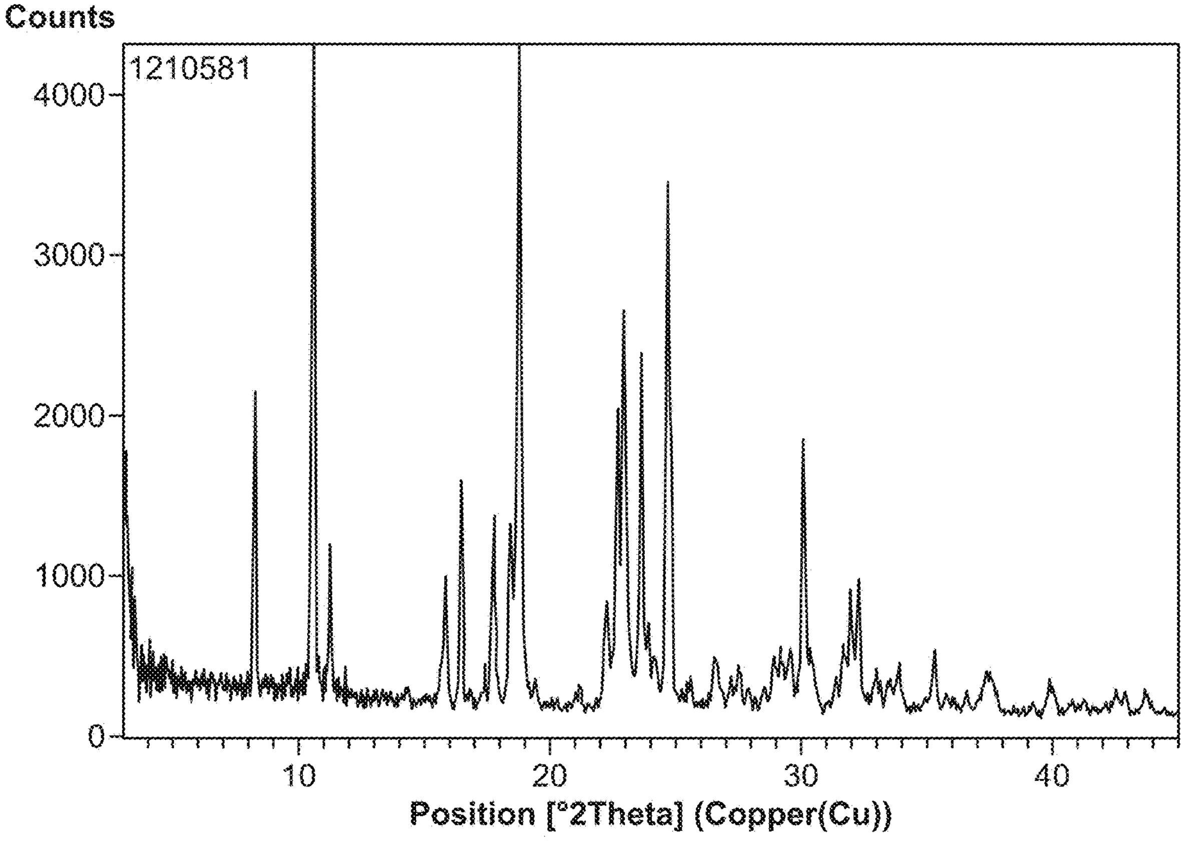
FIG. 6 is an X-ray powder diffractogram (XRPD) of Form A of Compound A.
Figure 7:
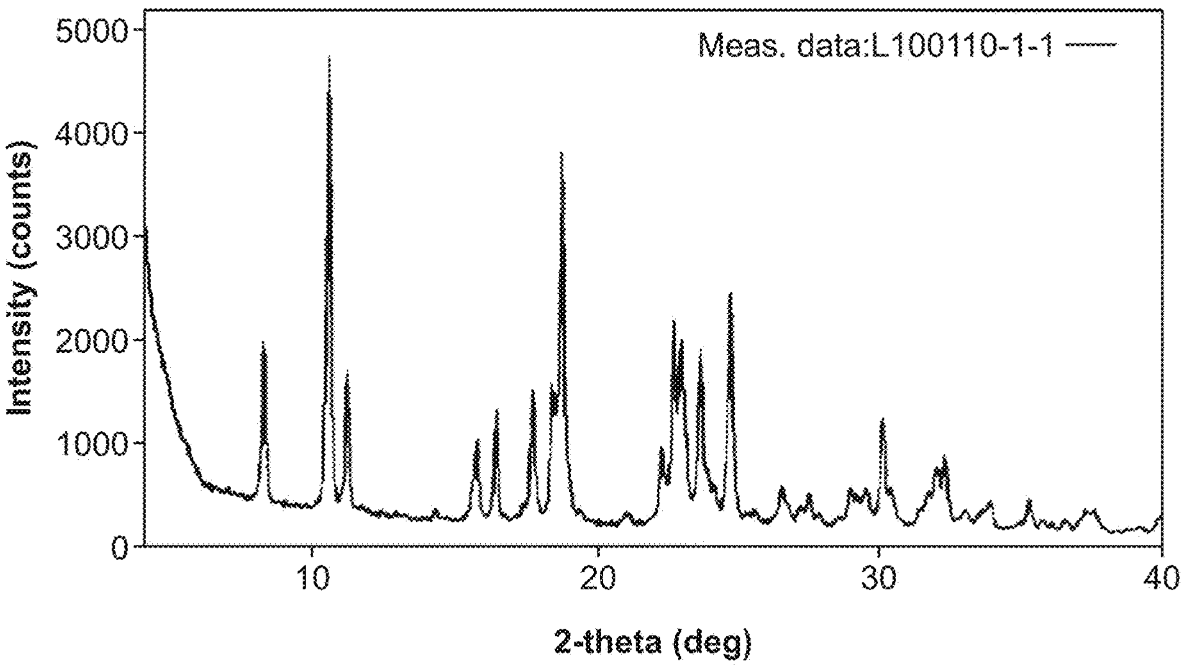
FIG. 7 is an X-ray powder diffraction (XRPD) pattern of an anhydrous crystalline form (Form A) of Compound A.
Figure 8:
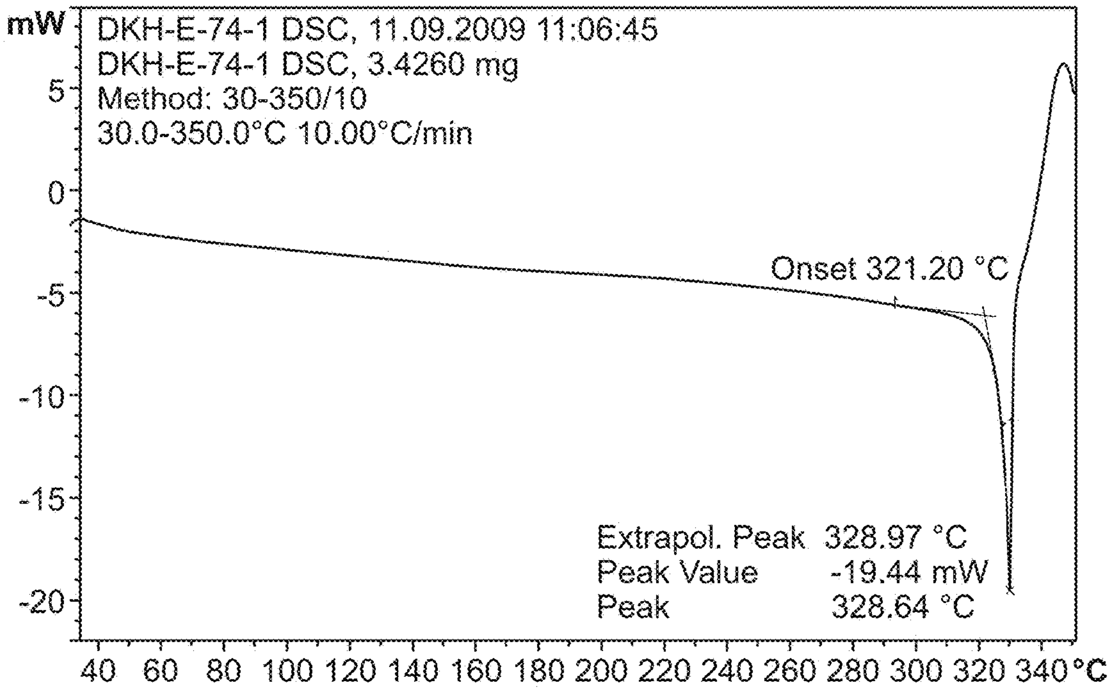
FIG. 8 is a differential scanning calorimetry (DSC) diagram of Form A of Compound A.

In some embodiments, the morphic form (Form A) of Compound A is characterized by an X-ray powder diffraction pattern including peaks at about 10.5, 18.7, 22.9, 23.6, and 24.7 degrees 2θ, wherein the x-ray powder diffraction pattern is obtained using a Cu Ka radiation source (1.54 Å). In some embodiments, the X-ray powder diffraction pattern further includes peaks at about 8.2, 11.2, 15.7, 16.4, 17.7, 30.0, and 32.2 degrees 2θ. In some embodiments, the X-ray powder diffraction pattern of Form A can further include one or more peaks from Table P-1. In some embodiments, Form A has an X-ray diffraction pattern substantially similar to that set forth in FIG. 6. In some embodiments, Form A has an X-ray diffraction pattern substantially similar to that set forth in FIG. 7. In embodiments, Form A is characterized by an onset melting temperature of about 321° C. and a differential scanning calorimetry (DSC) diagram that includes an endothermic peak at about 329° C. In embodiments, the DSC diagram is substantially the same as that shown in FIG. 8.

In some embodiments, the morphic form of Compound A is a hydrate. In embodiments, the hydrate is monohydrate. In embodiments, the hydrate is dihydrate.

Figure 9:
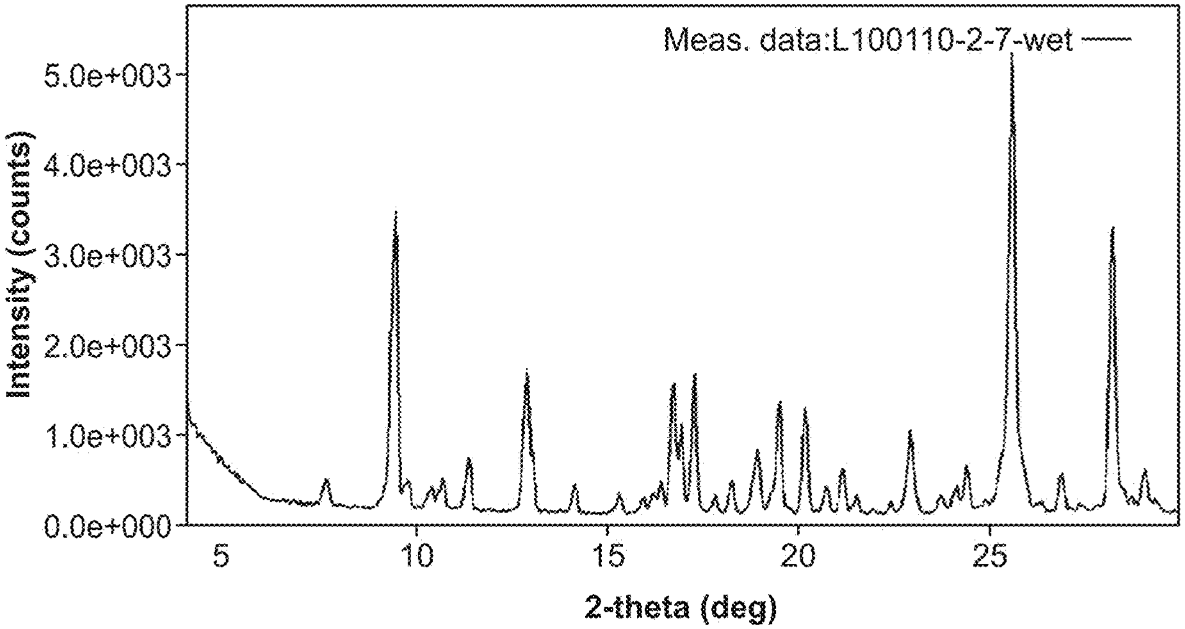
FIG. 9 is an XRPD pattern of a methyl isobutyl ketone (MIBK) solvate (Form G) of Compound A.

In some embodiments, the morphic form (Form G) of Compound A is characterized by an X-ray powder diffraction pattern including peaks at about 9.50, 12.9, 16.7, 17.3, 19.5, 20.2, 25.6, and 28.3 degrees 2θ, wherein the x-ray powder diffraction pattern is obtained using a Cu Ka radiation source (1.54 Å). In some embodiments, the X-ray powder diffraction pattern of Form G can further include one or more peaks from Table P-2. In some embodiments, Form G has an X-ray diffraction pattern substantially similar to that set forth in FIG. 9.

Figure 10:
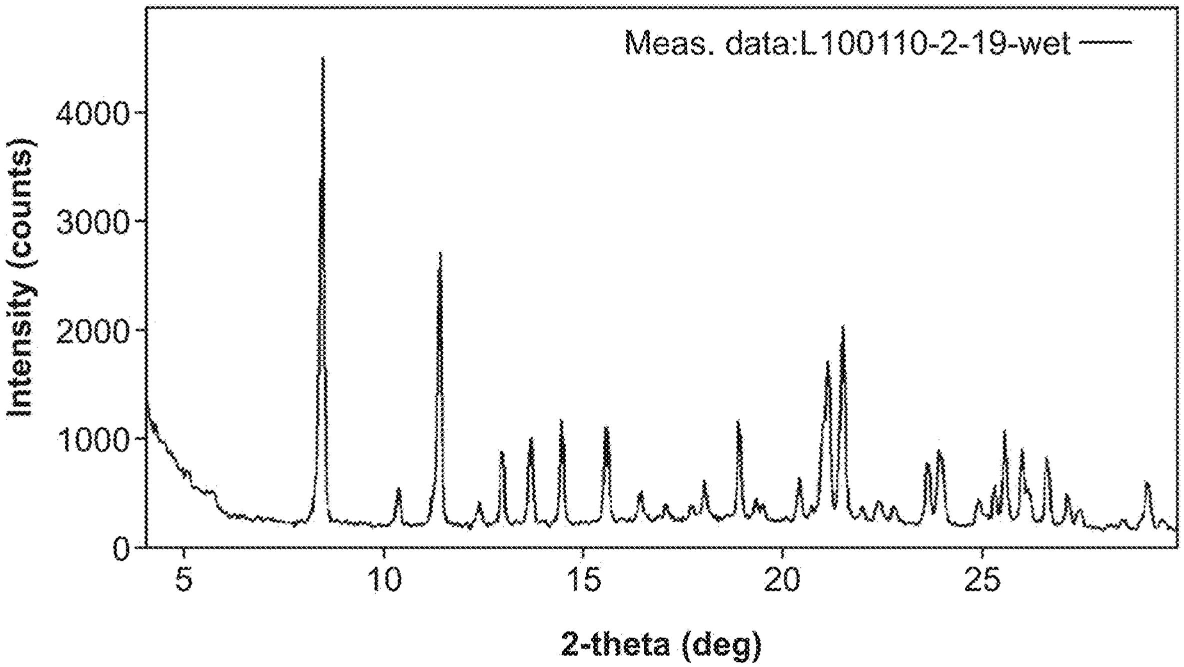
FIG. 10 is an XRPD pattern of a dimethyl acetamide solvate (Form K) of Compound A.

In some embodiments, the morphic form (Form K) of Compound A is characterized by an X-ray powder diffraction pattern including peaks at about 8.42, 11.4, 14.5, 18.9, 21.1, and 21.6 degrees 2θ, wherein the x-ray powder diffraction pattern is obtained using a Cu Ka radiation source (1.54 Å). In some embodiments, the X-ray powder diffraction pattern of Form K can further include one or more peaks from Table 3. In some embodiments, Form K has an X-ray diffraction pattern substantially similar to that set forth in FIG. 10.

TABLE P-1

| XRPD peak positions of Form A | | | |
|---|---|---|---|
| 2-θ | d (A°) | Height (counts) | Relative Intensity, % |
| 8.27 | 10.68878 | 1607 | 37 |
| 10.56 | 8.37014 | 4379 | 100 |
| 11.21 | 7.8855 | 1470 | 34 |
| 15.81 | 5.59963 | 660 | 15 |
| 16.43 | 5.38989 | 1085 | 25 |
| 17.72 | 5.00087 | 1342 | 31 |
| 18.45 | 4.80591 | 1166 | 27 |
| 18.75 | 4.72983 | 3414 | 78 |
| 22.30 | 3.98389 | 772 | 18 |
| 22.70 | 3.91432 | 1990 | 45 |
| 22.99 | 3.86513 | 1803 | 41 |
| 23.63 | 3.7622 | 1491 | 34 |
| 24.72 | 3.59862 | 2192 | 50 |
| 26.57 | 3.35183 | 274 | 6 |
| 27.49 | 3.24143 | 268 | 6 |
| 29.00 | 3.07664 | 323 | 7 |
| 29.52 | 3.02378 | 259 | 6 |
| 30.13 | 2.96403 | 922 | 21 |
| 32.04 | 2.79156 | 414 | 9 |
| 32.33 | 2.76688 | 423 | 10 |
| 35.25 | 2.54415 | 265 | 6 |

TABLE P-2

| XRPD peak positions of Form G | | | |
|---|---|---|---|
| 2-θ | d (A°) | Height (counts) | Relative Intensity, % |
| 7.71 | 11.45694 | 321 | 6 |
| 9.50 | 9.29954 | 3351 | 64 |
| 9.80 | 9.02038 | 264 | 5 |
| 10.70 | 8.26425 | 335 | 6 |
| 11.42 | 7.74427 | 573 | 11 |
| 12.91 | 6.85398 | 1574 | 30 |
| 13.06 | 6.77304 | 630 | 12 |
| 14.16 | 6.25129 | 331 | 6 |
| 15.32 | 5.78082 | 242 | 5 |
| 16.39 | 5.40376 | 342 | 7 |
| 16.72 | 5.29747 | 1503 | 29 |
| 16.93 | 5.23349 | 953 | 18 |
| 17.28 | 5.12802 | 1583 | 30 |
| 18.26 | 4.85418 | 367 | 7 |
| 18.95 | 4.67825 | 651 | 13 |
| 19.52 | 4.545 | 1324 | 25 |
| 20.20 | 4.39282 | 1156 | 22 |
| 20.75 | 4.27707 | 290 | 6 |
| 21.17 | 4.19266 | 499 | 10 |
| 22.94 | 3.87415 | 805 | 15 |
| 24.11 | 3.68838 | 255 | 5 |
| 24.39 | 3.64666 | 481 | 9 |
| 25.59 | 3.47856 | 5204 | 100 |
| 26.91 | 3.31057 | 389 | 7 |
| 28.26 | 3.15574 | 3363 | 65 |
| 29.10 | 3.06569 | 428 | 8 |

TABLE P-3

| XRPD peak positions of Form K | | | |
|---|---|---|---|
| 2-θ | d (A°) | Height (counts) | Relative Intensity, % |
| 8.42 | 10.48827 | 4822 | 100 |
| 10.36 | 8.53374 | 365 | 8 |
| 11.37 | 7.77279 | 2754 | 57 |
| 12.96 | 6.8237 | 817 | 17 |
| 13.67 | 6.47249 | 872 | 18 |
| 14.45 | 6.12352 | 983 | 20 |
| 15.56 | 5.69196 | 922 | 19 |
| 16.42 | 5.39359 | 285 | 6 |
| 18.04 | 4.9142 | 354 | 7 |
| 18.90 | 4.69153 | 988 | 21 |
| 20.46 | 4.33778 | 392 | 8 |
| 21.14 | 4.19865 | 1327 | 28 |
| 21.56 | 4.11889 | 1755 | 36 |
| 23.65 | 3.75927 | 574 | 12 |
| 23.96 | 3.71172 | 688 | 14 |
| 24.94 | 3.5668 | 226 | 5 |
| 25.32 | 3.51471 | 366 | 8 |
| 25.57 | 3.48028 | 819 | 17 |
| 26.03 | 3.42028 | 694 | 14 |
| 26.20 | 3.39821 | 284 | 6 |
| 26.66 | 3.34086 | 646 | 13 |
| 27.20 | 3.27634 | 293 | 6 |
| 29.25 | 3.0512 | 417 | 9 |

Dosage and Administration of Thyroid Hormone Receptor Agonists

The thyroid hormone receptor beta agonists contemplated in the methods described herein can be administered orally or parenterally (e.g., subcutaneously). For thyroid hormone receptor beta agonists that are approved for at least one indication by the Food and Drug administration, the route of administration can be as described in their FDA-approved label. In some aspects, the thyroid hormone receptor beta agonists are administered orally.

The thyroid hormone receptor beta agonists, including the thyroid hormone receptor beta agonists contemplated by the methods described herein are currently used, and in some cases approved for use by the Food and Drug Administration for the treatment of non-alcoholic steatohepatitis (NASH) (e.g., non-cirrhotic NASH).

In some aspects of the methods described herein, the thyroid hormone receptor beta agonists are administered at doses that are equivalent to the doses indicated on their label as the recommended doses for the treatment of non-alcoholic steatohepatitis (NASH) (e.g., non-cirrhotic NASH). In some aspects of the methods described herein, the thyroid hormone receptor beta agonists are administered at doses that are lower than the doses indicated on their label as the doses recommended for the treatment of non-alcoholic steatohepatitis (NASH) (e.g., non-cirrhotic NASH) (i.e., doses that represent a certain percentage of the dose indicated on their label as the doses recommended for the treatment of non-alcoholic steatohepatitis (NASH) (e.g., non-cirrhotic NASH)). In some aspects of the methods described herein, the thyroid hormone receptor beta agonist is administered at a dose that is between 10% and 90%, between 20% and 90%, between 30% and 90%, between 40% and 90%, between 50% and 90%, between 60% and 90%, between 70% and 90%, between 80% and 90%, between 10% and 80%, between 20% and 80%, between 30% and 80%, between 40% and 80%, between 50% and 80%, between 60% and 80%, between 70% and 80%, between 10% and 70%, between 20% and 70%, between 30% and 70%, between 40% and 70%, between 50% and 70%, between 60% and 70%, between 10% and 60%, between 20% and 60%, between 30% and 60%, between 40% and 60%, between 50% and 60%, between 10% and 50%, between 20% and 50%, between 30% and 50%, between 40% and 50%, between 10% and 40%, between 20% and 40%, between 30% and 40%, between 10% and 30%, between 20% and 30% and between 10% and 20% of the doses indicated for the treatment of non-alcoholic steatohepatitis (NASH) (e.g., non-cirrhotic NASH).

In some aspects, the thyroid hormone receptor beta agonist is administered at a dose that is between 10% and 90% of the dose indicated for the treatment of non-alcoholic steatohepatitis (NASH) (e.g., non-cirrhotic NASH). In some aspects, the thyroid hormone receptor beta agonist is administered at a dose that is between 20% and 90% of the dose indicated for the treatment of non-alcoholic steatohepatitis (NASH) (e.g., non-cirrhotic NASH). In some aspects, the thyroid hormone receptor beta agonist is administered at a dose that is between 30% and 90% of the dose indicated for the treatment of non-alcoholic steatohepatitis (NASH) (e.g., non-cirrhotic NASH). In some aspects, the thyroid hormone receptor beta agonist is administered at a dose that is between 40% and 90% of the dose indicated for the treatment of non-alcoholic steatohepatitis (NASH) (e.g., non-cirrhotic NASH). In some aspects, the thyroid hormone receptor beta agonist is administered at a dose that is between 50% and 90% of the dose indicated for the treatment of non-alcoholic steatohepatitis (NASH) (e.g., non-cirrhotic NASH). In some aspects, the thyroid hormone receptor beta agonist is administered at a dose that is between 60% and 90% of the dose indicated for the treatment of non-alcoholic steatohepatitis (NASH) (e.g., non-cirrhotic NASH). In some aspects, the thyroid hormone receptor beta agonist is administered at a dose that is between 70% and 90% of the dose indicated for the treatment of non-alcoholic steatohepatitis (NASH) (e.g., non-cirrhotic NASH). In some aspects, the thyroid hormone receptor beta agonist is administered at a dose that is between 80% and 90% of the dose indicated for the treatment of non-alcoholic steatohepatitis (NASH) (e.g., non-cirrhotic NASH). In some aspects, the thyroid hormone receptor beta agonist is administered at a dose that is between 10% and 80% of the dose indicated for the treatment of non-alcoholic steatohepatitis (NASH) (e.g., non-cirrhotic NASH). In some aspects, the thyroid hormone receptor beta agonist is administered at a dose that is between 20% and 80% of the dose indicated for the treatment of non-alcoholic steatohepatitis (NASH) (e.g., non-cirrhotic NASH). In some aspects, the thyroid hormone receptor beta agonist is administered at a dose that is between 30% and 80% of the dose indicated for the treatment of non-alcoholic steatohepatitis (NASH) (e.g., non-cirrhotic NASH). In some aspects, the thyroid hormone receptor beta agonist is administered at a dose that is between 40% and 80% of the dose indicated for the treatment of non-alcoholic steatohepatitis (NASH) (e.g., non-cirrhotic NASH). In some aspects, the thyroid hormone receptor beta agonist is administered at a dose that is between 50% and 80% of the dose indicated for the treatment of non-alcoholic steatohepatitis (NASH) (e.g., non-cirrhotic NASH). In some aspects, the thyroid hormone receptor beta agonist is administered at a dose that is between 60% and 80% of the dose indicated for the treatment of non-alcoholic steatohepatitis (NASH) (e.g., non-cirrhotic NASH). In some aspects, the thyroid hormone receptor beta agonist is administered at a dose that is between 70% and 80% of the dose indicated for the treatment of non-alcoholic steatohepatitis (NASH) (e.g., non-cirrhotic NASH). In some aspects, the thyroid hormone receptor beta agonist is administered at a dose that is between 10% and 70% of the dose indicated for the treatment of non-alcoholic steatohepatitis (NASH) (e.g., non-cirrhotic NASH). In some aspects, the thyroid hormone receptor beta agonist is administered at a dose that is between 20% and 70% of the dose indicated for the treatment of non-alcoholic steatohepatitis (NASH) (e.g., non-cirrhotic NASH). In some aspects, the thyroid hormone receptor beta agonist is administered at a dose that is between 30% and 70% of the dose indicated for the treatment of non-alcoholic steatohepatitis (NASH) (e.g., non-cirrhotic NASH). In some aspects, the thyroid hormone receptor beta agonist is administered at a dose that is between 40% and 70% of the dose indicated for the treatment of non-alcoholic steatohepatitis (NASH) (e.g., non-cirrhotic NASH). In some aspects, the thyroid hormone receptor beta agonist is administered at a dose that is between 50% and 70% of the dose indicated for the treatment of non-alcoholic steatohepatitis (NASH) (e.g., non-cirrhotic NASH). In some aspects, the thyroid hormone receptor beta agonist is administered at a dose that is between 60% and 70% of the dose indicated for the treatment of non-alcoholic steatohepatitis (NASH) (e.g., non-cirrhotic NASH). In some aspects, the thyroid hormone receptor beta agonist is administered at a dose that is between 10% and 60% of the dose indicated for the treatment of non-alcoholic steatohepatitis (NASH) (e.g., non-cirrhotic NASH). In some aspects, the thyroid hormone receptor beta agonist is administered at a dose that is between 20% and 60% of the dose indicated for the treatment of non-alcoholic steatohepatitis (NASH) (e.g., non-cirrhotic NASH). In some aspects, the thyroid hormone receptor beta agonist is administered at a dose that is between 30% and 60% of the dose indicated for the treatment of non-alcoholic steatohepatitis (NASH) (e.g., non-cirrhotic NASH). In some aspects, the thyroid hormone receptor beta agonist is administered at a dose that is between 40% and 60% of the dose indicated for the treatment of non-alcoholic steatohepatitis (NASH) (e.g., non-cirrhotic NASH). In some aspects, the thyroid hormone receptor beta agonist is administered at a dose that is between 50% and 60% of the dose indicated for the treatment of non-alcoholic steatohepatitis (NASH) (e.g., non-cirrhotic NASH). In some aspects, the thyroid hormone receptor beta agonist is administered at a dose that is between 10% and 50% of the dose indicated for the treatment of non-alcoholic steatohepatitis (NASH) (e.g., non-cirrhotic NASH). In some aspects, the thyroid hormone receptor beta agonist is administered at a dose that is between 20% and 50% of the dose indicated for the treatment of non-alcoholic steatohepatitis (NASH) (e.g., non-cirrhotic NASH). In some aspects, the thyroid hormone receptor beta agonist is administered at a dose that is between 30% and 50% of the dose indicated for the treatment of non-alcoholic steatohepatitis (NASH) (e.g., non-cirrhotic NASH). In some aspects, the thyroid hormone receptor beta agonist is administered at a dose that is between 40% and 50% of the dose indicated for the treatment of non-alcoholic steatohepatitis (NASH) (e.g., non-cirrhotic NASH). In some aspects, the thyroid hormone receptor beta agonist is administered at a dose that is between 10% and 40% of the dose indicated for the treatment of non-alcoholic steatohepatitis (NASH) (e.g., non-cirrhotic NASH). In some aspects, the thyroid hormone receptor beta agonist is administered at a dose that is between 20% and 40% of the dose indicated for the treatment of non-alcoholic steatohepatitis (NASH) (e.g., non-cirrhotic NASH). In some aspects, the thyroid hormone receptor beta agonist is administered at a dose that is between 30% and 40% of the dose indicated for the treatment of non-alcoholic steatohepatitis (NASH) (e.g., non-cirrhotic NASH). In some aspects, the thyroid hormone receptor beta agonist is administered at a dose that is between 10% and 30% of the dose indicated for the treatment of non-alcoholic steatohepatitis (NASH) (e.g., non-cirrhotic NASH). In some aspects, the thyroid hormone receptor beta agonist is administered at a dose that is between 20% and 30% of the dose indicated for the treatment of non-alcoholic steatohepatitis (NASH) (e.g., non-cirrhotic NASH). In some aspects, the thyroid hormone receptor beta agonist is administered at a dose that is between 10% and 20% of the dose indicated for the treatment of non-alcoholic steatohepatitis (NASH) (e.g., non-cirrhotic NASH).

The thyroid hormone receptor beta agonists can be administered at various dosing frequencies as part of the methods described herein. In certain aspects, the thyroid hormone receptor beta agonists are administered at the frequencies indicated on their labels for the treatment of one of their approved indications. In certain aspects, the thyroid hormone receptor beta agonists are administered at the frequencies indicated on their labels as maintenance regimens for the treatment of for the treatment of non-alcoholic steatohepatitis (NASH) (e.g., non-cirrhotic NASH). In some aspects, the thyroid hormone receptor beta agonists are administered daily (e.g., once or twice daily) or intermittently (e.g., every other day, on a M/W/F schedule, weekly, biweekly, monthly, bimonthly, etc). In some aspects, the thyroid hormone receptor beta agonists are administered daily (e.g., once or twice daily). In some aspects, the thyroid hormone receptor beta agonists are administered intermittently (e.g., every other day, on a M/W/F schedule, weekly, biweekly, monthly, bimonthly, etc).

In some embodiments, the thyroid hormone receptor beta agonist is resmetirom, and the dose indicated for the treatment of NASH (e.g., non-cirrhotic NASH) is 80 mg administered once daily for a patient with a weight of ≤100 kg and 100 mg administered once daily for a patient with a weight of ≥100 kg.

Methods of Treatment

In some aspects, embodiments provided herein relate to a method of treating fatty liver disease/steatotic liver disease in a subject in need thereof, the method comprising administering to the subject a combination of a FASN inhibitor as defined in any of the embodiments described herein and a thyroid hormone receptor beta agonist as defined in any of the embodiments described herein.

In some aspects, embodiments provided herein relate to a method of treating nonalcoholic steatohepatitis/metabolic dysfunction-associated steatohepatitis (NASH/MASH) in a subject in need thereof, the method comprising administering to the subject a combination of a FASN inhibitor as defined in any of the embodiments described herein and a thyroid hormone receptor beta agonist as defined in any of the embodiments described herein. In some embodiments, the NASH/MASH is NASH/MASH with moderate to severe fibrosis (e.g., a fibrosis score of 2 or 3). In some embodiments, treating the non-alcoholic steatohepatitis comprises preventing the progression of at least one symptom of non-alcoholic steatohepatitis. In some embodiments, the symptom is selected from elevated levels of AST; elevated levels of ALT; elevated levels of GGT; elevated levels of liver triglycerides; elevated levels of cholesterol; liver steatosis; liver inflammation; liver ballooning; liver fibrosis; and NAFLD activity score. In some embodiments, treating the NASH/MASH comprises an improvement of liver fibrosis in the subject of ≥1 stage without worsening of NASH/MASH.

In some embodiments, treating the NASH/MASH comprises resolution of NASH/MASH without worsening of fibrosis in the subject.

In some aspects, embodiments provided herein relate to a method of treating nonalcoholic fatty liver disease/metabolic dysfunction-associated steatotic liver disease (NAFLD/MASLD) in a subject in need thereof, the method comprising administering to the subject a combination of a FASN inhibitor as defined in any of the embodiments described herein and a thyroid hormone receptor beta agonist as defined in any of the embodiments described herein.

In some aspects, embodiments provided herein relate to a method of treating metabolic syndrome in a subject in need thereof, the method comprising administering to the subject a combination of a FASN inhibitor as defined in any of the embodiments described herein and a thyroid hormone receptor beta agonist as defined in any of the embodiments described herein.

In some aspects, embodiments provided herein relate to a method of treating Type II diabetes in a subject in need thereof, the method comprising administering to the subject a combination of a FASN inhibitor as defined in any of the embodiments described herein and a thyroid hormone receptor beta agonist as defined in any of the embodiments described herein.

In some aspects, embodiments provided herein relate to a method of treating atherosclerosis in a subject in need thereof, the method comprising administering to the subject a combination of a FASN inhibitor as defined in any of the embodiments described herein and a thyroid hormone receptor beta agonist as defined in any of the embodiments described herein.

In some aspects, embodiments provided herein relate to a method of treating liver cirrhosis in a subject in need thereof, the method comprising administering to the subject a combination of a FASN inhibitor as defined in any of the embodiments described herein and a thyroid hormone receptor beta agonist as defined in any of the embodiments described herein.

In some aspects, embodiments provided herein relate to a method of treating liver cancer (e.g., hepatocellular carcinoma) in a subject in need thereof, the method comprising administering to the subject a combination of a FASN inhibitor as defined in any of the embodiments described herein and a thyroid hormone receptor beta agonist as defined in any of the embodiments described herein. In some embodiments, the liver cancer has developed from NASH/MASH or NAFLD/MASLD. In some embodiments, the liver cancer is hepatocellular carcinoma. In some embodiments, the liver cancer is cholangiocarcinoma.

In some aspects, embodiments provided herein relate to a method of treating a disease or condition in which interleukin 1 beta (IL1β) levels are elevated in a subject in need thereof, the method comprising administering to the subject a combination of a FASN inhibitor as defined in any of the embodiments described herein and a thyroid hormone receptor beta agonist as defined in any of the embodiments described herein. In some embodiments, the disease or condition is selected from Familial Mediterranean fever (FMF), Pyogenic arthritis, pyoderma gangrenosum, acne (PAPA), Cryopyrin-associated periodic syndromes (CAPS), Hyper IgD syndrome (HIDS), Adult and juvenile Still disease, Schnitzler syndrome, TNF receptor-associated periodic syndrome (TRAPS), Blau syndrome; Sweet syndrome, Deficiency in IL-1 receptor antagonist (DIRA), Recurrent idiopathic pericarditis, Macrophage activation syndrome (MAS), Urticarial vasculitis, Antisynthetase syndrome, Relapsing chondritis, Behçet disease, Erdheim-Chester syndrome (histiocytosis), Synovitis, acne, pustulosis, hyperostosis, osteitis (SAPHO), Rheumatoid arthritis, Periodic fever, aphthous stomatitis, pharyngitis, adenitis syndrome (PFAPA), Urate crystal arthritis (gout), Type 2 diabetes, Smoldering multiple myeloma, Postmyocardial infarction heart failure, Osteoarthritis, Transfusion-related acute lung injury, Ventilator-induced lung injury, Pulmonary fibrosis including Idiopathic, Chronic obstructive pulmonary disease and Asthma. In some embodiments, the disease or condition is acne.

In some aspects, embodiments provided herein relate to a method of treating a disease or condition in which regulatory T cells ($T_{reg}$) are reduced or suppressed in a subject in need thereof, the method comprising administering to the subject a combination of a FASN inhibitor as defined in any of the embodiments described herein and a thyroid hormone receptor beta agonist as defined in any of the embodiments described herein. In some embodiments, $T_{reg}$ cells are suppressed.

In some aspects, embodiments provided herein relate to a method of treating a disease or condition in which t-helper ($T_h$) cell levels are elevated in a subject in need thereof, the method comprising administering to the subject a combination of a FASN inhibitor as defined in any of the embodiments described herein and a thyroid hormone receptor beta agonist as defined in any of the embodiments described herein. In some embodiments, the elevated t-helper cell is $T_h1$, $T_h2$, $T_h9$, or. $T_h17$. In some embodiments, the elevated t-helper cell is $T_{17}$. In some embodiments, the disease or condition is selected from Psoriasis, Rheumatoid arthritis, Multiple sclerosis, Ankylosing spondylitis, inflammatory bowel disease, asthma, tumorigenesis, and transplant rejection.

In some aspects, embodiments provided herein relate to a method of reversing established nonalcoholic steatohepatitis/metabolic dysfunction-associated steatohepatitis (NASH/MASH) in a subject in need thereof, the method comprising administering to the subject a combination of a FASN inhibitor as defined in any of the embodiments described herein and a thyroid hormone receptor beta agonist as defined in any of the embodiments described herein.

In some aspects, embodiments provided herein relate to a method of treating liver fibrosis in a subject in need thereof, the method comprising administering to the subject a combination of a FASN inhibitor as defined in any of the embodiments described herein and a thyroid hormone receptor beta agonist as defined in any of the embodiments described herein.

In some aspects, embodiments provided herein relate to a method of reducing fibrotic gene expression in a subject in need thereof, the method comprising administering to the subject a combination of a FASN inhibitor as defined in any of the embodiments described herein and a thyroid hormone receptor beta agonist as defined in any of the embodiments described herein.

In some aspects, embodiments provided herein relate to a method of reducing triglycerides in a subject in need thereof, the method comprising administering to the subject a combination of a FASN inhibitor as defined in any of the embodiments described herein and a thyroid hormone receptor beta agonist as defined in any of the embodiments described herein.

In some embodiments, the combination of FASN inhibitor and thyroid hormone receptor-beta agonist is synergistic.

In some embodiments of the methods provided herein, such as those described above (or below), the fatty acid synthase inhibitor has a formula of:

(a) Formula (IX)

(IX)

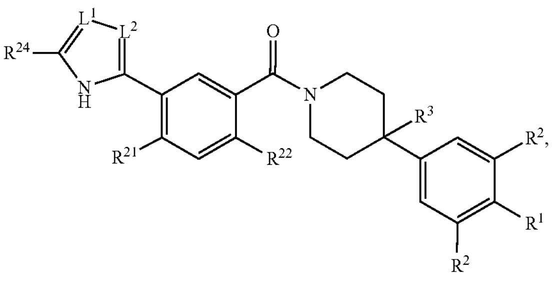

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

$C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

$L^1$ is $CR^{23}$ or N;

$L^2$ is CH or N;

at least one of $L^1$ or $L^2$ is N; and $R^{23}$ is H or $C_1$-$C_4$ straight or branched alkyl; or (b) Formula (X):

(X)

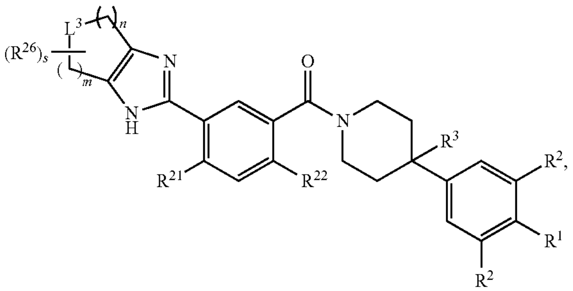

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

the $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH or halogen;

$L^3$ is $C(R^{60})_2$, O or $NR^{50}$;

each $R^{60}$ is independently H, —OH, —CN, —$O_t$—($C_3$-$C_5$ cycloalkyl), —O—($C_1$-$C_4$ straight or branched alkyl), or —C(O)—N$(R^{601})_2$ wherein:

t is 0 or 1, and the $C_3$-$C_5$ cycloalkyl optionally includes an oxygen or nitrogen heteroatom;

each $R^{50}$ is independently H, —C(O)—$O_t$—($C_1$-$C_4$ straight or branched alkyl), —C(O)—$O_t$—($C_3$-$C_5$ cyclic alkyl), —$C_3$-$C_5$ cyclic alkyl optionally containing an oxygen or nitrogen heteroatom, —C(O)—N$(R^{501})_2$, $C_1$-$C_4$ straight or branched alkyl wherein:

t is 0 or 1, and the $C_3$-$C_5$ cycloalkyl optionally includes an oxygen or nitrogen heteroatom;

n is 1, 2 or 3;

m is 1 or 2;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom $R^{22}$ is H, halogen, $C_1$-$C_2$ alkyl;

each $R^{26}$ is independently —OH, —CN, halogen, $C_1$-$C_4$ straight or branched alkyl, —($C_1$-$C_4$ alkyl)$_t$-$O_t$—($C_3$-$C_5$ cycloalkyl), —($C_1$-$C_4$ alkyl)$_t$-O—($C_1$-$C_4$ straight or branched alkyl), —C(O)—$O_t$—($C_1$-$C_4$ alkyl), or —C(O)—N$(R^{501})_2$ wherein:

t is 0 or 1, and the $C_3$-$C_5$ cycloalkyl optionally includes an oxygen or nitrogen heteroatom;

s is 0, 1 or 2;

each $R^{601}$ and $R^{501}$ is independently H or $C_1$-$C_4$ straight or branched alkyl; and wherein two of $R^{26}$, $R^{60}$, $R^{50}$, $R^{501}$ and $R^{601}$ optionally join to form a ring wherein the two of $R^{26}$, $R^{60}$, $R^{50}$, $R^{501}$ and $R^{601}$ may be two $R^{26}$, two $R^{60}$, two $R^{50}$, two $R^{501}$ or two $R^{601}$; or (c) Formula (VI-J)

(VI-J)

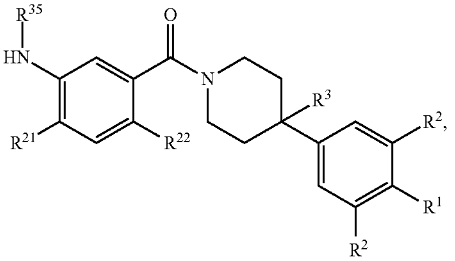

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

the $C_3$-$C_5$ cycloalkyl optionally includes an oxygen or nitrogen heteroatom; and when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is cyclobutyl, azetidin-1-yl, or cyclopropyl;

$R^{22}$ is H, halogen, or $C_1$-$C_2$ alkyl;

$R^{35}$ is —C(O)—$R^{351}$, —C(O)—NH$R^{351}$, —C(O)—O—$R^{351}$ or $S(O)_2R^{351}$; and $R^{351}$ is $C_1$-$C_6$ straight or branched alkyl, cycloalkyl, heterocyclyl, aryl or heteroaryl; or (d) Formula (XII):

(XII)

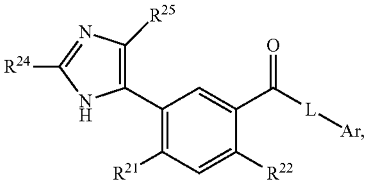

or pharmaceutically acceptable salts thereof, wherein:

L-Ar is

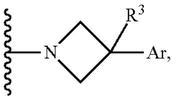 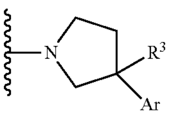 or 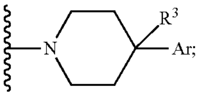

Ar is

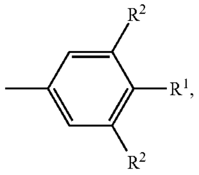 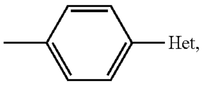

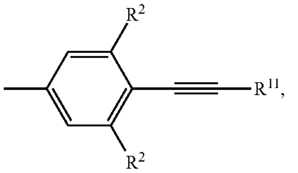

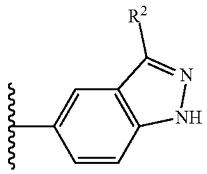 or 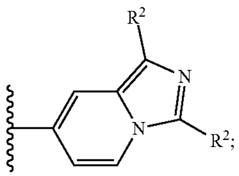

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl;

$R^{24}$ is H, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_6$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl), wherein:

t is 0 or 1;

u is 0 or 1;

with the proviso that when u is 1, t is 1; and each $R^{241}$ is independently H or $C_1$-$C_2$ alkyl; and $R^{25}$ is halogen, —CN, —($C_1$-$C_4$ alkyl)-CN, $C_1$-$C_2$ alkyl or cyclopropyl; or (e) Formula (XIII):

(XIII)

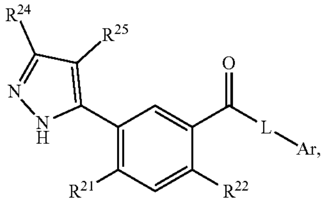

or pharmaceutically acceptable salts thereof, wherein:

L-Ar is

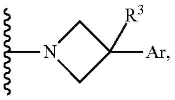 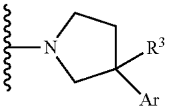 or 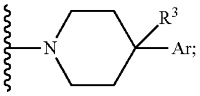

Ar is

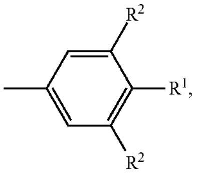 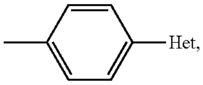

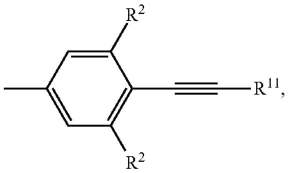

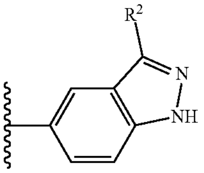 or 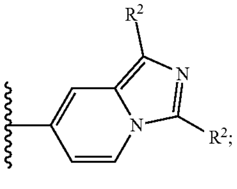

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and each $R^{24}$ and $R^{25}$ is independently H, halogen, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_5$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl), wherein:

each t is independently 0 or 1;

each u is independently 0 or 1; and each $R^{241}$ is independently H or $C_1$-$C_2$ alkyl; or (f) Formula (XIV):

(XIV)

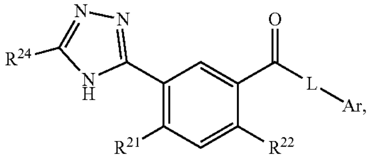

or pharmaceutically acceptable salts thereof, wherein:

L-Ar is

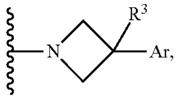 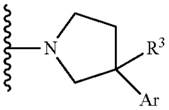 or

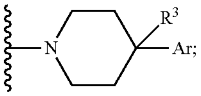

Ar is

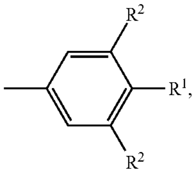 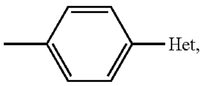

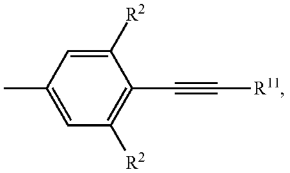 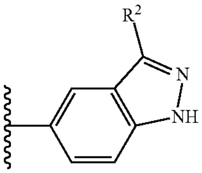 or

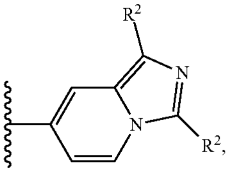

with the proviso that when L-Ar is

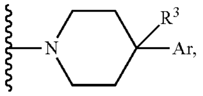

Ar is not

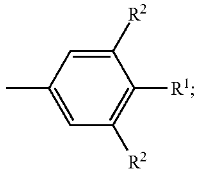

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl; and $R^{24}$ is H, $C_1$-$C_4$ alkyl, —($C_1$-$C_4$ alkyl)-OH, —($C_1$-$C_4$ alkyl)$_t$-N($R^{241}$)$_2$, —($C_1$-$C_4$ alkyl)$_t$-O$_t$—($C_3$-$C_5$ cycloalkyl), —($C_1$-$C_4$ alkyl)$_t$-O$_t$-(4- to 6-membered heterocycle) or —($C_1$-$C_4$ alkyl)$_t$-O—($C_1$-$C_4$ alkyl), wherein:

each t is independently 0 or 1; and each $R^{241}$ is independently H or $C_1$-$C_2$ alkyl; or (g) Formula (XV):

(XV)

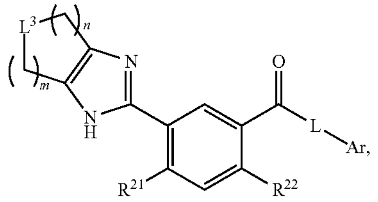

or pharmaceutically acceptable salts thereof, wherein:

$L^3$ is —$CH_2$—, —$CHR^{50}$—, —O—, —$NR^{50}$, —NC(O)$R^{50}$— or —NC(O)$OR^{50}$—, wherein $R^{50}$ is $C_1$-$C_6$ alkyl, $C_3$-$C_5$ cycloalkyl, or 4- to 6-membered heterocycle;

n is 1, 2, or 3;

m is 1 or 2 with the proviso that n+m≥3;

L-Ar is

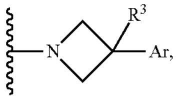

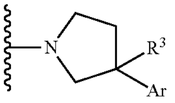

or

-continued

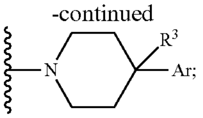

Ar is

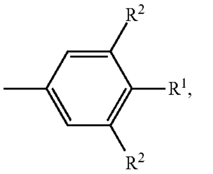

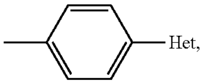

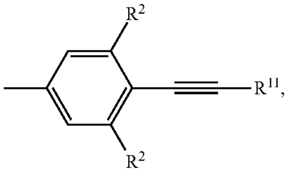

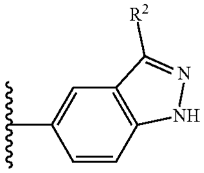

or

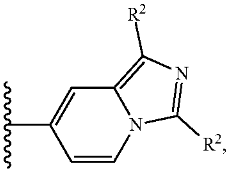

with the proviso that when L-Ar is

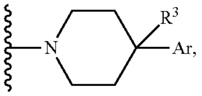

Ar is not

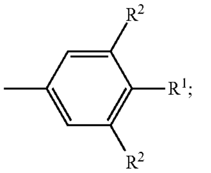

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or a 4- to 6-membered heterocycle; and $R^{22}$ is H, halogen, or $C_1$-$C_2$ alkyl; or (h) Formula (XVI):

(XVI)

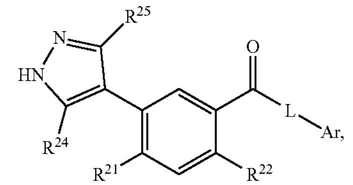

or pharmaceutically acceptable salts thereof, wherein:

L-Ar is

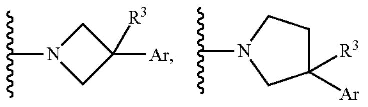

or

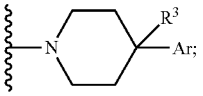

Ar is

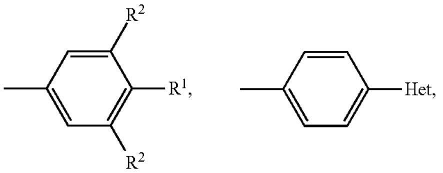

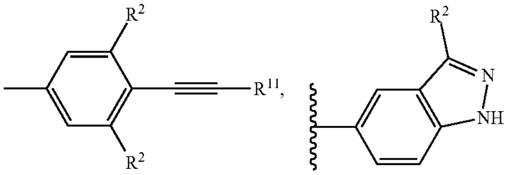

or

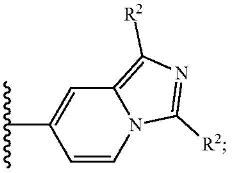

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and each of $R^{24}$ and $R^{25}$ is independently H, —$C_1$-$C_4$ alkyl, or halogen; or (i) Formula (XVII):

(XVII)

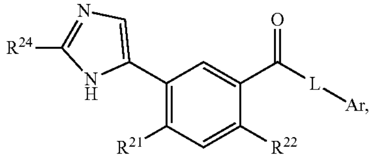

or pharmaceutically acceptable salts thereof, wherein:

L-Ar is

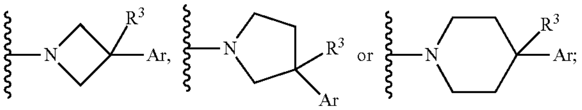

Ar is

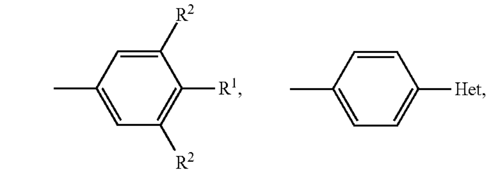

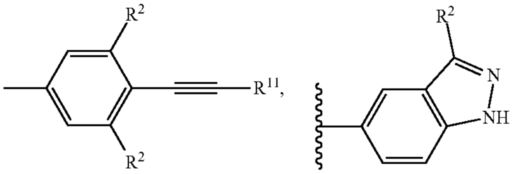

or

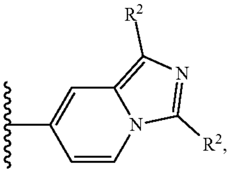

with the proviso that when L-Ar is

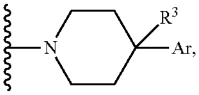

Ar is not

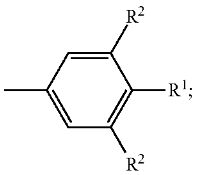

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and $R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_5$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl), wherein:

t is 0 or 1;

u is 0 or 1;

with the proviso that when u is 1, t is 1; and $R^{241}$ is H or $C_1$-$C_2$ alkyl; or (j) Formula (XVIII):

(XVIII)

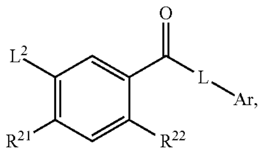

or pharmaceutically acceptable salts thereof, wherein:

L-Ar is

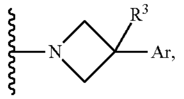

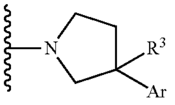

or

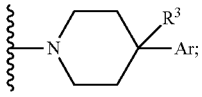

Ar is

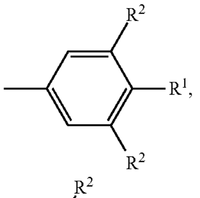

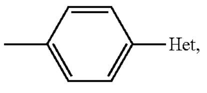

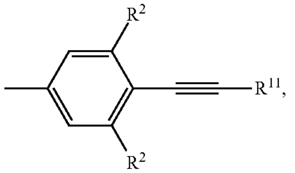

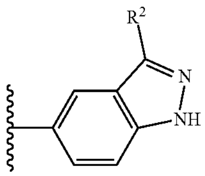

or

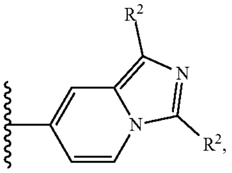

with the proviso that when L-Ar is

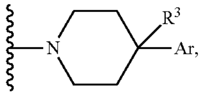

Ar is not

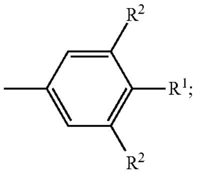

$L^2$ is —$NHR^{35}$ or —C(O)$NHR^{351}$, wherein $R^{351}$ is $C_1$-$C_6$ alkyl, $C_3$-$C_5$ cycloalkyl, 4- to 6-membered heterocycle, aryl or heteroaryl;

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle)$_t$-O—($C_1$-$C_4$ alkyl) wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl; and $R^{35}$ is —C(O)$R^{351}$, —C(O)$NHR^{351}$, C(O)$OR^{351}$ or S(O)$_2R^{351}$ wherein $R^{351}$ is $C_1$-$C_6$ alkyl, $C_3$-$C_5$ cycloalkyl, 4- to 6-membered heterocycle, aryl or heteroaryl; or (k) Formula (XIX):

(XIX)

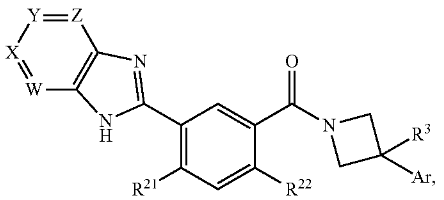

or pharmaceutically acceptable salts thereof, wherein:

each W, X, Y and Z is independently —N— or —$CR^{26}$— with the proviso that not more than 2 of W, X, Y and Z are —N—;

each $R^{26}$ is independently H, $C_1$-$C_4$ alkyl, —O—($C_1$-$C_4$ alkyl), —N($R^{27}$)$_2$, —S(O)$_2$—($C_1$-$C_4$ alkyl), or —C(O)—($C_1$-$C_4$ alkyl);

each $R^{27}$ is independently H or $C_1$-$C_4$ alkyl or both $R^{27}$ are $C_1$-$C_4$ alkyl and join to form a 3- to 6-membered ring together with the N to which they are attached and wherein the ring optionally includes one oxygen atom as one of the members of the ring;

Ar is

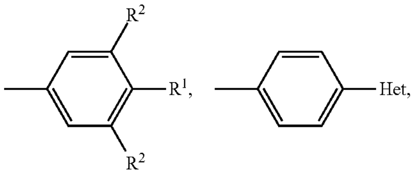

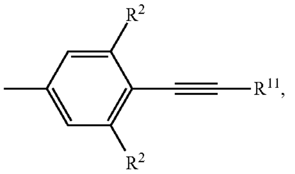

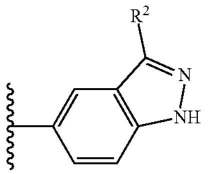

or

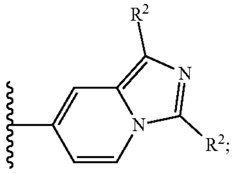

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle), —O—($C_1$-$C_4$ alkyl) wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or a 4- to 6-membered heterocycle; and $R^{22}$ is H, halogen or $C_1$-$C_2$ alkyl; or (l) Formula (XX):

(XX)

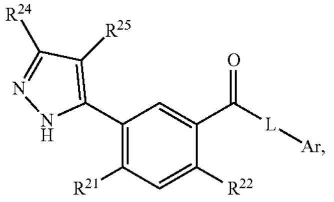

or a pharmaceutically acceptable salt thereof, wherein:

L-Ar is

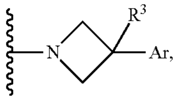

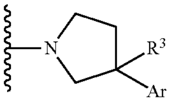

or

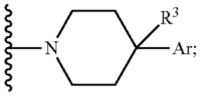

Ar is

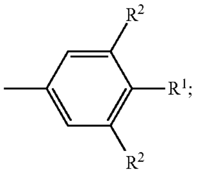

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogen;

each $R^2$ is independently hydrogen, halogen or $C_1$-$C_4$ alkyl;

$R^3$ is H or F;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl;

$R^{24}$ is —O—($C_1$-$C_4$ alkyl), —O—($C_1$-$C_4$ alkyl)-O—($C_1$-$C_4$ alkyl), —O—($C_3$-$C_5$ cycloalkyl), or —O-(4- to 6-membered heterocycle), wherein $R^{24}$ is optionally substituted with one or more hydroxyl or halogen; and $R^{25}$ is H, halogen, $C_1$-$C_4$ alkyl or $C_3$-$C_5$ cycloalkyl, wherein $R^{25}$ is optionally substituted with one or more halogen; or (m) Formula (XI):

(XI)

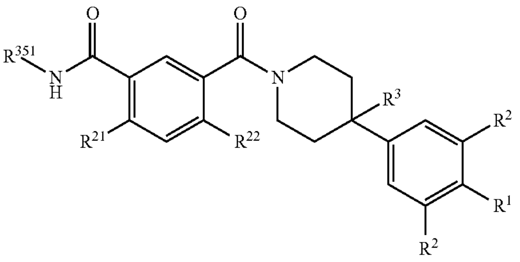

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

the $C_3$-$C_5$ cycloalkyl optionally includes an oxygen or nitrogen heteroatom; and when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is cyclobutyl, azetidin-1-yl, or cyclopropyl;

$R^{22}$ is H, halogen, $C_1$-$C_2$ alkyl; and $R^{351}$ is $C_1$-$C_2$ alkyl or $C_2$—O—($C_1$ or $C_2$ alkyl).

In some embodiments of the methods provided herein, such as those described above (or below), the fatty acid synthase inhibitor is a compound selected from the group consisting of:

Ar is

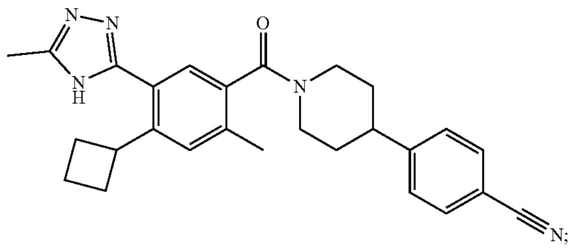

(denifanstat)

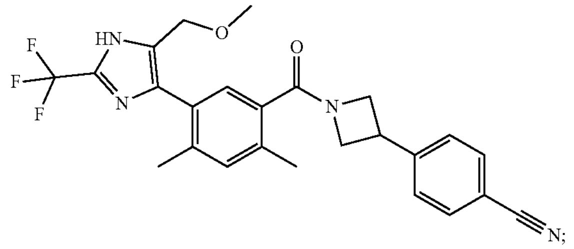

(TVB-3664)

(Compound 005-2)

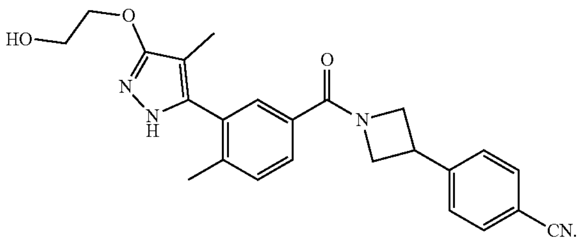

In some embodiments of the methods provided herein, such as those described above (or below), the fatty acid synthase inhibitor is a compound selected from the group consisting of:

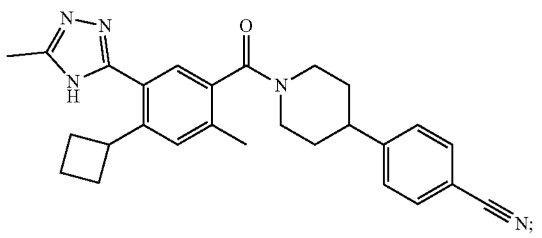

and (denifanstat)

(Compound 005-2)

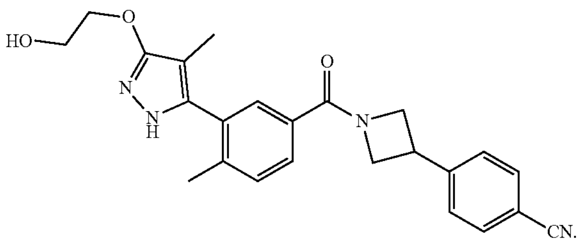

In some embodiments of the methods provided herein, such as those described above (or below), the fatty acid synthase inhibitor is

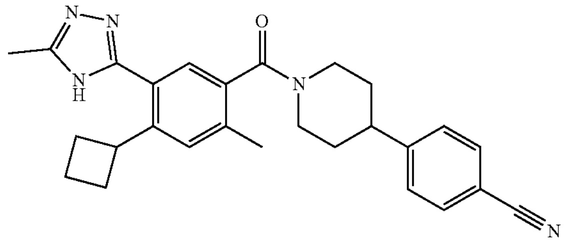 [SMILES: Cc1nnc(-c2cc(C(=O)N3CCC(c4ccc(C#N)cc4)CC3)c(C)cc2C2CCC2)[nH]1]

(denifanstat);

In some embodiments of the methods provided herein, such as those described above (or below), the fatty acid synthase inhibitor is

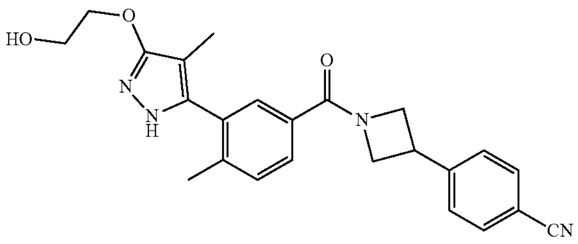 [SMILES: Cc1ccc(C(=O)N2CC(c3ccc(C#N)cc3)C2)cc1-c1[nH]nc(OCCO)c1C]

(Compound 005-2).

In some embodiments of the methods provided herein, such as those described above (or below), the fatty acid synthase inhibitor is denifanstat or a pharmaceutically acceptable salt thereof, including all possible tautomers of denifanstat.

In some embodiments of the methods provided herein, such as those described above (or below), the fatty acid synthase inhibitor is TVB-3664 or a pharmaceutically acceptable salt thereof.

In some embodiments of the methods provided herein, such as those described above (or below), the thyroid hormone receptor-beta agonist is selected from:

VK2809

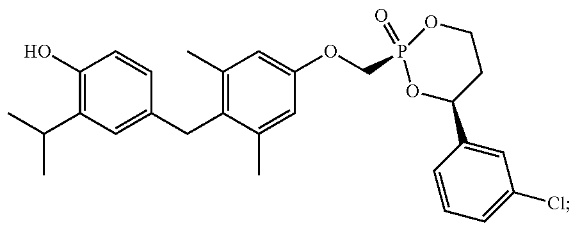

TERN-501

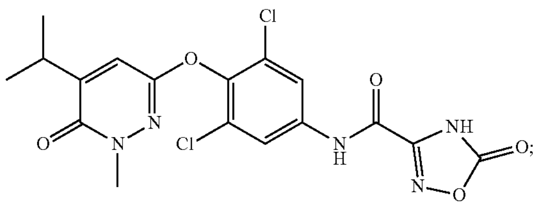

and ALG-055009.

In some embodiments of the methods provided herein, such as those described above (or below), the thyroid hormone receptor-beta agonist is a compound of formula (XXI):

(XXI)

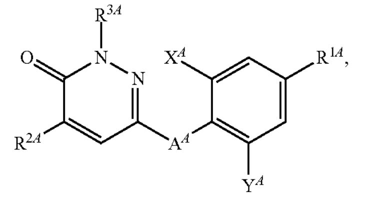

or a pharmaceutically acceptable salt thereof, wherein:

$A^A$ is O, $CH_2$, S, SO or $SO_2$;

$X^A$ and $Y^A$ are each independently selected from the group consisting of Br, Cl and $CH_3$;

$R^{1A}$ is selected from the group consisting of: $-(CH_2)_n$ COOH, $-OCH_2COOH$, $-NHC(=O)COOH$, $-NHCH_2COOH$,

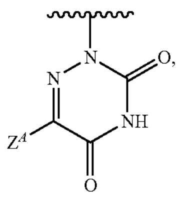

and

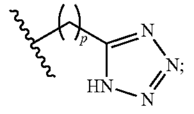

$Z^A$ is H, or $-C\equiv N$;

$R^{2A}$ is lower alkyl having from 1 to 4 C atoms;

$R^{3A}$ is H or lower alkyl;

n is 1 or 2;

p is 1 or 2.

In some embodiments of the methods provided herein, such as those described above (or below), the thyroid hormone receptor-beta agonist is resmetirom (also known as MGL-3196):

(Compound A)

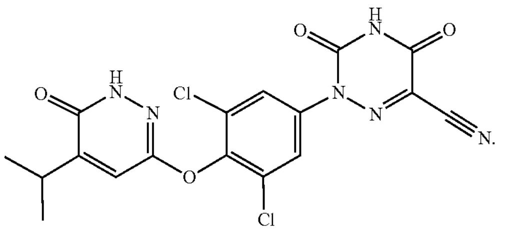

Throughout the disclosure, references to "methods of treatment" are meant to encompass uses of compounds, compositions and combinations in the methods of treatment described therein, compounds, compositions and combinations for use in treating the diseases recited herein, as well as use of the compounds, compositions and combinations described herein in the manufacturing of medicaments for the treatment of the diseases recited herein.

Synthesis of Compounds

Also described herein are methods of synthesizing the fatty acid synthase inhibitors of the present disclosure. Fatty acid synthase inhibitors of the present disclosure can be synthesized as indicated in SYNTHETIC SCHEMES 1-13 below.

Scheme 1

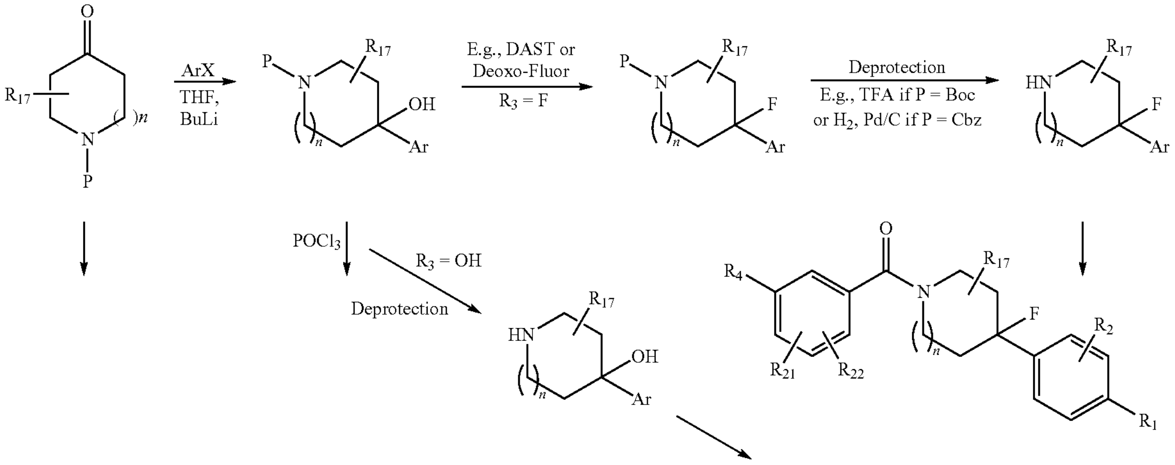

-continued

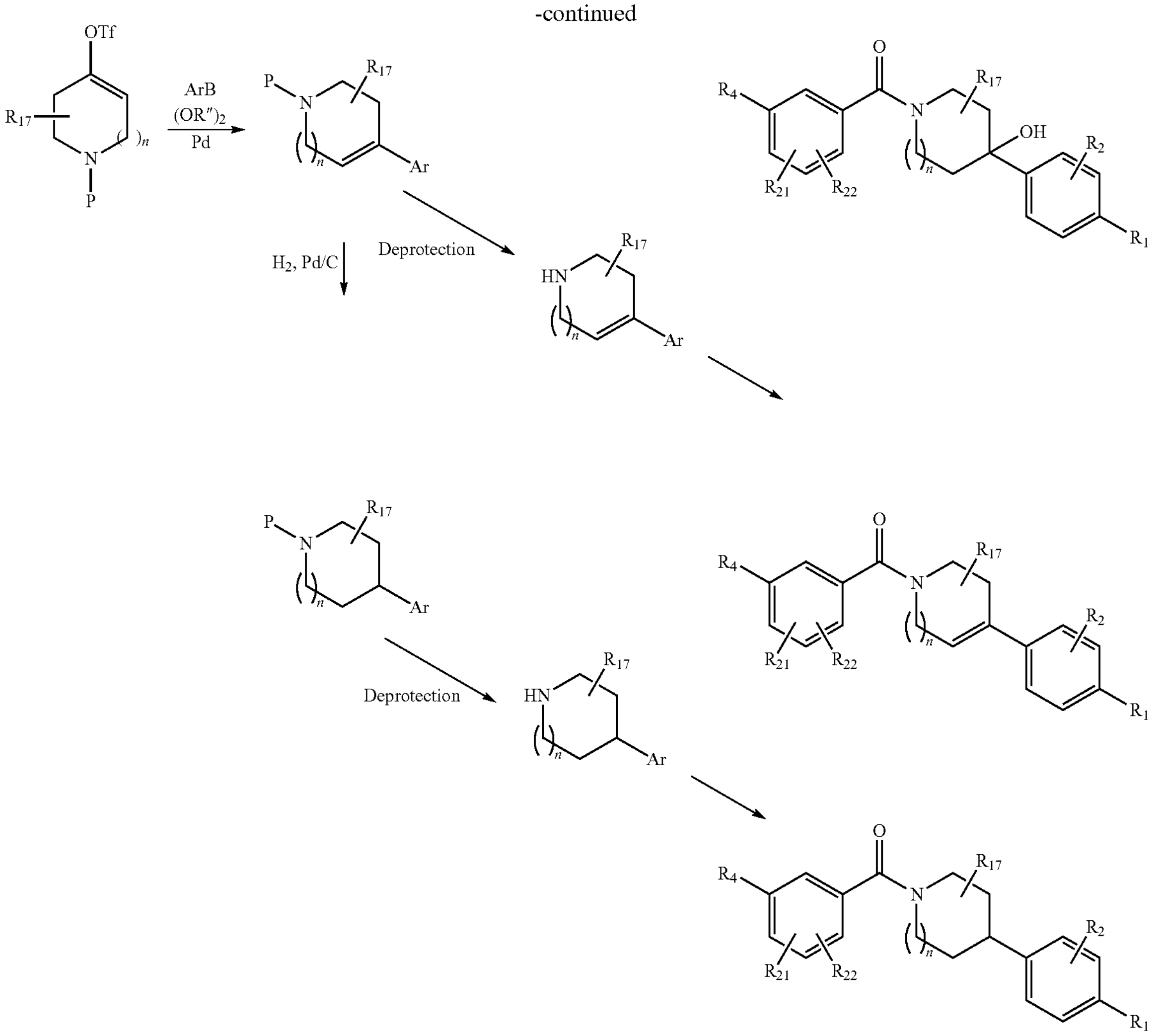

wherein:

R" is hydrogen or alkyl;

$R_1$ is hydrogen, cyano, halo, $C_{1-6}$ alkyl, $C_{1-6}$ alkoxy, —C(═O)N($R_{13}$)($R_{14}$), —$(CH_2)_q$C(═O)N($R_{13}$)($R_{14}$), $CF_3$, —$OCF_3$, or —S(═O)$_2R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —S(═O)$_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(═O)$_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino; and $R_{17}$ is hydrogen or alkyl.

Scheme 2

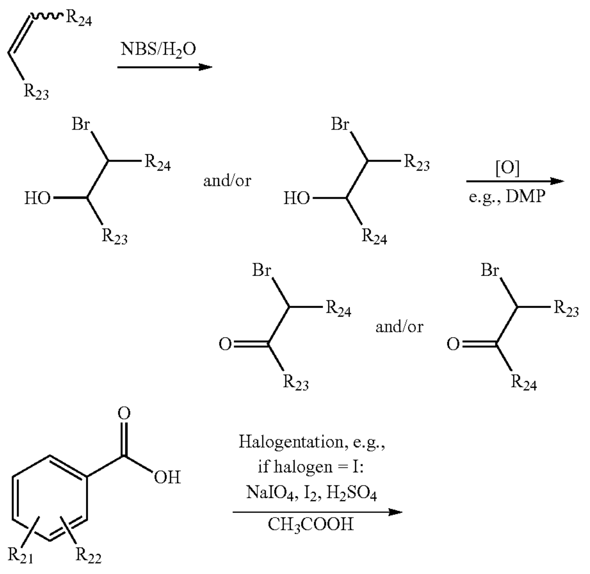

-continued

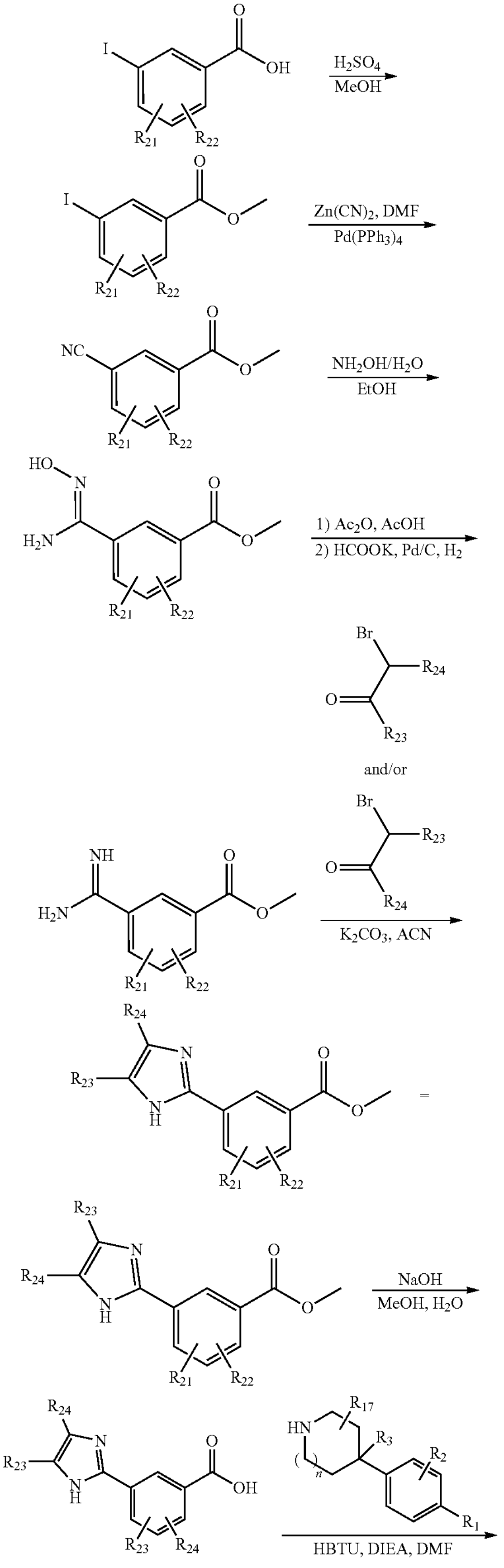

-continued

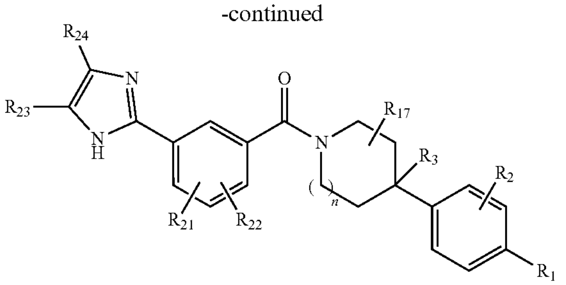

wherein:

$R_1$ is hydrogen, cyano, halo, $C_{1-6}$ alkyl, $C_{1-6}$ alkoxy, —C(=O)N($R_{13}$)($R_{14}$), —$(CH_2)_q$C(=O)N($R_{13}$)($R_{14}$), $CF_3$, —$OCF_3$, or —S(=O)$_2R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-4}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —S(=O)$_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino;

$R_{23}$ is hydrogen, —N($R_{13}$)($R_{14}$), $C_{1-6}$ alkyl, $C_{1-6}$ alkoxy, is absent if $L^{11}$ is N, or $R_{23}$ and $R_{24}$ taken together with the atoms to which they are attached join together to form a heterocyclyl, heteroaryl, or cycloalkyl; and $R_{24}$ is hydrogen, —N($R_{13}$)($R_{14}$), $C_{1-6}$ alkyl, $C_{1-6}$ alkoxy, —($C_{1-6}$ alkoxy) (heterocyclyl), heterocyclyl, or $R_{23}$ and $R_{24}$ taken together with the atoms to which they are attached join together to form a heterocyclyl, heteroaryl, or cycloalkyl.

Scheme 3

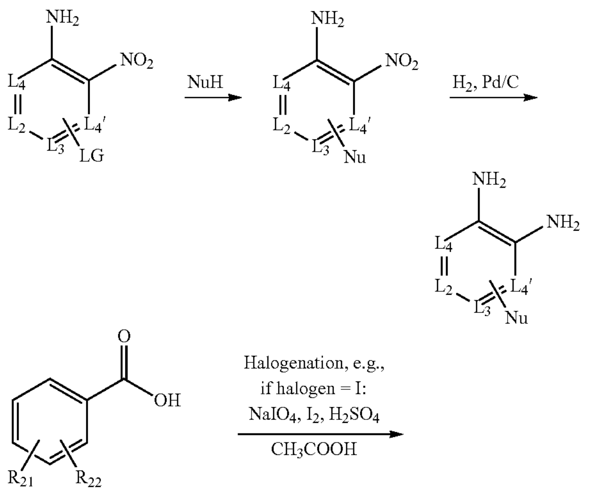

-continued

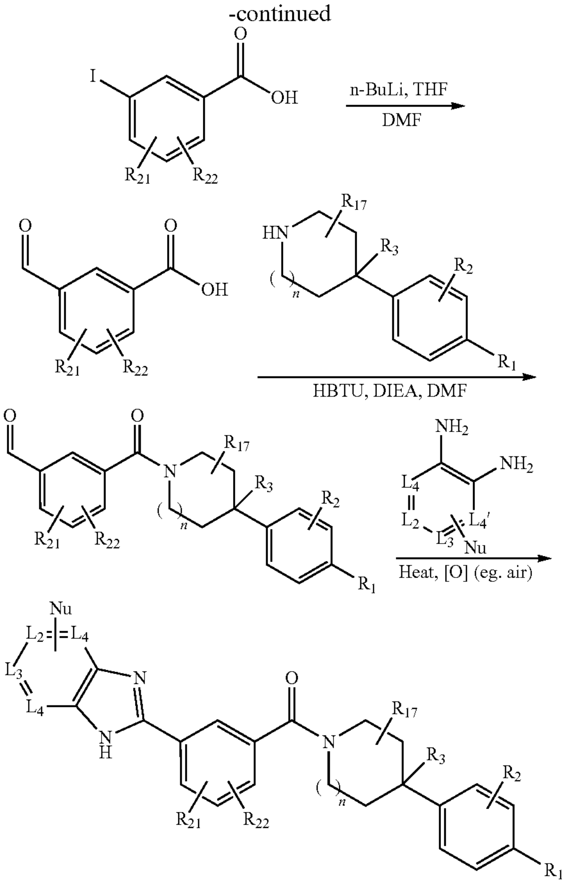

wherein:

LG is a leaving group;

Nu is a nucleophile;

$L_2$, $L_3$, $L_4$, and $L_4$ are each independently CH or N;

$R_1$ is hydrogen, cyano, halo, $C_{1-6}$ alkyl, $C_{1-6}$ alkoxy, $-C(=O)N(R_{13})(R_{14})$, $-(CH_2)_qC(=O)N(R_{13})(R_{14})$, $CF_3$, $-OCF_3$, or $-S(=O)_2R_{20}$;

q is 0, 1, 2, 3, or 4;

$R_{20}$ is hydrogen or $C_{1-6}$ alkyl, $C_{1-6}$ alkoxy, or $-N(R_{13})(R_{14})$;

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, $-OCF_3$, or $-S(=O)_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, $-N(R_{15}R_{16})$, or $-S(=O)_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino; and $R_{17}$ is hydrogen or alkyl.

Scheme 4

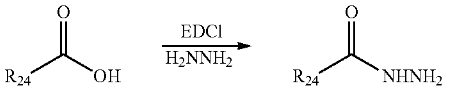

-continued

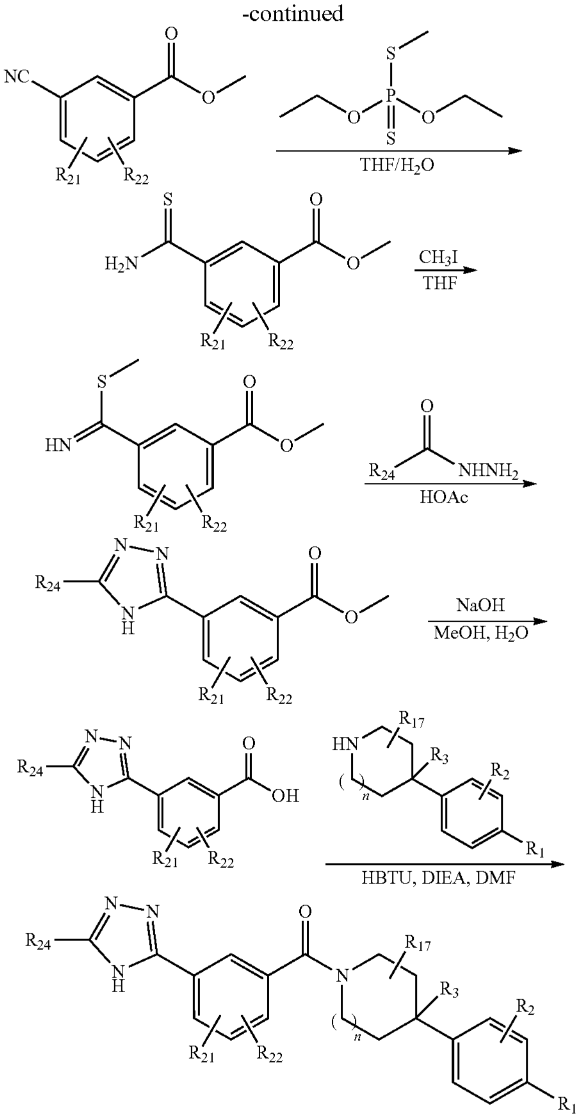

wherein:

$R_1$ is hydrogen, cyano, halo, $C_{1-6}$ alkyl, $C_{1-6}$ alkoxy, $-C(=O)N(R_{13})(R_{14})$, $-(CH_2)_qC(=O)N(R_{13})(R_{14})$, $CF_3$, $-OCF_3$, or $-S(=O)_2R_{20}$;

q is 0, 1, 2, 3, or 4;

$R_{20}$ is hydrogen or $C_{1-6}$ alkyl, $C_{1-6}$ alkoxy, or $-N(R_{13})(R_{14})$;

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, $-OCF_3$, or $-S(=O)_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, $-N(R_{15}R_{16})$, or $-S(=O)_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino;

$R_{17}$ is hydrogen or alkyl; and $R_{24}$ is hydrogen, $-N(R_{13})(R_{14})$, $C_{1-6}$ alkyl, $C_{1-6}$ alkoxy, $-(C_{1-6}$ alkoxy) (heterocyclyl), or heterocyclyl.

Scheme 5

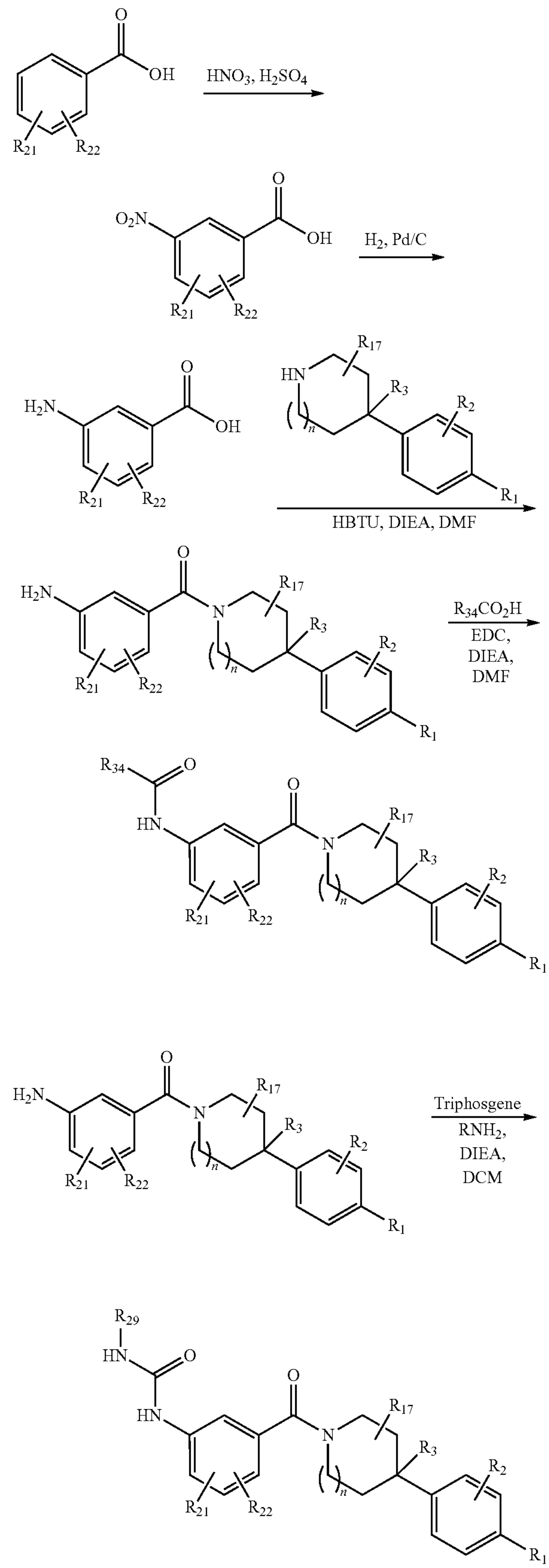

-continued

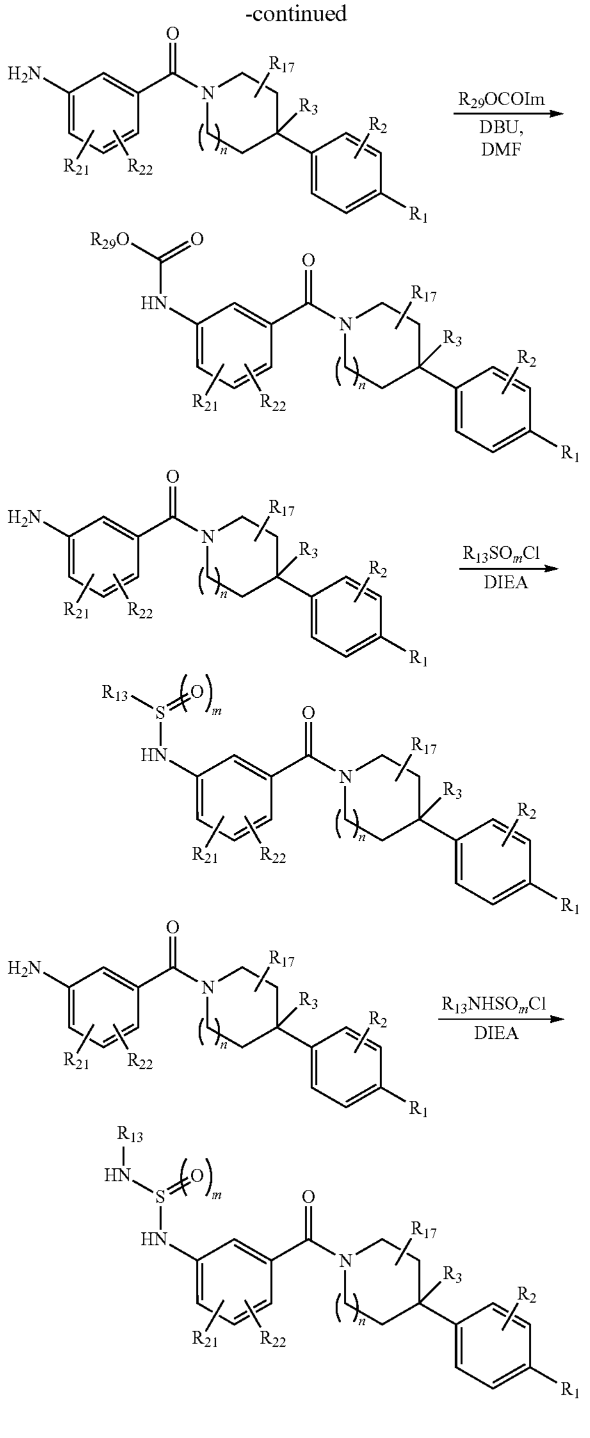

wherein:

$R_1$ is hydrogen, cyano, halo, $C_{1-6}$ alkyl, $C_{1-6}$ alkoxy, $—C(=O)N(R_{13})(R_{14})$, $—(CH_2)_qC(=O)N(R_{13})(R_{14})$, $CF_3$, $—OCF_3$, or $—S(=O)_2R_{20}$;

q is 0, 1, 2, 3, or 4;

$R_{20}$ is hydrogen or $C_{1-6}$ alkyl, $C_{1-6}$ alkoxy, or $—N(R_{13})(R_{14})$;

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, $—OCF_3$, or $—S(=O)_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —$N(R_{15}R_{16})$, or —$S(=O)_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino;

$R_{17}$ is hydrogen or alkyl;

$R_{24}$ is hydrogen, —$N(R_{13})(R_{14})$, $C_{1-6}$ alkyl, $C_{1-6}$ alkoxy, —($C_{1-6}$ alkoxy) (heterocyclyl), or heterocyclyl;

$R_{29}$ is hydrogen, $C_{1-6}$ alkyl, $C_{1-6}$ alkoxy, hydroxyalkyl, heteroaryl, heterocyclyl, —$N(R_{15}R_{16})$, —$C(=O)R_{46}$, or —$R_{48}C(=O)R_{47}$;

$R_{34}$ is hydrogen, $C_{1-6}$ alkyl, $C_{1-6}$ alkoxy, cycloalkyl, hydroxyl, hydroxyalkyl, aryl, heterocyclyl, heteroaryl, alkylamino, $CF_3$, —$OCF_3$, —$S(=O)_2R_{20}$, or —$N(R_{15}R_{16})$; and m 0, 1, or 2.

Schemes 6-13 provides a synthesis for exemplary compounds of formula IX wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

$C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{23}$ is H or $C_1$-$C_4$ straight or branched alkyl; and $R^{24}$ is H, $C_1$-$C_4$ straight or branched alkyl, —$(C_1$-$C_4$ alkyl$)_t$-OH, $(C_1$-$C_4$ alkyl$)_t$-$O_t$-($C_3$-$C_5$ cycloalkyl), or —$(C_1$-$C_4$ alkyl$)_t$-O—($C_1$-$C_4$ straight or branched alkyl)

wherein:

t is 0 or 1; and the $C_3$-$C_5$ cycloalkyl optionally includes an oxygen or nitrogen heteroatom.

Scheme 6

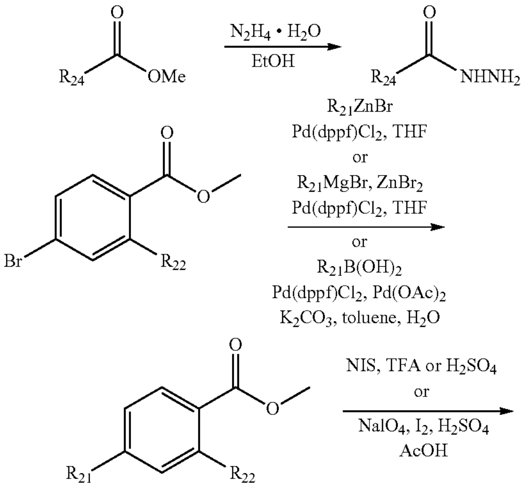

-continued

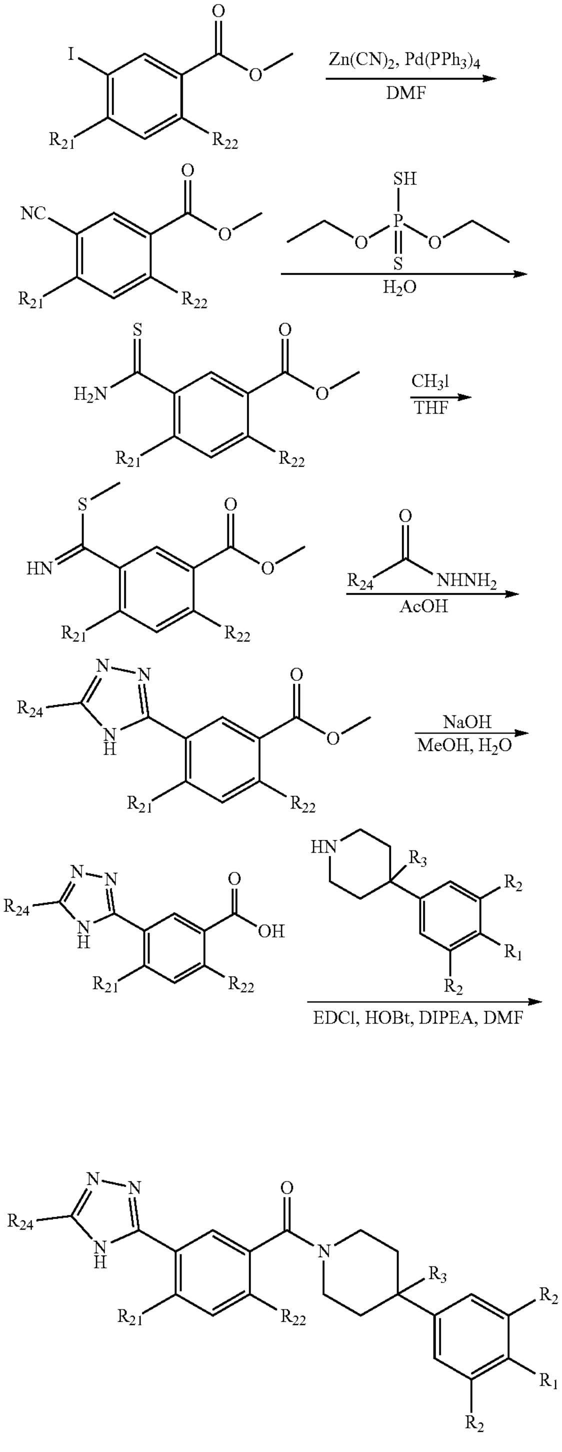

Scheme 7

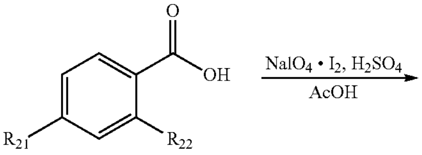

-continued
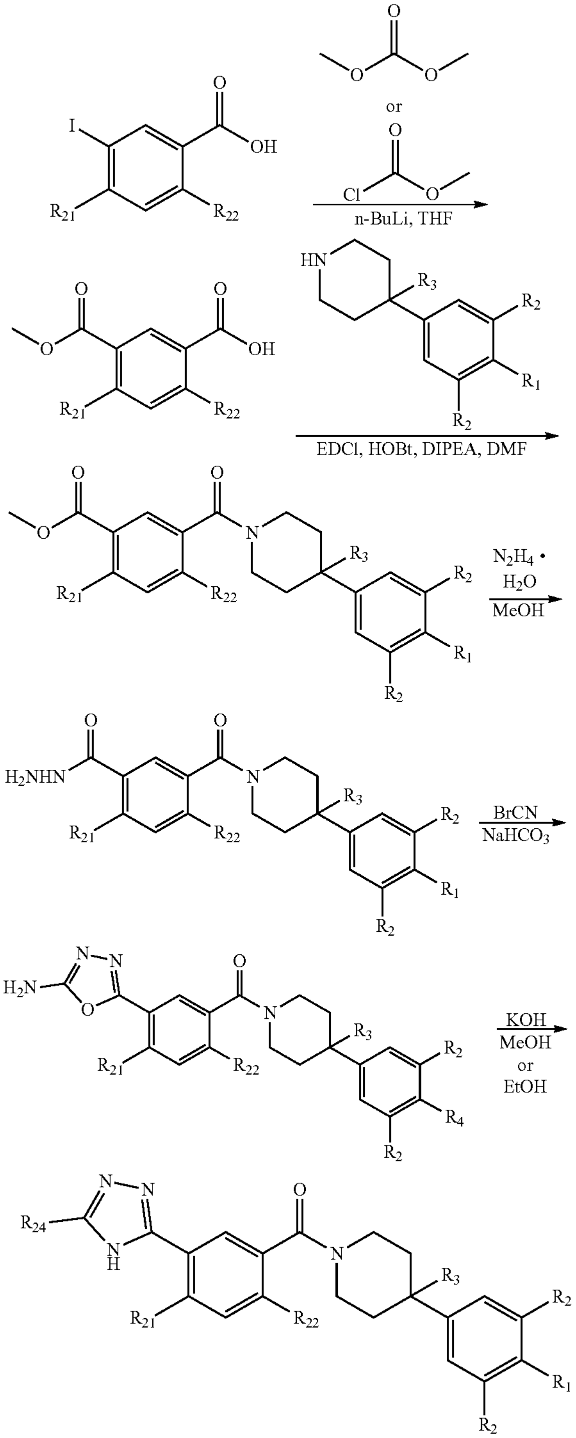
Scheme 8
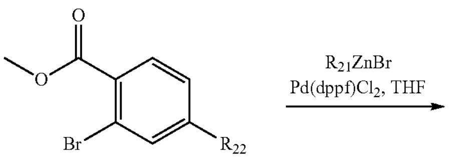
-continued
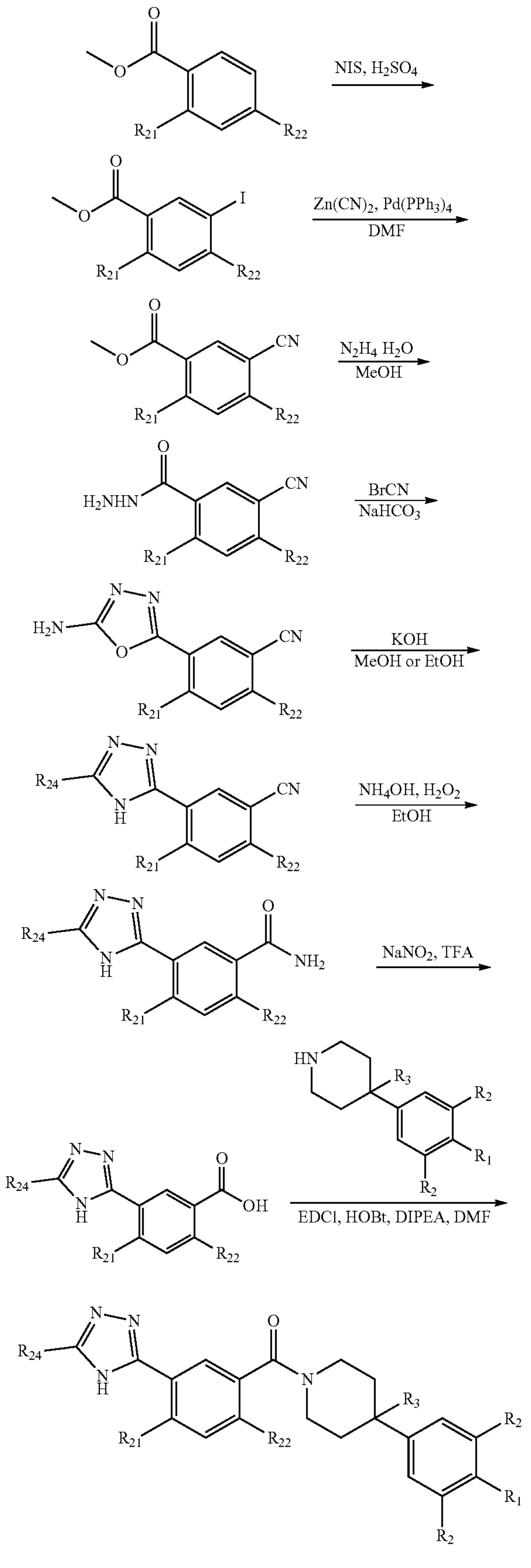

Scheme 9
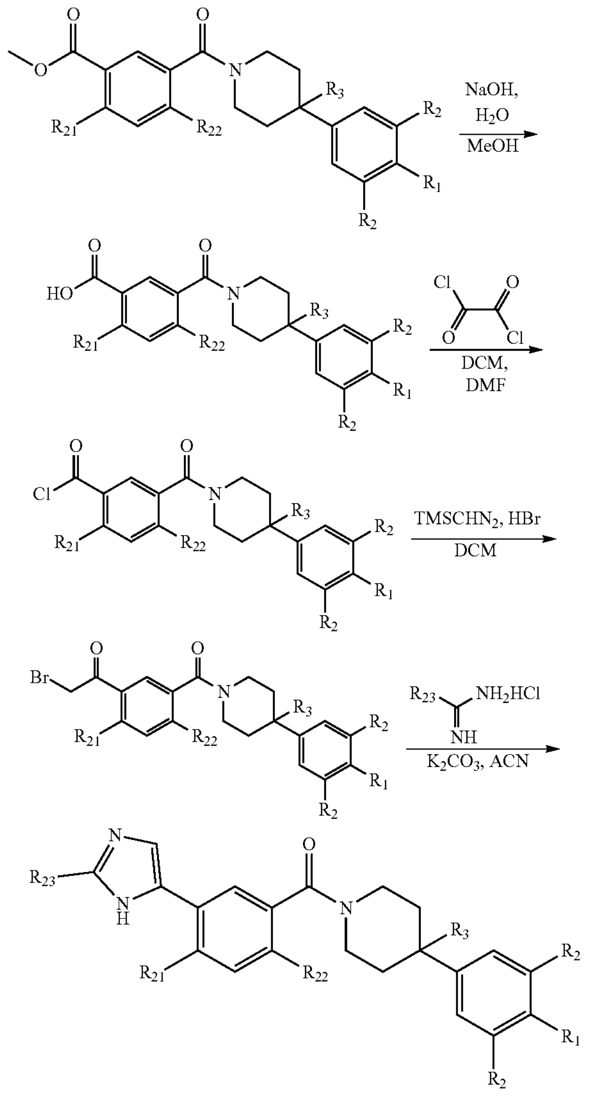
Scheme 10
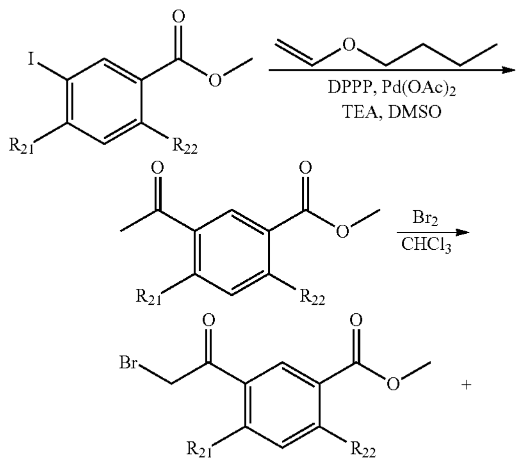
-continued
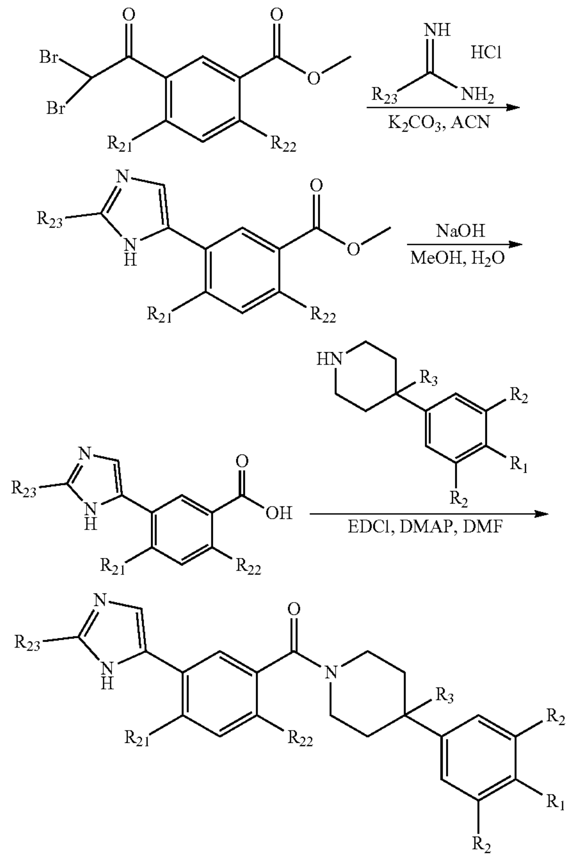
Scheme 11
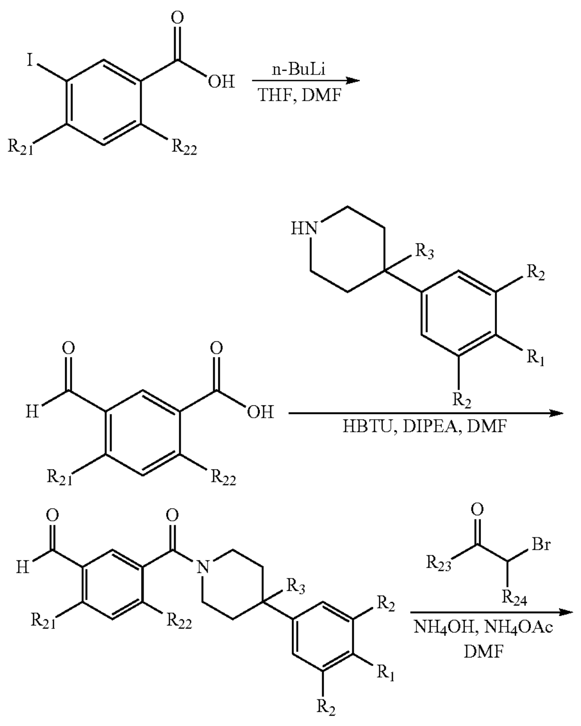

-continued
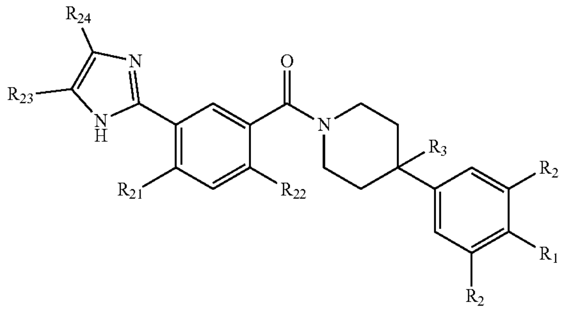
Scheme 12
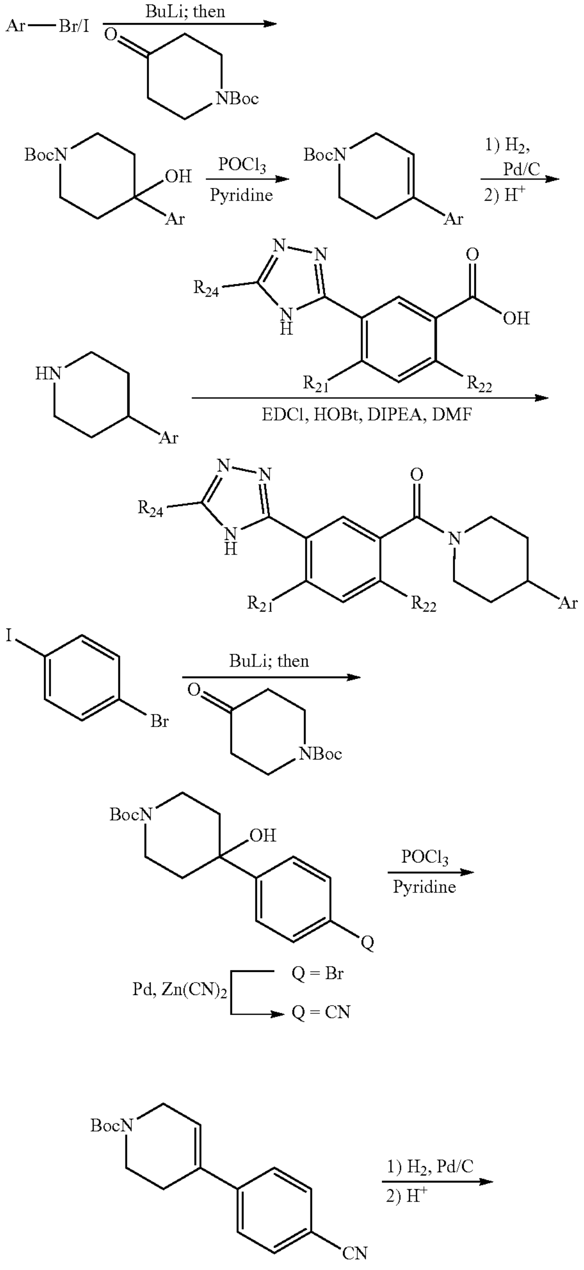
-continued
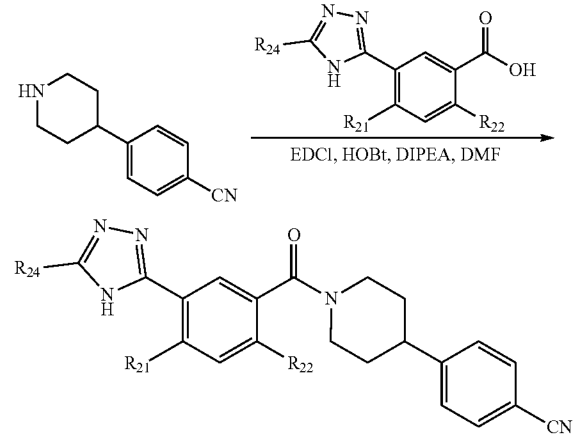
Scheme 13
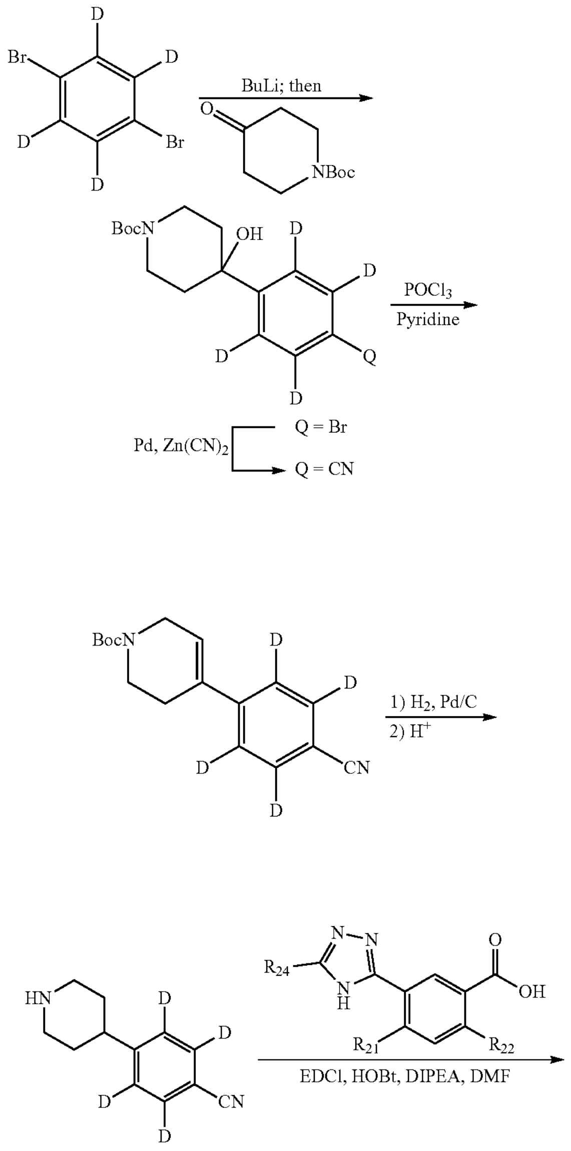

-continued

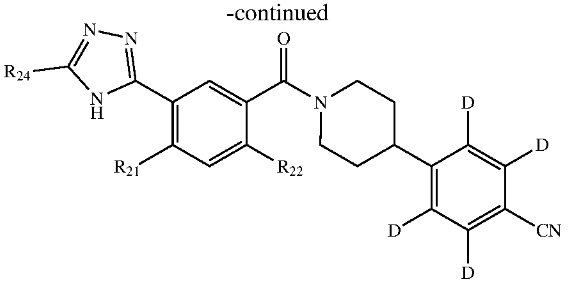

Additional methods for producing particular compounds according to the present disclosure are provided in the EXAMPLES. One skilled in the art will recognize that other compounds of structures can be made by modifications to the specifically disclosed schemes employing methods known to those of skill in the art. Additional examples can be found in Table C-1, Table C-2, and Table C-3.

Many such techniques are well known in the art. However, many of the known techniques are elaborated in Compendium of Organic Synthetic Methods (Vol. 1, 1971; Vol. 2, 1974; Vol. 3, 1977; Vol. 4, 1980; Vol. 5, 1984; and Vol. 6 as well as March in Advanced Organic Chemistry (1985); Comprehensive Organic Synthesis. Selectivity, Strategy & Efficiency in Modern Organic Chemistry. In 9 Volumes (1993); Advanced Organic Chemistry Part B: Reactions and Synthesis, Second Edition (1983); Advanced Organic Chemistry, Reactions, Mechanisms, and Structure, Second Edition (1977); Protecting Groups in Organic Synthesis, Second Edition; and Comprehensive Organic Transformations (1999).

Fatty Acid Synthesis Pathway

Various aspects of the present disclosure relate to compositions and methods that modulate the activity of the fatty acid synthesis pathway to treat a viral infection or treat cancer. The fatty acid synthesis pathway in humans can use four enzymes: 1) acetyl-CoA carboxylase citrate lyase, which can synthesize acetyl-CoA; and 4) fatty acid synthase, which can catalyze NADPH-dependent synthesis of fatty acids from acetyl-CoA and malonyl-CoA. In various aspects, the present disclosure relates to treatment of viral infections and cancer by modulating the activity of the fatty acid synthase protein.

The final products of fatty acid synthase are free fatty acids which can use separate enzymatic derivatization with coenzyme-A for incorporation into other products. In humans, fatty acid synthesis can occur in two sites: the liver, where palmitic acid can be made (Roncari, (1974) *Can. J. Biochem.*, 52:221-230) and lactating mammary gland, where $C_{10}$-$C_{14}$ fatty acids can be made (Thompson, et al., (1985) *Pediatr. Res.*, 19:139-143).

Fatty acids can be synthesized in the cytoplasm from acetyl-CoA. Acetyl-CoA can be generated from pyruvate by pyruvate dehydrogenase (PDH) and by β-oxidation of fatty acids in the mitochondria. A "citrate shuttle" can transport acetyl-CoA from the mitochondria to the cytoplasm. Acetyl-CoA can react with oxaloacetate to yield citrate, and a tricarboxylate translocase can transport citrate from the mitochondria to the cytosol. In the cytoplasm, citrate can be cleaved back to oxaloacetate and acetyl-CoA, a reaction that can be catalyzed by ATP-citrate lyase. Oxaloacetate can be converted back to pyruvate for re-entry into mitochondria.

Acetyl-CoA can be converted to malonyl-CoA. Acetyl-CoA carboxylase (ACC) is a complex multifunctional, biotin-containing, enzyme system that can catalyze carboxylation of acetyl-CoA to malonyl-CoA. This conversion is an irreversible, rate-limiting step in fatty acid synthesis. ACC can carry out three functions: biotin carboxyl carrier protein, biotin carboxylase and carboxyltransferase. ATP-dependent carboxylation of biotin, a prosthetic group (cofactor) can be followed by transfer of the carboxyl group to acetyl-CoA.

$$HCO_3^- + ATP + acetyl\text{-}CoA \text{ -> } ADP + P_i + malonyl\text{-}CoA$$

There are two ACC forms, alpha and beta, encoded by two different genes ACC-alpha (also known as ACC, ACAC, ACC1, ACCA, and ACACA) can encode protein highly enriched in lipogenic tissues. Multiple alternatively spliced transcript variants divergent in the sequence and encoding distinct isoforms have been found for this gene. ACC-beta (also known as ACC2, ACCB, HACC275, and ACACB) can encode protein thought to control fatty acid oxidation by means of the ability of malonyl-CoA to inhibit carnitine-palmitoyl-CoA transferase I, the rate-limiting step in fatty acid uptake and oxidation by mitochondria. ACC-beta may be involved in the regulation of fatty acid oxidation, rather than fatty acid biosynthesis. There is evidence for the presence of two ACC-beta isoforms.

ACC can be regulated by the phosphorylation/dephosphorylation of targeted serine residues. For example, AMP-activated kinase (AMPK) can phosphorylate ACC, and this phosphorylation can inhibit the ability of ACC to produce malonyl-CoA. On ACACA, AMPK can phosphorylate Ser79, Ser1200, and Ser1215 (Park S. H. et al. (2002) *J. Appl. Physiol.* 92:2475-82). AMPK can phosphorylate Ser218 on ACACB (Hardie D. G. (1992) *Biochim. Biophys. Acta* 1123:231-8). Also, cAMP-dependent protein kinase (Protein Kinase A, or PKA) can phosphorylate ACC.

ACC can be regulated by allosteric transformation by citrate or palmitoyl-CoA. For example, citrate can be a positive effector (i.e., citrate can allosterically activate ACC). Citrate concentration can be high when there is adequate acetyl-CoA entering the Krebs Cycle. Excess acetyl-CoA can then be converted via malonyl-CoA to fatty acids. Palmitoyl-CoA can be a negative effector. Palmitoyl-CoA, which is the product of Fatty Acid Synthase (FASN), can promote the inactive conformation of ACC, which can reduce production of malonyl-CoA (a feedback inhibition process). AMP can regulate fatty acid synthesis by regulating the availability of malonyl-CoA. Insulin binding a receptor can activate a phosphatase to dephosphorylate ACC, which can remove the inhibitory effect.

The fatty acid synthase gene (also known as FAS, OA-519, SDR27X1; MGC14367; MGC15706; FASN) is involved in fatty acid synthesis. The enzyme encoded by this gene is a multifunctional protein of approximately 272 kDa with multiple domains, each with distinct enzyme activities that can play a role in fatty acid biosynthesis. FASN can catalyze the synthesis of palmitate from acetyl-CoA and malonyl-CoA, in the presence of NADPH, into long-chain saturated fatty acids. In some cancer cell lines, FASN protein has been found to be fused with estrogen receptor-alpha (ER-alpha), in which the N-terminus of FASN is fused in-frame with the C-terminus of ER-alpha.

FASN protein can exist in the cytosol as a dimer of identical subunits. FASN consists of three catalytic domains in the N-terminal section (-ketoacyl synthase (KS), malonyl/acetyltransferase (MAT), and dehydrase (DH)). The N-terminal section is separated by a core region of about 600 amino acids from four C-terminal domains (enoyl reductase (ER), -ketoacyl reductase (KR), acyl carrier protein (ACP), and thioesterase (TE)). The crystal structure of a mammalian fatty acid synthase has been reported (Maier T. et al. (2008) *Science* 321:1315-1322). Each of the catalytic domains of FASN can be targeted in the methods of treating viral infection of the provided invention.

The enzymatic steps of fatty acid synthesis can involve decarboxylative condensation, reduction, dehydration, and another reduction and can result in a saturated acyl moiety. NADPH can be an electron donor in reductive reactions.

Utility in Metabolic Disorders

In various aspects, the therapeutic combinations of the present disclosure have utility in the treating of metabolic diseases. FASN has been demonstrated to be involved in regulation of glucose, lipids and cholesterol metabolism. Mice with a liver-specific inactivation of FASN have normal physiology unless fed a zero-fat diet, in which case they develop hypoglycemia and fatty liver, both of which are reversed with dietary fat. (Chakravarthy, M. V., et al. (2005) *Cell Metabolism* 1:309-322). Db/+ mice fed a high fructose diet exhibit reduced liver triglyceride levels and improved insulin sensitivity when treated for 28 days with platensimycin, a covalent inhibitor of FASN. (Wu, M. et al. (2011) *PNAS* 108(13):5378-5383). Ambient glucose levels are also reduced in db/db mice following treatment with platensimycin. These results provide evidence that inhibiting FASN can yield therapeutically relevant benefits in animal models of diabetes and related metabolic disorders. Thus the disclosed FASN inhibitors are useful in the treatment of disorders characterized by dysregulation in these systems. Without limitation, examples include steatosis and diabetes.

Non-alcoholic fatty liver disease/metabolic dysfunction-associated steatotic liver disease (NAFLD/MASLD), a condition in which the liver contains more than 5% fat by weight which is not caused by alcohol consumption, is a disease which currently affects ~20-30% of the US and general western world population, and is associated with a significant increased risk of morbidity extending beyond the liver to cardiovascular disease, chronic kidney disease and malignancy. Obesity and the metabolic syndrome are two key risk factors for NAFLD/MASLD which are characterized as an imbalance in energy utilization and storage. This imbalance leads to dysregulated metabolic pathways and inflammatory responses that drive further changes leading to liver damage and comorbid conditions. Along with the progression of metabolic syndrome, NAFLD/MASLD leads to more advanced liver disease starting with non-alcoholic steatohepatitis/metabolic dysfunction-associated steatohepatitis (NASH/MASH) which can then progress to significant liver diseases including cirrhosis and hepatocellular carcinoma.

The synthesis of fatty acids in the liver, a pathway termed hepatic de novo lipogenesis (DNL), is increased in subjects with metabolic syndrome and NAFLD/MASLD. The DNL pathway not only produces fatty acids that contribute to elevated liver stores of triglycerides, but the fatty acids that are produced are saturated fatty acid species, primarily palmitate (C16:0), which contribute to signaling events that increase liver inflammation. Free palmitate fatty acid has also been implicated in liver inflammation processes such as macrophage recruitment and activation of endoplasmic reticulum stress response.

Thyroid hormone, through activation of its β-receptor in hepatocytes, plays a central role in liver function impacting a range of health parameters from levels of serum cholesterol and triglycerides to the pathological buildup of fat in the liver. THR-β action is key to proper liver function, including regulation of mitochondrial activity such as breakdown of liver fat and control of the level of normal, healthy mitochondria. Patients with NASH/MASH have reduced levels of THR-β receptor activity in the liver.

Accordingly, in various aspects, the present disclosure provides methods for treating NASH/MASH or symptoms of NASH/MASH in a subject, the method comprising administering to a subject in need of such treatment an effective amount of a fatty acid synthase inhibitor in combination with a thyroid hormone receptor agonist (e.g., a THR-beta agonist), wherein the thyroid hormone receptor agonist has a formula (XXI) and the fatty acid synthase inhibitor has a formula (I), (II), (III), (IV), (V), (VI), (VI-J), (VII), (VIII), (IX), (X), (XI), (XII), (XIII), (XIV), (XV), (XVI), (XVII), (XVIII), (XIX), (XX), or as provided in Table C-1, Table C-2, or Table C-3. In further aspects, the therapeutic combinations can be used for the manufacture of a medicament for treating NASH/MASH or symptoms of NASH/MASH. In further aspects, the therapeutic combinations can be used for treating NASH/MASH or symptoms of NASH/MASH. In some embodiments, the NASH/MASH is established in the subject, and treatment with a compound of the present disclosure can reduce or eliminate the symptoms and etiology of NASH/MASH, e.g., general steatosis, steatosis of the liver, steatohepatitis, inflammation, inflammation of the liver, lysosomal acid lipase deficiency, and liver cirrhosis, etc. In other embodiments, the treatment is used prophylactically to prevent the onset of non-alcoholic fatty liver disease/metabolic dysfunction-associated steatotic liver disease (NAFLD/MASLD), the onset of NASH/MASH, the progression of NAFLD/MASLD to NASH/MASH or halt progression of NASH/MASH disease. Whether treating prophylactically or established NAFLD/MASLD or NASH/MASH disease, the treatment of steatotic liver disease reduces the risk factors associated with establishment or progressing diabetes, liver cancer, cardiovascular disease, high triglycerides, kidney disease and metabolic syndrome.

Accordingly, in some embodiments, the present disclosure provides a method of treating non-alcoholic steatohepatitis comprising administering to the subject in need thereof a fatty acid synthase inhibitor in combination with a thyroid hormone receptor agonist (e.g., a THR-beta agonist), wherein the thyroid hormone receptor agonist has a formula (XXI) and the fatty acid synthase inhibitor has a formula (I), (II), (III), (IV), (V), (VI), (VI-J), (VII), (VIII), (IX), (X), (XI), (XII), (XIII), (XIV), (XV), (XVI), (XVII), (XVIII), (XIX), (XX), or as provided in Table C-1, Table C-2, or Table C-3 wherein the method comprises reversing at least one symptom of established non-alcoholic steatohepatitis. In some embodiments, the method comprises preventing the progression of at least one symptom of non-alcoholic steatohepatitis. In some embodiments, the symptom is selected from elevated levels of AST; elevated levels of ALT; elevated levels of GGT; elevated levels of liver triglycerides; elevated levels of cholesterol; liver steatosis; liver inflammation; liver ballooning; liver fibrosis; and NAFLD activity score.

Furthermore, as set forth in Example 6, compounds of the present disclosure (e.g., Compound 002-386) were found to reduce fibrotic gene expression in human liver cells. Accordingly, in some embodiments, the therapeutic combinations of the disclosure can reduce fibrotic gene expression (e.g., Col 1a1, αSMA, βPDGFR, TGFbR1, TIMP1, TIMP2, and/or MMP2). In some embodiments, the gene expression can return after withdrawal of the compounds (e.g., Compound 002-386). Accordingly, without wishing to be bound by theory, the downregulation of the fibrotic genes is not a toxic effect of a compound of the present disclosure.

Accordingly, in various aspects, the present disclosure provides methods for reducing fibrotic gene expression in a subject (e.g., in the subject's liver cells), the method comprising administering to a subject in need of such treatment an effective amount of a fatty acid synthase inhibitor in combination with a thyroid hormone receptor agonist (e.g., a THR-beta agonist), wherein the thyroid hormone receptor agonist has a formula (XXI) and the fatty acid synthase inhibitor has a formula (I), (II), (III), (IV), (V), (VI), (VI-J), (VII), (VIII), (IX), (X), (XI), (XII), (XIII), (XIV), (XV), (XVI), (XVII), (XVIII), (XIX), (XX), or as provided in Table C-1, Table C-2, or Table C-3. In further aspects, the therapeutic combinations can be used for the manufacture of a medicament for reducing fibrotic gene expression (e.g., in liver cells). In further aspects, the therapeutic combinations can be used for reducing fibrotic gene expression (e.g., in liver cells).

Cardiovascular disease is closely linked to the progression of metabolic syndrome. However, NAFLD/MASLD is also a strong predictor of cardiovascular disease, such as increased risk of carotid atherosclerotic plaques and endothelial dysfunction, which is independent of the existence of metabolic syndrome (Francis W. B., et. als., "De novo lipogenesis in the liver in health and disease: more than just a shunting yard for glucose." *Biol. Rev.* (2016), 91, pp. 452-468). NAFLD/MASLD has also been implicated as an independent factor contributing to the development of type II diabetes. The rate of incidence of pre-diabetes or type II diabetes is 2.6 times higher in individuals with NAFLD/MASLD, suggesting an independent role in the pathogenesis of type II diabetes beyond initial insulin resistance (Francis W. B., *Biol. Rev.* (2016), pp. 452-468; Bac, J. C., et. als., "Combined effect of nonalcoholic fatty liver disease and impaired fasting glucose on the development of type 2 diabetes." *Diabetes Care,* 2011, 34, 727-729). Therefore DNL is an important pathway for therapeutic intervention to reduce the consequences associated with metabolic syndrome and NAFLD/MASLD (Bae, J. C., *Diabetes Care,* 2011, 727-729).

NAFLD/MASLD and NASH/MASH have been associated with obesity and diabetes in humans with high fat and high caloric diets. The synthesis of fatty acids in the liver (i.e., synthesized via the hepatic de novo lipogenesis (DNL) pathway), is increased in subjects with metabolic syndrome and NAFLD/MASLD. One of the key enzymes in DNL is fatty acid synthase (FASN). While there are promising associations between FASN, DNL and NAFLD/MASLD, there is very little evidence that direct inhibition of FASN is a competent mechanism for treating NAFLD/MASLD or controlling the progression of hepatic steatosis. Some literature reports of direct intervention at FASN by gene knock out or small molecule inhibitors give results which suggest an exacerbation of liver steatosis; the exact opposite effect needed to treat NAFLD/MASLD or NASH/MASH. These results teach that FASN inhibition would not be expected to reduce hepatic steatosis or be a suitable mechanism to control the underlying metabolic dysregulation or inflammation signaling which drive the progression of steatotic liver disease.

For example, liver-specific FASN knockout mice have been shown to have normal livers when maintained on a standard diet. Unexpectedly, when on a zero-fat/high carbohydrate diet, the mice develop fatty livers (hepatic steatosis) and hypoglycemia showing that complete inhibition of FASN in the liver of a mammal on a fat-restricted diet results in the development of NAFLD/MASLD, the precursor of NASH/MASH (Chakravarthy, M. V., et al., "New hepatic fat activates PPARalpha to maintain glucose, lipid, and cholesterol homeostasis," *Cell Metabol.* 1(5), 2005, 309-322). When the knockout mice are fed a normal diet, no effect on metabolism or development of hepatic steatosis resulting from complete inhibition of FASN by knockout is observed indicating that FASN inhibition in the liver would either have no effect on a mammal consuming a fat-containing diet or would induce a fatty liver state (leading to NAFLD/MASLD and NASH/MASH) in a mammal consuming a low fat/high carbohydrate diet, providing the opposite effect needed for treating NASH/MASH.

Small molecule inhibitors of FASN have been used to assess insulin resistance and hepatic steatosis. In a recent study in obese insulin resistant Zucker rats (Type II diabetes model), inhibition of de novo lipogenesis with a small molecule FASN inhibitor did not improve insulin sensitivity and actually increased the level of fat in the liver (i.e., hepatic steatosis). FASN inhibitors have also been shown to inhibit hepatic de novo lipogenesis, but resulted in increased hepatic steatosis or fat deposits in the liver ("A Novel Fatty Acid Synthase Inhibitor (FASi) Suppresses De Novo Lipogenesis but induces Hepatic Steatosis, Dermatitis and does not enhance Insulin Sensitivity in Obese Zucker Rats," Am. Diabetes Assoc. 68th Scientific Sessions, Jun. 6-10, 2008, San Francisco, CA, poster 58 LB; WO2008059214). These studies show that direct inhibition of FASN reduces fat synthesis in the liver, but results in acceleration in the development of NAFLD/MASLD and NASH/MASH in an obese diabetic mammal. Thus, FASN inhibition would not be expected to have a therapeutic effect on steatotic liver disease in obese and diabetic individuals who have the highest risk of developing NAFLD/MASLD and NASH/MASH disease.

The therapeutic methods and combinations of the present application are useful for controlling NAFLD/MASLD in rodents, reducing pro-inflammatory cytokines, such as IL-1β, and modulating T cell differentiation from pro-inflammatory cells, such as $Th_{17}$ cells, to anti-inflammatory $T_{reg}$ cells. The FASN inhibitors of the present application can be used to treat various aspects of metabolic syndrome including non-alcoholic liver disease (NAFLD/MASLD) and the more advanced disease, non-alcoholic steatohepatitis (NASH/MASH). If left untreated, these liver dysfunction disease states can progress to significant liver diseases, including liver cirrhosis, a state in which the liver shows steatosis, inflammation, fibrosis, steatohepatitis, and may progress to liver cancer (hepatocellular carcinoma). Liver cirrhosis can have direct health consequences due to the liver dysfunction including spider angiomata or spider nevi, palmar erythema, gynecomastia, hypogonadism, ascites, fetor hepaticus, jaundice, portal hypertension which causes splenomegaly, esophageal varices, caput medusa, Hepatic encephalopathy, and acute kidney injury (particularly hepatorenal syndrome). In some embodiments, the therapeutic combinations of the present disclosure can be used to treat metabolic syndrome, non-alcoholic liver disease (NAFLD/MASLD), non-alcoholic steatohepatitis (NASH/MASH), liver cirrhosis, liver fibrosis, and/or liver cancer (hepatocellular carcinoma, cholangiocarcinoma). In some embodiments, the therapeutic combinations of the present disclosure can be used to treat type II diabetes. In some embodiments, the therapeutic combinations of the present disclosure can be used to treat atherosclerosis.

The therapeutic methods and combinations of the present application can also be used to treat inflammatory diseases by inducing changes in inflammation inducing cytokines. Example of inflammatory diseases that can be treated with therapeutic combinations of the present application, include, but are not limited to, inflammatory diseases involving IL-1beta, such as diseases responsive to IL-1beta blockade or associated with increased IL-1beta expression. In some embodiments, a disease or condition wherein IL-1beta is elevated, or that is modulated by IL-1beta, is selected from Familial Mediterranean fever (FMF); Pyogenic arthritis, pyoderma gangrenosum, acne (PAPA); Cryopyrin-associated periodic syndromes (CAPS); Hyper IgD syndrome (HIDS); Adult and juvenile Still disease; Schnitzler syndrome; TNF receptor-associated periodic syndrome (TRAPS); Blau syndrome; Sweet syndrome; Deficiency in IL-1 receptor antagonist (DIRA); Recurrent idiopathic pericarditis; Macrophage activation syndrome (MAS); Urticarial vasculitis; Antisynthetase syndrome; Relapsing chondritis; Behçet disease; Erdheim-Chester syndrome (histiocytosis); Synovitis, acne, pustulosis, hyperostosis, osteitis (SAPHO); Rheumatoid arthritis; Periodic fever, aphthous stomatitis, pharyngitis, adenitis syndrome (PFAPA); Urate crystal arthritis (gout); Type 2 diabetes; Smoldering multiple myeloma; Postmyocardial infarction heart failure; Osteoarthritis; Transfusion-related acute lung injury; Ventilator-induced lung injury; Pulmonary fibrosis including Idiopathic; Chronic obstructive pulmonary disease (COPD); and Asthma. In some embodiments, a disease or condition wherein IL-1beta is elevated, or that is modulated by IL-1beta, is acne.

The therapeutic methods and combinations of the present application can also be used to treat disease or conditions associated with elevated levels of inflammatory T cells and/or reduced or inadequate levels of anti-inflammatory T cells, or to treat diseases or conditions in which the modulation of differentiation of white blood cells (i.e., T cells) away from T helper cells and increasing anti-inflammatory T regulatory ($T_{reg}$) cells would be beneficial. $T_{reg}$ cells are essential for immune tolerance and play a crucial role in the limitation of excessive immune and inflammatory responses executed by T helper cells (i.e., $Th_1$, $Th_2$, $Th_9$, $Th_{17}$, etc.). Thus, shunting the differentiation of T helper cells to regulatory T cells by FASN inhibition can be used to treat inflammatory diseases.

Treatment with a therapeutic method or combination of the present application can inhibit the maturation of T cells to T helper inflammatory cells (T-helper cells that can be inhibited include, but are not limited to, $Th_1$, $Th_2$, $Th_9$, and $Th_{17}$) and promotes their differentiation into $T_{reg}$ cells. Naive CD4+ cells differentiate into T helper and regulatory T cells to execute their immunologic function. The differentiation depends on the presence of cytokines. While T helper cells such as $Th_{17}$ cells play an important role in the protective immune response against intracellular pathogens, excessive immune responses exerted by these T helper cells also cause autoimmune and inflammatory diseases. Examples of immune-mediated diseases that can be treated by the FASN inhibitors of the present application include, but are not limited to, psoriasis, rheumatoid arthritis, multiple sclerosis, ankylosing spondylitis, inflammatory bowel disease (IBD), Chronic obstructive pulmonary disease (COPD), asthma, tumorigenesis, and transplant rejection. (Laura, A., et. al., "$Th_{17}$ cells in human disease," *Immunol. Rev.* 223, 2008, 87-113; Lee, Y., et. al. "Unexpected targets and triggers of autoimmunity. *J. Clin. Immunol.,* 34 Suppl 1, 2014, S56-60)

In various aspects, the disclosed therapeutic methods and combinations are useful in the treatment of nonalcoholic fatty acid disease (NAFLD/MASLD), non-alcoholic steatohepatitis (NASH/MASH), steatosis and diabetes. In one embodiment, the present disclosure relates to a method of treating non-alcoholic steatohepatitis (NASH/MASH) with A FASN inhibitor compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)).

In another embodiment, the present disclosure relates to a method of treating non-alcoholic steatohepatitis (NASH/MASH) with a FASN inhibitor compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)).

In another embodiment, the present disclosure relates to a method of treating metabolic syndrome. In one embodiment, the present disclosure relates to a method of treating metabolic syndrome with a compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)).

In another embodiment, the present disclosure relates to a method of treating type II diabetes. In one embodiment, the present disclosure relates to a method of treating type II diabetes with a compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)).

In another embodiment, the present disclosure relates to a method of treating atherosclerosis. In one embodiment, the present disclosure relates to a method of treating atherosclerosis with a compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)).

In another embodiment, the present disclosure relates to a method of treating liver cirrhosis. In one embodiment, the present disclosure relates to a method of treating liver cirrhosis with a compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)).

In another embodiment, the present disclosure relates to a method of treating liver fibrosis. In one embodiment, the present disclosure relates to a method of treating liver fibrosis with a compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)).

In another embodiment, the present disclosure relates to a method of treating inflammation. In one embodiment, the present disclosure relates to a method of treating inflammation with a compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)).

In another embodiment, the present disclosure relates to a method of treating a disease or condition in which interleukin 1 beta (IL1β) levels are elevated. In one embodiment, the present disclosure relates to a method of treating a disease or condition in which interleukin 1 beta (IL1β) levels are elevated with a compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)). In some embodiments, the disease or condition in which interleukin 1 beta (IL1β) levels are elevated is selected from Familial Mediterranean fever (FMF), Pyogenic arthritis, pyoderma gangrenosum, acne (PAPA), Cryopyrin-associated periodic syndromes (CAPS), Hyper IgD syndrome (HIDS), Adult and juvenile Still disease, Schnitzler syndrome, TNF receptor-associated periodic syndrome (TRAPS), Blau syndrome; Sweet syndrome, Deficiency in IL-1 receptor antagonist (DIRA), Recurrent idiopathic pericarditis, Macrophage activation syndrome (MAS), Urticarial vasculitis, Antisynthetase syndrome, Relapsing chondritis, Behçet disease, Erdheim-Chester syndrome (histiocytosis), Synovitis, acne, pustulosis, hyperostosis, osteitis (SAPHO), Rheumatoid arthritis, Periodic fever, aphthous stomatitis, pharyngitis, adenitis syndrome (PFAPA), Urate crystal arthritis (gout), Type 2 diabetes, Smoldering multiple myeloma, Postmyocardial infarction heart failure, Osteoarthritis, Transfusion-related acute lung injury, Ventilator-induced lung injury, Pulmonary fibrosis including Idiopathic, Chronic obstructive pulmonary disease and Asthma.

In another embodiment, the present disclosure relates to a method of treating a disease or condition in which t-helper ($T_h$) cell levels are elevated. In one embodiment, the present disclosure relates to a method of treating a disease or condition in which t-helper ($T_h$) cell levels are elevated with a compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)). In some embodiments, the disease or condition in which t-helper ($T_h$) cell levels are elevated is selected from Psoriasis, Rheumatoid arthritis, Multiple sclerosis, Ankylosing spondylitis, inflammatory bowel disease, asthma, tumorigenesis and transplant rejection.

In another embodiment, the present disclosure relates to a method of treating a disease or condition in which regulatory t cells ($T_{reg}$) are reduced or suppressed. In one embodiment, the present disclosure relates to a method of treating a disease or condition in which regulatory t cells ($T_{reg}$) are reduced or suppressed with a compound of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (i.e., of formula (XXI)). In some embodiments, the disease or condition in which regulatory t cells ($T_{reg}$) are reduced or suppressed is selected from Psoriasis, Rheumatoid arthritis, Multiple sclerosis, Ankylosing spondylitis, inflammatory bowel disease, asthma, tumorigenesis and transplant rejection.

Anticancer Activity

In various aspects, the disclosed therapeutic combinations are useful in the treatment of liver cancer. In one embodiment, the present disclosure related to a method of treating liver cancer with a fatty acid synthase inhibitor of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (e.g., a compound of Formula (XXI)). In some embodiments, the liver cancer is a liver cancer that has developed from NAFLD/MASLD or NASH/MASH. In some embodiments, the liver cancer is a hepatocellular carcinoma. In some embodiments, the liver cancer is a hepatocellular carcinoma that has developed from NAFLD/MASLD or NASH/MASH. In some embodiments, the liver cancer is cholangiocarcinoma.

Rapidly proliferating cancer cells activate the fatty acid synthesis pathway to supply the high levels of lipids needed for membrane assembly and oxidative metabolism. (Flavin, R. et al. (2010) *Future Oncology.* 6(4):551-562) Inhibitors of fatty acid synthesis have demonstrated in vivo activity in preclinical cancer models. (Orita, H. et al. (2007) *Clinical Cancer Research.* 13(23):7139-7145 and Puig, T. et al. (2011) *Breast Cancer Research,* 13(6):R131) Additionally, fatty acid synthesis supports new blood vessel formation and inhibitors of this pathway have activity in in vitro models of angiogenesis. (Browne, C. D., et al. (2006) *The FASEB Journal,* 20(12):2027-2035). The presently disclosed compounds demonstrated the ability to selectively induce cell-cycle arrest in HUVEC cells without causing general cell death by apoptosis. See EXAMPLES.

The cancer treatment of the present invention includes an anti-tumor effect that may be assessed by conventional means such as the response rate, the time to disease progression and/or the survival rate. Anti-tumor effects of the present invention include, but are not limited to, inhibition of tumor growth, tumor growth delay, regression of tumor, shrinkage of tumor, increased time to regrowth of tumor on cessation of treatment and slowing of disease progression. For example, it is expected that when the combination of the present invention is administered to a warm-blooded animal such as a human, in need of treatment for cancer involving a solid tumor, such a method of treatment will produce an effect, as measured by, for example, one or more of: the extent of the anti-tumor effect, the response rate, the time to disease progression and the survival rate.

In various aspects, the disclosed therapeutic combinations are useful in the reducing triglycerides in a subject in need thereof. In one embodiment, the present disclosure relates to a method of reducing triglycerides with a fatty acid synthase inhibitor of the disclosure (e.g., a compound of Formula (I), (II), (III), (IV), (IV), (V), (VI), (VI-J), (VII), (VIII), (IX), (X), (XI), (XII), (XIII), (XIV), (XV), (XVI), (XVII), (XVIII), (XIX) or (XX)) in combination with a thyroid receptor hormone agonist (e.g., a compound of Formula (XXI)).

Inhibition of Fatty Acid Synthesis

Reducing the activity of the fatty acid synthesis pathway, e.g., FASN gene expression or FASN protein activity, is also referred to as "inhibiting" the fatty acid synthesis pathway, e.g., FASN gene expression or FASN protein activity. The term "inhibits" and its grammatical conjugations, such as "inhibitory," do not require complete inhibition, but refer to a reduction in fatty acid synthesis activity, e.g., FASN gene expression or FASN protein activity. In another aspect, such reduction is by at least 50%, at least 75%, at least 90%, and can be by at least 95% of the activity of the enzyme in the absence of the inhibitory effect, e.g., in the absence of an inhibitor. Conversely, the phrase "does not inhibit" and its grammatical conjugations refer to situations where there is less than 20%, less than 10%, and can be less than 5%, of reduction in enzyme activity in the presence of the agent. Further the phrase “does not substantially inhibit” and its grammatical conjugations refer to situations where there is less than 30%, less than 20%, and in some aspects less than 10% of reduction in enzyme activity in the presence of the agent.

Increasing the activity of the fatty acid synthesis pathway, e.g., FASN gene expression or FASN protein activity, is also referred to as “activating” the fatty acid synthesis pathway, e.g., FASN gene expression or FASN protein activity. The term “activated” and its grammatical conjugations, such as “activating,” do not require complete activation, but refer to an increase in fatty acid synthesis pathway activity, e.g., FASN gene expression or FASN protein activity. In another aspect such increase is by at least 50%, at least 75%, at least 90%, and can be by at least 95% of the activity of the enzyme in the absence of the activation effect, e.g., in the absence of an activator. Conversely, the phrase “does not activate” and its grammatical conjugations refer to situations where there is less than 20%, less than 10%, and can be less than 5%, of an increase in enzyme activity in the presence of the agent. Further the phrase “does not substantially activate” and its grammatical conjugations refer to situations where there is less than 30%, less than 20%, and in another aspect less than 10% of an increase in enzyme activity in the presence of the agent.

The ability to reduce enzyme activity is a measure of the potency or the activity of an agent, or combination of agents, towards or against the enzyme. Potency can be measured by cell free, whole cell and/or in vivo assays in terms of IC50, $K_i$ and/or ED50 values. An IC50 value represents the concentration of an agent required to inhibit enzyme activity by half (50%) under a given set of conditions. A $K_i$ value represents the equilibrium affinity constant for the binding of an inhibiting agent to the enzyme. An ED50 value represents the dose of an agent required to effect a half-maximal response in a biological assay. Further details of these measures will be appreciated by those of ordinary skill in the art, and can be found in standard texts on biochemistry, enzymology, and the like.

Formulations, Routes of Administration, and Effective Doses

Yet another aspect of the present invention relates to formulations, routes of administration and effective doses for the compounds of the instant invention.

In some embodiments of the methods of the disclosure, the fatty acid synthase inhibitor and the thyroid receptor hormone agonist (e.g., a thyroid receptor hormone-beta agonist; e.g., a compound of Formula (XXI)) are administered sequentially.

In some embodiments of the methods of the disclosure, the fatty acid synthase inhibitor and the thyroid receptor hormone agonist (e.g., a thyroid receptor hormone-beta agonist; e.g., a compound of Formula (XXI)) are administered simultaneously.

In some embodiments of the methods of the disclosure, the fatty acid synthase inhibitor and the thyroid receptor hormone agonist (e.g., a thyroid receptor hormone-beta agonist; e.g., a compound of Formula (XXI)) are formulated in separate dosage forms.

In some embodiments of the methods of the disclosure, the fatty acid synthase inhibitor and the thyroid receptor hormone agonist (e.g., a thyroid receptor hormone-beta agonist; e.g., a compound of Formula (XXI)) are formulated in the same dosage form.

The dosage forms contemplated herein can contain any of the doses and dose combinations recited in the methods described herein.

Compounds of the invention can be administered as pharmaceutical formulations including those suitable for oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various aspects, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another aspect, the pharmaceutical preparation is substantially free of preservatives. In another aspect, the pharmaceutical preparation can contain at least one preservative. General methodology on pharmaceutical dosage forms is found in Ansel et al., Pharmaceutical Dosage Forms and Drug Delivery Systems (Lippencott Williams & Wilkins, Baltimore Md. (1999)). It will be recognized that, while any suitable carrier known to those of ordinary skill in the art can be employed to administer the compositions of this invention, the type of carrier will vary depending on the mode of administration.

Compounds can also be encapsulated within liposomes using well-known technology. Biodegradable microspheres can also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The compound can be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, “Liposomes,” Drug Carriers in Biology and Medicine, pp. 2.sup.87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug can be adjusted, the pH of the solution buffered and the isotonicity adjusted to be compatible with intravenous injection, as is well known in the art.

The compounds of the invention can be formulated as a sterile solution or suspension, in suitable vehicles, well known in the art. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described in Remington "The Science and Practice of Pharmacy" ($20^{th}$ Ed., Lippincott Williams & Wilkins, Baltimore MD), the teachings of which are incorporated by reference in their entirety herein.

The agents or their pharmaceutically acceptable salts can be provided alone or in combination with one or more other agents or with one or more other forms. For example, a formulation can comprise one or more agents in particular proportions, depending on the relative potencies of each agent and the intended indication. For example, in compositions for targeting two different host targets, and where potencies are similar, about a 1:1 ratio of agents can be used. The two forms can be formulated together, in the same dosage unit e.g., in one cream, suppository, tablet, capsule, aerosol spray, or packet of powder to be dissolved in a beverage; or each form can be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" means those salts which retain the biological effectiveness and properties of the agents used in the present invention, and which are not biologically or otherwise undesirable. For example, a pharmaceutically acceptable salt does not interfere with the beneficial effect of an agent of the invention in inhibiting the fatty acid synthesis pathway, e.g., inhibiting FASN gene expression or FASN protein activity.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the agent(s) contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the agents used in the present invention, and which are not biologically or otherwise undesirable. For example, the ester or amide does not interfere with the beneficial effect of an agent of the invention in inhibiting the fatty acid synthesis pathway, e.g., inhibiting FASN gene expression or FASN protein activity. Typical esters include ethyl, methyl, isobutyl, ethylene glycol, and the like. Typical amides include unsubstituted amides, alkyl amides, dialkyl amides, and the like.

In another aspect, an agent can be administered in combination with one or more other compounds, forms, and/or agents, e.g., as described above. Pharmaceutical compositions comprising combinations of a fatty acid synthesis pathway inhibitor e.g., an inhibitor or FASN gene expression or FASN protein activity with one or more other active agents can be formulated to comprise certain molar ratios. For example, molar ratios of about 99:1 to about 1:99 of a fatty acid synthesis pathway inhibitor e.g., an inhibitor of FASN gene expression or FASN protein activity, to the other active agent can be used. In some subset of the aspects, the range of molar ratios of fatty acid synthesis pathway inhibitor e.g., an inhibitor of FASN gene expression or FASN protein activity: other active agent is selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of a fatty acid synthesis pathway inhibitor e.g., an inhibitor of FASN gene expression or FASN protein activity: other active agent can be about 1:9, and in another aspect can be about 1:1. The two agents, forms and/or compounds can be formulated together, in the same dosage unit e.g., in one cream, suppository, tablet, capsule, or packet of powder to be dissolved in a beverage; or each agent, form, and/or compound can be formulated in separate units, e.g., two creams, suppositories, tablets, two capsules, a tablet and a liquid for dissolving the tablet, an aerosol spray a packet of powder and a liquid for dissolving the powder, etc.

The agent(s) (or pharmaceutically acceptable salts, esters or amides thereof) can be administered per se or in the form of a pharmaceutical composition wherein the active agent(s) is in an admixture or mixture with one or more pharmaceutically acceptable carriers. A pharmaceutical composition, as used herein, can be any composition prepared for administration to a subject. Pharmaceutical compositions for use in accordance with the present invention can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) useful in the present invention, or pharmaceutically acceptable salts, esters, or amides thereof, can be delivered to a patient using a number of routes or modes of administration, including oral, buccal, topical, rectal, transdermal, transmucosal, subcutaneous, intravenous, and intramuscular applications, as well as by inhalation.

For oral administration, the agents can be formulated readily by combining the active agent(s) with pharmaceutically acceptable carriers well known in the art. Such carriers enable the agents of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Generally, the agents of the invention will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions for oral use can contain agent(s) of this invention with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

In another aspect, oils or non-aqueous solvents can be required to bring the agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23:238-252 (1965) and Szoka et al., Proc. Natl Acad. Sci. USA 75:4194-4198 (1978), incorporated herein by reference. Ligands can also be attached to the liposomes to direct these compositions to particular sites of action. Agents of this invention can also be integrated into foodstuffs, e.g., cream cheese, butter, salad dressing, or ice cream to facilitate solubilization, administration, and/or compliance in certain patient populations.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as sodium alginate. The agents can also be formulated as a sustained release preparation.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents can be dissolved or suspended in suitable liquids, such as fatty oils, liquid paraffin, or liquid polyethylene glycols. In addition, stabilizers can be added. All formulations for oral administration should be in dosages suitable for administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or can contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Suitable fillers or carriers with which the compositions can be administered include agar, alcohol, fats, lactose, starch, cellulose derivatives, polysaccharides, polyvinylpyrrolidone, silica, sterile saline and the like, or mixtures thereof used in suitable amounts. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

A syrup or suspension can be made by adding the active compound to a concentrated, aqueous solution of a sugar, e.g., sucrose, to which can also be added any accessory ingredients. Such accessory ingredients can include flavoring, an agent to retard crystallization of the sugar or an agent to increase the solubility of any other ingredient, e.g., as a polyhydric alcohol, for example, glycerol or sorbitol.

When formulating compounds of the invention for oral administration, it can be desirable to utilize gastroretentive formulations to enhance absorption from the gastrointestinal (GI) tract. A formulation which is retained in the stomach for several hours can release compounds of the invention slowly and provide a sustained release that can be used in methods of the invention. Disclosure of such gastro-retentive formulations are found in Klausner, E. A.; Lavy, E.; Barta, M.; Cserepes, E.; Friedman, M.; Hoffman, A. 2003 "Novel gastroretentive dosage forms: evaluation of gastroretentivity and its effect on levodopa in humans." Pharm. Res. 20, 1466-73, Hoffman, A.; Stepensky, D.; Lavy, E.; Eyal, S. Klausner, E.; Friedman, M. 2004 "Pharmacokinetic and pharmacodynamic aspects of gastroretentive dosage forms" Int. J. Pharm. 11, 141-53, Streubel, A.; Siepmann, J.; Bodmeier, R.; 2006 "Gastroretentive drug delivery systems" Exp. Opin. Drug Deliver. 3, 217-3, and Chavanpatil, M. D.; Jain, P.; Chaudhari, S.; Shear, R.; Vavia, P. R. "Novel sustained release, swellable and bioadhesive gastroretentive drug delivery system for olfoxacin" Int. J. Pharm. 2006 epub March 24. Expandable, floating and bioadhesive techniques can be utilized to maximize absorption of the compounds of the invention.

The compounds of the invention can be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic) acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In a preferred aspect, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, the active compound can be formulated in aqueous solutions, specifically in physiologically compatible buffers such as Hanks solution, Ringer's solution, or physiological saline buffer. The solution can contain formulatory agents such as suspending, stabilizing and/or dispersing agents. Alternatively, the active compound can be in powder form for constitution with a suitable vehicle, e.g., sterile pyrogen-free water, before use. In another aspect, the pharmaceutical composition does not comprise an adjuvant or any other substance added to enhance the immune response stimulated by the peptide. In another aspect, the pharmaceutical composition comprises a substance that inhibits an immune response to the peptide. Methods of formulation are known in the art, for example, as disclosed in Remington's Pharmaceutical Sciences, latest edition, Mack Publishing Co., Easton P.

In addition to the formulations described previously, the agents can also be formulated as a depot preparation. Such long acting formulations can be administered by implantation or transcutaneous delivery (for example subcutaneously or intramuscularly), intramuscular injection or use of a transdermal patch. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

In another aspect, pharmaceutical compositions comprising one or more agents of the present invention exert local and regional effects when administered topically or injected at or near particular sites of infection. Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, can be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In another aspect, local/topical formulations comprising a fatty acid synthesis pathway inhibitor e.g., an inhibitor of FASN gene expression or FASN protein activity, are used to treat epidermal or mucosal viral infections.

Pharmaceutical compositions of the present invention can contain a cosmetically or dermatologically acceptable carrier. Such carriers are compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, an agent or combination of agents of the instant invention can be formulated in an oleaginous hydrocarbon base, an anhydrous absorption base, a water-in-oil absorption base, an oil-in-water water-removable base and/or a water-soluble base. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Ointments and creams can, for example, be formulated with an aqueous or oily base with the addition of suitable thickening and/or gelling agents. Lotions can be formulated with an aqueous or oily base and will in general also containing one or more emulsifying agents, stabilizing agents, dispersing agents, suspending agents, thickening agents, or coloring agents. The construction and use of transdermal patches for the delivery of pharmaceutical agents is well known in the art. Sec, e.g., U.S. Pat. Nos. 5,023,252, 4,992,445 and 5,001,139. Such patches can be constructed for continuous, pulsatile, or on demand delivery of pharmaceutical agents.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

The compositions according to the present invention can be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions can be prepared according to conventional methods. Other than the agents of the invention, the amounts of the various constituents of the compositions according to the invention are those conventionally used in the art. These compositions in particular constitute protection, treatment or care creams, milks, lotions, gels or foams for the face, for the hands, for the body and/or for the mucous membranes, or for cleansing the skin. The compositions can also consist of solid preparations constituting soaps or cleansing bars.

Compositions of the present invention can also contain adjuvants common to the cosmetic and dermatological fields, such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants can be introduced into the fatty phase, into the aqueous phase and/or into the lipid vesicles.

In another aspect, ocular viral infections can be effectively treated with ophthalmic solutions, suspensions, ointments or inserts comprising an agent or combination of agents of the present invention. Eye drops can be prepared by dissolving the active ingredient in a sterile aqueous solution such as physiological saline, buffering solution, etc., or by combining powder compositions to be dissolved before use. Other vehicles can be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions can be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents can be employed at a level of from about 0.01% to 2% by weight.

The compositions of the invention can be packaged in multidose form. Preservatives can be preferred to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, such preservatives can be employed at a level of from 0.004% to 0.02%. In the compositions of the present application the preservative, preferably benzalkonium chloride, can be employed at a level of from 0.001% to less than 0.01%, e.g., from 0.001% to 0.008%, preferably about 0.005% by weight. It has been found that a concentration of benzalkonium chloride of 0.005% can be sufficient to preserve the compositions of the present invention from microbial attack.

In another aspect, the agents of the present invention are delivered in soluble rather than suspension form, which allows for more rapid and quantitative absorption to the sites of action. In general, formulations such as jellies, creams, lotions, suppositories and ointments can provide an area with more extended exposure to the agents of the present invention, while formulations in solution, e.g., sprays, provide more immediate, short-term exposure.

In another aspect relating to topical/local application, the pharmaceutical compositions can include one or more penetration enhancers. For example, the formulations can comprise suitable solid or gel phase carriers or excipients that increase penetration or help delivery of agents or combinations of agents of the invention across a permeability barrier, e.g., the skin. Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl) pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In another aspect, the pharmaceutical compositions will include one or more such penetration enhancers.

In another aspect, the pharmaceutical compositions for local/topical application can include one or more antimicrobial preservatives such as quaternary ammonium compounds, organic mercurials, p-hydroxy benzoates, aromatic alcohols, chlorobutanol, and the like.

Gastrointestinal viral infections can be effectively treated with orally- or rectally delivered solutions, suspensions, ointments, enemas and/or suppositories comprising an agent or combination of agents of the present invention.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that the agent or combination of agents of the present invention is carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants useful in the present invention include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998. Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as the ethers. An aerosol formulation of the invention can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present invention can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

The aerosol formulation can be packaged under pressure and can be formulated as an aerosol using solutions, suspensions, emulsions, powders and semisolid preparations. For example, a solution aerosol formulation can comprise a solution of an agent of the invention such as a fatty acid synthesis pathway inhibitor e.g., an inhibitor of FASN gene expression or FASN protein activity, in (substantially) pure propellant or as a mixture of propellant and solvent. The solvent can be used to dissolve the agent and/or retard the evaporation of the propellant. Solvents useful in the invention include, for example, water, ethanol and glycols. Any combination of suitable solvents can be use, optionally combined with preservatives, antioxidants, and/or other aerosol components.

An aerosol formulation can also be a dispersion or suspension. A suspension aerosol formulation can comprise a suspension of an agent or combination of agents of the instant invention, e.g., a fatty acid synthesis pathway inhibitor, e.g., an inhibitor of FASN gene expression or FASN protein activity, and a dispersing agent. Dispersing agents useful in the invention include, for example, sorbitan trioleate, oleyl alcohol, oleic acid, lecithin and corn oil. A suspension aerosol formulation can also include lubricants, preservatives, antioxidant, and/or other aerosol components.

An aerosol formulation can similarly be formulated as an emulsion. An emulsion aerosol formulation can include, for example, an alcohol such as ethanol, a surfactant, water and a propellant, as well as an agent or combination of agents of the invention, e.g., a fatty acid synthesis pathway, e.g., an inhibitor of FASN gene expression or FASN protein activity. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

The compounds of the invention can be formulated for administration as suppositories. A low melting wax, such as a mixture of triglycerides, fatty acid glycerides, Witepsol S55 (trademark of Dynamite Nobel Chemical, Germany), or cocoa butter is first melted and the active component is dispersed homogeneously, for example, by stirring. The molten homogeneous mixture is then poured into convenient sized molds, allowed to cool, and to solidify.

The compounds of the invention can be formulated for vaginal administration. Pessaries, tampons, creams, gels, pastes, foams or sprays containing in addition to the active ingredient such carriers as are known in the art to be appropriate.

It is envisioned additionally, that the compounds of the invention can be attached releasably to biocompatible polymers for use in sustained release formulations on, in or attached to inserts for topical, intraocular, periocular, or systemic administration. The controlled release from a biocompatible polymer can be utilized with a water soluble polymer to form an instillable formulation, as well. The controlled release from a biocompatible polymer, such as for example, PLGA microspheres or nanospheres, can be utilized in a formulation suitable for intra ocular implantation or injection for sustained release administration, as well. Any suitable biodegradable and biocompatible polymer can be used.

Pharmaceutical compositions suitable for use in the present invention include compositions wherein the active ingredients are present in an effective amount, i.e., in an amount effective to achieve therapeutic and/or prophylactic benefit in a host with at least one viral infection or in a subject having cancer. The actual amount effective for a particular application will depend on the condition or conditions being treated, the condition of the subject, the formulation, and the route of administration, as well as other factors known to those of skill in the art. Determination of an effective amount of a fatty acid synthesis pathway inhibitor e.g., an inhibitor of FASN gene expression or FASN protein activity, is well within the capabilities of those skilled in the art, in light of the disclosure herein, and will be determined using routine optimization techniques.

The effective amount for use in humans can be determined from animal models. For example, a dose for humans can be formulated to achieve circulating, liver, topical and/or gastrointestinal concentrations that have been found to be effective in animals. One skilled in the art can determine the effective amount for human use, especially in light of the animal model experimental data described herein. Based on animal data, and other types of similar data, those skilled in the art can determine the effective amounts of compositions of the present invention appropriate for humans.

The effective amount when referring to an agent or combination of agents of the invention will generally mean the dose ranges, modes of administration, formulations, etc., that have been recommended or approved by any of the various regulatory or advisory organizations in the medical or pharmaceutical arts (e.g., FDA, AMA) or by the manufacturer or supplier.

Further, appropriate doses for a fatty acid synthesis pathway inhibitor e.g., an inhibitor of FASN gene expression or FASN protein activity, can be determined based on in vitro experimental results. For example, the in vitro potency of an agent in inhibiting a fatty acid synthesis pathway component, e.g., FASN gene expression or FASN protein activity, provides information useful in the development of effective in vivo dosages to achieve similar biological effects.

In some aspects, the FASN inhibitor is administered at a dose of 10-100 mg. In some aspects, the FASN inhibitor is administered at a dose of 10-90 mg. In some aspects, the FASN inhibitor is administered at a dose of 10-80 mg. In some aspects, the FASN inhibitor is administered at a dose of 10-70 mg. In some aspects, the FASN inhibitor is administered at a dose of 10-60 mg. In some aspects, the FASN inhibitor is administered at a dose of 10-50 mg. In some aspects, the FASN inhibitor is administered at a dose of 10-40 mg. In some aspects, the FASN inhibitor is administered at a dose of 10-30 mg. In some aspects, the FASN inhibitor is administered at a dose of 10-20 mg. In some aspects, the FASN inhibitor is administered at a dose of 20-100 mg. In some aspects, the FASN inhibitor is administered at a dose of 20-90 mg. In some aspects, the FASN inhibitor is administered at a dose of 20-80 mg. In some aspects, the FASN inhibitor is administered at a dose of 20-70 mg. In some aspects, the FASN inhibitor is administered at a dose of 20-60 mg. In some aspects, the FASN inhibitor is administered at a dose of 20-50 mg. In some aspects, the FASN inhibitor is administered at a dose of 20-40 mg. In some aspects, the FASN inhibitor is administered at a dose of 20-30 mg. In some aspects, the FASN inhibitor is administered at a dose of 30-100 mg. In some aspects, the FASN inhibitor is administered at a dose of 30-90 mg. In some aspects, the FASN inhibitor is administered at a dose of 30-80 mg. In some aspects, the FASN inhibitor is administered at a dose of 30-70 mg. In some aspects, the FASN inhibitor is administered at a dose of 30-60 mg. In some aspects, the FASN inhibitor is administered at a dose of 30-50 mg. In some aspects, the FASN inhibitor is administered at a dose of 30-40 mg. In some aspects, the FASN inhibitor is administered at a dose of 40-100 mg. In some aspects, the FASN inhibitor is administered at a dose of 40-90 mg. In some aspects, the FASN inhibitor is administered at a dose of 40-80 mg. In some aspects, the FASN inhibitor is administered at a dose of 40-70 mg. In some aspects, the FASN inhibitor is administered at a dose of 40-60 mg. In some aspects, the FASN inhibitor is administered at a dose of 40-50 mg. In some aspects, the FASN inhibitor is administered at a dose of 50-100 mg. In some aspects, the FASN inhibitor is administered at a dose of 50-90 mg. In some aspects, the FASN inhibitor is administered at a dose of 50-80 mg. In some aspects, the FASN inhibitor is administered at a dose of 50-70 mg. In some aspects, the FASN inhibitor is administered at a dose of 50-60 mg. In some aspects, the FASN inhibitor is administered at a dose of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg.

In some aspects, the FASN inhibitor is administered at a dose of 10 mg, 15 mg, 20 mg, 25 mg, 30 mg, 35 mg, 40 mg, 45 mg or 50 mg.

In some aspects, the FASN inhibitor is administered at a dose of 20 mg, 25 mg, 30 mg, 35 mg, 40 mg, 45 mg or 50 mg.

In some aspects, the FASN inhibitor is administered at a dose of 10 mg. In some aspects, the FASN inhibitor is administered at a dose of 15 mg. In some aspects, the FASN inhibitor is administered at a dose of 20 mg. In some aspects, the FASN inhibitor is administered at a dose of 25 mg. In some aspects, the FASN inhibitor is administered at a dose of 30 mg. In some aspects, the FASN inhibitor is administered at a dose of 35 mg. In some aspects, the FASN inhibitor is administered at a dose of 40 mg. In some aspects, the FASN inhibitor is administered at a dose of 45 mg. In some aspects, the FASN inhibitor is administered at a dose of 50 mg. In some aspects, the FASN inhibitor is administered at a dose of 55 mg. In some aspects, the FASN inhibitor is administered at a dose of 60 mg. In some aspects, the FASN inhibitor is administered at a dose of 65 mg. In some aspects, the FASN inhibitor is administered at a dose of 70 mg. In some aspects, the FASN inhibitor is administered at a dose of 75 mg. In some aspects, the FASN inhibitor is administered at a dose of 80 mg. In some aspects, the FASN inhibitor is administered at a dose of 85 mg. In some aspects, the FASN inhibitor is administered at a dose of 90 mg. In some aspects, the FASN inhibitor is administered at a dose of 95 mg. In some aspects, the FASN inhibitor is administered at a dose of 100 mg.

In some aspects, the FASN inhibitor is administered once or twice daily. In some aspects, the FASN inhibitor is administered once daily. In some aspects, the FASN inhibitor is administered twice daily. In some aspects, the FASN inhibitor is administered intermittently, for example administration once every two days, every three days, every five days, once a week, once or twice a month, and the like. In some aspects, the FASN inhibitor is administered three times a week. In some aspects, the FASN inhibitor is administered on an on/off/on/off/on/off/off schedule (e.g., a Monday, Wednesday, Friday schedule. In some aspects, the FASN inhibitor is administered twice a week. In some aspects, the FASN inhibitor is administered once a week. In some aspects, the FASN inhibitor is administered orally.

In some aspects, the FASN inhibitor and the thyroid hormone receptor beta agonist are administered as a fixed-dose combination. In some aspects, the FASN inhibitor and the thyroid hormone receptor beta agonist are administered as separate dosage units. In some aspects, the FASN inhibitor and the thyroid hormone receptor beta agonist are administered concurrently. In some aspects, the FASN inhibitor and the thyroid hormone receptor beta agonist are administered sequentially. In some aspects, the FASN inhibitor and the thyroid hormone receptor beta agonist are administered on the same dosing schedule. In some aspects, the FASN inhibitor and the thyroid hormone receptor beta agonist are administered on different dosing schedules. In another aspect, the amount, forms, and/or amounts of the different agents and/or forms can be varied at different times of administration.

A person of skill in the art would be able to monitor in a patient the effect of administration of a particular agent.

Having now generally described various aspects and aspects of the invention, the same will be more readily understood through reference to the following examples which are provided by way of illustration, and are not intended to be limiting, unless specified.

SELECTED EMBODIMENTS

Embodiment 1. A method of treating steatotic liver disease in a subject in need thereof, the method comprising administering to the subject a fatty acid synthase inhibitor and a thyroid hormone receptor-beta agonist.

Embodiment 2. A method of treating nonalcoholic steatohepatitis/metabolic dysfunction-associated steatohepatitis (NASH/MASH) in a subject in need thereof, the method comprising administering to the subject a fatty acid synthase inhibitor and a thyroid hormone receptor-beta agonist.

Embodiment 3. The method of embodiment 2, wherein treating the nonalcoholic steatohepatitis/metabolic dysfunction-associated steatohepatitis (NASH/MASH) comprises preventing the progression of at least one symptom of nonalcoholic steatohepatitis/metabolic dysfunction-associated steatohepatitis (NASH/MASH).

Embodiment 4. The method of embodiment 2 or 3, wherein the symptom is selected from elevated levels of AST; elevated levels of ALT; elevated levels of GGT; elevated levels of liver triglycerides; elevated levels of cholesterol; liver steatosis; liver inflammation; liver ballooning; liver fibrosis; and NAFLD activity score.

Embodiment 5. A method of treating fatty liver disease/metabolic dysfunction-associated steatotic liver disease (NAFLD/MASLD) in a subject in need thereof, the method comprising administering to the subject a fatty acid synthase inhibitor and a thyroid hormone receptor-beta agonist.

Embodiment 6. A method of treating metabolic syndrome in a subject in need thereof, the method comprising administering to the subject a fatty acid synthase inhibitor and a thyroid hormone receptor-beta agonist.

Embodiment 7. A method of treating type II diabetes in a subject in need thereof, the method comprising administering to the subject a fatty acid synthase inhibitor and a thyroid hormone receptor-beta agonist.

Embodiment 8. A method of treating atherosclerosis in a subject in need thereof, the method comprising administering to the subject a fatty acid synthase inhibitor and a thyroid hormone receptor-beta agonist.

Embodiment 9. A method of treating liver cirrhosis in a subject in need thereof, the method comprising administering to the subject a fatty acid synthase inhibitor and a thyroid hormone receptor-beta agonist.

Embodiment 10. A method of treating liver cancer in a subject in need thereof, the method comprising administering to the subject a fatty acid synthase inhibitor and a thyroid hormone receptor-beta agonist.

Embodiment 11. The method of embodiment 10, wherein the liver cancer has developed from NAFLD/MASLD or NASH/MASH.

Embodiment 12. The method of embodiment 11, wherein the liver cancer is cholangiocarcinoma.

Embodiment 13. The method of embodiment 11, wherein the liver cancer is hepatocellular carcinoma.

Embodiment 14. The method of embodiment 13, wherein the hepatocellular carcinoma has developed from NAFLD/MASLD or NASH/MASH.

Embodiment 15. A method of treating a disease or condition in which interleukin 1 beta (IL1βlevels are elevated in a subject in need thereof, the method comprising administering to the subject a fatty acid synthase inhibitor and a thyroid hormone receptor-beta agonist.

Embodiment 16. The method of embodiment 15, wherein the disease or condition is selected from Familial Mediterranean fever (FMF), Pyogenic arthritis, pyoderma gangrenosum, acne (PAPA), Cryopyrin-associated periodic syndromes (CAPS), Hyper IgD syndrome (HIDS), Adult and juvenile Still disease, Schnitzler syndrome, TNF receptor-associated periodic syndrome (TRAPS), Blau syndrome; Sweet syndrome, Deficiency in IL-1 receptor antagonist (DIRA), Recurrent idiopathic pericarditis, Macrophage activation syndrome (MAS), Urticarial vasculitis, Antisynthetase syndrome, Relapsing chondritis, Behçet disease, Erdheim-Chester syndrome (histiocytosis), Synovitis, acne, pustulosis, hyperostosis, osteitis (SAPHO), Rheumatoid arthritis, Periodic fever, aphthous stomatitis, pharyngitis, adenitis syndrome (PFAPA), Urate crystal arthritis (gout), Type 2 diabetes, Smoldering multiple myeloma, Postmyocardial infarction heart failure, Osteoarthritis, Transfusion-related acute lung injury, Ventilator-induced lung injury, Pulmonary fibrosis including Idiopathic, Chronic obstructive pulmonary disease and Asthma.

Embodiment 17. A method of treating a disease or condition in which regulatory t cells ($T_{reg}$) are reduced or suppressed in a subject in need thereof, the method comprising administering to the subject a fatty acid synthase inhibitor and a thyroid hormone receptor-beta agonist.

Embodiment 18. The method of embodiment 17, wherein $T_{reg}$ cells are suppressed.

Embodiment 19. A method of treating a disease or condition in which t-helper ($T_h$) cell levels are elevated in a subject in need thereof, the method comprising administering to the subject a fatty acid synthase inhibitor and a thyroid hormone receptor-beta agonist.

Embodiment 20. The method of embodiment 19, wherein the elevated t-helper cell is $T_h1$, $T_h2$, $T_h9$, or. $T_h17$.

Embodiment 21. The method of embodiment 20, wherein the elevated t-helper cell is $T_{17}$.

Embodiment 22. The method of any one of embodiments 17-21, wherein the disease or condition is selected from Psoriasis, Rheumatoid arthritis, Multiple sclerosis, Ankylosing spondylitis, inflammatory bowel disease, asthma, tumorigenesis and transplant rejection.

Embodiment 23. A method of reversing established nonalcoholic steatohepatitis/metabolic dysfunction-associated steatohepatitis (NASH/MASH) in a subject in need thereof, the method comprising administering to the subject a fatty acid synthase inhibitor and a thyroid hormone receptor-beta agonist.

Embodiment 24. A method of treating liver fibrosis in a subject in need thereof, the method comprising administering to the subject a fatty acid synthase inhibitor and a thyroid hormone receptor-beta agonist.

Embodiment 25. A method of reducing fibrotic gene expression in a subject in need thereof, the method comprising administering to the subject a fatty acid synthase inhibitor and a thyroid hormone receptor-beta agonist.

Embodiment 26. A method of reducing triglycerides in a subject in need thereof, the method comprising administering to the subject a fatty acid synthase inhibitor and a thyroid hormone receptor-beta agonist.

Embodiment 27. A method of improving or restoring liver function in a subject in need thereof, the method comprising administering to the subject a fatty acid synthase inhibitor and a thyroid hormone receptor-beta agonist.

Embodiment 28. A method of treating NASH/MASH with moderate to severe fibrosis in a subject in need thereof, the method comprising administering to the subject fatty acid synthase inhibitor and a thyroid hormone receptor-beta agonist.

Embodiment 29. The method of embodiment 28, wherein the subject has an improvement in liver fibrosis ≥1 stage without worsening of NASH/MASH.

Embodiment 30. The method of embodiment 28, wherein the subject has resolution of NASH/MASH without worsening of fibrosis.

Embodiment 31. The method of any one of embodiments 1-30, wherein the thyroid hormone receptor-beta agonist has a formula (XXI):

(XXI)

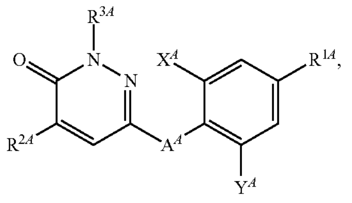

or a pharmaceutically acceptable salt thereof, wherein:

$A^A$ is O, $CH_2$, S, SO or $SO_2$;

$X^A$ and $Y^A$ are each independently selected from the group consisting of Br, Cl and $CH_3$;

$R^{1A}$ is selected from the group consisting of: $-(CH_2)_n$ COOH, $-OCH_2COOH$, $-NHC(=O)COOH$, $-NHCH_2COOH$,

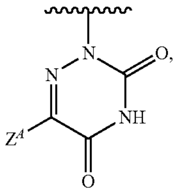 and 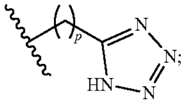

$Z^A$ is H, or $-C \equiv N$;

$R^{2A}$ is lower alkyl having from 1 to 4 C atoms;

$R^{3A}$ is H or lower alkyl;

n is 1 or 2;

p is 1 or 2.

Embodiment 32. The method of any one of embodiments 1-31, wherein the fatty acid synthase inhibitor has a formula of:

(a) Formula (IX)

(IX)

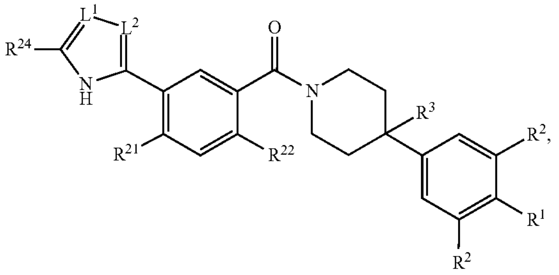

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

$C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

$L^1$ is $CR^{23}$ or N;

$L^2$ is CH or N;

at least one of $L^1$ or $L^2$ is N; and $R^{23}$ is H or $C_1$-$C_4$ straight or branched alkyl; or (b) Formula (X):

(X)

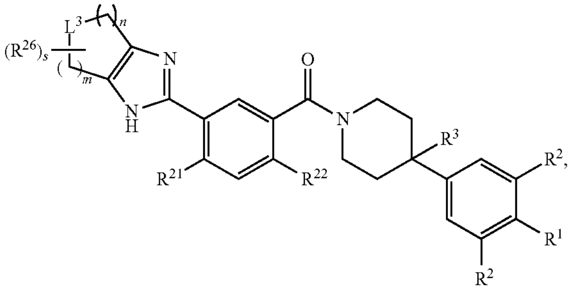

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

the $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH or halogen;

$L^3$ is $C(R^{60})_2$, O or $NR^{50}$;

each $R^{60}$ is independently H, —OH, —CN, —O$_t$—($C_3$-$C_5$ cycloalkyl), —O—($C_1$-$C_4$ straight or branched alkyl), or —C(O)—N($R^{601}$)$_2$ wherein:

t is 0 or 1, and the $C_3$-$C_5$ cycloalkyl optionally includes an oxygen or nitrogen heteroatom;

each $R^{50}$ is independently H, —C(O)—O$_t$—($C_1$-$C_4$ straight or branched alkyl), —C(O)—O$_t$—($C_3$-$C_5$ cyclic alkyl), —$C_3$-$C_5$ cyclic alkyl optionally containing an oxygen or nitrogen heteroatom, —C(O)—N($R^{501}$)$_2$, $C_1$-$C_4$ straight or branched alkyl wherein:

t is 0 or 1, and the $C_3$-$C_5$ cycloalkyl optionally includes an oxygen or nitrogen heteroatom;

n is 1, 2 or 3;

m is 1 or 2;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom $R^{22}$ is H, halogen, $C_1$-$C_2$ alkyl;

each $R^{26}$ is independently —OH, —CN, halogen, $C_1$-$C_4$ straight or branched alkyl, $(C_1$-$C_4$ alkyl$)_t$-$O_t$—$(C_3$-$C_5$ cycloalkyl), —$(C_1$-$C_4$ alkyl$)_t$-O—$(C_1$-$C_4$ straight or branched alkyl), —C(O)—$O_t$—$(C_1$-$C_4$ alkyl), or —C(O)—$N(R^{501})_2$ wherein:

t is 0 or 1, and the $C_3$-$C_5$ cycloalkyl optionally includes an oxygen or nitrogen heteroatom;

s is 0, 1 or 2;

each $R^{601}$ and $R^{501}$ is independently H or $C_1$-$C_4$ straight or branched alkyl; and wherein two of $R^{26}$, $R^{60}$, $R^{50}$, $R^{501}$ and $R^{601}$ optionally join to form a ring wherein the two of $R^{26}$, $R^{60}$, $R^{50}$, $R^{501}$ and $R^{601}$ may be two $R^{26}$, two $R^{60}$, two $R^{50}$, two $R^{501}$ or two $R^{601}$; or (c) Formula (VI-J)

(VI-J)

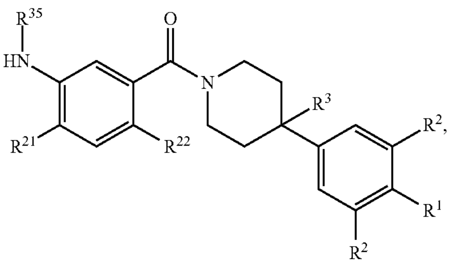

or a pharmaceutically acceptable salt thereof, wherein:

$R^1$ is H, —CN, halogen, $C_1$-$C_4$ straight or branched alkyl, —O—$(C_3$-$C_8$ cycloalkyl), —O—$(C_1$-$C_4$ straight or branched alkyl) wherein:

the $C_3$-$C_8$ cycloalkyl optionally includes an oxygen or nitrogen heteroatom; and when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is cyclobutyl, azetidin-1-yl, or cyclopropyl;

$R^{22}$ is H, halogen, or $C_1$-$C_2$ alkyl;

$R^{35}$ is —C(O)—$R^{351}$, —C(O)—$NHR^{351}$, —C(O)—O—$R^{351}$ or $S(O)_2R^{351}$; and $R^{351}$ is $C_1$-$C_6$ straight or branched alkyl, cycloalkyl, heterocyclyl, aryl or heteroaryl; or (d) Formula (XII):

(XII)

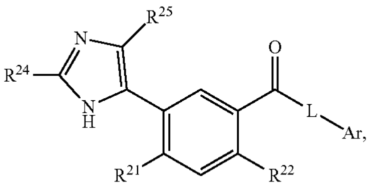

or pharmaceutically acceptable salts thereof, wherein:

L-Ar is

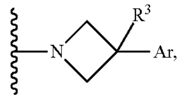

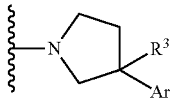

or

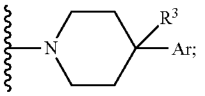

Ar is

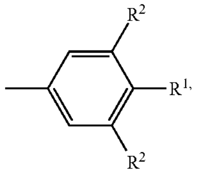

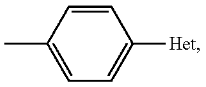

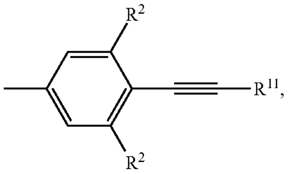

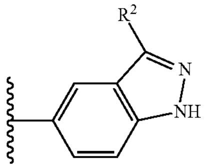

or

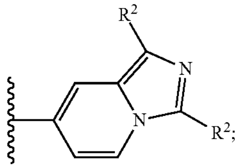

Het is a 5- to 6-membered heteroaryl;

$R^1$ is H, —CN, halogen, $C_1$-$C_4$ alkyl, —O—$(C_3$-$C_5$ cycloalkyl), —O-(4- to 6-membered heterocycle) or —O—$(C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_8$ cycloalkyl or 4- to 6-membered heterocycle;

$R^{22}$ is H, halogen, or $C_1$-$C_2$ alkyl;

$R^{24}$ is H, —CN, —$(C_1$-$C_4$ alkyl)-CN, $C_1$-$C_4$ alkyl, —$(C_1$-$C_4$ alkyl)-OH, —$(C_1$-$C_4$ alkyl)-$N(R^{241})_2$, —$(C_1$-$C_4$ alkyl$)_t$-$O_u$—$(C_3$-$C_6$ cycloalkyl), —$(C_1$-$C_4$ alkyl$)_t$-$O_u$-(4- to 6-membered heterocycle) or —$(C_1$-$C_4$ alkyl)-O—$(C_1$-$C_4$ alkyl), wherein:

t is 0 or 1;

u is 0 or 1;

with the proviso that when u is 1, t is 1; and each $R^{241}$ is independently H or $C_1$-$C_2$ alkyl; and $R^{25}$ is halogen, —CN, —$(C_1$-$C_4$ alkyl)-CN, $C_1$-$C_2$ alkyl or cyclopropyl; or (e) Formula (XIII):

(XIII)

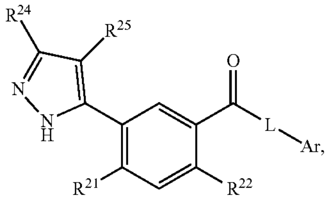

or pharmaceutically acceptable salts thereof, wherein:

L-Ar is

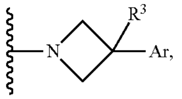

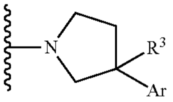

or

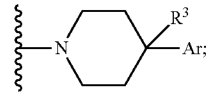

Ar is

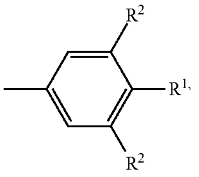

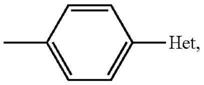

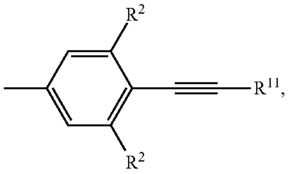

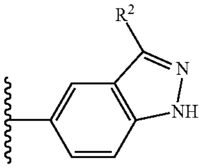

or

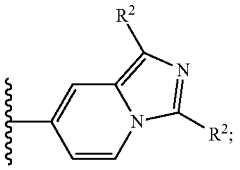

Het is a 5- to 6-membered heteroaryl;

$R^1$ is H, —CN, halogen, $C_1$-$C_4$ alkyl, —O—($C_3$-$C_8$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_8$ cycloalkyl or 4- to 6-membered heterocycle;

$R^{22}$ is H, halogen or $C_1$-$C_2$ alkyl; and each $R^{24}$ and $R^{25}$ is independently H, halogen, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_8$ cycloalkyl), —($C_1$-$C_4$ alkyl)$_t$-O$_u$-(4- to 6-membered heterocycle) or —($C_1$-$C_4$ alkyl)$_t$-O—($C_1$-$C_4$ alkyl), wherein:

each t is independently 0 or 1;

each u is independently 0 or 1; and each $R^{241}$ is independently H or $C_1$-$C_2$ alkyl; or (f) Formula (XIV):

(XIV)

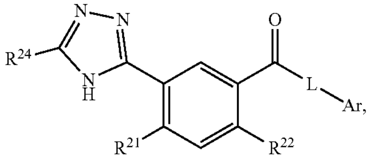

or pharmaceutically acceptable salts thereof, wherein:

L-Ar is

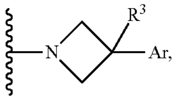

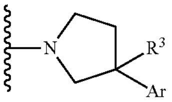

or

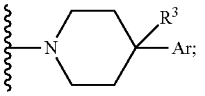

Ar is

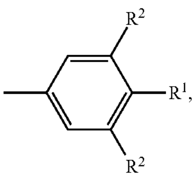

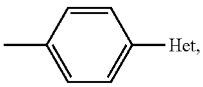

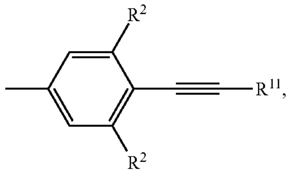

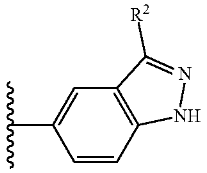

or

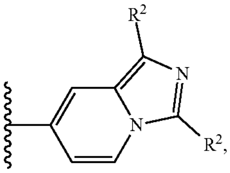

with the proviso that when L-Ar is

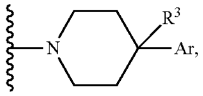

Ar is not

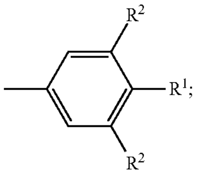

Het is a 5- to 6-membered heteroaryl;

$R^1$ is H, —CN, halogen, $C_1$-$C_4$ alkyl, —O—($C_3$-$C_8$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_8$ cycloalkyl or 4- to 6-membered heterocycle;

$R^{22}$ is H, halogen, or $C_1$-$C_2$ alkyl; and $R^{24}$ is H, $C_1$-$C_4$ alkyl, —($C_1$-$C_4$ alkyl)-OH, —($C_1$-$C_4$ alkyl), —N($R^{241}$)$_2$, —($C_1$-$C_4$ alkyl)$_t$-$O_t$—($C_3$-$C_5$ cycloalkyl), —($C_1$-$C_4$ alkyl)$_t$-$O_t$-(4- to 6-membered heterocycle) or —($C_1$-$C_4$ alkyl)-O—($C_1$-$C_4$ alkyl), wherein:

each t is independently 0 or 1; and each $R^{241}$ is independently H or $C_1$-$C_2$ alkyl; or (g) Formula (XV):

(XV)

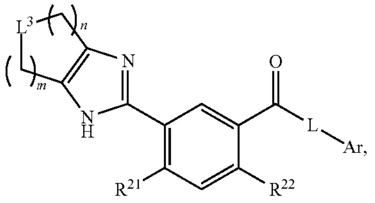

or pharmaceutically acceptable salts thereof, wherein:

$L^3$ is —$CH_2$—, —$CHR^{50}$—, —O—, —$NR^{50}$—, —NC(O)$R^{50}$— or —NC(O)O$R^{50}$—, wherein $R^{50}$ is $C_1$-$C_6$ alkyl, $C_3$-$C_5$ cycloalkyl, or 4- to 6-membered heterocycle;

n is 1, 2, or 3;

m is 1 or 2 with the proviso that n+m≥3;

L-Ar is

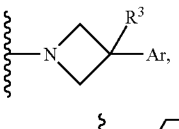

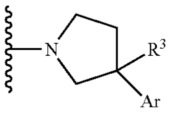

or

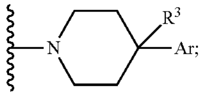

Ar is

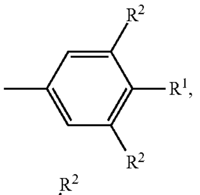

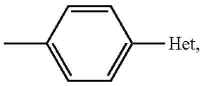

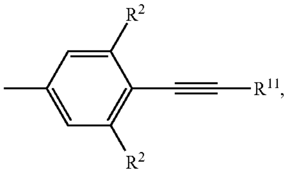

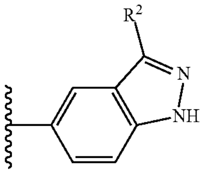

or

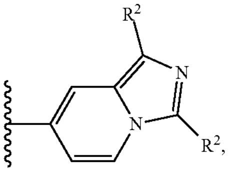

with the proviso that when L-Ar is

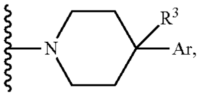

Ar is not

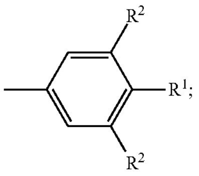

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_8$ cycloalkyl or a 4- to 6-membered heterocycle; and $R^{22}$ is H, halogen, or $C_1$-$C_2$ alkyl; or (h) Formula (XVI):

(XVI)

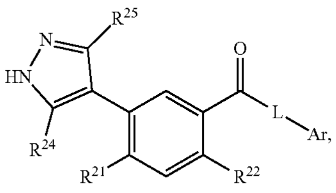

or pharmaceutically acceptable salts thereof, wherein:

L-Ar is

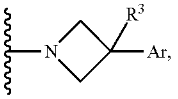

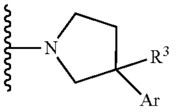

or

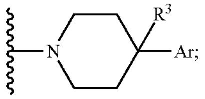

Ar is

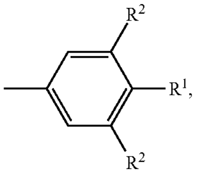

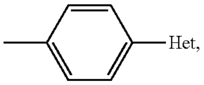

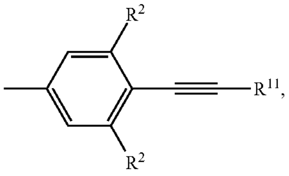

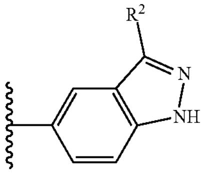

or

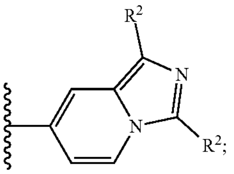

Het is a 5- to 6-membered heteroaryl;

$R^1$ is H, —CN, halogen, $C_1$-$C_4$ alkyl, —O—($C_3$-$C_8$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and each of $R^{24}$ and $R^{25}$ is independently H, —$C_1$-$C_4$ alkyl, or halogen; or (i) Formula (XVII):

(XVII)

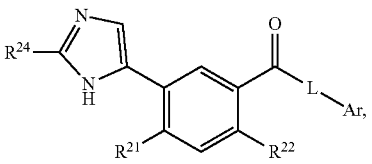

or pharmaceutically acceptable salts thereof, wherein:

L-Ar is

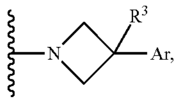

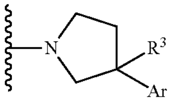

or

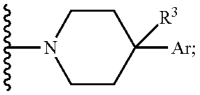

Ar is

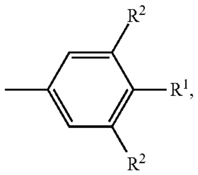

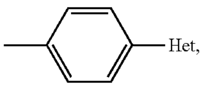

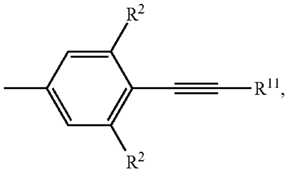

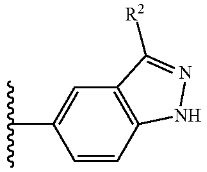

or

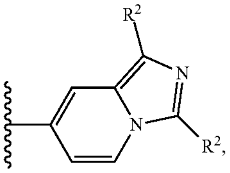

with the proviso that when L-Ar is

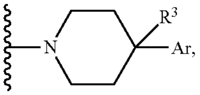

Ar is not

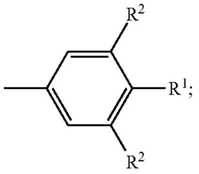

Het is a 5- to 6-membered heteroaryl;

$R^1$ is H, —CN, halogen, $C_1$-$C_4$ alkyl, —O—($C_3$-$C_8$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_8$ cycloalkyl or 4- to 6-membered heterocycle;

$R^{22}$ is H, halogen or $C_1$-$C_2$ alkyl; and $R^{24}$ is H, $C_1$-$C_4$ alkyl, —($C_1$-$C_4$ alkyl)-OH, —($C_1$-$C_4$ alkyl)-$N(R^{241})_2$, —($C_1$-$C_4$ alkyl)$_t$-$O_u$—($C_3$-$C_5$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl), wherein:

t is 0 or 1;

u is 0 or 1;

with the proviso that when u is 1, t is 1; and $R^{241}$ is H or $C_1$-$C_2$ alkyl; or (j) Formula (XVIII):

(XVIII)

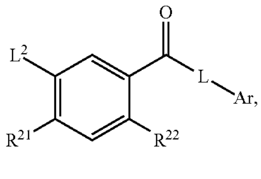

or pharmaceutically acceptable salts thereof, wherein:

L-Ar is

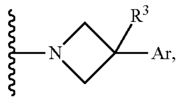

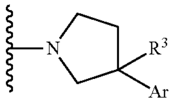 or

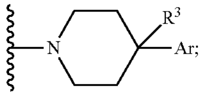

Ar is

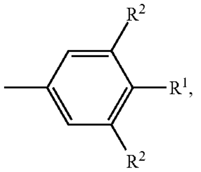

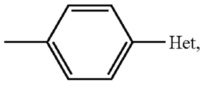

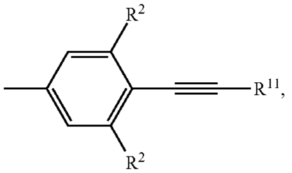

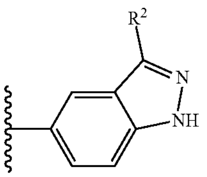 or 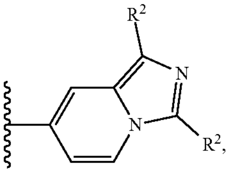

with the proviso that when L-Ar is

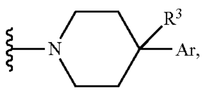

Ar is not

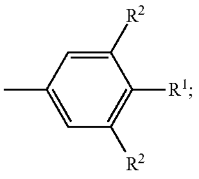

$L^2$ is —$NHR^{35}$ or —C(O)$NHR^{351}$, wherein $R^{351}$ is $C_1$-$C_6$ alkyl, $C_3$-$C_8$ cycloalkyl, 4- to 6-membered heterocycle, aryl or heteroaryl;

Het is a 5- to 6-membered heteroaryl;

$R^1$ is H, —CN, halogen, $C_1$-$C_4$ alkyl, —O—($C_3$-$C_8$ cycloalkyl), —O-(4- to 6-membered heterocycle)$_t$-O—($C_1$-$C_4$ alkyl) wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_8$ cycloalkyl or 4- to 6-membered heterocycle;

$R^{22}$ is H, halogen, or $C_1$-$C_2$ alkyl; and $R^{35}$ is —C(O)$R^{351}$, —C(O)$NHR^{351}$, C(O)$OR^{351}$ or S(O)$_2R^{351}$ wherein $R^{351}$ is $C_1$-$C_6$ alkyl, $C_3$-$C_5$ cycloalkyl, 4- to 6-membered heterocycle, aryl or heteroaryl; or (k) Formula (XIX):

(XIX)

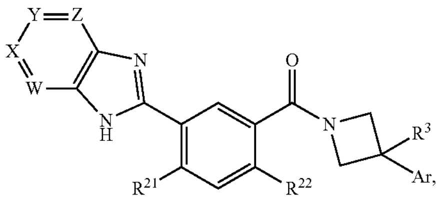

or pharmaceutically acceptable salts thereof, wherein:

each W, X, Y and Z is independently —N— or —$CR^{26}$— with the proviso that not more than 2 of W, X, Y and Z are —N—;

each $R^{26}$ is independently H, $C_1$-$C_4$ alkyl, —O—($C_1$-$C_4$ alkyl), —$N(R^{27})_2$, —$S(O)_2$—($C_1$-$C_4$ alkyl), or —C(O)—($C_1$-$C_4$ alkyl);

each $R^{27}$ is independently H or $C_1$-$C_4$ alkyl or both $R^{27}$ are $C_1$-$C_4$ alkyl and join to form a 3- to 6-membered ring together with the N to which they are attached and wherein the ring optionally includes one oxygen atom as one of the members of the ring;

Ar is

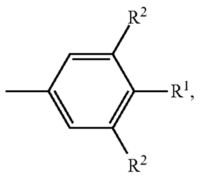

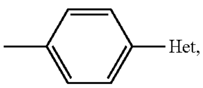

-continued

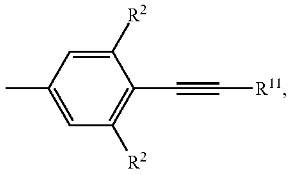

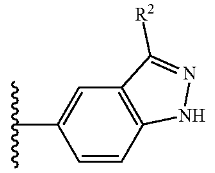

or

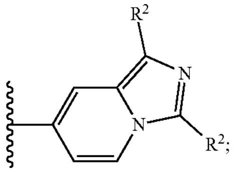

Het is a 5- to 6-membered heteroaryl;

$R^1$ is H, —CN, halogen, $C_1$-$C_4$ alkyl, —O—($C_3$-$C_8$ cycloalkyl), —O-(4- to 6-membered heterocycle), —O—($C_1$-$C_4$ alkyl) wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_8$ cycloalkyl or a 4- to 6-membered heterocycle; and $R^{22}$ is H, halogen or $C_1$-$C_2$ alkyl; or (l) Formula (XX):

(XX)

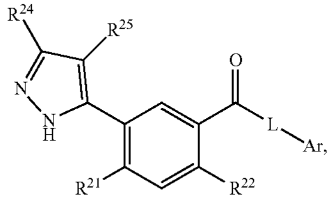

or a pharmaceutically acceptable salt thereof, wherein:

L-Ar is

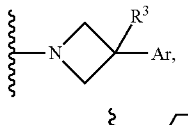

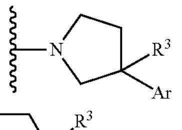

or

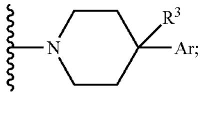

Ar is

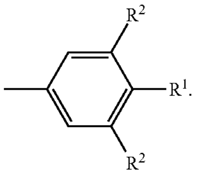

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogen;

each $R^2$ is independently hydrogen, halogen or $C_1$-$C_4$ alkyl;

$R^3$ is H or F;

$R^{21}$ is H, halogen, $C_1$-$C_4$ alkyl, $C_3$-$C_8$ cycloalkyl or 4- to 6-membered heterocycle;

$R^{22}$ is H, halogen or $C_1$-$C_2$ alkyl;

$R^{24}$ is —O—($C_1$-$C_4$ alkyl), —O—($C_1$-$C_4$ alkyl)-O—($C_1$-$C_4$ alkyl), —O—($C_3$-$C_8$ cycloalkyl), or —O-(4- to 6-membered heterocycle), wherein $R^{24}$ is optionally substituted with one or more hydroxyl or halogen; and $R^{25}$ is H, halogen, $C_1$-$C_4$ alkyl or $C_3$-$C_8$ cycloalkyl, wherein $R^{25}$ is optionally substituted with one or more halogen; or (m) Formula (XI):

(XI)

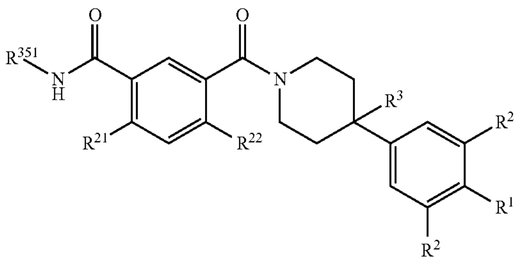

or a pharmaceutically acceptable salt thereof, wherein:

$R^1$ is H, —CN, halogen, $C_1$-$C_4$ straight or branched alkyl, —O—($C_3$-$C_8$ cycloalkyl), —O—($C_1$-$C_4$ straight or branched alkyl) wherein:

the $C_3$-$C_8$ cycloalkyl optionally includes an oxygen or nitrogen heteroatom; and when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is cyclobutyl, azetidin-1-yl, or cyclopropyl;

$R^{22}$ is H, halogen, $C_1$-$C_2$ alkyl; and $R^{351}$ is $C_1$-$C_2$ alkyl or $C_2$—O—($C_1$ or $C_2$ alkyl).

Embodiment 33. The method of any one of embodiments 1-32, wherein the fatty acid synthase inhibitor has a Formula (IX).

Embodiment 34. The method of any one of embodiments 1-32, wherein the fatty acid synthase inhibitor has a Formula (X).

Embodiment 35. The method of any one of embodiments 1-32, wherein the fatty acid synthase inhibitor has a Formula (XII).

Embodiment 36. The method of any one of embodiments 1-32, wherein the fatty acid synthase inhibitor has a Formula (XIV).

Embodiment 37. The method of any one of embodiments 1-32, wherein the fatty acid synthase inhibitor has a Formula (XV).

Embodiment 38. The method of any one of embodiments 1-32, wherein the fatty acid synthase inhibitor has a Formula (XX).

Embodiment 39. The method of any one of embodiments 1-32, wherein the fatty acid synthase inhibitor is:

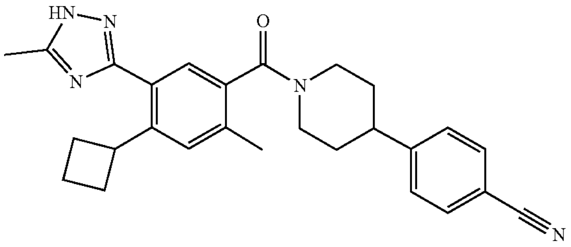 [SMILES: Cc1nc(-c2cc(C(=O)N3CCC(c4ccc(C#N)cc4)CC3)c(C)cc2C2CCC2)n[nH]1]

Embodiment 40. The method of any one of embodiments 1-32, wherein the fatty acid synthase inhibitor is:

(Compound 005-2)

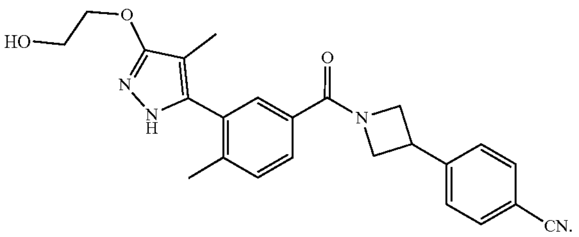

Embodiment 41. The method of any one of embodiments 1-40, wherein the thyroid hormone receptor-beta agonist is selected from resmetirom, VK2809, TERN-501 and ALG-055009.

Embodiment 42. The method of any one of embodiments 1-40, wherein the thyroid hormone receptor-beta agonist is resmetirom, having the formula:

(Compound A)

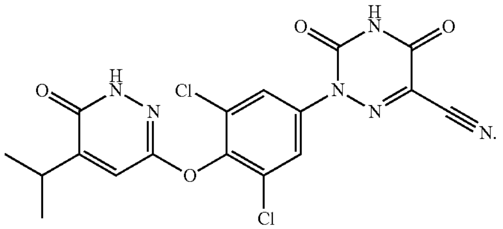

Embodiment 43. The method of any one of embodiments 1-42, wherein the fatty acid synthase inhibitor and the thyroid hormone receptor-beta agonist are administered sequentially.

Embodiment 44. The method of any one of embodiments 1-42, wherein the fatty acid synthase inhibitor and the thyroid hormone receptor-beta agonist are administered simultaneously.

Embodiment 45. The method of embodiment 44, wherein the FASN inhibitor and the thyroid hormone receptor-beta agonist are administered on the same dosing schedule.

Embodiment 46. The method of embodiment 44, wherein the FASN inhibitor and the thyroid hormone receptor-beta agonist are administered on different dosing schedules.

Embodiment 47. The method of any one of embodiments 1-46, wherein the fatty acid synthase inhibitor and the thyroid hormone receptor-beta agonist are formulated in separate dosage forms.

Embodiment 48. The method of any one of embodiments 1-44, wherein the fatty acid synthase inhibitor and the thyroid hormone receptor-beta agonist are formulated in the same dosage form.

Embodiment 49. The method of any one of embodiments 1-42, wherein the compound A (resmetirom) is a polymorph of Form A.

Embodiment 50. The method of any one of embodiments 1-49, wherein the FASN inhibitor and the thyroid hormone receptor beta agonist are administered in synergistically effective amounts.

Embodiment 51. The method of any one of embodiments 1-50, wherein the FASN inhibitor is administered at a dose of 10-100 mg.

Embodiment 52. The method of any one of embodiments 1-50, wherein the FASN inhibitor is administered at a dose of 10-90 mg.

Embodiment 53. The method of any one of embodiments 1-50, wherein the FASN inhibitor is administered at a dose of 10-80 mg.

Embodiment 54. The method of any one of embodiments 1-50, wherein the FASN inhibitor is administered at a dose of 10-70 mg.

Embodiment 55. The method of any one of embodiments 1-50, wherein the FASN inhibitor is administered at a dose of 10-60 mg.

Embodiment 56. The method of any one of embodiments 1-50, wherein the FASN inhibitor is administered at a dose of 10-50 mg.

Embodiment 57. The method of any one of embodiments 1-50, wherein the FASN inhibitor is administered at a dose of 10-40 mg.

Embodiment 58. The method of any one of embodiments 1-50, wherein the FASN inhibitor is administered at a dose of 10-30 mg.

Embodiment 59. The method of any one of embodiments 1-50, wherein the FASN inhibitor is administered at a dose of 10-20 mg.

Embodiment 60. The method of any one of embodiments 1-50, wherein the FASN inhibitor is administered at a dose of 20-100 mg.

Embodiment 61. The method of any one of embodiments 1-50, wherein the FASN inhibitor is administered at a dose of 20-90 mg.

Embodiment 62. The method of any one of embodiments 1-50, wherein the FASN inhibitor is administered at a dose of 20-80 mg.

Embodiment 63. The method of any one of embodiments 1-50, wherein the FASN inhibitor is administered at a dose of 20-70 mg.

Embodiment 64. The method of any one of embodiments 1-50, wherein the FASN inhibitor is administered at a dose of 20-60 mg.

Embodiment 65. The method of any one of embodiments 1-50, wherein the FASN inhibitor is administered at a dose of 20-50 mg.

Embodiment 66. The method of any one of embodiments 1-50, wherein the FASN inhibitor is administered at a dose of 20-40 mg.

Embodiment 67. The method of any one of embodiments 1-50, wherein the FASN inhibitor is administered at a dose of 20-30 mg.

Embodiment 68. The method of any one of embodiments 1-50, wherein the FASN inhibitor is administered at a dose of 30-100 mg.

Embodiment 69. The method of any one of embodiments 1-50, wherein the FASN inhibitor is administered at a dose of 30-90 mg.

Embodiment 70. The method of any one of embodiments 1-50, wherein the FASN inhibitor is administered at a dose of 30-80 mg.

Embodiment 71. The method of any one of embodiments 1-50, wherein the FASN inhibitor is administered at a dose of 30-70 mg.

Embodiment 72. The method of any one of embodiments 1-50, wherein the FASN inhibitor is administered at a dose of 30-60 mg.

Embodiment 73. The method of any one of embodiments 1-50, wherein the FASN inhibitor is administered at a dose of 30-50 mg.

Embodiment 74. The method of any one of embodiments 1-50, wherein the FASN inhibitor is administered at a dose of 30-40 mg.

Embodiment 75. The method of any one of embodiments 1-50, wherein the FASN inhibitor is administered at a dose of 40-100 mg.

Embodiment 76. The method of any one of embodiments 1-50, wherein the FASN inhibitor is administered at a dose of 40-90 mg.

Embodiment 77. The method of any one of embodiments 1-50, wherein the FASN inhibitor is administered at a dose of 40-80 mg.

Embodiment 78. The method of any one of embodiments 1-50, wherein the FASN inhibitor is administered at a dose of 40-70 mg.

Embodiment 79. The method of any one of embodiments 1-50, wherein the FASN inhibitor is administered at a dose of 40-60 mg.

Embodiment 80. The method of any one of embodiments 1-50, wherein the FASN inhibitor is administered at a dose of 40-50 mg.

Embodiment 81. The method of any one of embodiments 1-50, wherein the FASN inhibitor is administered at a dose of 50-100 mg.

Embodiment 82. The method of any one of embodiments 1-50, wherein the FASN inhibitor is administered at a dose of 50-90 mg.

Embodiment 83. The method of any one of embodiments 1-50, wherein the FASN inhibitor is administered at a dose of 50-80 mg.

Embodiment 84. The method of any one of embodiments 1-50, wherein the FASN inhibitor is administered at a dose of 50-70 mg.

Embodiment 85. The method of any one of embodiments 1-50, wherein the FASN inhibitor is administered at a dose of 50-60 mg.

Embodiment 86. The method of any one of embodiments 1-50, wherein the FASN inhibitor is administered at a dose of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg.

Embodiment 87. The method of any one of embodiments 1-50, wherein the FASN inhibitor is administered at a dose of 10 mg, 15 mg, 20 mg, 25 mg, 30 mg, 35 mg, 40 mg, 45 mg or 50 mg.

Embodiment 88. The method of any one of embodiments 1-93, wherein the FASN inhibitor is administered at a dose of 20 mg, 25 mg, 30 mg, 35 mg, 40 mg, 45 mg or 50 mg.

Embodiment 89. The method of any one of embodiments 1-50, wherein the FASN inhibitor is administered at a dose of 10 mg.

Embodiment 90. The method of any one of embodiments 1-50, wherein the FASN inhibitor is administered at a dose of 15 mg.

Embodiment 91. The method of any one of embodiments 1-50, wherein the FASN inhibitor is administered at a dose of 20 mg.

Embodiment 92. The method of any one of embodiments 1-50, wherein the FASN inhibitor is administered at a dose of 25 mg.

Embodiment 93. The method of any one of embodiments 1-50, wherein the FASN inhibitor is administered at a dose of 30 mg.

Embodiment 94. The method of any one of embodiments 1-50, wherein the FASN inhibitor is administered at a dose of 35 mg.

Embodiment 95. The method of any one of embodiments 1-50, wherein the FASN inhibitor is administered at a dose of 40 mg.

Embodiment 96. The method of any one of embodiments 1-50, wherein the FASN inhibitor is administered at a dose of 45 mg.

Embodiment 97. The method of any one of embodiments 1-50, wherein the FASN inhibitor is administered at a dose of 50 mg.

Embodiment 98. The method of any one of embodiments 1-50, wherein the FASN inhibitor is administered at a dose of 55 mg.

Embodiment 99. The method of any one of embodiments 1-50, wherein the FASN inhibitor is administered at a dose of 60 mg.

Embodiment 100. The method of any one of embodiments 1-50, wherein the FASN inhibitor is administered at a dose of 65 mg.

Embodiment 101. The method of any one of embodiments 1-50, wherein the FASN inhibitor is administered at a dose of 70 mg.

Embodiment 102. The method of any one of embodiments 1-50, wherein the FASN inhibitor is administered at a dose of 75 mg.

Embodiment 103. The method of any one of embodiments 1-50, wherein the FASN inhibitor is administered at a dose of 80 mg.

Embodiment 104. The method of any one of embodiments 1-50, wherein the FASN inhibitor is administered at a dose of 85 mg.

Embodiment 105. The method of any one of embodiments 1-50, wherein the FASN inhibitor is administered at a dose of 90 mg.

Embodiment 106. The method of any one of embodiments 1-50, wherein the FASN inhibitor is administered at a dose of 95 mg.

Embodiment 107. The method of any one of embodiments 1-50, wherein the FASN inhibitor is administered at a dose of 100 mg.

Embodiment 108. The method of any one of embodiments 1-107, wherein the FASN inhibitor is administered once or twice daily.

Embodiment 109. The method of any one of embodiments 1-107, wherein the FASN inhibitor is administered once daily.

Embodiment 110. The method of any one of embodiments 1-107, wherein the FASN inhibitor is administered twice daily.

Embodiment 111. The method of any one of embodiments 1-107, wherein the FASN inhibitor is administered intermittently.

Embodiment 112. The method of any one of embodiments 1-107, wherein the FASN inhibitor is administered three times a week.

Embodiment 113. The method of any one of embodiments 1-107, wherein the FASN inhibitor is administered on an on/off/on/off/on/off/off schedule (e.g., a Monday, Wednesday, Friday schedule.

Embodiment 114. The method of any one of embodiments 1-107, wherein the FASN inhibitor is administered twice a week.

Embodiment 115. The method of any one of embodiments 1-107, wherein the FASN inhibitor is administered once a week.

Embodiment 116. The method of any one of embodiments 1-115, wherein the FASN inhibitor is administered orally.

Embodiment 117. The method of any one of embodiments 1-116, wherein the thyroid hormone receptor beta agonist is administered at a dose that is equivalent to the single-agent dose indicated for treating NASH/MASH.

Embodiment 118. The method of any one of embodiments 1-116, wherein the thyroid hormone receptor beta agonist is administered at a dose that is between 10% and 90% of the single-agent dose indicated for treating NASH/MASH.

Embodiment 119. The method of any one of embodiments 1-116, wherein the thyroid hormone receptor beta agonist is administered at a dose that is between 20% and 90% of the single-agent dose indicated for treating NASH/MASH.

Embodiment 120. The method of any one of embodiments 1-116, wherein the thyroid hormone receptor beta agonist is administered at a dose that is between 30% and 90% of the single-agent dose indicated for treating NASH/MASH.

Embodiment 121. The method of any one of embodiments 1-116, wherein the thyroid hormone receptor beta agonist is administered at a dose that is between 40% and 90% of the single-agent dose indicated for treating NASH/MASH.

Embodiment 122. The method of any one of embodiments 1-116, wherein the thyroid hormone receptor beta agonist is administered at a dose that is between 50% and 90% of the single-agent dose indicated for treating NASH/MASH.

Embodiment 123. The method of any one of embodiments 1-116, wherein the thyroid hormone receptor beta agonist is administered at a dose that is between 60% and 90% of the single-agent dose indicated for treating NASH/MASH.

Embodiment 124. The method of any one of embodiments 1-116, wherein the thyroid hormone receptor beta agonist is administered at a dose that is between 70% and 90% of the single-agent dose indicated for treating NASH/MASH.

Embodiment 125. The method of any one of embodiments 1-116, wherein the thyroid hormone receptor beta agonist is administered at a dose that is between 80% and 90% of the single-agent dose indicated for treating NASH/MASH.

Embodiment 126. The method of any one of embodiments 1-116, wherein the thyroid hormone receptor beta agonist is administered at a dose that is between 10% and 80% of the single-agent dose indicated for treating NASH/MASH.

Embodiment 127. The method of any one of embodiments 1-116, wherein the thyroid hormone receptor beta agonist is administered at a dose that is between 20% and 80% of the single-agent dose indicated for treating NASH/MASH.

Embodiment 128. The method of any one of embodiments 1-116, wherein the thyroid hormone receptor beta agonist is administered at a dose that is between 30% and 80% of the single-agent dose indicated for treating NASH/MASH.

Embodiment 129. The method of any one of embodiments 1-116, wherein the thyroid hormone receptor beta agonist is administered at a dose that is between 40% and 80% of the single-agent dose indicated for treating NASH/MASH.

Embodiment 130. The method of any one of embodiments 1-116, wherein the thyroid hormone receptor beta agonist is administered at a dose that is between 50% and 80% of the single-agent dose indicated for treating NASH/MASH.

Embodiment 131. The method of any one of embodiments 1-116, wherein the thyroid hormone receptor beta agonist is administered at a dose that is between 60% and 80% of the single-agent dose indicated for treating NASH/MASH.

Embodiment 132. The method of any one of embodiments 1-116, wherein the thyroid hormone receptor beta agonist is administered at a dose that is between 70% and 80% of the single-agent dose indicated for treating NASH/MASH.

Embodiment 133. The method of any one of embodiments 1-116, wherein the thyroid hormone receptor beta agonist is administered at a dose that is between 10% and 70% of the single-agent dose indicated for treating NASH/MASH.

Embodiment 134. The method of any one of embodiments 1-116, wherein the thyroid hormone receptor beta agonist is administered at a dose that is between 20% and 70% of the single-agent dose indicated for treating NASH/MASH.

Embodiment 135. The method of any one of embodiments 1-116, wherein the thyroid hormone receptor beta agonist is administered at a dose that is between 30% and 70% of the single-agent dose indicated for treating NASH/MASH.

Embodiment 136. The method of any one of embodiments 1-116, wherein the thyroid hormone receptor beta agonist is administered at a dose that is between 40% and 70% of the single-agent dose indicated for treating NASH/MASH.

Embodiment 137. The method of any one of embodiments 1-116, wherein the thyroid hormone receptor beta agonist is administered at a dose that is between 50% and 70% of the single-agent dose indicated for treating NASH/MASH.

Embodiment 138. The method of any one of embodiments 1-116, wherein the thyroid hormone receptor beta agonist is administered at a dose that is between 60% and 70% of the single-agent dose indicated for treating NASH/MASH.

Embodiment 139. The method of any one of embodiments 1-116, wherein the thyroid hormone receptor beta agonist is administered at a dose that is between 10% and 60% of the single-agent dose indicated for treating NASH/MASH.

Embodiment 140. The method of any one of embodiments 1-116, wherein the thyroid hormone receptor beta agonist is administered at a dose that is between 20% and 60% of the single-agent dose indicated for treating NASH/MASH.

Embodiment 141. The method of any one of embodiments 1-116, wherein the thyroid hormone receptor beta agonist is administered at a dose that is between 30% and 60% of the single-agent dose indicated for treating NASH/MASH.

Embodiment 142. The method of any one of embodiments 1-116, wherein the thyroid hormone receptor beta agonist is administered at a dose that is between 40% and 60% of the single-agent dose indicated for treating NASH/MASH.

Embodiment 143. The method of any one of embodiments 1-116, wherein the thyroid hormone receptor beta agonist is administered at a dose that is between 50% and 60% of the single-agent dose indicated for treating NASH/MASH.

Embodiment 144. The method of any one of embodiments 1-116, wherein the thyroid hormone receptor beta agonist is administered at a dose that is between 10% and 50% of the single-agent dose indicated for treating NASH/MASH.

Embodiment 145. The method of any one of embodiments 1-116, wherein the thyroid hormone receptor beta agonist is administered at a dose that is between 20% and 50% of the single-agent dose indicated for treating NASH/MASH.

Embodiment 146. The method of any one of embodiments 1-116, wherein the thyroid hormone receptor beta agonist is administered at a dose that is between 30% and 50% of the single-agent dose indicated for treating NASH/MASH.

Embodiment 147. The method of any one of embodiments 1-116, wherein the thyroid hormone receptor beta agonist is administered at a dose that is between 40% and 50% of the single-agent dose indicated for treating NASH/MASH.

Embodiment 148. The method of any one of embodiments 1-116, wherein the thyroid hormone receptor beta agonist is administered at a dose that is between 10% and 40% of the single-agent dose indicated for treating NASH/MASH.

Embodiment 149. The method of any one of embodiments 1-116, wherein the thyroid hormone receptor beta agonist is administered at a dose that is between 20% and 40% of the single-agent dose indicated for treating NASH/MASH.

Embodiment 150. The method of any one of embodiments 1-116, wherein the thyroid hormone receptor beta agonist is administered at a dose that is between 30% and 40% of the single-agent dose indicated for treating NASH/MASH.

Embodiment 151. The method of any one of embodiments 1-116, wherein the thyroid hormone receptor beta agonist is administered at a dose that is between 10% and 30% of the single-agent dose indicated for treating NASH/MASH.

Embodiment 152. The method of any one of embodiments 1-116, wherein the thyroid hormone receptor beta agonist is administered at a dose that is between 20% and 30% of the single-agent dose indicated for treating NASH/MASH.

Embodiment 153. The method of any one of embodiments 1-116, wherein the thyroid hormone receptor beta agonist is administered at a dose that is between 10% and 20% of the single-agent dose indicated for treating NASH/MASH.

Embodiment 154. The method of any one of embodiments 117-153 wherein the single-agent dose of thyroid hormone receptor beta agonist indicated for treating NASH/MASH is 80 mg once daily for a patient with a body weight of ≤100 kg and 100 mg once daily for a patient with a body weight of ≥100 kg.

Embodiment 155. The method of any one of embodiments 1-153 wherein the thyroid hormone receptor beta agonist is administered at a dose of 80 mg once daily for a patient with a body weight of ≤100 kg and 100 mg once daily for a patient with a body weight of ≥100 kg.

Embodiment 156. The method of any one of embodiments 1-155 wherein the subject has been diagnosed with a comorbidity.

Embodiment 157. The method of embodiment 156, wherein the comorbidity is obesity, type 2 diabetes or a combination of both.

Embodiment 158. The method of embodiment 156, wherein the comorbidity is obesity.

Embodiment 159. The method of embodiment 156, wherein the comorbidity is type 2 diabetes.

Embodiment 160. The method of embodiment 156, wherein the comorbidity is a combination of obesity and type 2 diabetes.

Embodiment 161. A pharmaceutical formulation comprising Compound 001-152 or a pharmaceutically acceptable salt thereof and Compound A or a pharmaceutically acceptable salt thereof.

Embodiment 162. A pharmaceutical formulation comprising Compound 001-152 or a pharmaceutically acceptable salt thereof and a polymorph of Form A of the Compound A.

Embodiment 163. A pharmaceutical formulation comprising a FASN inhibitor or a pharmaceutically acceptable salt thereof and a thyroid hormone receptor agonist or a pharmaceutically acceptable salt thereof.

EXAMPLES

Synthetic Example 1-Synthesis of Compounds of the Present Disclosure

General: All reactions and manipulations described were carried out in well ventilated fume-hoods. Operations and reactions carried out at elevated or reduced pressure were carried out behind blast shields. Abbreviations: ACN, acetonitrile; AcOH, acetic acid; AIBN, azobisisobutyronitrile; BuLi, butyl lithium; CDI, 1,1'-Carbonyldiimidazole; DBU, 1,8-Diazabicyclo[5.4.0]undec-7-ene; DCE, 1,2-dichloroethane; DCM, dichloromethane or methylene chloride; DIEA, N,N-Diisopropylethylamine; DMAP, 4-dimethylaminopyridine; DMF, N,N-dimethylformamide; DMSO, dimethylsulfoxide; EDC, 1-ethyl-3-(3-dimethylaminopropyl) carbodiimide; EDCI, 1-ethyl-3-(3-dimethylaminopropyl) carbodiimide hydrochloride; EtOAc, ethyl acetate; EtOH, Ethanol; HATU, 2-(1H-7-Azabenzotriazol-1-yl)-1,1,3,3-tetramethyl uronium hexafluorophosphate; HBTU, O-Benzotriazole-N,N,N',N'-tetramethyl-uronium-hexafluoro-phosphate or 2-(1H-Benzotriazole-1-yl)-1,1,3,3-tetramethylaminium hexafluorophosphate; HMPA, hexamethylphosphoramide; HOAc, acetic acid; HOBT, 1-Hydroxybenzotriazole; LDA, lithium diisopropylamine; MeOH, methanol; MsCl, methanesulfonyl chloride; MsOH, methanesulfonic acid; NBS, N-bromosuccinimide; NIS, N-iodosuccinimide; PE, petroleum ether; PTAT, phenyltrimethylammonium tribromide; PTSA, p-toluenesulfonic acid; Py, pyridine; Pyr, pyridine; TEA, triethylamine; TFA, trifluoroacetic acid; THF, tetrahydrofuran; TMSCl, chlorotrimethylsilane; TsOH, p-toluenesulfonic acid. Exemplary syntheses are disclosed below. Additional syntheses are found in International Application Publication Nos. WO2012/122391, WO2014/008197, and WO2015/105860, each of which are incorporated by reference herein in their entireties.

Compound 001-152

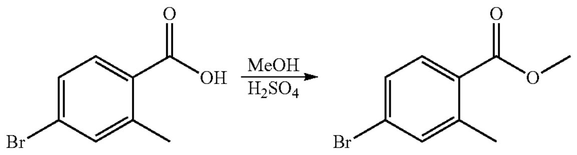

Compound 001-152.1. Methyl 4-bromo-2-methylbenzoate. To a solution of 4-bromo-2-methylbenzoic acid (5.11 g, 23.8 mmol, 1.0 equiv) in methanol (25 mL) was added dropwise ulfuric acid (2.0 mL) over about 3 minutes (mildly exothermic). The resulting mixture was refluxed for 4 hours. After cooling to room temperature, the reaction mixture was carefully quenched into saturated aqueous $NaHCO_3$ (100 mL) (note-significant gas evolution) and extracted with dichloromethane (200 mL×1 then 50 mL×1). The combined organic phases were washed with a mixture of brine/saturated $NaHCO_3$ (9:1) (50 mL), dried ($Na_2SO_4$), and concentrated under reduced pressure to obtain compound 001-152.1 as a colorless oil (5.28 g, 97%). $^1H$ NMR (400 MHz, $CDCl_3$): δ 7.78 (d, J=8.0 Hz, 1H), 7.42 (d, J=1.6 Hz, 1H), 7.38 (dd, J=1.6 Hz, 1H), 3.89 (s, 3H), 2.58 (s, 3H).

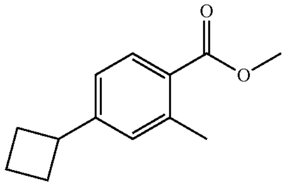

Compound 001-152.2. Methyl 4-cyclobutyl-2-methylbenzoate. Cyclobutylzinc(II) bromide (50 ml, 0.5 M in THF, 25.0 mmol) was added to a mixture of methyl 4-bromo-2-methylbenzoate (compound 152.1, 5.2 g, 22.7 mmol) and $PdCl_2(dppf)CH_2Cl_2$ (1.85 g, 2.27 mmol). The mixture was degassed and the flask was filled with argon through a balloon. The mixture was heated at 65° C. under argon for 24 hours. The mixture was cooled to 0° C. and quenched with water (10 ml). The mixture was diluted with EtOAc (200 ml), washed with water then with brine. The EtOAc layer was dried ($Na_2SO_4$), concentrated under reduced pressure, and purified using column (silica gel) chromatography (hexanes:EtOAc 30:1 to 20:1). Yield: 4.1 g, clear oil, 89.1%. $^1H$ NMR (400 MHz, Chloroform-d) δ 7.86 (d, 1H), 7.12-7.02 (m, 2H), 3.88 (s, 3H), 3.59-3.48 (m, 1H), 2.59 (s, 3H), 2.35 (m, 2H), 2.22-1.96 (m, 3H), 1.86-1.84 (m, 1H).

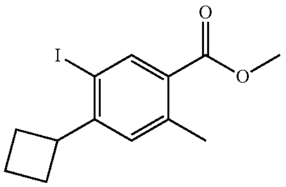 [SMILES: COC(=O)c1cc(I)c(C2CCC2)cc1C]

Compound 001-152.3. Methyl 4-cyclobutyl-5-iodo-2-methylbenzoate. N-Iodosuccinimide (3.52 g, 15.6 mmol) was added portionwise to a solution of methyl 4-cyclobutyl-2-methylbenzoate (compound 152.2, 3.2 g, 15.6 mmol) in concentrated sulfuric acid (25 ml) at 0° C. The mixture was stirred at 0° C. for 30 min and at RT for 2 hours. The mixture turned very thick. The mixture was cooled to 0° C. again and MeOH (30 ml) was added. The mixture was heated at 60° C. for 2 hours. The methanol was removed under reduced pressure and the residue was poured into ice water (100 ml). The mixture was extracted with EtOAc (2×). The combined organic layers were washed with brine, then aq. 1N $NaHCO_3$ (note-significant gas evolution), dried ($Na_2SO_4$) and concentrated. The residue was purified using column (silica gel) chromatography (hexanes:EtOAc 30:1 to 20:1). Yield: 4.17 g, light yellow oil, 81%. $^1H$ NMR (400 MHz, Chloroform-d) δ 8.33 (s, 1H), 7.14 (s, 1H), 3.87 (s, 3H), 3.67-3.54 (m, 1H), 2.57 (s, 3H), 2.51-2.40 (m, 2H), 2.14-1.97 (m, 3H), 1.82-1.79 (m, 1H).

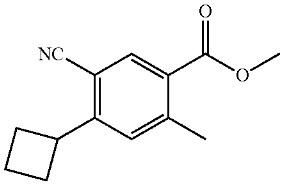 [SMILES: COC(=O)c1cc(C#N)c(C2CCC2)cc1C]

Compound 001-152.4. Methyl 5-cyano-4-cyclobutyl-2-methylbenzoate. A mixture of methyl 4-cyclobutyl-5-iodo-2-methylbenzoate (compound 152.3, 4.17 g, 12.64 mmol), $Zn(CN)_2$ (2.96 g, 25.21 mmol) and $Pd(PPh_3)_4$ (0.73 g, 0.63 mmol) in DMF (30 ml) was degassed and the flask was filled with argon through a balloon. The mixture was heated at 100° C. under argon overnight. After cooling to ambient temperature, the mixture was quenched with saturated aq. $FeSO_4$ (20 ml) and diluted with EtOAc (200 ml). The greenish solid was removed by filtration through celite. The filtrate was partitioned between water and EtOAc. The EtOAc layer was washed with brine, dried ($Na_2SO_4$), and concentrated. The residue was purified using column (silica gel) chromatography (hexanes:EtOAc 30:1 to 20:1). Yield: 2.55 g, white solid, 88%. $^1H$ NMR (400 MHz, Chloroform-d) δ 8.16 (s, 1H), 7.28 (s, 1H), 3.90 (s, 3H), 3.86-3.82 (m, 1H), 2.68 (s, 3H), 2.55-2.45 (m, 2H), 2.27-2.04 (m, 3H), 1.89-1.87 (m, 1H).

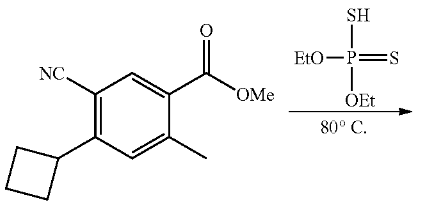

-continued

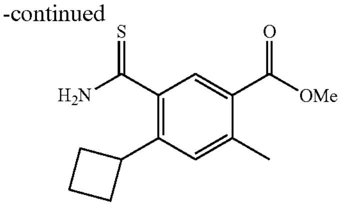

Compound 001-152.5. Methyl 5-carbamothioyl-4-cyclobutyl-2-methylbenzoate. To a round-bottom flask were added methyl 5-cyano-4-cyclobutyl-2-methylbenzoate (compound 152.4, 3.63 g, 0.015 mol), O,O'-diethyl dithiophosphate (10 mL) and water (1 mL). The reaction mixture was heated to 80° C. for 3 hours (CAUTION: significant gas evolution occurs—this and all other reactions described herein should be carried out in well ventilated fume hoods). After cooling to room temperature, the reaction mixture was partitioned between ethyl acetate (50 mL) and water (50 mL). The combined organic layers were washed successively with saturated aqueous $NaHCO_3$ (50 mL) and brine (50 mL), dried over $Na_2SO_4$, and concentrated in vacuo. Purification by $SiO_2$ flash chromatography (hexanes/ethyl acetate=80/20 to 50/50) afforded methyl 5-carbamothioyl-4-cyclobutyl-2-methylbenzoate as a yellow solid (3.06 g, 78% yield). m/z (ES+) 264 $(M+H)^+$. $^1H$ NMR (400 MHz, $CDCl_3$): δ 7.93 (s, 1H), 7.82 (s, 1H), 7.26 (s, 1H), 6.92 (s, 1H), 4.19 (m, 1H), 3.89 (s, 3H), 2.64 (s, 3H), 2.40 (m, 2H), 2.29-2.15 (m, 2H), 2.12-2.00 (m, 1H), 1.95-1.84 (m, 1H).

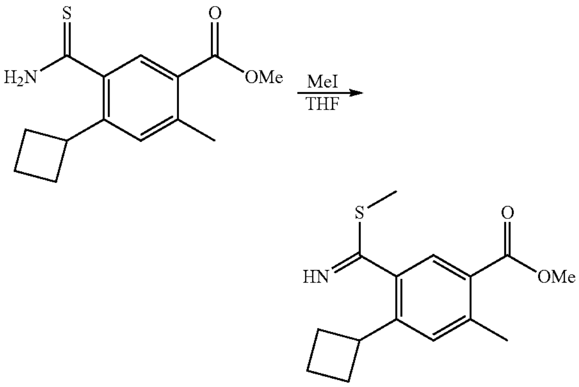

Compound 001-152.6. Methyl 4-cyclobutyl-5-(imino(methylthio)methyl)-2-methylbenzoate. To a round-bottom flask was added methyl 5-carbamothioyl-4-cyclobutyl-2-methylbenzoate (compound 001-152.5, 861 mg, 3.27 mmol) in THF (10 mL). Iodomethane (912 mg, 6.42 mmol) was added dropwise and the reaction mixture was stirred at room temperature for 7 hours. The reaction mixture was concentrated in vacuo and purified by $SiO_2$ flash chromatography (ethyl acetate to ethyl acetate/methanol=95/5) to afford methyl 4-cyclobutyl-5-(imino(methylthio)methyl)-2-methylbenzoate as a yellowish oil (807 mg, 89% yield). m/z (ES+) 278 $(M+H)^+$. $^1H$ NMR (400 MHz, DMSO-$d_6$): δ 7.67 (s, 1H), 7.40 (s, 1H), 3.88-3.71 (m, 4H), 2.57 (s, 3H), 2.44 (s, 3H), 2.22-2.19 (m, 2H), 2.12 (m, 2H), 1.98-1.86 (m, 1H), 1.82-1.70 (m, 1H).

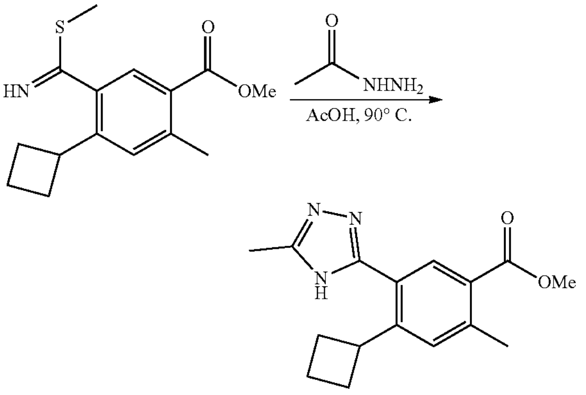

Compound 001-152.7. Methyl 4-cyclobutyl-2-methyl-5-(5-methyl-4H-1,2,4-triazol-3-yl)benzoate. To a round-bottom flask were added methyl 4-cyclobutyl-5-(imino(methylthio)methyl)-2-methylbenzoate (compound 001-152.6, 556 mg, 0.002 mol) and acetohydrazide (223 mg, 0.003 mol) in 6 mL acetic acid. The reaction mixture was heated to 90° C. for 3 hours. After cooling to room temperature, the reaction mixture was partitioned between water (50 mL) and ethyl acetate (50 mL). The organic layer was washed with brine (2×50 mL), dried over $Na_2SO_4$, and concentrated in vacuo. Purification via $SiO_2$ flash chromatography (hexanes/ethyl acetate=50/50 to 30/70) afforded the title compound as a white solid (243 mg, 43% yield). m/z (ES+) 286 $(M+H)^+$. $^1H$ NMR (400 MHz, $CDCl_3$): δ 8.23 (s, 1H), 7.32 (s, 1H), 4.24-4.05 (m, 1H), 3.89 (s, 3H), 2.69 (s, 3H), 2.54 (s, 3H), 2.23-2.20 (m, 2H), 2.16-2.05 (m, 2H), 2.05-1.88 (m, 1H), 1.88-1.71 (m, 1H).

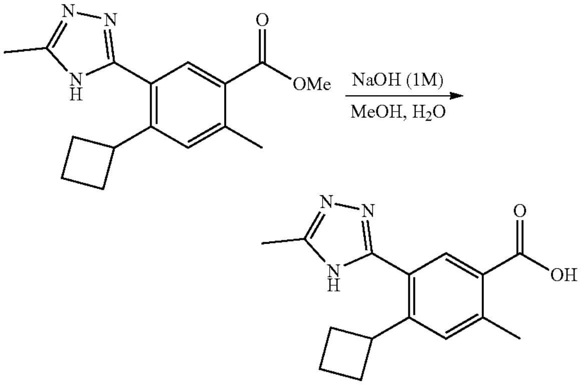

Compound 001-152.8. 4-Cyclobutyl-2-methyl-5-(5-methyl-4H-1,2,4-triazol-3-yl)benzoic acid. To a solution of methyl 4-cyclobutyl-2-methyl-5-(5-methyl-4H-1,2,4-triazol-3-yl)benzoate (compound 152.7, 240 mg, 0.842 mmol) in methanol (5 mL) was added aqueous NaOH (6 mL, 1M). The resulting mixture was heated to 50° C. for 6 hours. After cooling to ambient temperature, the reaction mixture was acidified with 1N HCl to pH 2 and extracted with ethyl acetate (3×50 mL). The combined organic layers were washed with brine (50 mL), dried over $Na_2SO_4$, and concentrated in vacuo to afford 4-cyclobutyl-2-methyl-5-(5-methyl-4H-1,2,4-triazol-3-yl)benzoic acid (260 mg, quantitative) as a white solid. m/z (ES+) 272 $(M+H)^+$.

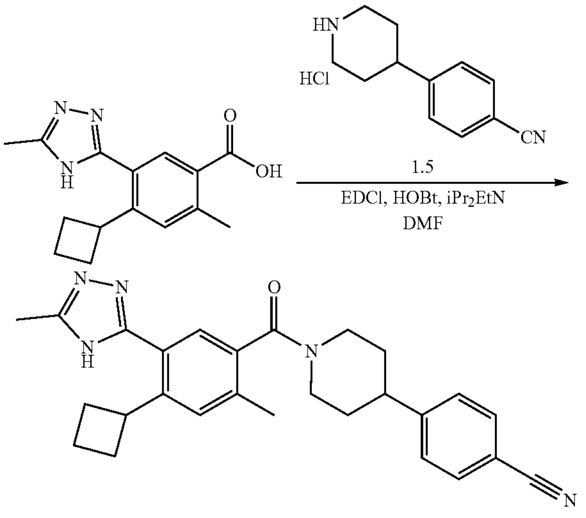

Compound 001-152. 4-(1-(4-Cyclobutyl-2-methyl-5-(5-methyl-4H-1,2,4-triazol-3-yl)benzoyl) piperidin-4-yl)benzonitrile. To a solution of 4-cyclobutyl-2-methyl-5-(5-methyl-4H-1,2,4-triazol-3-yl)benzoic acid (compound 001-152.8, 260 mg, 0.95 mmol) in DMF (4 mL) were added 4-(piperidin-4-yl)benzonitrile hydrochloride salt (232 mg, 1.045 mmol), EDC (272 mg, 1.425 mmol), HOBt (39 mg, 0.285 mmol), and DIEA (367.7 mg, 2.85 mmol). The resulting mixture was stirred at room temperature for 16 hours. The mixture was quenched with saturated aqueous $NaHCO_3$ (20 mL) and extracted with ethyl acetate (2×50 mL). The combined organic layers were washed with brine (50 mL), dried over $Na_2SO_4$, filtered, and concentrated in vacuo. Purification via $SiO_2$ column chromatography (dichloromethane/methanol=95/5) afforded 4-(1-(4-cyclobutyl-2-methyl-5-(5-methyl-4H-1,2,4-triazol-3-yl)benzoyl) piperidin-4-yl)benzonitrile as a white solid (193 mg, 44% yield). m/z (ES+) 440 $(M+H)^+$. $^1H$ NMR (300 MHz, $CD_3OD$): δ 7.69 (d, J=5.4 Hz, 2H), 7.56-7.30 (m, 4H), 1 proton obscured by methanol solvent peak, 4.10-3.98 (m, 1H), 3.64 (t, J=10.7 Hz, 1H), 3.33-3.21 (m, 1H), 3.00 (t, J=8.9 Hz, 2H), 2.58 (s, 3H), 2.48 and 2.38 (2 singlets, amide rotamers, $ArCH_3$, 3H), 2.28-1.92 (m, 6H), 1.92-1.55 (m, 4H). 1H NMR (400 MHz, DMSO-$d_6$): δ 13.66 (s, 1H), 7.77 (d, J=8.0 Hz, 2H), 7.62-7.34 (m, 4H), 4.78-4.63 (m, 1H), 4.31 (br s, 1H), 3.45 (br s, 1H), 3.15 (app t, J=12.3 Hz, 1H), 2.99-2.78 (m, 2H), 2.44-1.80 (m, 12H), 1.80-1.37 (m, 4H).

Compound 005-2

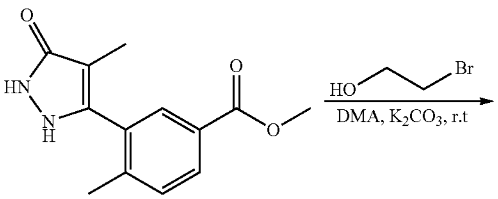

-continued

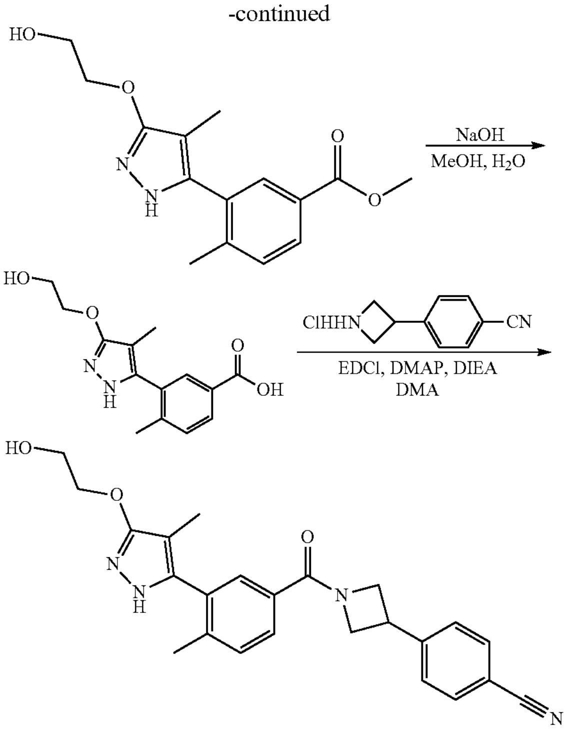

2

Compound 005-2.1. To a solution of methyl 4-methyl-3-(4-methyl-5-oxo-2,5-dihydro-1H-pyrazol-3-yl)benzoate (40 g, 163 mmol, 1.00 equiv) in DMA (800 mL) was added potassium carbonate (112 g, 813 mmol, 5.00 equiv) and 2-bromoethan-1-ol (141 g, 1138 mmol, 7.00 equiv). The mixture was stirred for 4 h at 25° C., then diluted with 1000 mL of $H_2O$. The aqueous phase was extracted with 5×1000 mL of ethyl acetate and the combined organic layers were washed with 2×1000 mL of brine, dried over anhydrous sodium sulfate and concentrated under vacuum. The residue was applied onto a silica gel column with ethyl acetate/petroleum ether (1:10-1:1) as eluent to yield 30 g (64%) of methyl 3-(3-(2-hydroxyethoxy)-4-methyl-1H-pyrazol-5-yl)-4-methylbenzoate as light yellow oil.

005-2.2. To a solution of methyl 3-(3-(2-hydroxyethoxy)-4-methyl-1H-pyrazol-5-yl)-4-methylbenzoate (30 g, 103 mmol, 1.00 equiv) in methanol (500 mL) was added a solution of sodium hydroxide (41 g, 1025 mmol, 10.0 equiv) in water (300 mL). The mixture was stirred for 2 h at room temperature. The resulting mixture was concentrated under vacuum and the pH value of the solution was adjusted to 4-5 with hydrogen chloride (2 mol/L). The solids were collected by filtration. This resulted in 20 g (71%) of 3-(3-(2-hydroxyethoxy)-4-methyl-1H-pyrazol-5-yl)-4-methylbenzoic acid as a light yellow solid.

005-2.3. To a solution of 3-(3-(2-hydroxyethoxy)-4-methyl-1H-pyrazol-5-yl)-4-methylbenzoic acid (20.0 g, 72.5 mmol, 1.00 equiv) in DCM (500 mL) was added EDCI (16.7 g, 87.0 mmol, 1.20 equiv), 4-dimethylaminopyridine (1.77 g, 14.5 mmol, 0.20 equiv), DIEA (23.4 g, 181 mmol, 2.50 equiv) and 4-(azetidin-3-yl)benzonitrile hydrochloride (15.5 g, 79.7 mmol, 1.10 equiv). The resulting solution was stirred for overnight at room temperature. The resulting solution was diluted with 500 mL of $H_2O$. The resulting solution was extracted with 3×500 mL of ethyl acetate and the combined organic layers were washed with 2×500 mL of $NH_4Cl$ (sat.), 2×500 mL of brine and dried over anhydrous sodium sulfate and concentrated under vacuum. The residue was purified by a silica gel chromatography with CH2Cl2/MeOH (50/1-30/1) as cluent to furnish 21.0 g (67%) of 4-(1-(3-(3-(2-hydroxyethoxy)-4-methyl-1H-pyrazol-5-yl)-4-methylbenzoyl) azetidin-3-yl)benzonitrile (Compound 005-2) as a white solid.

Additional example compounds are found in Table C-1, Table C-2, and Table C-3.

BIOLOGICAL EXAMPLES

Example 1—FASN Inhibition by FASN Inhibitors of the Present Disclosure

Determination of FASN biochemical activity: The FASN enzyme was isolated from SKBr3 cells. SKBr3 is a human breast cancer cell-line with high levels of FASN expression. It is estimated that FASN comprises about 25% of the cytosolic proteins in this cell line. SKBr3 cells were homogenized in a dounce homogenizer then centrifuged for 15 minutes at 4° C. to remove particulate matter. The supernatant was then analyzed for protein content, diluted to the appropriate concentration, and used to measure FASN activity. The presence of FASN was confirmed by western blot analysis. A similar method for isolation of FASN from SKBr3 cells is described in Teresa, P. et al. (*Clin. Cancer Res.* 2009; 15(24), 7608-7615).

FASN activity of the SKBr3 cell extract was determined by measuring either NADPH oxidation or the amount of thiol-containing coenzyme A (CoA) released during the fatty acid synthase reaction. The dye CPM (7-diethylamino-3-(4'-maleimidyl-phenyl)-4-methylcoumarin) contains a thiol reactive group that increases its fluorescence emission on reaction with the sulfhydryl group of CoA. The biochemical activities shown in Tables C-1-C-3 were determined using the fluorescence measurement of CoA release via a procedure described in Chung C. C. et al. (Assay and Drug Development Technologies, 2008, 6 (3), 361-374).

Example 2—Effects of FASN Inhibitors on Fatty Liver Disease/Steatotic Liver Disease in Mice The impact a FASN inhibitor of the present application on steatosis was determined in C57BL/6 male mice on a high fat diet (HFD).

This example describes the effects of Compound 002-386.

(Compound 002-386)

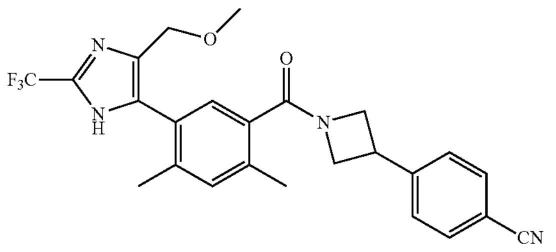

2 groups of 5 male C57BL/6NCrSim mice were employed vehicle and FASN inhibitor treated groups, which were 4-5 weeks old at the start of dosing. Mice were allowed unrestricted access to a diet high in fat (Research Diets cat. No. D09100301: 40% kcal partially hydrogenated vegetable oil shortening and by weight 20% fructose and 2% cholesterol). In addition, all animals received once-daily oral doses of vehicle or 10 mg per kg of mouse body weight of a FASN inhibitor of the application for 57 consecutive days. At sacrifice, the right liver lobe was placed in a preservative (10% neutral buffered formalin) followed by preparation of liver samples for microscopic evaluation by a licensed pathologist. Liver samples were either stained for fat using Oil Red O stain or collagen with Masson's trichrome stain.

Slides were prepared from right liver lobes and stained with Oil Red O for fat and Masson's Trichrome for collagen. Animals receiving vehicle for 57 days while on a HFD developed severe fat deposits inside the liver cells. The liver cells were enlarged and filled with small vesicles of lipid as indicated by the Oil Red O staining. There was no significant inflammation or accumulation of collagen. Animals on HFD which received Compound 002-386 at 10 mg/kg for 57 days had no evidence of fat deposits inside the liver cells and appeared normal. These results demonstrate that prophylactic once daily dosing of 10 mg/kg Compound 002-386 inhibited the development of steatosis in this model. These results support the utility of FASN inhibitors in the treatment of NAFLD/MASLD, NASH, metabolic syndrome and Type II diabetes.

TABLE 1

Study 1 histopathologic evaluation of stained sections of liver and ranked hepatic steatosis severity

| Test Article | Animal | Oil Red O for Intracellular Lipid | Trichrome for General Histology and Fibrosis |
|---|---|---|---|
| Vehicle | 1 | 4 | 4 |
| Vehicle | 2 | 4 | 4 |
| Vehicle | 3 | 3 | 4 |
| Vehicle | 4 | 3 | 4 |
| Vehicle | 5 | 3 | 4 |
| Compound 002-386 @ 10 mg/kg | 6 | 0 | 0 |
| Compound 002-386 @, 10 mg/kg | 7 | 0 | 0 |
| Compound 002-386 @ 10 mg/kg | 8 | 0 | 0 |
| Compound 002-386 @ 10 mg/kg | 9 | 0 | 0 |
| Compound 002-386 @ 10 mg/kg | 10 | 0 | 0 |

A second study employed 3 groups of 5 male C57BL/6J mice (vehicle for 28 days, vehicle for 57 days and vehicle for 28 days followed by treatment with a FASN inhibitor compound of the application for 29 days) which were 4-5 weeks old at the start of dosing. Mice were allowed unrestricted access to a diet high in fat (Research Diets cat. No. D09100301: 40% kcal partially hydrogenated vegetable oil shortening and by weight 20% fructose and 2% cholesterol). At sacrifice, the right liver lobe was placed in a preservative (10% neutral buffered formalin) followed by preparation of liver samples for microscopic evaluation by a licensed pathologist. Liver samples were either stained for fat using Oil Red O stain or collagen with Masson's trichrome stain.

Animals dosed with vehicle for 57 days while on a HFD developed severe fat deposits inside the liver cells. Fewer and much smaller fat deposits were observed in the livers from animals which were dosed with vehicle for 28 days followed by Compound 002-386 for 29 days even though these animals had received the HFD for a total of 57 days. These results demonstrate that therapeutic, once daily dosing of 10 mg/kg Compound 002-386 inhibited progression of hepatic steatosis in this model.

TABLE 2

Study 2 histopathologic evaluation of stained sections of liver and ranked hepatic steatosis severity

| Group | Animal | Overall Hepatic changes | Histopathologic findings |
|---|---|---|---|
| 1 Vehicle 28 Days | 1 | moderate[3] | Variable-sized vacuoles throughout section |
| | 2 | moderate[3] | Variable-sized vacuoles throughout section |
| | 3 | marked[4] | Some enlargement/ballooning of hepatocytes numerous variable-sized vacuoles |
| | 4 | moderate[3] | Variable-sized vacuoles throughout section with few large vacuoles |
| | 5 | moderate[3] | Variable-sized vacuoles throughout section |
| | 6 | minimal[1] | Few small vacuoles identified |
| | 7 | moderate[3] | Variable-sized vacuoles throughout section with few large/ballooning hepatocytes |
| | 8 | mild[2] | Small single and multiple vacuoles within hepatocytes |
| | 9 | marked[4] | Focus of cellular alteration (fatty change) enlargement/ballooning of hepatocytes numerous large vacuoles |
| | 10 | marked[4] | Numerous large vacuoles enlargement/ballooning of hepatocytes foci of necrosis |
| 2 Vehicle 57 Days Group | 11 | severe[5] | Diffuse enlargement/ballooning of hepatocytes cytoplasmic rarefaction, scattered large vacuoles |
| | 12 | severe[5] | Diffuse enlargement/ballooning of hepatocytes cytoplasmic rarefaction, large vacuoles in subcapsular region |
| | 13 | marked[4] | Numerous variable-sized vacuoles throughout section |
| | 14 | marked[4] | Some enlargement of hepatocytes numerous variable-sized vacuoles throughout section |
| | 15 | severe[5] | Diffuse enlargement/ballooning of hepatocytes cytoplasmic rarefaction, large vacuoles in subcapsular region |
| | 16 | severe[5] | Diffuse enlargement/ballooning of hepatocytes cytoplasmic rarefaction, large vacuoles in subcapsular region |
| | 17 | severe[5] | Diffuse enlargement/ballooning of hepatocytes cytoplasmic rarefaction, few vacuoles in subcapsular region |
| | 18 | moderate[3] | Variable-sized vacuoles some enlargement of hepatocytes |
| | 19 | severe[5] | Diffuse enlargement/ballooning of hepatocytes cytoplasmic rarefaction, large scattered vacuoles |
| | 20 | marked[4] | Some enlargement of hepatocytes few vacuoles |
| 3 Vehicle 28 Days; C Compound 002-386 29 days | 21 | marked[4] | Multifocal enlargement/ballooning of hepatocytes, occasional large vacuoles |
| | 22 | marked[4] | Multifocal enlargement/ballooning of hepatocytes; numerous variable-sized vacuoles throughout section |
| | 23 | moderate[3] | Numerous small vacuoles; some enlargement/ballooning of hepatocytes |
| | 24 | marked[4] | Multifocal enlargement of hepatocytes numerous variable-sized vacuoles throughout |
| | 25 | marked[4] | Numerous variable-sized vacuoles throughout section |
| | 26 | severe[5] | Diffuse enlargement/ballooning of hepatocytes cytoplasmic rarefaction; numerous small and large vacuoles |
| | 27 | marked[4] | Multifocal enlargement/ballooning of hepatocytes; numerous variable-sized vacuoles throughout section |
| | 28 | moderate[3] | Scattered variable-sized vacuoles |
| | 29 | moderate[3] | Scattered variable-sized vacuoles |
| | 30 | moderate[3] | Scattered variable-sized vacuoles |

Hepatic Steatosis Scoring System: 0=Normal—Tissue considered to be normal under the conditions of the study and considering the age, sex and strain of the animal concerned Alterations may be present which, under other circumstances, would be considered deviations from normal. 1=Minimal—The amount of change barely exceeds that which is considered to be within normal limits. 2=Mild—In general, the lesion is easily identified but of limited severity. The lesion probably does not produce any functional impairment. 3=Moderate—The lesion is prominent but there is significant potential for increased severity. Limited tissue or organ dysfunction is possible. 4=Severe—

The degree is either as complete as considered possible or great enough in intensity or extent to expect significant tissue or organ dysfunction.

Example 3—Effects of FASN Inhibitors on IL-1β Levels In Vivo and In Vitro

The impact of a FASN inhibitor of the present application on IL-1β levels was evaluated in vivo and in vitro. This example describes the effects of Compound 002-386, Compound 6B and Compound 242A.

Compound 6B

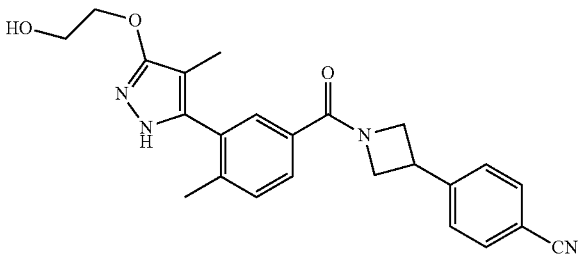

Compound 242A

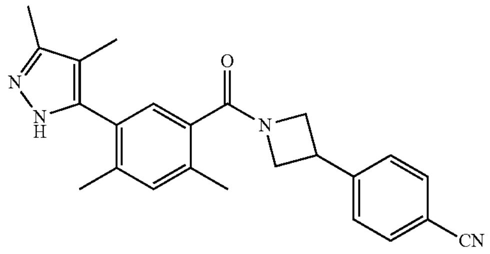

Fast-Fed Study in Rats

Female Sprague Dawley rats were fasted for 12 hours and then two groups were dosed orally with a FASN inhibitor of the application at 60 mg/kg of body weight or 100 mg/kg. A separate control group was dosed with the formulation vehicle material. One hour later, the animals were allowed to feed for 6 hours followed by a 5 hour fast and then given an additional 10 hours of feeding. Blood samples were collected at time points to determine the level of IL-1β.

High Fat Study in Mice

Two groups of male C57BL/6J mice were dosed orally once daily with a FASN inhibitor of the application at 3 mg/kg or 10 mg/kg. A separate control group was dosed with the formulation vehicle material. Blood samples were collected at time points to determine the level of IL-1β.

Human IL-1b Study

Blood from healthy donors was treated with an anticoagulant and peripheral blood mononuclear cells (PBMC) were isolated. The adherent monocyte cells in the PBMC were selected by allowing cells to attach to tissue culture dishes.

The FASN inhibitors of the application lowered the level of IL-1β beta in blood serum which resulted after food intake in fasted rats or which occurred in mice fed a high fat diet. The release of IL-1β from freshly isolated human blood cells was also reduced by treatment with a FASN inhibitor. These results support the utility of FASN inhibitors in the treatment of inflammatory conditions that occur in NAFLD/MASLD, NASH, metabolic syndrome, Type II diabetes and other inflammatory diseases.

Treatment with Compound 6B prior to feeding reduced the IL-1 beta response over this complete time course and by 22 hours the reduction was over 5 fold.

After 14 and 37 days on a high fat diet, the level of IL-1β was determined in blood serum of the mice. Mice treated with Compound 002-386 had reduced levels of IL-1β beta at both 14 and 37 days, both before reintroduction of food and after feeding (1 hr data), compared to mice which received vehicle.

Stimulation with either LPS or LTA plus DMSO, the solvent for Compound 242A, resulted in secretion of IL-1 beta. Compound 242A treatment of PBMC, which is a mixed population of mononuclear cells including both lymphocytes and monocytes, reduced the level of IL-1 beta resulting from either LPS or LTA stimulation. For monocytes, Compound 242A treatment reduced the level of IL-1 beta resulting from LTA stimulation whereas there was only a slight reduction after LPS stimulation.

Example 4—Effects of Fasn Inhibitors on T-Cell Differentiation

The impact of FASN inhibitors on the differentiation of naive CD4+ T cells, isolated from mouse or human blood, into pro-inflammatory $T_h17$ cells and anti-inflammatory $T_{reg}$ cells was examined. This example describes the effects of Compound 002-386 and Compound 001-152.

Compound 152

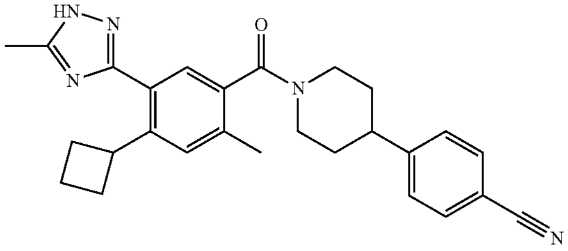

Naive T-Cell Isolation Procedure

Naive CD4+ T cells were isolated ex vivo from whole blood collected in sodium citrate tubes and enriched with Dynabeads™ Untouched mouse (Cat #11415D) or human (Cat #11346D) CD4+ T Cells Isolation Kits (Thermo Fisher). Naive mouse CD4+ T cells were plated into 48-well tissue culture plates (Costar) with 1 μg/mL anti-CD3 and anti-CD28 antibody coated beads. Differentiation of naive mouse CD4+ T cells to generate mouse $Th_{17}$ cell cultures used medium containing the following additives for 4 days: anti-IL-2 (30 ng/mL) (R&D Systems); recombinant mouse IL-6 (Peprotech) (10 ng/ml); recombinant human TGFbeta (1 ng/ml) (Peprotech); recombinant mouse IL-1beta (10 ng/mL) (Peprotech); recombinant mouse IL-23 (10 ng/mL) (R&D Systems); anti-IL-4 antibody (20 ng/ml) (Biocell); and anti-IFNgamma antibody (50 ng/ml) (Biocell). $Th_{17}$ cells were cultured in IMDM GlutaMAX medium (Life Technologies) supplemented with 10% heat-inactivated FCS (Biochrom), 500 U penicillin-streptomycin (Life Technologies).

Differentiation Procedure-Human T-Cells

Naive human CD4+ T cells were plated into 48-well tissue culture plates (Costar) with 1 μg/mL anti-CD3 with anti-CD28 antibody coated beads. See Endo et al., 2015, Cell Reports 12:1042-1055. Differentiation of naive human CD4+ T cells to generate human $Th_{17}$ cultures used medium containing the following additives for 4 days: anti-IL-2 (30 ng/mL) (R&D Systems); recombinant human IL-6 (10 ng/ml) (BD Biosciences); recombinant human TGFbeta (1 ng/ml) (BD Biosciences); recombinant human IL-1beta (10 ng/mL) (BD Biosciences); recombinant human IL-23 (10 ng/mL) (BD Biosciences); anti-IL-4 antibody (20 ng/ml) (R&D Systems); and anti-IFNgamma antibody (50 ng/mL) (R&D Systems). $Th_{17}$ cells were cultured in IMDM GlutaMAX medium (Life Technologies) supplemented with 10% heat-inactivated FCS (Biochrom), 500 U penicillin-streptomycin (Life Technologies).

Flow Cytometry

For mouse cells, monoclonal antibodies specific to the following antigens (and labeled with the indicated fluorescent markers) were used: CD4 PerCP (GK1.5; 1:800), (Affymetrix/eBioscience); Foxp3 Alexa488 (FJK-16s; 1:400), (Affymetrix/eBioscience); and IL-17A PE and IL-17A PE (eBio17B7; 1:400 and 1:200), (Affymetrix/eBioscience).

For human cells, monoclonal antibodies specific to the following antigens (and labeled with the indicated fluorescent markers) were used: Foxp3 FITC (236A/E7; 1:100) (Affymetrix/eBioscience); IL-17A PE-Cy7 (eBio64DEC17; 1:100) (Affymetrix/eBioscience); and CD4 PerCP (SK3; 1:200) (BD Biosciences).

For analysis of surface markers, cells were stained in PBS containing 0.25% BSA and 0.02% azide. Dead cells were excluded by LIVE/DEAD Fixable Dead Cell Stain Kit (Life Technologies).

For intracellular cytokine staining, cells were treated with Brefeldin A (5 mg/mL) for 2 h and stained using the Fixation/Permeabilization Kit (BD Biosciences) according to the manufacturer's instruction.

Quantitation of fluorescent cells and their intensity were acquired on a FACSCalibur (BD Biosciences), and data were analyzed with CELLQuest software.

FASN inhibition (50 nM Compound 002-386) of mouse CD4+ naive T cells with 4 days of $Th_{17}$ differentiation conditions inhibits $Th_{17}$ cell differentiation and stimulates $T_{reg}$ differentiation. IL-17+Th17 cells fall from 41.2% of the CD4+ population to 3.9%, while FoxP3+ Treg cells increase from 0.04% to 23.8% of the CD4+ population with Compound 002-386 treatment.

FASN inhibition (50 nM Compound 002-386) of human CD4+ naive T cells from two different donors with 4 days of $Th_{17}$ differentiation conditions inhibits $TH_{17}$ cell differentiation and stimulates $T_{reg}$ differentiation. IL-17+TH17 cells fall from 31% to 1.7% (donor 1) and from 37.2% to 1.6% (donor 2) of the CD4+ population, while FoxP3+ Treg cells increase from 0.05% to 24.2% (donor 1) and from 1.1% to 30.2% (donor 2) of the CD4+ population with Compound 002-386 treatment.

FASN inhibition (100 nM Compound 152) of human CD4+ naive T cells from two different donors with 4 days of Th17 differentiation conditions inhibits $TH_{17}$ cell differentiation and stimulates $T_{reg}$ differentiation. IL-17+TH17 cells fall from 30% to 10.3% (donor 1) and from 30.2% to 6.4% (donor 2) of the CD4+ population, while FoxP3+ Treg cells increase from 0.06% to 26.1% (donor 1) and from 0.04% to 20.4% (donor 2) of the CD4+ population with Compound 002-386 treatment.

The data clearly indicates that when naive CD4+ T cells are stimulated to differentiate under pro-inflammatory conditions to generate $Th_{17}$ inflammatory cells, FASN is required for this process and inhibition of FASN with small molecule inhibitors such as Compound 002-386 or Compound 152 prevents this pro-inflammatory differentiation and steers differentiation to the production of anti-inflammatory $T_{reg}$ cells instead. These results support the utility of FASN inhibitors in the treatment of inflammatory conditions that occur in NAFLD/MASLD, NASH/MASH, metabolic syndrome, Type II diabetes and other inflammatory diseases.

While preferred aspects of the present invention have been shown and described herein, it will be obvious to those skilled in the art that such aspects are provided by way of example only. Numerous variations, changes, and substitutions will now occur to those skilled in the art without departing from the invention. It should be understood that various alternatives to the aspects of the invention described herein can be employed in practicing the invention. It is intended that the following claims define the scope of the invention and that methods and structures within the scope of these claims and their equivalents be covered thereby.

Example 5—Compound 002-386 Reverses Multiple Components of NASH in Mice

The ability of compound 002-386 to reverse the symptoms of established diet-induced nonalcoholic steatohepatitis in mice was investigated.

C57BL/6J mice were fed a high-fat/fructose/cholesterol diet (HFFCD) for 44 weeks. For an additional eight weeks, animals continued a high-fat/fructose/cholesterol diet and received oral once-per-day treatments of either Compound 002-386, the anti-fibrotic pirfenidone, both Compound 002-386 and pirfenidone, or vehicle control. At the end of the study, analyses included histological assessment (NAFLD Activity Score (NAS) and Fibrosis Stage), gene expression (liver) total triglyceride and cholesterol content (liver and plasma), levels of alanine transaminase (ALT), and aspartate transaminase (AST) in plasma and serum cytokine levels.

Methods

Liver biopsy: Mice were anesthetized with isoflurane (2-3%) in atmospheric air. A small abdominal incision was made in the midline and the left lateral lobe of the liver was exposed. A cone shaped wedge of liver tissue (approximately 50 mg) was excised from the distal portion of the lobe and fixated in 10% neutral buffered formalin (4% formaldehyde) for histology. The cut surface of the liver was instantly electrocoagulated using bipolar coagulation (ERBE VIO 100 electrosurgical unit). The liver was returned to the abdominal cavity, the abdominal wall was sutured and the skin was closed with staplers. For post-operative recovery mice received carprofen (5 mg/kg) administered subcutaneously on OP day and post-OP day 1 and 2.

Blood sampling: During anesthesia with isoflurane, the abdominal cavity was opened and cardiac blood was drawn with a regular syringe into EDTA tubes or with a coated (heparine/EDTA) vacutainer. Blood was placed at 4° C.

Plasma preparation: Blood was centrifuged at 2000 g for 10 minutes. The plasma supernatants were transferred to new tubes and immediately frozen in liquid nitrogen and stored at −80° C.

Blood and plasma assays (triglycerides (TG), total-cholesterol (TC), alanine transaminase (ALT), aspartate transaminase (AST)): Blood samples were collected in heparinized tubes and plasma was separated and stored at −80° C. until analysis. TG, TC, ALT, AST were measured using commercial kits (Roche Diagnostics, Germany) on the Cobas™ C-501 autoanalyzer according to the manufacturer's instructions.

NAFLD activity score (NAS) and fibrosis stage: Liver samples were fixed in formalin, paraffin embedded, and sections were stained with hematoxylin and eosin (H&E) and Sirius Red. Samples were scored for NAS and fibrosis stage (outlined below) using of the clinical criteria outlined by Kleiner et al. 2005. Total NAS score represented the sum of scores for steatosis, inflammation, and ballooning, and ranges from 0-8.

TABLE 3

| NAS and Fibrosis Stage Evaluation Guidelines | | |
|---|---|---|
| Steatosis | <5% | 0 |
| | 5-33% | 1 |
| | >33-66% | 2 |
| | >66% | 3 |
| Lobular inflammation | No foci | 0 |
| | <2 foci/200× | 1 |
| | 2-4 foci/200× | 2 |
| | >4 foci/200× | 3 |
| Ballooning degeneration | None | 0 |
| | Few | 1 |
| | Many cells/prominent ballooning | 2 |
| Fibrosis | None | 0 |
| | Perisinusoidal or periportal | 1 |
| | Perisinusoidal & | 2 |
| | portal/periportal | 3 |
| | Bridging fibrosis | 4 |
| | Cirrhosis | |

Liver tissue assays: Hydroxyproline is a major component of collagen and the total content of collagen in liver was determined by colorimetric detection of hydroxyproline using a QZBhypro, Quickzyme hydroxyproline assay. Homogenized liver tissue was hydrolyzed by hydrochloric acid and the supernatant transferred to a 96 well plate. The oxidized hydroxyproline was reacted with 4-(Dimethyl-amino) benzaldehyde (DMAB), which resulted in a colorimetric product proportional to the hydroxyproline present. Absorbance was measured at 560 nm.

The triglyceride content in liver was determined using the Triglyceride reagent (Cat. no. 22-045-795, Roche Diagnostics, Germany) on the Cobas™ C-111 autoanalyzer. Homogenized liver tissue was heated to 80-100° C. twice, centrifuged in a microcentrifuge and the triglyceride content was measured in the supernatant.

The cholesterol content in liver was determined using the Cholesterol reagent (Cat. no. 22-045-780, Roche Diagnostics, Germany) on the Cobas™ C-111 antoanalyzer. Homogenized liver tissue was heated to 80-100° C. twice, centrifuged in a microcentrifuge and the cholesterol content was measured in the supernatant.

Histological staining procedures: In brief, slides with paraffin embedded sections were de-paraffinated in xylene and rehydrated in series of graded ethanol.

Hematoxylin & Eosin (H&E) staining: The slides were incubated in Mayer's Hematoxylin (Dako), washed in tap water, stained in Eosin Y solution (Sigma-Aldrich), hydrated, mounted with Pertex, and then allowed to dry before scanning.

Sirius red staining: The slides were incubated in Weigert's iron hematoxylin (Sigma-Aldrich), washed in tap water, stained in Picro-sirius red (Sigma-Aldrich), and washed twice in acidified water. Excess water was removed by shaking the slides and the slides were then hydrated in three changes of 100% ethanol, cleared in xylene and mounted with Pertex and allowed to dry before scanning.

Type I collagen IHC staining: Type I collagen (Southern Biotech, Cat. 1310-01) IHC was performed using standard procedures. Briefly, after antigen retrieval and blocking of endogenous peroxidase activity, slides were incubated with primary antibody. The primary antibody was detected using a polymeric HRP-linker antibody conjugate. Next, the primary antibody was visualized with DAB as chromogen. Finally, sections were counterstained in hematoxylin and cover-slipped.

Galectin-3 IHC staining: Galectin-3 (Biolegend, Cat. #125402) IHC were performed using standard procedures. Briefly, after antigen retrieval and blocking of endogenous peroxidase activity, slides were incubated with primary antibody. The primary antibody was detected using a linker secondary antibody followed by amplification using a polymeric HRP-linker antibody conjugate. Next, the primary antibody was visualized with DAB as chromogen. Finally, sections were counterstained in hematoxylin and cover-slipped.

IHC and steatosis quantification: IHC-positive staining was quantified by image analysis using the Visiomorph software (Visiopharm, Denmark). Visiomorph protocols are designed to analyse the virtual slides in two steps. The first step is crude detection of the tissue at low magnification (1× objective). The liver capsule is excluded. The second step is detection of IHC-positive staining at high magnification (10× objective). The quantitative estimates of IHC-positive staining are calculated as an area fraction (AF) according to Equation 1:

$$AF_{IHC-pos.} = \frac{Area_{IHC-pos.}}{Area_{fat} + Area_{tissue} + Area_{IHC-pos.}}$$

Quantitative assessment of steatosis: Steatosis was quantified on H&E stained slides by image analysis using the Visiomorph software (Visiopharm, Denmark). Visiomorph protocols analyse the virtual slides in two steps. The first step is crude tissue detection at low magnification (1× objective). The second step is detection of steatosis at high magnification (20× objective). The quantitative estimates of steatosis are calculated as an area fraction according to Equation 2:

$$AF_{steatosis} = \frac{Area_{steatosis}}{Area_{tissue} + Area_{steatosis}}$$

Results

In this diet-induced biopsy-confirmed mouse model of NASH, FASN inhibition with Compound 002-386 reduced hepatocyte ballooning, hepatic inflammation and steatosis, lowered plasma ALT and AST levels, diminished liver triglyceride and cholesterol and established a signature consistent with resolution of fibrosis including reduced expression of collagens, alpha-SMA and TIMP1 and increased expression of MMP9. Co-administration of pirfenidone further reduced liver fibrosis while maintaining the beneficial effects specific to FASN inhibition.

FASN inhibition by Compound 002-386, alone or in combination with the anti-fibrotic pirfenidone improved liver function.

FASN inhibition by Compound 002-386 reduced adverse liver symptoms alone or in combination with an antifibrotic.

Example 6—Compound 002-386 Affects Gene Expression in Hepatic Stellate Cells

The relative mRNA expression of fibrotic genes in immortalized human hepatic stellate cells (LX-2 cells) treated with Compound 002-386 or sorafenib was investigated.

Methods

Cell lines: Primary human hepatic stellate cells (phHSCs) and immortalized human hepatic stellate cells (LX-2) were used.

Compound 002-386 and Sorafenib small molecules: Compound 002-386 was dissolved in DMSO at 1, 3, 10 and 30 μM concentration stock solution followed by a series of working concentrations of 5, 15, 50 and 150 nM in DMEM cell culture medium supplemented with 0.1% BSA without antibiotic. For the positive control, the cells were treated in parallel with, a kinase inhibitor, sorafenib at 7.5 μM concentration dissolved in DMSO.

Experimental Protocol: At the beginning of each experiment, stellate cells were serum-starved overnight in Dulbecco's Modified Eagle Medium (DMEM) supplied with 0.1% BSA (without antibiotic) to synchronize metabolic activities of the cells. The cells were then exposed to different working concentrations of either Compound 002-386 or sorafenib for 24, 48 and 72 hours.

Cell and gene analysis: Cell proliferation and cell apoptosis were assessed by dye. Fibrogenic gene expression was assessed by real time PCR of (i) alpha smooth muscle actin; (ii) collagen I; (iii) beta PDGF receptor; (iv) MMP2; (v) TIMP1; and (vi) TIMP2.

Cell cytotoxicity assay: 5,000 LX-2 cells or 10,000 phHSCs were plated per well in 96 well plates. Cells were starved overnight in DMEM supplemented with 0.1% BSA (without antibiotic) to synchronize metabolic activities of the cells. Cells were then incubated with different concentrations of Compound 002-386 for the indicated durations and MTS assays were accomplished using CellTiter 96 AQueous One Solution Cell Proliferation Assay kit according to manufacturer protocol.

Cell proliferation assay: 5,000 LX-2 cells or 10,000 phHSCs were plated per well in 96 well plates. After overnight serum starvation in DMEM supplemented with 0.1% BSA (without antibiotic) the cells were exposed to Compound 002-386 at indicated concentrations. At 24 and 48 hours of drug exposure the cells were labeled with BrdU for either 2 hours (for LX-2 cells) or 16 hours (for phHSCs) at 37° C. The cell proliferation ELISA, BrdU colorimetric kit was used following the manufacturer's instructions.

Cell viability assay: 150,000 LX-2 cells or 200,000 phHSCs per well were plated on 6-well plates. Cells were starved overnight in DMEM supplemented with 0.1% BSA (without antibiotic) to synchronize metabolic activities of the cells. Cells were then incubated with Compound 002-386 at the indicated concentrations and durations. Cells were harvested and mixed (1:1) with 0.4% trypan blue stain. The viability of the cells was immediately counted in a Countess automated cell counter.

Fibrogenic gene expression in hepatic stellate cells by RT-qPCR: The following fibrogenic gene expressions were quantified by RT-qPCR: (1) Collagen1α1 (Col1α1); (2) Alpha Smooth Muscle Actin (αSMA); (3) Beta PDGF receptor (β-PDGFR); (4) Transforming growth factor-β receptor1 (TGFβ-R1); (5) Tissue inhibitor of metalloproteinase-1 (TIMP1); (6) Tissue inhibitor of metalloproteinase-2 (TIMP2); and (7) Matrix Metalloproteinase 2 (MMP2).

The kinase inhibitor Sorafenib (7.5 μM concentration) small molecule was used as positive control and run in parallel. 150,000 LX-2 cells or 200,000 phHSCs per well were plated on 6-well plates. Cells were starved overnight in DMEM supplemented with 0.1% BSA (without antibiotic) to synchronize metabolic activities of the cells. Cells were then incubated with either Compound 002-386 or sorafenib at the indicated concentrations and durations. Cells were harvested and total RNA was extracted using RNeasy Mini Kit. 0.5 μg of total RNA was used for reverse transcription with an RNA to cDNA EcoDry Premix (Double Primed) Kit. Expression of fibrogenic genes were measured by qPCR using custom designed primers and iQ SYBR Green Supermix on a LightCycler 480 II instrument. Glyceraldehyde-3-phosphate dehydrogenase (GAPDH) was used as a housekeeping gene where the expression (Ct value) was constant throughout different doses of Compound 002-386 as well as sorafenib. Fibrogenic genes were normalized to GAPDH.

Experimental data analysis: Each experiment was repeated at least three times. The data analysis was accomplished by using appropriate scientific and statistical software. Standard error (±SE) was calculated according to student t-test. Unless otherwise specified, P values smaller than 0.05 were considered statistically significant.

Results

In vitro, FASN inhibition with Compound 002-386 dose-dependently reduced fibrogenic gene expression by real time PCR LX-2 liver cells.

The rescue of fibrogenic gene expression at 48 hours after withdrawal of the compound suggests the downregulation of the genes are not a toxic effect of the compound.

Example 7—Efficacy of Compound 001-152 Monotherapy and Combination Therapy Using InSphero 3DInSight™ Liver Disease Models The effect of Compound 001-152 on lipid accumulation in the InSight™ Liver Co-Culture model was investigated. In the investigation, the effect of Compound 001-152 alone or in combination with other compounds targeting different aspects of non-alcoholic steatohepatitis (NASH) was evaluated. For each of the compounds, two concentrations were tested, alone as well as in combination with two concentrations of Compound 001-152. After a 7 day treatment with dosings at days 0, 2 and 5, intratissue lipid accumulation was measured using Triglyceride-Glo™ Assay (Promega). In addition, metabolic activity of the treated Liver Microtissues (MTs) and cytotoxicity were assessed by measurement of ATP content at day 7 of treatment (CellTiter-Glo® 2.0 Cell Viability Assay, Promega) and LDH release between days 0-2, days 2-5 and days 5-7 (LDH-Glo™ Cytotoxicity Assay, Promega), respectively. Leftover supernatant collected on treatment days 2, 5 and 7 were stored frozen for further analysis.

Material and Methods

Microtissue Model: 3D InSight™ Human Liver Microtissues

Microtissues were co-cultured with cryopreserved primary human hepatocytes (IPHH) and cryopreserved primary human non-parenchymal cells (IPHN), the major human hepatic cell types.

Experimental Setup: The duration of treatment was 7 days, a study timeline is shown in FIG. 1C. Cells were dosed on days 0, 2 and 5. Experimental readout measurements comprised collection and freezing of supernatants for LDH measurement on days 2, 5 and 7. Measurement of LDH released into supernatant was analyzed using an LDH-Glo™ Cytotoxicity Assay (Promega). Measurement of ATP content in single MTs after 7 days of treatment with was analyzed using a Cell Titer Glo™ 2.0 Cell Viability Assay (Promega). Measurement of intratissue triglyceride (TG) content after 7 days of treatment was analyzed using a Triglyceride-Glo™ Assay (Promega). Cell supernatants were collected and frozen for further analysis on days 2, 5 and 7.

Culture Medium: 3D InSight™ Human Liver Maintenance Medium 10×. The medium does not contain BSA.

Compound: Compound 001-152 was provided as a powder. A 12 mM stock was prepared in DMSO and aliquots were stored at −80° C. Dosing concentration of Compound 001-152 was 30 nM or 3 μM.

Culture Conditions: The MTs were treated in 96-well Akura™ plates covered with Microclime® lids (Labcyte, USA) and were incubated in a humidified cell culture incubator (37° C., 5% $CO_2$).

Anti-NASH Drug Candidates, Tested Alone and in Combination with Compound 001-152:

- Elafibranor (PPAR α/γ agonist, MedChemExpress), 1 μM or 10 μM
- Obeticholic Acid (OCA, FXR agonist, MedChernExpress), 0.1 μM or 1 μM
- Tropifexor (FXR agonist, Achemblock), 0.2 nM or 20 nM
- Compound A, 50 nM or 3 μM Assay Control Compounds:

Chlorpromazine (SigmaAldrich) was included in every run of Hepatotoxicity Testing to control MTs' response to a toxic insult. A 15 μM concentration was used.

Firsocostat (ND-630, MedChernExpress) was included in all tests of lipid accumulation as a positive control for inhibition of lipid accumulation. A 0.5 μM or 2 μM concentration was used.

Endpoint Assay-Triglyceride (TG) Content:

Total TG content in MTs at day 7 of treatment was measured with Triglyceride-Glo™ Assay (Promega), according to InSphero AG protocol. The amount of glycerol/MT [pmol/MT] was calculated using linear regression to a standard curve. Values were plotted as mean±Standard Deviation including individual values with GraphPad Prism® (Version 8). An unpaired, two-tailed t-test with Welch's correction vs day 7 vehicle control (*p<0.05) was used to calculate significant changes in TG content. The n of microtissues/treatment group was a minimum of 5.

Results and Conclusions

In a human liver microtissue model of hepatic de novo lipogenesis (DNL) condition as measured by intratissue Triglyceride content, Compound 001-152 (30 nM and 3 uM) single agent reduced cellular triglycerides in vitro (FIG. 1A), which indicates potential to reduce liver fat. Combination of Compound 001-152 with Compound A enhanced the effect of Compound A and the combination showed an increased efficacy overall versus single agent. Improved TG reduction was observed in the combination treatment as compared to Compound A alone (FIG. 1A).

Example 8—Efficacy of Compound 001-152 Monotherapy and Combination Therapy Using InSphero 3DInSight™ NASH Disease Model The effects of Compound 001-152 alone or in combination with other compounds targeting different aspects of NASH in InSphero's 3DInSight™ Liver NASH Model were investigated. For each of the compounds, two concentrations were tested, alone as well as in combination with two concentrations of Compound 001-152. InSphero's 10-day NASH treatment scheme was applied with compound dosing at days 0, 3, 5 and 7 of treatment. The effect of Compound 001-152 alone and in combination with other compounds was measured by assessment of changes of NASH hallmarks, including, but not limited to, lipid accumulation, inflammation, and fibrosis. At day 5 of treatment, secreted cytokine levels were measured (LUMINEX™), at days 7 and 10 released procollagen 1 was quantified and at day 10 of treatment intratissue triglyceride content was determined. The release of lactate dehydrogenase (LDH) into culture supernatant was measured at days 3, 5, 7 and 10, in order to detect possible cytotoxicity caused by the treatments. After first data evaluation, released procollagen 3 was measured in supernatants of selected day 10 samples.

Material and Methods

Microtissue Model: 3D InSight™ Human Liver Microtissues

Microtissues were co-cultured with cryopreserved primary human hepatocytes (IPHH), cryopreserved primary human non-parenchymal cells (IPHN), and cryopreserved primary human hepatic stellate cells (IPHS), the major human hepatic cell types.

Figure 2A:
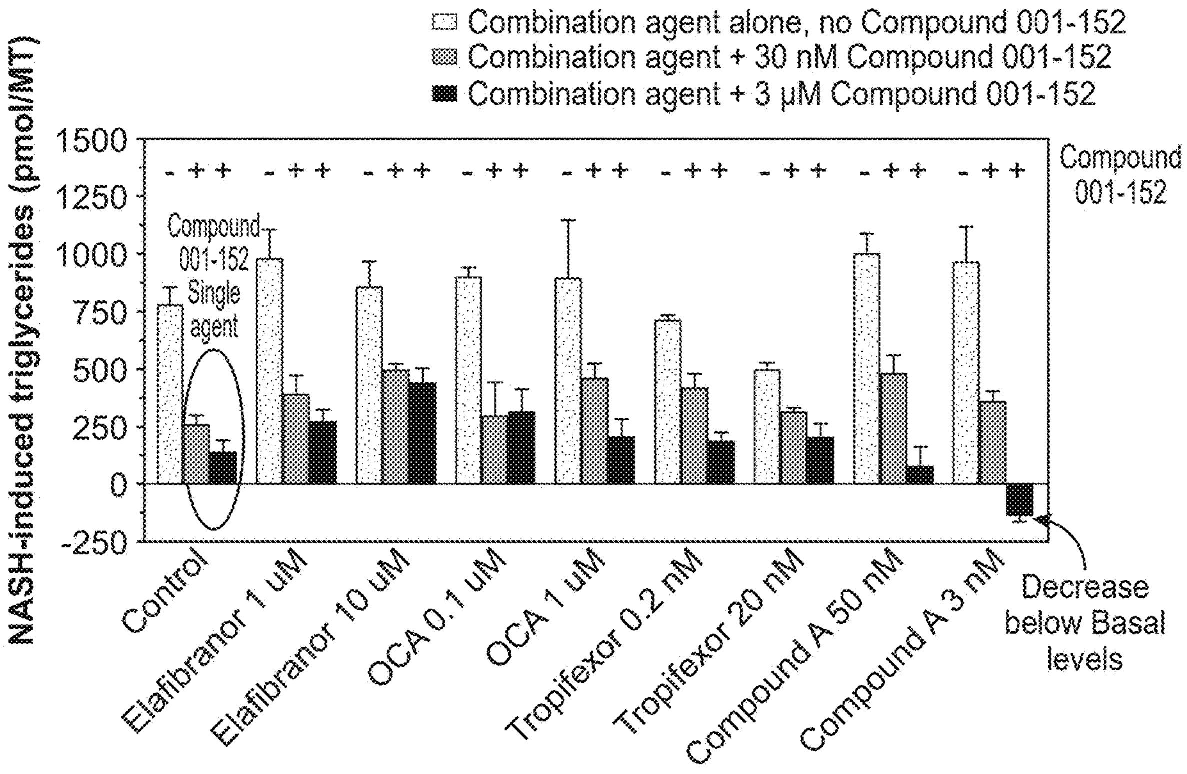
FIG. 2A is a graph showing NASH-induced intratissue triglyceride levels following administration of Compound 001-152 as a single agent, and in combination with other agents, including Compound A. The graph illustrates that, in a human liver microtissue model, Compound 001-152 single agent reduced cellular triglycerides. Other agents in development for NASH did not reduce triglycerides as effectively (see speckled bars). Combination of Compound 001-152 with those agents (grey and black bars) reduced triglycerides more effectively. Combination of Compound 001-152 with Compound A (Resmetirom or MGL-3196) reduced TG content below basal levels. Graphs depict median and interquartile range.
Figure 2B:
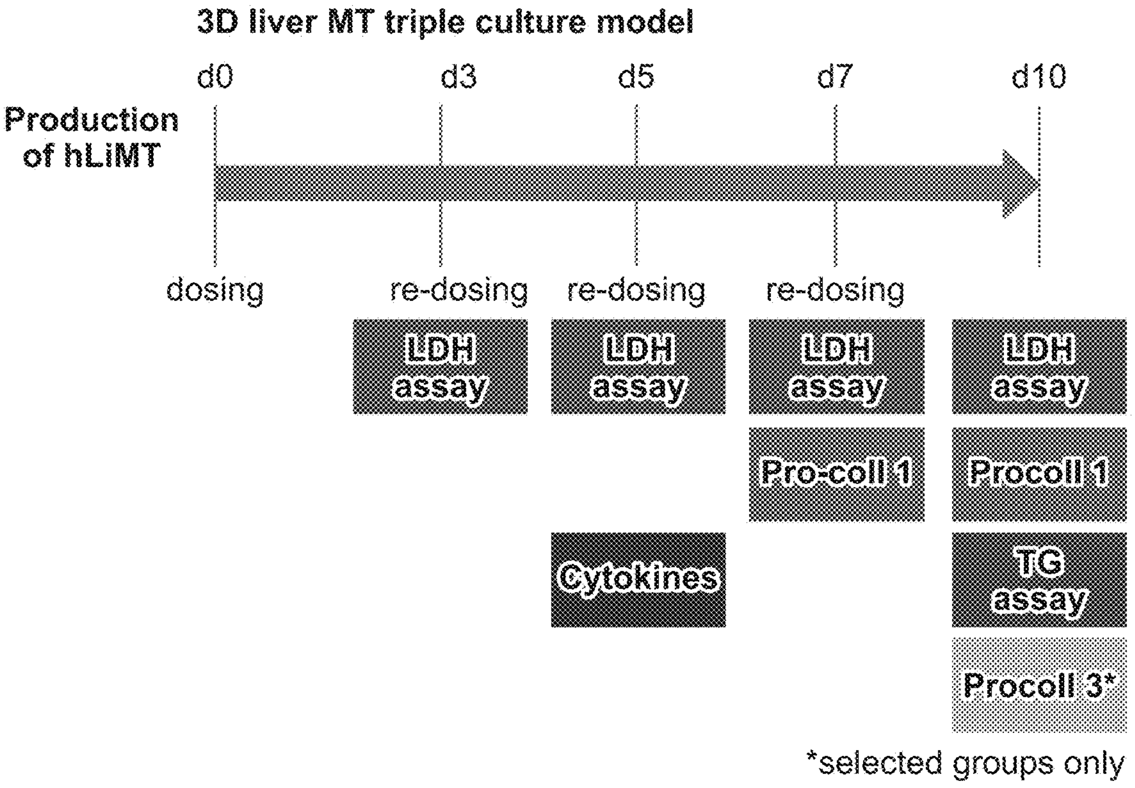
FIG. 2B is a chart showing the study timeline.

Experimental Setup: The duration of treatment was 10 days, a study timeline is shown in FIG. 2B. Cells were dosed on days 0, 3, 5 and 10. Experimental readout measurements comprised collection and freezing of supernatants for LDH measurement on days 3, 5, 7 and 10. Measurement of LDH released into supernatant was analyzed using an LDH-Glo™ Cytotoxicity Assay (Promega). Measurement of intratissue triglyceride (TG) content after 10 days of treatment was analyzed using a Triglyceride-Glo™ Assay (Promega). Cell supernatants were collected and frozen for measurement of cytokine release at day 5 of treatment. Measurement of IL-6, IL-8, IP-10, MCP-1, MIP-1α and TNF-α content was analyzed using Magnetic Luminex® Performance Assay, Human XL Cytokine Discovery Base Kit (R&D systems).

Cell supernatants were collected and frozen for measurement of procollagen 1 released into supernatant at days 7 and 10 of treatment. Measurement of procollagen 1 was analyzed using human procollagen type 1 kit (Cisbio). Leftover supernatants collected on days 3, 5, 7 and 10 of treatment were kept frozen at −20° C. for further analysis after execution of all above mentioned readouts.

Culture Medium: InSight™ Physiological Medium.

Compound: Compound 001-152 was provided as a powder. A 12 mM stock was prepared in DMSO and aliquots were stored at −80° C. Dosing concentration of Compound 001-152 was 30 nM or 3 μM.

Culture Conditions: The MTs were treated in 96-well Akura™ plates covered with Microclime® lids (Labcyte, USA) and were incubated in a humidified cell culture incubator (37° C., 5% $CO_2$).

Anti-NASH drug candidates, tested alone and in combination with Compound 001-152:

- Elafibranor (PPAR α/γ agonist, MedChemExpress), 1 μM or 10 μM
- Obeticholic Acid (OCA, FXR agonist, MedChernExpress), 0.1 μM or 1 μM
- Tropifexor (FXR agonist, Achemblock), 0.2 nM or 20 nM
- Compound A, 50 nM or 3 μM Assay Control Compounds:

Chlorpromazine (SigmaAldrich) was included in every run of Hepatotoxicity Testing to control MTs' response to a toxic insult. A 15 μM concentration was used.

Firsocostat (ND-630, MedChernExpress) was included in all tests of lipid accumulation as a positive control for inhibition of lipid accumulation. A 0.5 μM or 2 μM concentration was used.

Selonsertib (MedChemExpress) was included as a positive control compound with anti-inflammatory properties. A 10 μM concentration was used.

Alk5i (SB525334) (Selleckchem), was included as a positive control (tool compound) acting anti-fibrotic. A 0.5 μM concentration was used.

Assays

Cytokine levels in supernatants: The amounts of IL-6, IL-8, IP-10, MCP-1, MIP-1α and TNF-α present in the supernatant on day 5 of treatment were analyzed using a Magnetic Luminex® Performance Assay, Human XL Cytokine Discovery Base Kit (R&D systems), according to InSphero AG protocol. Amounts of cytokine were expressed as absolute concentrations calculated from a standard curve with Luminex xPONENT software. All values are described as mean±standard deviation (SD) calculated in GraphPad Prism® (Version 8) software. Unpaired, two-tailed t-test with Welch's correction vs day 10 NASH 0.2% DMSO control was performed with GraphPad Prism® (Version 8), *$p<0.05$. The n of microtissues/treatment group was 6; for groups with ≥3 values falling below lower limit of quantification (LLOQ) the whole treatment group was considered <LLOQ.

Procollagen 1 content in supernatants: Procollagen type 1 levels in supernatants collected on days 7 and 10 of treatment were measured with the human procollagen type 1 kit (sandwich assay using HTRF® technology, Cisbio), according to InSphero AG protocol. Concentrations were calculated with GraphPad Prism® (Version 8) software using a 4-parametric fit to a standard curve. Concentrations were normalized to incubation times. Results graphs show mean values±SD. Unpaired, two-tailed t-test with Welch's correction vs day 10 NASH 0.2% DMSO control was performed with GraphPad Prism® (Version 8), *$p<0.05$. The n of microtissues/treatment group was 6; for groups with ≥3 values falling below lowest standard value the whole treatment group was considered <LLOQ.

Endpoint Assay—Triglyceride (TG) content:

Total TG content in MTs at day 10 of treatment was measured with Triglyceride-Glo™ Assay (Promega), according to InSphero AG protocol. The amount of glycerol/MT [pmol/MT] was calculated a using linear regression to a standard curve. Values were plotted as mean±Standard Deviation including individual values with GraphPad Prism® (Version 8). An unpaired, two-tailed t-test with Welch's correction vs day 10 NASH 0.2% DMSO control (*$p<0.05$) was used to calculate significant changes in TG content. The n of microtissues/treatment group was a minimum of 6.

Procollagen 3 Content in Supernatants:

Procollagen type 3 levels in supernatants collected on day 10 of treatment were measured with the N-Terminal Procollagen Type III Peptide (PIIINP) ELISA (Cisbio), according to InSphero AG protocol. Concentrations were calculated using a linear fit to a standard curve. To identify outliers, Grubb's test (alpha=0.05) was run. Mean values±SD are shown in results graphs. Unpaired, two-tailed t-test with Welch's correction vs day 10 NASH 0.2% DMSO control was performed with GraphPad Prism® (Version 8), *$p<0.05$. The n of microtissues/treatment group was 6. For the following groups, an outlier was detected using Grubb's test: Selonsertib 10 μM, OCA 1 μM+Compound 001-152 3 μM, Tropifexor 20 nM+Compound 001-152 3 μM. These three values were excluded from analysis.

Results and Conclusions

Figure 1B:
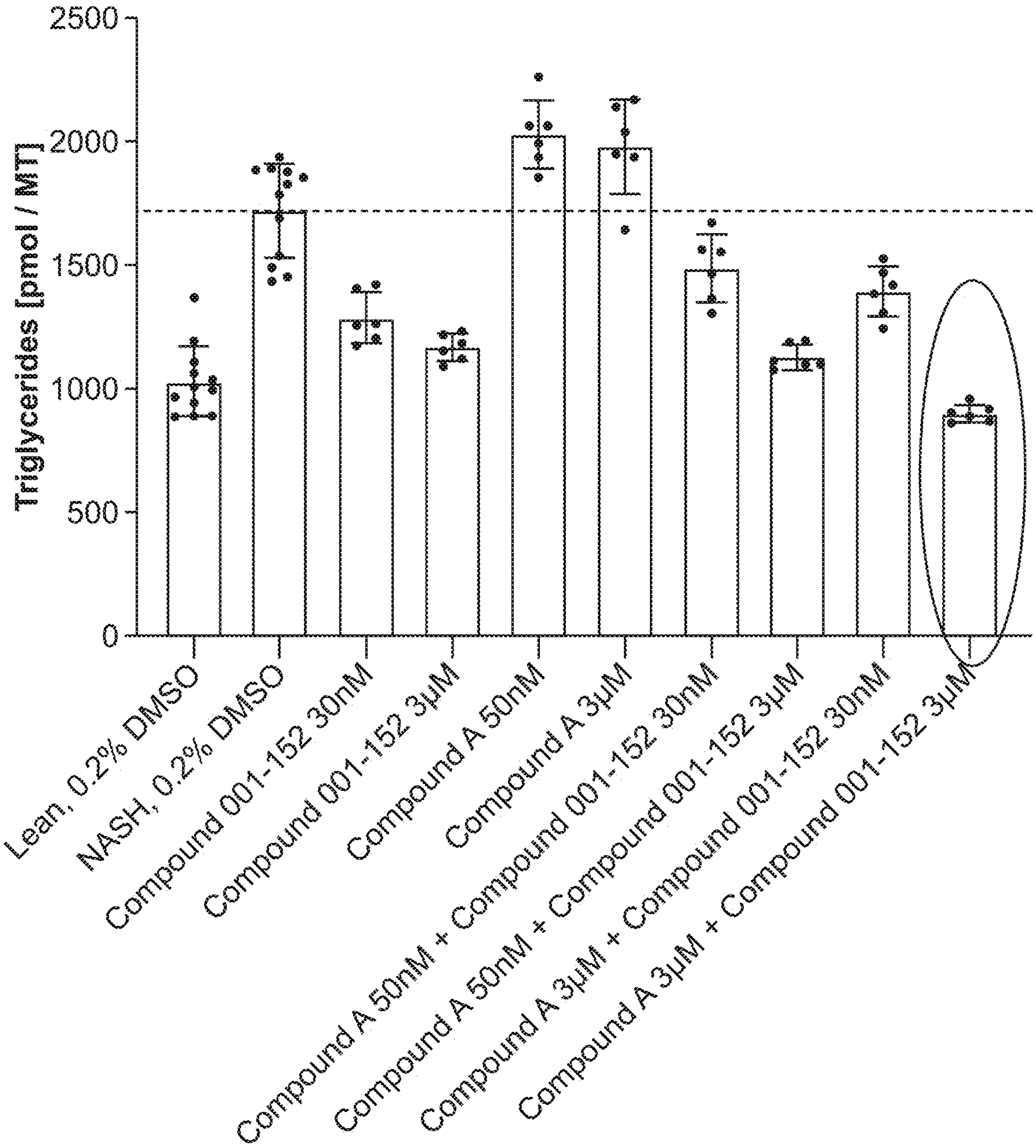
FIG. 1B is a graph showing the effect of Compound 001-152 and Compound A in a human liver microtissue model in NASH condition as measured by intratissue Triglyceride content. The model includes stellate cells and includes pro-inflammatory stimulation with lipopolysaccharides (LPS). This liver microtissue model comprises hepatocytes, liver endothelial cells, and hepatic stellate cells. Liver microtissue was treated for 10 days. To model increased lipid accumulation within hepatocytes, and inflammation and fibrosis processes, microtissues were treated with sugar, free fatty acids (FFA), and lipopolysaccharides (LPS). Graphs depict Mean±Standard Deviation (SD). A two-tailed t-test with Welch's correction *$p<0.05$ was used.
Figure 1C:
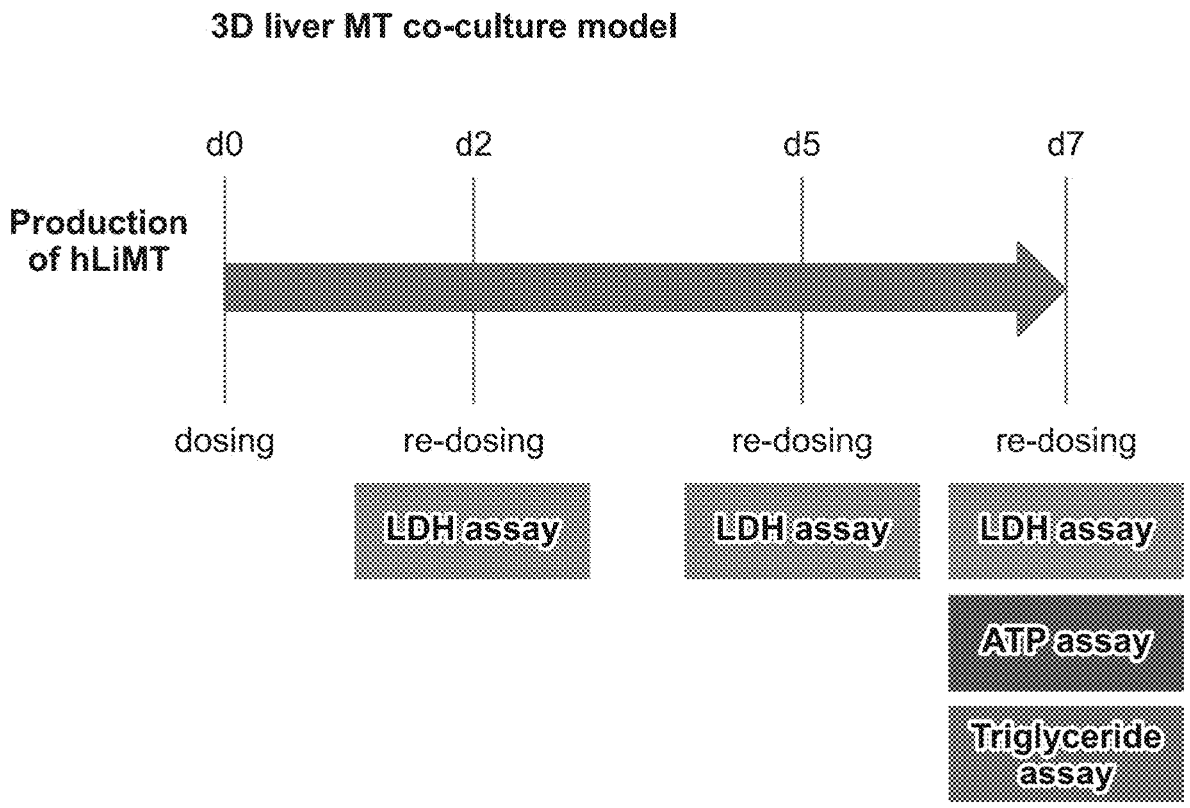
FIG. 1C is a chart showing the study timeline.

In a human liver microtissue model of NASH condition as measured by intratissue Triglyceride content, Compound 001-152 (30 nM and 3 μM) single agent reduced cellular triglycerides in vitro, which indicates potential to reduce liver fat (FIG. 1B). Other agents in development for NASH ("Combination agent" in FIG. 2A) did not reduce NASH-induced TG as effectively (FIG. 2A). Combination of Compound 001-152 with Compound A enhanced the effect of Compound A and the combination showed an increased efficacy overall versus single agent. Improved TG reduction was observed in the combination treatment as compared to Compound A alone (FIG. 1B). This model is a more aggressive NASH model that includes stellate cells and includes pro-inflammatory stimulation with LPS. Combination of Compound 001-152 with different agents in development for NASH (grey and black bars compared to speckled for agent in FIG. 2A). The combination of Compound 001-152 and Compound A (Resmetirom) reduced NASH-induced TG content below basal levels (FIG. 2A).

Figures 3, 4A:
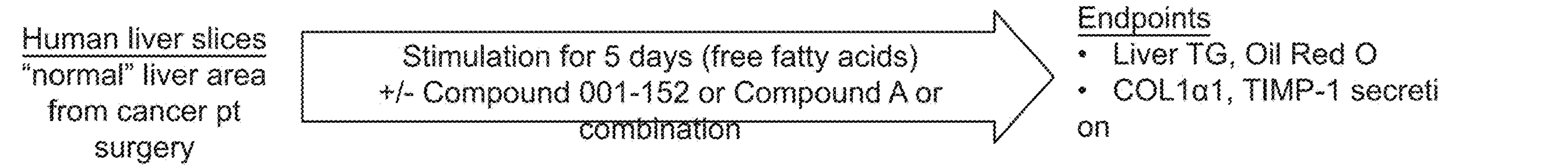
FIG. 3 is a chart depicting in a human liver microtissue model, the combination showed improved and/or more consistent decreases in inflammation markers MIP1a, IL-8 and TNFa (columns 7,8), and IP10 (columns 5,6) than single agent treatments (columns 1,2 for Compound A and 3,4 for Compound 001-152). The combination also showed improved decreases in the fibrosis marker Collagen 1 (columns 7, 8) compared to single agents. These results indicate that the combination of Compound 001-152 and Compound A has potential to improve efficacy of inflammation and fibrosis pathways beyond that observed with single agent treatment. In the chart, "MGL" denotes Compound A, "U" indicates an increase of fold change of NASH inflammation or fibrosis markers, and "D" indicates a decrease of fold change of NASH inflammation or fibrosis markers; the magnitude of the effect is reflected in the grayscale tone of the fields, with darker gray representing a more pronounced effect. Black fields indicate that no data was collected.
FIG. 4A is a schematic showing the study design.

The combination of Compound 001-152 and Compound A (Resmetirom) showed improved decreases in inflammation markers MIP1a, IL-8 and TNFa (FIG. 3, columns 7,8), and IP10 (FIG. 3, columns 5,6) as compared to single agent treatments (FIG. 3, columns 1,2 for Compound A and FIG. 3, columns 3,4 for Compound 001-152). The combination showed improved decreases in the fibrosis marker Collagen 1 (FIG. 3, columns 7, 8) as compared to single agents.

Example 9—Evaluation of Precision Cut Liver Slice In Vitro Human NASH Model

Precision Cut Liver Slice (PCLS) Preparation and Culture:

PCLSs were prepared from resected liver tissue and rested for 24 hours to allow the post-slicing stress period to elapse before experiments began. Subsequently, PCLSs were cultured without exogenous challenge (Table 4, Group 1 only) or with exogenous challenge via a combination of lipids conjugated to Fatty Acid depleted BSA (Table 4, Groups 2-10) for a further 5 days (144 hrs total). From 24 hrs onward, PCLSs were cultured in the presence or absence of ALK5i at a single high dose (10 μM), Compound 001-152 at two (2) escalating doses (1 μM, 3 μM), Compound A at two (2) escalating doses (3 μM, 10 μM) or a combination of Compound 001-152+Compound A at low (1 μM+3 μM) or high doses (3 μM+10 μM). In addition, from 72 hrs onward, PCLSs were cultured in the presence of Compound 001-152 at a single high dose (3 μM). PCLS culture media, including lipids and compounds, was refreshed at 24 hrs intervals. All PCLSs were harvested at 144 hrs.

Study Groups:

Ten (10) different groups with n=6 or n=8 human PCLSs (total n=68 per donor) were investigated as shown in Table 4. PCLSs were prepared from an n=1 individual human liver. The human livers are normal margins of near-to-normal human liver obtained during a surgical resection.

TABLE 4

| Study Groups Overview | | | | | | |
|---|---|---|---|---|---|---|
| Group | Challenge (24-144 hrs) | Intervention | Dose | Intervention Duration | Harvest | PCLS |
| 1 | Control | Vehicle | — | None | 144 hrs | n = 8 |
| 2 | Lipids | Vehicle | — | 24-144 hrs | 144 hrs | n = 8 |
| 3 | Lipids | Compound 001-152 | 1 μM | 24-144 hrs | 144 hrs | n = 8 |
| 4 | Lipids | Compound 001-152 | 3 μM | 24-144 hrs | 144 hrs | n = 8 |
| 5 | Lipids | Compound A | 3 μM | 24-144 hrs | 144 hrs | n = 6 |
| 6 | Lipids | Compound A | 10 μM | 24-144 hrs | 144 hrs | n = 6 |
| 7 | Lipids | Compound 001-152 + Compound A | 1 μM + 3 μM | 24-144 hrs | 144 hrs | n = 6 |
| 8 | Lipids | Compound 001-152 + Compound A | 3 μM + 10 μM | 24-144 hrs | 144 hrs | n = 6 |
| 9 | Lipids | ALK5i | 10 μM | 24-144 hrs | 144 hrs | n = 6 |
| 10 | Lipids | Compound 001-152 | 3 μM | 72-144 hrs | 144 hrs | n = 6 |
| | | | | | Total | n = 68 |

Harvest and Analysis

PCLS Harvest:

Tissue culture supernatant (n=3 or n=4 per group) were collected every 24 hrs and snap frozen for quantification of the soluble outputs described below. At harvest, n=2 PCLSs were harvested for a triglyceride assay, n=2 PCLSs were harvested for frozen sections (Oil Red O staining), n=2 PCLSs were formalin-fixed, paraffin embedded (FFPE) for immunohistochemistry, and n=2 PCLSs were snap frozen for RNA isolation (Table 4, Groups 1-4 only).

PCLS Function and Viability Analysis:

Tissue culture levels of markers of liver damage (Lactate Dehydrogenase (LDH) and Aspartate Transaminase (AST)) and hepatocyte function/viability (Albumin) were quantified on all PCLSs at all-time points (n=173 samples total; n=3 at 24 hrs, n=34 at 48 hrs, 72 hrs, 96 hrs, 120 hrs and 144 hrs). Albumin secretion was quantified by ELISA as a marker of PCLS's integrity and function (n=173 samples per donor).

Soluble Outputs Analysis:

Levels of collagen 1α1 (FIG. 4B), IL-6, and TIMP-1 in the tissue culture supernatants (n=173 samples per donor) were quantified using R&D Duoset ELISA kits.

Results and Conclusions

Figure 4B:
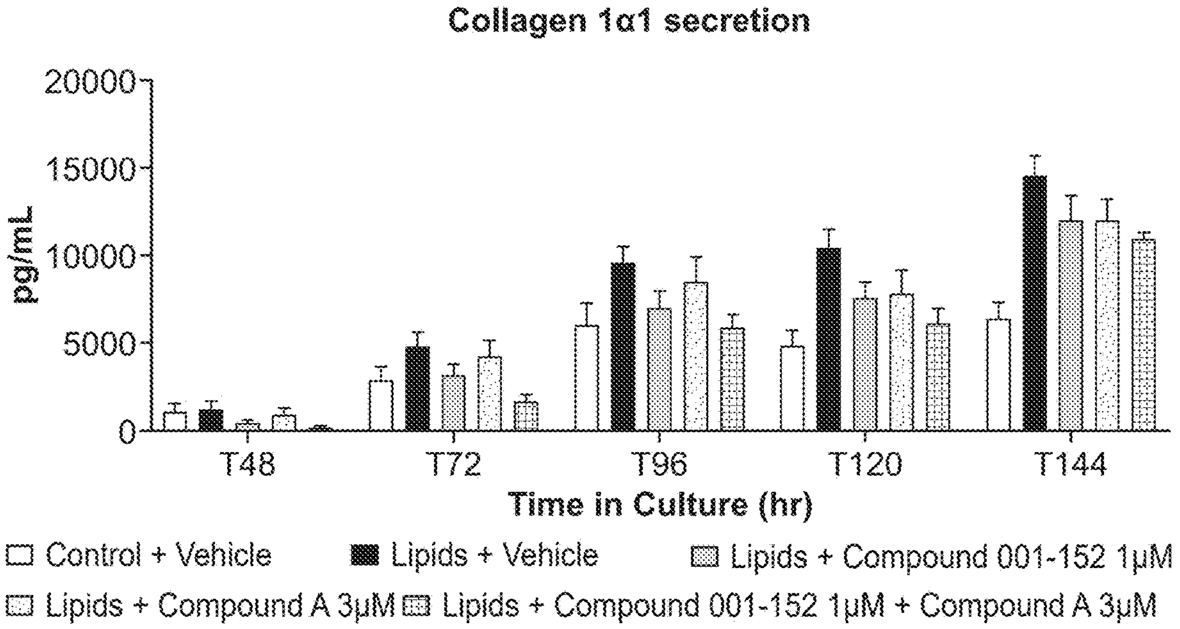
FIG. 4B is a graph showing the effect of the combination of Compound 001-152 and Compound A on collagen 1α1 in human liver slices cultured in conditions to mimic human NASH. The graph demonstrates that the combination of Compound 001-152 and Compound A improved suppression of the fibrosis marker collagen 1α1 compared to single agents (see T72 and later timepoints).

In human liver slices cultured in conditions to mimic human NASH, the combination of Compound 001-152 and Compound A showed improved suppression of the fibrosis marker collagen 1α1 as compared to single agents (FIG. 4B, T72 and later timepoints). Compound 001-152 showed a dose and time-dependent decrease in collagen 1α1, suggestive of decreased fibrogenic activity.

Example 10—Evaluation of Human Primary Hepatic Stellate Cell In Vitro Human NASH Model In Vitro Cell Model:

Primary isolated human stellate cells (HSC) were investigated in the study. The cells were maintained under standard culture conditions and in established culture medium.

Study Model: Viability screening and in vitro fibrosis study, 24 well plate format, 4 day stimulation with recombinant human TGF-β1. In this study, 2.5 and 10 ng/ML TGF-β1 were used.

Test Substances:

1. Name: Compound 001-152

Pharmacological class: fatty acid synthase inhibitor

2. Name: Compound A

Pharmacological class: THR-β agonist

3. Name: LY-364947

Pharmacological class: TGFβR-I/ALK5 inhibitor; a positive control for functional TGF-β1-mediated cell activation.

Experimental Design: In Vitro Fibrosis Study

Primary HSCs were seeded on t=day−1 and cultured in 24 well plates for 24 hours. On t=day 0, the culture medium was replaced with culture medium containing the test compounds Compound 001-152 or Compound A, or both, in 6 test concentrations (respectively as 3 nM-10 nM-30 nM-100 nM-300 nM-1000 nM and 10 nM-30 nM-100 nM-300 nM-1000 nM-3000 nM, each condition in triplo). Two hours after addition of test compounds, cells were stimulated with 2.5 or 10 ng/mL human recombinant TGF-β1. Control treatments included no stimulation (n=4), stimulation with 2.5 or 10 ng/mL TGF-β1 only (n=4), and stimulation with 2.5 or 10 ng/ml TGF-β1 in combination with 5 μM LY-364947 (ALK-5 inhibitor reference compound, n=4). Cells were incubated for an additional 96 hours (t=day 4). Conditioned medium samples were collected for expression analysis of secreted proteins. All wells were used for an alamarBlue assay to assess cell viability/metabolic activity. A separate plate was used at t=day 0 as reference for the alamarBlue assay. Next, the cell-matrix fraction was collected for measurement of total collagen and cell protein levels. Conditioned medium samples were collected for measurement of PAI-1.

Test Compound; Test Concentrations:

Compound 001-152: 3 nM-10 nM-30 nM-100 nM-300 nM-1000 nM

Compound A 10 nM-30 nM-100 nM-300 nM-1000 nM-3000 nM

Both test compounds were dissolved in DMSO. Working concentrations were prepared from a stock concentration that is 1000-fold that of the highest working concentration. All controls were incubated with the same DMSO concentration as that present in the highest working concentration.

Sample Collection and Analyses:

Conditioned culture medium and acid-solubilized cell-matrix protein lysates were collected for further analysis.

AlamarBlue assay for viability/metabolic activity. Performed according to manufacturer's protocol. Cells were incubated with alamarBlue reagent working solution for 45-60 minutes. Medium samples were collected and reagent conversion into a fluorescent product was measured using a plate reader.

Total Collagen assay was performed according to the manufacturer's protocol.

Total Protein assay, for use with the Total Collagen assay, was performed according to the manufacturer's protocol. Protein levels were used to correct for differences in cell contents between samples.

Statistics:

Significance of differences between the groups was calculated either parametrically or non-parametrically, using the computer program SPSS. For nonparametric calculations, a Kruskal-Wallis test for several independent samples was used, followed by a Mann-Whitney U-test for independent samples. For parametric calculations, a One-way ANOVA for multiple comparisons was used, followed by Dunnett or Bonferroni's correction. A P-value≤0.05 was considered statistically significant.

Results and Conclusions

Figure 5:
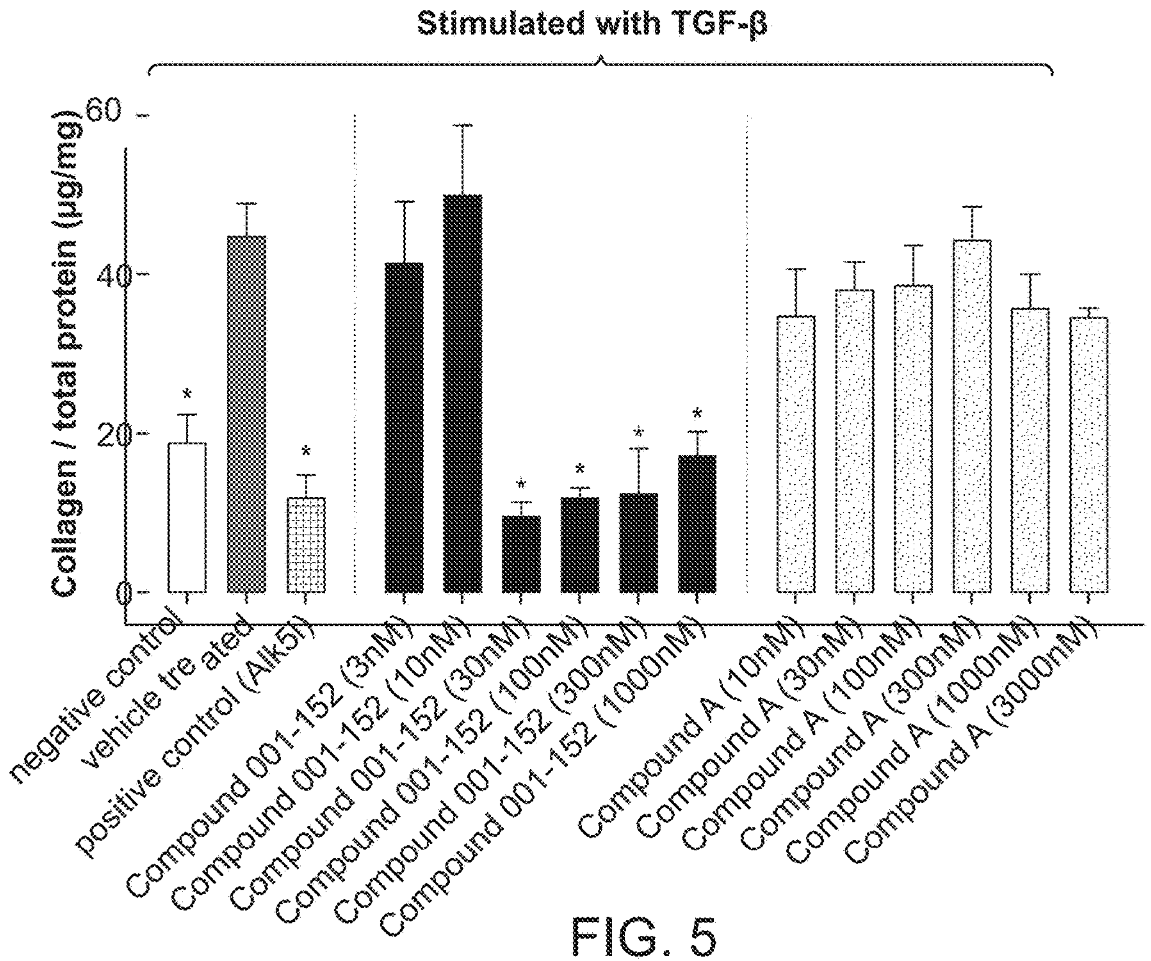
FIG. 5 is a graph showing the effect of Compound 001-152 and Compound A on collagen production in human primary hepatic stellate cells stimulated with 10 ng/ml TGF-beta in 4 day treatments. Compound 001-152 inhibits collagen production directly (no other cell types are present in this model). * denotes p<0.05 vs vehicle control.

In human primary hepatic stellate cells, FIG. 5 shows Compound 001-152 inhibits collagen production directly whereas cells treated with Compound A did not display the same effect. Primary human hepatic stellate cells were stimulated with 10 ng/ml TGF-β for 4 days. * denotes $p<0.05$ vs vehicle control.

The highest drug concentrations used exceed clinically relevant plasma exposure levels, for both agents. Compound 001-152 at 30 nM and higher (at or above the $IC_{50}$) inhibits as effectively as positive control Alk5 inhibitor. Compound 001-152, but not resmetirom (Compound A), shows inhibition of collagen production in primary human hepatic stellate cells suggesting a direct fibrosis effect.

Example 11—Combination of Fatty Acid Synthase (FASN) Inhibitor and Thyroid Hormone Receptor Beta (THRβ) Agonist, Resmetirom, Improved Markers of NASH and Cardiovascular Health in LDL Receptor Knockout NASH Mice This study was designed to evaluate FASN inhibitor alone and in combination with resmetirom on plasma biomarkers and liver histology in LDL receptor knockout (Ldlr−/−. Leiden) NASH mice. FASN inhibitor and resmetirom were also evaluated in vitro in hepatic stellate cells (HSCs) for direct anti-fibrotic effects.

Method:

Male Ldlr−/−. Leiden mice were fed with fast food diet (FFD) for 18 weeks to induce NASH features and treated with either TVB-3664 (a surrogate FASN inhibitor for denifanstat, 5 mg/kg, PO, QD) or THRb agonist resmetirom (MGL-3196, 3 mg/kg, PO, QD) alone or in combination for 10 weeks. Endpoints included liver enzymes, lipids and liver histology. Primary human HSCs were stimulated by TGF-b1 and treated with denifanstat or resmetirom at various concentrations (TNO, Netherlands).

Figure 11A:
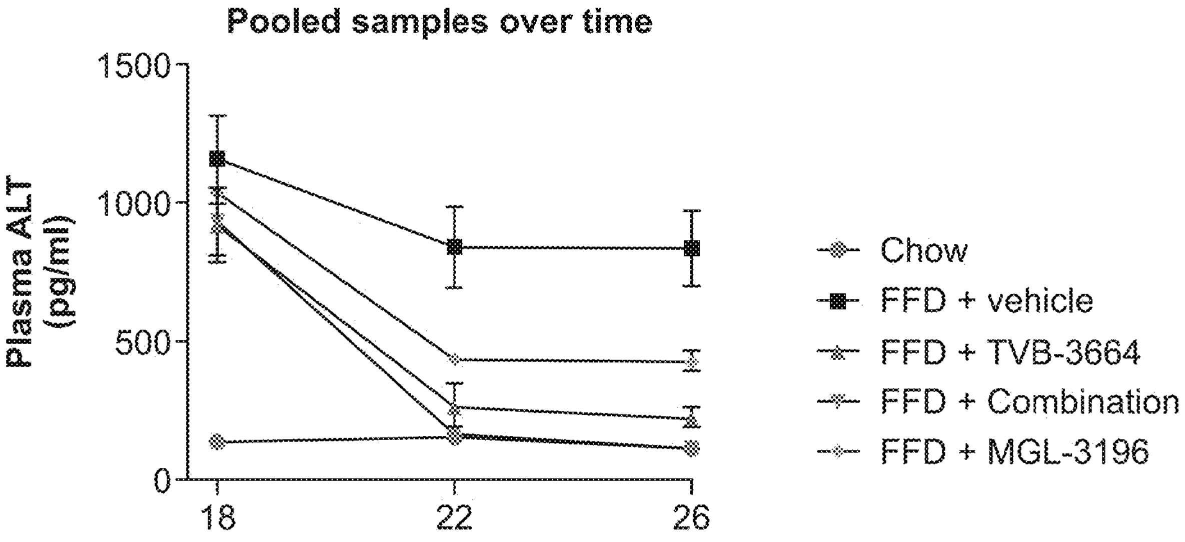
FIG. 11A shows the changes in plasma ALT over time in male LDL receptor knockout (Ldlr−/−) mice after being fed with fast-food diet (FFD) for 18 weeks to induce MASH features. Figures represent data mean+SD with *p<0.05, p<0.01 and *p<0.001 vs FFD-vehicle. Treatment groups: Control normal chow n=8; vehicle, TVB-3664, MGL-3196, combination n=14~15 (Example 11).
Figure 11B:
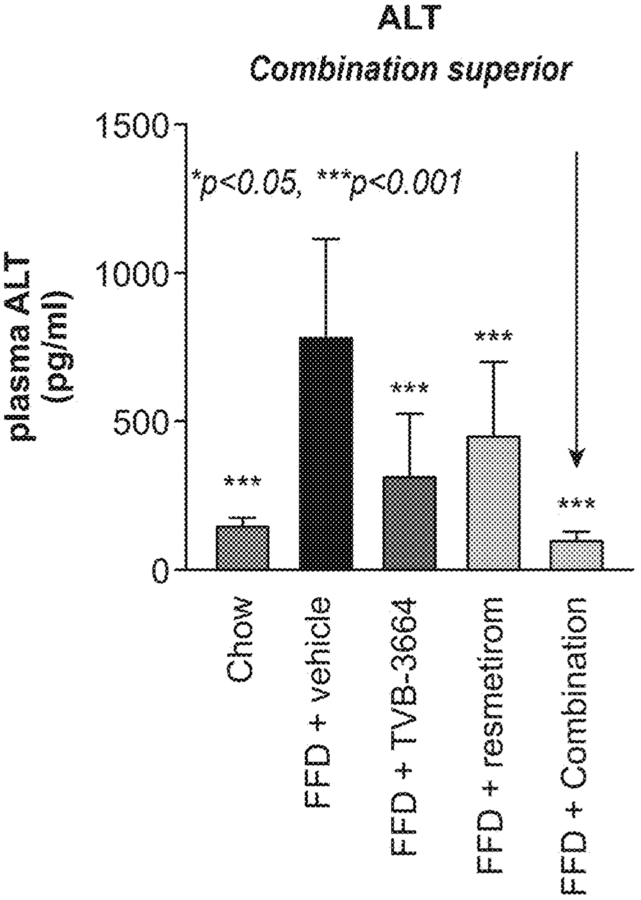
FIG. 11B shows the changes in plasma ALT at day 28 of treatment in male LDL receptor knockout (Ldlr−/−) mice after being fed with fast-food diet (FFD) for 18 weeks to induce MASH features. Figures represent data mean+SD with *p<0.05, and ***p<0.001 vs FFD-vehicle. Treatment groups: Control normal chow n=8; vehicle, TVB-3664, MGL-3196, combination n=14~15 (Example 11).
Figure 12A:
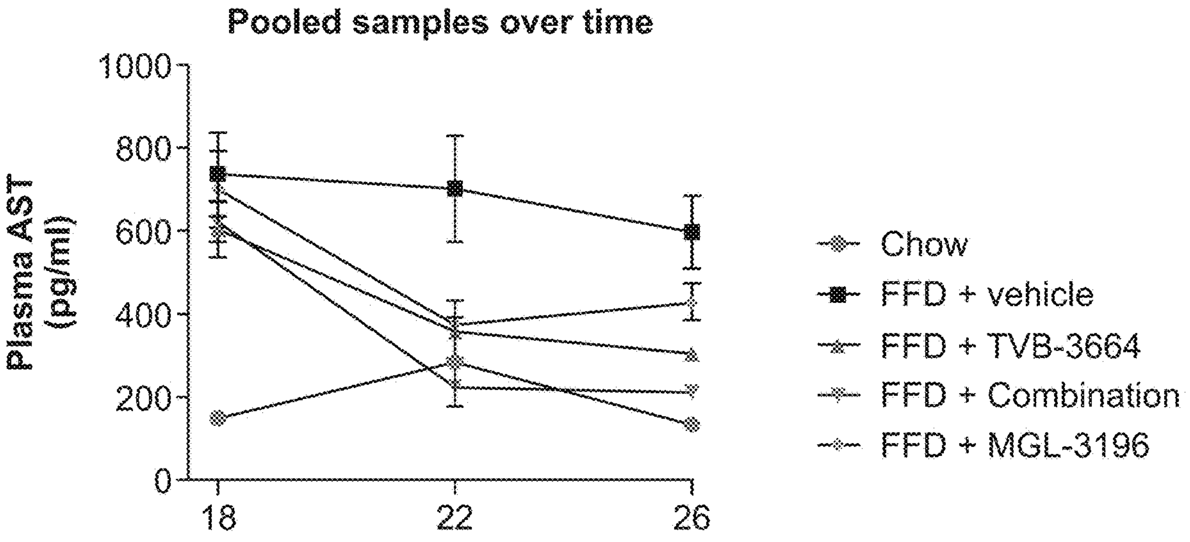
FIG. 12A shows the changes in plasma AST over time in male LDL receptor knockout (Ldlr−/−) mice after being fed with fast-food diet (FFD) for 18 weeks to induce MASH features. Figures represent data mean+SD with *p<0.05, p<0.01 and *p<0.001 vs FFD-vehicle. Treatment groups: Control normal chow n=8; vehicle, TVB-3664, MGL-3196, combination n=14~15 (Example 11).
Figure 12B:
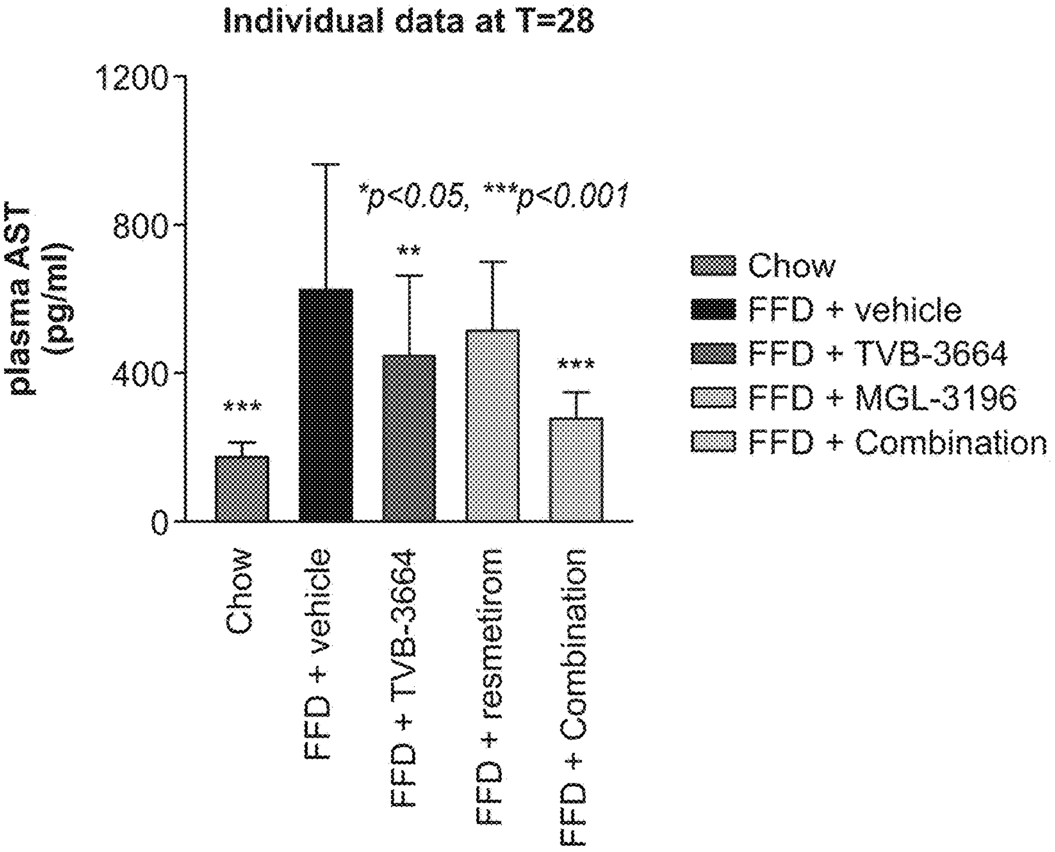
FIG. 12B shows the changes in plasma AST at day 28 of treatment in male LDL receptor knockout (Ldlr−/−) mice after being fed with fast-food diet (FFD) for 18 weeks to induce MASH features. Figures represent data mean+SD with *p<0.05, and ***p<0.001 vs FFD-vehicle. Treatment groups: Control normal chow n=8; vehicle, TVB-3664, MGL-3196, combination n=14~15 (Example 11).
Figure 13:
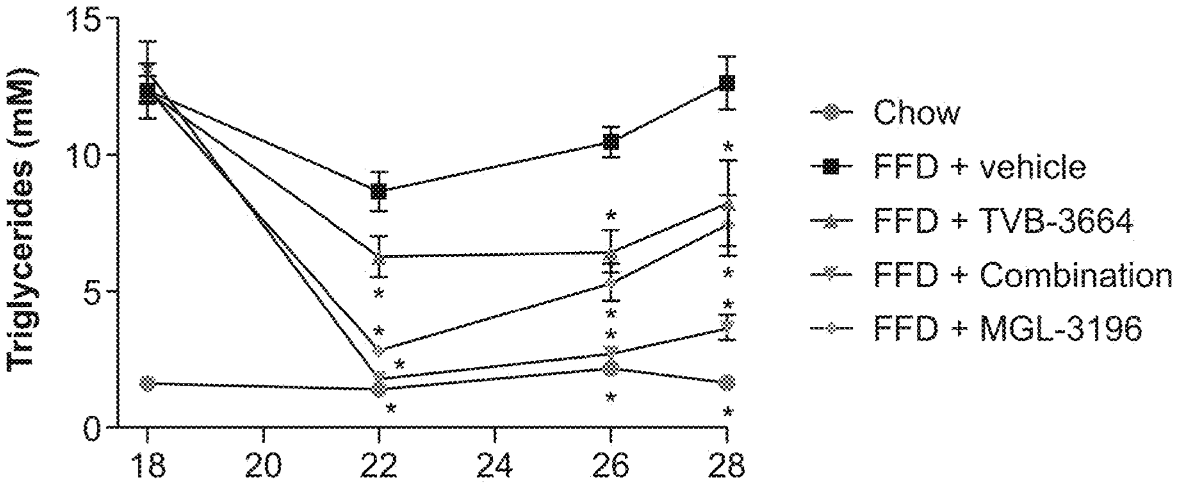
FIG. 13 shows the changes in plasma triglycerides over time in male LDL receptor knockout (Ldlr−/−) mice after being fed with fast-food diet (FFD) for 18 weeks to induce MASH features. Figures represent data mean+SD with *p<0.05, p<0.01 and *p<0.001 vs FFD-vehicle. Treatment groups: Control normal chow n=8; vehicle, TVB-3664, MGL-3196, combination n=14~15 (Example 11).
Figure 14:
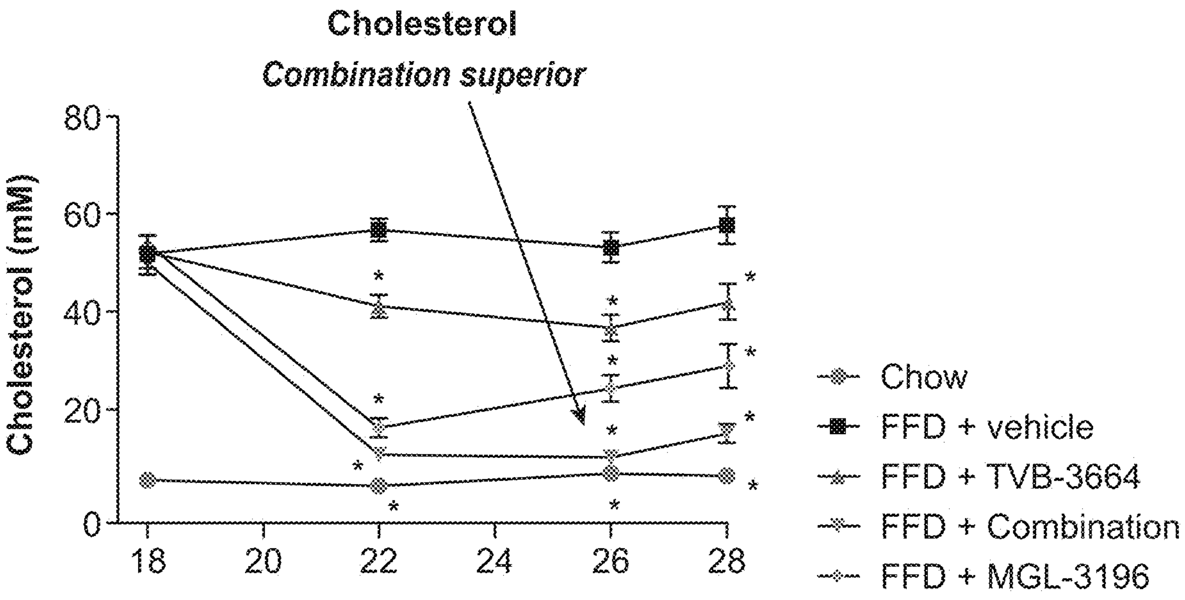
FIG. 14 shows the changes in plasma cholesterol over time in male LDL receptor knockout (Ldlr−/−) mice after being fed with fast-food diet (FFD) for 18 weeks to induce MASH features. Figures represent data mean+SD with *p<0.05, p<0.01 and *p<0.001 vs FFD-vehicle. Treatment groups: Control normal chow n=8; vehicle, TVB-3664, MGL-3196, combination n=14~15 (Example 11).

Results:

FFD feeding significantly increased plasma ALT/AST, total cholesterols and triglycerides in Ldlr−/− mice. TVB-3664 or resmetirom alone rapidly reduced plasma ALT/AST, total cholesterols and triglycerides with 4 weeks treatment and these reductions were sustained until end of the study (10 weeks); importantly, combination of TVB-3664/resmetirom showed further additive improvement compared to either agent alone. FIG. 11A and FIG. 11B show the reduction in ALT over time and at 28 days, respectively. FIG. 12A and FIG. 12B show the reduction in AST over time and at 28 days, respectively. FIG. 13 and FIG. 14 show the reduction in triglycerides and cholesterol, respectively, over time.

Figure 15:
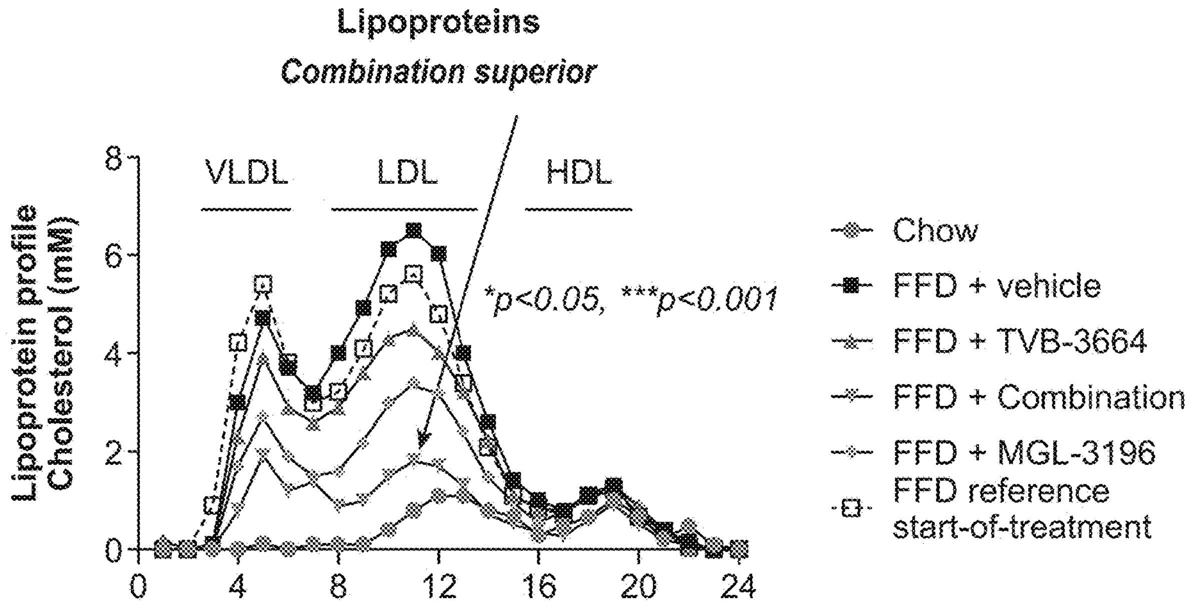
FIG. 15 shows the changes in plasma lipoproteins in male LDL receptor knockout (Ldlr−/−) mice after being fed with fast-food diet (FFD) for 18 weeks to induce MASH features. Figures represent data mean+SD with *p<0.05, p<0.01 and *p<0.001 vs FFD-vehicle. Treatment groups: Control normal chow n=8; vehicle, TVB-3664, MGL-3196, combination n=14~15; the lipoprotein profile at the beginning of treatment for the FFD-vehicle group is included for reference (Example 11).

Lipoprotein analysis showed that LDL-C and VLDL-C were highly induced by FFD and both were significantly reduced by TVB-3664 or resmetirom alone and further reduced by the combination (FIG. 15).

Figure 16:
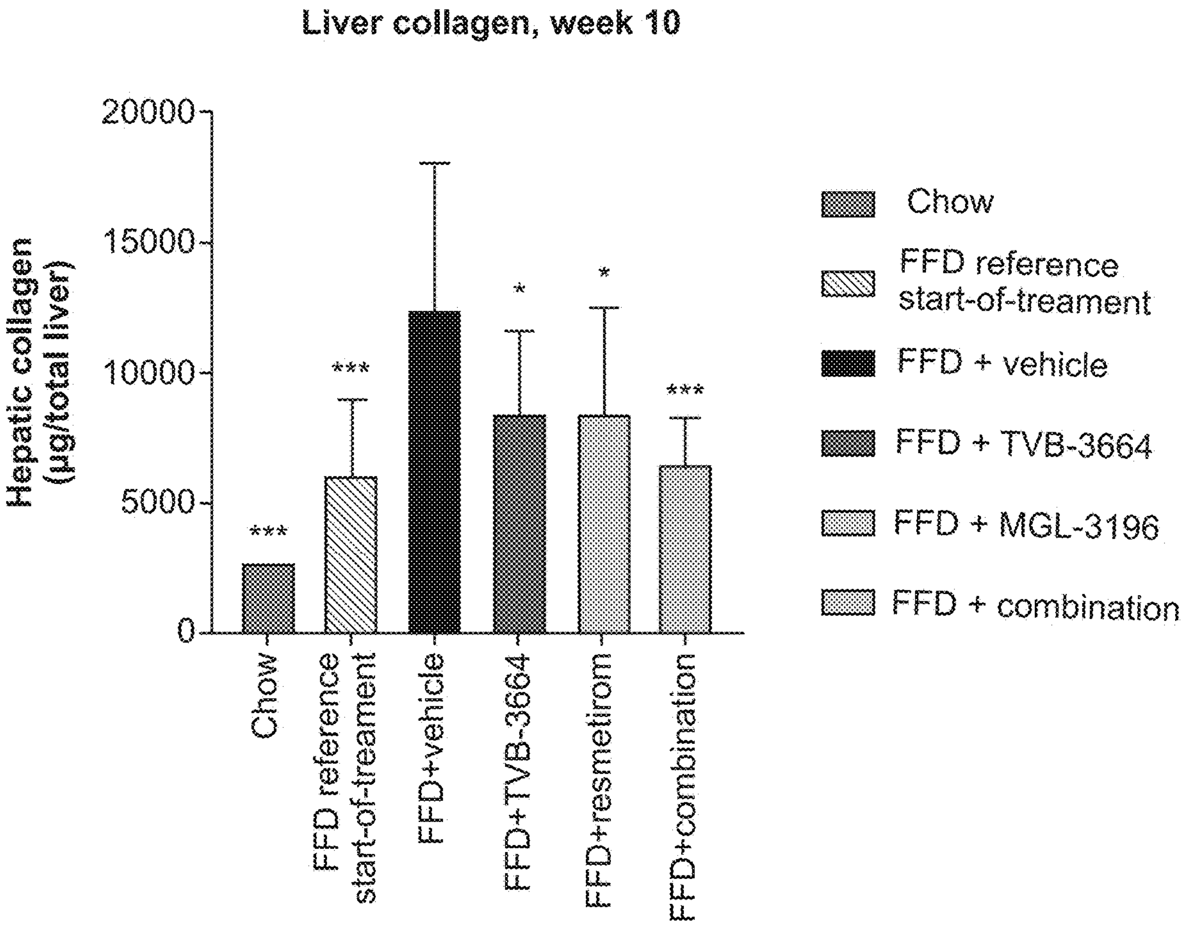
FIG. 16 shows the changes in hepatic collagen in male LDL receptor knockout (Ldlr−/−) mice after being fed with fast-food diet (FFD) for 18 weeks to induce MASH features. Data shown is after 10 weeks of treatment. Figures represent data mean+SD with *p<0.05, p<0.01 and *p<0.001 vs FFD-vehicle. Treatment groups: Control normal chow n=8; vehicle, TVB-3664, MGL-3196, combination n=14~15; the hepatic collagen profile at the beginning of treatment for the FFD-vehicle group is included for reference (Example 11).
Figure 17:
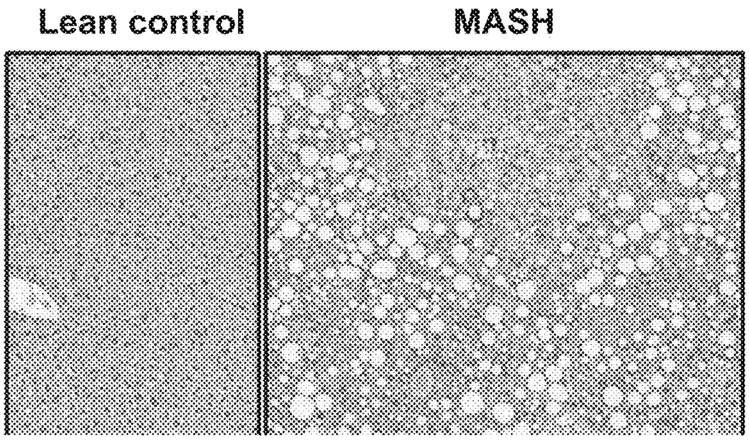
FIG. 17 shows the changes in total steatosis by histopathology in male LDL receptor knockout (Ldlr−/−) mice after being fed with fast-food diet (FFD) for 18 weeks to induce MASH features. Data shown is after 10 weeks of treatment. Figures represent data mean+SD with *p<0.05, p<0.01 and *p<0.001 vs FFD-vehicle. Treatment groups: Control normal chow n=8; vehicle, TVB-3664, MGL-3196, combination n=14~15; the steatosis profile at the beginning of treatment for the FFD-vehicle group is included for reference (Example 11). Inset figure is an exemplary slide showing the difference between a lean control and a MASH slide as visualised in the experiment.
Figure 17:
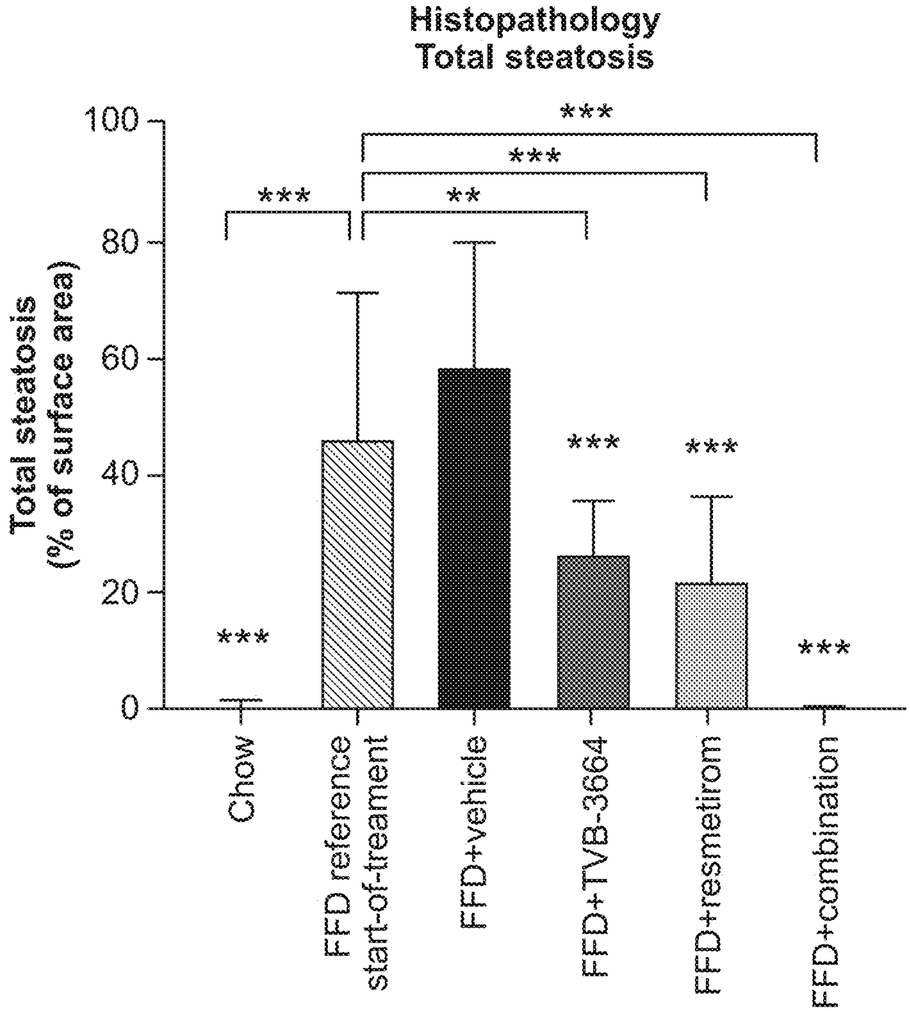
Figure 18:
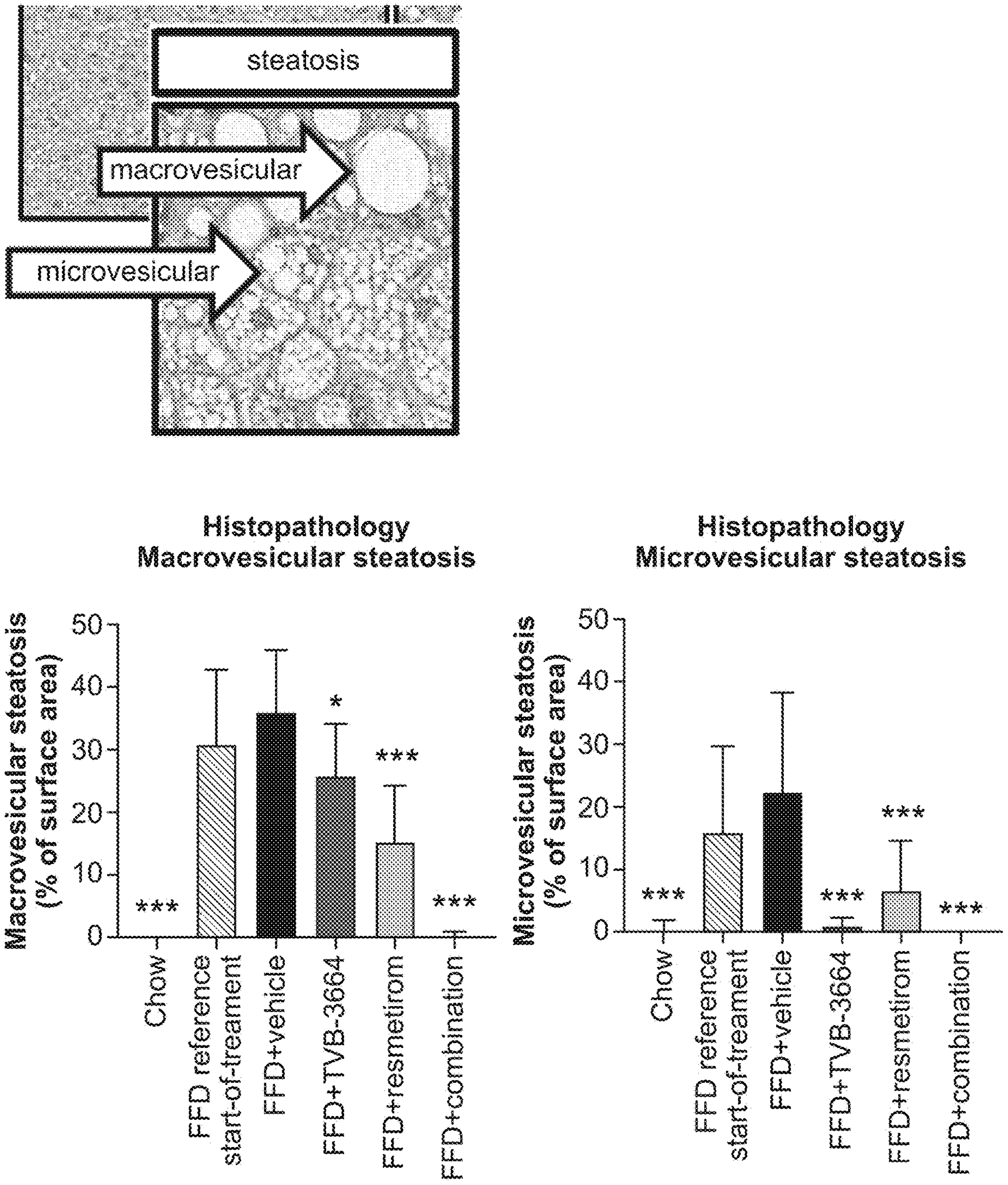
FIG. 18 shows the changes in microvesicular and macrovesicular steatosis by histopathology in male LDL receptor knockout (Ldlr−/−) mice after being fed with fast-food diet (FFD) for 18 weeks to induce MASH features. Data shown is after 10 weeks of treatment. Figures represent data mean+SD with *p<0.05, p<0.01 and *p<0.001 vs FFD-vehicle. Treatment groups: Control normal chow n=8; vehicle, TVB-3664, MGL-3196, combination n=14~15; the microvesicular and macrovesicular steatosis profile at the beginning of treatment for the FFD-vehicle group is included for reference (Example 11). Inset figure is an exemplary slide showing the difference between a lean control and a MASH slide with macrovesicular and microvesicular steatosis as visualised in the experiment.
Figure 19:
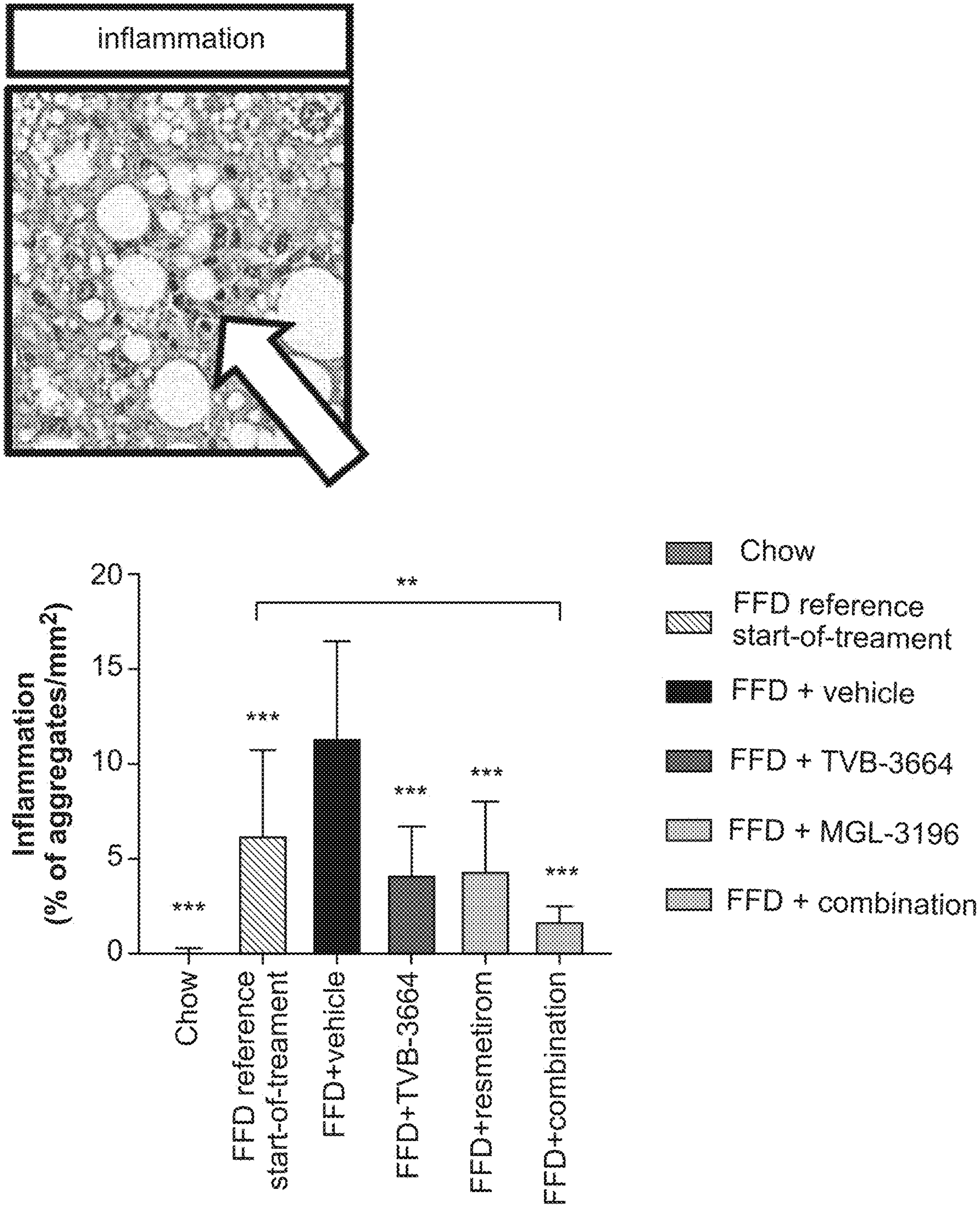
FIG. 19 shows the changes in inflammation by histopathology in male LDL receptor knockout (Ldlr−/−) mice after being fed with fast-food diet (FFD) for 18 weeks to induce MASH features. Data shown is after 10 weeks of treatment. Figures represent data mean+SD with *p<0.05, p<0.01 and *p<0.001 vs FFD-vehicle. Treatment groups: Control normal chow n=8; vehicle, TVB-3664, MGL-3196, combination n=14~15; the inflammation profile at the beginning of treatment for the FFD-vehicle group is included for reference (Example 11). Inset figure is an exemplary slide showing the visualization of inflammation.
Figure 20:
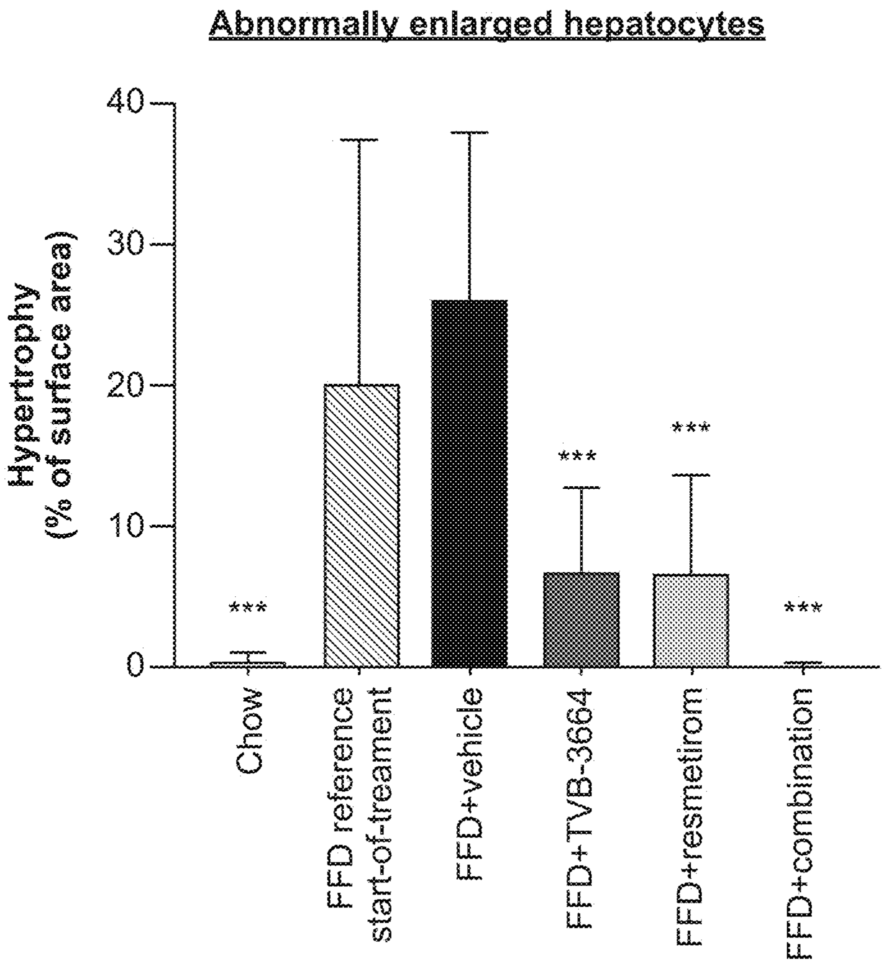
FIG. 20 shows the changes in abnormally enlarged hepatocytes (hypertrophy as % of surface area) by histopathology in male LDL receptor knockout (Ldlr−/−) mice after being fed with fast-food diet (FFD) for 18 weeks to induce MASH features. Data shown is after 10 weeks of treatment. Figures represent data mean+SD with *$p<0.05$, $p<0.01$ and *$p<0.001$ vs FFD-vehicle. Treatment groups: Control normal chow n=8; vehicle, TVB-3664, MGL-3196, combination n=14~15; the profile at the beginning of treatment for the FFD-vehicle group is included for reference (Example 11).

The combination also resulted in significant further reduction compared to either agent alone in liver collagen (FIG. 16), total steatosis (FIG. 17), macrovesicular steatosis (FIG. 18), inflammation (FIG. 19) and abnormally enlarged hepatocytes (FIG. 20). In primary human HSCs, TGF-b1-stimulated collagen1α1 production and plasminogen 1 (PAI-1) secretion were decreased by denifanstat, but not resmetirom, in a dose-dependent manner.

Conclusion

Combination of FASN inhibitor and THRb agonist resmetirom showed further ALT/AST improvement and lipid lowering compared to either agent alone in a mouse model of dyslipidemia and NASH/MASH. In vitro, denifanstat, but not resmetirom, directly reduced collagen production. These results suggest that complementary MOAs of denifanstat (DNL inhibition and direct anti-fibrotic effect) and resmetirom (lipid burning) combination could provide added benefit and support future clinical evaluation of this combination for NASH/MASH.

Example 12—Combination of Fatty Acid Synthase (FASN) Inhibitor and Thyroid Hormone Receptor Beta (THRβ) Agonist Resmetirom Shows Synergistic Improvement of NAFLD Activity Score (NAS) within 6-Weeks in Diet-Induced Obese Mice with Biopsy-Confirmed Metabolic Dysfunction-Associated Steatohepatitis (MASH)

This study was designed to evaluate FASN inhibitor alone and in combination with RES on liver histology in biopsy-confirmed MASH mice.

Method: Male C57BL/6J Gubra-Amylin-MASH (GAN) diet-induced obese mice with histologically confirmed NAS (≥5) and fibrosis stage (F1-F3) were randomized and treated with either TVB-3664 (a surrogate FASN inhibitor for denifanstat, 5 mg/kg, PO, QD) or resmetirom (RES; MGL-3196) (3 mg/kg, PO, QD) individually or in combination for 6 weeks (n=10-12 for each group, Gubra, Denmark). Treatment groups are NC (normal chow diet control); VEH (MASH vehicle control); FASN (TVB-3664, FASN inhibitor, surrogate for denifanstat); RES (resmetirom) and COMBO (combination of TVB-3664 and resmetirom).

Figure 21:
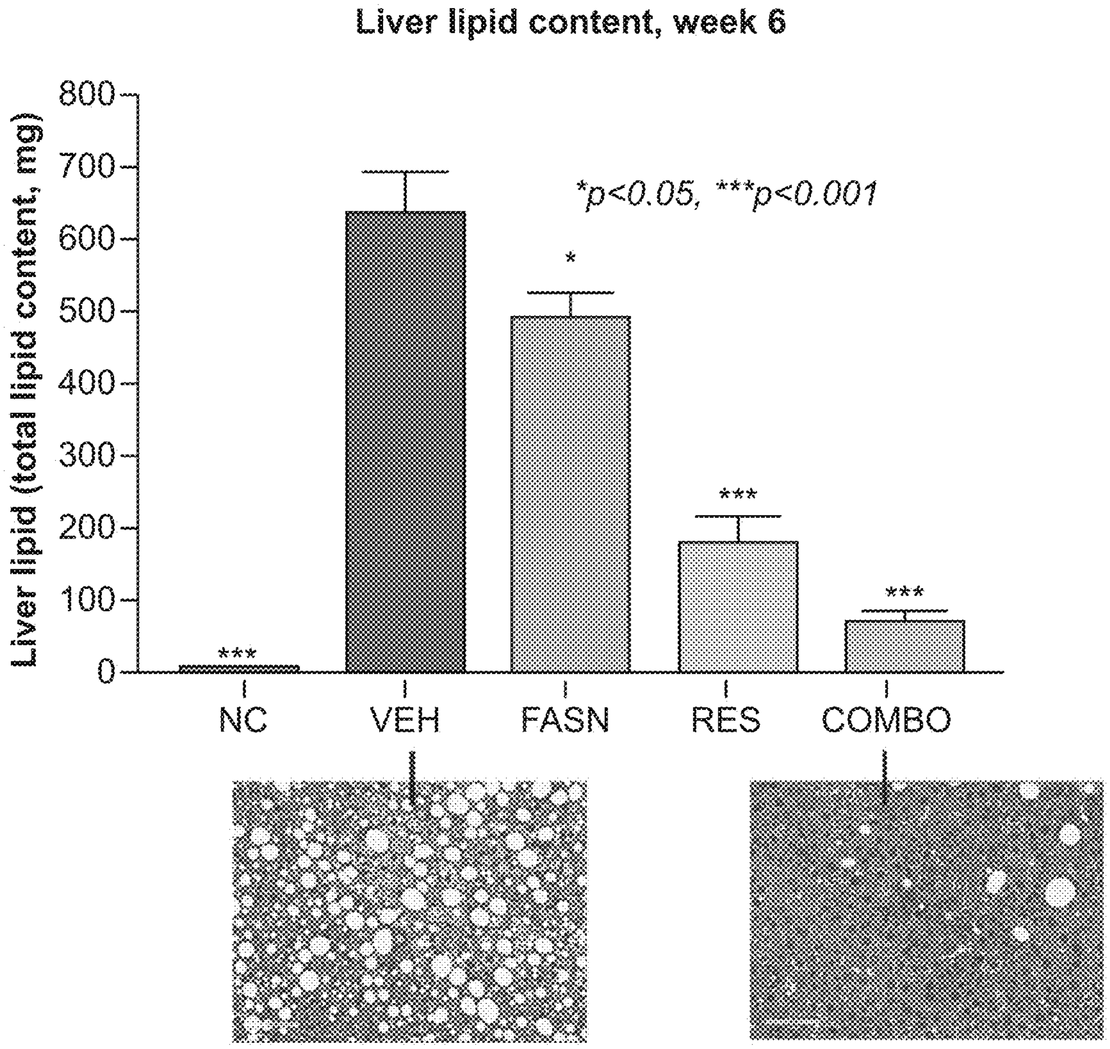
FIG. 21 shows the liver lipid content at 6 weeks in a DIO (diet induced obese) MASH Gubra mouse model (Example 12). The groups are NC (normal chow diet control); VEH (MASH vehicle control); FASN (TVB-3664, FASN inhibitor, surrogate for denifanstat); RES (resmetirom) and COMBO (combination of TVB-3664 and resmetirom).
Figure 22:
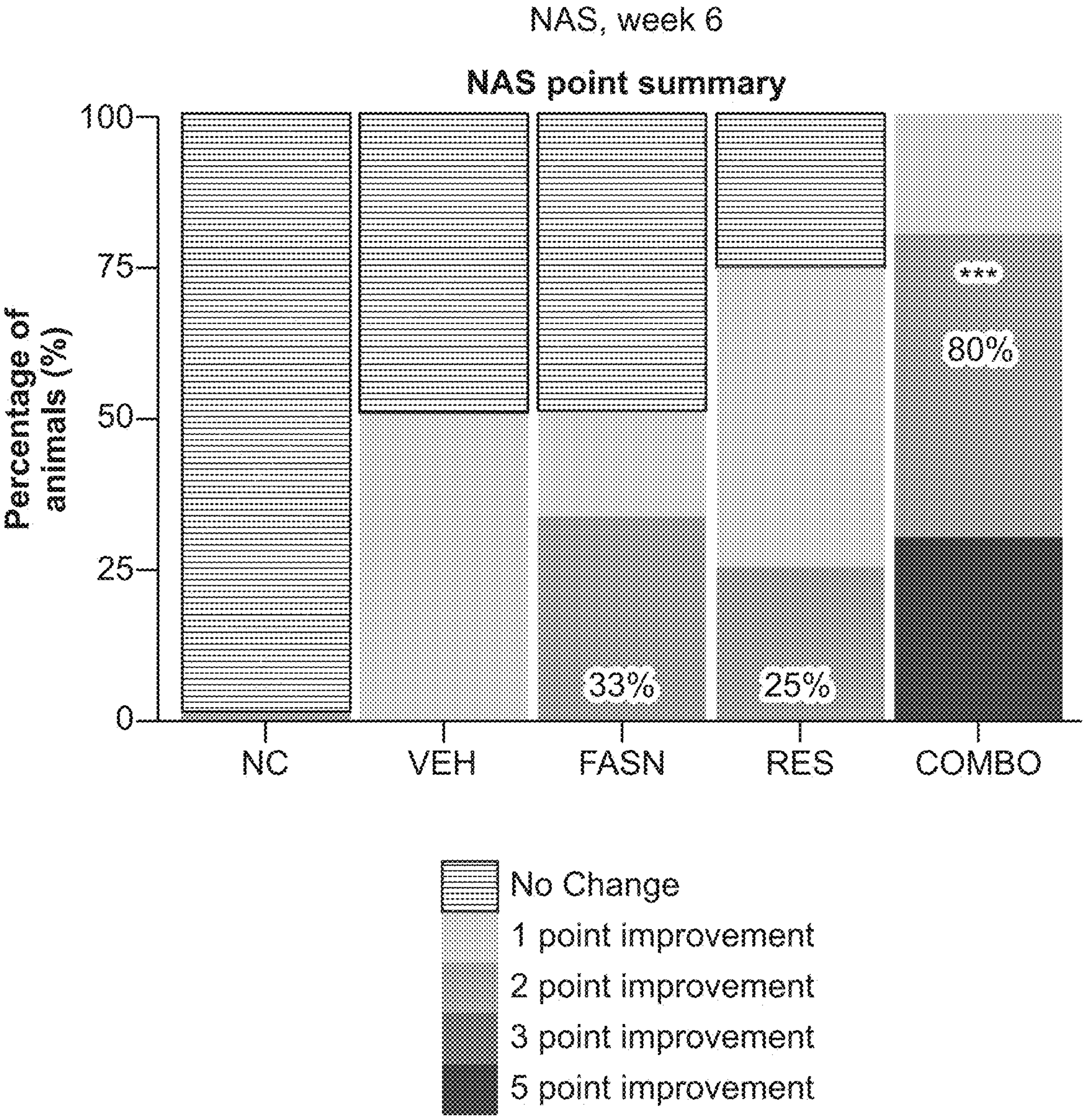
FIG. 22 shows the change in NAS points at 6 weeks in a DIO (diet induced obese) MASH Gubra mouse model (Example 12). The groups are NC (normal chow diet control); VEH (MASH vehicle control); FASN (TVB-3664, FASN inhibitor, surrogate for denifanstat); RES (resmetirom) and COMBO (combination of TVB-3664 and resmetirom).

Results: With a 6-week treatment of established MASH, the response rate (RR) for reduction of NAS≥2-points was 33% for TVB-3664 (FASN), 25% for resmetirom (RES), 0% for vehicle VEH and 80% for the combination (COMBO). Remarkably, 100% of combination-treated mice showed at least 1-point and 30% had ≥3-point NAS improvement. For steatosis, the RR for 1-point reduction was 17% for TVB-3664, 50% for RES and 100% for the combination, with a 2-point reduction in 80% combination animals (FIG. 22). This was consistent with significant reduction of % hepatocytes with lipid droplets and % area of liver lipids in drug-treated groups (FIG. 21). For lobular inflammation, the 1-point RR was 42% for TVB-3664, 8% for RES with a 2-point reduction in 10% combination animals. Some ballooning hepatocytes (ballooning score 1) were present before initiation of treatment and all treatments decreased the ballooning score to 0.

Conclusion: Combination of FASN inhibitor and THRb agonist RES had a synergistic effect on histological improvement of NAS compared to single agents within 6-weeks in a mouse model of MASH. These results suggest that the complementary MOAs of denifanstat (directly decrease lipid synthesis, inflammation and fibrosis) and RES (increase lipid burning) combined could provide added benefit and support future clinical evaluation of this combination for MASH.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

All publications and patent applications cited in this specification are herein incorporated by reference as if each individual publication or patent application were specifically and individually indicated to be incorporated by reference.

The invention claimed is:

1. A pharmaceutical composition comprising a therapeutically effective amount of:

a fatty acid synthase (FASN) inhibitor of formula:

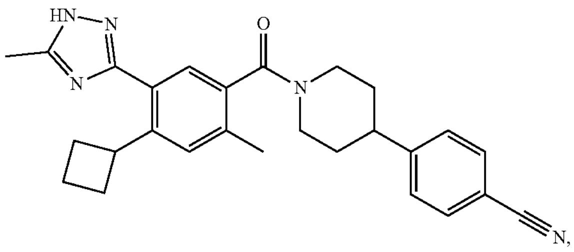

(denifanstat)

or a pharmaceutically acceptable salt thereof, and;

a thyroid hormone receptor-beta (THR-B) agonist of formula:

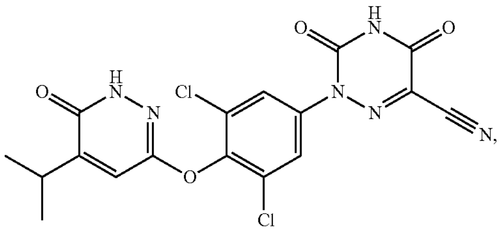

(resmetirom)

or a pharmaceutically acceptable salt thereof.

2. The pharmaceutical composition of claim 1, wherein the pharmaceutical composition comprising the therapeutically effective amount is a fixed-dose combination.

3. The pharmaceutical composition of claim 1, wherein the pharmaceutical composition comprising the therapeutically effective amount is a fixed-dose combination comprising from 25 to 50 mg of denifanstat.

4. A method of treating nonalcoholic steatohepatitis/metabolic dysfunction-associated steatohepatitis (NASH/MASH) in a subject in need thereof, the method comprising administering to the subject the pharmaceutical composition of claim 1.

5. The method of claim 4, wherein the pharmaceutical composition is administered once daily.

6. The method of claim 4, wherein the subject has moderate to severe fibrosis.

7. The method of claim 4, wherein the subject has severe fibrosis.

8. A method of treating nonalcoholic steatohepatitis/metabolic dysfunction-associated steatohepatitis (NASH/MASH) in a subject in need thereof, the method comprising administering to the subject the pharmaceutical composition of claim 2.

9. The method of claim 8, wherein the pharmaceutical composition is administered once daily.

10. The method of claim 8, wherein the subject has moderate to severe fibrosis.

11. The method of claim 8, wherein the subject has severe fibrosis.

12. A method of treating nonalcoholic steatohepatitis/metabolic dysfunction-associated steatohepatitis (NASH/MASH) in a subject in need thereof, the method comprising administering to the subject the pharmaceutical composition of claim 3.

13. The method of claim 12, wherein the pharmaceutical composition is administered once daily.

14. The method of claim 12, wherein the subject has moderate to severe fibrosis.

15. The method of claim 12, wherein the subject has severe fibrosis.

16. A method of producing improvement in liver fibrosis ≥1 stage without worsening of NASH/MASH in a subject in need thereof, the method comprising administering to the subject the pharmaceutical composition of claim 1.

17. A method of producing improvement in liver fibrosis ≥1 stage without worsening of NASH/MASH in a subject in need thereof, the method comprising administering to the subject the pharmaceutical composition of claim 2.

18. A method of producing improvement in liver fibrosis ≥1 stage without worsening of NASH/MASH in a subject in need thereof, the method comprising administering to the subject the pharmaceutical composition of claim 3.

* * * * *